US007803387B2

(12) United States Patent
Arico et al.

(10) Patent No.: US 7,803,387 B2
(45) Date of Patent: Sep. 28, 2010

(54) HETEROLOGOUS EXPRESSION OF NEISSERIAL PROTEINS

(75) Inventors: Maria Beatrice Arico, Siena (IT); Maurizio Comanducci, Siena (IT); Cesira Galeotti, Montegriggioni (IT); Vega Masignani, Siena (IT); Marizia Monica Guiliani, Siena (IT); Mariagrazia Pizza, Siena (IT)

(73) Assignee: Novartis Vaccines and Diagnostics SRL, Siena (IT)

( * ) Notice: Subject to any disclaimer, the term of this patent is extended or adjusted under 35 U.S.C. 154(b) by 1138 days.

(21) Appl. No.: 10/220,481

(22) PCT Filed: Feb. 28, 2001

(86) PCT No.: PCT/IB01/00452

§ 371 (c)(1), (2), (4) Date: Aug. 13, 2003

(87) PCT Pub. No.: WO01/64922

PCT Pub. Date: Sep. 7, 2001

(65) Prior Publication Data

US 2004/0110670 A1 Jun. 10, 2004

(30) Foreign Application Priority Data

Feb. 28, 2000 (GB) ................................ 0004695.3
Nov. 13, 2000 (GB) ................................ 0027675.8

(51) Int. Cl.

*A61K 39/095* (2006.01)
*A61K 39/38* (2006.01)
*A61K 38/00* (2006.01)
*C12P 1/00* (2006.01)
*C12P 39/00* (2006.01)

(52) U.S. Cl. .............. 424/250.1; 424/184.1; 424/249.1; 435/41; 435/42; 530/300; 530/324

(58) Field of Classification Search .............. 424/184.1, 424/249.1, 250.1; 435/41, 42, 69.7; 530/300, 530/324

See application file for complete search history.

(56) References Cited

U.S. PATENT DOCUMENTS 5,547,670 A 8/1996 Goldstein et al.
5,914,254 A 6/1999 Mascarenhas et al.
6,013,267 A 1/2000 Blake et al.
6,028,049 A 2/2000 Jacobs et al.

FOREIGN PATENT DOCUMENTS

| | | | |
|---|---|---|---|
| FR | 2 720 408 | A1 | 12/1995 |
| WO | WO 92/16643 | A1 | 10/1992 |
| WO | WO 97/13860 | A1 | 4/1997 |
| WO | WO 97/28273 | A1 | 8/1997 |
| WO | WO 99/24578 | A2 | 5/1999 |
| WO | WO 99/36544 | A2 | 7/1999 |
| WO | WO 99/57280 | * | 11/1999 |
| WO | WO 99/57280 | A2 | 11/1999 |
| WO | WO 99/57289 | * | 11/1999 |
| WO | WO 99/57820 | * | 11/1999 |
| WO | WO 00/22430 | A2 | 4/2000 |

OTHER PUBLICATIONS

Renauld-Mongenie (Journal of Bacteriology, Oct. 1997, p. 6400-6407).*
Thomas E. Creighton, in his book, "Proteins: Structures and Molecular Properties, 1984", (pp. 314-315).*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second paragraph).*
Greenspan et al. (Nature Biotechnology 17: 936-937, 1999).*
Bowie et al (Science, 1990, 257:1306-1310).*
Guillen et al., "Expression in *Escherichia coli* and immunological characterization of a hybrid class 1-P64K protein from *Neisseria meningitidis," Biotecnologia Aplicada* 13(4):271-275, 1996.
Legrain et al., "Production of lipidated meningococcal transferrin binding protein 2 in *Escherichia coli," Protein Expression and Purification* 6:570-578, 1995.
Renauld-Mongénie et al., "Identification of human transferrin-binding sites within meningococcal transferrin-binding protein B," *J. Bacteriology* 179(20):6400-6407, 1997.
Brandhorst T. et al, Effects of Leader Sequences upon the Heterologous Expression of Restriction in *Aspergillus nidulans* and *Aspergillus niger*, CJM, 41, 7, 1995, pp. 601-611.

* cited by examiner

*Primary Examiner*—Vanessa L. Ford
(74) *Attorney, Agent, or Firm*—Amy Hessler; Helen Lee; Robert Gorman

(57) ABSTRACT

Alternative and improved approaches to the heterologous expression of the proteins of *Neisseria meningitidis* and *Neisseria gonorrhoeae*. These approaches typically affect the level of expression, the ease of purification, the cellular localization, and/or the immunological properties of the expressed protein.

8 Claims, 13 Drawing Sheets

ELISA: *POSITIVE*

*FIGURE 4*
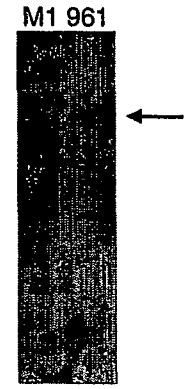
*PURIFICATION*
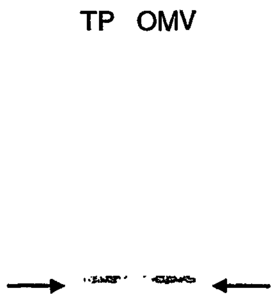
*WESTERN BLOT*
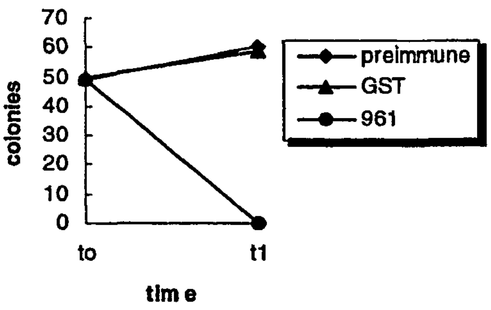
*BACTERICIDAL ASSAY*
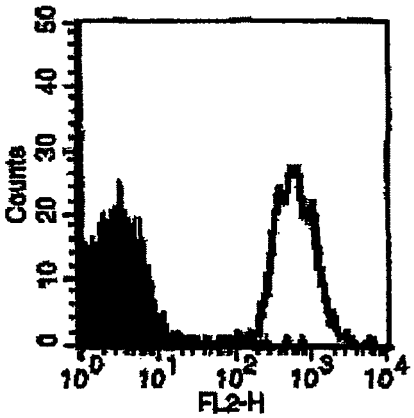
*FACS*
*ELISA:* *POSITIVE*

FIGURE 7

```
          <A----------------------<Δ1----------------------------------
MC58    1 MFKRSVIAMACIFALSACGGGGGGSPDVKSADTLSKPAAPVVSEKETEAKEDAPQAGSQG
2996    1 MFERSVIAMACIFALSACGGGGGGSPDVKSADTLSKPAAPVVAEKETEVKEDAPQAGSQG

          ---------<Δ2-------------------------------------------------
MC58   61 QGAPSAQGSQDMAAVSEENTGNGGAVTADNPKNEDEVAQNDMPQNAAGTDSSTPNHTPDP
2996   61 QGAPSTQGSQDMAAVSAENTGNGGAATTDKPKNEDEGPQNDMPQN...............

          ------------------------------------------------------<Δ3----
MC58  121 NMLAGNMENQATDAGESSQPANQPDMANAADGMQGDDPSAGGQNAGNTAAQGANQAGNNQ
2996  106 ................................................SAESANQTGNNQ

          --------------------A><B-------------------------------------
MC58  181 AAGSSDPIPASNPAPANGGSNFGRVDLANGVLIDGPSQNITLTHCKGDSCSGNNFLDEEV
2996  118 PADSSDSAPASNPAPANGGSNFGRVDLANGVLIDGPSQNITLTHCKGDSCNGDNLLDEEA

          ---------------------------------------------B>
MC58  241 QLKSEFEKLSDADKISNYKKDGKNDKFVGLVADSVQMKGINQYIIFYKPK..PTSFARFR
2996  178 PSKSEFENLNESERIEKYKKDGKSDKFTNLVATAVQANGTNKYVIIYKDKSASSSSARFR

                         <C--------------------------------------------
MC58  299 RSARSRRSLPAEMPLIPVNQADTLIVDGEAVSLTGHSGNIFAPEGNYRYLTYGAEKLPGG
2996  238 RSARSRRSLPAEMPLIPVNQADTLIVDGEAVSLTGHSGNIFAPEGNYRYLTYGAEKLPGG

          -------------------------------------------------------------
MC58  359 SYALRVQGEPAKGEMLAGAAVYNGEVLHFHTENGRPYPTRGRFAAKVDFGSKSVDGIIDS
2996  298 SYALRVQGEPAKGEMLAGTAVYNGEVLHFHTENGRPYPTRGRFAAKVDFGSKSVDGIIDS

          -------------------------------------------------------------
MC58  419 GDDLHMGTQKFKAAIDGNGFKGTWTENGSGDVSGKFYGPAGEEVAGKYSYRPTDAEKGGF
2996  358 GDDLHMGTQKFKAAIDGNGFKGTWTENGGGDVSGRFYGPAGEEVAGKYSYRPTDAEKGGF

          --------C>
MC58  479 GVFAGKKEQD*
2996  418 GVFAGKKEQD*
```

FIGURE 13
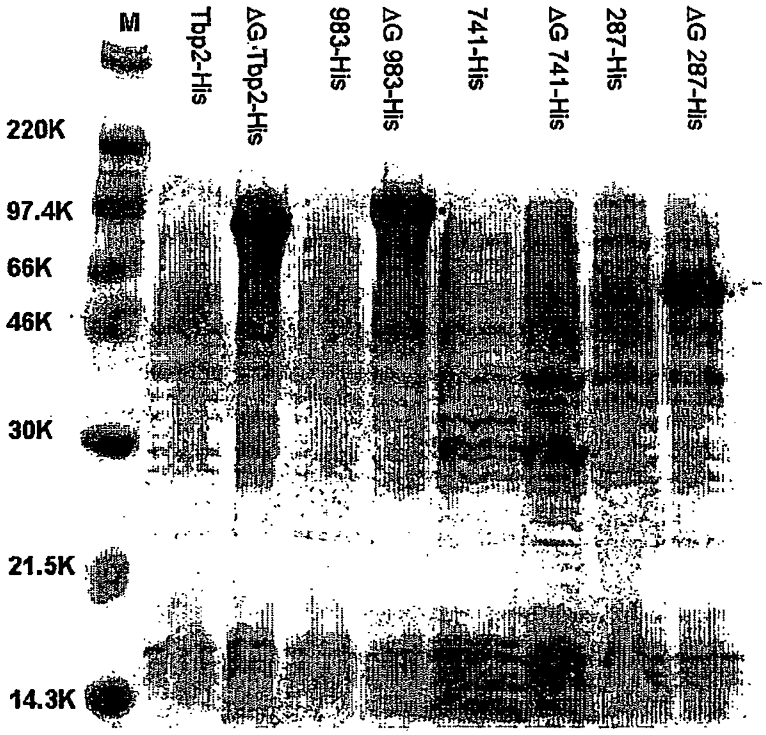
FIGURE 14
FIGURE 14A — ΔG287—919
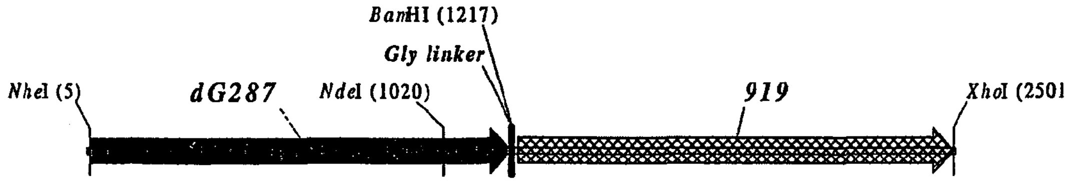
FIGURE 14B — ΔG287—953
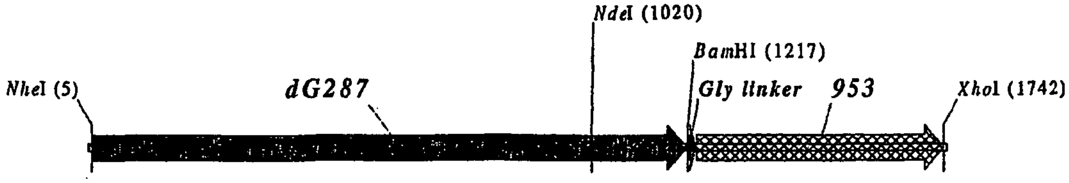

FIGURE 14C — ΔG287—961
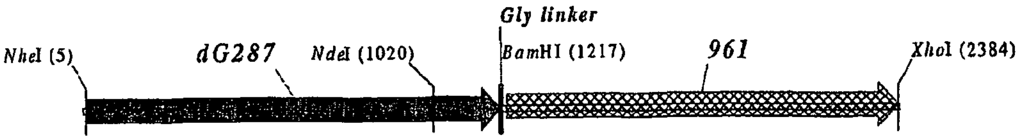
FIGURE 14D — ΔG287NZ—919
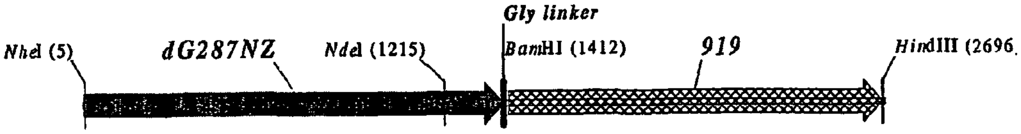
FIGURE 14E — ΔG287NZ—953
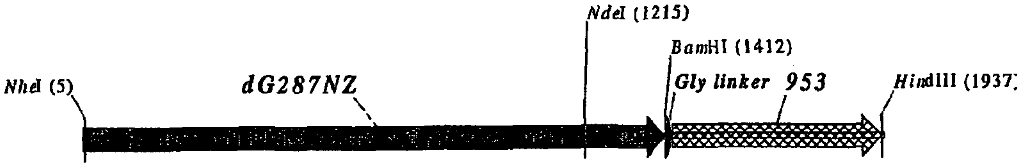
FIGURE 14F — ΔG287NZ—961
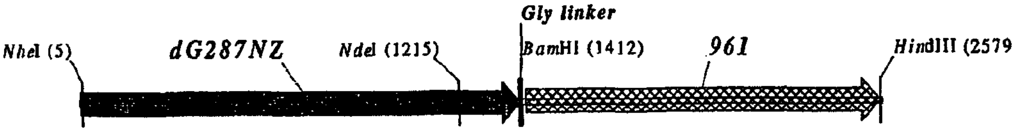
FIGURE 14G — ΔG983-ORF46.1
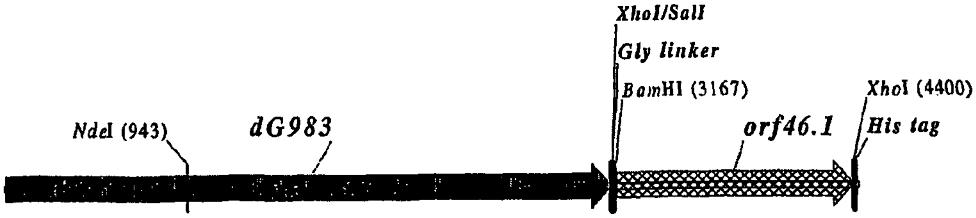

FIGURE 14H — ΔG983-741
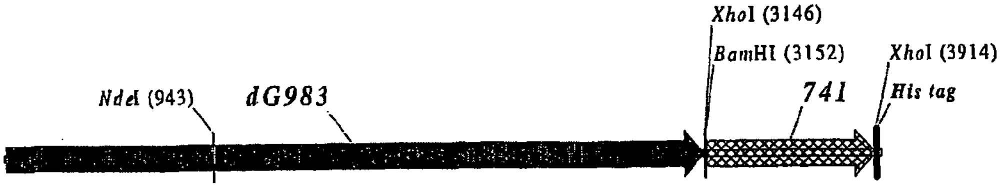
FIGURE 14I — ΔG983-961
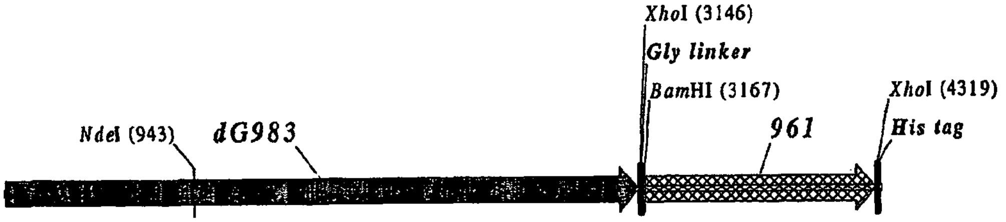
FIGURE 14J — ΔG983-961c
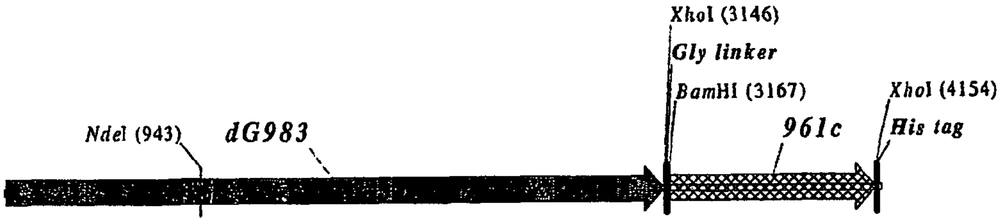
FIGURE 14K — ΔG741-961
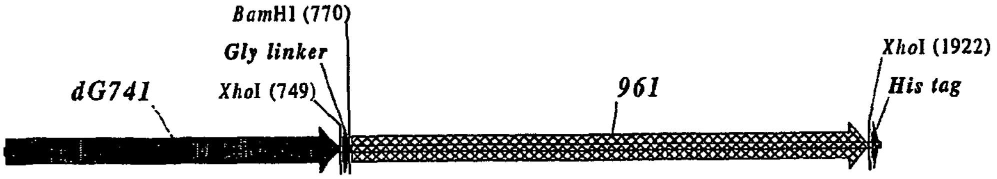
FIGURE 14L — ΔG741-961c
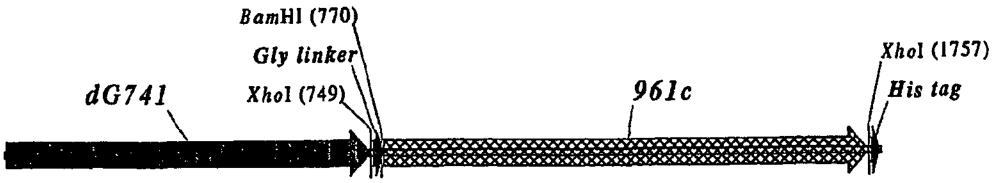

FIGURE 14M — ΔG741-983
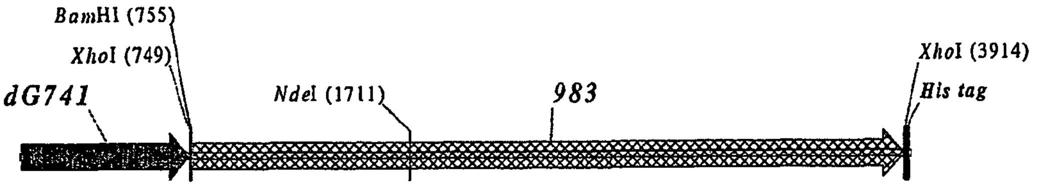
FIGURE 14N — ΔG741-ORF46.1
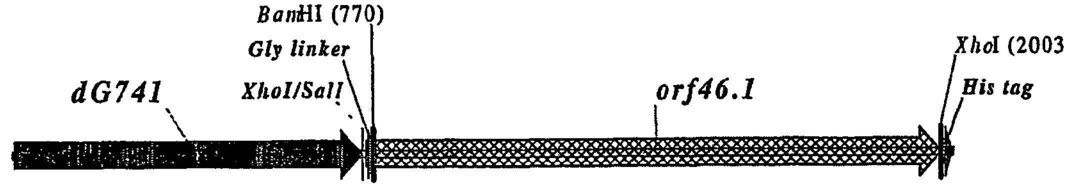
FIGURE 14O — ORF46.1-741
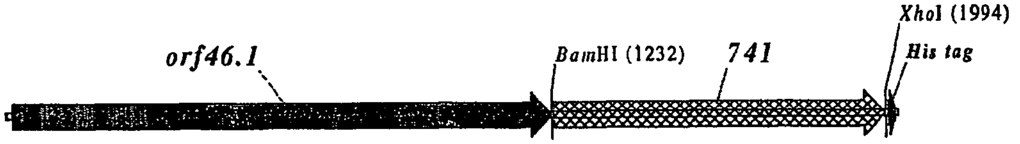
FIGURE 14P — ORF46.1-961
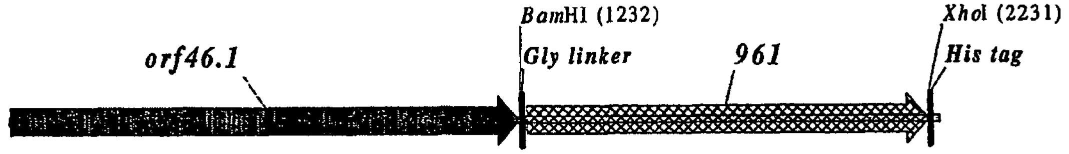
FIGURE 14Q — ORF46.1—961c
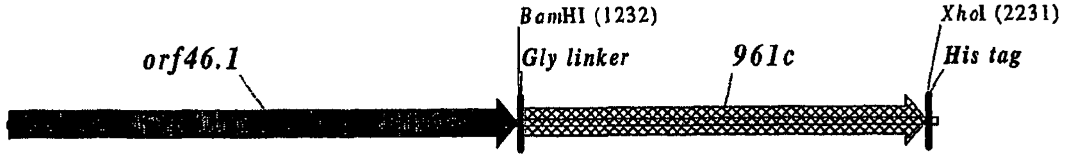

FIGURE 14R — 961-ORF46.1
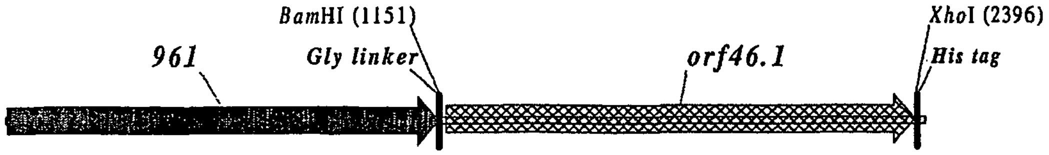
FIGURE 14S — 961-741
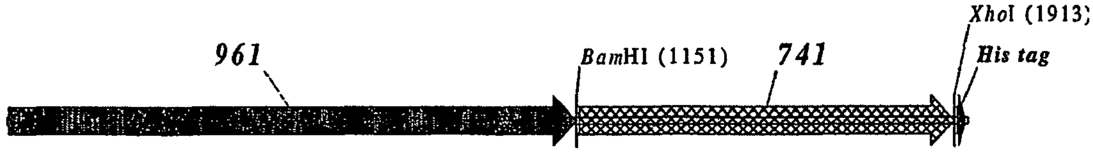
FIGURE 14T — 961-983
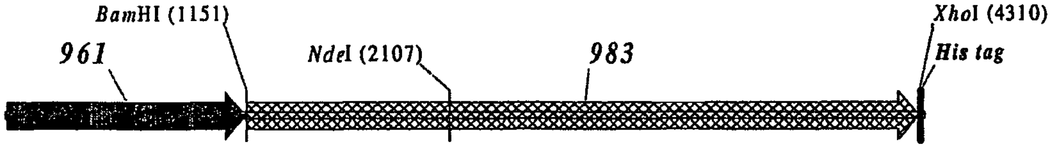
FIGURE 14U — 961c-ORF46.1
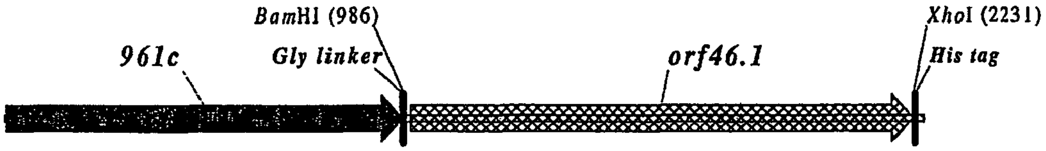
FIGURE 14V — 961c-741
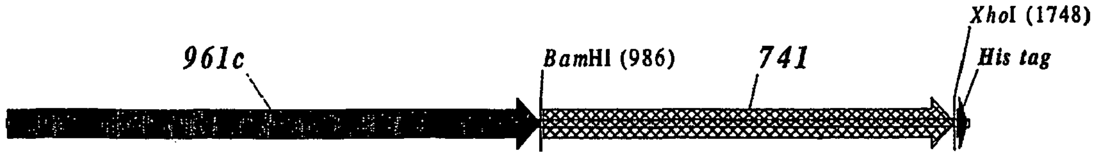

FIGURE 14W — 961c-983
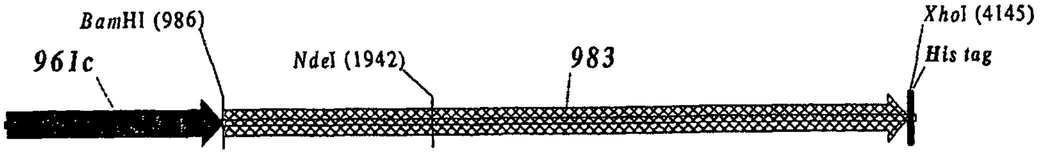
FIGURE 14X — 961cL-ORF46.1
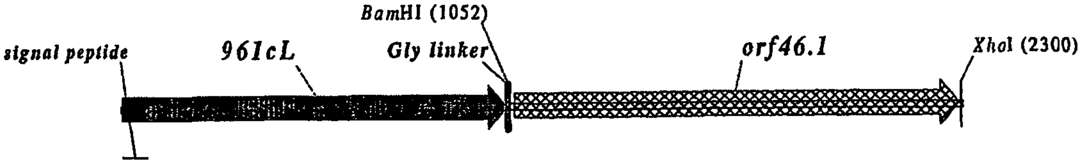
FIGURE 14Y — 961cL-741
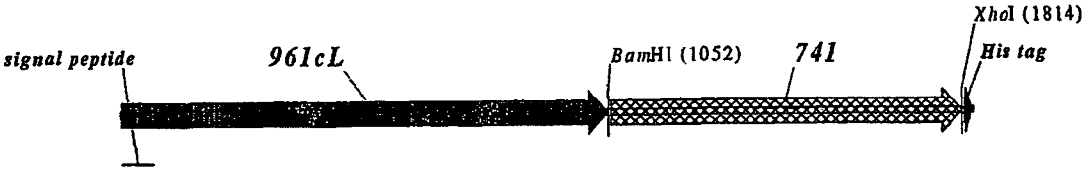
FIGURE 14Z — 961cL-983
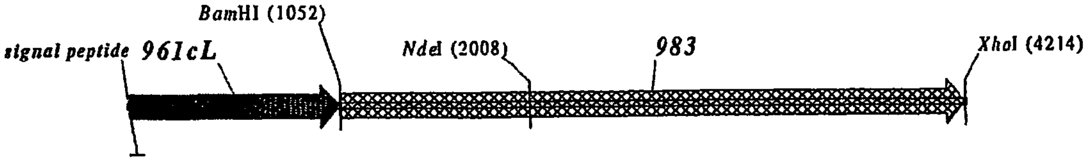

HETEROLOGOUS EXPRESSION OF NEISSERIAL PROTEINS

All documents cited herein are incorporated by reference in their entirety.

This application is a §371 filing from PCT/IB01/00452, filed Feb. 28, 2001, which claims priority from GB 0004695.3, filed Feb. 28, 2000 and GB 0027675.8, filed Nov. 13, 2000, from which applications priority is claimed pursuant to the provisions of 35 U.S.C. §§119/120 and which applications are incorporated by reference herein in their entireties.

TECHNICAL FIELD

This invention is in the field of protein expression. In particular, it relates to the heterologous expression of proteins from *Neisseria* (e.g. *N.gonorrhoeae* or, preferably, *N.meningitidis*).

BACKGROUND ART

International patent applications WO99/24578, WO99/36544, WO99/57280 and WO00/22430 disclose proteins from *Neisseria meningitidis* and *Neisseria gonorrhoeae*. These proteins are typically described as being expressed in *E.coli* (i.e. heterologous expression) as either N-terminal GST-fusions or C-terminal His-tag fusions, although other expression systems, including expression in native *Neisseria*, are also disclosed.

It is an object of the present invention to provide alternative and improved approaches for the heterologous expression of these proteins. These approaches will typically affect the level of expression, the ease of purification, the cellular localisation of expression, and/or the immunological properties of the expressed protein.

DISCLOSURE OF THE INVENTION

Nomenclature Herein

The 2166 protein sequences disclosed in WO99/24578, WO99/36544 and WO99/57280 are referred to herein by the following SEQ# numbers:

| Application | Protein sequences | SEQ# herein |
|---|---|---|
| WO99/24578 | Even SEQ IDs 2-892 | SEQ#s 1-446 |
| WO99/36544 | Even SEQ IDs 2-90 | SEQ#s 447-491 |
| WO99/57280 | Even SEQ IDs 2-3020 | SEQ#s 492-2001 |
| | Even SEQ IDs 3040-3114 | SEQ#s 2002-2039 |
| | SEQ IDs 3115-3241 | SEQ#s 2040-2166 |

In addition to this SEQ# numbering, the naming conventions used in WO99/24578, WO99/36544 and WO99/57280 are also used (e.g. 'ORF4', 'ORF40', 'ORF40-1' etc. as used in WO99/24578 and WO99/36544; 'm919', 'g919' and 'a919' etc. as used in WO99/57280).

The 2160 proteins NMB0001 to NM2160 from Tettelin et al. [*Science* (2000) 287:1809-1815] are referred to herein as SEQ#s 2167-4326 [see also WO00/66791].

The term 'protein of the invention' as used herein refers to a protein comprising:

(a) one of sequences SEQ#s 1-4326; or (b) a sequence having sequence identity to one of SEQ#s 1-4326; or (c) a fragment of one of SEQ#s 1-4326.

The degree of 'sequence identity' referred to in (b) is preferably greater than 50% (eg. 60%, 70%, 80%, 90%, 95%, 99% or more). This includes mutants and allelic variants [e.g. see WO00/66741]. Identity is preferably determined by the Smith-Waterman homology search algorithm as implemented in the MPSRCH program (Oxford Molecular), using an affine gap search with parameters gap open penalty=12 and gap extension penalty=1. Typically, 50% identity or more between two proteins is considered to be an indication of functional equivalence.

The 'fragment' referred to in (c) should comprise at least n consecutive amino acids from one of SEQ#s 1-4326 and, depending on the particular sequence, n is 7 or more (eg. 8, 10, 12, 14, 16, 18, 20, 25, 30, 35, 40, 50, 60, 70, 80, 90, 100 or more). Preferably the fragment comprises an epitope from one of SEQ#s 1-4326. Preferred fragments are those disclosed in WO0/71574 and WO01/04316.

Preferred proteins of the invention are found in *N.meningitidis* serogroup B.

Preferred proteins for use according to the invention are those of serogroup B *N.meningitidis* strain 2996 or strain 394/98 (a New Zealand strain). Unless otherwise stated, proteins mentioned herein are from *N.meningitidis* strain 2996. It will be appreciated, however, that the invention is not in general limited by strain. References to a particular protein (e.g. '287', '919' etc.) may be taken to include that protein from any strain.

Non-Fusion Expression

In a first approach to heterologous expression, no fusion partner is used, and the native leader peptide (if present) is used. This will typically prevent any 'interference' from fusion partners and may alter cellular localisation and/or post-translational modification and/or folding in the heterologous host.

Thus the invention provides a method for the heterologous expression of a protein of the invention, in which (a) no fusion partner is used, and (b) the protein's native leader peptide (if present) is used.

The method will typically involve the step of preparing an vector for expressing a protein of the invention, such that the first expressed amino acid is the first amino acid (methionine) of said protein, and last expressed amino acid is the last amino acid of said protein (i.e. the codon preceding the native STOP codon).

This approach is preferably used for the expression of the following proteins using the native leader peptide: 111, 149, 206, 225-1, 235, 247-1, 274, 283, 286, 292, 401, 406, 502-1, 503, 519-1, 525-1, 552, 556, 557, 570, 576-1, 580, 583, 664, 759, 907, 913, 920-1, 936-1, 953, 961, 983, 989, Orf4, Orf7-1, Orf9-1, Orf23, Orf25, Orf37, Orf38, Orf40, Orf40.1, Orf40.2, Orf72-1, Orf76-1, Orf85-2, Orf91, Orf97-1, Orf119, Orf143.1, NMB0109 and NMB2050. The suffix 'L' used herein in the name of a protein indicates expression in this manner using the native leader peptide.

Proteins which are preferably expressed using this approach using no fusion partner and which have no native leader peptide include: 008, 105, 117-1, 121-1, 122-1, 128-1, 148, 216, 243, 308, 593, 652, 726, 926, 982, Orf83-1 and Orf143-1.

Advantageously, it is used for the expression of ORF25 or ORF40, resulting in a protein which induces better anti-bactericidal antibodies than GST- or His-fusions.

This approach is particularly suited for expressing lipoproteins.

Leader-Peptide Substitution

In a second approach to heterologous expression, the native leader peptide of a protein of the invention is replaced by that of a different protein. In addition, it is preferred that no fusion partner is used. Whilst using a protein's own leader peptide in heterologous hosts can often localise the protein to its 'natural' cellular location, in some cases the leader sequence is not efficiently recognised by the heterologous host. In such cases, a leader peptide known to drive protein targeting efficiently can be used instead.

Thus the invention provides a method for the heterologous expression of a protein of the invention, in which (a) the protein's leader peptide is replaced by the leader peptide from a different protein and, optionally, (b) no fusion partner is used.

The method will typically involve the steps of: obtaining nucleic acid encoding a protein of the invention; manipulating said nucleic acid to remove nucleotides that encode the protein's leader peptide and to introduce nucleotides that encode a different protein's leader peptide. The resulting nucleic acid may be inserted into an expression vector, or may already be part of an expression vector. The expressed protein win consist of the replacement leader peptide at the N-terminus, followed by the protein of the invention minus its leader peptide.

The leader peptide is preferably from another protein of the invention (e.g. one of SEQ#s 1-4326), but may also be from an *E.coli* protein (e.g. the OmpA leader peptide) or an *Erwinia carotovora* protein (e.g. the PelB leader peptide), for instance.

A particularly useful replacement leader peptide is that of ORF4. This leader is able to direct lipidation in *E.coli*, improving cellular localisation, and is particularly useful for the expression of proteins 287, 919 and ΔG287. The leader peptide and N-terminal domains of 961 are also particularly useful.

Another useful replacement leader peptide is that of *E.coli* OmpA. This leader is able to direct membrane localisation of *E.coli*. It is particularly advantageous for the expression of ORF1, resulting in a protein which induces better anti-bactericidal antibodies than both fusions and protein expressed from its own leader peptide.

Another useful replacement leader peptide is MKKYLFSAA (SEQ ID NO:621). This can direct secretion into culture medium, and is extremely short and active. The use of this leader peptide is not restricted to the expression of Neisserial proteins—it may be used to direct the expression of any protein (particularly bacterial proteins).

Leader-Peptide Deletion

In a third approach to heterologous expression, the native leader peptide of a protein of the invention is deleted. In addition, it is preferred that no fusion partner is used.

Thus the invention provides a method for the heterologous expression of a protein of the invention, in which (a) the protein's leader peptide is deleted and, optionally, (b) no fusion partner is used.

The method will typically involve the steps of: obtaining nucleic acid encoding a protein of the invention; manipulating said nucleic acid to remove nucleotides that encode the protein's leader peptide. The resulting nucleic acid may be inserted into an expression vector, or may already be part of an expression vector. The first amino acid of the expressed protein will be that of the mature native protein.

This method can increase the levels of expression. For protein 919, for example, expression levels in *E.coli* are much higher when the leader peptide is deleted. Increased expression may be due to altered localisation in the absence of the leader peptide.

The method is preferably used for the expression of 919, ORF46, 961, 050-1, 760 and 287.

Domain-Based Expression

In a fourth approach to heterologous expression, the protein is expressed as domains. This may be used in association with fusion systems (e.g. GST or His-tag fusions).

Thus the invention provides a method for the heterologous expression of a protein of the invention, in which (a) at least one domain in the protein is deleted and, optionally, (b) no fusion partner is used.

The method will typically involve the steps of: obtaining nucleic acid encoding a protein of the invention; manipulating said nucleic acid to remove at least one domain from within the protein. The resulting nucleic acid may be inserted into an expression vector, or may already be part of an expression vector. Where no fusion partners are used, the first amino acid of the expressed protein will be that of a domain of the protein.

A protein is typically divided into notional domains by aligning it with known sequences in databases and then determining regions of the protein which show different alignment patterns from each other.

The method is preferably used for the expression of protein 287. This protein can be notionally split into three domains, referred to as A B & C (see FIG. 5). Domain B aligns strongly with IgA proteases, domain C aligns strongly with transferrin-binding proteins, and domain A shows no strong alignment with database sequences. An alignment of polymorphic forms of 287 is disclosed in WO00/66741.

Once a protein has been divided into domains, these can be (a) expressed singly (b) deleted from with the protein e.g. protein ABCD→ABD, ACD, BCD etc. or (c) rearranged e.g. protein ABC→ACB, CAB etc. These three strategies can be combined with fusion partners is desired.

ORF46 has also been notionally split into two domains—a first domain (amino acids 1-433) which is well-conserved between species and serogroups, and a second domain (amino acids 433-608) which is not well-conserved. The second domain is preferably deleted. An alignment of polymorphic forms of ORF46 is disclosed in WO00/66741.

Protein 564 has also been split into domains (FIG. 8), as have protein 961 (FIG. 12) and protein 502 (amino acids 28-167 of the MC58 protein).

Hybrid Proteins

In a fifth approach to heterologous expression, two or more (e.g. 3, 4, 5, 6 or more) proteins of the invention are expressed as a single hybrid protein. It is preferred that no non-Neisserial fusion partner (e.g. GST or poly-His) is used.

This offers two advantages. Firstly, a protein that may be unstable or poorly expressed on its own can be assisted by adding a suitable hybrid partner that overcomes the problem. Secondly, commercial manufacture is simplified—only one expression and purification need be employed in order to produce two separately-useful proteins.

Thus the invention provides a method for the simultaneous heterologous expression of two or more proteins of the invention, in which said two or more proteins of the invention are fused (i.e. they are translated as a single polypeptide chain).

The method will typically involve the steps of: obtaining a first nucleic acid encoding a first protein of the invention; obtaining a second nucleic acid encoding a second protein of the invention; ligating the first and second nucleic acids. The resulting nucleic acid may be inserted into an expression vector, or may already be part of an expression vector.

Preferably, the constituent proteins in a hybrid protein according to the invention will be from the same strain.

The fused proteins in the hybrid may be joined directly, or may be joined via a linker peptide e.g. via a poly-glycine linker (i.e. $G_n$ where n=3, 4, 5, 6, 7, 8, 9, 10 or more) or via a short peptide sequence which facilitates cloning. It is evidently preferred not to join a ΔG protein to the C-terminus of a poly-glycine linker.

The fused proteins may lack native leader peptides or may include the leader peptide sequence of the N-terminal fusion partner.

The method is well suited to the expression of proteins orf1, orf4, orf25, orf40, orf46/46.1, orf83, 233, 287, 292L, 564, 687, 741, 907, 919, 953, 961 and 983.

The 42 hybrids indicated by 'X' in the following table of form $NH_2$-A-B—COOH are preferred:

| ↓A B→ | ORF46.1 | 287 | 741 | 919 | 953 | 961 | 983 |
|---|---|---|---|---|---|---|---|
| ORF46.1 | | X | X | X | X | X | X |
| 287 | X | | X | X | X | X | X |
| 741 | X | X | | X | X | X | X |
| 919 | X | X | X | | X | X | X |
| 953 | X | X | X | X | | X | X |
| 961 | X | X | X | X | X | | X |
| 983 | X | X | X | X | X | X | |

Preferred proteins to be expressed as hybrids are thus ORF46.1, 287, 741, 919, 953, 961 and 983. These may be used in their essentially full-length form, or poly-glycine deletions (ΔG) forms may be used (e.g. ΔG-287, ΔGTbp2, ΔG741, ΔG983 etc.), or truncated forms may be used (e.g. Δ1-287, Δ2-287 etc.), or domain-deleted versions may be used (e.g. 287B, 287C, 287BC, $ORF46_{1-433}$, $ORF46_{433-608}$, ORF46, 961c etc.).

Particularly preferred are: (a) a hybrid protein comprising 919 and 287; (b) a hybrid protein comprising 953 and 287; (c) a hybrid protein comprising 287 and ORF46.1; (d) a hybrid protein comprising ORF1 and ORF46.1; (e) a hybrid protein comprising 919 and ORF46.1; (f) a hybrid protein comprising ORF46.1 and 919; (g) a hybrid protein comprising ORF46.1, 287 and 919; (h) a hybrid protein comprising 919 and 519; and (i) a hybrid protein comprising ORF97 and 225. Further embodiments are shown in FIG. 14.

Where 287 is used, it is preferably at the C-terminal end of a hybrid; if it is to be used at the N-terminus, if is preferred to use a ΔG form of 287 is used (e.g. as the N-terminus of a hybrid with ORF46.1, 919, 953 or 961).

Where 287 is used, this is preferably from strain 2996 or from strain 394/98.

Where 961 is used, this is preferably at the N-terminus. Domain forms of 961 may be used.

Alignments of polymorphic forms of ORF46, 287, 919 and 953 are disclosed in WO00/66741. Any of these polymorphs can be used according to the present invention.

Temperature

In a sixth approach to heterologous expression, proteins of the invention are expressed at a low temperature.

Expressed Neisserial proteins (e.g. 919) may be toxic to *E.coli*, which can be avoided by expressing the toxic protein at a temperature at which its toxic activity is not manifested.

Thus the present invention provides a method for the heterologous expression of a protein of the invention, in which expression of a protein of the invention is carried out at a temperature at which a toxic activity of the protein is not manifested.

A preferred temperature is around 30° C. This is particularly suited to the expression of 919.

Mutations

As discussed above, expressed Neisserial proteins may be toxic to *E.coli*. This toxicity can be avoided by mutating the protein to reduce or eliminate the toxic activity. In particular, mutations to reduce or eliminate toxic enzymatic activity can be used, preferably using site-directed mutagenesis.

In a seventh approach to heterologous expression, therefore, an expressed protein is mutated to reduce or eliminate toxic activity.

Thus the invention provides a method for the heterologous expression of a protein of the invention, in which protein is mutated to reduce or eliminate toxic activity.

The method is preferably used for the expression of protein 907, 919 or 922. A preferred mutation in 907 is at Glu-117 (e.g. Glu→Gly), preferred mutations in 919 are at Glu-255 (e.g. Glu→Gly) and/or Glu-323 (e.g. Glu→Gly); preferred mutations in 922 are at Glu-164 (e.g. Glu→Gly), Ser-213 (e.g. Ser→Gly) and/or Asn-348 (e.g. Asn→Gly).

Alternative Vectors

In a eighth approach to heterologous expression, an alternative vector used to express the protein. This may be to improve expression yields, for instance, or to utilise plasmids that are already approved for GMP use.

Thus the invention provides a method for the heterologous expression of a protein of the invention, in which an alternative vector is used. The alternative vector is preferably pSM214, with no fusion partners. Leader peptides may or may not be included.

This approach is particularly useful for protein 953. Expression and localisation of 953 with its native leader peptide expressed from pSM214 is much better than from the pET vector.

pSM214 may also be used with: ΔG287, Δ2-287, Δ3-287, Δ4-287, Orf46.1, 961L, 961, 961(MC58), 961c, 961c-L, 919, 953 and ΔG287-Orf46.1.

Another suitable vector is, pET-24b (Novagen; uses kanamycin resistance), again using no fusion partners. pET-24b is preferred for use with: ΔG287K, Δ2-287K, Δ3-287K, Δ4287K, Orf46.1-K, Orf46A-K, 961-K (MC58), 961a-K, 961b-K, 961c-K, 961c-L-K, 961d-K, ΔG287-919-K, ΔG287-Orf46.1-K and ΔG287-961-K.

Multimeric Form

In a ninth approach to heterologous expression, a protein is expressed or purified such that it adopts a particular multimeric form.

This approach is particularly suited to protein 953. Purification of one particular multimeric form of 953 (the monomeric form) gives a protein with greater bactericidal activity than other forms (the dimeric form).

Proteins 287 and 919 may be purified in dimeric forms.

Protein 961 may be purified in a 180 kDa oligomeric form (e.g. a tetramer).

Lipidation

In a tenth approach to heterologous expression, a protein is expressed as a lipidated protein.

Thus the invention provides a method for the heterologous expression of a protein of the invention, in which the protein is expressed as a lipidated protein.

This is particularly useful for the expression of 919, 287, ORF4, 406, 576-1, and ORF25. Polymorphic forms of 919, 287 and ORF4 are disclosed in WO00/66741.

The method will typically involve the use of an appropriate leader peptide without using an N-terminal fusion partner.

C-Terminal Deletions

In an eleventh approach to heterologous expression, the C-terminus of a protein of the invention is mutated. In addition, it is preferred that no fusion partner is used.

Thus the invention provides a method for the heterologous expression of a protein of the invention, in which (a) the protein's C-terminus region is mutated and, optionally, (b) no fusion partner is used.

The method will typically involve the steps of: obtaining nucleic acid encoding a protein of the invention; manipulating said nucleic acid to mutate nucleotides that encode the protein's C-terminus portion. The resulting nucleic acid may be inserted into an expression vector, or may already be part of an expression vector. The first amino acid of the expressed protein will be that of the mature native protein.

The mutation may be a substitution, insertion or, preferably, a deletion.

This method can increase the levels of expression, particularly for proteins 730, ORF29 and ORF46. For protein 730, a C-terminus region of around 65 to around 214 amino acids may be deleted; for ORF46, the C-terminus region of around 175 amino acids may be deleted; for ORF29, the C-terminus may be deleted to leave around 230-370 N-terminal amino acids.

Leader Peptide Mutation

In a twelfth approach to heterologous expression, the leader peptide of the protein is mutated. This is particularly useful for the expression of protein 919.

Thus the invention provides a method for the heterologous expression of a protein of the invention, in which the protein's leader peptide is mutated.

The method will typically involve the steps of: obtaining nucleic acid encoding a protein of the invention; and manipulating said nucleic acid to mutate nucleotides within the leader peptide. The resulting nucleic acid may be inserted into an expression vector, or may already be part of an expression vector.

Poly-Glycine Deletion

In a thirteenth approach to heterologous expression, poly-glycine stretches in wild-type sequences are mutated. This enhances protein expression.

The poly-glycine stretch has the sequence $(Gly)_n$, where $n \geqq 4$ (e.g. 5, 6, 7, 8, 9 or more). This stretch is mutated to disrupt or remove the $(Gly)_n$. This may be by deletion (e.g. CGGGGS (SEQ ID NO:622)→CGGGS (SEQ ID NO:623), CGGS (SEQ ID NO:624), CGS or CS), by substitution (e.g. CGGGGS (SEQ ID NO:622)→CGXGGS (SEQ ID NO:625), CGXXGS (SEQ ID NO:626), CGXGXS (SEQ ID NO:627) etc.), and/or by insertion (e.g. CGGGGS (SEQ ID NO:622)→CGGXGGS (SEQ ID NO:628), CGXGGGS (SEQ ID NO:629), etc.).

This approach is not restricted to Neisserial proteins—it may be used for any protein (particularly bacterial proteins) to enhance heterologous expression. For Neisserial proteins, however, it is particularly suitable for expressing 287, 741, 983 and Thp2. An alignment of polymorphic forms of 287 is disclosed in WO00/66741.

Thus the invention provides a method for the heterologous expression of a protein of the invention, in which (a) a poly-glycine stretch within the protein is mutated.

The method will typically involve the steps of: obtaining nucleic acid encoding a protein of the invention; and manipulating said nucleic acid to mutate nucleotides that encode a poly-glycine stretch within the protein sequence. The resulting nucleic acid may be inserted into an expression vector, or may already be part of an expression vector.

Conversely, the opposite approach (i.e. introduction of poly-glycine stretches) can be used to suppress or diminish expression of a given heterologous protein.

Heterologous Host

Whilst expression of the proteins of the invention may take place in the native host (i.e. the organism in which the protein is expressed in nature), the present invention utilises a heterologous host. The heterologous host may be prokaryotic or eukaryotic. It is preferably *E.coli*, but other suitable hosts include *Bacillus subtilis, Vibrio cholerae, Salmonella typhi, Salmonenna typhimurium, Neisseria meningitidis, Neisseria gonorrhoeae, Neisseria lactamica, Neisseria cinerea, Mycobateria* (e.g. *M.tuberculosis*), yeast etc.

Vectors etc.

As well as the methods described above, the invention provides (a) nucleic acid and vectors useful in these methods (b) host cells containing said vectors (c) proteins expressed or expressable by the methods (d) compositions comprising these proteins, which may be suitable as vaccines, for instance, or as diagnostic reagents, or as immunogenic compositions (e) these compositions for use as medicaments (e.g. as vaccines) or as diagnostic reagents (f) the use of these compositions in the manufacture of (1) a medicament for treating or preventing infection due to Neisserial bacteria (2) a diagnostic reagent for detecting the presence of Neisserial bacteria or of antibodies raised against Neisserial bacteria, and/or (3) a reagent which can raise antibodies against Neisserial bacteria and (g) a method of treating a patient, comprising administering to the patient a therapeutically effective amount of these compositions.

Sequences

The invention also provides a protein or a nucleic acid having any of the sequences set out in the following examples. It also provides proteins and nucleic acid having sequence identity to these. As described above, the degree of 'sequence identity' is preferably greater than 50% (eg. 60%, 70%, 80%, 90%, 95%, 99% or more).

Furthermore, the invention provides nucleic acid which can hybridise to the nucleic acid disclosed in the examples, preferably under "high stringency" conditions (eg. 65° C. in a 0.1×SSC, 0.5% SDS solution).

The invention also provides nucleic acid encoding proteins according to the invention.

It should also be appreciated that the invention provides nucleic acid comprising sequences complementary to those described above (eg. for antisense or probing purposes).

Nucleic acid according to the invention can, of course, be prepared in many ways (eg. by chemical synthesis, from genomic or cDNA libraries, from the organism itself etc.) and can take various forms (eg. single stranded, double stranded, vectors, probes etc.).

In addition, the term "nucleic acid" includes DNA and RNA, and also their analogues, such as those containing modified backbones, and also peptide nucleic acids (PNA) etc.

BRIEF DESCRIPTION OF DRAWINGS

FIG. 4 shows similar data for protein 961.

FIGS. 6 & 7 (SEQ ID NOS:619 and 620) show deletions within domain A.

FIG. 13 shows SDS-PAGE of ΔG proteins. Dots show the main recombinant product.

FIG. 14 shows 26 hybrid proteins according to the invention.

MODES FOR CARRYING OUT THE INVENTION

Example 1

919 and its Leader Peptide

Figure 1:
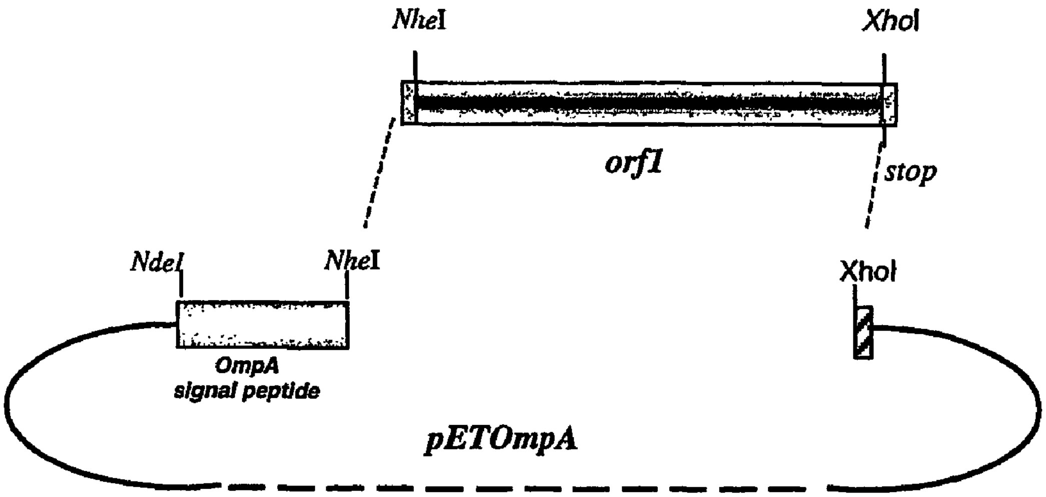
FIGS. 1 and 2 show constructs used to express proteins using heterologous leader peptides.

Protein 919 from *N.meningitidis* (serogroup B, strain 2996) has the following sequence (SEQ ID NO:1):

```
  1 MKKYLFRAAL YGIAAAILAA CQSKSIQTFP QPDTSVINGP
                                        DRPVGIPDPA
 51 GTTVGGGGAV YTVVPHLSLP HWAAQDFAKS LQSFRLGCAN
                                        LKNRQGWQDV
101 CAQAFQTPVH SFQAKQFFER YFTPWQVAGN GSLAGTVTGY
                                        YBPVLKGDDR
151 RTAQARPPIY GIPDDFISVP LPAGLRSGKA LVRIRQTGKN
                                        SGTIDNTGGT
201 HTADLSRFPI TARTTAIKGR FEGSEFLPYH TRNQINGGAL
                                        DGKAPILGYA
251 EDPVELFFMH IQGSGRLKTP SGKYIRIGYA DKNEHPYVSI
                                        GRYMADKGYL
301 KLGQTSMQGI KAYMRQNPQR LABVLGQNPS YIFFRELAGS
                                        SNDGPVGALG
351 TPLMGEYAGA VDRHYITLGA PLFVATAHPV TRKALNRLIM
                                        AQDTGBAIKG
401 AVRVDYFWGY GDEAGELAGK QKTTGYVWQL LPNGMKPEYR P*
```

The leader peptide is underlined.

The sequences of 919 from other strains can be found in FIGS. 7 and 18 of WO00/66741.

Example 2 of WO99/57280 discloses the expression of protein 919 as a His-fusion in *E.coli*. The protein is a good surface-exposed immunogen.

Three alternative expression strategies were used for 919:

1) 919 without its leader peptide (and without the mature N-terminal cysteine) and without any fusion partner ('919$^{untagged}$') (SEQ ID NO:2):

```
  1 QBKSIQTPP QPDTSVINGP DRPVGIPDPA GTTVGGGQAV
                                        YTVVPHLSLP
 50 HWAAQDFAKS LQSFRLGCAN LKNRQGWQDV CAQAPQTPVH
                                        SFQAKQFFER
100 YFTPWQVAGN GSLAGTVTGY YBPVLKGDDR RTAQARPPIY
                                        GIPDDFISVP
```

-continued

```
150 LPAGLRSGKA LVRIRQTGKN SGTIDNTGGT HTADLSPPPI
                                        TARTTAIKGR
200 FEGSRFLPYH TRNQINGGAL DGKAPILGYA EDPVBLFFMH
                                        IQGSGELKTP
250 SGKYIRIGYA DKNEHPYVSI GRYMADKGYL KLGQTBMQGI
                                        KAYMRQNPQR
300 LAEVLGQNPS YIFFRELAGB SNDGPVGALG TPLMGEYAGA
                                        VDRHYITLGA
350 PLFVATAHPV TRKALNRLIM AQDTGSAIKG AVRVDYFWGY
                                        GDBAGELAGK
400 QKTTGYVWQL LPNGMKPEYR P*
```

The leader peptide and cysteine were omitted by designing the 5'-end amplification primer downstream from the predicted leader sequence.

2) 919 with its own leader peptide but without any fusion partner ('919L'); and 3) 919 with the leader peptide (MKTFFKTLSAAALALILAA (SEQ ID NO:630)) from ORF4 ('919LOrf4') (SEQ ID NO:3).

```
  1 MKTFFKTLSAAALALILAA CQSKSIQTFP QPDTSVINGP
                                        DRPVGIPDPA
 50 GTTVGGGGAV YTVVPELSLP HWAAQDFAKS LQSFRLGCAN
                                        LKNRQGWQDV
100 CAQAFQTPVH SPQAKQFFER YFTPWQVAGN GSLAGTVTGY
                                        YEPVLKGDDR
150 RTAQARFPIY GIPDDFISVP LPAGLRSGKA LVRIRQTGKN
                                        SGTIDNTGGT
200 HTADLSRFPI TARTTAIKGR FEGSRFLPYH TRNQINGGAL
                                        DGKAPILGYA
250 EDPVELFFMH IQGSGRLKTP SGKYIRIGYA DKNEHPYVSI
                                        GRYMADKGYL
300 KLGQTSMQGI KSYHRQNPQR LAEVLGQNPS YIFFRELAGS
                                        SNDGPVGALG
350 TPLMGEYAGA VDRHYITLGA PLFVATAHPV TRKALNRLIM
                                        AQDTGSAIKG
400 AVRVDYFWGY GDEAGELAGK QKTTGYVWQL LPNGMKPEYR P*
```

To make this construct, the entire sequence encoding the ORF4 leader peptide was included in the 5'-primer as a tail (primer 919Lorf4 For). A NheI restriction site was generated by a double nucleotide change in the sequence coding for the ORF4 leader (no amino acid changes), to allow different genes to be fused to the ORF4 leader peptide sequence. A stop codon was included in all the 3'-end primer sequences.

All three forms of the protein were expressed and could be purified.

The '919L' and '919LOrf4' expression products were both lipidated, as shown by the incorporation of [$^3$]-palmitate label. 919$^{untagged}$ did not incorporate the $^3$H label and was located intracellularly.

919LOrf4 could be purified more easily than 919L. It was purified and used to immunise mice. The resulting sera gave excellent results in FACS and ELISA tests, and also in the bactericidal assay. The lipoprotein was shown to be localised in the outer membrane.

919$^{untagged}$ gave excellent ELISA titres and high serum bactericidal activity. FACS confirmed its cell surface location.

Example 2

919 and Expression Temperature

Growth of *E.coli* expressing the 919Orf4 protein at 37° C. resulted in lysis of the bacteria. In order to overcome this problem, the recombinant bacteria were grown at 30° C. Lysis was prevented without preventing expression.

Example 3

Mutation of 907, 919 and 922

It was hypothesised that proteins 907, 919 and 922 are murein hydrolases, and more particularly lytic transglycosylases. Murein hydrolases are located on the outer membrane and participate in the degradation of peptidoglycan.

The purified proteins $919^{untagged}$, 919Lorf4, 919-His (i.e. with a C-terminus His-tag) and 922-His were thus tested for murein hydrolase activity [Ursinus & Holtje (1994) *J. Bact.* 176:338-343]. Two different assays were used, one determining the degradation of insoluble murein sacculus into soluble muropeptides and the other measuring breakdown of poly $(MurNAc\text{-}GlcNAc)_{n>30}$ glycan strands.

The first assay uses murein sacculi radiolabelled with meso-2,6-diamino-3,4,5-[$^{3}$H]pimelic acid as substrate. Enzyme (3-10 μg total) was incubated for 45 minutes at 37° C. in a total volume of 100 μl comprising 10 mM Tris-maleate (pH 5.5), 10 mM $MgCl_2$, 0.2% v/v Triton X-100 and [$^{3}$H] $A_2$pm labelled murein sacculi (about 10000 cpm). The assay mixture was placed on ice for 15 minutes with 100 μl of 1% w/v N-acetyl-N,N,N-trimethylammonium for 15 minutes and precipitated material pelleted by centrifugation at 1000 g for 15 minutes. The radioactivity in the supernatant was measured by liquid scintillation counting. *E.coli* soluble lytic transglycosylase Slt70 was used as a positive control for the assay; the negative control comprised the above assay solution without enzyme.

All proteins except 919-His gave positive results in the first assay.

The second assay monitors the hydrolysis of poly(MurNAc-GlcNAc)glycan strands. Purified strands, poly$(MurNAc\text{-}GlcNAc)_{n>30}$ labelled with N-acetyl-D-1-[$^{3}$H]glucosamine were incubated with 3 μg of 919L in 10 mM Tris-maleate (pH 5.5), 10 mM $MgCl_2$ and 0.2% v/v Triton X-100 for 30 min at 37° C. The reaction was stopped by boiling for 5 minutes and the pH of the sample adjusted to about 3.5 by addition of 10 μl of 20% v/v phosphoric acid. Substrate and product were separated by reversed phase HPLC on a Nucleosil 300 $C_{18}$ column as described by Harz et. al. [*Anal. Biochem.* (1990) 190:120-128]. The *E.coli* lytic transglycosylase Mlt A was used as a positive control in the assay. The negative control was performed in the absence of enzyme.

By this assay, the ability of 919LOrf4 to hydrolyse isolated glycan strands was demonstrated when anhydrodisaccharide subunits were separated from the oligosaccharide by HPLC.

Protein 919Lorf4 was chosen for kinetic analyses. The activity of 919Lorf4 was enhanced 3.7-fold by the addition of 0.2% v/v Triton X-100 in the assay buffer. The presence of Triton X-100 had no effect on the activity of $919^{untagged}$. The effect of pH on enzyme activity was determined in Tris-Maleate buffer over a range of 5.0 to 8.0. The optimal pH for the reaction was determined to be 5.5. Over the temperature range 18° C. to 42° C., maximum activity was observed at 37° C. The effect of various ions on murein hydrolase activity was determined by performing the reaction in the presence of a variety of ions at a final concentration of 10 mM. Maximum activity was found with $Mg^{2+}$, which stimulated activity 2.1-fold. $Mn^{2+}$ and $Ca^{2+}$ also stimulated enzyme activity to a similar extent while the addition $Ni^{2+}$ and EDTA had no significant effect In contrast, both $Fe^{2+}$ and $Zn^{2+}$ significantly inhibited enzyme activity.

The structures of the reaction products resulting from the digestion of unlabelled *E.coli* murein sacculus were analysed by reversed-phase HPLC as described by Glauner [*Anal. Biochem.* (1988) 172:451-464]. Murein sacculi digested with the muramidase Cellosyl were used to calibrate and standardise the Hypersil ODS column. The major reaction products were 1,6 anhydrodisaccharide tetra and tri peptides, demonstrating the formation of 1,6 anhydromuraminic acid intramolecular bond.

These results demonstrate experimentally that 919 is a murein hydrolase and in particular a member of the lytic transglycosylase family of enzymes. Furthermore the ability of 922-His to hydrolyse murein sacculi suggests this protein is also a lytic transglycosylase.

This activity may help to explain the toxic effects of 919 when expressed in *E.coli.*

In order to eliminate the enzymatic activity, rational mutagenesis was used. 907, 919 and 922 show fairly low homology to three membrane-bound lipidated murein lytic transglycosylases from *E.coli:*

919 (441aa) is 27.3% identical over 440aa overlap to *E.coli* MLTA (p46885);

922 (369aa) is 38.7% identical over 310aa overlap to *E.coli* MLTB (P41052); and 907-2 (207aa) is 26.8% identical over 149aa overlap to *E.coli* MLTC (P52066).

907-2 also shares homology with *E.coli* MLTD (P23931) and Slt70 (P03810), a soluble lytic transglycosylase that is located in the periplasmic space. No significant sequence homology can be detected among 919, 922 and 907-2, and the same is true among the corresponding MLTA, MLTB and MLTC proteins.

Crystal structures are available for Slt70 [1QTEA; 1QTEB; Thunnissen et al. (1995) *Biochemistry* 34:12729-12737] and for Slt35 [1LTM; 1QUS; 1QUT; van Asselt et al. (1999) *Structure Fold Des* 7:1167-80] which is a soluble form of the 40 kDa MLTB.

The catalytic residue (a glutamic acid) has been identified for both Slt70 and MLTB.

In the case of Slt70, mutagenesis studies have demonstrated that even a conservative substitution of the catalytic Glu505 with a glutamine (Gln) causes the complete loss of enzymatic activity. Although Slt35 has no obvious sequence similarity to Slt70, their catalytic domains shows a surprising similarity. The corresponding catalytic residue in MLTB is Glu162.

Another residue which is believed to play an important role in the correct folding of the enzymatic cleft is a well-conserved glycine (Gly) downstream of the glutamic acid. Recently, Terrak et al. [*Mol. Microbiol.* (1999) 34:350-64] have suggested the presence of another important residue which is an aromatic amino acid located around 70-75 residues downstream of the catalytic glutamic acid.

Sequence alignment of Slt70 (SEQ ID NO:5) with 907-2 (SEQ ID NO:4) and of MLTB (SEQ ID NO:7) with 922 (SEQ ID NO:6) were performed in order to identify the corresponding catalytic residues in the MenB antigens.

The two alignments in the region of the catalytic domain are reported below:

907-2/Slt70:

```
                 90        100       110    ▼120       130       140
907-2.pep       ERRRLLVNIQYESSRAG--LDTQIVLGLIEVESAFRQYAISGVGARGLMQVMPFWKNYIG
                ||  |  |  ::   :|  :  : :::: :  |||:   : | |T| T|||:||   ::
slty_ecoli      ERFPLAYNDLFKRYTSGKEIPQSYAMAIARQESAWNPKVKSPVGASGLMQIMPGTATHTV
                     480       490       500   ▲  510       520       530
                                               GLU505
```

922/MLTB

```
                  150       160  ▼    170       180       190       200
922.pep         VAQKYGVPAELIVAVIGIETNYGKNTGSFRVADALATLGFDYPRRAGFFQKELVELLKLA
                : | |||| |:||::||:|| :T:   T:  |:  ||||||:|:|||||  :|:  ||   :| :|
mltb_ecoli      AWQVYGVPPEIIVGIIGVETRWGRVMGKTRILDALATLSFNYPRRAEYFSGELETFLLMA
                     150       160 ▲     170       180       190       200
                                  GLU162

                  210       220       230       240       250       260
922.pep         KEEGGDVFAFKGSYAGAMGMPQFMPSSYRKWAVDYDGDGHRDIWGNVGDVAASVANYMKQ
                ::|   | :  :|||:|||||:  ||||||T:::|||::||||  ::|   |  |:  :|||||:|
mltb_ecoli      RDEQDDPLNLKGSFAGAMGYGQFMPSSYKQYAVDFSGDGHINLWDPV-DAIGSVANYFKA
                     210       220       230       240       250       260
```

From these alignments, it results that the corresponding catalytic glutamate in 907-2 is Glu117, whereas in 922 is Glu164. Both antigens also share downstream glycines that could have a structural role in the folding of the enzymatic cleft (in bold), and 922 has a conserved aromatic residue around 70aa downstream (in bold).

In the case of protein 919, no 3D structure is available for its *E. coli* homologue MLTA, and nothing is known about a possible catalytic residue. Nevertheless, three amino acids in 919 (SEQ ID NO:8) are predicted as catalytic residues by alignment with MLTA (SEQ ID NO:9):

919/MLTA

```
                240       250    ▼   260 □ □  270 □      280       290
919.pep           ALDGKAPILGYAEDPVELFFMHIQGSGRLKTPSGKYIRI-GYADKNEHPYVSIGRYMADK
                  ||: |  ||:|::: :: |:| :||||  :    :|: : : :|| || | | |||: : |:
mlta_ecoli.p      ALSDKY-ILAYSNSLMDNFIMDVQGSGYIDFGDGSPLNFFSYAGKNGHAYRSIGKVLIDR
                            170       180       190       200       210

                   300       310       320  ▼    330□ □□  340      ◊ 350    ◊
919.pep           GYLKLGQTSMQGIKSYMRQNPQ-RLAEVLGQNPSYIFFRELAGSSNDGPV-GALGTPLMG
                  | :|   : |||:|: : : : : :: |:| ||||::||:  : :     || || ::||:|
mlta_ecoli.p      GEVKKEDMSMQAIRHWGETHSEAEVRELLEQNPSFVFFKPQSFA----PVKGASAVPLVG
                220       230       240       250       260       270

                     360 ▼      ○      380            390       400      ◊◊ 410
919.pep           EYAGAVDRHYITLGAPLFVATAHPVTRKALN-----RLIMAQDTGSAIKGAVRVDYFWGY
                  : : | ||  |  |: |:: :    :    :|     ||::| |:|:||||   :  |  : |
mlta_ecoli.p      RASVASDRSIIPPGTTLLAEVPLLDNNGKFNGQYELRLMVALDVGGAIKGQ-HFDIYQGI
                      280       290       300          310       320       330

                        420        ○
919.pep           GDEAGELAGKQKTTGYVWQLLP
                  | |||: ||   :   | || |
mlta_ecoli.p      GPEAGHRAGWYNHYGRVWVLKT
                        340       350
```

The three possible catalytic residues are shown by the symbol ▼:

1) Glu255 (Asp in MLTA), followed by three conserved glycines (Gly263, Gly265 and Gly272) and three conserved aromatic residues located approximately 75-77 residues downstream. These downstream residues are shown by □.

2) Glu323 (conserved in MLTA), followed by 2 conserved glycines (Gly347 and Gly355) and two conserved aromatic residues located 84-85 residues downstream (Tyr406 or Phe407). These downstream residues are shown by ◊.

3) Asp362 (instead of the expected Glu), followed by one glycine (Gly 369) and a conserved aromatic residue (Trp428). These downstream residues are shown by ○.

Alignments of polymorphic forms of 919 are disclosed in WO00/66741.

Based on the prediction of catalytic residues, three mutants of the 919 and one mutant of 907, containing each a single amino acid substitution, have been generated. The glutamic acids in position 255 and 323 and the aspartic acids in position 362 of the 919 protein and the glutamic acid in position 117 of the 907 protein, were replaced with glycine residues using PCR-based SDM. To do this, internal primers containing a codon change from Glu or Asp to Gly were designed:

| Primers | SEQ ID No: | Sequences | Codon change |
|---|---|---|---|
| 919-E255 for | 10 | CGAAGACCCCGTCGgtCTTTTTTTTATG | GAA→Ggt |
| 919-E255 rev | 11 | GTGCATAAAAAAAAGacCGACGGGGTCT | |
| 919-E323 for | 12 | AACGCCTCGCCGgtGTTTTGGGTCA | GAA→Ggt |
| 919-E323 rev | 13 | TTTGACCCAAAACacCGGCGAGGCG | |
| 919-D362 for | 14 | TGCCGGCGCAGTCGgtCGGCACTACT | GAC→Ggt |
| 919-D362 rev | 15 | TAATGTATGCCGacCGACTGCGCCG | |
| 907-E117 for | 16 | TGATTGAGGTGGgtAGCGCGTTCCG | GAA→Ggt |
| 907-E117 rev | 17 | GGCGGAACGCGCTacCCACCTCAAT | |

Underlined nucleotides code for glycine; the mutated nucleotides are in lower case.

Underlined nucleotides code for glycine; the mutated nucleotides are in lower case.

To generate the 919-E255, 919-E323 and 919-E362 mutants, PCR was performed using 20 ng of the pET 919-LOrf4 DNA as template, and the following primer pairs:
1) Orf4L for/919-E255 rev
2) 919-E255 for/919L rev
3) Orf4L for/919-E323 rev
4) 919-E323 for/919L rev
5) Orf4L for/919-D362 rev
6) 919-D362 for/919L rev The second round of PCR was performed using the product of PCR 1-2, 3-4 or 5-6 as template, and as forward and reverse primers the "Orf4L for" and "919L rev" respectively.

For the mutant 907-E117, PCR have been performed using 200 ng of chromosomal DNA of the 2996 strain as template and the following primer pairs:
7) 907L for/907-E117 rev
8) 907-E117 for/907L rev The second round of PCR was performed using the products of PCR 7 and 8 as templates and the oligos "907L for" and "907L rev" as primers.

The PCR fragments containing each mutation were processed following the standard procedure, digested with NdeI and XhoI restriction enzymes and cloned into pET-21b+ vector. The presence of each mutation was confirmed by sequence analysis.

Mutation of Glu117 to Gly in 907 is carried out similarly, as is mutation of residues Glu164, Ser213 and Asn348 in 922.

The E255G mutant of 919 shows a 50% reduction in activity; the E323G mutant shows a 70% reduction in activity; the E362G mutant shows no reduction in activity.

Example 4

Multimeric Form

287-GST, 919$^{untagged}$ and 953-His were subjected to gel filtration for analysis of quaternary structure or preparative purposes. The molecular weight of the native proteins was estimated using either FPLC Superose 12 (H/R 10/30) or Superdex 75 gel filtration columns (Pharmacia). The buffers used for chromatography for 287, 919 and 953 were 50 mM Tris-HCl (pH 8.0), 20 mM Bicine (pH 8.5) and 50 mM Bicine (pH 8.0), respectively.

Additionally each buffer contained 150-200 mM NaCl and 10% v/v glycerol. Proteins were dialysed against the appropriate buffer and applied in a volume of 200 µl. Gel filtration was performed with a flow rate of 0.5-2.0 ml/min and the eluate monitored at 280 nm. Fractions were collected and analysed by SDS-PAGE. Blue dextran 2000 and the molecular weight standards ribonuclease A, chymotrypsin A ovalbumin, albumin (Pharmacia) were used to calibrate the column.

The molecular weight of the sample was estimated from a calibration curve of $K_{av}$ vs. log $M_r$ of the standards. Before gel filtration, 287-GST was digested with thrombin to cleave the GST moiety.

The estimated molecular weights for 287, 919 and 953-His were 73 kDa, 47 kDa and 43 kDa respectively. These results suggest 919 is monomeric while both 287 and 953 are principally dimeric in their nature. In the case of 953-His, two peaks were observed during gel filtration. The major peak (80%) represented a dimeric conformation of 953 while the minor peak (20%) had the expected size of a monomer. The monomeric form of 953 was found to have greater bactericidal activity than the dimer.

Example 5 pSM214 and pET-24b Vectors 953 protein with its native leader peptide and no fusion partners was expressed from the pET vector and also from pSM214 [Velati Bellini et al. (1991) *J. Biotechnol.* 18, 177-192].

The 953 sequence was cloned as a full-length gene into pSM214 using the *E. coli* mM294-1 strain as a host. To do this, the entire DNA sequence of the 953 gene (from ATG to the STOP codon) was amplified by PCR using the following primers:

953L for/2 CCGGAATTCTTATGAAAAAAATCATCT-TCGCCGC Eco RI (SEQ ID NO:18)

953L rev/2 GCCCAAGCTTTTATTGTTTGGCTGC-CTCGATT Hind III (SEQ ID NO:19)

which contain EcoRI and HindIII restriction sites, respectively. The amplified fragment was digested with EcoRI and HindIII and ligated with the pSM214 vector digested with the same two enzymes. The ligated plasmid was transformed into *E. coli* mM294-1 cells (by incubation in ice for 65 minutes at 37° C.) and bacterial cells plated on LB agar containing 20 µg/ml of chloramphenicol.

Recombinant colonies were grown over-night at 37° C. in 4 ml of LB broth containing 20 µg/ml of chloramphenicol; bacterial cells were centrifuged and plasmid DNA extracted as and analysed by restriction with EcoRI and HindIII. To analyse the ability of the recombinant colonies to express the protein, they were inoculated in LB broth containing 20 µg/ml of chloramphenicol and let to grown for 16 hours at 37° C. Bacterial cells were centrifuged and resuspended in PBS. Expression of the protein was analysed by SDS-PAGE and Coomassie Blue staining.

Expression levels were unexpectedly high from the pSM214 plasmid.

Oligos used to clone sequences into pSM-214 vectors were as follows:

| | | | | |
|---|---|---|---|---|
| ΔG287 | Fwd | CCGGAATTCTTATG-TCGCCCGATGTTAAATCGGCGGA | SEQ ID NO: 20 | EcoRI |
| (pSM-214) | Rev | GCCCAAGCTT-**TCA**ATCCTGCTCTTTTTTGCCG | SEQ ID NO: 21 | HindIII |
| Δ2 287 | Fwd | CCGGAATTTCTTATG-AGCCAAGATATGGCGGCAGT | SEQ ID NO: 22 | EcoRI |
| (pSM-214) | Rev | GCCCAAGCTT-**TCA**AATCCTGCTCTTTTTTGCCG | SEQ ID NO: 23 | HindIII |
| Δ3 287 | Fwd | CCGGAATTCTTATG-TCCGCCGAATCCGCAAATCA | SEQ ID NO: 24 | EcoRI |
| (pSM-214) | Rev | GCCCAAGCTT-**TCA**ATCCTGCTCTTTTTTGCCG | SEQ ID NO: 25 | HindIII |
| Δ4 287 | Fwd | CCGGAATTCTTATG-GGAAGGGTTGATTTGGCTAATG | SEQ ID NO: 26 | EcoRI |
| (pSM-214) | Rev | GCCCAAGCTT-**TCA**ATCCTGCTCTTTTTTTGCCG | SEQ ID NO: 27 | HindIII |
| Orf46.1 | Fwd | CCGGAATTCTTATG-TCAGATTTGGCAAACGATTCTT | SEQ ID NO: 28 | EcoRI |
| (pSM-214) | Rev | GCCCAAGCTT-**TTA**CGTATCATATTTCACGTGCTTC | SEQ ID NO: 29 | HindIII |
| ΔG287. Orf46.1 | Fwd | CCGGAATTCTTATG-TCGCCCGATGTTAAATCGGCGGA | SEQ ID NO: 30 | EcoRI |
| (pSM-214) | Rev | GCCCAAGCTT-**TTA**CGTATCATATTTCACGTGCTTC | SEQ ID NO: 31 | HindIII |
| 919 | Fwd | CCGGAATTCTTATG-CAAAGCAAGAGCATCCAAACCT | SEQ ID NO: 32 | EcoRI |
| (pSM-214) | Rev | GCCCAAGCTT-**TTA**CGGGCGGTATTCGGGCT | SEQ ID NO: 33 | HindIII |
| 961L | Fwd | CCGAATTCATATG-AAACACTTTCCATCC | SEQ ID NO: 34 | EcoRI |
| (pSM-214) | Rev | GCCCAAGCTT-**TTA**CCACTCGTAATTGAC | SEQ ID NO: 35 | HindIII |
| 961 | Fwd | CCGGAATTCATATG-GCCACAAGCGACGAC | SEQ ID NO: 36 | EcoRI |
| (pSM-214) | Rev | GCCCAAGCTT-**TTA**CCACTCGTAATTGAC | SEQ ID NO: 37 | HindIII |
| 961c L | Fwd | CCGGAATTCTTATG-AAACACTTTCCATCC | SEQ ID NO: 38 | EcoRI |
| pSM-214 | Rev | GCCCAAGCTT-**TCA**ACCCACGTTGTAAGGTTG | SEQ ID NO: 39 | HindIII |
| 961c | Fwd | CCGGAATTCTTATG-GCCACAAACGACGACG | SEQ ID NO: 40 | EcoRI |
| pSM-214 | Rev | GCCCAAGCTT-**TCA**ACCCACGTTGTAAGGTTG | SEQ ID NO: 41 | HindIII |
| 953 | Fwd | CCGGAATTCTTATG-GCCACCTACAAAGTGGACGA | SEQ ID NO: 42 | EcoRI |
| (pSM-214) | Rev | GCCCAAGCTT-**TTA**TTGTTTGGCTGCCTCGATT | SEQ ID NO: 43 | HindIII |

These sequences were manipulated, cloned and expressed as described for 953L.

For the pET-24 vector, sequences were cloned and the proteins expressed in pET-24 as described below for pET21. pET2 has the same sequence as pET-21, but with the kanamycin resistance cassette instead of ampicillin cassette.

Oligonucleotides used to clone sequences into pET-24b vector were:

| | | | | |
|---|---|---|---|---|
| ΔG 287 K | Fwd | CGCGGATCCGCTAGC-CCCGATGTrAAATCGGC§ | SEQ ID NO: 44 | NheI |
| | Rev | CCCGCTCCGAG-**TCA**ATCCTGCTCTTTTTTGCC * | SEQ ID NO: 45 | XhoI |
| Δ2 287 K | Fwd | CGCGGATCCGCTAGC-CAAGATATGOCGGCAGT§ | SEQ ID NO: 46 | NheI |
| Δ3 287 K | Fwd | CGCGGATCCGCTAGC-GCCGAATCCGCAAATCA§ | SEQ ID NO: 47 | NheI |
| Δ4 287 K | Fwd | CGCGCTAGC-GGAAGGGTTGATTTGGCTAATGG§ | SEQ ID NO: 48 | NheI |
| Orf46.1 K | Fwd | GGGAATTCCATATG-GGCATTTCCCGCAAAATATC | SEQ ID NO: 49 | NdeI |
| | Rev | CCCGCTCGAC-**TTA**ACGTATCATATTTCACGTGC | SEQ ID NO: 50 | XhoI |
| Orf46A K | Fwd | GGGAATTCCATATG-GGCATTTCCCGCAAAATATC | SEQ ID NO: 51 | NdeI |
| | Rev | CCCGCTCGAG-**TTA**TTCTATGCCTTGTGCGGCAT | SEQ ID NO: 52 | XhoI |
| 961 K | Fwd | CGCGGATCCCATATG-GCCACAAGCGACGACGA | SEQ ID NO: 53 | NdeI |
| (MC58) | Rev | CCCGCTCGAG-**TTA**CCACTCGTAATTGAC | SEQ ID NO: 54 | XhoI |
| 961a K | Fwd | CGCGGATCCCATATG-GCCACAAACGACG | SEQ ID NO: 55 | NdeI |
| | Rev | CCCGCTCGAG-**TCA**TTTAGCAATATTATCTTTGTTC | SEQ ID NO: 56 | XhoI |
| 961b K | Fwd | CGCGGATCCCATATG-AAAGCAAACAGTGCCGAC | SEQ ID NO: 57 | NdeI |
| | Rev | CCCGCTCGAG-**TTA**CCACTCGTAATTGAC | SEQ ID NO: 58 | XhoI |
| 961c K | Fwd | CGCGGATCCCATATG-GCCACAAACGACG | SEQ ID NO: 59 | NdeI |
| | Rev | CCCGCTCGAG-**TTA**ACCCACGTTGTAAGGT | SEQ ID NO: 60 | XhoI |
| 961cL K | Fwd | CGCGGATCCCATATG-ATGAAACACTTTCCATCC | SEQ ID NO: 61 | NdeI |
| | Rev | CCCGCTCGAG-**TTA**ACCCACGTTGTAAGGT | SEQ ID NO: 62 | XhoI |

-continued

| | | | | |
|---|---|---|---|---|
| 961d K | Fwd | CGCGGATCCCATATG-GCCACAAACGACG | SEQ ID NO: 63 | NdeI |
| | Rev | CCCGCTCGAG-**TCA**GTCTGACACTGTTTTATCC | SEQ ID NO: 64 | XhoI |
| ΔG 287-919 K | Fwd | CGCGGATCCGCTAGC-CCCGATGTTAAATCGGC | SEQ ID NO: 65 | NheI |
| | Rev | CCCGCTCGAG-**TTA**ACGGGCGGTATTCGG | SEQ ID NO: 66 | XhoI |
| ΔG 287-Orf46.1 K | Fwd | CGCGGATCCGCTAGC-CCCGATGTTAAATCGGC | SEQ ID NO: 67 | NheI |
| | Rev | CCCGCTCGAG-**TTA**CGTATCATATTTCACGTGC | SEQ ID NO: 68 | XhoI |
| ΔG 287-961 K | Fwd | CGCGGATCCGCTAGC-CCCGATGTTAAATCGGC | SEQ ID NO: 69 | NheI |
| | Rev | CCCGCTCGAG-**TTA**CCACTCGTAATTGAC | SEQ ID NO: 70 | XhoI |

* This primer was used as a Reverse primer for all the 287 forms.

§ Forward primers used in combination with the ΔG278 K reverse primer.

Example 6

ORF1 and its Leader Peptide

ORF1 from *N.meningitidis* (serogroup B, strain MC58) is predicted to be an outer membrane or secreted protein. It has the following sequence (SEQ ID NO:71):

```
   1 MKTTDKRTTE THRKAPKTGR IRFSPAYLAI CLSFGILPQA WAGHTYFGIN
  51 YQYYRDFAEN KGKFAVGAKD IEVYNKKGEL VGKSMTKAPM IDFSVVSRNG
 101 VAALVGDQYI VSVAHNGGYN NVDFGAEGRN PDQHRFTYKI VKRNNYKAGT
 151 KGHPYGGDYH MPRLHKFVTD AEPVEMTSYM DGRKYIDQNN YPDRVRIGAG
 201 RQYWRSDEDE PNNRESSYHI ASAYSWLVGG NTFAQNGSGG GTVNLGSEKI
 251 KHSPYGFLPT GGSFGDSGSP MFIYDAQKQK WLINGVLQTG NPYIGKSNGF
 301 QLVRKDWFYD EIFAGDTHSV FYEPRQNGKY SFNDDNNGTG KINAKHEHNS
 351 LPNRLKTRTV QLFNVSLSET AREPVYHAAG GVNSYRPRLN NGENISFIDE
 401 GKGELILTSN INQGAGGLYF QGDFTVSPEN NETWQGAGVH ISEDSTVTWK
 451 VNGVANDRLS KIGKGTLHVQ AKGENQGSIS VGDGTVILDQ QADDKGKKQA
 501 FSEIGLVSGR GTVQLNADNQ FNPDKLYFGF RGGRLDLNGH SLSFHRIQNT
 551 DEGAMIVNHN QDKESTVTIT GNKDIATTGN NNSLDSKKEI AYNGWPGEKD
 601 TTKTNGRLNL VYQPAAEDRT LLLSGGTNLN GNITQTNGKL FFSGRPTPHA
 651 YNHLNDHWSQ KEGIPRGEIV WDNDWINRTF KAENFQIKGG QAVVSRNVAK
 701 VKGDWHLSNH AQAVFGVAPH QSHTICTRSD WTGLTNCVEK TITDDKVIAS
 751 LTKTDISGNV DLADHAHLNL TGLATLNGNL SANGDTRYTV SHNATQNGNL
 801 SLVGNAQATF NQATLNGNTS ASGNASFNLS DHAVQNGSLT LSGNAKANVS
```

-continued

```
 851 HSALNGNVSL ADKAVFHFES SRFTGQISGG KDTALHLKDS EWTLPSGTEL
 901 GNLNLDNATI TLNSAYRHDA AGAQTGSATD APRRRSRRSR RSLLSVTPPT
 951 SVESEFNTLT VNGKLNGQGT FRFMSELFGY RSDKLKLAES SEGTYTLAVN
1001 NTGNEPASLE QLTVVEGKDN KPLSENLNFT LQNEHVDAGA WRYQLIRKDG
1051 EFRLHNPVKE QELSDKLGKA EAKKQAEKDN AQSLDALIAA GRDAVEKTES
1101 VAEPARQAGG ENVGINQAEE EKKRVQADKD TALAKQREAE TRPATTAFPR
1151 ARRARRDLPQ LQPQPQPQPQ RDLISRYANS GLSEFSATLN SVFAVQDELD
1201 RVFAEDRRNA VWTSGIRDTK HYRSQDFRAY RQQTDLRQIG MQKHLGSGRV
1251 GILFSHNRTE NTFDDGIGNS ARLAHGAVFG QYGIDRFYIG ISAGAGFSSG
1301 SLSDGIGGKI RRRVLHYGIQ ARYRAGFGGF GIEPHIGATR YFVQKADYRY
1351 ENVNIATPGL AFNRYRAGIK ADYSFKPAQH ISITPYLSLS YTDAASGKVR
1401 TRVNTAVLAQ DFGKTRSAEW GVNAEIKGFT LSLHAAAAKG PQLEAQHSAG
1451 IKLGYRW*
```

The leader peptide is underlined.

A polymorphic form of ORF1 is disclosed in WO99/55873.

Three expression strategies have been used for ORF1:

1) ORF1 using a His tag, following WO99/24578 (ORF1-His);
2) ORF1 with its own leader peptide but without any fusion partner ('ORF1L'); and
3) ORF1 with the leader peptide (MKKTAIAIAVALAGFATVAQA (SEQ ID NO:72)) from *E. coli* OmpA ('Orf1LOmpA') (SEQ ID NO:73):

```
MKKTAIAIAVALAGGATVAQAASAGTYFGINYQYYRDFAENKGKFAVGADKIEVYNKKGELVGKSMTKAPMIDFSV
VSRNGVAALVGDQYIVSVAHNGGYNNVDFGAEGRNPDQHRFTYKIVKRNNYKAGTKGHPYGGDYHMPRLHKFVTDAE
PVEMTSYDGRKYIDQNNYPDRVRIGAGRQYWRSDEDEPNNRESSYHIASAYSWLVGGNTFAQNGSGGGTVNLGSEK
IKHSPYQFLPTGGSFGDSGSPMFIYDAQKQKWLINGVLQTGNPYIGKSNGFQLVRKDWFYDEIFAGDTHSVFYEPRQ
NGKYSFNDDNGTGKINAKHEHNSLPNRILKTRTVQLFNVSLSETAREPVYHAAGGVNSYRPLNNGENISFIDEGKG
ELILTSNINQGAGGLYFQGDFTVSPENNETWQGAGVHISEDSTVTWKVNGVANDRLSKIGKGTLHVQAKGENQGSIS
VGDGTVILDQQADDKQKKQAFSEIGLVSGRGTVQLNADNQFNPDKLYFGFRGGBLDLNGHSLSFHRIQNTDEGAMIV
NHNQDKESTVTITGDIATTGIQNNSLDSKKEIAYNGWFGDEKDTTKTNGRLNLVYQPAAEDRTLLLSGGTNLNGNIT
QTNGKLFFSGRPTPHAYNHLNDHWSQKEGIPRGEIVWDNDWINRTFKAENFQIKGGQAVVSRNVAKVKGDWHLSNHA
QAVFGVAPHQSHTICTRSDWTGLTNCVERTITDDKVIASLTKTDISNGVDLADHAHLNLTGALTLNGNLSANGDTRY
TVSHNATQNGNLSLVGNAQATPNQATIMGNTSASGNASFNLSDHAVQNGSLTLSGNAKANVSHSALNGNVSLADKAV
FHFESSRFTGQISGGKDTALHLKDSEWTLPSGTELGNLNDNATITLNSAYRHDAAGAQTGSATDAPRRRSRRSRRS
LLSVTPPTSVESRFNTLTVNGKLNGQGTFRFMSELFGYRSDKLKAESSEGTYYTLAVNNTGNEASLEQLTVVEGKD
NKPLSENLNFTLQNEHVDAGWRYQLIRKDGEFRLHNPVKEQELSDKLGKAEAKKQAEKDNAQSDALIAAGRDAVE
KTSEVAEPARQAGGENVGIMQAEEEKKRVQADKDTALAKQREAETRPATTAFPRARRARRDLPQLQPAPAPAPARDL
ISRYANSGLSEFSATLNSFVAVQDELDRVFAEDRRNAVWTSGIRDTKHYRSQDFAYRQQTDLRQIGMQKNLGSGRV
GILFSNGRTENTFDDGIGNSARLAHGAVGGYGIDRFYIGISAGAGFSSGSLSDGIGGKIRRRVLHGIQARYRAGF
GGFGIEPHIGATRYFVQADYRYENVIATPGLAFNRYRAGIKADYSFKPAQHISITPYLSLSYTDAASGKVRTRVN
TAVLAQDFQKTRSAEWGVNAEIKGFTLSLHAAAAGPQLEAQHSAGIKLGYRW*
```

To make this construct, the clone pET911LOmpA (see below) was digested with the NheI and XhoI restriction enzymes and the fragment corresponding to the vector carrying the OmpA leader sequence was purified (pETLOmpA). The ORF1 gene coding for the mature protein was amplified using the oligonucleotides ORF1-For and ORF1-Rev (including the NheI and XhoI restriction sites, respectively), digested with NheI and XhoI and ligated to the purified pETOmpA fragment (see FIG. 1). An additional AS dipeptide was introduced by the NheI site.

Figure 3:
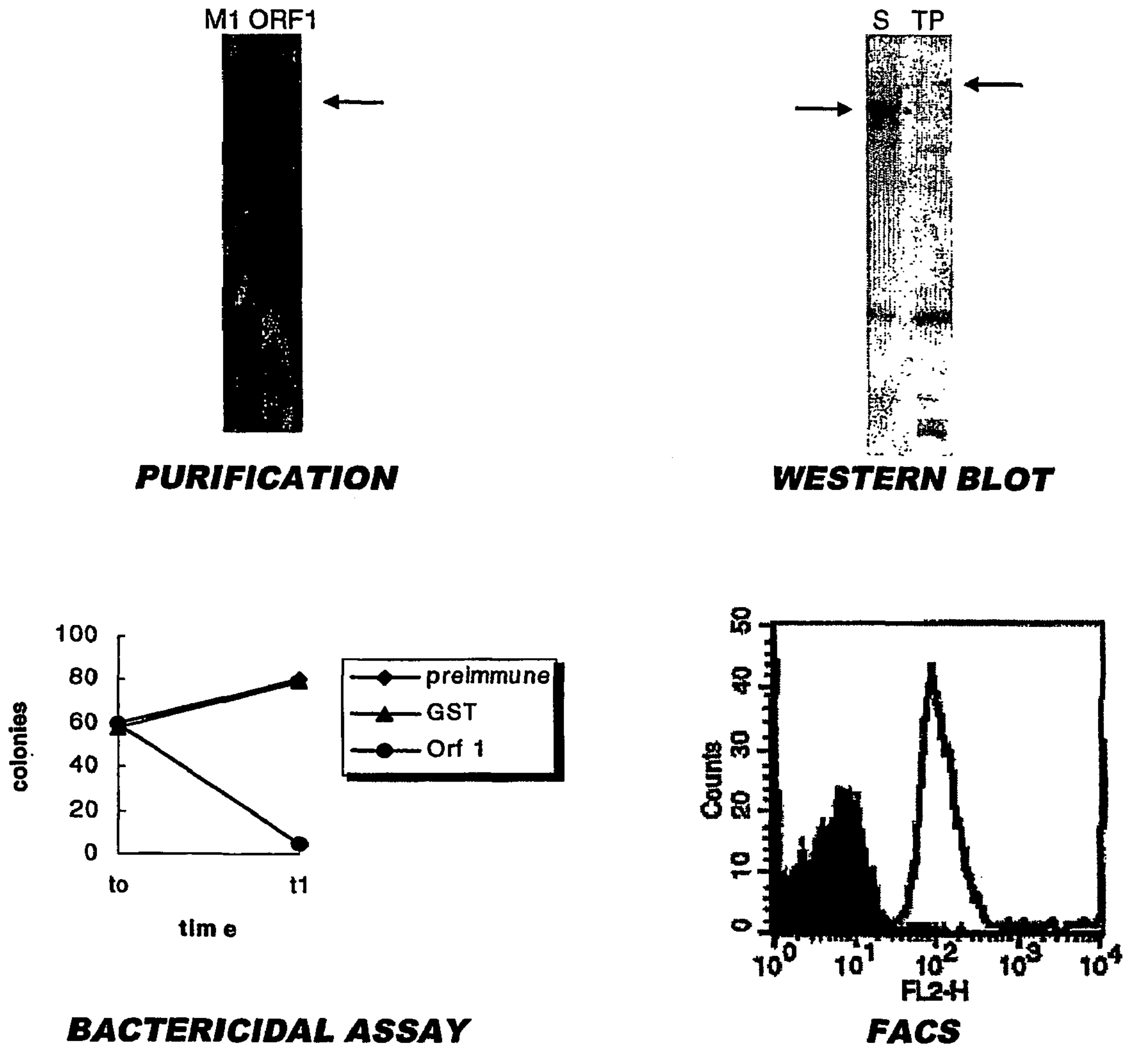
FIG. 3 shows expression data for ORF1.

All three forms of the protein were expressed. The His-tagged protein could be purified and was confirmed as surface exposed, and possibly secreted (see FIG. 3). The protein was used to immunise mice, and the resulting sera gave excellent results in the bactericidal assay.

ORF1LOmpA was purified as total membranes, and was localised in both the inner and outer membranes. Unexpectedly, sera raised against ORF1LOmpA show even better ELISA and anti-bactericidal properties than those raised against the His-tagged protein.

ORF1L was purified as outer membranes, where it is localised.

Example 7

Protein 911 and its Leader Peptide

Protein 911 from *N.meningitidis* (serogroup B, strain MC58) has the following sequence (SEQ ID NO:74):

```
  1 MKKNILEFWV GLFVLIGAAA VAFLAFRVAG GAAFGGSDKT
                                       YAVYADFGDI
 51 GGLKVNAPVK SAGVLVGRVG AIGLDPKSYQ ARVRLDLDGK
```

-continued

```
                                       YQFSSDVSAQ
101 ILTBGLLGEQ YIGLQQGGDT ENLAAGDTIS VTSSAMVLEN
                                       LIQKPHTSFA
151 RKNADGGNAE KAAE*
```

The leader peptide is underlined.

Three expression strategies have been used for 911:

1) 911 with its own leader peptide but without any fusion partner ('911L');

2) 911 with the leader peptide from *E.coli* OmpA ('911LOmpA'). To make this construct, the entire sequence encoding the OmpA leader peptide was included in the 5'-primer as a tail (primer 911LOmpA Forward). A NheI restriction site was inserted between the sequence coding for the OmpA leader peptide and the 911 gene encoding the predicted mature protein (insertion of one amino acid, a serine), to allow the use of this construct to clone different genes downstream the OmpA leader peptide sequence.

3) 911 with the leader peptide (MKYLLPTAAAGLLLAAQPAMA (SEQ ID NO:75)) from *Erwinia carotovora* PelB ('911LpelB3').

To make this construct, the 5'-end PCR primer was designed downstream from the leader sequence and included the NcoI restriction site in order to have the 911 fused directly to the PelB leader sequence; the 3'-end primer included the STOP codon. The expression vector used was pET22b+ (Novagen), which carries the coding sequence for the PelB leader peptide. The NcoI site introduces an additional methionine after the PelB sequence.

All three forms of the protein were expressed. ELISA titres were highest using 911L, with 919LOmpA also giving good results.

Example 8

ORF46

The complete ORF46 protein from *N.meningitidis* (serogroup B, strain 2996) has the following sequence (SEQ ID NO:76):

```
  1 LGISRKISLI LSILAVCLPM HAHASDLAND SFIRQVLDRQ
                                          HFEPDGKYHL
 51 FGSRGELAER SGHIGLGKIQ SHQLGNLMIQ QAAIKGNIGY
                                          IVRFSDHGHE
101 VHSPFDNHAS HSDSDEAGSP VDGFSLYRIH WDGYEHHPAD
                                          GYDGPQGGGY
151 PAPKGAPDIY SYDIKGVAQN IRLNLTDNRS TGQRLADRFH
                                          NAGSNLTQGV
201 GDGFKRATRY SPELDRSGNA AEAFNGTADI VKNIIGAAGE
                                          IVQAGDAVQG
251 ISEGSNIAVM HGLGLLSTEN KMARINDLAD MAQLKDYAAA
                                          AIRDWAVQNP
301 NAAQGIEAVS NIFMAAIPIK GIGAVRGKYG LGGITAHPIK
                                          RSQMGAIALP
351 KGKSAVSDNF ADAAYAKYPS PYHSRNIRSN LEQRYGKENI
                                          TSSTVPPSNG
401 KNVKLADQRH PKTGVPFDGK GFPNFEKHVK YDTKLDIQEL
                                          SGQGIPKAKP
451 VSDAKPRWEV DRKLNKLTTR EQVEKNVQEI RNGNKNSNFS
                                          QHAQLEEEIN
501 KLKSADEINF ADGMGKFTDS MNDKAPSPLV KSVKENGFTN
                                          PVVRYVEING
551 KAYIVRGNNR VFAAEYLGRI HELKFKKVDF PVPNTSWKNP
                                          TDVLNESGNV
601 KRPRYRSK*
```

The leader peptide is underlined.

The sequences of ORF46 from other strains can be found in WO00/66741.

Three expression strategies have been used for ORF46:

1) ORF46 with its own leader peptide but without any fusion partner ('ORF46-2L');
2) ORF46 without its leader peptide and without any fusion partner ('ORF46-2'), with the leader peptide omitted by designing the 5'-end amplification primer downstream from the predicted leader sequence (SEQ ID NO:77):

```
  1 SDLANDSFIR QVLDRQHFEP DGKYHLFGSR GELAERSGHI
                                          GLGKIQSHQL
 51 GNLHIQQAAI KGNIGYIVRF SDHGHEVHSP FDNHASHSDS
                                          DEAGSPVDGF
101 SLYPJHWDGY EHHPADGYDG PQGGGYPAPK GARDIYSYDI
                                          KGVAQNIRLN
151 LTDNRSTGQR LADRFHNAGS MTLTQGVGDGF KRATRYSPEL
                                          DRSGNAAEAF
201 NGTADIVKNI IGAAGEIVGA GDAVQGISEG SNIAVMHGLG
                                          LLSTENKMAR
```

-continued

```
251 INDLADMAQL KDYAAAAIRD WAVQNPNAAQ GIEAVSNIFM
                                          AAIPIKGIGA
301 VRGKYGLGGI TAHPIKRSQM GAIALPKGKS AVSDNFADAA
                                          YARYPBPYHS
351 RNIRSNLEQR YGKENITSST VPPSNGKNVK LADQRHPKTG
                                          VPPDGKGFPN
401 FEKHVKYDTK LDIQELSGGG IPKAKPVBDA KPRNHVDRKL
                                          NKLTTREQVE
451 KNVQEIRNGN KNSNFSQHAQ LEREINKLKS ADEINFADGM
                                          GKFTDSMNDK
501 APSRLVKSVK ENGFTNPVVE YVBINGKAYI VRGNNRVFAA
                                          EYLGRIHELK
551 FKKVDFPVPN TSWKNPTDVL NESGNVKRPR YRSK*
```

3) ORF46 as a truncated protein, consisting of the first 433 amino acids ('ORF46.1L'), constructed by designing PCR primers to amplify a partial sequence corresponding to aa 1-433.

A STOP codon was included in the 3'-end primer sequences.

ORF46-2L is expressed at a very low level to *E.coli*. Removal of its leader peptide (ORF46-2) does not solve this problem. The truncated ORF46.1L form (first 433 amino acids, which are well conserved between serogroups and species), however, is well-expressed and gives excellent results in ELISA test and in the bactericidal assay.

ORF46.1 has also been used as the basis of hybrid proteins. It has been fused with 287, 919, and ORF1. The hybrid proteins were generally insoluble, but gave some good ELISA and bactericidal results (against the homologous 2996 strain):

| Protein | ELISA | Bactericidal Ab |
|---|---|---|
| Orf1-Orf46.1-His | 850 | 256 |
| 919-Orf46.1-His | 12900 | 512 |
| 919-287-Orf46-His | n.d. | n.d. |
| Orf46.1-287His | 150 | 8192 |
| Orf46.1-919His | 2800 | 2048 |
| Orf46.1-287-919His | 3200 | 16384 |

For comparison, 'triple' hybrids of ORF46.1, 287 (either as a GST fusion, or in ΔG287 form) and 919 were constructed and tested against various strains (including the homologous 2996 strain) versus a simple mixture of the three antigens. FCA was used as adjuvant:

| | 2996 | BZ232 | MC58 | NGH38 | F6124 | BZ133 |
|---|---|---|---|---|---|---|
| Mixture | 8192 | 256 | 512 | 1024 | >2048 | >2048 |
| ORF46.1-287-919his | 16384 | 256 | 4096 | 8192 | 8192 | 8192 |
| ΔG287-919-ORF46.1his | 8192 | 64 | 4096 | 8192 | 8192 | 16384 |
| ΔG287-ORF46.1-919his | 4096 | 128 | 256 | 8192 | 512 | 1024 |

Again, the hybrids show equivalent or superior immunological activity.

Hybrids of two proteins (strain 2996) were compared to the individual proteins against various heterologous strains:

| | 1000 | MC58 | F6124 (MenA) |
|---|---|---|---|
| ORF46.1-His | <4 | 4096 | <4 |
| ORF1-His | 8 | 256 | 128 |
| ORF1-ORF46.1-His | 1024 | 512 | 1024 |

Again, the hybrid shows equivalent or superior immunological activity.

Example 9

Protein 961

The complete 961 protein from *N.meningitidis* (serogroup B, strain MC58) has the following sequence (SEQ ID NO:78):

```
  1 MSMKHFPAKV LTTAILATFC SGALAATSDD DVKKAATVAI VAAYNNGQEI
 51 NGFKAGETIY DIGEDGTITQ KDATAADVEA DDFKGLGLKK VVTNLTKTVN
101 ENKQNVDAKV KAAESEIEKL TTKLADTDAA LADTDAALDE TTNALNKLGE
151 NITTFAEETK TNIVKIDEKL EAVADTVDKH AEAFNDIADS LDETNTKADE
201 AVKTANEAKQ TAEETKQNVD AKVKAAETAA GKAEAAAGTA NTAADKAEAV
251 AAKVTDIKAD IATNKADIAK NSARIDSLDK NVANLEKETR QGLAEQAALS
301 GLFQPYNVGR FNVTAAVGGY KSESAVAIGT GFRFTENFAA KAGVAVGTSS
351 GSSAAYHVGV NYEW*
```

The leader peptide is underlined.

Three approaches to 961 expression were used:

1) 961 using a GST fusion, following WO99/57280 ('GST961');
2) 961 with its own leader peptide but without any fusion partner ('961L'); and
3) 961 without its leader peptide and without any fusion partner ('961$^{untagged}$'), with the leader peptide omitted by designing the 5'-end PCR primer downstream from the predicted leader sequence.

All three forms of the protein were expressed. The GST-fusion protein could be purified and antibodies against it confirmed that 961 is surface exposed (FIG. 4). The protein was used to immunise mice, and the resulting sera gave excellent results in the bactericidal assay. 961L could also be purified and gave very high ELISA titres.

Protein 961 appears to be phase variable. Furthermore, it is not found in all strains of *N.meningitidis*.

Example 10

Protein 287

Protein 287 from *N.meningitidis* (serogroup B, strain 2996) has the following sequence (SEQ ID NO:79):

```
  1 MFERSVIAMA CIFALSACGG GGGQSPDVKS ADTLSKPAAP VVAEKETEVK
 51 EDAPQAGSQG QGAPSTQGSQ DMAAVSAENT GNGGAATTDK PKNEDEGPQN
101 DMPQNSAESA NQTGNNQPAD SSDSAPASNP APANGGSNFG RVDLANGVLI
151 DGPSQNITLT HCKGDSCNGD NLLDEEAPSK SEFENLNESE RIEKYKKDGK
201 SDKFTNLVAT AVQANGTNKY VIIYKDKSAS SSSARFRRSA RSRRSLPAEM
251 PLIPVNQADT LIVDGEAVSL TGHSGNIFAP EGNYRYLTYG AEKLPGGSYA
301 LRVQGEPAKG EMLAGTAVYN GEVLHFHTEN GRPYPTRGRF AAKVDFGSKS
351 VDGIIDSGDD LHMGTQKFKA AIDGNGFKGT WTENGGGDVS GRFYGPAGEE
401 VAGKYSYRPT DAEKGGFGVF AGKKEQD*
```

The leader peptide is shown underlined.

Figure 5:
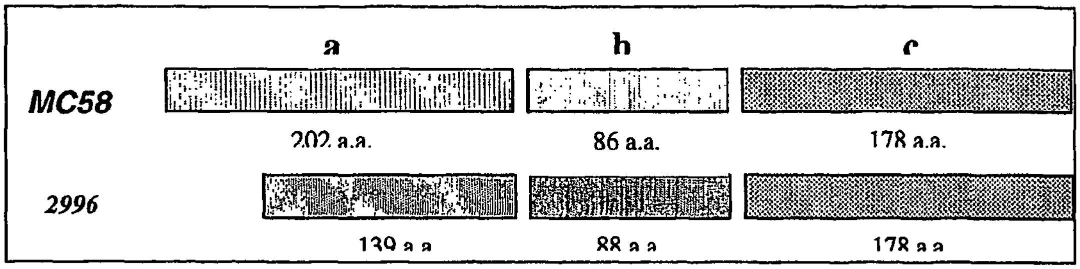
FIG. 5 shows domains of protein 287.

The sequences of 287 from other strains can be found in FIGS. 5 and 15 of WO00/66741.

Example 9 of WO99/57280 discloses the expression of 287 as a GST-fusion in *E.coli*.

A number of further approaches to expressing 287 in *E.coli* have been used, including:

1) 287 as a His-tagged fusion ('287-His');
2) 287 with its own leader peptide but without any fusion partner ('287L');
3) 287 with the ORF4 leader peptide and without any fusion partner ('287LOrf4'); and
4) 287 without its leader peptide and without any fusion partner ('287$^{untagged}$') (SEQ ID NO:80):

```
  1 CGGGQGGSPD VKSADTLSKP AAPVVAEKET EVKEDAPQAG SQGQGAPSTQ
 51 GSQDMAAVSA ENTGNGGAAT TDKPKNEDEG PQNDHPQNSA ESANQTGNNQ
101 PADSSDSAPA SNPAPANGGS NFGRVDLANG VLIDGPSQNI TLTHCKGDSC
153 NGDNLLDEEA PSKSEPENLN ESERIEKYKK DGKSDKFTNL VATAVQANGT
```

-continued

```
201 NKYVIIYKDK SASSSSARFR RSARSRRSLP AEMPLIPVNQ
                                         ADTLIVDGEA
251 VSLTQHSGNI FAPEGNYRYL TYGAEKLPGG SYALRVQGEP
                                         AKGEMLAGTA
301 VYNGEVLHFH TENGRPYPTR GRFAAKVDFG SKSVDGIIDS
                                         GDDLHHGTQK
351 FKAAIDGNGF KGTWTENGGG DVSGRPYGPA GEEVAGRYSY
                                         RPTDAEKGGF
401 GVFAGKKEQD *
```

All these proteins could be expressed and purified '287L' and '287LOrf4' were confirmed as lipoproteins.

Figure 2:
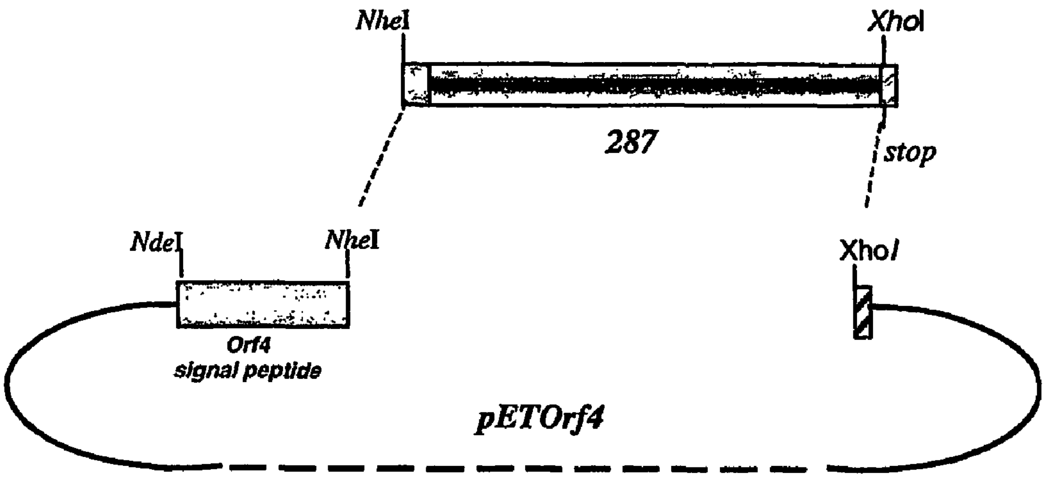

As shown in FIG. 2, '287LOrf4' was constructed by digesting 919LOrf4 with NheI and XhoI. The entire ORF4 leader peptide was restored by the addition of a DNA sequence coding for the missing amino acids, as a tail, in the 5'-end primer (287LOrf4 for), fused to 287 coding sequence. The 287 gene coding for the mature protein was amplified using the oligonucleotides 287LOrf4 For and Rev (including the NheI and XhoI sites, respectively), digested with NheI and XhoI and ligated to the purified pETOrf4 fragment.

Example 11

Further Non-Fusion Proteins with/without Native Leader Peptides

A similar approach was adopted for *E.coli* expression of further proteins from WO99/24578, WO99/36544 and WO99/57280.

The following were expressed without a fusion partner: 008, 105, 117-1, 121-1, 122-1, 128-1, 148, 216, 243, 308, 593, 652, 726, 982, and Orf143-1. Protein 117-1 was confirmed as surface-exposed by FACS and gave high ELISA titres.

The following were expressed with the native leader peptide but without a fusion partner: 111, 149, 206, 225-1, 235, 247-1, 274, 283, 286, 292, 401, 406, 502-1, 503, 519-1, 525-1, 552, 556, 557, 570, 576-1, 580, 583, 664, 759, 907, 913, 920-1, 926, 936-1, 953, 961, 983, 989, Orf4, Orf7-1, Orf9-1, Orf23, Orf25, Orf37, Orf38, Orf40, Orf40.1, Orf40.2, Orf72-1, Orf76-1, Orf85-2, Orf91, Orf97-1, Orf119, Orf143.1. These proteins are given the suffix 'L'.

His-tagged protein 760 was expressed with and without its leader peptide. The deletion of the signal peptide greatly increased expression levels. The protein could be purified most easily using 2M urea for solubilisation.

His-tagged protein 264 was well-expressed using its own signal peptide, and the 30 kDa protein gave positive Western blot results.

All proteins were successfully expressed.

The localisation of 593, 121-1, 128-1, 593, 726, and 982 in the cytoplasm was confirmed.

The localisation of 920-1L, 953L, ORF9-1L, ORF85-2L, ORF97-1L, 570L, 580L and 664L in the periplasm was confirmed.

The localisation of ORF40L in the outer membrane, and 008 and 519-1L in the inner membrane was confirmed. ORF25L, ORF4L, 406L, 576-1L were all confirmed as being localised in the membrane.

Protein 206 was found not to be a lipoprotein.

ORF25 and ORF40 expressed with their native leader peptides but without fusion partners, and protein 593 expressed without its native leader peptide and without a fusion partner, raised good anti-bactericidal sera. Surprisingly, the forms of ORF25 and ORF40 expressed without fusion partners and using their own leader peptides (i.e. 'ORF25L' and 'ORF40L') give better results in the bactericidal assay than the fusion proteins.

Proteins 920L and 953L were subjected to N-terminal sequencing, giving HRVWVETAH (SEQ ID NO:81) and ATYKVDEYHANARFAF (SEQ ID NO:82), respectively. This sequencing confirms that the predicted leader peptides were cleaved and, when combined with the periplasmic location, confirms that the proteins are correctly processed and localised by *E. coli* when expressed from their native leader peptides.

The N-terminal sequence of protein 519.1L localised in the inner membrane was MEFFIILLA (SEQ ID NO:83), indicating that the leader sequence is not cleaved. It may therefore function as both an uncleaved leader sequence and a transmembrane anchor in a manner similar to the leader peptide of PBP1 from *N.gonorrhoeae* [Ropp & Nicholas (1997) *J Bact.* 179:2783-2787.]. Indeed the N-terminal region exhibits strong hydrophobic character and is predicted by the Tmpred. program to be transmembrane.

Example 12

Lipoproteins

The incorporation of palmitate in recombinant lipoproteins was demonstrated by the method of Kraft et. al. [*J. Bact.* (1998) 180:3441-3447.]. Single colonies harbouring the plasmid of interest were grown overnight at 37° C. in 20 ml of LB/Amp (100 μg/ml) liquid culture. The culture was diluted to an $OD_{550}$ of 0.1 in 5.0 ml of fresh medium LB/Amp medium containing 5 μC/ml [$^3$H] palmitate (Amersham). When the $OD_{550}$ of the culture reached 0.4-0.8, recombinant lipoprotein was induced for 1 hour with IPTG (final concentration 1.0 mM). Bacteria were harvested by centrifugation in a bench top centrifuge at 2700 g for 15 min and washed twice with 1.0 ml cold PBS. Cells were resuspended in 120 μl of 20 mM Tris-HCl (pH 8.0), 1 mM EDTA, 1.0% w/v SDS and lysed by boiling for 10 min. After centrifugation at 13000 g for 10 min the supernatant was collected and proteins precipitated by the addition of 1.2 ml cold acetone and left for 1 hour at −20° C. Protein was pelleted by centrifugation at 13000 g for 10 min and resuspended in 20-50 μl (calculated to standardise loading with respect to the final O.D of the culture) of 1.0% w/v SDS. An aliquot of 15 μl was boiled with 5 μl of SDS-PAGE sample buffer and analysed by SDS-PAGE. After electrophoresis gels were fixed for 1 hour in 10% v/v acetic acid and soaked for 30 minutes in Amplify solution (Amersham). The gel was vacuum-dried under heat and exposed to Hyperfilm (Kodak) overnight −80° C.

Incorporation of the [$^3$H] palmitate label, confirming lipidation, was found for the following proteins: Orf4L, Orf25L, 287L, 287LOrf4, 406.L, 576L, 926L, 919L and 919LOrf4.

Example 13

Domains in 287

Based on homology of different regions of 287 to proteins that belong to different functional classes, it was split into three 'domains', as shown in FIG. 5. The second domain shows homology to IgA proteases, and the third domain shows homology to transferrin-binding proteins.

Each of the three 'domains' shows a different degree of sequence conservation between *N.meningitidis* strains—domain C is 98% identical, domain A is 83% identical, whilst domain B is only 71% identical. Note that protein 287 in strain MC58 is 61 amino acids longer than that of strain 2996.

An alignment of the two sequences is shown in FIG. 7, and alignments for various strains are disclosed in WO0/66741 (see FIGS. 5 and 15 therein).

The three domains were expressed individually as C-terminal His-tagged proteins. This was done for the MC58 and 2996 strains, using the following constructs:

287a-MC58 (aa 1-202), 287b-MC58 (aa 203-288), 287c-MC58 (aa 311-488).

287a-2996 (aa 1-139), 287b-2996 (aa 140-225), 287c-2996 (aa 250-427).

To make these constructs, the stop codon sequence was omitted in the 3'-end primer sequence. The 5' primers included the NheI restriction site, and the 3' primers included a XhoI as a tail, in order to direct the cloning of each amplified fragment into the expression vector pET21b+ using NdeI-XhoI, NheI-XhoI or NdeI-HindIII restriction sites.

All six constructs could be expressed, but 287b-MC8 required denaturation and refolding for solubilisation.

Deletion of domain A is described below ('Δ4 287-His').

Immunological data (serum bactericidal assay) were also obtained using the various domains from strain 2996, against the homologous and heterologous MenB strains, as well as MenA (F6124 strain) and MenC (BZ133 strain):

| | 2996 | BZ232 | MC58 | NGH38 | 394/98 | MenA | MenC |
|---|---|---|---|---|---|---|---|
| 287-His | 32000 | 16 | 4096 | 4096 | 512 | 8000 | 16000 |
| 287(B)-His | 256 | — | — | — | — | 16 | — |
| 287(C)-His | 256 | — | 32 | 512 | 32 | 2048 | >2048 |
| 287(B–C)-His | 64000 | 128 | 4096 | 64000 | 1024 | 64000 | 32000 |

Using the domains of strain MC58, the following results were obtained:

| | MC58 | 2996 | BZ232 | NGH38 | 394/98 | MenA | MenC |
|---|---|---|---|---|---|---|---|
| 287-His | 4096 | 32000 | 16 | 4096 | 512 | 8000 | 16000 |
| 287(B)-His | 128 | 128 | — | — | — | — | 128 |
| 287(C)-His | — | 16 | — | 1024 | — | 512 | — |
| 287(B–C)-His | 16000 | 64000 | 128 | 64000 | 512 | 64000 | >8000 |

Example 14

Deletions in 287

Figure 6:
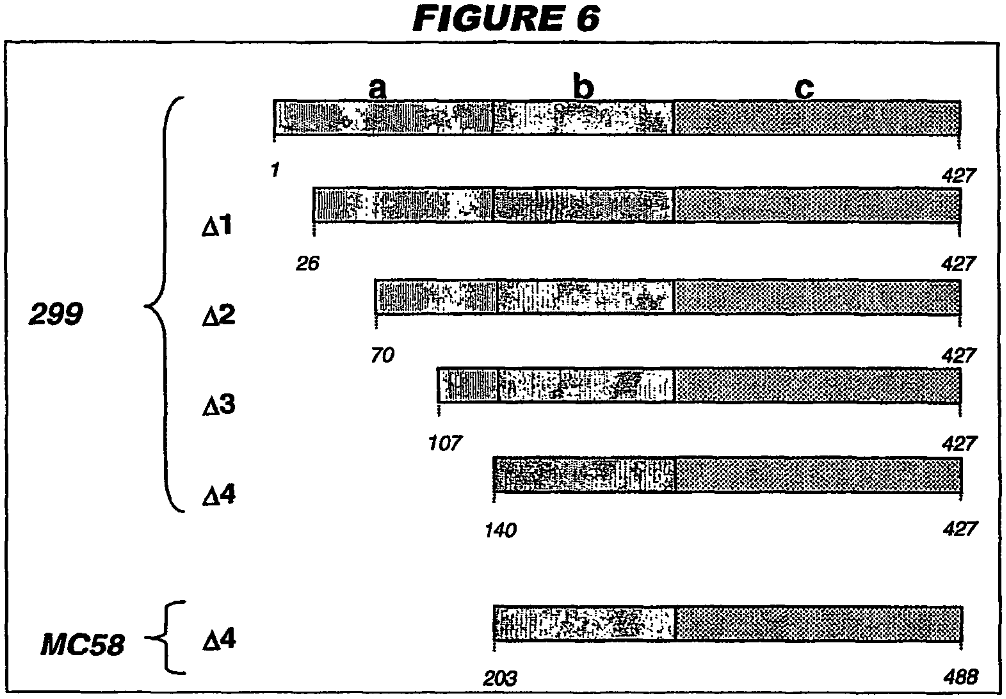

As well as expressing individual domains, 287 was also expressed (as a C-terminal His-tagged protein) by making progressive deletions within the first domain. These Four deletion mutants of protein 287 from strain 2996 were used (FIG. 6):

1) '287-His', consisting of amino acids 18-427 (i.e. leader peptide deleted);

2) 'Δ1 287-His', consisting of amino acids 26-427;

3) 'Δ2 287-His', consisting of amino acids 70-427;

4) 'Δ3 287-His', consisting of amino acids 107-427; and

5) 'Δ4 287-His', consisting of amino acids 140-427 (=287-bc).

The 'Δ4' protein was also made for strain MC58 ('Δ4 287MC58-His'; aa 203-488).

The constructs were made in the same way as 287a/b/c, as described above.

All six constructs could be expressed and protein could be purified. Expression of 287-His was, however, quite poor.

Expression was also high when the C-terminal His-tags were omitted.

Immunological data (serum bactericidal assay) were also obtained using the deletion mutants, against the homologous (2996) and heterologous MenB strains, as well as MenA (F6124 strain) and MenC (BZ133 strain):

| | 2996 | BZ232 | MC58 | NGH38 | 394/98 | MenA | MenC |
|---|---|---|---|---|---|---|---|
| 287-his | 32000 | 16 | 4096 | 4096 | 512 | 8000 | 16000 |
| Δ1 287-His | 16000 | 128 | 4096 | 4096 | 1024 | 8000 | 16000 |
| Δ2 287-His | 16000 | 128 | 4096 | >2048 | 512 | 16000 | >8000 |
| Δ3 287-His | 16000 | 128 | 4096 | >2048 | 512 | 16000 | >8000 |
| Δ4 287-His | 64000 | 128 | 4096 | 64000 | 1024 | 64000 | 32000 |

The same high activity for the Δ4 deletion was seen using the sequence from strain MC58.

As well as showing superior expression characteristics, therefore, the mutants are immunologically equivalent or superior.

Example 15

Poly-Glycine Deletions

The 'Δ1287-His' construct of the previous example differs from 287-His and from '287$^{untagged}$' only by a short N-terminal deletion (GGGGGGS) (SEQ ID NO:631). Using an expression vector which replaces the deleted serine with a codon present in the Nhe cloning site, however, this amounts to a deletion only of (Gly)$_6$ (SEQ ID NO:632). Thus, the deletion of this (Gly)$_6$ sequence (SEQ ID NO:632) has been shown to have a dramatic effect on protein expression.

The protein lacking the N-terminal amino acids up to GGGGGG (SEQ ID NO:632) is called 'ΔG 287'. In strain MC58, its sequence (leader peptide underlined) is (SEQ ID NO:84):

```
                        → ΔG287
  1 MFKRSVIAMA CIFALSACGG GGGGSPDVKS ADTLSKPAAP
                                    VVSEKETEAK
 51 EDAPQAGSQG QGAPSAQGSQ DMAAVSEENT GNGGAVTADN
                                    PKNBDEVAQN
101 DMPQNAAGTD SSTPNHTPDP NMLAGNNENQ ATDAGESSQP
                                    ANQPDMANAA
151 DGMQGDDPSA GGQNAGNTAA QGANQAGNNQ AAGSSDPIPA
                                    SNPAPANGGS
201 NFGRVDLANG VLIDGPSQNI TLTHCKGDSC SGNNFLDBEV
                                    QLKSEFEKLS
251 DADKISNYKK DGKNDKFVGL VADSVQMKGI NQYIIFYKPK
                                    PTSFARPRRS
301 ARSEPSLPAE MPLIPVNQAD TLIVDGEAVS LTGHSGNIFA
                                    PEGNYRYLTY
351 GAEKLPGGSY ALRVQGEPAK GEKLAGAAVY NGEVLRFHTE
                                    NGRPYPTRGR
401 FAAKVDFGSK SVDGIIDSGD DLMHGDQKFK AAIDGNGFKG
                                    TWTENGSGDV
451 SGKFYGPAGE EVAGKYSYRP TDAEKGGFGV FAGKKEQD*
```

ΔG287, with or without His-tag ('ΔG287-His' and 'ΔG287K', respectively), are expressed at very good levels in comparison with the '287-His' or '287$^{untagged}$'.

On the basis of gene variability data, variants of ΔG287-His were expressed in E.coli from a number of MenB strains, in particular from strains 2996, MC58, 1000, and BZ232. The results were also good.

It was hypothesised that poly-Gly deletion might be a general strategy to improve expression. Other MenB lipoproteins containing similar (Gly)$_n$ motifs (near the N-terminus, downstream of a cysteine) were therefore identified, namely Tbp2 (NMB0460) (SEQ ID NO:85), 741 (NMB 1870) (SEQ ID NO:86) and 983 (NMB1969) (SEQ ID NO:87):

```
TBP2                    → ΔGTbp2
  1 MNNPLVNQAA MVLPVFLLSA CWGGGSFDL DSVDTEAPRP
                                    APKYQDVFSE
```

-continued
```
 51 KPQAQKDQGG YGFAMRLKRR NWYPQAKEDB VKLDESDWEA
                                    TGLPDEPKEL
101 PKRQRSVIEK VRTDSDNNIY SSPYLKPSNH QNGNTGNGIN
                                    QPKNQAXDYE
151 NFKYVYSGWF YKHAKREFNL KVBPKSAKNG DDGYIFYHGK
                                    EPSRQLPASG
201 KITYKGVWHF ATDTKKGQKF REIIQPSKBQ GDRYSGFSGD
                                    DGEEYSNKNK
251 STLTDGQEGY GFTSNLEVDF HNKKLTGKLI RNNANTDNNQ
                                    ATTTQYYSLE
301 AQVTGNRPNG KATATDKPQQ NSETKBHPFV SDSSSLSGGF
                                    FGPQGEELGF
351 RPLSDDQKVA VVGSAKTKDK PANGNTAAAS GGTDAAASNG
                                    AAGTSSENGK
401 LTTVLDAVEL KLGDKEVQKL DNFSNAAQLV VDGIMIPLLP
                                    EASESGNNQA
451 NQGTNGGTAF TRKFDHTPES DKKDAQAGTQ TNGAQTASNT
                                    AGDTNGKTKT
501 YEVEVCCSNL NYLKYGMLTR KNSKSAMQAG ESSSQADAKT
                                    EQVEQSMFLQ
551 GERTDEKEIP SEQNIVYRGS WYGYIANDKS TSWSGNASNA
                                    TSGNRAEFTV
601 NFADKKITGT LTADNRQEAT FTIDGNIKDN GFEGTAKTAE
                                    SGFDLDQSNT
651 TRTPKAYITD AKVQGGPYGP KAEELGGWFA YPGDKQTKNA
                                    TNASGNSSAT
701 VVFGAKRQQP VR*
                        → ΔG741
741
  1 VNRTAPCCLS LTTALILTAC SSGGGGVAAD IGAGLADALT
                                    APLDHKDKGL
 51 QSLTLDQSVR KNEKLKLAAQ GAEKTYGNGD SLNTGKLKND
                                    KVSRFDFIRQ
101 IEVDGQLITL ESGEFQVYKQ SHSALTAFQT EQIQDSEHSG
                                    KMVAKRQFRI
151 GDIAGEHTSF DKLPEGGRAT YRGTAFGSDD AGGKLTYTID
                                    FAAKQGNGKI
201 EHLKSPELNV DLAAADIKPD GKRHAVISGS VLYNQAEKGS
                                    YSLGIFGGKA
251 QEVAGSAEVK TVNGIRHIGL AAKQ*
                        → ΔG983
983
  1 MRTTPTPPTK TDXPTAMALA VATTLSACLG GGGGGTSAPD
                                    FNAGGTGIGS
 51 NSRATTAKSA AVSYAGIKNE HCKDRSNLCA GRDDVAVTDR
                                    DAKINAPPPN
101 LHTGDFPNPN DAYKNLINLK PAIEAGYTGR GVEVGIVDTG
                                    ESVGSISFPE
151 LYGRKEHGYN ENYKNYTAYM RKEAPEDGGG KDIEASFDDE
                                    AVIETEAKPT
201 DIRHVKEIGR IDLVSHIIGG RSVDGRPAGG IAPDATLHIM
                                    NTNDETKNEM
251 MVAAIRNAWV KLGERGVPJV NNSPGTTSRA GTADLFQIAN
                                    SEEQYRQALL
301 DYSGGDKTDE GIRLMQQSDY GNLSYHIRNK NMLFXFSTGN
                                    DAQAQPNTYA
```

-continued

```
 351 LLPFYEKDAQ KGIITVAGVD RSGEKFKREM YGRPGTEPLE
                                     YGSNHCGITA

 401 MWCLSAPYEA SVRPTRTNPI QIAGTSFSAP IVTGTAALLL
                                     QKTPWMSNDN

 451 LRTTLLTTAQ DIGAVGVDSK FGWGLLDAGK AMNGPASFPF
                                     GDPTADTKGT

 501 SDIAYSFRND ISGTGGLIKK GGSQLQLHGN NTYTGKTIIE
                                     GGSLVLYGNN

 551 KSDMRVETKG ALIYNGAASG GSLNSDGIVY LADTDQSGAN
                                     ETVHIKGSLQ

 601 LDGKGTLYTR LGKLLKVDGT AIIGGKLYMS ARGKGAGYLN
                                     STGRRVPFLS

 651 AAKIGQDYSF FTNIETDGGL LASLDSVEKT AGSEGDTLSY
                                     YVRRGNAART

 701 ASAAAHSAPA GLKHAVEQGG SNLENLMVEL DASESSATPE
                                     TVETAAADRT

 751 DMPGIRPYGA TFRAAAAVQH ANAADGVRIF NSLAATVYAD
                                     STAAHADMQG

 801 RRLKAVSDGL DHNGTGLRVI AQTQQDGGTW EQGGVEGKMR
                                     GSTQTVGIAA

 851 KTGENTTAAA TLGMGRSTWS ENSANAKTDS ISLFAGIRHD
                                     AGDIGYLKGL

 901 FSYGRYKNSI SRSTGADEHA EGSVNGTLMQ LGALGGVNVP
                                     FAATGDLTVE

 951 GGLRYDLLKQ DAFAEKGSAL GWSGNSLTEG TLVGLAGLKL
                                     SQPLSDKAVL

1001 FATAGVERDL NGRDYTVTGG FTGATAATGK TGARMNPHTR
                                     LVAGLGADVE

1051 FGNGWNGLAR YSYAGSKQYG NHSGRVGVGY RF*
```

Tbp2 and 741 genes were from strain MC58; 983 and 287 genes were from strain 2996. These were cloned in pET vector and expressed in *E.coli* without the sequence coding for their leader peptides or as "ΔG forms", both fused to a C-terminal His-tag. In each case, the same effect was seen—expression was good in the clones carrying the deletion of the poly-glycine stretch, and poor or absent if the glycines were present in the expressed protein:

| ORF | Express. | Purification | Bact. Activity |
|---|---|---|---|
| 287-His(2996) | +/− | + | + |
| '287*untagged*'(2996) | +/− | nd | nd |
| ΔG287-His(2996) | + | + | + |
| ΔG287K(2996) | + | + | + |
| ΔG287-His(MC58) | + | + | + |
| ΔG287-His(1000) | + | + | + |
| ΔG287-His(BZ232) | + | + | + |
| Tbp2-His(MC58) | +/− | nd | nd |
| ΔGTbp2-His(MC58) | + | + | |
| 741-His(MC58) | +/− | nd | nd |
| ΔG741-His(MC58) | + | + | |
| 983-His (2996) | | | |
| ΔG983-His (2996) | + | + | |

SDS-PAGE of the proteins is shown in FIG. 13.

ΔG287 and Hybrids

ΔG287 proteins were made and purified for strains MC58, 1000 and BZ232. Each of these gave high ELISA titres and also serum bactericidal titres of >8192. ΔG287K, expressed from pET-24b, gave excellent titres in ELISA and the serum bactericidal assay. ΔG-287-ORF46.1K may also be expressed in pET-24b.

ΔG287 was also fused directly in-frame upstream of 919 (SEQ ID NOS:88 and 89), 953 (SEQ ID NOS:90 and 91), 961 (SEQ ID NOS:92 and 93) (sequences shown below) and ORF46.1:

ΔG287-919

```
  1 ATGGCTAGCC CCGATGTTAA ATCGGCGGAC ACGCTGTCAA AACCGGCCGC

 51 TCCTGTTGTT GCTGAAAAAG AQACAGAGGT AAAAGAAGAT GCGCCACAGG

101 CAGGTTCTCA AGGACAGGGC GCGCCATCCA CACAAGGCAG CCAAGATATG

151 GCGGCAGTTT CGGCAGAAAA TACAGGCAAT GGCGGTGCGG CAACAACGGA

201 CAAACCCAAA AATGAAGACG AGGGACCGCA AAATGATATG CCGCAAAATT

251 CCGCCGAATC CGCAAATCAA ACAGGGAACA ACCAACCCGC CGATTCTTCA

301 GATTCCGCCC CCGCGTCAAA CCCTGCACCT GCGAATGGCG GTAGCAATTT

351 TGGAAGGGTT GATTTGGCTA ATGGCGTTTT GATTGATGGG CCGTCGCAAA

401 ATATAACGTT GACCCACTGT AAAGGCGATT CTTGTAATGG TGATAATTTA

451 TTGGATGAAG AAGCACCGTC AAAATCAGAA TTTGAAAATT TAAATGAGTC

501 TGAACGAATT GAGAAATATA AGAAAGATGG GAAAAGCGAT AAATATACTA

551 ATTTGGTTGC GACAGCAGTT CAAGCTAATG GAAATAACAA ATATGTCATC

601 ATTTATAAAG ACAAGTCCGC TTCATCTTCA TCTGCGCGAT TCAGGCGTTC

651 TGCACGGTCG AGGAGGTCGC TTCCTGCCGA GATGCCGCTA ATCCCCGTCA

701 ATCAGGCGGA TACGCTGATT GTCGATGGGG AAGCGGTCAG CCTGACGGGG
```

-continued

751 CATTCCGGCA ATATCTTCGC GCCCGAAGGG AATTACCGGT ATCTGACTTA

801 CGGGGCGGAA AAATTGCCCG GCGGATCGTA TGCCCTCCGT GTGCAAGGCG

851 AACCGGCAAA AGGCGAAATG CTTGCTGGCA CGGCCGTGTA CAACGGCGAA

901 GTGCTGCATT TTCATACGOA AAACGGCCGT CCGTACCCGA CTAGAGGCAG

951 GTTTGCCGCA AAAGTCGATT TCGGCAGCAA ATCTGTGGAC GGCATTATCG

1001 ACAGCGGCGA TGATTTGCAT ATGGGTACGC AAAAATTCAA AGCCGCCATC

1051 GATGGAAACG GCTTTAAGGG GACTTGGACG GAAAATGGCG GCGGGGATGT

1101 TTCCGGAAGG TTTTACGGCC CGGCCOGCGA GGAAGTGGCG GGAAAATACA

1151 GCTATCGCCC GACAGATGCG GAAAAGGGCG GATTCGGCGT GTTTGCCGGC

1201 AAAAAAGAGC AGGATGGATC CGGAGGAGGA GGATGCCAAA GCAAGAGCAT

1251 CCAAACCTTT CCGCAACCCG ACACATCCGT CATCAACGGC CCGGACCGGC

1301 CGGTCGGCAT CCCCGACCCC GCCGGAACGA CGGTCGGCGG CGGCGGGGCC

1351 GTCTATACCG TTGTACCGCA CCTGTCCCTG CCCCACTGGG CGGCGCAGGA

1401 TTTCGCCAAA AGCCTGCAAT CCTTCCGCCT CGGCTGCGCC AATTTGAAAA

1451 ACCGCCAAGG CTGGCAGGAT GTGTGCGCCC AAGCCTTTCA AACCCCCGTC

1501 CATTCCTTTC AGGCAAAACA GTTTTTTGAA CGCTATTTCA CGCCGTGGCA

1551 GGTTGCAGGC AACGGAAGCC TTGCCGGTAC GGTTACCGGC TATTACGAGC

1601 CGGTGCTGAA GGGCGACGAC AGGCGGACGG CACAAGCCCG CTTCCCGATT

1651 TACGGTATTC CCGACGATTT TATCTCCGTC CCCCTGCCTG CCGGTTTGCG

1701 GAGCGGAAAA GCCCTTGTCC GCATCAGGCA GACGGGAAAA AACAGCGGCA

1751 CAATCGACAA TACCGGCGGC ACACATACCG CCGACCTCTC CCGATTCCCC

1801 ATCACCGCGC GCACAACGGC AATCAAAGGC AGGTTTGAAG GAAGCCGCTT

1851 CCTCCCCTAC CACACGCGCA ACCAAATCAA CGGCGGCGCG CTTGACGGCA

1901 AAGCCCCGAT ACTCGGTTAC GCCGAAGACC CCGTCGAACT TTTTTTTATG

1951 CACATCCAAG GCTCGGGCCG TCTGAAAACC CCGTCCGGCA AATACATCCG

2001 CATCGGCTAT GCCGACAAAA ACGAACATCC CTACGTTTCC ATCGGACGCT

2051 ATATGGCGGA CAAAGGCTAC CTCAAGCTCG GGCAGACCTC GATGCAGGGC

2101 ATCAAAGCCT ATATGCGGCA AAATCCGCAA CGCCTCGCCG AAGTTTTGGG

2151 TCAAAACCCC AGCTATATCT TTTTCCGCGA GCTTGCCGGA AGCAGCAATG

2201 ACGGTCCCGT CGGCOCACTG GGCACGCCGT TGATGGGGGA ATATGCCGGC

2251 GCAGTCGACC GGCACTACAT TACCTTGGGC GCGCCCTTAT TTGTCGCCAC

2301 CGCCCATCCG GTTACCCGCA AAGCCCTCAA CCGCCTGATT ATGGCGCAGG

2351 ATACCGGCAG CGCGATTAAA GGCGCGGTGC GCGTGGATTA TTTTTGGGGA

2401 TACGGCGACG AAGCCGGCGA ACTTGCCGGC AAACAGAAAA CCACGGGTTA

2451 CGTCTGGCAG CTCCTACCCA ACGGTATGAA GCCCGAATAC CGCCCGTAAC

2501 TCGAG

1 MASPDVKSAD TLSKPAAPVV AEKETEVKED APQAGSQGQG APSTQGSQDM

51 AAVSAENTGN GGAATTDKPK NEDEGPQNDM PQNSAESANQ TGNNQPADSS

101 DSAPASNPAP ANGGSNFGRV DLANGVLIDG PSQNITLTHC KGDSCNGDNL

151 LDEEAPSKSE FENLNESERI EKYKKDGKSD KFTNLVATAV QANGTNKYVI

-continued

201 IYKDKSASSS SAPPRRSARS RRSLPAEMPL IPVNQADTLI VDGEAVSLTG

251 HSGNIFAPEG NYRYLTYGAE KLPGGSYMJR VQGEPAXGEM LAGTAVYNGE

301 VLHFHTENGR PYPTRGRPAA KVDFGSKSVD GIIDSGDDLH HGTQKFKAAI

351 DGNGFKGTWT ENGGGDVSGR FYGPAGEEVA GKYSYRPTDA EKGGFGVFAG

401 KKEQDGSGGG GCQSKSIQTP PQPDTSVING PDEPVGIPDP AGTTVGOGGA

451 VYTVVPELSL PHWAAQDFAK SLQSFRLGCA NLKNRQGWQD VCAQAFQTPV

501 HSFQAKQFFE RYFTPWQVAG NGSLAGTVTG YYEPVLKGDD RRTAQARFPI

551 YGIPDDFISV PLPAGLRSGK ALVRIRQTGK NSGTIDNTGG THTADLSRFP

601 ITARTTAIKG RFEGSRPLPY HTRNQINGGA LDGKAPILGY AEDPVELFFM

651 HIQGSGRLKT PSGKYIRIGY ADKNEHPYVS IGRYMADKGY LKLGQTSMQG

701 IKAYMRQNPQ RLAEVLGQNP SYIPFRELAD SBIWGPVGMJ GTPIMGEYAG

751 AVDRHYITLG APLFVATAHP VTRKALNELI MAQDTGSAIK GAVRVDYFWG

801 YGDEAGELAG KQKTTGYVWQ LLPNGMKPEY RP*

ΔG287-953

1 ATGGCTAGCC CCGATGTTAA ATCGGCGGAC ACGCTGTCAA AACCGGCCGC

51 TCCTGTTGTT GCTGAAAAAG AGACAGAGGT AAAAGAAGAT GCGCCACAGG

101 CAGGTTCTCA AGGACAGGGC GCGCCATCCA CACAAGGCAG CCAAGATATG

151 GCGGCAGTTT CGGCAGAAAA TACAGGCAAT GGCGGTGCGG CAACAACGGA

201 CAAACCCAAA AATGAAGACG AGGGACCGCA AAATGATATG CCGCAAAATT

251 CCGCCGAATC CGCAAATCAA ACAGGGAACA ACCAACCCGC CGATTCTTCA

301 GATTCCGCCC CCGCGTCAAA CCCTGCACCT GCGAATGGCG GTAGCAATTT

351 TGGAAGGGTT GATTTGGCTA ATGGCGTTTT GATTGATGGG CCGTCGCAAA

401 ATATAACGTT GACCCACTGT AAAGGCGATT CTTGTAATGG TGATAATTTA

451 TTGGATGAAG AAGCACCGTC AAAATCAGAA TTTGAAAATT TAAATGAGTC

501 TGAACGAATT GAGAAATATA AGAAAGATGG GAAAAGCGAT AAATTTACTA

551 ATTTGGTTGC GACAGCAGTT CAAGCTAATG GAACTAACAA ATATGTCATC

601 ATTTATAAAG ACAAGTCCGC TTCATCTTCA TCTGCGCGAT TCAGGCGTTC

651 TGCACGGTCG AGGAGGTCGC TTCCTGCCGA GATGCCGCTA ATCCCCGTCA

701 ATCAGGCGGA TACGCTGATT GTCGATGGGG AAGCGGTCAG CCTGACGAGG

751 CATTCCGGCA ATATCTTCGC GCCCGAAGGG AATTACCGGT ATCTGACTTA

801 CGGGGCGGAA AAATTGCCCG GCGGATCGTA TGCCCTCCGT GTGCAAGGCG

851 AACCGGCAAA AGGCGAAATG CTTGCTGGCA CGGCCGTGTA CAACGGCGAA

901 GTGCTGCATT TTCATACGGA AAACGGCCGT CCGTACCCGA CTAGAGGCAG

951 GTTTGCCGCA AAAGTCGATT TCGGCAGCAA ATCTGTGGAC GGCATTATCG

1001 ACAGCGGCGA TGATTTGCAT ATGGGTACGC AAAAATTCAA AGCCGCCATC

1051 GATGGAAACG GCTTTAAGGG GACTTGGACG GAAAATGGCG GCGGGGATGT

1101 TTCCGGAAGG TTTTACGGCC CGCCCCGCGA GGAAGTGGCG GGAAAATACA

1151 GCTATCGCCC GACAGATGCG GAAAAGGGCG GATTCGGCGT GTTTGCCGGC

1201 AAAAAAGAGC AGGATGGATC CGGAGGAGGA GGAGCCACCT ACAAAGTGGA

1251 CGAATATCAC GCCAACGCCC GTTTCGCCAT CGACCATTTC AACACCAGCA

1301 CCAACGTCGG CGGTTTTTAC GGTCTGACCG GTTCCGTCGA GTTCGACCAA

-continued

```
1351 GCAAAACGCG ACGGTAAAAT CGACATCACC ATCCCCGTTG CCAACCTGCA

1401 AAGCGGTTCG CAACACTTTA CCGACCACCT GAAATCAGCC GACATCTTCG

1451 ATGCCGCCCA ATATCCGGAC ATCCGCTTTG TTTCCACCAA ATTCAACTTC

1501 AACGGCAAAA AACTGGTTTC CGTTGACGGC AACCTGACCA TGCACGGCAA

1551 AACCGCCCCC GTCAAACTCA AAGCCGAAAA ATTCAACTGC TACCAAAGCC

1601 CGATGGCGAA AACCGAAGTT TGCGGCGGCG ACTTCAGCAC CACCATCGAC

1651 CGCACCAAAT GGGGCGTGGA CTACCTCGTT AACGTTGGTA TGACCAAAAG

1701 CGTCCGCATC GACATCCAAA TCGAGGCAGC CAAACAATAA CTCGAG
```

```
  1 MASPDVKSAD TLSKPAAPVV AEKETEVKED APQAGSQGQG APSTQGSQDM

 51 AAVSAENTGN GGAATTDKPK NBDEGPQNDM PQNSAESANQ TGNNQPADSS

101 DSAPASNPAP ANGGSNFGRV DLANGVLIDG PSQNITLTHC KGDSCNGDNL

151 LDEEAPSKSE FENLNESERI ERYKKDGKSD KFTNLVATAV QANGTNKYVI

201 IYKDKSASSS SARFRRSARS RRSLPAEMPL IPVNQADTLI VDGRAVSLTG

251 RSGNIFAPEG NYRYLTYGAE KLPGGSYALR VQGEPAKGEH LAGTAVYNGE

301 VLHFETENGR PYPTRGRFAA KVDFGSKSVD GIIDSGDDLH MGTQKFKAAI

351 DGNGFKGTWT ENGGGDVSGR PYGPAGBEVA GKYSYRPTDA EKGGFGVFAG

401 KKEQDGSGGG GATYRVDEYH ANAPPAIDHF NTSTNVGGFY GLTGSVBFDQ

451 AXRDGKIDIT IPVANLQSGS QHFTDHLKSA DIFDAAQYPD IRFVSTKFNF

501 NGKKLVSVDG NLTMHGKTAP VKLKAEKFNC YQSPMAKTEV CGGDFSTTID

551 RTKWGVDYLV NVVGMTKSVRI DIQIEAAKQ*
```

ΔG287-961
```
  1 ATGGCTAGCC CCGATGTTAA ATCGGCGGAC ACGCTGTCAA AACCGGCCGC

 51 TCCTGTTGTT GCTGAAAAAG AGACAGAGGT AAAAGAAGAT GCGCCACAGG

101 CAGGTTCTCA AGGACAGGGC GCGCCATCCA CACAAGGCAG CCAAGATATG

151 GCGGCAGTTT CGGCAGAAAA TACAGGCAAT GGCGGTGCGG CAACAACGGA

201 CAAACCCAAA AATGAAGACG AGGGACCGCA AAATGATATG CCGCAAAATT

251 CCGCCGAATC CGCAAATCAA ACAGGGAACA ACCAACCCGC CGATTCTTCA

301 GATTCCGCCC CCGCGTCAAA CCCTGCACCT GCGAATGGCG GTAGCAATTT

351 TGGAAGGGTT GATYTGGCTA ATGGCGTTTT GATTGATGGG CCGTCGCAAA

401 ATATAACGTT GACCCACTGT AAAGGCGATT CTTGTAATGG TGATAATTTA

451 TTGGATGAAG AAGCACCGTC AAAATCAGAA TTTGAAAATT TAAATGAGTC

501 TGAACGAATT GAAAAATATA AGAAAGATGG GAAAAGCGAT AAATTTACTA

551 ATTTGGTTGC GACAGCAGTT CAAGCTAATG GAACTAACAA ATATGTCATC

601 ATTTATAAAG ACAAGTCCGC TTCATCTTCA TCTGCGCGAT TCAGGCGTTC

651 TGCACGGTCG AAGAGGTCGC TTCCTGCCGA GATGCCGCTA ATCCCCGTCA

701 ATCAGGCGGA TACGCTGATT GTCGATGGGG AAGCGGTCAG CCTGACGGGG

751 CATTCCGGCA ATATCTTCGC GCCCGAAGGG AATTACCGGT ATCTGACTTA

801 CGGGGCGGAA AAATTGCCCG GCGGATCGTA TGCCCTCCGT GTGCAAGGCG

851 AACCGQCAAA AGGCGAAATG CTTGCTGGCA CGGCCGTGTA CAACGGCGAA

901 GTGCTGCATT TTCATACGGA AAACGGCCGT CCGTACCCGA CTAGAGGCAG
```

-continued

951 GTTTGCCGCA AAAGTCGATT TCGGCAGCAA ATCTGTGGAC GGCATTATCG

1001 ACAGCGGCGA TGATTTGCAT ATGGGTACGC AAAAATTCAA AGCCGCCATC

1051 GATGGAAACG GCTTTAAGGG GACTTGGACG GAAAATGGCG GCGGGGATGT

1101 TTCCGGAAGG TTTTACGGCC CGGCCGGCGA GGAAGTGGCG GGAAAATACA

1151 GCTATCGCCC GACAGATGCG GAAAAGGGCG GATTCGGCGT GTTTGCCGGC

1201 AAAAAAGAGC AGGATGGATC CGGAGGAGGA GGAGCCACAA ACGACGACGA

1251 TGTTAAAAAA GCTGCCAGTG TGGCCATTGC TGCTGCCTAC AACAATGGCC

1301 AAGAAATCAA CGGTTTCAAA GCTGGAGAGA CCATCTACGA CATTGATGAA

1351 GACGGCACAA TTACCAAAAA AGACGCAACT GCAGCCGATG TTGAAGCCGA

1401 CGACTTTAAA GGTCTGGGTC TGAAAAAAGT CGTGACTAAC CTGACCAAAA

1451 CCGTCAATGA AAACAAACAA AACGTCGATG CCAAAGTAAA AGCTGCAGAA

1501 TCTGAAATAG AAAAGTTAAC AACCAAGTTA GCAGACACTG ATGCCGCTTT

1551 AGCAGATACT GATGCCGCTC TGGATGCAAC CACCAACGCC TTGAATAAAT

1601 TGGGAGAAAA TATAACGACA TTTGCTGAAG AGACTAAGAC AAATATCGTA

1651 AAAATTGATG AAAAATTAGA AGCCGTGGCT GATACCGTGG ACAAGCATGC

1701 CGAAGCATTC AACGATATCG CCGATTCATT GGATGAAACC AACACTAAGG

1751 CAGACGAAGC CGTCAAAACC GCCAATGAAG CCAAACAGAC GGCCGAAGAA

1801 ACCAAACAAA ACGTCGATGC CAAAGTAAAA GCTGCAGAAA CTGCAGCAGG

1851 CAAAGCCGAA GCTGCCGCTG GCACAGCTAA TACTGCAGCC GACAAGGCCG

1901 AAGCTGTCGC TGCAAAAGTT ACCGACATCA AAGCTGATAT CGCTACGAAC

1951 AAAGATAATA TTGCTAAAAA AGCAAACAGT GCCGACGTGT ACACCAGAGA

2001 AGAGTCTGAC AGCAAATTTG TCAGAATTGA TGGTCTGAAC GCTACTACCG

2051 AAAAATTGGA CACACGCTTG GCTTCTGCTG AAAAATCCAT TGCCGATCAC

2101 GATACTCGCC TGAACGGTTT GGATAAAACA GTGTCAGACC TGCGCAAAGA

2151 AACCCGCCAA GGCCTTGCAG AACAAGCCGC GCTCTCCGGT CTGTTCCAAC

2201 CTTACAACGT GGGTCGGTTC AATGTAACGG CTGCAGTCGG CGGCTACAAA

2251 TCCGAATCGG CAGTCGCCAT CGGTACCGGC TTCCGCTTTA CCGAAAACTT

2301 TGCCGCCAAA GCAGGCGTGG CAGTCGGCAC TTCGTCCGGT TCTTCCGCAG

2351 CCTACCATGT CGGCGTCAAT TACGAGTGGT AACTCGAG

1 MASPDVKSAD TLSKPAAPVV AEKETEVKED APQAGSQGQG APSTQGSQDM

51 AAVSAENTGN GGAATTDKPK NEDEGPQNDM PQNSAESANQ TGNNQPADSS

101 DSAPASNPAP ANGGSNFGRV DLANGVLIDG PSQNITLTHC KGDSCNGDNL

151 LDEEAPSKSE FENLNESERI EKYKKDGKSD KFTNLVATAV QANGTNKYVI

201 IYKDKSASSS SARFRSARS ERSLPAEHPL IPVNQADTLI VDGEAVSLTG

251 HSGNIFAPEG NYRYLTYGAE KLPGGSYALR VQGBPAKGEK LAGTAVNGE

301 VYJHFHTENGR PYPTRGRPAA KVDFGSKSVD GIIDSGDDLH MGTQKPKAAI

351 DGNGFKGTWT ENGGGDVSGR FYGPAGEEVA GKYSYRPTDA EKGGPGVFAG

401 KKEQDGSGGG GATNDDDVKK AATVAIAAAY NNGQEINGFK AGETIYDIDE

451 DGTITKKDAT AADVEADDFK GLGLKKVVTN LTKTVNENQK NVDAXVXAAE

501 SEIEKLTTKL ADTDAALADT DAALDAFTNA LNKLGENITT FAEETKTNZV

-continued

```
551  KIDEKLEAVA DTVDKHARAF NDIADSLDET NTKADEAVKT ANEAKQTAEE

601  TKQNVDAKVK AAETAAGKAE AAAGTANTAA DKAEAVAAKV TDIKADIATN

651  KDNIAXKANS ADVYTREESD SKFVRIDGLN ATTEKLDTRL ASAEKSIADH

701  DTRLNGLDKT VSDLRKETRQ GLAEQAALSG LPQPYNVGRP NVTAAVGGYK

751  SESAVAIGTG FRPTENFAAK AGVAVGTSSG SSAAYHVGVN YEW*
```

| | ELISA | Bactericidal |
|---|---|---|
| ΔG287-953-His | 3834 | 65536 |
| ΔG287-961-His | 108627 | 65536 |

The bactericidal efficacy (homologous strain) of antibodies raised against the hybrid proteins was compared with antibodies raised against simple mixtures of the component antigens (using 287-GST) for 919 and ORF46.1:

| | Mixture with 287 | Hybrid with ΔG287 |
|---|---|---|
| 919 | 32000 | 128000 |
| ORF46.1 | 128 | 16000 |

Data for bactericidal activity against heterologous MenB strains and against serotypes A and C were also obtained:

| | 919 | | ORF46.1 | |
|---|---|---|---|---|
| Strain | Mixture | Hybrid | Mixture | Hybrid |
| NGH38 | 1024 | 32000 | — | 16384 |
| MC58 | 512 | 8192 | — | 512 |
| BZ232 | 512 | 512 | — | — |
| MenA (F6124) | 512 | 32000 | — | 8192 |
| MenC (C11) | >2048 | >2048 | — | — |
| MenC (BZ133) | >4096 | 64000 | — | 8192 |

The hybrid proteins with ΔG287 at the N-terminus are therefore immunologically superior to simple mixtures, with ΔG287-ORF46.1 being particularly effective, even against heterologous strains. ΔG287-ORF46.1K may be expressed in pET-24b.

The same hybrid proteins were made using New Zealand strain 394/98 rather than 2996:

ΔG287NZ-919
(SEQ ID NOS: 94 and 95)

```
1    ATGGCTAGCC CCGATGTCAA GTCGGCGGAC ACGCTGTCAA AACCTGCCGC

51   CCCTGTTGTT TCTGAAAAAG AGACAGAGGC AAAGGAAGAT GCGCCACAGG

101  CAGGTTCTCA AGGACAGGGC GCGCCATCCG CACAAGGCGG TCAAGATATG

151  GCGGCGGTTT CGGAAGAAAA TACAGQCAAT GGCGGTGCGG CAGCAACGGA

201  CAAACCCAAA AATGAAGACG AGGGGGCGCA AAATGATATG CCGCAAAATG

251  CCGCCGATAC AGATAGTTTG ACACCGAATC ACACCCCGGC TTCGAATATG

301  CCGGCCGGAA ATATGGAAAA CCAAGCACCG GATGCCGGGG AATCGGAGCA

351  GCCGGCAAAC CAACCGGATA TGGCAAATAC GGCGGACGGA ATGCAGGGTG

401  ACGATCCGTC GGCAGGCGGG GAAAATGCCG GCAATACGGC TGCCCAAGGT

451  ACAAATCAAG CCGAAAACAA TCAAACCGCC GGTTCTCAAA ATCCTGCCTC

501  TTCAACCAAT CCTAGCGCCA CGAATAGCGG TGGTGATTTT GGAAAGACGA

551  ACGTGGGCAA TTCTGTTGTG ATTGACGGGC CGTCGCAAAA TATAACGTTG

601  ACCCACTGTA AAGGCGATTC TTGTAGTGGC AATAATTTCT TGGATGAAGA

651  AGTACAGCTA AAATCAGAAT TTGAAAAATT AAGTGATGCA GACAAAATAA

701  GTAATTACAA GAAAGATGGG AAGAATGACG GGAAGAATGA TAAATTTGTC

751  GGTTTGGTTG CCQATAGTGT GCAGATGAAG GGAATCAATC AATATATTAT

801  CTTTTATAAA CCTAAACCCA CTTCATTTGC GCGATTTAGG CGTTCTGCAC

851  GGTCGAGGCG GTCGCTTCCG GCCGATATGC CGCTGATTCC CGTCAATCAG

901  GCGGATACGC TGATTGTCGA TGGGGAAGCG GTCAGCCTGA CGGGGCATTC
```

-continued

```
951 CGGCAATATC TTCGCGCCCG AAGGGAATTA CCGGTATCTG ACTTACGGGG

1001 CGGAAAAATT GCCCGGCGGA TCGTATGCCC TCCGTGTTCA AGGCGAACCT

1051 TCAAAAGGCG AAATGCTCGC GGGCACGGCA GTGTACAACG GCGAAGTGCT

1101 GCATTTTCAT ACGGAAAACG GCCGTCCGTC CCCGTCCAGA GGCAGGTTTG

1151 CCGCAAAAGT CGATTTCGGC AGCAAATCTG TGGACGGCAT TATCGACAGC

1201 GGCGATGGTT TGCATATGGG TACGCAAAAA TTCAAAGCCG CCATCGATGG

1251 AAACGGCTTT AAGGGGACTT GGACGGAAAA TGGCGGCGGG GATGTTTCCG

1301 GAAAGTTTTA CGGCCCGGCC GGCGAGGAAG TGGCGGGAAA ATACAGCTAT

1351 CGCCCAACAG ATGCGGAAAA GGGCGGATTC GGCGTGTTTG CCGGCAAAAA

1401 AGAGCAGGAT GGATCCGGAG GAGGAGGATG CCAAAGCAAG AGCATCCAAA

1451 CCTTTCCGCA ACCCGACACA TCCGTCATCA ACGGCCCGGA CCGGCCGGTC

1501 GGCATCCCCG ACCCCGCCGG AACGACGGTC GGCGGCGGCG GGGCCGTCTA

1551 TACCGTTGTA CCGCACCTGT CCCTGCCCCA CTGGGCGGCG CAGGATTTCG

1601 CCAAAAGCCT GCAATCCTTC CGCCTCGGCT GCGCCAATTT GAAAAACCGC

1651 CAAGGCTGGC AGGATGTGTG CGCCCAAGCC TTTCAAkCCC CCGTCCATTC

1701 CTTTCAGGCA AAACAGTTTT TTGAACGCTA TTTCACGCCG TGGCAGGTTG

1751 CAGGCAACGG AAGCCTTGCC GGTACGGTTA CCGGCTATTA CGAGCCGGTG

1801 CTGAkGGGCG AGGACAGGCG GACGGCACAA GCCCGCTTCC CGATTTACGG

1851 TATTCCCGAC GATTTTATCT CCGTCCCCCT GCCTGCCGGT TTGCGGAGCG

1901 GAAAAGCCCT TGTCCGCATC AGGCAGACGG GAAAAAACAG CGGCACAATC

1951 GACAATACCG GCGGCACACA TACCGCCGAC CTCTCCCGAT TCCCCATCAC

2001 CGCGCGCACA ACGGCAATCA AAGCAAGGTT TGAAGGAAGC CGCTTCCTCC

2051 CCTACCACAC GCGCAACCAA ATCAACGGCG GCGCGCTTGA CGGCAAAGCC

2101 CCGATACTCG GTTACGCCGA AGACCCCGTC GAACTTTTTT TTATGCACAT

2151 CCAAGGCTCG GGCCGTCTGA AAACCCCGTC CGGCAAATAC ATCCGCATCG

2201 GCTATGCCGA CAAAAACGAA CATCCCTACG TTTCCATCGG ACGCTATATG

2251 GCGGACAAAG GCTACCTCAA GCTCGGGCAG ACCTCGATGC AGGGCATCAA

2301 AGCCTATATG CGGCAAAATC CGCAACGCCT CGCCGAAGTT TTGGGTCAAA

2351 ACCCCAGCTA TATCTTTTTC CGCGAGCTTG CCGGAAGCAG CAATGACGGT

2401 CCCGTCGGCG CACTGGGCAC GCCGTTGATG GGGGAATATG CCGGCGCAGT

2451 CGACCGGCAC TACATTACCT TGGGCGCGCC CTTATTTGTC GCCACCGCCC

2501 ATCCGGTTAC CCGCAAAGCC CTCAACCGCC TGATTATGGC GCAGGATACC

2551 GGCAGCGCGA TTAAAGGCGC GGTGCGCGTG GATTATTTTT GGGGATACGG

2601 CGACGAAGCC GGCGAACTTG CCGGCAAACA GAAAACCACG GGTTACGTCT

2651 GGCAGCTCCT ACCCAACGGT ATGAAGCCCG AATACCGCCC GTAAAAGCTT

1 MASPDVKSAD TLBKPAAPVV SEKETEAKED APQAGSQGQG APSAQGGQDH

51 AAVSEENTGN GGAAATDKPK NEDEGAQNDM PQNAADTDSL TPNHTPASNH

101 PAGNMENQAP DAGESEQPAN QPDMANTADG HQGDDPSAGG ENAGNTAAQG

151 TNQAENNQTA GSQNPASSTN PSATNSGGDF GRTNVGNSVV IDGPSQNITL

201 THCKGDSCSG NNPLDEEVQL KSEFEKLSDA DKISNYKKDG KNDGKNDKFV
```

-continued

251 GLVADSVQHK GINQYZIFYK PKPTSFARFR RSARSRRSLP AEHPLIPVNQ

301 ADTLIVDGEA VSLTGHSGNI FAPEGNYRYL TYGAEKLPGG SYALRVQGEP

351 SRGEHLAGTA VYNGEVLHFH TENGRPSPSR GRFAAKVDFG SKSVDGIIDS

401 GDGLHMGTQK FKAAIDGNGF KGTWTENGGG DVSGKFYGPA GEEVAGKYSY

451 RPTDAEKGGF GVFAGKKEQD GSGGGGCQSK SIQTFPQPDT SVINGPDRPV

501 GIPDPAGTTV GGGGAVYTVV PHLSLPHWAA QDFAKSLQSF RLGCANLKNR

551 QGWQDVCAQA FQTPVHSFQA KQFFERYFTP WQVAGNGSLA GTVTGYYEPV

601 LKGDDRRTAQ ARFPIYGIPD DPISVPLPAG LRSGKALVRZ RQTGKNSGTI

651 DNTGGTHTAD LSRFPITART TAIRGEPEGS EPLPYHTRNQ INGGALDGKA

701 PILGYAEDPV ELFFMHIQGS GRLKTPSGKY IRIGYADKNE HPYVSIGRYM

751 ADKGYLKLGQ TSMQGIKAYH RQNPQRLAEV LGQNPSYZFF RELAGSSNDG

801 PVGALGTPLM GEYAGAVDEH YITLGAPLFV ATAHPVTRKA LNRLIMAQDT

851 GSAIKGAVRV DYFWGYGDEA GELAGKQKTT GYVWQLLPNG HKPEYRP*

ΔG287NZ-953
(SEQ ID NOS: 96 and 97)

1 ATGGCTAGCC CCGATGTCAA GTCGGCGGAC ACGCTGTCAA AACCTGCCGC

51 CCCTGTTGTT TCTGAAAAAG AGACAGAGGC AAAGGAAGAT GCGCCACAGG

101 CAGGTTCTCA AGGACAGGGC GCGCCATCCG CACAAGGCGG TCAAGATATG

151 GCGGCGGTTT CGGAAGAAAA TACAGGCAAT GGCGGTGCGG CAGCAACGGA

201 CAAACCCAAA AATGAAGACG AGGGGGCGCA AAATGATATG CCGCAAAATG

251 CCGCCGATAC AGATAGTTTG ACACCGAATC ACACCCCGGC TTCGAATATG

301 CCGGCCGGAA ATATGGAAAA CCAAGCACCG GATGCCGGGG AATCGGAGCA

351 GCCGGCAAAC CAACCGGATA TGGCAAATAC GGCGGACGGA ATGCAGGGTG

401 ACGATCCGTC GGCAGGCGGG GAAAATGCCG GCAATACGGC TGCCCAAGGT

451 ACAAATCAAG CCGAAAACAA TCAAACCGCC GGTTCTCAAA ATCCTGCCTC

501 TTCAACCAAT CCTAGCGCCA CGAATAGCGG TGGTGATTTT GGAAGGACGA

551 ACGTGGGCAA TTCTGTTGTG ATTGACGGGC CGTCGCAAAA TATAACGTTG

601 ACCCACTGTA AAGGCGATTC TTGTAGTGGC AATAATTTCT TGGATGAAGA

651 AGTACAGCTA AAATCAGAAT TTGAAAAATT AAGTGATGCA GACAAAATAA

701 GTAATTACAA GAAAGATGGG AAGAATGACG GGAAGAATGA TAAATTTGTC

751 GGTTTGGTTG CCGATAGTGT GCAGATGAAG GGAATCAATC AATATATTAT

801 CTTTTATAAA CCTAAACCCA CTTCATTTGC GCGATTTADG CGTTCTGCAC

851 GGTCGAGGCG GTCGCTTCCG GCCGAGATGC CGCTGATTCC CGTCAATCAG

901 GCGGATACGC TGATTGTCGA TGGGGAAGCG GTCAGCCTGA CGGGGCATTC

951 CGGCAATATC TTCGCGCCCG AAGGGAAATA CCGGTATCTG ACTTACGGGG

1001 CGGAAAAATT GCCCGGCGGA TCGTATGCCC TCCGTGTTCA AGGCGAACCT

1051 TCAAAAGGCG AAATGCTCGC GGGCACGGCA GTGTACAACG GCGAAGTGCT

1101 GCATTTTCAT ACGGAAAACG GCCGTCCGTC CCCGTCCAGA GGCAGGTTTG

1151 CCGCAAAAGT CGATTTCGGC AGCAAATCTG TGGACGGCAT TATCGACAGC

1201 GGCGATGGTT TGCATATGGG TACGCAAAAA TTCAAAGCCG CCATCGATGG

1251 AAACGGCTTT AAGGGGACTT GGACGGAAAA TGGCGGCGGG GATGTTTCCG

-continued

```
1301 GAAAGTTTTA CGGCCCGGCC GGCGAGGAAG TGGCGGGAAA ATACAGCTAT
1351 CGCCCAACAG ATGCGGAAAA GGGCGGATTC GGCGTGTTTG CCGGCAAAAA
1401 AGAGCAGGAT GGATCCGGAG GAGGAGGAGC CACCTACAAA GTGGACGAAT
1451 ATCACGCCAA CGCCCGTTTC GCCATCGACC ATTTCAACAC CAGCACCAAC
1501 GTCGGCGGTT TTTACGGTCT GACCGGTTCC GTCGAGTTCG ACCAAGCAAA
1551 ACGCGACGGT AAAATCGAGA TCACCATCCC CGTTGCCAAC CTGCAAAGCG
1601 GTTCGCAACA CTTTACCGAC CACCTGAAAT CAGCCGACAT CTTCGATGCC
1651 GCCCAATATC CGGACATCCG CTTTGTTTCC ACCAAATTCA ACTTCAACGG
1701 CAAAAAACTG GTTTCCGTTG ACGGCAACCT GACCATOCAC GGCAAAACCG
1751 CCCCCGTCAA ACTCAAAGCC GAAAAATTCA ACTGCTACCA AAGCCCGATG
1801 GCGAAAACCG AAGTTTGCGG CGGCGACTTC AGCACCACCA TCGACCGCAC
1851 CAAATGGGGC GTGGACTACC TCGTTAACGT TGGTATGACC AAAAGCGTCC
1901 GCATCGACAT CCAAATCGAG GCAGCCAAAC AATAAAAGCT T

   1 MASPDVKSAD TLSKPAAPVV SEKBTEAKED APQAGSQGQG APSAQGGQDM
  51 AAVSEENTGN GGAAATDKPK NEDEGAQNDM PQNAADTDSL TPNHTPASNM
 101 PAGNMENQAP DAGESEQPAN QPDMANTADG MQGDDPSAGG ENAGNTAAQG
 151 TNQAENNQTA GSQNPASSTN PSATNSGGDF GRTNVGNSVV IDGPSQNITL
 201 THCKGDSCSG NNFLNEEVQL KSEPEKLSDA DKISNYKKDG KNDGKNDKFV
 251 GLVADSVQMK GINQYIIFYK PKPTSFARPR RSARSRRSLP AEMPLIPVNQ
 301 ADTLIVDGEA VSLTGHSGNI FAPEGNYRYL TYGAEKLPGG SYALRVQGEP
 351 SKGENLAGTA VYNGEVLHFH TENGRPSPSR GRPAAKVDPG SKSVDGIIDB
 401 GDGLHMGTQK PKAAIDGNGF KGTWTENGGG DVSGKFYGPA GEEVAGRYSY
 451 RPTDAEKGGF GVFAGKKEQD GSGGGGATYK VDEYHANARF AIDHFNTSTN
 501 VGGFYGLTGS VEFDQAKRDG KIDITIPVAN LQSGSQHFTD NLKSADIFDA
 551 AQYPDIRFVS TKFNFNGKKL VSVDGNLTMH GKTAPVKLKA EKFNCYQSPM
 601 AKTEVCGGDF STTIDRTKWG VDYLVNVGMT KSVRIDIQIE AAKQ*
```

ΔG2B7NZ-961
(SEQ ID NOS: 98 and 99)

```
   1 ATGGCTAGCC CCGATGTCAA GTCGGCGGAC ACGCTGTCAA AACCTGCCGC
  51 CCCTGTTGTT TCTGAAAAAG AGACAGAGGC AAAGGAAGAT GCGCCACAGG
 101 CAGGTTCTCA AGGACAGGGC GCGCCATCCG CACAAGGCGG TCAAGATATC
 151 GCGGCGGTTT CGGAAGAAAA TACAGGCAAT GGCGGTGCGG CAGCAACGGA
 201 CAAACCCAAA AATGAAGACG AGGGGGCGCA AAATGATATG CCGCAAAATG
 251 CCGCCGATAC AGATAGTTTG ACACCGAATC ACACCCCGGC TTCGAATATG
 301 CCGGCCGGAA ATATGGAAAA CCAAGCACCG GATGCCGGGG AATCGGAGCA
 351 GCCGGCAAAC CAACCGGATA TGGCAAATAC GGCGGACGGA ATGCAGGGTG
 401 ACGATCCGTC GGCAGGCGGG GAAAATGCCG GCAATACGGC TGCCCAAGGT
 451 ACAAATCAAG CCGAAAACAA TCAAACCGCC GGTTCTCAAA ATCCTGCCTC
 501 TTCAACCAAT CCTAGCGCCA CGAATAGCGG TGGTGATTTT GGAAGGACGA
 551 ACGTGGGCAA TTCTGTTGTG ATTGACGGGC CGTCGCAAAA TATAACGTTG
 601 ACCCAGTGTA AAGGCGATTC TTGTAGTGGC AATAATTTCT TGGATGAAGA
```

-continued

```
 651 AGTACAGCTA AAATCAGAAT TTGAAAAATT AAGTGATGCA GACAAAATAA
 701 GTAAATACAA GAAAGATGGG AAGAATGACG GGAAGAATGA TAAATTTGTC
 751 GGTTTGGTTG CCGATAGTGT GCAGATGAAG GGAATCAATC AATATATTAT
 801 CTTTTATAAA CCTAAACCCA CTTCATTTGC GCGATTTAGG CGTTCTGCAC
 851 GGTCGAGGCG GTCGCTTCCG GCCGAGATGC CGCTGATTCC CGTCAATCAG
 901 GCGGATACGC TGATTGTCGA TGGGGAAGCG GTCAGCCTGA CGGGGCATTC
 951 CGGCAATATC TTCGCGCCCG AAGGGAATTA CCGGTATCTG ACTTACGGGG
 001 CGGAAAAATT GCCCGGCGGA TCGTATGCCC TCCGTGTTCA AGGCGAACCT
1051 TCAAAAGGCG AAATGCTCGC GGGCACGGCA GTGTACAACG GCGAAGTGCT
1101 GCATTTTCAT ACGGAAAACG GCCGTCCGTC CCCGTCCAGA GGCAGGTTTG
1151 CCGCAAAAGT CGATTTCGGC AGCAAATCTG TGGACGGCAT TATCGACAGC
1201 GGCGATGGTT TGCATATGGG TACGCAAAAA TTCAAAGCCG CCATCGATGG
1251 AAACGGCTTT AAGGGGACTT GGACGGAAAA TGGCGGCGGG GATGTTTCCG
1301 GAAAGTTTTA CGGCCCGGCC GGCGAGGAAG TGGCGGGAAA ATACAGCTAT
1351 CGCCCAACAG ATGCGGAAAA GGGCGGATTC GGCGTGTTTG CCGGCAAAAA
1401 AGAGCAGGAT GGATCCGGAG GAGGAGGAGC CACAAACGAC GACGATGTTA
1451 AAAAAGCTGC CACTGTGGCC ATTGCTGCTG CCTACAACAA TGGCCAAGAA
1501 ATCAACGGTT TCAAAGCTGG AGAGACCATC TACGACATTG ATGAAGACGG
1551 CACAATTACC AAAAAAGACG CAACTGCAGC CGATGTTGAA GCCGACGACT
1601 TTAAAGGTCT GGGTCTGAAA AAAGTCGTGA CTAACCTGAC CAAAACCGTC
1651 AATGAAAACA AACAAAACGT CGATGCCAAA GTAAAAGCTG CAGAATCTGA
1701 AATAGAAAAG TTAACAAcCA AGTTAGCAGA CACTGATGCC GCTTTAGCAG
1751 ATACTGATGC CGCTCTGGAT GCAACCACCA ACGCCTTGAA TAAATTGGGA
1801 GAAAATATAA CGACATTTGC TGAAGAGACT AAGACAAATA TCGTAAAAAT
1851 TGATGAAAAA TTAGAAGCCG TGGCTGATAC CGTCGACAAG CATGCCGAAG
1901 CATTCAACGA TATCGCCGAT TCATTGGATG AAACCAACAC TAAGGCAGAC
1951 GAAGCCGTCA AAACCGCCAA TGAAGCCAAA CAGACGGCCG AAGAAACCAA
2001 ACAAAACGTC GATGCCAAAG TAAAAGCTGC AGAAACTGCA GCAGGCAAAG
2051 CCQAAGOTGC CGCTGGCACA GCTAATACTG CAGCCGACAA GGCCGAAGCT
2101 GTCGCTGCAA AAGTTACCGA CATCAAAGCT GATATCGCTA CGAACAAAGA
2151 TAATATTGCT AAAAAAGCAA ACAGTGCCGA CGTGTACACC AGAGAAGAGT
2201 CTGACAGCAA ATTTGTCAGA ATTGATGGTC TGAACGCTAC TACCGAAAAA
2251 TTGGACACAC GCTTGGCTTC TGCTGAAAAA TCCATTGCCG ATCACGATAC
2301 TCGCCTGAAC GGTTTGGATA AAACAGTGTC AQACCTGCGC AAAGAAACCC
2351 GCCAAGGCCT TGCAGAACAA GCCGCGCTCT CCGGTCTGTT CCAACCTTAC
2401 AACGTGGGTC GGTTCAATGT AACGGCTGCA GTCGGCGGCT ACAAATCCGA
2451 ATCGGCAGTC GCCATCGGTA CCGGCTTCCG CTTTACCGAA AACTTTGCCG
2501 CCAAAGCAGG CGTGGCAGTC GGCACTTCGT CCGGTTCTTC CGCAGCCTAC
2551 CATGTCGGCG TCAATTACGA GTGGTAAAAG CTT
   1 MASPDVKSAD TLSKPAAPVV SBKETEAXBD APQAGSQGQG APSAQGGQDM
```

-continued

```
51  AAVSEENTGN GGAAATDKPK NEDEGAQNDM PQNAADTDSL TPNHTPASNH

101 PAGNMENQAP DAGESEQPAN QPDMANTADG HQGDDPSAGG ENAGNTAAQG

151 TNQAENNQTA GSQNPASSTN PSATNSGGDF GRTNVGNSVV IDGPSQNITL

201 THCKGDSCSG NNFLDEEVQL KSEFEKLSDA DKISNYKKDG KNDGKNDKFV

251 GLVADSVQKM GINQYIIFYK PKPTSFARPR RSARSERSLP AEHPLIPVNQ

301 ADTLIVDGEA VSLTGHSGNI FAPEGNYRYL TYGAEKLPGG SYALRVQGEP

351 SKGEMLAGTA VYKGEVLHFH TBNGRPSPSR GEPAAKVDFG SKBVDGIIDS

401 GDGLHMGTQK FKAAIDGNGF RGTWTENGGG DVSGKFYGPA GERVAGRYSY

451 RPTDAEKGGF GVFAGKKEQD GSGGGGATND DDVKKAATVA IAAAYNNGQE

501 INGFKAGETI YDIDEDGTIT KKDATAADVE ADDFKGIGLK KVVTNLTKTV

551 NENKQNVDAK VRAAESEIEK LTTKLADTDA ALADTDAALD ATTNMJNKLG

601 ENITTFAEET KTNIVKIDEK LEAVADTVDK HAEAFNDIAD SLDETNTKAD

651 EAVKTANEAK QTAEETKQNV DAKVKAAETA AGKAEAAAGT ANTAADKAEA

701 VAAXVTDIKA DIATNKDNIA KKANSADVYT REESDSKFVR IDGLNATTEK

751 LDTELASAEK SIADHDTRLN GLDKTVSDLR KETRQGLAEQ AALSGLFQPY

801 NVGEFNVTAA VGGYKSESAV AIGTGFEPTE NFAAKAGVAV GTSSGSSAAY

851 HVGVNYEW*
```

ΔG983 and Hybrids

Bactericidal titres generated in response to ΔG983 (His-fusion) were measured against various strains, including the homologous 2996 strain:

| | 2996 | NGH38 | BZ133 |
|---|---|---|---|
| ΔG983 | 512 | 128 | 128 |

ΔG983 was also expressed as a hybrid, with ORF46.1 (SEQ ID NOS:100 and 101), 741 (SEQ ID NOS:102 and 103), 961 (SEQ ID NOS:104 and 105) or 961c (SEQ ID NOS:106 and 107) at its C-terminus:

ΔG983-ORF46.1

```
1   ATGACTTCTG CGCCCGACAA CAATGCAGGC GGTACCGGTA TCGGCAGCAA

51  CAGCAGAGCA ACAACAGCGA AATCAGCAGC AGTATCTTAC GCCGGTATCA

101 AGAACGAAAT GTGCAAAGAC AGAAGCATGC TCTGTGCCGG TCGGQATGAC

151 GTTGCGGTTA CAGACAGGGA TGCCAAAATC AATGCCCCCC CCCCGAATCT

201 GCATACCGGA GACTTTCCAA ACCCAAATGA CGCATACAAG AATTTGATCA

251 ACCTCAAACC TGCAATTGAA GCAGGCTATA CAGGACGCGG GGTAGAGGTA

301 GGTATCGTCG ACACAGGCGA ATCCGTCGGC AGCATATCCT TTCCCGAACT

351 GTATGGCAGA AAAGAACACG GCTATAACGA AAATTACAAA AACTATACGG

401 CGTATATGCG GAAGGAAGCG CCTGAAGAGG GAGGCGGTAA ACACATTGAA

451 GCTTCTTTCG ACGATGAGGC CGTTATAGAG ACTGAAGCAA ACCCGACGGA

501 TATCCGCCAC GTAAAAQAAA TCGGACACAT CGATTTGGTC TCCCATATTA

551 TTGGCGGGCG TTCCGTGGAC GGCAGACCTG CAGGCGGTAT TGCGCCCGAT

601 GCGACGCTAC ACATAATGAA TACGAATGAT GAAACCAAGA ACGAAATGAT

651 GGTTGCAGCC ATCCGCAATG CATGGGTCAA GCTGGGCGAA CGTGGCGTGC
```

-continued

701 GCATCGTCAA TAACAGTTTT GGAACAACAT CGAGGGCAGG CACTGCCGAC
751 CTTTTCCAAA TAGCCAATTC GGAGGAGCAG TACCGCCAAG CGTTGCTCGA
801 CTATTCCGGC GGTGATAAAA CAGACGAGGG TATCCGCCTG ATGCAACAGA
851 GCGATTACGG CAACCTGTCC TACCACATCC GTAATAAAAA CATGCTTTTC
901 ATCTTTTCGA CAGGCAATGA CGCACAAGCT CAGCCCAACA CATATGCCCT
951 ATTGCCATTT TATGAAAAAG ACGCTCAAAA AGGCATTATC ACAGTCGCAG
1001 GCGTAGACCG CAGTGGAGAA AAGTTCAAAC GGGAAATGTA TGGAGAACCG
1051 GGTACAGAAC CGCTTGAGTA TGGCTCCAAC CATTGCGGAA TTACTGCCAT
1101 GTGGTGCCTG TCGGCACCCT ATGAAGCAAG CGTCCGTTPC ACCCGTACAA
1151 ACCCGATTCA AATTGCCGGA ACATCCTTTT CCGCACCCAT CGTAACCGGC
1201 ACGGCGGCTC TGCTGCTGCA GAAATACCCG TGGATGAGCA ACGACAACCT
1251 GCGTACCACG TTGCTGACGA CGGCTCAGGA CATCGGTGCA GTCGGCGTGG
1301 ACAGCAAGTT CGGCTGGGGA CTGCTGGATG CGGGTAAGGC CATGAACGGA
1351 CCCGCGTCCT TTCCGTTCGG CGACTTTACC GCCGATACGA AAGGTACATC
1401 CGATATTGCC TACTCCTTCC GTAACGACAT TTCAGGCACG GGCGGCCTGA
1451 TCAAAAAAGG CGGCAGCCAA CTGCAACTGC ACGGCAACAA CACCTATACG
1501 GGCAAAACCA TTATCGAAGG CGGTTCGCTG GTGTTGTACG GCAACAACAA
1551 ATCGGATATG CGCGTCGAAA CCAAAGGTGC GCTGATTTAT AACGGGGCGG
1601 CATCCGGCGG CAGCCTGAAC AGCGACGGCA TTGTCTATCT GGCAGATACC
1651 GACCAATCCG GCGCAAACGA AACCGTACAC ATCAAAGGCA GTCTGCAGCT
1701 GGACGGCAAA GGTACGCTGT ACACACGTTT GGGCAAACTG CTGAAAGTGG
1751 ACGGTACGGC GATTATCGGC GGCAAGCTGT ACATGTCGGC ACGCGGCAAG
1801 GGGGCAGGCT ATCTCAACAG TACCGGACGA CGTGTTCCCT TCCTGAGTGC
1851 CGCCAAAATC GGGCAGGATT ATTCTTTCTT CACAAACATC GAAACCGACG
1901 GCGGCCTGCT GGCTTCCCTC GACAGCGTCG AAAAAACAGC GGGCAGTGAA
1951 GGCGACACGC TGTCCTATTA TGTCCGTCGC GGCAATGCGG CACGGACTGC
2001 TTCGGCAGCG GCACATTCCG CGCCCGCCGG TCTGAAACAC GCCGTAGAAC
2051 AGGGCGGCAG CAATCTGGAA AACCTGATGG TCGAACTGGA TGCCTCCGAA
2101 TCATCCGCAA CACCCGAGAC GGTTGAAACT GCGGCAGCCG ACCGCACAGA
2151 TATGCCGGGC ATCCGCCCCT ACGGCGCAAC TTTCCGCGCA GCGGCAGCCG
2201 TACAGCATGC GAATGCCGCC GACGGTGTAC GCATCTTCAA CAGTCTCGCC
2251 GCTACCGTCT ATGCCGACAG TACCGCCGCC CATGCCGATA TGCAGGGACG
2301 CCGCCTGAAA GCCGTATCGG ACGGGTTGGA CCACAACGGC ACGGGTCTGC
2351 GCGTCATCGC GCAAACCCAA CAGGACGGTG GAACGTGGGA ACAGGGCGGT
2401 GTTGAAGGCA AAATGCGCGG CAGTACCCAA ACCGTCGGCA TTGCCGCQAA
2451 AACCGGCGAA AATACGACAG CAGCCGCCAC ACTGGGCATG GGACGCAGCA
2501 CATGGAGCGA AAACAGTGCA AATGCAAAAA CCGACAGCAT TAGTCTGTTT
2551 GCAGGCATAC GGCACGATGC GGGCGATATC GGCTATCTCA AAGGCCTGTT
2601 CTCCTACGGA CGCTACAAAA ACAGCATCAG CCGCAGCACC GGTGCGGACG
2651 AACATGCGGA AGGCAGCGTC AACGGCACGC TGATGCAGCT GGGCGCACTG

-continued

2701 GGCGGTGTCA ACGTTCCGTT TGCCGCAACG GGAGATTTGA CGGTCGAAGG

2751 CGGTCTGCGC TACGACCTGC TCAAACAGGA TGCATTCGCC GAAAAAGGCA

2801 GTGCTTTGGG CTGGAGCGGC AACAGCCTCA CTGAAGGCAC GCTGGTCGGA

2851 CTCGCGGGTC TGAAGCTGTC GCAACCCTTG AGCGATAAAG CCGTCCTGTT

2901 TGCAACGGCG GGCGTGGAAC GCGACCTGAA CGGACGCGAC TACAGGGTAA

2951 CGGGCGGCTT TACCGGCGCG ACTGCAGCAA CCGGCAAGAC GGGGGCACGC

3001 AATATGCCGC ACACCCGTCT GGTTGCCGGC CTGGGCGCGG ATGTCGAATT

3051 CGGCAACGGC TGGAACGGCT TGGCACGTTA CAGCTAQGCC GGTTCCAAAC

3101 AGTACGGCAA CCACAGCGGA CGAGTCGGCG TAGGCTACCG GTTCCTCGAC

3151 GGTGGCGGAG GCACTGGATC CTCAGATTTG GCAAACGATT CTTTTATCCG

3201 GCAGGTTCTC GACCGTCAGC ATTTCGAACC CGACGGGAAA TACCACCTAT

3251 TCGGCAGCAG GGGGGAACTT GCCGAGCGCA GCGGCCATAT CGGATTGGGA

3301 AAAATACAAA GCCATCAGTT GGGCAACCTG ATGATTCAAC AGGCGGCCAT

3351 TAAAGGAAAT ATCGGCTACA TTGTCCGCTT TTCCGATCAC GGGCACGAAG

3401 TCCATTCCCC CTTCGACAAC CATGCCTCAC ATTCCGATTC TGATQAAGCC

3451 GGTAGTCCCG TTGACGGATT TAGCCTTTAC CGCATCCATT GGGACGGATA

3501 CGAACACCAT CCCGCCGACG GCTATGAQGG GCCACAGGGC GGCGGCTATC

3551 CCGCTCCCAA AGGCGCGAGG GATATATACA GCTACGACAT AAAAGGCGTT

3601 GCCCAAAATA TCCGCCTCAA CCTGACCGkC AACCGCAGCA CCGGACAACG

3651 GCTTGCCGAC CGTTTCCACA ATGCCGGTAG TATGCTGACG CAAGGAGTAG

3701 GCGACGGATT CAAACGCGCC ACCCGATACA GCCCCGAGCT GGACAGATCG

3751 GGCAATGCCG CCGAAGCCTT CAACGGCACT GCAGATATCG TTAAAAACAT

3801 CATCGGCGCG GCAGGAGAAA TTGTCGGCGC AGGCGATGCC GTGCAGGGCA

3851 TAAGCGAAGG CTCAAACATT GCTGTCATGC ACGGCTTGGG TCTGCTTTCC

3901 ACCGAAAACA AGATGGCGCG CATCAACGAT TTGGCAGATA TGGCGCAACT

3951 CAAAGACTAT GCCGCAGCAG CCATCCGCGA TTGGGCAGTC CAAAACCCCA

4001 ATGCCGCACA AGGCATAGAA GCCGTCAGCA ATATCTTTAT GGCAGCCATC

4051 CCCATCAAAG GGATTGQAGC TGTTCGGGGA AAATACGGCT TGGGCGGCAT

4101 CACGGCACAT CCTATCAAGC GGTCGCAGAT GGGCGCGATC GCATTGCCGA

4151 AAGGGAAATC CGCCGTCAGC GACAATTTTG CCGATGCGGC ATACGCCAAA

4201 TACCCGTCCC CTTACCATTC CCGAAATATC CGTTCAAACT TGGAGCAGCG

4251 TTACGGCAAA GAAAACATCA CCTCCTCAAC CGTGCCGCCG TCAAACGGCA

4301 AAAATGTCAA ACTGGCAGAC CAACGCCACC CGAAGACAGG CGTACCGTTT

4351 GACGGTAAAG GGTTTCCGAA TTTTGAGAAG CACGTGAAAT ATGATACGCT

4401 CGAGCACCAC CACCACCACC ACTGA

1 MTSAPDFNAG GTGIGSNSRA TTAKSAAVSY AGIKNEMCKD RSMLCAGRDD

51 VAVTDRDAKI NAPPPNLHTG DFPNPNDAYK NLINLKPAIE AGYTGRGVEV

101 GIVDTGESVG SISPPELYGR KEHGYNENYK NYTAYMRKEA PEDGGGKDIE

151 ASFDDEAVIE TRAKPTDIRH VKEIGHIDLV SHIIGGRSVD GRPAGGIAPD

201 ATLHIMNTND BTKNEMMVAA IENAWVKLGE RGVRIVNNSF GTTSRAGTAD

-continued

251 LFQIANSEBQ YRQALLDYSG GDKTDEGIEL MQQSDYGNLS YHIRNKNMLF

301 IFSTGNDAQA QPNTYALLPF YEKDAQKGII TVAGVDRSGE KFKREMYGEP

351 GTEPLBYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKANNG

451 PASFPFGDFT ADTKGTSDIA YSPRNDISGT GGLIKKGGSQ LQLHGNNTYT

501 GKTIIEGGSL VLYGNNKSDM RVBTKGMJIY NGAASGGSLN SDGIVYLADT

551 DQSGANETVH IKGSLQLDQK GTLYTRLGKL LKVDGTAIIG GKLYMSARGK

601 GAGYLNSTGR RVPFLSAAKI GQDYSFFTNI ETDGGLLASL DSVBKTAGSE

651 GDTLSYYVER GNAARTASAA AHSAPAGLKH AVEQGGSNLE NLMVELDASE

701 SSATPBTVET AAADRTDMPG IRPYGATFRA AAAVQHANAA DGVRIFNSLA

751 ATVYADSTAA HADMQGRRLK AVSDGLDHNG TGLRVIAQTQ QDGGTWEQGG

801 VEGKMRGSTQ TVGIAAKTGE NTTAAATLGM GRSTWSENSA NAKTDSISLF

851 AGIRHDAGDI GYLKGLFSYG RYKNSISRST GADEHAEGSV NGTLNQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEPGNG WNGLARYSYA GSKQYGNHSG RVGVGYRFLD

1051 GGGGTGSSDL ANDSFIRQVL DRQHFEPDGK YHLFGSRGEL AERSGHIGLG

1101 KIQSHQLGNL MIQQAAIKGN ZGYIVRPSDH GHEVHSPFDN HASHSDSDEA

1151 GSPVDGFSLY RIHWDGYEHH PADGYDGPQG GGYPAPKGAR DIYSYDIKGV

1201 AQNIELNLTD NRSTGQRLAD RPHNAGSMLT QGVGDGFKRA TRYSPELDRS

1251 GNAAEAFNGT ADIVKNIIGA AGBIVGAGDA VQGISEGSNI AVMHGLGLLS

1301 TENKMARIND LADMAQLKDY AAAAIRDWAV QNPNAAQGIE AVSNIFKAAI

1351 PIKGIGAVRG KYGLGGITAR PIKRSQMGAI ALPKGKSAVS DNFADAAYAK

1401 YPSPYHSRNI RSNLEQRYGK ENITSSTVPP SNGDKVKLAD QRHPKTGVPF

1451 DGKGFPNFEK HVKYDTLEHH HHHH*

ΔG983-741

1 ATGACTTCTG CGCCCGACTT CAATGCAGGC GGTACCGGTA TCGGCAGCAA

51 CAGCAGACCA ACAACAGCGA AATCAGCAGC AGTATCTTAC GCCGGTATCA

101 AGAACGAAAT GTGCAAAGkC AGAAGCATGC TCTGTGCCGG TCGGGATGAC

151 GTTGCGGTTA CAGACAGGGA TGCCAAAATC AATGCCCCCC CCCCGAATCT

201 GCATACCGGA GACTTTCCAA ACCCAAATGA CGCATACAAG AATTTGATCA

251 ACCTCAAACC TGCAATTGAA GCAGGCTATA CAGGACGCGG GGTAGAGGTA

301 GGTATCGTCG ACACAGGCGA ATCCGTCGGC AGCATATCCT TTCCCGAACT

351 GTATGGCAGA AAAGAACACG GCTATAACQA AAATTACAAA AACTATACGG

401 CGTATATGCG GAAGGAAGCG CCTGAAGACG GAGGCGGTAA AGACATTGAA

451 GCTTCTTTCG ACGATGAGGC CGTTATAGAG ACTGAAGCAA AGCCGACGGA

501 TATCCGCCAC GTAAAAGAAA TCGGACACAT CGATTTGGTC TCCCATATTA

551 TTGGCGGGCG TTCCGTGGAC GGCAGACCTG CAGGCGGTAT TGCGCCCGAT

601 GCGACGCTAC ACATAATGAA TACGAATGAT GAAACCAAGA ACGAAATGAT

651 GGTTGCAGCC ATCCGCAATG CATGGGTCAA GCTGGGCGAA CGTGGCGTGC

-continued

```
701   GCATCGTCAA TAACAGTTTT GGAACAACAT CGAGGGCAGG CACTGCCGAC
751   CTTTTCCAAA TAGCCAATTC GGAGGAGCAG TACCGCCAAG CGTTGCTCGA
801   CTATTCCGGC GGTGATAAAA CAGACGAGGG TATCCGCCTG ATGCAkCAGA
851   GCGATTACGQ CAACCTGTCC TACCACATCC GTAATAAAAA CATGCTTTTC
901   ATCTTTTCGA CAGGCAATQA CGCACAAGCT CAGCCCAAQA CATATGCCCT
951   ATTGCCATTT TATGAAAAAG ACGCTCAAAA AGGCATTATC ACAGTCGCAG
1001  GCGTAGACCG CAGTGGAGAA AAGTTCAAAC GGGAAATGTA TGGAGAACCG
1051  GGTACAGAAC CGCTTGAGTA TGGCTCCAAC CATTGCGGAA TTACTGCCAT
1101  GTGGTGCCTG TCGGCACCCT ATGAAGCAAG CGTCCGTTTC ACCCGTACAA
1151  ACCCGATTCA AATTGCCGGA ACATCCTTTT CCGCACCCAT CGTAACCGGC
1201  ACGGCGGCTC TGCTGCTGCA GAAATACCCG TGGATGAGCA ACGACAACCT
1251  GCGTACCACG TTGCTGACGA CGGCTCAGGA CATCGGTGCA GTCGGCGTGG
1301  ACAGCAAGTT CGGCTGGGGA CTGCTGGATG CGGGTAAGGC CATGAACGGA
1351  CCCGCGTCCT TTCCGTTCGG CGACTTTACC GCCGATACGA AAGGTACATC
1401  CGATATTGCC TACTCCTTCC GTAACGACAT TTCAGGCACG GGCGGCCTGA
1451  TCAAAAAAGG CGGCAGCCAA CTGCAAATGC ACGGCAACAT CACCTATACG
1501  GGCAAAACCA TTATCGAAGG CGGTTCGCTG GTGTTGTACG GCAACAACAA
1551  ATCGGATATG CGCGTCGAAA CCAAAGGTGC GCTGATTTAT AACGGGGCGG
1601  CATCCGGCGG CAGCCTGAAC AGCGACGGCA TTGTCTATCT GGCAGATACC
1651  GACCAATCCG GCGCAAACGA AACCGTACAC ATCAAAGGCA GTCTGCAGCT
1701  GGACGGCAAA GGTACGCTGT ACACACGTTT GGGCAAACTG CTGAAAGTGG
1751  ACGGTACGGC GATTATCGGC GGCAAGCTGT ACATGTCGGC ACGCGGCAAG
1801  GGGGCAGGCT ATCTCAACAG TACCGGACGA CGTGTTCCCT TCCTGAGTGC
1851  CGCCAAAATC GGGCAGGATT ATTCTTTCTT CACAAACATC GAAACCGACG
1901  GCGGCCTGCT GGCTTCCCTC GACAGCGTCG AAAAAACAGC GGGCAGTGAA
1951  GGCGACACGC TGTCCTATTA TGTCCGTCGC GGCAATGCGG CACGGACTGC
2001  TTCGGCAGCG GCACATTCCG OGCCCGCCGG TCTGAAACAC GCCGTAGAAC
2051  AGGGCGGCAG CAATCTGGAA AACCTGATGG ICGAACTGGA TGCCTCCGAA
2101  TCATCCGCAA CACCCGAGAC GGTTGAAACT GCGGCAGCCG ACCGCACAGA
2151  TATGCCGGGC ATCCGCCCCT ACGGCGCAAC TTTCCGCGCA GCGGCAGCCG
2201  TACAGCATGC GAATGCCGCC GACGGTGTAC GCATCTTCAA CAGTCTCGCC
2251  GCTACCGTCT ATGCCGACAG TACCGCCGCC CATGCCGATA TGCAGGGACG
2301  CCGCCTGAAA GCCGTATCGG ACGGGTTGGA CCACAACGGC ACGGGTCTGC
2351  GCGTCATCGC GCAAACCCAA CAGGACGGTG GAACGTGGGA ACAGGGCGGT
2401  GTTGAAGGCA AAATGCGCGG CAGTACCCAA ACCGTCGGCA TTGCCGCGAA
2451  AACCGGCGAA AATACGACAG CAGCCGCCAC ACTGGGCATG GGACGCAGCA
2501  CATGGAGCGA AAACAGTGCA AATGCAAAAA CCGACAGCAT TAGTCTGTTT
2551  GCAGGCATAC GGCACGATGC GGGCGATATC GGCTATCTCA AAGGCCTGTT
2601  CTCCTACGGA CGCTACAAAA ACAGCATCAG CCGCAGCACC GGTGCGGACG
2651  AACATGCGGA AGGCAGCGTC AACGGCACGC TGATGCAGCT GGGCGCACTG
```

-continued

```
2701   GGCGGTGTCA ACGTTCCGTT TGCCGCAACG GGAGATTTGA CGGTCGAAGG
2751   CGGTGTGCGC TACGACCTGC TCAAACAGGA TGCATTCGCC GAAAAAGGCA
2801   GTGCTTTGGG CTGGAGCGGC AACAGCCTCA CTGAAGGCAC GCTGGTCGGA
2851   CTCGCGGGTC TGAAGCTGTC GCAACCCTTG AGCGATAAAG CCGTCCTGTT
2901   TGCAACGGCG GOCGTGGAAC GCGACCTGAT CGGACGCGAC TACACGGTAA
2951   CGGGCGGCTT TACCGGCGCG ACTGCAGCAA CCGGCAAGAC GGGGGCACGC
3001   AATATGCCGC ACACCCGTCT GGTTGCCGGC CTGGGCGCGG ATGTCGAATT
3051   CGGCAACGGC TGGAACGGCT TGGCACGTTA CAGCTACGCC GGTTCCAAAC
3101   AGTACGGCAA CCACAGCGGA CGAGTCGGCG TAGGCTACCG GTTCCTCGA
3151   GGATCCGGAG GGGGTGGTGT CGCCGCCGAC ATCGGTGCGG GGCTTGCCGA
3201   TGCACTAACC GCACCGCTCG ACCATAAAGA CAAAGGTTTG CAGTCTTTGA
3251   CGCTGGATCA GTCCGTCAGG AAAAACGAGA AACTGAAGCT GGCGGCACAA
3301   GGTGCGGAAA AAACTTATGG AAACGGTGAC AGCCTCAATA CGGGCAAATT
3351   GAAGAACGAC AAGGTCAGCC GTTTCGACTT TATCCGCCAA ATCGAAGTGG
3401   ACGGGCAGCT CATTACCTTG GAGAGTGGAG AGTTCCAAGT ATACAAACAA
3451   AGCCATTCCG CCTTAACCGC CTTTCAGACC GAGCAAATAC AAGATTCGGA
3501   GCATTCCGGG AAGATGGTTG CGAAACGCCA GTTCAGAATC GGCGACATAG
3551   CGGGCGAACA TACATCTTTT GACAAGCTTC CCGAAGGCGG CAGGGCGACA
3601   TATCGCGGGA CGGCGTTCGG TTCAGACGAT GCCGGCGGAA AACTGACCTA
3651   CACCATAGAT TTCGCCGCCA AGCAGGGAAA CGGCAAAATC GAACATTTGA
3701   AATCGCCAGA ACTCAATGTC GACCTGGCCG CCGCCGATAT CAAGCCGGAT
3751   GGAAAACGCC ATGCCGTCAT CAGCGGTTCC GTCCTTTACA ACCAAGCCGA
3801   GAAAGGCAGT TACTCCCTCG GTATCTTTGG CGGAAAAGCC CAGGAAGTTG
3851   CCGGCAGCGC GGAAGTGAAA ACCGTAAACG GCATACGCCA TATCGGCCTT
3901   GCCGCCAAGC AACTCGAGCA CCACCACCAC CACCACTGA

1      MTSAPDFNAG GTGIGSNBRA TTAKSAAVSY AGIKNEHCKD RSMLCAGRDD
51     VAVTDRDAKI NAPPPNLHTG DFPNPNDAYK NLINLKPAIE AGYTGRGVZV
101    GXVDTGBSVQ SISFPELYGR KEHGYNENYK NYTAYMRKEA PBDGGGKDIB
151    ASFDDEAVIE TEAKPTDIRH VKEIGHIDLV SHIIGGRSVD GRPAGGIAPD
201    ATLHIMNTND ETKNEMMVAA IRNAWVKLGB RGVRIVNNSF GTTSRAGTAD
251    LFQLANSEBQ YRQALLDYSG GDKTDEGIRL MQQSDYGNLS YHIRNKNMLF
301    IFSTGNDAQA QPNTYALLPF YBKDAQKGII TVAGVDRSGE KFKRENYGEP
351    GTEPLEYGSN HCGITAMWCL SAPYEASVRP TRTNPIQIAG TSFSAPIVTG
401    TAALLLQKYP WMSNDNLRTT LLTTAQDIGA VGVDSKFGWG LLDAGKAMNG
451    PASFPFGDFT ADTKGTSDIA YSFENDISGT GGLIKKGGSQ LQLHGNNTYT
501    GKTIIEGGSL VLYGNNKSDN RVETKGALIY NQAASGGSLN SDGIVYLADT
551    DQSGANETVH IKGSLQLDGK GTLYTRLGKL LKVDGTAIIG GKLYMSARGK
601    GAGYLNSTGR RVPPLBAAKI GQDYBPFTNI HTDGGLLASL DSVEKTAGSE
651    GDTLSYYVRR GNAARTASAA AHSAPAGLKH AVEQGGSNLE NLMVELDABE
701    SSATPETVBT AAADRTDMPG IRPYGATFRA AAAVQHANAA DGVRIFNSLA
```

-continued

751 ATVYADSTAA HADMQGRRLK AVSDGLDHNG TGLRVIAQTQ QDGGTWBQGG

801 VHGKMRGSTQ TVGIAAKTGE NTTAAATLGM GRSTWBENSA NAKTDSISLP

851 AGIRHDAGDI GYLKGLFBYG RYKNSISEST GADBHAEGSV NGTLMQLGAL

901 GGVNVPFAAT GDLTVEGGLR YDLLKQDAFA HKGSALQWSG NSLTEQTLVG

951 LAGLKLSQPL SDKAVLFATA GVERDLNGRD YTVTGGFTGA TAATGKTGAR

1001 NHPHTRLVAG LGADVHFGNG WNGLARYSYA GSKQYGNHSG RVGVGYRFLE

1051 GSGGGGVAAD IGAGLADALT APLDHKDKGL QSLTLDQSVR KNEKLKLAAQ

1101 GAEKTYGNGD SLNTGKLKND KVSPPDFIRQ IEVDGQLITL ESGEFQVYXQ

1151 SHSALTAPQT EQIQDSEHSG KMVAKRQFRI GDIAGEHTFP DKLPEGGRAT

1201 YRGTAFGSDD AGGKLTYTID FAAKQGNGKI EHLKSPELNV DLAAADIKPD

1251 GKPHAVISGS VLYNQAEKGS YSLGIFOGKA QEVAGSAEVK TVNGIEHIGL

1301 AAKQLEHHHH HH*

ΔG983-961

1 ATGACTTCTG CGCCCGACTT CAATGCAGGC GGTACCGGTA TCGGCAGCAA

51 CAGCAGAGCA ACAACAGCGA AATCAGCAGC AGTATCTTAC GCCGGTATCA

101 AGAACGAAAT GTGCAAAGAC AGAAGCATGC TCTGTGCCGG TCGGGATGAC

151 GTTGCGGTTA CAGACAGGGA TGCCAAAATC AATGCCCCCC CCCCGAATCT

201 GCATACCGGA GACTTTCCAA ACCCAAATGA CGCATACAAG AATTTGATCA

251 ACCTCAAACC TGCAATTGAA GCAGGCTATA CAGGAQGCGG GGTAGAGGTA

301 GGTATCGTCG ACACAGGCGA ATCCGTCGGC AGCATATCCT TTCCCGAACT

351 GTATGGCAGA AAAGAACACG GCTATAACGA AAATTACAAA AACTATACGG

401 CGTATATGCG GAAGGAAGCG CCTGAAGACG GAGGCGGTAA AGACATTGAA

451 GCTTCTTTCG ACGATGAGGC CGTTATAGAG ACTGAAGCAA AGCCGACGGA

501 TATCCGCCAC GTAAAAGAAA TCGGACACAT CGATTTGGTC TCCCATATTA

551 TTGGCGGGCG TTCCGTGGAC GGCAGACCTG CAGGCGGTAT TGCGCCCGAT

601 GCGACGCTAC ACATAATGAA TACGAATGAT GAAACCAAGA ACGAAATGAT

651 GGTTGCAGCC ATCCGCAATG CATGGGTCAA GCTGGGCGAA CGTGGCGTGC

701 GCATCGTCAA TAACAGTTTT GGAACAACAT CGAGGGCAGG CACTGCCGAC

751 CTTTTCCAAA TAGCCAATTC GGAGGAGCAG TACCGCCAAG CGTTGCTCGA

801 CTATTCCGGC GGTGATAAAA CAGACGAGGC TATCCGCCTG ATGCAACAGA

851 GCGATTACGG CAACCTGTCC TACCACATCC GTAATAAAAA CATGCTTTTC

901 ATCTTTTCGA CAGGCAATGA CGCACAAGCT CAGCCCAACA CATATGCCCT

951 ATTGCCATTT TATGAAAAAG ACGCTCAAAA AGGCATTATC ACAQTCGCAG

1001 GCGTAQACCG CAGTGGAGAA AAGTTCAAAC GGGAAATGTA TGGAGAACCG

1051 GGTACAGAAC CGCTTGAGTA TGGCTCCAAC CATTGCGGAA TTACTGCCAT

1101 GTGGTGCCTG TCGGCACCCT ATGAAGCAAG CGTCCGTTTC ACCCGTACAA

1151 ACCCGATTCA AATTGCCGGA ACATCCTTTT CCGCACCCAT CGTAACCGGC

1201 ACGGCGGCTC TGCTGCTGCA GAAATAGCCG TGGATGAGCA ACGACAACCT

1251 GCGTACCACG TTGCTGACGA CGGCTCAGGA CATCGGTGCA GTCGGCGTGG

1301 ACAGCAAGTT CGGCTGGGGA CTGCTGGATG CGGGTAAGGC CATGAACGGA

1351 CCCGCGTCCT TTCCGTTCGG CGACTTTACC GCCGATACGA AAGGTACATC

-continued

```
1401  CGATATTGCC TACTCCTTCC GTAACGACAT TTCAGGCACG GGCGGCCTGA
1451  TCAAAAAAGG CGGCAGCCAA CTGCAACTGC ACGGCAACAA CACCTATACG
1501  GGCAAAACCA TTATCGAAGG CGGTTCGCTG GTGTTGTACG GCAACAACAA
1551  ATCGGATATG CGCGTCGAAA CCAAAGGTGC GCTGATTTAT AACGGGGCGG
1601  CATCCGGCGG CAGCCTGAAC AGCGACGGCA TTGTCTATCT GGCAGATACC
1651  GACCAATCCG GCGCAAACGA AACCGTACAC ATCAAAGGCA GTCTGCAGCT
1701  GGACGGCAAA GGTACGCTGT ACACACGTTT GGGCAAAGTG CTGAAAGTGG
1751  ACGGTACGGC GATTATCGGC GGCAAGCTGT ACATGTCGGC ACGCGGCAAG
1801  GGGGCAGGCT ATCTCAACAG TACCGGACGA CGTGTTCCCT TCCTGAGTGC
1851  CGCCAAAATC GGGCAGGATT ATTCTTTCTT CACAAACATC GAAACCGACG
1901  GCGGCCTGCT GGCTTCCCTC GACAGCGTCG AAAAAACAGC GGGCAGTGAA
1951  GGCGACACGC TGTCCTATTA TGTCCGTCGC GGCAATGCGG CACGGACTGC
2001  TTCGGCAGCG GCACATTCCG CGCCCGCCGG TCTGAAACAC GCCGTAGAAC
2051  AGGGCGGCAG CAATCTGGAA AACCTGATGG TCGAACTGGA TGCCTCCGAA
2101  TCATCCGCAA CACCCGAGAC GGTTGAAACT GCGGCAGCCG ACCGCACAGA
2151  TATGCCGGGC ATCCGCCCCT ACGGCGCAAC TTTCCGCGCA GCGGCAGCCG
2201  TACAGCATGC GAATGCCGCC GACGGTGTAC GCATCTTCAA CAGTCTCGCC
2251  GCTACCGTCT ATGCCGACAG TACCGCCGCC CATGCCGATA TGCAGGGAGG
2301  CCGCCTGAAA GCCGTATCGG ACGGGTTGGA CCACAACGGC ACGGGTCTGC
2351  GCGTCATCGC GCAAACCCAA CAGGACGGTG GAACGTGGGA ACAGCGCGGT
2401  GTTGAAGCCA AAATGCGCGG CAGTACCCAA ACCGTCGGCA TTGCCGCGAA
2451  AACCGGCGAA AATACGACAG CAGCCGCCAC ACTGGGCATG GGACGCAGCA
2501  CATGGAGCGA AAACAGTGCA AATGCAAAAA CCGACAGCAT TAGTCTGTTT
2551  GCAGGCATAC GGCACGATGC GGGCGATATC GGCTATCTCA AAGGCCTGTT
2601  CTCCTACGGA CGCTACAAAA ACAGCATCAG CCGCAGCACC GGTGCGGACG
2651  AACATGCGGA AGGCAGCGTC AACGGCACGC TGATGCAGCT GGGCGCACTG
2701  GGCGGTGTCA ACGTTCCGTT TGCCGCAACG GGAGATTTGA CGGTCGAAGG
2751  CGGTCTGCGC TACGACCTGC TCAAACADGA TGCATTCGCC GAAAAAGGCA
2801  GTGCTTTGGG CTGGAGCGGC AACAGCCTCA CTGAAGGCAC GCTGGTCGGA
2851  CTCGCGGGTC TGAAGCTGTC GCAACCCTTG AGCGATAAAG CCGTCCTGTT
2901  TGCAACGGCG GGCGTGGAAC GCGACCTGAA CGGACGCGAC TACACGGTAA
2951  CGGGCGGCTT TACCGGCGCG ACTGCAGCAA CCGGCAAGAC GGGGGCACGC
3001  AATATGCCGC ACACCCGTCT GGTTGCCGGC CTGGGCGCGG ATGTCGAATT
3051  CGGCAACGGC TGGAACGGCT TGGCACGTTA CAGCTACGCC GGTTCCAAAC
3101  AGTACGGCAA CCACAGCGGA CGAGTCGGCG TAGGCTACCG GTTCCTCGAG
3151  GGTGGCGGAG GCACTGGATC CGCCACAAAC GACGACGATG TTAAAAAAGC
3201  TGCCACTGTG GCCATTGCTG CTGCCTACAA CAATGGCCAA GAAATCAACG
3251  GTTTCAAAGC TGGAGAGACC ATCTACGACA TTGATGAAGA CGGCACAATT
3301  ACCAAAAAAG ACGCAACTGC AGCCGATGTT GAAGCCGACG ACTTTAAAGG
3351  TCTGGGTCTG AAAAAAGTCG TGACTAACCT GACCAAAACC GTCAATGAAA
```

-continued

```
3401 ACAAACAAAA CGTCGATGCC AAAGTAAAAG CTGCAGAATC TGAAATAGAA
3451 AAGTTAACAA CCAAGTTAGC AGACACTGAT GCCGCTTTAG CAGATACTGA
3501 TGCCGCTCTG QATGCAACCA CCAACGCCTT GAATAAATTG GGAGAAAATA
3551 TAACGACATT TGCTGAAGAG ACTAAGACAA ATATCGTAAA AATTGATGAA
3601 AAATTAGAAG CCGTGGCTGA TACCGTCGAC AAGCATGCCG AAGCATTCAA
3651 CGATATCGCC GATTCATTGG ATGAAACCAA CACTAAGGCA GACGAAGCCG
3701 TCAAAACCGC CAATGAAGCC AAACAGACGG CCGAAGAAAC CAAACAAAAC
3751 GTCGATGCCA AAGTAAAAGC TGCAGAAACT GCAGCAGGCA AAGCCGAAGC
3801 TGCCGCTGGC ACAGCTAATA CTGCAGCCGA CAAGGCCGAA GCTGTCGCTG
3851 CAAAAGTTAC CGACATCAAA GCTGATATCG CTACGAACAA AGATAATATT
3901 GCTAAAAAAG CAAACAGTGC CGACGTGTAC ACCAGAGAAG AGTCTGACAG
3951 CAAATTTGTC AGAATTGATG GTCTGAACGC TACTACCGAA AAATTGGACA
4001 CACGCTTGGC TTCTGCTGAA AAATCCATTG CCGATCACGA TACTCGCCTG
4051 AACGGTTTGG ATAAAACAGT GTCAGACCTG CGCAAAGAAA CCCGCCAAGG
4101 CCTTGCAGAA CAAGCCGCGC TCTCCGGTCT GTTCCAACCT TACAACGTGG
4151 GTCGGTTCAA TGTAACGGCT GCAGTCGGCG GCTACAAATC CGAATCGGCA
4201 GTCGCCATCG GTACCGGCTT CCGCTTTACC GAAAACTTTG CCGCCAAAGC
4251 AGGCGTGGCA GTCGGCACTT CGTCCGGTTC TTCCGCAGCC TACCATGTCG
4301 GCGTCAATTA CGAGTGGCTC GAGCACCACC ACCACCACCA CTGA

   1 MTSAPDFNAG GTGIGSNSRA TTAKSAAVSY AGIKNRMCKD RSMLCAGRDD
  51 VAVTDRDAKI NAPPPNLHTG DFPNPNDAYK NLINLKPAIE AGYTGRGVEV
 101 GIVDTGBSVG SISFPELYGR KEHGYNENYK NYTAYNRKEA PEDGGGKDIE
 151 ASFDDEAVIE TEAKPTDIEH VKEIGHIDLV SHIIGGRSVD GRPAGGIAPD
 201 ATLHIMNTND ETKNEMMVAA IRNAWVKLGE RGVRIVNNSF GTTSRAGTAD
 251 LFQIANSEEQ YRQALLDYSG GDKTDEGIRL MQQSDYGNLS YHIRNKNMLF
 301 IFSTGNDAQA QPNTYALLPF YRKDAQRGII TVAGVDRSGE KFKREHYGEP
 351 GTEPLEYGSN HCGITAMWCL BAPYEASVRF TRTNPIQIAG TSFSAPIVTG
 401 TAALLLQKYP WMSNDNLRTT LLTTAQDIGA VGVDSKFGWG LLDAGKAMNG
 451 PASFPFGDFT ADTKGTSDIA YSFRIWISGT GGLIKKGGSQ LQLHGNNTYT
 501 GKTIIEGGSL VLYGNNKBDM RVETKGMJZY NGAABGGSLN SDGIVYLADT
 551 DQSGANETVH IKGSLQLDGK GTLYTRLGKL LRVDGTAIIG GKLYHSARGK
 601 GAGYLNSTGR RVPFLSAAKI GQDYSFFTNI BTDGGLLABL DSVEKTAGSE
 651 GDTLSYYVRR GNAARTASAA AHSAPAGLKH AVRQGGSNLE NLMVELDASE
 701 SSATPBTVET AAADRTDMPG IRPYGATFRA AAAVQHANAA DGVRIPNSLA
 751 ATVYADSTAA HADMQGRRLK AVSDGLDHNG TGLRVZAQTQ QDGGTWEQGQ
 801 VEGKMRGSTQ TVGIAAKTGE NTTAAATLGM GRBTWSENSA NAKTDBISLF
 851 AGIRHDAGDI GYLKGLFBYG RYKNSISRST GADEHAEGSV NGTLMQLGAL
 901 GGVNVPFAAT GDLTVRGGLR YDLLKQDAPA EKGSALGWSG NSLTEGTLVG
 951 LAGLKLSQPL SDKAVLFATA GVERDLNGRD YTVTGGFTGA TAATGKTGAR
1001 NMPHTRLVAG LGADVEFGNG WNGLARYSYA GSKQYGNHSG RVGVGYRPLB
```

-continued

1051 GGGGTGSATN DDDVKKAATV AIAAAYNNGQ EINGFKAGET IYDIDEDGTI

1101 TKKDATAADV EADDFKGLGL KKVVTNLTKT VNENKQNVDA KVKAAESBIB

1151 KLTTKLADTD AALADTDAAL DATTNALNKL GENITTFAEE TKTNIVKIDE

1201 KLEAVADTVD KHAEAPNDIA DSLDETNTKA DEAVKTAUEA KQTABETKQN

1251 VDAKVKAABT AAGKAEAAAG TANTAADKAE AVAAKVTDIK ADIATNKDNI

1301 AKKANSADVY TREESDSKFV RIDGLNATTE KLDTRLASAE KSIADHDTRL

1351 NGLDKTVSDL RKETRQGLAE QAALSGLFQP YNVGRFNVTA AVGGYKSESA

1401 VAIGTGFRFT ENFAAKAGVA VGTSSGSSAA YHVGVNYEWL EHHHHHH*

ΔG983-961c

1 ATGACTTCTG CGCCCGACTT CAATGCAGGC GGTACCGGTA TCGGCAGCAA

51 CAGCAGAGCA ACAACAGCGA AATCAGCAGC AGTATCTTAC GCCGGTATCA

101 AGAACGAAAT GTGCAAAGAC AGAAGCATGC TCTGTGCCGG TCGGGATGAC

151 GTTGCGGTTA CAGACAGQGA TGCCAAAATC AATGCCCCCC CCCCGAATCT

201 GGATACCOGA GACTTTCCAA ACCCAAATGA CGCATACAAG AATTTGATCA

251 ACCTCAAACC TGCAATTGAA GCAGGCTATA CAGGACGCGG GGTAGAGGTA

301 GGTATCGTCG ACACAGGCGA ATCCGTCGGC AGCATATCCT TTCCCGAACT

351 GTATGGCAGA AAAGAACACG GCTATAACGA AAATTACAAA AACTATACGG

401 CGTATATGCG GAAGGAAGCG CCTGAAGACG GAGGCGGTAA AGACATTGAA

451 GCTTCTTTCG ACGATGAGGC CGTTATAGAG ACTGAAGCAA AGCCGACGGA

501 TATCCGCCAC GTAAAAGAAA TCGGACACAT CGATTTGGTC TCCCATATTA

551 TTGGCGGGCG TTCCGTGGAC GGCAGACCTG CAGGCGGTAT TGCGCCCGAT

601 GCGACGCTAC ACATAATGAA TACGAATGAT GAAACCAAGA ACGAAATGAT

651 GGTTGCAGCC ATCCGCAATG CATGGGTCAA GCTGGGCGAA CGTGGCGTGC

701 GCATCGTCAA TAACAGTTTT GGAACAACAT CGAGGGCAGG CACTGCCGAC

751 CTTTTCCAAA TAGCCAATTC GGAGGAGCAG TACCGCCAAG CGTTGCTCGA

801 CTATTCCGGC GGTGATAAAA CAGACGAGGG TATCCGCCTG ATGCAACAGA

851 GCGATTACGG CAACCTGTCC TACCACATCC GTAATAAAAA CATGCTTTTC

901 ATCTTTTCGA CAGGCAATGA CGCACAAGCT CAGCCCAACA CATATGCCCT

951 ATTGCCATTT TATGAAAAAG ACGCTCAAAA AGGCATTATC ACAGTCGCAG

1001 GCGTAGACCG CAGTGGAGAA AAGTTCAAAC GGGAAATGTA TGGAGAACCG

1051 GGTACAGAAC CGCTTGAGTA TGGCTCCAAC CATTGCGGAA TTACTGCCAT

1101 GTGGTGCCTG TCGGCACCCT ATGAAGCAAG CGTCCGTTTC ACCCGTACAA

1151 ACCCGATTCA AATTGCCGGA ACATCCTTTT CCGCACCCAT CGTAACCGGC

1201 ACGGCGGCTC TGCTGCTGCA GAAATACCCG TGGATGAGCA ACGACAACCT

1251 GCGTACCACG TTGCTGACGA CGGCTCAGGA CATCGGTGCA GTCGGCGTGG

1301 ACAGCAAGTT CGGCTGGGGA CTGCTGGATG CGGGTAAGGC CATGAACGGA

1351 CCCGCGTCCT TTCCGTTCGG CGACTTTACC GCCGATACGA AAGGTACATC

1401 CGATATTGCC TACTCCTTCC GTAACGACAT TTCAGGCACG GGCGGCCTGA

1451 TCAAAAAAGG CGGCAGCCAA CTGCAACTGC ACGGCAACAA CACCTATACG

1501 GGCAAAACCA TTATCGAAGG CGGTTCGCTG GTGTTGTACG GCAACAACAA

-continued

1551 ATCGGATATG CGCGTCGAAA CCAAAGGTGC GCTGATTTAT AACGGGGCGG

1601 CATCCGGCGG CAGCCTGAAC AGCGACGGCA TTGTCTATCT GGCAGATACC

1651 GACCAATCCG GCGCAAACGA AACCGTACAC ATCAAAGGCA GTCTGCAGCT

1701 GGACGGCAAA GGTACGCTGT ACACACGTTT GGGCAAACTG CTGAAAGTGG

1751 ACGGTACGGC GATTATCGGC GGCAAGCTGT ACATGTCGGC ACGCGGCAAG

1801 GGGGCAGGCT ATCTCAACAG TACCGGACGA CGTGTTCCCT TCCTGAGTGC

1851 CGCCAAAATC GGGCAGQATT ATTCTTTCTT CACAAACATC GAAACCGACG

1901 GCGGCCTGCT GGCTTCCCTC GACAGCGTCG AAAAAACAGC GGGCAGTGAA

1951 GGCGACACGC TGTCCTATTA TGTCCGTCGC GGCAATGCGG CACGGACTGC

2001 TTCGGCAGCG GCACATTCCG CGCCCOCCGG TCTGAAACAC GCCGTAGAAC

2051 AGGGCGGCAG CAATCTGGAA AACCTGATGG TCGAACTGQA TGCCTCCGAA

2101 TCATCCGCAA CACCCGAGAC GGTTGAAACT GCGGCAGCCG ACCGCACAGA

2151 TATGCCGGGC ATCCGCCCCT ACGGCGCAAC TTTCCGCGCA GCGGCAGCCG

2201 TACAGCATGC GAATGCCGCC GACGGTGTAC GCATCTTCAA CAGTCTCGCC

2251 GCTACCGTCT ATGCCGACAG TACCGCCGCC CATGCCGATA TGCAGGGACG

2301 CCGCCTGAAA GCCGTATCGG ACGGGTTGGA CCACAACGGC ACGGGTCTGC

2351 GCGTCATCGC GCAAACCCAA CAGGAQGGTG GAACGTGGGA ACAGGGCGGT

2401 GTTGAAGGCA AAATGCGCGG CAGTACCCAA ACCGTCGGCA TTGCCGCGAA

2451 AACCGGCGAA AATACGACAG CAGCCGCCAC ACTGGGCATG GGACGCAGCA

2501 CATGGAGCGA AAACAGTGCA AATGCAAAAA CCGACAGCAT TAGTCTGTTT

2551 GCAGGCATAC GGCACGATGC GGGCGATATC GGCTATCTCA AAGGCCTGTT

2601 CTCCTACGGA CGCTACAAAA ACAGCATCAG CCGCAGCACC GGTGCGGACG

2651 AACATGCGGA AGOCAGCGTC AACGGCACGC TGATGCAGCT GGGCGCACTG

2701 GGCGGTGTCA ACGTTCCGTT TGCCGCAACG GGAGATTTGA CGGTCGAAGG

2751 CGGTCTGCGC TACGACCTGC TCAAACAGGA TGCATTCGCC GAAAAAGGCA

2801 GTGCTTTGGG CTGGAGCGGC AACAGCCTCA CTGAAGGCAC GCTGGTCGGA

2851 CTCGCGGGTC TGAAGCTGTC GCAACCCTTG AGCGATAAAG CCGTCCTGTT

2901 TGCAACGGCG GGCGTGGAAC GCGACCTGAA CGGACGCGAC TACACGGTAA

2951 CGGGCGGCTT TACCGGCGCG ACTGCAGCAA CCGGCAAGAC GGGGGCACGC

3001 AATATGCCGC ACACCCGTCT GGTTGCCGGC CTGGGCGCGG ATGTCGAATT

3051 CGGCAACGGC TGGAACGGCT TGGCACGTTA CAGCTACGCC GGTTCCAAAC

3101 AGTACGGCAA CCACAGCGGA CGAGTCGGCG TAGGCTACCG GTTCCTCGAG

3151 GGTGOCGGAG GCACTGGATC CGCCACAAAC GACGACGATG TTAAAAAAGC

3201 TGCCACTGTG GCCATTGCTG CTGCCTACAA CAATGGCCAA GAAATCAACG

3251 GTTTCAAAGC TGGAGAGACC ATCTACGACA TTGATGAAGA CGGCACAATT

3301 ACCAAAAAAG ACGCAACTGC AGCCGATGTT GAAGCCGACG ACTTTAAkGG

3351 TCTGGGTCTG AAAAAAGTCG TGACTAACCT GACCAAAACC GTCAATGAAA

3401 ACAAACAAAA CGTCGATGCC AAAGTAAAAG CTGCAGAATC TGAAATAGAk

3451 AAGTTAACAA CCAAGTTAGC AGACAGTGAT GCCGCTTTAG CAGATACTGA

3501 TGCCGCTCTG GATGCAACCA CCAAGGCCTT GAATAAATTG GGAGAAAATA

-continued

```
3551 TAACGACATT TGCTGAAGAG ACTAAGACAA ATATCGTAAA AATTGATGAA
3601 AAATTAGAAG CCGTGGCTGA TACCGTCGAC AAGCATGCCG AAGCATTCAA
3651 CGATATCGCC GATTCATTGG ATGAAACCAA CACTAAGGCA GACGAAGCCG
3701 TCAAAACCGC CAATGAAGCC AAACAGACGG CCGAAGAAAC CAAACAAAAC
3751 GTCGATGCCA AAGTAAAAGC TGCAGAAACT GCAGCAGGCA AAGCCGAAGC
3801 TGCCGCTGGC ACAGCTAATA CTGCAGCCGA CAAGGCCGAA GCTGTCGCTG
3851 CAAAAGTTAC CGACATCAAA GCTGATATCG CTACGAACAA AGATAATATT
3901 GCTAAAAAAG CAAACAGTGC CGACGTGTAC ACCAGAGAAG AGTCTGACAG
3951 CAAATTTGTC AGAATTGATG GTCTGAACGC TACTACCGAA AAATTGGACA
4001 CACGCTTGGC TTCTGCTGAA AAATCCATTG CCGATCACGA TACTCGCCTG
4051 AACGGTTTGG ATAAAACAGT GTCAGACCTG CGCAAAGAAA CCCGCCAAGG
4101 CCTTGCAGAA CAAGCCGCGC TCTCCGGTCT GTTCCAACCT TACAACGTGG
4151 GTCTCGAGCA CCACCACCAC CACCACTGA

   1 MTSAPDFNAG GTGIGSNSRA TTAXSAAVSY AGIKNEHCKD RSNLCAGRDD
  51 VAVTDRDAKI NAPPPNLHTG DFPNPNDAYK NLINLKPAIE AGYTGRGVEV
 101 GIVDTGESVG SISFPELYGR KERGYNENYK NYTAYMEKEA PEDGGGKDIE
 151 ASFDDEAVIE TEAKPTDThH VKEIGHIDLV SHIIGGRSVD GRPAGGIAPD
 201 ATLHIMNTND ETKNEMMVAA IPNAWVKLGE RGVRIVNNSP GTTSRAGTAD
 251 LFQIANSEEQ YRQALLDYSG GDKTDEGIRL MQQSDYGNLS YHIRNKNMLF
 301 IFSTGNDAQA QPNTYALLPF YEKDAQKGII TVAGVDRSGE KFKEEMYGEP
 351 GTEPLEYGSN HCGITAMWCL SAPYBASVRP TRTNPIQIAG TSPSAPIVTG
 401 TAALLLQKYP WMSNDNLRTT LLTTAQDIGA VGVDSKEGWG LLDAGKAMNG
 451 PASFPFGDFT ADTKGTSDIA YSFENDISGT GGLIDCGGSQ LQLHGNNTYT
 501 QKTIIEGGSL VLYGNNKSDH RVETKGALIY NGAASGGSLN SDGIVYLADT
 551 DQSGANETVH IKGSLQLDGK GTLYTRLGKL LKVDGTAIIG GKLYMSARGK
 601 GAGYLNSTGR RVPFLSAAKI GQDYSFFTNI ETDGGLLASL DSVEKTAGSE
 651 GDTLSYYVRR GNAARTASAA AHSAPAGLKH AVEQGGSNLE NLMVBLDASE
 701 SSATPETVET AAADRTDMPG IRPYGATFRA AAAVQHANAA DGVRIPNSLA
 751 ATVYADSTAA HADMQGPELK AVSDGLDHNG TGLRVIAQTQ QDGGTWEQGG
 801 VHGKHRGSTQ TVGIAAKTGE NTTAAATLGM GRSTWSENSA NAKTDSISLF
 851 AGIEHDAGDI GYLKGLPSYG RYENSISRST GADEHAEGSV NGTLKQLGAL
 901 GGVNVPFAAT GDLTVBGGLR YDLLKQDAPA EKGSALGWSG NSLTEGTLVG
 951 LAGLKLSQPL SDKAVLPATA GVERDLNGED YTVTGGFTGA TAATGKTGAR
1001 NMPHTRLVAG LGADVEFGNG WNGLARYSYA GSKQYGNHSG RVGVGYRFLE
1051 GGGGTGSATN DDDVKKAATV AIAAAYNNGQ BINGFKkGET IYDIDEDGTI
1101 TKKDATAADV EADDFKGLGL KKVVTNLTKT VNENKQNVDA KVKAAESEIE
1151 KLTTKLADTD AALADTDAAL DATTNALNKL GENITTFAEE TKTNIVKIDE
1201 KLEAVADTVD KHAEAFNDIA DSLDETNTKA DEAVKTANEA KQTAEETKQN
1251 VDAKVKAAET AAGKAEAAAG TANTAADKAE AVAAKVTDIK ADIATNKDNI
1301 AERANSADVY TRERSDSKFV RIDGLNATTE KLDTRLASAE KSIADHDTRL
```

-continued

```
1351 NGLDKTVSDL RKETRQGLAE QAALBGLFQP YNVGLEHHHH HH*
```

ΔG741 and Hybrids

Bactericidal titres generated in response to ΔG741 (His-fusion) were measured against various strains, including the homologous 2996 strain:

| | 2996 | MC58 | NGH38 | F6124 | BZ133 |
|---|---|---|---|---|---|
| ΔG741 | 512 | 131072 | >2048 | 16384 | >2048 |

As can be seen, the ΔG741-induced anti-bactericidal titre is particularly high against heterologous strain MC58.

ΔG741 was also fused directly in-frame upstream of proteins 961 (SEQ ID NOS:108 and 109), 961c (SEQ ID NOS: 110 and 111), 983 (SEQ ID NOS:112 and 113) and ORF46.1 (SEQ ID NOS:114 and 115):

ΔG741-961

```
   1 ATGGTCGCCG CCGACATCGG TGCGGGGCTT GCCGATGCAC TAACCGCACC
  51 GCTCGACCAT AAAGACAAAG GTTTGCAGTC TTTGACGCTG GATCAGTCCG
 101 TCAGGAAAAA CGAGAAACTG AAGCTGGCGG CACAAGGTGC GGAAAAAACT
 151 TATGGAAACG GTGACAGCCT CAATACGGGC AAATTGAAGA ACGACAAGGT
 201 CAGCCGTTTC GACTTTATCC GCCAAATCGA AGTGGACGGG CAGCTCATTA
 251 CCTTGGAGAG TGGAGAGTTC CAAGTATACA AACAAAGCCA TTCCGCCTTA
 301 ACCGCCTTTC AGACCGAGCA AATACAAGAT TCGGAGCATT CCGGGAAGAT
 351 GGTTGCGAAA CGCCAGTTCA GAATCGGCGA CATAGCGGGC GAACATACAT
 401 CTTTTGACAA GCTTCCCGAA GGCGGCAGGG CGACATATCG CGGGACGGCG
 451 TTCGGTTCAG ACGATGCCGG CGGAAAACTG ACCTACACCA TAGATTTCGC
 501 CGCCAAGCAG GGAAACGGCA AAATCGAACA TTTGAAATCG CCAGAACTCA
 551 ATGTCGACCT GGCCGCCGCC GATATCAAGC CGGATGGAAA AOGCCATGCC
 601 GTCATCAGCG GTTCCGTCCT TTACAACCAA GCCGAGAAAG GCAGTTACTC
 651 CCTCGGTATC TTTGGCGGAA AAGCCCAGGA AGTTGCCGGC AGCGCGGAAG
 701 TGAAAACCGT AAACGGCATA CGCCATATCG GCCTTGCCGC CAAGCAACTC
 751 GAGGGTGGCG GAGGCACTGG ATCCGCCACA AACGACGACG ATGTTAAAAA
 801 AGCTGCCACT GTGGCCATTG CTGCTGCCTA CAACAATGGC CAAGAAATCA
 851 ACGGTTTCAA AGCTGGAGAG ACCATCTACG ACATTGATGA AGACGGCACA
 901 ATTACCAAAA AAGACGCAAC TGCAGCCGAT GTTGAAGCCG ACGACTTTAA
 951 AGGTCTGGGT CTGAAAAAAG TCGTGACTAA CCTGACCAAA ACCGTCAATG
1001 AAAACAAACA AAACGTCGAT GCCAAAGTAA AAGCTGCAGA ATCTGAAATA
1051 GAAAAGTTAA CAACCAAGTT AGCAGACACT GATGCCGCTT TAGCAGATAC
1101 TGATGCCGCT CTGGATGCAA CCACCAACGC CTTGAATAAA TTGGGAGAAA
1151 ATATAACGAC ATTTGCTGAA GAGACTAAGA CAAATATCGT AAAAATTGAT
1201 GAAAAATTAG AAGCCGTGGC TGATACCGTC GACAAGCATG CCGAAGCATT
1251 CAACGATATC GCCGATTCAT TGGATGAAAC CAACACTAAG GCAGACGAAG
1301 CCGTCAAAAC CGCCAATGAA GCCAAACAGA CGGCCGAAGA AACCAAACAA
1351 AACGTCGATG CCAAAGTAAA AGCTGCAGAA ACTGCAGCAG GCAAAGCCGA
1401 AGCTGCCGCT GGCACAGCTA ATACTGCAGC CGACAAGGCC GAAGCTGTCG
1451 CTGCAAAAGT TACCGACATC AAAGCTGATA TCGCTACGAA CAAAGATAAT
1501 ATTGCTAAAA AAGCAAACAG TGCCGACGTG TACACCAGAG AAGAGTCTGA
```

-continued

```
1551 CAGCAAATTT GTCAGAATTG ATGGTCTGAA CGCTACTACC GAAAAATTGG
1601 ACACACGCTT GGCTTCTGCT GAAAAATCCA TTGCCGATCA CGATACTCGC
1651 CTGAACGGTT TGGATAAAAC AGTGTCAGAC CTGCGCAAAG AAACCCGCCA
1701 AGGCCTTGCA GAACAAGCCG CGCTCTCCGG TCTGTTCCAA CCTTACAACG
1751 TGGGTCGGTT CAATGTAACG GCTGCAGTCG GCGGCTACAA ATCCGAATCG
1802 GCAGTCGCCA TCGGTACCGG CTTCCGCTTT ACCGAAAACT TTGCCGCCAA
1851 AGCAGGCGTG GCAGTCGGCA CTTCGTCCGG TTCTTCCGCA GCCTACCATG
1901 TCGGCGTCAA TTACGAGTGG CTCGAGCACC ACCACCACCA CCACTGA
   1 MVAADIGAGL ADMJTAPLDH KDKGLQSLTL DQSVRKNEKL KLAAQGAEKT
  51 YGNGDSLNTG KLKNDKVSRF DFIRQIEVDG QLITLESGBF QVYKQSHSAL
 101 TAPQTEQIQD SEHSGKMVAK RQFRIGDIAG EHTSFDKLPE GGRATYRGTA
 151 FGSDDAGGKL TYTIDFAAXQ GNGKIEHLKS PELNVDLAAA DIKPDGKEEA
 201 VISGSVLYNQ AEKGSYSLGI FGGKAQEVAG SAEVKTVNGI RHIGLAAKQL
 251 EGGGGTGSAT NDDDVKKAAT VAIAAAYNNG QEINGFKAGE TIYDIDBDGT
 301 ITKKDATAAD VEADDFKGLG LKKVVTNLTK TVNENKQNVD AKVKAAESEI
 351 EKLTTKLADT DAALADTDAA LDATTNALNK LGRNZTTFAB BTKTNIVKID
 401 EKLEAVADTV DKHAEAFNDI ADSLDETNTK ADEAVKTANE AKQTAEETKQ
 451 NVDAKVKAAB TAAGRAEAAA GTANTAADRA EAVAAKVTDI KADIATNKDN
 501 IAKKANSADV YTREESDSKF VRIDGLNATT ELKDTRLASA BKSIADHDTR
 551 LNGLDKTVSD LRKETRQGLA EQAALSGLFQ PYNVGRFNVT AAVGGYKSES
 601 AVAIGTGFRF TENFAAKAGV AVGTSSGSSA AYHVGVNYEW LHHHHHHH*

                    ΔG741-961c
   1 ATGGTCGCCG CCGACATCGG TGCGGGGCTT GCCGATGCAC TAACCGCACC
  51 GCTCGACCAT AAAGACAAAG GTTTGCAGTC TTTGACGCTG GATCAGTCCG
 101 TCAGGAAAAA CGAGAAACTG AAGCTGGCGG CACAAGGTGC GGAAAAAACT
 151 TATGGAAACG GTGACAGCCT CAATACGGGC AAATTGAAGA ACGACAAGGT
 201 CAGCCGTTTC GACTTTATCC GCCAAATCGA AGTGGACGGG CAGCTCATTA
 251 CCTTGGAGAG TGGAGAGTTC CAAGTATACA AACAAAGCCA TTCCGCCTTA
 301 ACCGCCTTTC AGACCGAGCA AATACAAGAT TCGGAGCATT CCGGGAAGAT
 351 GGTTGCGAAA CGCCAGTTCA GAATCGGCGA CATAGCGGGC GAACATACAT
 401 CTTTTGACAA GCTTCCCGAA GGCGGCAGGG CGACATATCG CGGGACGGCG
 451 TTCGGTTCAG ACGATGCCGG CGGAAAACTG ACCTACACCA TAGATTTCGC
 501 CGCCAAGCAG GGAAACGGCA AAATCGAACA TTTGAAATCG CCAGAACTCA
 551 ATGTCGACCT GGCCGCCGCC GATATCAAGC CGGATGGAAA ACGCCATGCC
 601 GTCATCAGCG GTTCCGTCCT TTACAACCAA GCCGAAAAAG GCAGTTACTC
 651 CCTCGGTATC TTTGGCGGAA AAGCCCAGGA AGTTGCCGGC AGCGCGGAAG
 701 TGAAAACCGT AAACGGCATA CGCCATATCG GCCTTGCCGC CAAGCAACTC
 751 GAGGGTGGCG GAGGCACTGG ATCCGCCACA AACGACGACG ATGTTAAAAA
 801 AGCTGCCACT GTGGCCATTG CTGCTGCCTA CAACAATGGC CAAGAAATCA
 851 ACGGTTTCAA AGCTGGAGAG ACCATCTACG ACATTGATGA AGACGGCACA
```

-continued

```
 901 ATTACCAAAA AAGACGCAAC TGCAGCCGAT GTTGAAGCCG ACGACTTTAA
 951 AGGTCTGGGT CTGAAAAAAG TCGTGACTAA CCTGACCAAA ACCGTCAATG
1001 AAAACAAACA AAACGTCGAT GCCAAAGTAA AAGCTGCAGA ATCTGAAATA
1051 GAAAAGTTAA CAACCAAGTT AGCAGACACT GATGCCGCTT TAGCAGATAC
1101 TGATGCCGCT CTGGATGCAA CCACCAACGC CTTGAATAAA TTGGGAGAAA
1151 ATATAACGAC ATTTGCTGAA GAGACTAAGA CAAATATCGT AAAAATTGAT
1201 GAAAAATTAG AAGCCGTGGC TGATACCGTC GACAAGCATG CCGAAGCATT
1251 CAACGATATC GCCGATTCAT TGGATGAAAC CAACACTAAG GCAGACGAAG
1301 CCGTCAAAAC CGCCAATGAA GCCAAACAGA CGGCCGAAGA AACCAAACAA
1351 AACGTCGATG CCAAAGTAAA AGCTGCAGAA ACTGCAGCAG GCAAAGCCGA
1401 AGCTGCCGCT GGCACAGCTA ATACTGCAGC CGACAAGGCC GAAGCTGTCG
1451 CTGCAAAAGT TACCGACATC AAAGCTGATA TCGCTACGAA CAAAGATAAT
1501 ATTGCTAAAA AAGCAAACAG TGCCGACGTG TACACCAGAG AAGAGTCTGA
1551 CAGCAAATTT GTCAGAATTG ATGGTCTGAA CGCTACTACC GAAAAATTGG
1601 ACACACGCTT GGCTTCTGCT GAAAAATCCA TTGCCGATCA CGATACTCGC
1651 CTGAACGGTT TGGATAAAAC AGTGTCAGAC CTGCGCAAAG AAACCCGCCA
1701 AGGCCTTGCA GAACAAGCCG CGCTCTCCGG TCTGTTCCAA CCTTACAACG
1751 TGGGTCTCGA GCACCACCAC CACCACCACT GA

   1 MVAADIGAGL ADALTAPLDH KDKGLQSLTL DQSVEXNEKL KLAAQGAEKT
  51 YGNGDSLNTG KLKNDKVSRF DFIRQIEVDG QLITLBSGEF QVYKQSHSAL
 101 TAPQTBQIQD SEHSGKMVAK RQFRIGDIAG EHTSFDKLPE GGRATYRGTA
 151 FGSDDAGGKL TYTIDFAAKQ GNGKIEHLKS PELNVDLAAA DIKPDGKRHA
 201 VISGSVLYNQ AEKGSYSLGI FGGKAQEVAG SAEVKTVNGI RHIGLAAXQL
 251 EGGGGTGSAT NDDDVKKAAT VAIAAAYNNG QHINGFKAGE TIYDIDEDGT
 301 ITKKDATAAD VEADDFRGLG LKKVVTNLTK TVNENKQNVD AKVKAAESEI
 351 EKLTTKLADT DAALADTDAA LDATTNALNK LGENITTFAE ETKTNIVKID
 401 EKLEAVADTV DKHAEAFNDI ADSLDETNTK ADEAVKTANE AKQTAEETKQ
 451 NVDAKVKAAE TAAGKAEAAA GTANTAADKA EAVAAKVTDI KADIATNKDN
 501 IAKKANSADV YTREESDSKF VRIDGLNATT EKLDTPLASA EKSIADHDTR
 551 LNGLDKTVSD LRKETRQGLA EQAALSGLPQ PYNVGLEHHH HHH*
```

ΔG741-983

```
   1 ATGGTCGCCG CCGACATCGG TGCGGGGCTT GCCGATGCAC TAACCGCACC
  51 GCTCGACCAT AAAGACAAAG GTTTGCAGTC TTTGACGCTG GATCAGTCCG
 101 TCAGGAAAAA CGAGAAACTG AAGCTGGCGG CACAAGGTGC GGAAAAAACT
 151 TATGGAAACG GTGACAGCCT CAATACGGGC AAATTGAAGA ACGACAAGGT
 201 CAGCCGTTTC GACTTTATCC GCCAAATCGA AGTGGACGGG CAGCTCATTA
 251 CCTTGGAGAG TGGAGAGTTC CAAGTATACA AACAAAGCCA TTCCGCCTTA
 301 ACCGCCTTTC AGACCGAGCA AATACAAGAT TCGGAGCATT CCGGGAAGAT
 351 GGTTGCGAAA CGCCAGTTCA GAATCGGCGA CATAGCGGGC GAACATACAT
 401 CTTTTGACAA GCTTCCCGAA GGCGGCAGGG CGACATATCG CGGGACGGCG
 451 TTCGGTTCAG ACGATGCCGG CGGAAAACTG ACCTACACCA TAGATTTCGC
```

-continued

```
501  CGCCAAGCAG GGAAACGGCA AAATCGAACA TTTGAAATCG CCAGAACTCA
551  ATGTCGACCT GGCCGCCGCC GATATCAAGC CGGATGGAAA ACGCCATGCC
601  GTCATCAGCG GTTCCGTCCT TTACAACCAA GCCGAGAAAG GCAGTTACTC
651  CCTCGGTATC TTTGGCGGAA AAGCCCAGGA AGTTGCCGGC AGCGCGGAAG
701  TGAAAACCGT AAACGGCATA CGCCATATCG GCCTTGCCGC CAAGCAACTC
751  GAGGGATCCG GCGGAGGCGG CACTTCTGCG CCCGACTTCA ATGCAGGCGG
801  TACCGGTATC GGCAGCAACA GCAGAGCAAC AACAGCGAAA TCAGCAGCAG
851  TATCTPACGC CGGTATCAAG AACGAAATGT GCAAAGACAG AAGCATGCTC
901  TGTGCCGGTC GGGATGACGT TGCGGTTACA GACAGGGATG CCAAAATCAA
951  TGCCCCCCCC CCGAATCTGC ATACCGGAGA CTTTCCAAAC CCAAATGACG
1001 CATACAAGAA TTTGATCAAC CTCAAACCTG CAATTGAAGC AGCCTATACA
1051 GGACGCGGGG TAGAGGTAGG TATCGTCGAC ACAGGCGAAT CCGTCGGCAG
1101 CATATCCTTT CCCGAACTGT ATGGCAGAAA AGAACACGGC TATAACGAAA
1151 ATTACAAAAA CTATACGGCG TATATGCGGA AGGAAGCGCC TGAAGACGGA
1201 GGCGGTAAAG ACATTGAAGC TTCTTTCGAC GATGAGGCCG TTATAGAGAC
1251 TGAAGCAAAG CCGACGGATA TCCGCCACGT AAAAGAAATC GGACACATCG
1301 ATTTGGTCTC CCATATTATT GGCGGGCGTT CCGTGGACGG CAGACCTGCA
1351 GGCGGTATTG CGCCCGATGC GACGCTACAC ATAATGAATA CGAATGATGA
1401 AACCAAGAAC GAAATGATGG TTGCAGCCAT CCGCAATGCA TGGGTCAAGC
1451 TGGGCGAACG TGGCGTGCGC ATCGTCAATA ACAGTTTTGG AACAACATCG
1501 AGGGCAGGCA CTGCCGACCT TTTCCAAATA GCCAATTCGG AGGAGCAGTA
1551 CCGCCAAGCG TTGCTCGACT ATTCCGGCGG TGATAAAACA GACGAGGGTA
1601 TCCGCCTGAT GCAACAGAGC GATTACGGCA ACCTGTCCTA CCACATCCGT
1651 AATAAAAACA TGCTTTTCAT CTTTTCGACA GGCAATGACG CACAAGCTCA
1701 GCCCAACACA TATGCCCTAT TGCCATTTTA TGAAAAAGAC GCTCAAAAAG
1751 GCATTATCAC AGTCGCAGGC GTAGACCOCA GTGGAGAAAA GTTCAAACGG
1801 GAAATGTATG GAGAACCGGG TACAGAACCG CTTGAGTATG GCTCCAACCA
1851 TTGCGGAATT ACTGCCATGT GGTGCCTGTC GGCACCCTAT GAAGCAAGCG
1901 TCCGTTTCAC CCGTACAAAC CCGATTCAAA TTGCCGGAAC ATCCTTTTCC
1951 GCACCCATCG TAACCGGCAC GGCGGCTCTG CTGCTGCAGA AATACCCGTG
2001 GATGAGCAAC GACAACCTGC GTACCACGTT GCTGACGACG GCTCAGGACA
2051 TCGGTGCAGT CGGCGTGGAC AGCAAGTTCG GCTGGGGACT GCTGGATGCG
2101 GGTAAGGCCA TGAACGGACC CGCGTCCTTT CCGTTCGGCG ACTTTACCGC
2151 CGATACGAAA GGTACATCCG ATATTGCCTA CTCCTTCCGT AACGACATTT
2201 CAGGCACGGG CGGCCTGATC AAAAAAGGCG GCAGCCAACT GCAACTGCAC
2251 GGCAACAACA CCTATACGGG CAAAACCATT ATCGAAGGCG GTTCGCTGGT
2301 GTTGTACGGC AACAACAAAT CGGATATGCG CGTCGAAACC AAAGGTGCGC
2351 TGATTTATAA CGGGGCGGCA TCCGGCGGCA GCCTGAACAG CGACGGCATT
2401 GTCTATCTGG CAGATACCGA CCAATCCGGC GCAAACGAAA CCGTACACAT
2451 CAAAGGCAGT CTGCAGCTGG ACGGCAAAGG TACGCTGTAC ACACGTTTGG
```

-continued

2501 GCAAACTGCT GAAAGTGGAC GGTACGGCGA TTATCGGCGG CAAGCTGTAC
2551 ATGTCGGCAC GCGGCAAGGG GGCAGGCTAT CTCAACAGTA CCGGACGACG
2601 TGTTCCCTTC CTGAGTGCCG CCAAAATCGG GCAGGATTAT TCTTTCTTCA
2651 CAAACATCGA AACCGACGGC GGCCTGCTGG CTTCCCTCGA CAGCGTCGAA
2701 AAAACAGCGG GCAGTGAAGG CGACACGCTG TCCTATTATG TCCGTCGCGG
2751 CAATGCGGCA CGGACTGCTT CGGCAGCGGC ACATTCCGCG CCCGCCGGTC
2801 TGAAACACGC CGTAGAACAG GGCGGCAGCA ATCTGGAAAA CCTGATGGTC
2851 GAACTGGATG CCTCCGAATC ATCCGCAACA CCCGAGACGG TTGAAACTGC
2901 GGCAGCCGAC CGCACAGATA TGCCGGGCAT CCGCCCCTAC GGCGCAACTT
2951 TCCGOGCAGC GGCAGCCGTA CAGCATGCGA ATGCCGCCGA CGGTGTACGC
3001 ATCTTCAACA GTCTCGCCGC TACCGTCTAT GCCGACAGTA CCGCCGCCCA
3051 TGCCGATATG CAGGGACGCC GCCTGAAAGC CGTATCGGAC GGGTTGGACC
3101 ACAACGGCAC GGGTCTGCGC GTCATCGCGC AAACCCAACA GGACGGTGGA
3151 ACGTGGGAAC AGGGCGGTGT TGAAGGCAAA ATGCGCGGCA GTACCCAAAC
3201 CGTCGGCATT GCCGCGAAAA CCGGCGAAAA TAAGACAGCA GCCGCCACAC
3251 TGGGCATGGG ACGCAGCACA TGGAGCGAAA ACAGTGCAAA TGCAAAAACC
3301 GACAGCATTA GTCTGTTTGC AGGCATACGG CACGATGCGG GCGATATCGG
3351 CTATCTCAAA GGCCTGTTCT CCTACGGACG CTACAAAAAC AGCATCAGCC
3401 GCAGCACCGG TGCGGACGAA CATGCGGAAG GCAGCGTCAA CGGCACGCTG
3451 ATGCAGCTGG GCGCACTGGG CGGTGTCAAC GTTCCGTTTG CCGCAACGGG
3501 AGATTTGACG GTCGAAGGCG GTCTGCGCTA CGACCTGCTC AAACAGGATG
3551 CATTCGCCGA AAAAGGCAGT GCTTTGGGCT GGAGCGGCAA CAGCCTCACT
3601 GAAGGCACGC TGGTCGGACT CGCGGGTCTG AACCTGTCGC AACCCTTGAG
3651 CGATAAAGCC GTCCTGTTTG CAACGGCGGG CGTGGAACGC GACCTGAACG
3701 GACGCGACTA CACGGTAACG GGCGGCTTTA CCGGCGCGAC TGCAGCAACC
3751 GGCAAGACGG GGGCACGCAA TATGCCGCAC ACCCGTCTGG TTGCCGGCCT
3801 GGGCGCGGAT GTCGAATTCG GCAACGGCTG GAACGGCTTG GCACGTTACA
3851 GCTACGCCGG TTCCAAACAG TACGGCAACC ACAGCGGACG AGTCGGCGTA
3901 GGCTACCGGT TCCTCGAGCA CCACCACCAC CACCACTGA

1 MVAADIGAQL ADALTAPLDH KDKGLQSLTL DQSVRKNEKL KLAAQGAEKT
51 YGNGDSLNTG KLKNDKVSRP DFIRQIEVDG QLITLESGEF QVYKQSHSAL
101 TAFQTEQIQD SEHSGKNVAK RQFRIGDIAG EHTSFDKLPE GGRATYRGTA
151 FGSDDAGGKL TYTIDFAAKQ GNGKIEHLKS PELNVDLAAA DIKPDGKRHA
201 VISGSVLYNQ ARKGSYSLGI FGGKAQEVAG SABVKTVNGI RHIGLAAKQL
251 EGSGGGGTSA PDPNAGGTGI GSNSRATTAK SAAVSYAGIK NEMCKDRBML
301 CAGRDDVAVT DRDAKINAPP PNLHTGDFPN PIWAYKNLIN LKPAIEAGYT
351 GRGVEVGIVD TGESVGSISF PELYGRKEHG YNENYKNYTA YHRKRAPEDG
401 GGKDIEASFD DEAVIHTEAK PTDIRHVKBI GHIDLVSHII GGRSVDGRPA
451 GGIAPDATLH IMNTNDETKN EMMVAAIRNA WVKLGERGVR IVNNSFGTTS
501 RAGTADLPQI ANSEBQYRQA LLDYSGGDKT DEGIPLMQQS DYGNLSYHIR

-continued

```
 551 NKNHLFIFST GNDAQAQPNT YALLPFYEKD AQKGIITVAG VDRSGEKFKR
 601 EMYGBPGTRP LEYGSNHCGI TANWOLSAPY EASVEFTRTN PIQIAGTSFS
 651 APIVTGTAAL LLQKYPWHSN DNLRTTLLTT AQDIGAVGVD SKFGWGLLDA
 701 GKAMNGPASF PFGDFTADTK GTSDIAYSFR NDISGTGGLI KKGGSQLQLH
 751 GNNTYTGRTI IEGGSLVLYG NNKSDMRVET KGALIYNGAA SGGSLNSDGI
 801 VYLADTDQSG ANETVHIKGS LQLDGKGTLY TRLGKLLKVD GTAIIGGKLY
 851 MSARGKGAGY LNSTGRRVPF LSAAKIGQDY SFFTNIBTDG GLLASLDSVB
 901 KTAGSEGDTL SYYVRRGNAA RTASAAAHSA PAGLKHAVEQ GGSNLENLMV
 951 ELDASESSAT PETVETAAAD RTDMPGIRPY GATFRAAAAV QHANAADGVR
1001 IFNSLAATVY ADSTAAHADH QGRRLKAVSD GLDHNGTGLR VIAQTQQDGG
1051 TWBQGGVEGK MRGSTQTVGI AAKTGENTTA AATLGMGRST WSENSANART
1101 DSISLFAGIR HDAGDIGYLK GLFSYGRYKN SISRSTGADE HAEGSVNGTL
1151 MQLGALGGVN VPFAATGDLT VEGGLRYDLL KQDAFAEKGS ALGWSGNSLT
1201 EGTLVGLAGL KLSQPLSDKA VLFATAGVER DLNGRDYTVT GGFTGATAAT
1251 GKTGARNMPH TRLVAGLGAD VBFGNGWNGL ARYSYAGSKQ YGNHSGRVGV
1301 GYRFLEHHHH HH*
```

ΔG741-ORF46.1

```
   1 ATGGTCGCCG CCGACATCGG TGCGGGGCTT GCCGATGCAC TAACCGCACC
  51 GCTCGACCAT AAAGACAAAG GTTTGCAGTC TTTGACGCTG GATCAGTCCG
 101 TCAGGAAAAA CGAGAAACTG AAGCTGGCGG CACAAGGTGC GGAAAAAACT
 151 TATGGAAACG GTGACAGCCT CAATACGGGC AAATTGAAGA ACGACAAGGT
 201 CAGCCGTTTC GACTTTATCC GCCAAATCGA AGTGGACGGG CAGCTCATTA
 251 CCTTGGAGAG TGGAGAGTTC CAAGTATACA AACAAAGCCA TTCCGCCTTA
 301 ACCGCCTTTC AGACCGAGCA AATACAAGAT TCGGAGCATT CCGGGAAGAT
 351 GGTTGCGAAA CGCCAGTTCA GAATCGGCGA CATAGCGGGC GAACATACAT
 401 CTTTTGACAA GCTTCCCGAA GGCGGCAGGG CGACATATCG CGGGACGGCG
 451 TTCGGTTCAG ACGATGCCGG CGGAAAACTG ACCTACACCA TAGATTTCGC
 501 CGCCAAGCAG GGAAACGGCA AAATCGAACA TTTGAAATCG CCAGAACTCA
 551 ATGTCGACCT GGCCGCCGCC GATATCAAGC CGGATGGAAA ACGCCATGCC
 601 GTCATCAGCG GTTCCGTCCT TTACAACCAA GCCGAGAGAG GCAGTTACTC
 651 CCTCGGTATC TTTGGCGGAA AAGCCCAGGA AGTTGCCGGC AGCGCGGAAG
 701 TGAAAACCGT AAACGGCATA CGCCATATCG GCCATGCCGC CAAGCAACTC
 751 GACGGTGGCG GAGGCACTGG ATCCTCAGAT TTGGCAAACG ATTCTTTTAT
 801 CCGGCAGGTT CTCGACCGTC AGCATTTCGA ACCCGACGGG AAATACCACC
 851 TATTCGGCAG CAGGGGGGAA CTTGCCGAGC GCAGCGGCCA TATCGGATTG
 901 GGAAAAATAC AAAGCCATCA GTTGGGCAAC CTGATGATTC AACAGGCGGC
 951 CATTAAAGGA AATATCGGCT ACATTGTCCG CTTTTCCGAT CACGGGCACG
1001 AAGTCCATTC CCCCTTCGAC AACCATGCCT CACATTCCGA TTCTGATGAA
1051 GCCGGTAGTC CCGTTGACGG ATTTAGCCTT TACCGCATCC ATTGGGACGG
1101 ATACGAACAC CATCCCGCCG ACGGCTATGA CGGGCCACAG GGCGGCGGCT
```

-continued

```
1151 ATCCCGCTCC CAAAGGCGCG AGGGATATAT ACAGCTAGGA CATAAAAGGC
1201 GTTGCCCAAA ATATCCGCCT CAACCTGACC GACAACCGCA GCACCGGACA
1251 ACGGCTTGCC GACCGTTTCC ACAATGCCGG TAGTATGCTG ACGCAAGGAG
1301 TAGGCGACGG ATTCAAACGC GCCACCCGAT ACAGCCCCGA GCTGGACAGA
1351 TCGGGCAATG CCGCCGAAGC CTTCAACGGC ACTGCAGATA TCGTTAAAAA
1401 CATCATCGGC GCGGCAGGAG AAATTGTCGG CGCAGOCGAT GCCGTGCAGG
1451 GCATAAGGGA AGGCTCAAAC ATTGCTGTCA TGCACGGCTT GGGTCTGCTT
1501 TCCACCGAAA ACAAGATGGC GCGCATCAAC GATTTGGCAG ATATGGCGCA
1551 ACTCAAAGAC TATGCCGCAG CAGCCATCCG CGATTGGGCA GTCCAAAACC
1601 CCAATGCCGC ACAAGGCATA GAAGCCGTCA GCAATATCTT TATGGCAGCC
1651 ATCCCCATCA AAGGGATTGG AGCTGTTCGG GGAAAATACG GCTTGGGCGG
1701 CATCACGGCA CATCCTATCA AGCGGTCGCA GATGGGCGCG ATCGCATTGC
1751 CGAAAGGGAA ATCCGCCGTC AGCGACAATT TTGCCGATGC GGCATACGCC
1801 AAATACCCGT CCCCTTACCA TTCCCGAAAT ATCCGTTCAA ACTTGGAGCA
1851 GCGTTACGGC AAAGAAAACA TCACCTCCTC AACCGTGCCG CCGTCAAACG
1901 GCAAAAATGT CAAACTGGCA GACCAACGCC ACCCGAAGAC AGGCGTACCG
1951 TTTGACGGTA AAGGGTTTCC GAATTTTGAG AAGCACGTGA AATATGATAC
2001 GCTCGAGCAC CACCACCACC ACCACTGA

1 MVAADIGAGL ADALTAPLDH KDKGLQSLTL DQSVRKNBKL KLAAQGAEKT
51 YGNGDSLNTG KLKNDKVSEP DFIRQIEVDG QLITLESGEF QVYKQSHSAL
101 TAFQTEQIQD SEHSGKMVAK RQFRIGDIAG EHTSFDKLPE GGEATYRGTA
151 PGSDDAGGKL TYTIDFAAKQ GNGKIEHLKS PELNVDLAAA DIKPDGKRHA
201 VISGSVLYNQ AEKGSYSLGI FGGKAQEVAG SAEVKTVNGI RHIGLAAKQL
251 DGGGGTGSSD LANDSFIRQV LDRQHFEPDG KYHLFGSRGE LAERSGHIGL
301 GKIQSHQLGN LHIQQAAIKG NIGYIVEPSD HGHEVESPFD NHASHSDSDE
351 AGSPVDGPSL YRIHWDGYEH HPADGYDGPQ GGQYPAPKGA RDIYSYDIKG
401 VAQNIRLNLT DNESTGQELA DRPHNAGSML TQGVGDGFKR ATRYSPBLDR
451 SGNAAEAFNG TADIVKNIIG AAGEIVGAGD AVQGISEGSN IAVMHGLGLL
501 STENKMAPJN DLADMAQLKD YAAAAIRDWA VQNPNAAQGI EAVSNIFMAA
551 IPIKGIGAVR GKYGLGGITA HPIKRSQMGA IALPKGKSAV SDNFADAAYA
601 KYPSPYHSRN IESNLEQRYG KENITSSTVP PSNGKNVKLA DQRHPRTGVP
651 FDGKGPPNFE KHVKYDTLEH HHHHH
```

Example 16

C-Terminal Fusions ('Hybrids') with 287/ΔG287

According to the invention, hybrids of two proteins A & B may be either $NH_2$-A-B—COOH or $NH_2$—B-A-COOH. The effect of this difference was investigated using protein 287 either C-terminal (in '287-His' form) or N-terminal (in ΔG287 form—sequences shown above) to 919, 953 and ORF46.1. A panel of strains was used, including homologous strain 2996. FCA was used as adjuvant:

| | 287 & 919 | | 287 & 953 | | 287 & ORF46.1 | |
|---|---|---|---|---|---|---|
| Strain | ΔG287-919 | 919-287 | ΔG287-953 | 953-287 | ΔG287-46.1 | 46.1-287 |
| 2996 | 128000 | 16000 | 65536 | 8192 | 16384 | 8192 |
| BZ232 | 256 | 128 | 128 | <4 | <4 | <4 |
| 1000 | 2048 | <4 | <4 | <4 | <4 | <4 |
| MC58 | 8192 | 1024 | 16384 | 1024 | 512 | 128 |
| NGH38 | 32000 | 2048 | >2048 | 4096 | 16384 | 4096 |
| 394/98 | 4096 | 32 | 256 | 128 | 128 | 16 |
| MenA (F6124) | 32000 | 2048 | >2048 | 32 | 8192 | 1024 |
| MenC (BZ133) | 64000 | >8192 | >8192 | <16 | 8192 | 2048 |

Better bactericidal titres are generally seen with 287 at the N-terminus (in the ΔG form)

When fused to protein 961 [$NH_2$-ΔG287-961COOH—sequence shown above], the resulting protein is insoluble and must be denatured and renatured for purification. Following renaturation, around 50% of the protein was found to remain insoluble. The soluble and insoluble proteins were compared, and much better bactericidal titres were obtained with the soluble protein (FCA as adjuvant):

| | 2996 | BZ232 | MC58 | NGH38 | F6124 | BZ133 |
|---|---|---|---|---|---|---|
| Soluble | 65536 | 128 | 4096 | >2048 | >2048 | 4096 |
| Insoluble | 8192 | <4 | <4 | 16 | n.d. | n.d. |

Titres with the insoluble form were, however, improved by using alum adjuvant instead:

| | | | | | | |
|---|---|---|---|---|---|---|
| Insoluble | 32768 | 128 | 4096 | >2048 | >2048 | 2048 |

Example 17

N-Terminal Fusions ('Hybrids') to 287

Expression of protein 287 as full-length with a C-terminal His-tag, or without its leader peptide but with a C-terminal His-tag, gives fairly low expression levels. Better expression is achieved using a N-terminal GST-fusion.

As an alternative to using GST as an N-terminal fusion partner, 287 was placed at the C-terminus of protein 919 ('919-287'), of protein 953 ('953-287'), and of proteins ORF46.1 ('ORF46.1-287'). In both cases, the leader peptides were deleted, and the hybrids were direct in-frame fusions.

To generate the 953-287 hybrid, the leader peptides of the two proteins were omitted by designing the forward primer downstream from the leader of each sequence; the stop codon sequence was omitted in the 953 reverse primer but included in the 287 reverse primer. For the 953 gene, the 5' and the 3' primers used for amplification included a NdeI and a BamHI restriction sites respectively, whereas for the amplification of the 287 gene the 5' and the 3' primers included a BamHI and a XhoI restriction sites respectively. In this way a sequential directional cloning of the two genes in pET21b+, using NdeI-BamHI (to clone the first gene) and subsequently BamHI-XhoI (to clone the second gene) could be achieved.

The 919-287 hybrid was obtained by cloning the sequence coding for the mature portion of 287 into the XhoI site at the 3'-end of the 919-His clone in pET21b+. The primers used for amplification of the 287 gene were designed for introducing a SalI restriction site at the 5'- and a XhoI site at the 3'- of the PCR fragment. Since the cohesive ends produced by the SalI and XhoI restriction enzymes are compatible, the 287 PCR product digested with SalI-XhoI could be inserted in the pET21b-919 clone cleaved with XhoI.

The ORF46.1-287 hybrid was obtained similarly.

The bactericidal efficacy (homologous strain) of antibodies raised against the hybrid proteins was compared with antibodies raised against simple mixtures of the component antigens:

| | Mixture with 287 | Hybrid with 287 |
|---|---|---|
| 919 | 32000 | 16000 |
| 953 | 8192 | 8192 |
| ORF46.1 | 128 | 8192 |

Data for bactericidal activity against heterologous MenB strains and against serotypes A and C were also obtained for 919-287 and 953-287:

| | 919 | | 953 | | ORF46.1 | |
|---|---|---|---|---|---|---|
| Strain | Mixture | Hybrid | Mixture | Hybrid | Mixture | Hybrid |
| MC58 | 512 | 1024 | 512 | 1024 | — | 1024 |
| NGH38 | 1024 | 2048 | 2048 | 4096 | — | 4096 |
| BZ232 | 512 | 128 | 1024 | 16 | — | — |
| MenA (F6124) | 512 | 2048 | 2048 | 32 | — | 1024 |
| MenC (C11) | >2048 | n.d. | >2048 | n.d. | — | n.d. |
| MenC (BZ133) | >4096 | >8192 | >4096 | <16 | — | 2048 |

Hybrids of ORF46.1 and 919 were also constructed. Best results (four-fold higher titre) were achieved with 919 at the N-terminus.

Hybrids 919-519His, ORF97-225His and 225-ORF97His were also tested These gave moderate ELISA fitres and bactericidal antibody responses.

Example 18

The Leader Peptide from ORF4

As shown above, the leader peptide of ORF4 can be fused to the mature sequence of other proteins (e.g. proteins 287 and 919). It is able to direct lipidation in *E.coli*.

Example 19

Domains in 564

Figure 8:
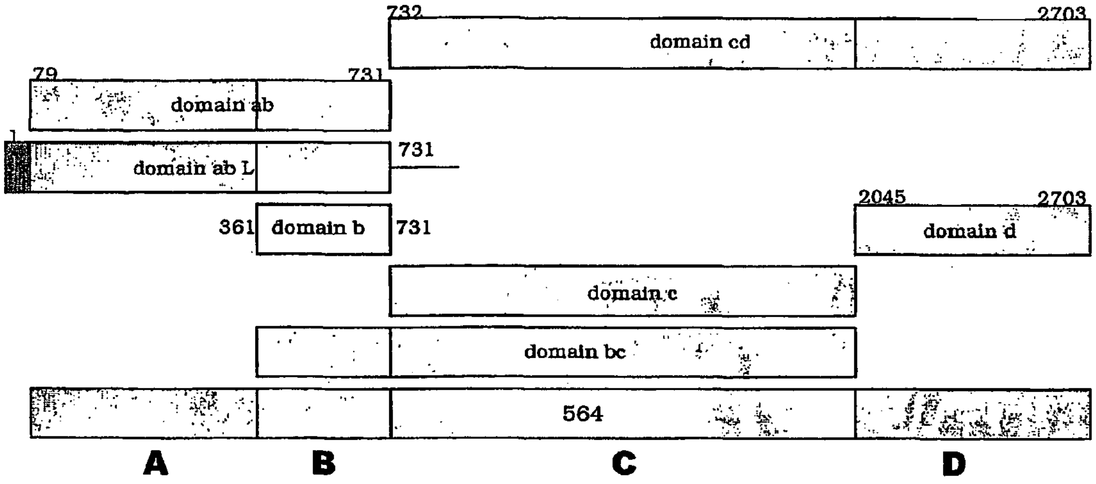
FIG. 8 shows domains of protein 564.

The protein '564' is very large (2073aa), and it is difficult to clone and express it in complete form. To facilitate expression, the protein has been divided into four domains, as shown in FIG. 8 (according to the MC58 sequence):

| | Domain | | | |
|---|---|---|---|---|
| | A | B | C | D |
| Amino Acids | 79-360 | 361-731 | 732-2044 | 2045-2073 |

These domains show the following homologies:

Domain A shows homology to other bacterial toxins:

gb|AAG03431.1|AE004443_9probable hemagglutinin [*Pseudoiuonas aeruginosa*] (38%)

gb|AAC31981.1|(139897) HecA [*Pectobacterium cbrysanthemi*] (45%)

emb|CAA36409.1|(X52156) filamentous hemagglutinin [*Bordetella pertussis*] (31%)

gb|AAC79757.1|(AF057695) large supernatant protein1 [*Haemophulus ducreyi*] (26%)

gb|AAA25657.1|(M30186) HpmA precursor [*Proteus mirabilis*] (29%)

Domain B shows no homology, and is specific to 564.

Domain C shows homology to:

gb|AAP84995.1|AE004032 HA-like secreted protein [*Xylella fastidiosa*] (33%)

gb|AAG05850.1|AE004673 hypothetical protein [*Pseudomonas aeruginosa*] (27%)

gb|AAFS8414.1AF237928 putative FHA [*Pasteurella multocisida*] (23%)

gb|AAC79757.1|(AF057695)large supernatant protein1 [*Haemophilus ducreyi*] (23%)

piR||S21010 FHA B precursor [*Bordetella pertussis*] (20%)

Domain D shows homology to other bacterial toxins:

gb|AAF84995.1|AE004032_14 HA-like secreted protein [*Xylella fastidiosa*] (29%)

Using the MC58 strain sequence, good intracellular expression of 564ab was obtained in the form of GST-fusions (no purification) and his-tagged protein; this domain-pair was also expressed as a lipoprotein, which showed moderate expression in the outer membrane/supernatant fraction.

The b domain showed moderate intracellular expression when expressed as a his-tagged product (no purification), and good expression as a GST-fusion.

The c domain showed good intracellular expression as a GST-fusion, but was insoluble. The d domain showed moderate intracellular expression as a his-tagged product (no purification). The cd protein domain-pair showed moderate intracellular expression (no purification) as a GST-fusion.

Good bactericidal assay titres were observed using the c domain and the bc pair.

Example 20

The 919 Leader Peptide

The 20mer leader peptide (SEQ ID NO:633) from 919 is discussed in example 1 above:

MKKYLFRAAL YGIAAAILAA

Figure 9:
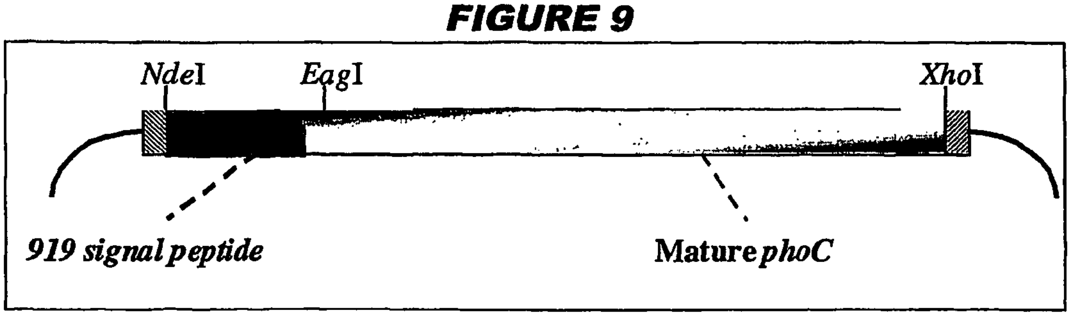
FIG. 9 shows the PhoC reporter gene driven by the 919 leader peptide.

As shown in example 1, deletion of this leader improves heterologous expression, as does substitution with the ORF4 leader peptide. The influence of the 919 leader on expression was investigated by fusing the coding sequence to the PhoC reporter gene from *Morganella morganii* [Thaller et al. (1994) *Microbiology* 140:1341-1350]. The construct (SEQ ID NO:116) was cloned in the pET21-b plasmid between the NdeI and XhoI sites (FIG. 9):

```
  1 MKKYLFRAAL YGIAAAILAA AIPAGNDATT KPDLYYLKNE QAIDSLKLLP
 51 PPPEVGSIQF LNDQAMYEKG RMLRNTERGK QAQADADLAA GGVATAFSGA
101 FGYPITEKDS PELYKLLTNM IEDAGDLATR SAKEHYMRIR PFAFYGTETC
151 NTKDQKKI1ST NGSYPSGHTS IGWATALVLA EVNPANQDAI LEEGYQLGQS
201 RVICGYHWQS DVDAARIVGS AAVATLHSDP AFQAQLAKAK QEFAQKSQK*
```

The level of expression of PhoC from this plasmid is >200-fold lower than that found for the same construct but containing the native PhoC signal peptide. The same result was obtained even after substitution of the T7 promoter with the *E.coli* Plac promoter. This means that the influence of the 919 leader sequence on expression does not depend on the promoter used.

In order to investigate if the results observed were due to some peculiarity of the 919 signal peptide nucleotide sequence (secondary structure formation, sensitivity to RNAases, etc.) or to protein instability induced by the presence of this signal peptide, a number of mutants were generated. The approach used was a substitution of nucleotides of the 919 signal peptide sequence by cloning synthetic linkers containing degenerate codons. In this way, mutants were obtained with nucleotide and/or amino acid substitutions.

Two different linkers were used, designed to produce mutations in two different regions of the 919 signal peptide sequence, in the first 19 base pairs (L1) (SEQ ID NO:117) and between bases 20-36 (S1) (SEQ ID NO:118).

```
L1: 5' T ATG AAa/g TAc/t c/tTN TTt/c a/cGC GCC GCC CTG TAC GGC ATC GCC GCC
    GCC ATC CTC GCC GCC GCG ATC CC 3'

S1: 5' T ATG AAA AAA TAC CTA TTC CGa/g GCN GCN c/tTa/g TAc/t GGc/g ATC GCC
    GCC GCC ATC CTC GCC GCC GCG ATC CC 3'
```

The alignment of some of the mutants obtained is given below.

```
L1 mutants:
9L1-a      ATGAAAAATACTTCCGCGCCGCC~~~~~~~~~~~~~~~~~~~~~~~~~~~~~~
           (SEQ ID NO: 119)

9L1-e      ATGAAAAAATACTTTTTCCGCGCCGCC~~~~~~~~~~~~~~~~~~~~~~~~~~~~~~
           (SEQ ID NO: 120)

9L1-d      ATGAAAAAATACTTTTTCCGCGCCGCC~~~~~~~~~~~~~~~~~~~~~~~~~~~~~~
           (SEQ ID NO: 121)

9L1-f      ATGAAAAAATATCTCTTTAGCGCCGCCCTGTACGGCATCGCCGCCGCCATCCTCGCCGCC
           (SEQ ID NO: 122)

919sp      ATGAAAAAATACCTATTCCGCGCCGCCCTGTACGGCATCGCCGCCGCCATCCTCGCCGCC
           (SEQ ID NO: 123)

9L1a       MKKYLFSAA~~~~~~~~~~~
           (SEQ ID NO: 124)

9L1e       MKKYFFRAA~~~~~~~~~~~
           (SEQ ID NO: 125)

9L1d       MKKYFFRAA~~~~~~~~~~~
           (SEQ ID NO: 126)

9L1f       MKKYLFSAALYGIAAAILAA
           (SEQ ID NO: 127)

919sp      MKKYLFRAALYGIAAAILAA (i.e. native signal peptide)
           (SEQ ID NO: 128)

S1 mutants:
9S1-e      ATGAAAAAATACCTATTC..................ATCGCCGCCGCCATCCTCGCCGCC
           (SEQ ID NO: 129)

9S1-c      ATGAAAAAATACCTATTCCGAGCTGCCCAATACGGCATCGCCGCCGCCATCCTCGCCGCC
           (SEQ ID NO: 130)

9S1-b      ATGAAAAAATACCTATTCCGGGCCGCCCAATACGGCATCGCCGCCGCCATCCTCGCCGCC
           (SEQ ID NO: 131)

9S1-i      ATGAAAAAATACCTATTCCGGGCGGCTTTGTACGGGATCGCCGCCGCCATCCTCGCCGCC
           (SEQ ID NO: 132)

919sp      ATGAAAAAATACCTATTCCGCGCCGCCCTGTACGGCATCGCCGCCGCCATCCTCGCCGCC
           (SEQ ID NO: 123)

9S1e       MKKYLF......IAAAILAA
           (SEQ ID NO: 133)

9S1c       MKKYLFRAAQYGIAAAILAA
           (SEQ ID NO: 134)

9S1b       MKKYLFRAAQYGIAAAILAA
           (SEQ ID NO: 135)

9S1i       MKKYLFRAALYGIAAAILAA
           (SEQ ID NO: 136)

919sp      MKKYLFRAALYGIAAAILAA
           (SEQ ID NO: 128)
```

As shown in the sequences alignments, most of the mutants analysed contain in-frame deletions which were unexpectedly produced by the host cells.

Figure 10:
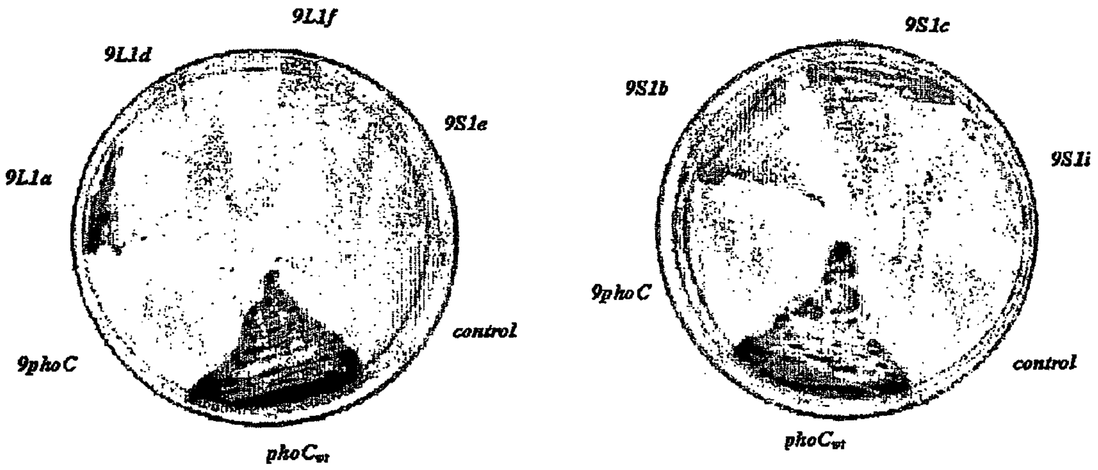
FIG. 10 shows the results obtained using mutants of the leader peptide.

Selection of the mutants was performed by transforming *E. coli* BL21(DE3) cells with DNA prepared from a mixture of L1 and S1 mutated clones. Single transformants were screened for high PhoC activity by streaking them onto LB plates containing 100 μg/ml ampicillin, 50 μg/ml methyl green, 1 mg/ml PDP (phenolphthaleindiphosphate). On this medium PhoC-producing cells become green (FIG. 10). for A quantitative analysis of PhoC produced by these mutants was carried out in liquid medium using pNPP as a substrate PhoC activity. The specific activities measured in cell extracts and supernatants of mutants grown in liquid medium for 0, 30, 90, 180 min. were:

| | 0 | 30 | 90 | 180 |
|---|---|---|---|---|
| CELL EXTRACTS | | | | |
| control | 0.00 | 0.00 | 0.00 | 0.00 |

-continued

| | 0 | 30 | 90 | 180 |
|---|---|---|---|---|
| 9phoC | 1.11 | 1.11 | 3.33 | 4.44 |
| 9S1e | 102.12 | 111.00 | 149.85 | 172.05 |
| 9L1a | 206.46 | 111.00 | 94.35 | 83.25 |
| 9L1d | 5.11 | 4.77 | 4.00 | 3.11 |
| 9L1f | 27.75 | 94.35 | 82.14 | 36.63 |
| 9S1b | 156.51 | 111.00 | 72.15 | 28.86 |
| 9S1c | 72.15 | 33.30 | 21.09 | 14.43 |
| 9S1i | 156.51 | 83.25 | 55.50 | 26.64 |
| phoCwt | 194.25 | 180.93 | 149.85 | 142.08 |
| SUPERNATANTS | | | | |
| control | 0.00 | 0.00 | 0.00 | 0.00 |
| 9phoC | 0.33 | 0.00 | 0.00 | 0.00 |
| 9S1e | 0.11 | 0.22 | 0.44 | 0.89 |
| 9L1a | 4.88 | 5.99 | 5.99 | 7.22 |
| 9L1d | 0.11 | 0.11 | 0.11 | 0.11 |
| 9L1f | 0.11 | 0.22 | 0.11 | 0.11 |
| 9S1b | 1.44 | 1.44 | 1.44 | 1.67 |
| 9S1c | 0.44 | 0.78 | 0.56 | 0.67 |
| 9S1i | 0.22 | 0.44 | 0.22 | 0.78 |
| phoCwt | 34.41 | 43.29 | 87.69 | 177.60 |

Some of the mutants produce high amounts of PhoC and in particular, mutant 9L1a can secrete PhoC in the culture medium. This is noteworthy since the signal peptide sequence of this mutant is only 9 amino acids long. This is the shortest signal peptide described to date.

Example 21

C-Terminal Deletions of Maf-Related Proteins

MafB-related proteins include 730, ORF46 and ORF29.

The 730 protein from MC58 has the following sequence (SEQ ID NO:137):

```
  1 VKPLRRLTNL LAACAVAAAA LIQPALAADL AQDPFITDNA
                                    QRQHYEPGGK

 51 YHLFGDPRGS VSDRTGKINV IQDYTHQMGN LLIQQANING
                                    TIGYHTRFSG

101 HGHEBHAPFD NHAADSASEE KGNVDEGPTV YRLNWEGHEH
                                    HPADAYDGPK

151 GGNYPKPTGA RDEYTYHVNG TARSIKTJNPT DTRSIRQRIS
                                    DNYSNLGSNF

201 SDRADEANRK NFEHNAKLDR WGNSMEFING VAAGALNPFI
                                    SAGEALGIGD

251 ILYGTRYAID KAAMRNIAPL PAEGKFAVIG GLGSVAGFEK
                                    NTREAVDRWI

301 QENPNAAETV EAVPNVAAAA KVAKLAKAAK PGKAAVSGDF
                                    ADSYKKKLAL

351 SDSARQLYQN AKYIREALDIH YEDLIRRXTD GSSKFINGRE
                                    IDAVTNDALI

401 AKRTISAID KPKNFLNQKN RKQIKATIEA ANQQGKRAEF
                                    WFKYGVHSQV

451 KSYIESKGGI VKTGLGD*
```

The leader peptide is underlined.

730 shows similar features to ORF46 (see example 8 above):

- as for Orf46, the conservation of the 730 sequence among MenB, MenA and gonococcus is high (>80%) only for the N-terminal portion. The C-terminus, from ~340, is highly divergent.
- its predicted secondary structure contains a hydrophobic segment spanning the central region of the molecule (aa. 227-247).
- expression of the full-length gene in *E. coli* gives very low yields of protein. Expression from tagged or untagged constructs where the signal peptide sequence has been omitted has a toxic effect on the host cells. In other words, the presence of the full-length mature protein in the cytoplasm is highly toxic for the host cell while its translocation to the periplasm (mediated by the signal peptide) has no detectable effect on cell viability. This "intracellular toxicity" of 730 is particularly high since clones for expression of the leaderless 730 can only be obtained at very low frequency using a recA genetic background (*E. coli* strains: HB 101 for cloning; HMS 174(DE3) for expression).

To overcome this toxicity, a similar approach was used for 730 as described in example 8 for ORF46. Four C-terminal truncated forms were obtained, each of which is well expressed. All were obtained from intracellular expression of His-tagged leaderless 730.

Form A consists of the N-terminal hydrophilic region of the mature protein (aa 28-226). This was purified as a soluble His-tagged product, having a higher-than-expected MW.

Form B extends to the end of the region conserved between serogroups (aa 28-340). This was purified as an insoluble His-tagged product.

Figure 11A:
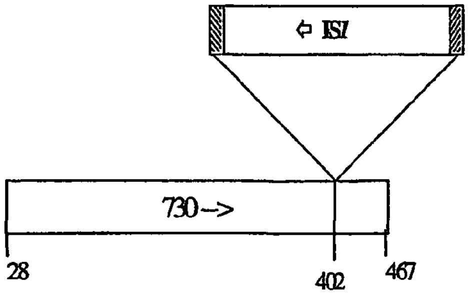
FIG. 11 shows insertion mutants of protein 730 (A: 730C1; B: 730-C2).
Figure 11B:
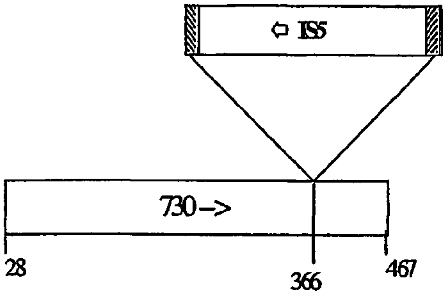

The C-terminal truncated forms named C1 and C2 were obtained after screening for clones expressing high levels of 730-His clones in strain HMS174(DE3). Briefly, the pET21b plasmid containing the His-tagged sequence coding for the full-length mature 730 protein was used to transform the recA strain HMS174(DE3). Transformants were obtained at low frequency which showed two phenotypes: large colonies and very small colonies. Several large and small colonies were analysed for expression of the 730-His clone. Only cells from large colonies over-expressed a protein recognised by anti-730A antibodies. However the protein over-expressed in different clones showed differences in molecular mass. Sequencing of two of the clones revealed that in both cases integration of an *E. coli* IS sequence had occurred within the sequence coding for the C terminal region of 730. The two integration events have produced in-frame fusion with 1 additional codon in the case of C1, and 12 additional codons in the case of C2 (FIG. 11). The resulting "mutant" forms of 730 have the following sequences:

```
730-C1 (due to an IS1 insertion - FIG. 11A)
(SEQ ID NO: 138)
  1 MADLAQDPFI TDNAQRQHYE PGGXYHLFGD PRGSVSDRTG
                                    KINVIQDYTH

 51 QMGNLLIQQA NINGTIGYHT RFSGHGHEEH APFDNHAADS
                                    ASEEKGNVDE

101 GFTVYRLNWE GHEHHPADAY DGPKGGNYPK PTGARDEYTY
                                    HVNGTARSIK

151 LNPTDTRSIR QRISDNYSNL GSNFSDRADE ANRKMFEHNA
                                    KLDRWGNSME

201 FINGVAAGAL NPFISAGEAL GIGDILYGTR YAIDKAAMRN
                                    IAPLPABGKF

251 AVIGGLGSVA GFEKNTREAV DRWIQENPNA AETVEAVFNV
                                    AAAAKVAKLA

301 KAAKPGKAAV SGDFADSYKK KLALSDSARQ LYQNAKYREA
                                    LDIHYEDLIR

352 RKTDGSSKFI NGREIDAVTN DALIQAR*
```

The additional amino acid produced by the insertion is underlined.

```
730-c2 (due to en IS5 insertion - FIG. 11B)
(SEQ ID NO: 139)
  1 MADLAQDPFI TDNAQRQHYE PGGKYHLFGD PRGSVSDRTG
                                      KINVIQDYTH

 51 QMGNLLIQQA NINGTIGYHT RFSGHGHEEH APFDNHAADS
                                      ASHEKGNVDE

101 GFTVYELNWE GHEHHPADAY DGPKGGNYPK PTGARDEYTY
                                      HVNGTARSIK

151 LNPTDTRSIR QRISDNYSNL GSNFSDRADE ANRKMFEHNA
                                      KLDRWGNSME

201 FINGVAAGAL NPFISAGEAL GIGDILYGTR YAIDKAAMRN
                                      IAPLPAEGKF

251 AVIGGLGSVA GFEKNTREAV DRWIQENPNA AETVEAVFNV
                                      AAAAKVAKLA

301 KAAKPGKAAV SGDFADSYKK KLALSDSARQ LYQNAXYREA
                                      LGKVRISGEI

352 LLG*
```

The additional amino acids produced by the insertion are underlined.

In conclusion, intracellular expression of the 730-C1 form gives very high level of protein and has no toxic effect on the host cells, whereas the presence of the native C-terminus is toxic. These data suggest that the “intracellular toxicity” of 730 is associated with the C-terminal 65 amino acids of the protein.

Equivalent truncation of ORF29 to the first 231 or 368 amino acids has been performed, using expression with or without the leader peptide (amino acids 1-26; deletion gives cytoplasmic expression) and with or without a His-tag.

Example 22

Domains in 961

Figure 12:
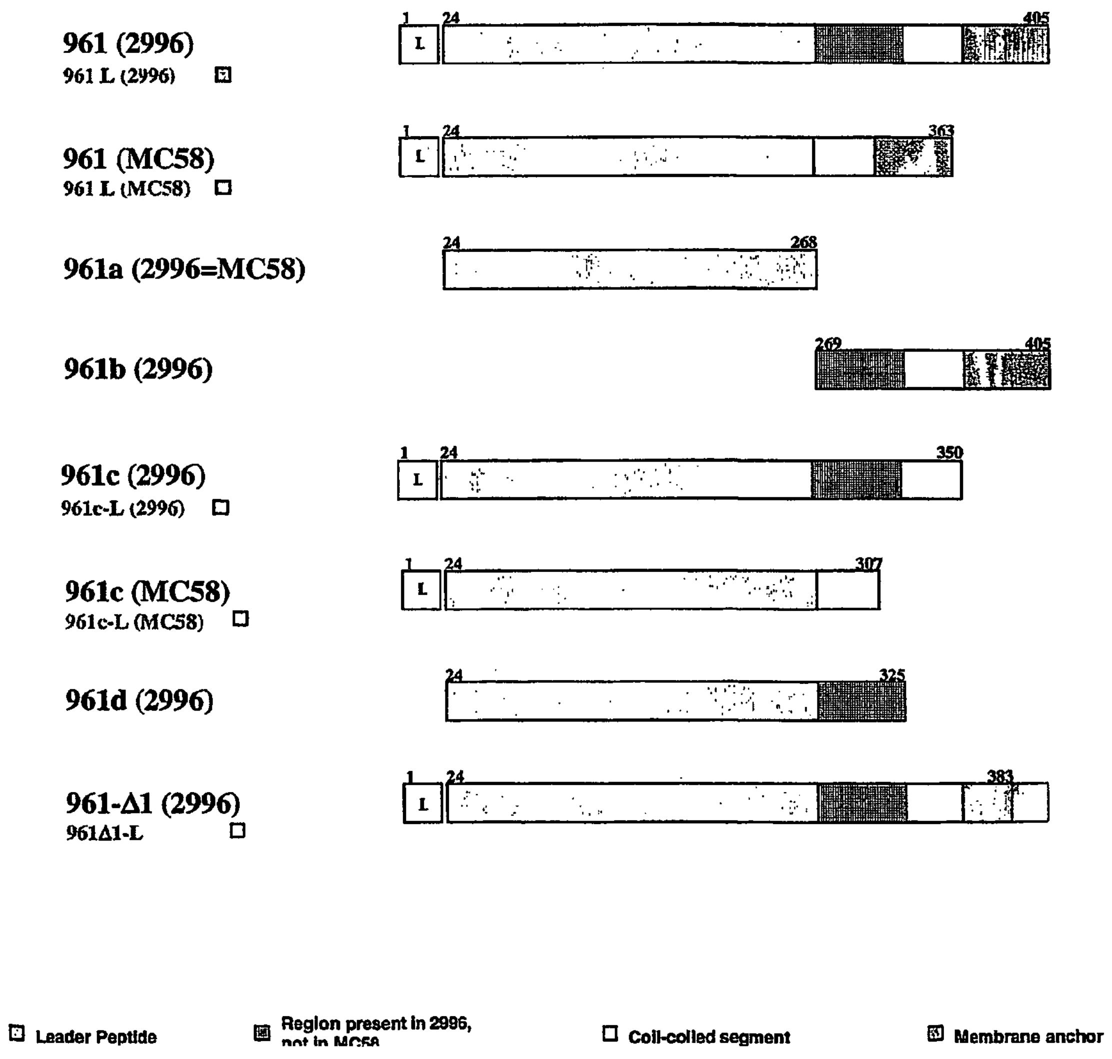
FIG. 12 shows domains of protein 961.

As described in example 9 above, the GST-fusion of 961 was the best-expressed in *E.coli*. To improve expression, the protein was divided into domains (FIG. 12).

The domains of 961 were designed on the basis of YadA (an adhesin produced by Yersinia which has been demonstrated to be an adhesin localized on the bacterial surface that forms oligomers that generate surface projection [Hoiczyk et al. (2000) *EMBO J* 19:5989-99]) and are: leader peptide, head domain, coiled-coil region (stalk), and membrane anchor domain.

These domains were expressed with or without the leader peptide, and optionally fused either to C-terminal His-tag or to N-terminal GST. *E.coli* clones expressing different domains of 961 were analyzed by SDS-PAGE and western blot for the production and localization of the expressed protein, from over-night (o/n) culture or after 3 hours induction with IPTG. The results were:

| | Total lysate (Western Blot) | Periplasm (Western Blot) | Supernatant (Western Blot) | OMV SDS-PAGE |
|---|---|---|---|---|
| 961 (o/n) | – | – | – | |
| 961 (IPTG) | +/– | – | – | |
| 961-L (o/n) | + | – | – | + |
| 961-L (IPTG) | + | – | – | + |
| 961c-L (o/n) | – | – | – | |
| 961c-L (IPTG) | + | + | + | |
| $961\Delta_1$-L (o/n) | – | – | – | |
| $961\Delta_1$-L (IPTG) | + | – | – | + |

The results show that in *E.coli*:

961-L is highly expressed and localized on the outer membrane. By western blot analysis two specific bands have been detected: one at ~45 kDa (the predicted molecular weight) and one at ~180 kDa, indicating that 961-L can form oligomers. Additionally, these aggregates are more expressed in the over-night culture (without IPTG induction). OMV preparations of this clone were used to immunize mice and serum was obtained. Using overnight culture (predominantly by oligomeric form) the serum was bactericidal; the IPTG-induced culture (predominantly monomeric) was not bactericidal.

$961\Delta_1$-L (with a partial deletion in the anchor region) is highly expressed and localized on the outer membrane, but does not form oligomers;

the 961c-L (without the anchor region) is produced in soluble form and exported in the supernatant.

Titres in ELISA and in the serum bactericidal assay using His-fusions were as follows:

| | ELISA | Bactericidal |
|---|---|---|
| 961a (aa 24-268) | 24397 | 4096 |
| 961b (aa 269-405) | 7763 | 64 |
| 961c-L | 29770 | 8192 |
| 961c (2996) | 30774 | >65536 |
| 961c (MC58) | 33437 | 16384 |
| 961d | 26069 | >65536 |

*E.coli* clones expressing different forms of 961 (961, 961-L, $961\Delta_1$-L and 961c-L) were used to investigate if the 961 is an adhesin (cf. YadA). An adhesion assay was performed using (a) the human epithelial cells and (b) *E.coli* clones after either over-night culture or three hours IPTG induction. 961-L grown over-night ($961\Delta_1$-L) and IPTG-induced 961c-L (the clones expressing protein on surface) adhere to human epithelial cells.

961c was also used in hybrid proteins (see above). As 961 and its domain variants direct efficient expression, they are ideally suited as the N-terminal portion of a hybrid protein.

Example 23

Further Hybrids

Further hybrid proteins of the invention are shown below (see also FIG. 14). These are advantageous when compared to the individual proteins:

```
ORF46.1-741
(SEQ ID NOS: 140 and 141)
  1   ATGTCAGATT TGGCAAACGA TTCTTTTATC CGGCAGGTTC TCGACCGTCA
```

-continued

```
51   GCATTTCGAA CCCGACGGGA AATACCACCT ATTCGGCAGC AGGGGGGAAC
101  TTGCCGAGCG CAGCGGCCAT ATCGGATTGG GAAAAATACA AAGCCATCAG
151  TTGGGCAACC TGATGATTCA ACAGGCGGCC ATTAAAGGAA ATATCGGCTA
201  CATTGTCCGC TTTTCCGATC ACGGGCACGA AGTCCATTCC CCCTTCGACA
251  ACCATGCCTC ACATTCCGAT TCTGATGAAG CCGGTAGTCC CGTTGACGGA
301  TTTAGCCTTT ACCGCATCCA TTGGGACGGA TACGAACACC ATCCCGCCGA
351  CGGCTATGAC GGGCCACAGG GCGGCGGCTA TCCCGCTCCC AAAGGCGCGA
401  GGGATATATA CAGCTACGAC ATAAAAGGCG TTGCCCAAAA TATCCGCCTC
451  AACCTGACCG ACAACCGCAG CACCGGACAA CGGCTTGCCG ACCGTTTCCA
501  CAATGCCGGT AGTATGCTGA CGCAAGGAGT AGGCGACGGA TTCAAACGCG
551  CCACCCGATA CAGCCCCGAG CTGGACAGAT CGGGCAATGC CGCCGAAGCC
601  TTCAACGGCA CTGCAGATAT CGTTAAAAAC ATCATCGGCG CGGCAGGAGA
651  AATTGTCGGC GCAGGCGATG CCGTGCAGGG CATAAGCGAA GGCTCAAACA
701  TTGCTGTCAT GCACGGCTTG GGTCTGCTTT CCACCGAAAA CAAGATGGCG
751  CGCATCAACG ATTTGGCAGA TATGGCGCAA CTCAAAGACT ATGCCGCAGC
801  AGCCATCCGC GATTGGGCAG TCCAAAACCC CAATGCCGCA CAAGGCATAG
851  AAGCCGTCAG CAATATCTTT ATGGCAGCCA TCCCCATCAA AGGGATTGGA
901  GCTGTTCGGG GAAAATACGG CTTGGGCGGC ATCACGGCAC ATCCTATCAA
951  GCGGTCGCAG ATGGGCGCGA TCGCATTGCC GAAAGGGAAA TCCGCCGTCA
1001 GCGACAATTT TGCCGATGCG GCATACGCCA AATACCCGTC CCCTTACCAT
1051 TCCCGAAATA TCCGTTCAAA CTTGGAGCAG CGTTACGGCA AAGAAAACAT
1101 CACCTCCTCA ACCGTGCCGC CGTCAAACGG CAAAAATGTC AAACTGGCAG
1151 ACCAACGCCA CCCGAAGACA GGCGTACCGT TTGACGGTAA AGGGTTTCCG
1201 AATTTTGAGA AGCACGTGAA ATATGATACG GGATCCGGAG GGGGTGGTGT
1251 CGCCGCCGAC ATCGGTGCGG GGCTTGCCGA TGCACTAACC GCACCGCTCG
1301 ACCATAAAGA CAAAGGTTTG CAGTCTTTGA CGCTGGATCA GTCCGTCAGG
1351 AAAAACGAGA AACTGAAGCT GGCGGCACAA GGTGCGGAAA AAACTTATGG
1402 AAACGGTGAC AGCCTCAATA CGGGCAAAAT GAAGAACGAC AAGGTCAGCC
1451 GTTTCQACTT TATCCGCCAA ATCGAAGTGG ACGGGCAGCT CATTACCTTG
1501 GAGAGTGGAG AGTTCCAAGT ATACAAACAA AGCCATTCCG CCTTAACCGC
1551 CTTTCAGACC GAGCAAATAC AAGATTCGGA GCATTCCGGG AAGATGGTTG
1601 CGAAACGCCA GTTCAGAATC GGCGACATAG CGGGCGAAQA TACATCTTTT
1651 GACAAGCTTC CCGAAGGCGG CAGGGCGACA TATCGCGGGA CGGCGTTCGG
1701 TTCAGACGAT GCCGGCGGAA AACTGACCTA CACCATAGAT TTCGCCGCCA
1751 AGCAGGGAAA CGGCAAAATC GAACATTTGA AATCGCCAGA ACTCAATGTC
1801 GACCTGGCCG CCGCCGATAT CAAGCCGGAT GGAAAACGCC ATGCCGTCAT
1851 CAGCGGTTCC GTCCTTTACA ACCAAGCCGA GAAAGGCAGT TACTCCCTCG
1901 GTATCTTTGG CGGAAAAGCC CAGGAAGTTG CCGGCAGCGC GGAAGTGAAA
1951 ACCGTAAACG GCATACGCCA TATCGGCCTT GCCGCCAAGC AACTCGAGCA
2001 CCACCACCAC CACCACTGA
```

-continued

```
  1 MSDLANDSFI RQVLDRQHFE PDGKYHLFGS RGELABRSGH IGLGKIQSHQ

 51 LGNIJMIQQAA IKGNIGYIVR FSDHGHEVHS PFDNHASHSD SDEAGSPVDG

101 FSLYRIHWDG YEHHPADGYD GPQGGGYPAP KGARDIYSYD IKGVAQNIEL

151 NLTDNRSTGQ RLADRFHNAG SMLTQGVGDG FKRATRYSPE LDRSGNAAEA

201 PNGTADIVKN IIGAAGEIVG AGDAVQGISE GSNIAVMHGL GLLSTENKMA

251 RINDLADMAQ IJKDYAAAAIR DWAVQNPNAA QGIEAVSNIF HAAIPIKGIG

301 AVRGKYGLGG IThHPIKRSQ MGAIALPKGK SAVSDNFADA AYAKYPSPYH

351 SRNIRSNLEQ RYGKENITSS TVPPSNGKNV KLADQRHPKT GVPFDGKGFP

401 NFEKHVKYDT GSGGGGVAAD IGAGLADALT APLDHKDKGL QSLTLDQSVR

451 RNEKLKLAAQ GABKTYGNGD SLNTGKLKND KVSRPDFIRQ IEVDGQLITL

501 ESGEFQVYKQ SHSALTAPQT BQIQDSEHSG KMVAKRQPRI GDIAGEHTSP

551 DKLPBGGRAT YRGTAFGSDD AGGKLTYTID FAAKQGNGKI EELKSPBLNV

601 DLAAADIKPD GKRHAVISGS VLYNQAEKGS YSLGIFGGKA QEVAGSABVK

651 TVNGIEHIGL AAKQLEHHHH HH*
```

ORF46.1-961
(SEQ ID NOS: 142 and 143)

```
     ATGTCAGATT TGGCAAACGA TTCTTTTATC CGGCAGGTTC TCGACCGTCA

  51 GCATTTCGAA CCCGACGGGA AATACCACCT ATTCGGCAGC AGGGGGGAAC

 101 TTGCCGAGCG CAGCGGCCAT ATOGGATTOG GAAAAATACA AAGCCATCAG

 151 TTGGGCAACC TGATGATTCA ACAGGCGGCC ATTAAAGGAA ATATCGGCTA

 201 CATTGTCCGC TTTTCCGATC ACGGGCACGA AGTCCATTCC CCCTTCGACA

 251 ACCATGCCTC ACATTCCGAT TCTGATGAAG CCGGTAGTCC CGTTGACGGA

 301 TTTAGCCTTT ACCGCATCCA TTGGGACGGA TACGAACACC ATCCCGCCGA

 351 CGGCTATGAC GGGCCACAGG GCGGCGGCTA TCCCGCTCCC AAAGGCGCGA

 401 GGGATATATA CAGOTACOAC ATAAAAGGCG TTGCCCAAAA TATCCGCCTC

 451 AACCTGACCG ACAACCGCAG CACCGGACAA CGGCTTGCCG ACCGTTTCCA

 501 CAATGCCGGT AGTATGCTGA CGCAAGGAGT AGGCGACGGA TTCAAACGCG

 551 CCACCCGATA CAGCCCCGAG CTGGACAGAT CGGGCAATGC CGCCGAAGCC

 601 TTCAACGGCA CTGCAGATAT CGTTAAAAAC ATCATCGGCG CGGCAGGAGA

 651 AATTGTCGGC GCAGGCGATG CCGTGCAGGG CATAAGCGAA GGCTCAAACA

 701 TTGCTGTCAT GCACGGCTTG GGTCTGCTTT CCACCGAAAA CAAGATGGCG

 751 CGCATCAACG ATTTGGCAGA TATGGCGCAA CTCAAAGACT ATGCCGCAGC

 801 AGCCATCCGC GATTGGGCAG TCCAAAACCC CAATGCCGCA CAAGGCATAG

 851 AAGCCGTCAG CAATATCTTT ATGGCAGCCA TCCCCATCAA AGGGATTGGA

 901 GCTGTTCGGG GAAAATACGG CTTGGGCGGC ATCACGGCAC ATCCTATCAA

 951 GCGGTCGCAG ATGGGCGCGA TCGCATTGCC GAAAGGGAAA TCCGCCGTCA

1001 GCGACAATTT TGCCGATGCG GCATACGCCA AATACCCGTC CCCTTACCAT

1051 TCCCGAAATA TCCGTTCAAA CTTGGAGCAG CGTTACGGCA AAGAAAACAT

1101 CACCTCCTCA ACCGTGCCGC CGTCAAACGG CAAAAATGTC AAACTGGCAG

1151 ACCAACGCCA CCCGAAGACA GGCGTACCGT TTGACGGTAA AGGGTTTCCG

1201 AATTTTGAGA AGCACGTGAA ATATGATACG GGATCCGGAG GAGGAGGAGC
```

-continued

```
1251 CACAAACGAC GACGATGTTA AAAAAGCTGC CACTGTGGCC ATTGCTGCTG
1301 CCTACAACAA TGGCCAAGAA ATCAACGGTT TCAAAGCTGG AGAGACCATC
1351 TACGACATTG ATGAAGACGG CACAATTACC AAAAAAGACG CAACTGCAGC
1401 CGATGTTGAA GCCGACGACT TTAAAGGTCT GGGTCTGAAA AAAGTCGTGA
1451 CTAACCTGAC CAAAACCGTC AATGAAAACA AACAAAACGT CGATGCCAAA
1501 GTAAAAGCTG CAGAATCTGA AATAGAAAAG TTAACAACCA AGTTAGCAGA
1551 CACTGATGCC GCTTTAGCAG ATACTGATGC CGCTCTGGAT GCAACCACCA
1601 ACGCCTTGAA TAAATTGGGA GAAAATATAA CGACATTTGC TGAAGAGACT
1651 AAGACAAATA TCGTAAAAAT TGATGAAAAA TTAGAAGCCG TGGCTGATAC
1701 CGTCGACAAG CATGCCGAAG CATTCAACGA TATCGCCGAT TCATTGGATG
1751 AAACCAACAC TAAGGCAGAC GAAGCCGTCA AAACCGCCAA TGAAGCCAAA
1801 CAGACGGCCG AAGAAACCAA ACAAAACGTC GATGCCAAAG TAAAAGCTGC
1851 AGAAACTGCA GCAGGCAAAG CCGAAGCTGC CGCTGGCACA GCTAATACTG
1901 CAGCCGACAA GGCCGAAGCT GTCGCTGCAA AAGTTACCGA CATCAAAGCT
1951 GATATCGCTA CGAACAAAGA TAATATTGCT AAAAAAGCAA ACAGTGCCGA
2001 CGTGTACACC AGAGAAGAGT CTGACAGCAA ATTTGTCAGA ATTGATGGTC
2051 TGAACGCTAC TACCGAAAAA TTGGACACAC GCTTGGCTTC TGCTGAAAAA
2101 TCCATTGCCG ATCACGATAC TCGCCTGAAC GGTTTGGATA AAACAGTGTC
2151 AGACCTGCGC AAAGAAACCC GCCAAGGCCT TGCAGAACAA GCCGCGCTCT
2201 CCGGTCTGTT CCAACCTTAC AACGTGGGTC GGTTCAATGT AACGGCTGCA
2251 GTCGGCGGCT ACAAATCCGA ATCGGCAGTC GCCATCGGTA CCGGCTTCCG
2301 CTTTACCGAA AACTTTGCCG CCAAAGCAGG CGTGGCAGTC GGCACTTCGT
2351 CCGGTTCTTC CGCAGCCTAC CATGTCGGCG TCAATTACGA GTGGCTCGAG
2401 CACCACCACC ACCACCACTG A

   1 MSDLPJWSFI RQVLDRQHFE PDGKYHLFGS RGELAERSGH IGLGKIQSHQ
  51 LGNLHIQQAA IKGNIGYIVR FSDHGHEVHS PFDNHASHSD SDEAGSPVDG
 101 FSLYPJHWDG YEHHPADGYD GPQGGGYPAP KGAEDIYSYD IKGVAQNIEL
 151 NLTDNRSTGQ RLADRFHNAG BMLTQGVGDG FKRATRYSPE LDRSGNAAEA
 201 FNGTADIVKN IIGAAGBIVG AGDAVQGISB GSNIAVMHGL GLLSTENKMA
 251 RINflLADMAQ LKDYAAAAIR DWAVQNPNAA QGIEAVSNIF MAAIPIKGIG
 301 AVRGKYGLGG ITAHPIKRSQ HGAIALPKGK SAVBDNFADA AYAKYPSPYH
 351 SRNIRBNLEQ RYGXENITSS TVPPSNGKNV KLADQRHPKT GVPFDGKGFP
 401 NFEKHVKYDT GSGGGGATND DDVKKAATVA IAAAYNNGQE INGFKAGETI
 451 YDIDEDGTIT KKDATAADVE ADDPKGLGLK KVVTNLTKTV NENKQNVDAK
 501 VKAAESHIEK LTTKLADTDA ALADTDAALD ATTNALNKLG ENITTFAEET
 551 KTNIVKIDEK LEAVADTVDK HAEAFNDIAD SLDETNTKAD EAVKTANEAK
 601 QTAEETKQNV DAKVKAABTA AGKAEAAAGT ANTAADKAEA VAAKVTDIKA
 651 DIATNKDNIA KKMISADVYT REESDSKFVR IDGLNATTEK LDTPLASAEK
 701 SIADHDTELN GLDRTVSDLR KETRQGLAEQ AALSGLPQPY NVGRFNVTAA
 751 VGGYKSESAV AIGTGFRFTE NKAAKAGVAV GTSSGSSAAY HVGVNYEWLE
```

-continued

```
 801 HHHHHH*

ORF46.1-961c
(SEQ ID NOS: 144 and 145)
   1 ATGTCAGATT TGGCAAACGA TTCTTTTATC CGGCAGGTTC TCGACCGTCA

  51 GCATTTCGAA CCCGACGGGA AATACCACCT ATTCGGCAGC AGGGGGGAAC

 101 TTGCCGAGCG CAGCGGCCAT ATCGGATTGG GAAAAATACA AAGCCATCAG

 151 TTGGGCAACC TGATGATTCA ACAGGCGGCC ATTAAAGGAA ATATCGGCTA

 201 CATTGTCCGC TTTTCCQATC ACGGGCACGA AGTCCATTCC CCCTTCGACA

 251 ACCATGCCTC ACATTCCGAT TCTGATGAAG CCGGTAGTCC CGTTGACGGA

 301 TTTAGCCTTT ACCGCATCCA TTGGGACGGA TACGAACACC ATCCCGCCGA

 351 CGGCTATGAC GGGCCACAGG GCGGCGGCTA TCCCGCTCCC AAAGGCGCGA

 401 GGGATATATA CAGCTACGAC ATAAAAGGCG TTGCCCAAAA TATCCGCCTC

 451 AACCTGACCG ACAACCGCAG CACCGGACAA CGGCTTGCCG ACCGTTTCCA

 501 CAATGCCGGT AGTATGCTGA CGCAAGGAGT AGGCGACGGA TTCAAACGCG

 551 CCACCCGATA CAGCCCCGAG CTGGACAGAT CGGGCAATGC CGCCGAAGCC

 601 TTCAACGGCA CTGCAGATAT CGTTAAAAAC ATCATCGGCG CGGCAGGAGA

 651 AATTGTCGGC GCAGGCGATG CCGTGCAGGG CATAAGCGAA GGCTCAAACA

 701 TTGCTGTCAT GCACGGCTTG GGTCTGCTTT CCACCGAAAA CAAGATGGCG

 751 CGCATCAACG ATTTGGCAGA TATGGCGCAA CTCAAAGACT ATGCCGCAGC

 801 AGCCATCCGC GATTGGGCAG TCCAAAACCC CAATGCCGCA CAAGGCATAG

 851 AAGCCGTCAG CAATATCTTT ATGGCAGCCA TCCCCATCAA AGGGATTGGA

 901 GCTGTTCGGG QAAAATACGG CTTGGGCGGC ATCACGGCAC ATCCTATCAA

 951 GCGGTCGCAG ATGGGCGCGA TCGCATTGCC GAAAGGGAAA TCCGCCGTCA

1001 GCGACAATTT TGCCGATGCG GCATACGCCA AATACCCGTC CCCTTACCAT

1051 TCCCGAAATA TCCGTTCAAA CTTGGAGCAG CGTTACGGCA AAGAAAACAT

1101 CACCTCCTCA ACCGTGCCGC CGTCAAACGG CAAAAATGTC AAACTGGCAQ

1151 ACCAACGCCA CCCGAAGACA GGCGTACCGT TTGACGGTAA AGGGTTTCCG

1201 AATTTTGAGA AGCACGTGAA ATATGATACG GGATCCGGAG GAGGAGGAGC

1251 CACAAACGAC GACGATGTTA AAAAAGCTGC CACTGTGGCC ATTGCTGCTG

1301 CCTACAACAA TGGCCAAGAA ATCAACGGTT TCAAAGCTOG AGAGACCATC

1351 TACGACATTG ATGAAGACGG CACAATTACC AAAAAAGACG CAACTGCAGC

1401 CGATGTTGAA GCCGACGACT TTAAAGGTCT GGGTCTGAAA AAAGTCGTGA

1451 CTAACCTGAC CAAAACCGTC AATGAAAACA AACAAAACGT CGATGCCAAP

1501 GTAAAAGCTG CAGAATCTGA AATAGAAAAG TTAACAACCA AGTTAGCAGA

1551 CACTGATGCC GCTTTAGCAG ATACTGATGC CGCTCTGGAT GCAACCACCA

1601 ACGCCTTGAA TAAATTGGGA GAAAATATAA CGACATTTGC TGAAGAGACT

1651 AAGACAAATA TCGTAAAAAT TGATGAAAAA TTAGAAGCCG TGGCTGATAC

1701 CGTCGACAAG CATGCCGAAG CATTCAACGA TATCQCCGAT TCATTGGATG

1751 AAACCAACAC TAAGGCAGAC GAAGCCGTCA AAACCGCCAA TGAAGCCAAA

1801 CAGACGGCCG AAGAAACCAA ACAAAACGTC GATGCCAAAG TAAAAGCTGC

1851 AGAAACTGCA GCAGGCAAAG CCGAAGCTGC CGCTGGCACA GCTAATACTG
```

-continued

```
1901 CAGCCGACAA GGCCGAAGCT GTCGCTGCAA AAGTTACCGA CATCAAAGCT
1951 GATATCGCTA CGAACAAAGA TAATATTGCT AAAAAAGCAA ACAGTGCCGA
2001 CGTGTACACC AGAGAAGAGT CTGACAGCAA ATTTGTCAGA ATTGATGGTC
2051 TGAACGCTAC TACCGAAAAA TTGGACACAC GCTTGGCTTC TGCTGAAAAA
2101 TCCATTGCCG ATCACGATAC TCGCCTGAAC GGTTTGGATA AAACAGTGTC
2151 AGACCTGCGC AAAGAAACCC GCCAAGGCCT TGCAGAACAA GCCGCGCTCT
2201 CCGGTCTGTT CCAACCTTAC AACGTGGGTO TCGAGCACCA CCACCACCAC
2251 CACTGA

   1 MSDLANDSFI RQVIJDRQHFE PDGKYHLFGS RGELAERSGH IGLGKIQSHQ
  51 LGNIJHIQQAA IKGNIGYIVR FSDHGHEVHS PFDNHASHSD SDEAGSPVDG
 101 FSLYRIHWDG YEHHPADGYD GPQGGGYPAP KGARDIYSYD IKGVAQNIRL
 151 NLTDNRSTGQ RLADRPHNAG SMLTQGVGDG FKRATRYSPE LDRSGNAAEA
 201 FNGTADIVKN IIGAAGBIVG AGDAVQGISE GSNIAVMIGL GLLSTENKMA
 251 RINDLAflHAQ LKDYAAAAIR DWAVQNPNAA QGIEAVSNIF MIAIPIRGIG
 301 AVRGKYGLGG ITAHPIKRSQ MGAIALPKGK SAVSDNFADA AYAKYPSPYH
 351 SRNIRSNLEQ RYGKENITSS TVPPSNGKNV KLADQRHPKT GVPFDGKGFP
 401 NFEKHVKYDT GSGGGGATND DDVKKAATVA IAAAYNNGQB INGFKAGETI
 451 YDIDEDGTIT KKDATAADVE ADDFKGLGLK KVVTNLTKTV NENKQNVDAX
 501 VKAABSEIEK LTTKLADTDA ALADTDAALD ATTNALNKLG ENITTFAEET
 551 KTNIVKIDBK LEAVADTVDK HAEAFNDIAD SLDETNTKAD EAVKTANEAK
 601 QTAEETKQNV DAKVKAAETA AGKAEAAAGT ANTAADKAEA VAAKVTDIRA
 651 DIATNKDNIA KKANSADVYT REESDSKFVR IDGLNATTRK LDTRLASAEK
 701 SIADHDTRLN GLDKTVSDLR KBTRQGLAEQ AALBGLFQPY NVGLEHHHHH
 751 H*
```

961-ORF46.1
(SEQ ID NOS: 146 and 147)

```
   1 ATGGCCACAA ACGACGACGA TGTTAAAAAA GCTGCCACTG TGGCCATTGC
  51 TGCTGCCTAC AACAATGGCC AAGAAATCAA CGGTTTCAAA GCTGGAGAGA
 101 CCATCTACGA CATTGATGAA GACGGCACAA TTACCAAAAA AGACGCAACT
 151 GCAGCCGATG TTGAAGCCGA CGACTTTAAA GGTCTGGGTC TGAAAAAAGT
 201 CGTGACTAAC CTGACCAAAA CCGTCAATGA AAACAAACAA AACGTCGATG
 251 CCAAAGTAAA AGCTGCAGAA TCTGAAATAG AAAAGTTAAC AACCAAGTTA
 301 GCAGACACTG ATGCCGCTTT AGCAGATACT GATGCCGCTC TGGATGCAAC
 351 CACCAACGCC TTGAATAAAT TGGGAGATAA TATAACGACA TTTGCTGAAG
 401 AGACTAAGAC AAATATCGTA AAAATTGATG AAAAATTAGA AGCCGTGGCT
 451 GATACCGTCG ACAAGCATGC CGAAGCATTC AACGATATCG CCGATTCATT
 501 GGATGAAACC AACACTAAGG CAGACGAAGC CGTCAAAACC GCCAATGAAG
 551 CCAAACAGAC GGCCGAAGAA ACCAAACAAA ACGTCGATGC CAAAGTAAAA
 601 GCTGCAGAAA CTGCAGCAGG CAAAGCCGAA GCTGCCGCTG GCACAGCTAA
 651 TACTGCAGCC GACAAGGCCG AAGCTGTCGC TGCAAAAGTT ACCGACATCA
 701 AAGCTGATAT CGGTACGAAC AAAGATAATA TTGCTAAAAA AGCAAACAGT
```

-continued

751 GCCGACGTGT ACACCAGAGA AGAGTCTGAC AGCAAATTTG TCAGAATTGA

801 TGGTCTGAAC GCTACTACCG AAAAATTGGA CACACGCTTG GCTTCTGCTG

851 AAAAATCCAT TGCCGATCAC GATACTCGCC TGAACGGTTT GGATAAAACA

901 GTGTCAGACC TGCGCAAAGA AACCCGCCAA GGCCTTGCAG AACAAGCCGC

951 GCTCTCCGGT CTGTTCCAAC CTTACAACGT GGGTCGGTTC AATGTAACGG

1001 CTGCAGTCGG CGGCTACAAA TCCGAATCGG CAGTCGCCAT CGGTACCGGC

1051 TTCCGCTTTA CCGAAAACTT TGCCGCCAAA GCAGGCGTGG CAGTCGGCAC

1101 TTCGTCCGGT TCTTCCGCAG CCTACCATGT CGGCGTCAAT TACGAGTGGG

1151 GATCCGGAGG AGGAGGATCA GATTTGGCAA ACGATTCTTT TATCCGGCAG

1201 GTTCTCGACC GTCAGCATTT CGAACCCGAC GGGAAATACC ACCTATTCGG

1251 CAGCAGGGGG GAACTTGCCG AGCGCAGCGG CCATATCGGA TTGGGAAAAA

1301 TACAAAGCCA TCAGTTGGGC AACCTGATGA TTCAACAGGC GGCCATTAAA

1351 GGAAATATCG GCTACATTGT CCGCTTTTCC GATCACGGGC ACGAAGTCCA

1401 TTCCCCCTTC GACAACCATG CCTCACATTC CGATTCTGAT GAAGCCGGTA

1451 GTCCCGTPGA CGGATTTAGC CTTTACCGCA TCCATTGGGA CGGATACGAA

1501 CACCATCCCG CCGACGGCTA TGACGGGCCA CAGGGCGGCG GCTATCCCGC

1551 TCCCAAAGGC GCGAGGGATA TATACAGCTA CGACATAAAA GGCGTTGCCC

1601 AAAATATCCG CCTCAACCTG ACCGACAACC GCAGCACCGG ACAACGGCTP

1651 GCCGACCGTT TCCACAATGC CGGTAGTATG CTGACGCAAG GAGTAGGCGA

1701 CGGATTCAAA CGCGCCACCC GATACAGCCC CGAGCTGGAC AGATCGGGCA

1751 ATGCCGCCGA AGCCTTCAAC GGCACTGCAG ATATCGTTAA AAACATCATC

1801 GGCGCGGCAG GAGAAATTGT CGGCGCAGGC GATGCCGTGC AGGGCATAAG

1851 CGAAGGCTCA AACATTGCTG TCATGCACGG CTTGGGTCTG CTTTCCACCG

1901 AAAACAAGAT GGCGCGCATC AACGATTTGG CAGATATGGC GCAACTCAAA

1951 GACTATGCCG CAGCAGCCAT CCGCGATTGG GCAGTCCAAA ACCCCAATGC

2001 CGCACAAGGC ATAGAAGCCG TCAGCAATAT CTTTATGGCA GCCATCCCCA

2051 TCAAAGGGAT TGGAGCTGTT CGGGGAAAAT ACGGCTTGGG CGGCATCACG

2101 GCACATCCTA TCAAGCGGTC GCAGATGGGC GCGATCGCAT TGCCGAAAGG

2151 GAAATCCGCC GTCAGCGACA ATTTTGCCGA TGCGGCATAC GCCAAATACC

2201 CGTCCCCTTA CCATTCCCGA AATATCCGTT CAAACTTGGA GCAGCGTTAC

2251 GGCAAAGAAA ACATCACCTC CTCAACCGTG CCGCCGTCAA ACGGCAAAAA

2301 TGTCAAACTG GCAGACCAAC GCCACCCGAA GACAGGOOTA CCGTTTGACG

2351 GTAAAGGGTT TCCGAATT1T GAGAAGCACG TGAAATATGA TACGCTCGAG

2401 CACCACCACC ACCACCACTG A

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALALT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKABAVAAKV TDIKADIATN KDNIAKKANS

251 ADVYTREESD SKFVRIDGLN ATTEKLDTRL ASAEKSIADH DTRLNGLDKT

-continued

301 VSDLEKETRQ GLAEQAALSG LFQPYNVGRF NVTAAVGGYK SESAVAIGTG

351 FRPTENFAAK AGVAVGTSSG SSAAYHVGVN YEWGSGGGGS DLANDSFIRQ

401 VLDRQHFEPD GKYHLFGSRG ELABRSGEIG LGKIQSHQLG NLMIQQAAIK

451 GNIGYIVRFS DHGHEVHSPF D14EASHSDSD EAGSPVDGFS LYRIHWDGYE

501 HHPAflGYDGP QGGGYPAPKG APDIYSYDIK GVAQNIRLNL TDNRSTGQRL

551 ADRFENAGSM LTQGVGDGPR RATRYSPELD RSGNAAEAPN GTADIVKNII

601 GAAGEIVGAG DAVQGISEGS NIAVHMGLGL LSTENKMARI NDLADHAQLK

651 DYAAAAIRDW AVQNPNAAQG IEAVSNIFHA AIPIKGIGAV RGKYGLGGIT

701 AHPIKRSQHG AIALPKGKSA VSDNFADAAY AKYPSPYHSR NIRSNLEQRY

751 GKENITSSTV PPSNGKNVKL ADQRHPKTGV PFDGKGFPNF EKHVKYDTLE

801 HHHHHH*

961-741
(SEQ ID NOS: 148 and 149)

1 ATGGCCACAA ACGACGACGA TGTTAAAAAA GCTGCCACTG TGGCCATTGC

51 TGCTGCCTAC AACAATGGCC AAGAAATCAA CGGTTTCAAA GCTGGAGAGA

101 CCATCTACGA CATTGATGAA GACGGCACAA TTACCAAAAA AGACGCAACT

151 GCAGCCGATG TTGAAGCCGA CGACTTTAAA GGTCTGGGTC TGAAAAAAGT

201 CGTGAVTAAC CTGACCAAAA CCGTCAATGA AAACAAACAA AACGTCGATG

251 CCAAAGTACA AGCTGCAGAA TCTGAAATAG AAAAGTTAAC AACCAAGTTA

301 GCAGACACTG ATGCCGGTTT AGCAGATACT GATGCCGCTC TGGATGCAAC

351 CACCAACGCC TTGAATAAAT TGGGAGAAAA TATAACGACA TTTGCTGAAG

401 AGACTAAGAC AAATATCGTA AAAATTGATG AAAAATTAGA AGCCGTGGCT

451 GATACCGTCG ACAAGCATGC CGAAGCATTC AACGATATCG CCGATTCATT

501 GGATGAAACC AACACTAAGG CAGACGAAGC CGTCAAAACC GCCAATGAAG

551 CCAAACAGAC GGCCGAAGAA ACCAAAQAAA ACGTCGATGC CAAAGTAAAA

601 GCTGCAGAAA CTGCAGCAGG CAAAGCCGAA GCTGCCGCTG GCACAGCTAA

651 TACTGCAGCC GACAAGGCCG AGGGTGTCGC TGCAAAAGTT ACCGACATCA

701 AAGCTGATAT CGGTACGAAC AAAGATAATA TTGCTAAAAA AGCAAACAGT

751 GCCGACGTGT ACACCAGAGA AGAGTCTGAC AGCAAATTTG TCAGAATTGA

801 TGGTCTGAAC GCTACTACCG AAAAATTGGA CACACGCTTG GCTTCTGCTG

851 AAAAATCCAT TGCCGATCAC GATACTCGCC TGAACGGTTT GGATAAAACA

901 GTGTCACACC TGCGCAAAGA AACCCGCCAA GGCCTTGCAG AACAAGCCGC

951 GCTCTCCGGT CTGTTCCAAC CTTACAACGT GGGTCGGTTC AATGTAACGG

1001 CTGCAGTCGG CGGCTACAAA TCCGAATCGG CAGTCGCCAT CGGTACCGGC

1051 TTCCGCTTTA CCGAAAACTT TGCCGCCAAA GCAGGCGTGG CAGTCGGCAC

1101 TTCGTCCGGT TCTTCCGCAG CCTACCATGT CGGCGTCAAT TACGAGTGGG

1151 GATCCGGAGG GGGTGGTGTC GCCGCCGACA TCGGTGCGGG GCTTGCCGAT

1201 GCACTAACCG CACCGCTCGA CCATAAAGAC AAAGGTTTGC AGTCTTTGAC

1251 GCTGGATCAG TCCGTCAGGA AAAACGAGAA ACTGAAGCTG GCGGCACAAG

1301 GTGCGGAAAA AACTTATGGA AACGGTGACA GCCTCAATAC GGGCAAATTG

1351 AAGAACGACA AGGTCAGCCG TTTCGACTTT ATCCGCCAAA TCGAAGTGGA

1401 CGGGCAGCTC ATTACCTTGG AGAGTGGAGA GTTCCAAGTA TACAAACAAA

-continued

1451 GCCATPCCGC CTTAACCGCC TTTCAGACCG AGCAAATACA AGATTCGGAG

1501 CATTCCGGGA AGATGGTTGC GAAACGCCAG TTCAGAATCG GCGACATAGC

1551 GGGCGAACAT ACATCTTTTG ACAAGCTTCC CGAAGGCGGC AGGGCGACAT

1601 ATCGCGGGAC GGCGTTCGGT TCAGACGATG CCGGCGGAAA ACTGACCTAC

1651 ACCATAGATT TCGCCGCCAA GCAGGGAAAC GGCAAAATCG AACATTTGAA

1701 ATCGCCAGAA CTCAATGTCG ACCTGGCCGC CGCCGATATC AAGCCGGATG

1751 GAAAACGCCA TGCCGTCATC AGCGGTTCCG TCCTTTACAA CCAAGCCGAG

1801 AAAGGCAGTT ACTCCCTCGG TATCTTTGGC GGAAAAGCCC AGGAAGTTGC

1851 CGGCAGCGCG GAAGTGAAAA CCGTAAACGG CATACGCCAT ATCGGCCTTG

1901 CCGCCAAGCA ACTCGAGCAC CACCACCACC ACCACTGA

1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAP NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTRBESD SKFVRIDGLN ATTEKLDTRL ASAEKSIADH DTRLNGLDKT

301 VSDIJRKETRQ GLAEQAALSG LFQPYNVGRP NVTAAVGGYK SESAVAIGTG

351 FRPTENFAAK AGVAVGTSSG SSAAYHVGVN YEWGSGGGGV DLANDSFIRQ

401 MJTAPLDHKD KGLQSLTLDQ SVRKNEKLKL AAQGAEKTYG NGDSLNTGKL

451 KNDKVSEFDF IRQIEVDGQL ITLESGEFQV YKQSHSALTA FQTEQIQDSE

501 HSGKMVAKRQ FRIGDIAGEH TSFDXLPEGG RATYRGTAFG SDDAGGKLTY

551 TIDFAAKQGN GKIEHIJKSPE LNVDLAAADI KPDGKRHAVI SGSVLYNQAE

601 KGSYSLGIFG GKAQEVAGSA EVKTVNGIRH IGLAAKQLEH HHHHH*

961-983
(SEQ ID NOS: 150 and 151)

1 ATGGCCACAA ACGACGAQGA TGTTAAAAAA GCTGCCACTG TGGCCATTGC

51 TGCTGCCTAC AACAATGGCC AAQAAATCAA CGGTTTCAAA GCTGGAGAGA

101 GCATGTACCA CATTGATGAA GACGGCACAA TTACCAAAAA AGACGCAACT

151 GCAGCCGATG TTGAACCGA CGACTTTAAA GGTCTGGGTC TGAAAAAAGT

201 CGTGACTAAC CTGACCAAAA CCGTCAATGA AAACAAACAA AACGTCGATG

251 CCAAAGTAAA AGCTGCAGAA TCTGAAATAG AAAAGTTAAC AACCAAGTTA

301 GCAGACACTG ATGCCGCTTT AGCAGATACT GATGCCGCTC TGGATGCAAC

351 CACCAACGCC TTGAATAAAT TGGGAGAAAA TATAACGACA TTTGCTGAAG

401 AGACTAAGAC AAATATCGTA AAAATTGATG AAAAATTAGA AGCCGTGGCT

451 GATACCGTCG ACAAGCATGC CGAAGCATTC AACQATATCG CCGATTCATT

501 GGATGAAACC AACACTAAGG CAGACGAAGC CGTCAAAACC GCCAATGAAG

551 CCAAACAGAC GGCCGAAGAA ACCAAACAAA ACGTCGATGC CAAAGTAAAA

601 GCTGCAGAAA CTGCAGCAGG CAAAGCCGAA GCTGCCGCTG GCACAGCTAA

651 TACTGCAGCC GACAAGGCCG AAGCTGTCGC TGCAAAAGTT ACCGACATCA

701 AAGCTGATAT CGCTACGAAC AAAGATAATA TTGCTAAAAA AGCAAACAGT

751 GCCGACGTGT ACACCAGAGA AGAGTCTGAC AGCAAATTTG TCAGAATTGA

-continued

```
801  TGGTCTGAAC GCTACTACCG AAAAATTGGA CACACGCTTG GCTTCTGCTG
851  AAAAATCCAT TGCCGATCAC GATACTCGCC TGAACGGTTT GGATAAAACA
901  GTGTCAGACC TGCGCAAAGA AACCCGCCAA GGCCTTGCAG AACAAGCCGC
951  GCTCTCCGGT CTGTTCCAAC CTTACAACGT GGGTCGGTTC AATGTAACGG
1001 CTGCAGTCGG CGGCTACAAA TCCGAATCGG CAGTCGCCAT CGGTACCGGC
1051 TTCCGCTTTA CCGAAAACTT TGCCGCCAAA GCAGGCGTGG CAGTCGGCAC
1101 TTCGTCCGGT TCTTCCGCAG CCTACCATGT CGGCGTCAAT TACGAGTGGG
1151 GATCCGGCGG AGGCGGCACT TCTGCGCCCG ACTTCAATGC AGGCGGTACC
1201 GGTATCGGCA GCAACAGCAG AGCAACAACA GCGAAATCAG CAGCAGTATC
1251 TTACGCCGGT ATCAAGAACG AAATGTGCAA AQACAGAAGC ATGCTCTGTG
1301 CCGGTCGGGA TGACGTTGCG GTTACAGACA GGGATGCCAA AATCAATGCC
1351 CCCCCCCCGA ATCTGCATAC CGGAGACTTT CCAAACCCAA ATGACGCATA
1401 CAAGAATTTG ATCAACCTCA AACCTGCAAT TGAAGCAGGC TATACAGGAC
1451 GCGGGGTAGA GGTAGGTATC GTCGACACAG GCGAATCCGT CGGCAGCATA
1501 TCCTTTCCCG AACTGTATGG CAGAAAAGAA CACGGGTATA ACGAAAATTA
1551 CAAAAACTAT ACGGCGTATA TGCGGAAGGA AGCGCCTGAA GACGGAGGCG
1601 GTAAAGACAT TGAAGCTTCT TTCGACGATG AGGCCGTTAT AGAGACTGAA
1651 GCAAAGCCGA CGGATATCCG CCACGTAAAA GAALTCGGAC ACATCGATTT
1701 GGTCTCCCAT ATTATTGGCG GGCGTTCCGT GGACGGCAGA CCTGCAGGCG
1751 GTATTGCGCC CGATGCGACG CTACACATAA TGAATACGAA TGATGAAACC
1801 AAGAACGAAA TGATGGTTGC AGCCATCCGC AATGCATGGG TCAAGCTGGG
1851 CGAACGTGGC GTGCGCATCG TCAATAACAG TTTTGGAACA ACATCGAGGG
1901 CAGGCACTGC CQACCTTTTC CAAATAGCCA ATTCGGAGGA GCAGTACCGC
1951 CAAGCGTTGC TCGACTATTC CGGCGGTGAT AAAACAGACG AGGGTATCCG
2001 CCTGATGCAA CAGAGCGATT ACGGCAACCT GTCCTACCAC ATCCGTAATA
2051 AAAACATGGT TTTCATCTTT TCGACAGGCA ATOACOCACA AGCTCAGCCC
2101 AACACATATG CCCTATTGCC ATTTTATGAA AAAGACGCTC AAAAAGGCAT
2151 TATCACAGTC GCAGGCGTAG ACCGCAGTGG AGAAAAGTTC AAACGGGAAA
2201 TGTATGGAGA ACCGGGTACA GAACCGCTTG AGTATGGCTC CAACCATTGC
2251 GGAATTACTG CCATGTGGTG CCTGTCGGCA CCCTATGAAG CAAGCGTCCG
2301 TTTCACCCGT ACAAACCCGA TTCAAATTGC CGGAACATCC TTTTCCGCAC
2351 CCATCGTAAC CGGCACGGCG GCTCTGCTGC TGCAGAAATA CCCGTGGATG
2401 AGCAACGACA ACCTGCGTAC CACGTTGCTG ACGACGGCTC AGGCCATCGG
2451 TGCAGTCGGC GTGGACAGCA AGTTCGGCTG GGGACTGCTG GATGCGGGTA
2501 AGGCCATGAA CGGACCCGCG TCCTTTCCGT TCGGCGACTT TACCGCCGAT
2551 ACGAAAGGTA CATCCGATAT TGCCTACTCC TTCCGTAACG ACATTTCAGG
2601 CACGGGCGGC CTGATCAAAA AAGGCGGCAG CCAACTGCAA CTGCACGGCA
2651 ACAACACCTA TACGGGCAAA ACCATTATCG AAGGCGGTTC GCTGGTGTTG
2701 TACGGCAACA ACAAATCGGA TATGCGCGTC GAAACCAAAG GTGCGCTGAT
2751 TTATAACGGG GCGGCATCCG GCGGCAGCCT GAACAGCGAC GGCATTGTCT
```

-continued

2801 ATCTGGCAGA TACCGACCAA TCCGGCGCAA ACGAAACCGT ACACATCAAA
2851 GGCAGTCTGC AGCTGGACGG CAAAGGTACG CTGTACACAC GTTTGGGCAA
2901 ACTGCTGAAA GTGGACGGTA CGGCGATTAT CGGCGGCAAG CTGTACATGT
2951 CGGCCGCGG CAACGGGGCA GGCTATCTCA ACACTACCGG ACGACGTGTT
3001 CCCTTCCTGA GTGCCGCCAA AATCGGGCAG GATTATTCTT TCTTCACAAA
3051 CATCGAAACC GACGGCGGCC TGCTGGCTTC CCTCGACAGC GCCGAAAAAA
3101 CAGCGGGCAG TGAAGGCGAC ACGCTGTCCT ATTATGTCCG TCGCGGCAAT
3151 GCGGCACGGA CTGCTTCGGC AGCGGCGCGT TCCGCGCCCG CCGGTCTGAA
3201 ACACGCCGTA GAACAGGGCG GCAGCAkTCT GGAAAACCTG ATGGTCGAAC
3251 TGGATGCCTC CQAATCATCC GCAACACCCG AGACGGTTGA AACTGCGGCA
3301 GCCGACCGCA CAGATATGCC GGGCATCCGC CCCTACGGCG CAACTTTCCG
3351 CGCAGCGGCA GCCGTACAGC ATGCGAATGC CGCCGACGGT GTACGCATCT
3401 TCAACAGTCT CGCCGCTACC GTCTATGCCG ACAGTACCGC CGCCCATGCC
3451 GATATGCAGG GACGCCGCCT GAAAGCCGTA TCGGACGGGT TGGACCACAA
3501 CGGCACGGGT CTGCGCGTCA TCGCGCAAAC CCAACAGGAC GGTGGAACGT
3551 GGGAACAGGG CQGTGTTGAA GGCAAAATGC GCGGCAGTAC CCAAACCGTC
3601 GGCATTGCCG CGAAAACCGG CGAAAATACG ACAGCAGCCG CCACACTGGG
3651 CATGGGACGC AGCACATGGA GCGAAAACAG TGCAAATGCA AAAACCGACA
3701 GCATTAGTCT GTTTGCAGGC ATACGGCACG ATGCGGGCGA TATCGGCTAT
3751 CTCAAAGGCC TGTTCTCCTA CGGACGCTAC AAAAACAGCA TCAGCCGCAG
3801 CACCGGTGCG GACGAACATG CGGAAGGCAG CGTCAACGGC ACGCTGATGC
3851 AGCTGGGCGC ACTGGGCGGT GTCAACGTTC CGTTTGCCGC AACGGGGGAT
3901 TTGAGGGTCG AACGCGGTCT GCGCTACGAC CTGCTCAAAG ACGATGCATT
3951 CGCCGAAAAA GGCAGTGCTT TGGGCTGGAG CGGCAACAGC CTCACTGAAG
4001 GCACGCTGGT CGGACTCGCG GGTCTGAAGC TGTCGCAACC CTTGAGCGAT
4051 AAAGCCGTCC TGTTTGCAAC GGCGGGCGTG GAACGCGACC TGAACGGACG
4101 CGACTACACG GTAACGGGCG GCTTTACCGG CGCGACTGCA GCACCCGGCA
4151 AGACGGGGGC ACGCAATATG CCGCACACCC GTCTGGTTGC CGGCCTGGGC
4201 GCGGATGTCG AATTCGGCAA CGGCTGGAAC GGCTTGGCAC GCTACAGCTA
4251 CGCCGGTTCC AAACAGTACG GCAACCACAG CGGACGAGTC GGCGTAGGCT
4301 ACCGGT4PCCT CGAGCACCAC CACCACCACC ACTGA
1 MATNDDDVKK AATVAIAAAY NNGQEINGFK AGETIYDIDE DGTITKKDAT
51 AADVEADDFK GLGLKKVVTN LTKTVNENKQ NVDAKVKAAB SEIEKLTTKL
101 ALTDAALADT DAALDATTNA LNKLGENITT FAEETKTNIV KIDEKLEAVA
151 DTVDKHAEAF NDIADSLDET NTKADEAVKT ANEAKQTARE TKQNVDARVK
201 AAETAAGKAE AAAGTAMTAA DLAEAVAALV TDIKADIATN KDNIAKKANS
251 ADVYTREESD SKFVRIDGLN ATTEKLDTEL ASAEKSIADH DTRLNGLDKT
301 VSDLRKETRQ GLABQAALSG LFQPYNVGRP NWlAAVGGYK SESAVAIGTG
351 FRFTENFAAK AGVAVGTSSG SSAAYHVGVN YEWGSGGGGT SAPDFNAGGT
401 GIGSNSRATT AKSAAVSYAG INMEMCKDRS MLCAGRDDVA VTDPDAXINA

-continued

```
 451 PPPNLHTGDF PNPNDAYKNL INLKPAIEAG YTGEQVEVGI VDTGESVGSI
 501 SFPELYGRKE HGYNENYKNY TAYMRKEAPB DGGGKDIEAS FDDEAVIETE
 551 AKPTDIREVK EIGHIDLVSH IIGGESVPGR PAGGIAPPAT LHIMNTNDET
 601 KNEMMVAAIR NAWVKLGERG VRIVNNSFGT TSRAGTADLF QIANSEEQYR
 651 QALLDYSGGD KTDRGIRLMQ QSDYGNLSYH IRKNKNLFIF STGNDAQAQP
 701 NTYALLPFYE KDAQKGIITV AGVDRSGEKF KRENYGEPGT EPLEYGSNHC
 751 GITAMWCLSA PYEASVRPTR TNPIQIAGTS FSAPIVTGTA ALLLQKYPWH
 801 SNDNLRTTLL TTAQDIGAVG VDSKFGWGLL DAGKAMNGPA SFPFGDFTAD
 851 TKGTSDIAYS FRNDISGTGG LIKKGGSQLQ LHGNNTYTGK TIIEGGSLVL
 901 YGNNKSDMRV ETKGALIYNG AASGGSLNSD GIVYLADTDQ SGANETVHIK
 951 GSLQIDGKGT LYTRLGKLLK VDGTAIIGGK LYMSAKGKGA GYLNSTGRRV
1001 PFLSAAKIGQ DYSPFTNIET DGGLLASLDS VEKTAGSEGD TLSYYVRPGN
1051 AARTABAAAH SAPAGLKHKV EQGGSNLENL HVBLDASBSS ATPETVHTAA
1101 ADRTDMPGIR PYGATFRAAA AVQHANAADG VRIFNSLAAT VYADSTAAHA
1151 DMQGRRLKAV TAAATLGMGR STSWENSANA KTDSISLFAG IRHDAGIGY
1201 GIAAKTGENT TAAATLGHGR STWSENSANA KTDSISLFAG IRHDAGDIGY
1251 LKGLFSYGRY KNSZSRSTQA DEHAEGSVNG TLNQLGALGG VNVPFAATGD
1301 LTVEGGLRYD LLKQDAPAEK GSALGWSGNS LTEGTLVGLA GIJKLSQPLSD
1351 KAVLFATAGV ERDLNGRDYT VTGGFTGATA ATGKTGARNM PHTRLVAGLG
1401 ADVEFGNGWN GLARYSYAGS KQYGNHSGRV GVGYRFLEHH HHHH*
```

961c-ORF46.1
(SEQ ID NOS: 152 and 153)

```
   1 ATGGCCACAA ACGACGACGA TGTTAAAAAA GCTGCCACTG TGGCCATTGC
  51 TGCTGCCTAC AACAATGGCC AAGAAATCAA CGGTTTCAAA GCTGGAGAGA
 101 CCATCTACGA CATTGATGAA GACGGCACAA TTACCAAAAA AGACGCAACT
 151 GCAGCCGATG TTGAAGCCGA CGACTTTAAA GGTCTGGGTC TGAAAAAAGT
 201 CGTGACTAAC CTGACCAAAA CCGTCAATGA AAACAAACAA AACGTCGATG
 251 CCAAAGTAAA AGCTGCAGAA TCTGAAATAG AAAAGTTAAC AACCAAGTTA
 301 GCAGACACTG ATGCCGCTTT AGCAGATACT GATGCCGCTC TGGATGCAAC
 351 CACCAACGCC TTGAATAAAT TGGGAGAAAA TATAACGACA TTTGCTGAAG
 401 AGACTAAGAC AAATATCGTA AAAATTGATG AAAAATTAGA AGCCGTGGCT
 451 GATACCGTCG ACAAGCATGC CGAAGCATTC AACGATATCG CCGATTCATT
 501 GGATGAAACC AACACTAAGG CAGACGAAGC CGTCAAAACC GCCAATGAAG
 551 CCAAACAGAC GGCCGAAGAA ACCAAACAAA ACGTCGATGC CAAAGTAAAA
 601 GCTGCAGAAA CTGCAGCAGG CAAAGCCGAA GCTGCCGTG GCACAGCTAA
 651 TACTGCAGCC GACAAGGCCG AAGCTGTCGC TGCAAAAGTT ACCGACATCA
 701 AAGCTGATAT CGCTACGAAC AAAGATAATA TTGCTAAAAA AGCAAACAGT
 751 GCCGACGTGT ACACCAGAGA AGAGTCTGAC AGCAAATTTG TCAGAATTGA
 801 TGGTCTGAAC GCTACTACCG AAAAATTGGA CACACGCTTG GCTTCTGCTG
 851 AAAAATCCAT TGCCGATCAC GATACTCGCC TGAACGGTTT GGATAAAACA
 901 GTGTCAGACC TGCGCAAAGA AACCCGCCAA GGCCTTGCAG AACAAGCCGC
```

-continued

```
 951 GCTCTCCGGT CTGTTCCAAC CTTACAACGT GGGTGGATCC GGAGGAGGAG
1001 GATCAGATTT GGCAAACGAT TCTTTTATCC GGCAGGTTCT CGACCGTCAQ
1051 CATTTCGAAC CCGACGGGAA ATACCACCTA TTCGGCAGCA GGGGGGAACT
1101 TGCCGAGCGC AGCGGCCATA TCGGATTGGG AAAAATACAA AGCCATCAGT
1151 TGGGCAACCT GATGATTCAA CAGGCGGCCA TTAAAGGAAA TATCGGCTAC
1201 ATTGTCCGCT TTTCCGATCA CGGGCACGAA GTCCATTCCC CCTTCGACAA
1251 CCATGCCTCA CATTCCGATT CTGATGAAGC CGGTAGTCCC GTTGACGGAT
1301 TTAGCCTTTA CCGCATCCAT TGGGACGGAT ACGAACACCA TCCCGCCGAC
1351 GGTTATGACG GGCCACAGGG CGGCGGCTAT CCCGCTCCCA AAGGCGCQAG
1401 GGATATATAC AGCTACGACA TAAAAGGCGT TGCCCAAAAT ATCCGCCTCA
1451 ACCTGACCGA CAACCGCAGC ACCGGACAAC GGCTTGCCGA CCGTTTCCAC
1501 AATGCCGGTA GTATGCTGAC GCAAGGAGTA GGCGACGGAT TCAAACGCGC
1551 CACCCGATAC AGCCCCGAGC TGGACAGATC GGGCAATGCC GCCGAAGCCT
1601 TCAACGGCAC TGCAGATATC GTTAAAAACA TCATCGGCGC GGCAGGAGAA
1651 ATTGTCGGCG CAGGCGATGC CGTGCAGGGC ATAAGCGAAG GCTCAAACAT
1701 TGCAGTCATG CACGGCTTGG GTCTGCTTTC CACCGAAAAC AAGATGGCGC
1751 GCATCAACGA TTTGGCAGAT ATGGCGCAAC TCAAAGACTA TGCCGCAGCA
1801 GCCATCCGCG ATTGGGCAGT CCAAAACCCC AATGCCGCAC AAGGCATAGA
1851 AGCCGTCAGC AATATCTTTA TGGCAGCCAT CCCCATCAAA GGGATTGGAG
1901 CTGTTCGGGG AAAATACGGC TTGGGCGGCA TCACGGCACA TCCTATCAAG
1951 CGGTCGCAGA TGGGCGCGAT CGCATTGCCG AAAGGGAAAT CCGCCGTCAG
2001 CGACAATTTT QCCGATGCGG CATACGCCAA ATACCCGTCC CCTTACCATT
2051 CCCGAAATAT CCGTTCAAAC TTGGAGCAGC GTTACGGCAA AGAAAACATC
2101 ACCTCCTCAA CCGTGCCGCC GTCAAACGGC AAAAATGTCA AACTGGCAGA
2151 CCAACGCCAC CCGAAGACAG GCGTACCGTT TGACGGTAAA GGGTTTCCGA
2201 ATTTTGAGAA GCACGTGAAA TATGATACGC TCGAGCACCA CCACCACCAC
2251 CACTGA

   1 MATNDDDVKK AATVAIAAAY NNGQEINGFK AGETIYDIDE DGTITKKDAT
  51 AADVEADDFK GLGLKKVVTN LTKTVNENKQ NVDAKVKAAE SBIEKLTTKL
 101 ADTDAALADT DAALDATTNA LNKLGENITT FAEETKTNIV KIDEKLEAVA
 151 DTVDIWAPAP NDIADSLDET NTKADEAVKT ANEAKQTAEE TKQNVDAKVK
 201 AABTAAGKAE AAAGTANTAA DKAEAVAAKV TDIKALLATN KDNIAKKANS
 251 ADVYTRBESD SKPVRIDGLN ATTEKLDTEL ASAEKSIADH DTRLNGLDKT
 301 VSDLRKETRQ GLAEQAALSG LFQPYNVGGS GGGGSDLAND SFIRQVLDRQ
 351 HFEPDGKYHL FGSRGELAER SGHIGLGKIQ SHQLGNLMIQ QAAIKGNIGY
 401 IVRFSDHGHE VHSPFDNHAS HSDSDEAGSP VDGFSLYRIH WDGYEHHPAD
 451 GYDGPQGGGY PAPKGAPDZY SYDIKGVAQN IRLNLTDNRS TGQRLADRFH
 501 NAGSNLTQGV GDGPKEATRY SPELDRSGNA AEAPNGTADI VKNIIGAAGE
 551 IVGAGDAVQG ISEGSNIAVM HGLGLLSTEN KMARINDLAD MAQLKDYAAA
 601 AIRDWAVQNP NAAQGIEAVS NIFMAAIPIK GIGAVEOKYG LGGITAHPIK
```

-continued

```
651 RSQMGAIALP KGKSAVSDNF ADAAYAKYPS PYHBRNIRBN LEQRYGKENI

701 TSSTVPPSNG KNVKLADQRH PKTGVPFDGK GPPNPEKBVK YDTLEHEHHH
```

961c-741
(SEQ ID NOS: 154 and 155)

```
   1 ATGGCCACAA ACGACGACGA TGTTAAAAAA GCTGCCACTG TGGCCATTGC

  51 TGCTGCCTAC AACAATGGCC AAGAAATCAA CGGTTTCAAA GCTGGAGAGA

 101 CCATCTACGA CATTGATGAA GACGGCACAA TTACCAAAAA AGACGCAACT

 151 GCAGCCGATG TTGAAGCCGA CGACTTTAAA GGTCTGGGTC TGAAAAAAGT

 201 CGTGACTAAC CTGACCAAAA CCGTCAATGA AAACAAACAA AACGTCGATG

 251 CCAAAGTAAA AGCTGCAGAA TCTGAAATAG AAAAGTTAAC AACCAAGTTA

 301 GCAGACACTG ATGCCGCTTT AGCAGATACT GATGCCGCTC TGGATGCAAC

 351 CACCAACGCC TTGAATAAAT TGGGAGAAAA TATAACGACA TTTGCTGAAG

 401 AGACTAAGAC AAATATCGTA AAAATTGATG AAAAATTAGA AGCCGTGGCT

 453 GATACCGTCG ACAAGCATGC CGAAGCATTC AACGATATCG CCGATTCATT

 501 GGATGAAACC AACACTAAGG CAGACGAAGC CGTCAAAACC GCCAATGAAG

 551 CCAAACAGCG GGCCGAAGAA ACCAAGCAAA ACGTCGATGC CAAAGTAAAA

 601 GCTGCAGAAA CTGCAGCAGG CAAAGCCGAA GCTGCCGCTG GCACAGCTAA

 651 TACTGCAGCC GACAAGGCCG AAGCTGTCGC TGCAAAATT ACCGACATCA

 701 AAGCTGATAT CGCTACGAAC AAAGATAATA TTGCTAAAAA AGCAAACAGT

 751 GCCGACGTGT ACACCAGAGA AGAGTCTGAC AGCAAATTTG TCAGAATTGA

 801 TGGTCTGAAC GCTACTACCG AAAAATTGGA CACACGCTTG GCTTCTGCTG

 851 AAAAATCCAT TGCCGATCAC GATACTCGCC TGAACGGTTT GGATAAAACA

 901 GTGTCAGACC TGCGCAAAGA AACCCGCCAA GGCCTTGCAG AACAAGCCGC

 951 GCTCTCCGGT CTGTTCCAAC CTTACAACGT GGGTGGATCC GGAGGGGGTG

1001 GTGTCGCCGC CGACATCGGT GCGGGGCTTG CCGATGCACT AACCGCACCG

1051 CTCGACCATA AAGACAAAGG TTTGCAGTCT TTGACGCTGG ATCAGTCCGT

1101 CAGGAAAAAC GAGAAACTGA AGCTGGCGGC ACAAGGTGCG GAAAAAACTT

1151 ATGGAAACGG TGACAGCCTC AATACGGGCA AATTGAAGAA CGACAAGGTC

1201 AGCCGTTTCG ACTTTATCCG CCAAATCGAA GTGGAQGGGC AGCTCATTAC

1251 CTTGGAGAGT GGAGAGTTCC AAGTATACAA ACAAAGCCAT TCCGCCTTAA

1301 CCGCCTTTCA GACCGAGCAA ATACAAGATT CGGAGCATTC CGGGAAGATG

1351 GTTGCGAAAC GCCAGTTCAG AATCGGCGAC ATAGCGGGCG AACATACATC

1401 TTTTGACAAG CTTCCCGAAG GCGGCAGGGC GACATATCGC GGGACGGCGT

1451 TCGGTTCAGA CGATGCCGGC GGAAAACTGA CCTACACCAT AGATTTCGCC

1501 GCCAAGCAGG GAAACGGCAA AATCGAACAT CTGAAATCGC CAGAACTCAA

1551 TGTCGACCTG GCCGCCGCCG ATATCAAGCC GGATGGAAAA CGCCATGCCG

1601 TCATCAGCGG TTCCGTCCTT TACAACCAAG CCGAGAAAGG CAGTTACTCC

1651 CTCGGTATCT TTGGCGGAAA AGCCCAGGAA GTTGCCGGCA GCGCGGAAGT

1701 GAAAACCGTA AACGGCATAC GCCATATCGG CCTTGCCGCC AAGCAACTCG

1751 AGCACCACCA CCACCACCAC TGA

   1 MATNDDDVKK AATVAIAAAY NNGQEINGFK AGETIYDIDE DGTITICKDAT
```

-continued

```
 51 AADVEADDFK GLGLKKVVTN LTKTVNENKQ NVDAKVKAAE SEIEKLTTKL
101 ADTDAALADT DAALDATTNA LNKLGBNITT FABETKTNIV KIDEKLEAVA
151 DTVDKHABAF NDIADSLDET NTKADEAVKT ANEAKQTAEE TKQNVDAKVK
201 AAETAAGKAE AAAGTANTAA DKAEAVAAKV TDZKADIATN KDNIAKKANS
251 ADVYTEEBSD SKPVRIDGLN ATTEKLDTEL ASAEKSIADH DTELNGLDKT
301 VSDLRXETRQ GLABQAALSG LFQPYNVGGS GGGGVAADIG AGLADALTAP
351 LDHDKGLQS LTLDQSVRKN EKLKLAAQGA EKTYGNGDSL NTGKLKNDKV
401 SEFDFIRQIE VDGQLITLES GEPQVYKQSH SALTAPQTEQ IQDSEHSGKH
451 VAKRQFRIGD IAGEHTSFDK LPBGGEATYR GTAPGSDDAG GKLTYTIDFA
501 AXQGNGKIEH LKSPELNVDL AAADIKPDGK RHAVISGSVL YNQA3KGSYS
551 LGIFGGKAQE VAGSAEVKTV NGIRHIGLAA KQLEHHHHHH *
```

961c-983
(SEQ ID NOS: 156 and 157)

```
   1 ATGGCCACAA ACGACGACGA TGTTAAAAAA GCTGCCACTG TGGCCATTGC
  51 TGCTGCCTAC AACAATGGCC AAGAAATCAA CGGTTTCAAA GCTGGAGAGA
 101 CCATCTACGA CATTGATGAA GACGGCACAA TTACCAAAAA AGACGCAACT
 151 GCAGCCGATG TTGAAGCCGA CGACTTTAAA GGTCTGGGTC TGAAAAAAGT
 201 CGTGACTAAC CTGACCAAAA CCGTCAATGA AAAAAAACAA AACGTCGATG
 251 CCAAAGTAAA AGCTGCAGAA TCTGAAATAG AAAAGTTAAC AACCAAGTTA
 301 GCAGACACTG ATGCCGCTTT AGCAGATACT GATGCCGCTC TGGATGCAAC
 351 CACCAACGCC TTGAATAAAT TGGGAGAAAA TATAACGACA TTTGCTGAAG
 401 AGACTAAGAC AAATATCGTA AAAATTGATG AAAAATTAGA AGCCGTGGCT
 451 GATACCGTCG ACAAGCATGC CGAAGCATTC AACGATATCG CCGATTCATT
 501 GGATGAAACC AACACTAAGG CAGACGAAGC CGTCAAAACC GCCAATGAAG
 551 CCAAACAGAC GGCCGAAGAA ACCAAACAAA ACGTCGATGC CAAAGTAAAA
 601 GCTGCAGAAA CTGCAGCAGG CAAAGCCGAA GCTGCCGCTG GCACAGCTAA
 651 TACTGCAGCC GACAAGGCCG AAGCTGTCGC TGCAAAAGTT ACCGACATCA
 701 AAGCTGATAT CGCTACGAAC AAAGATAATA TTGCTAAAAA AGCAAACAGT
 751 GCCGACGTGT ACACCAGAGA AGAGTCTGAC AGCAAATTTG TCAGAATTGA
 801 TGGTCTGAAC GCTACTACCG AAAAATTGGA CACACGCTTG GCTTCTGCTG
 851 AAAAATCCAT TGCCGATCAC GATACTCGCC TGAACGGTTT GGATAAAACA
 901 GTGTCAGACC TGCGCAAAGA AACCCGCCAA GGCCTTGCAG AACAAGCCGC
 953 GCTCTCCGGT CTGTTCCAAC CTTACAACGT GGGTGGATCC GGCGGAGGCG
1001 GCACTTCTGC GCCCGACTTC AATGCAGGCG GTACCGGTAT CGGCAGCAAC
1051 AGCAGAGCAA CAACAGCGAA ATCAGCAGCA GTATCTTACG CCGGTATCAA
1101 GAACGAAATG TGCAAAGACA GAAGCATGCT CTGTGCCGGT CGGGATGACG
1151 TTGCGGTTAC AGACAGGGAT GCCAAAATCA ATGCCCCCCC CCCGAATCTG
1201 CATACCGGAG ACTTTCCAAA CCCAAATGAC GCATACAAGA ATTTGATCAA
1251 CCTCAAACCT GCAATTGAAG CAGGCTATAC AGGACGCGGG GTAGAGGTAG
1301 GTATCGTCGA CACAGGCGAA TCCGTCGGCA GCATATCCTT TCCCGAACTG
1351 TATGGCAGAA AAGAACACGG CTATAACGAA AATTACAAAA AcTATACGGC
```

-continued

```
1401 GTATATGCGG AAGGAAGCGC CTGAAGACGG AGGCGGTAAA GACATTGAAG
1451 CTTCTTTCGA CGATGAGGCC GTTATAGAGA CTGAAGCAAA GCCGACGGAT
1501 ATCCGCCACG TAAAAGAAAT CGGACACATC GATTTGGTCT CCCATATTAT
1551 TGGCGGGCGT TCCGTGGACG GCAGACCTGC AGGCGGTATT GCGCCCGATG
1601 CGACGCTACA CATAATGAAT ACGAATGATG AAACCAAGAA CGAAATGATG
1651 GTTGCAGCCA TCCGCAATGC ATGGGTCAAG CTGGGCGAAC GTGGCGTGCG
1701 CATCGTCAAT AACAGTTTTG GAACAACATC GAGGGCAGGC ACTGCCGACC
1751 TTTTCCAAAT AGCCAATTCG GAGGAGCAGT ACCGCCAAGC GTTGCTCGAC
1801 TATTCCGGCG GTGATAAAAC AGACGAGGGT ATCCGCCTGA TGCAACAGAG
1851 CGATTACGGC AACCTGTCCT ACCACATCCG TAATAAAAAC ATGCTTTTCA
1901 TCTTTTCGAC AGGCAATQAC GCACAAGCTC AGCCCAACAC ATATGCCCTA
1951 TTGCCATTTT ATGAAAAAGA CGCTCAAAAA GGCATTATCA CAGTCGCAGG
2001 CGTAGACCGC AGTGGAGAAA AGTTCAAACG GGAAATGTAT GGAGAACCGG
2051 GTACAGAACC GCTCGAGTAT GGCTCCAACC ATTGCGGAAT TACTGCCATG
2101 TGGTGCCTGT CGGCACCCTA TGAAGCAAGC GTCCGTTTCA CCCGTACAAA
2151 CCCGATTCAA ATTGCCGGAA CATCCTTCC CGCACCCATC GTAACCGGCA
2201 CGGCGGCTCT GCTGCTGCAQ AAATACCCGT GGATGAGCAA CGACAACCTG
2251 CGTACCACGT TGCTGACGAC GGCTCAGGAC ATCGGTGCAG TCGGCGTGGA
2301 CAGCAAGTTC GGCTGGGGAC TGCTGGATGC GGGTAAGGCC ATGAACGGAC
2351 CCGCGTCCTT TCCGTTCGGC GACTTTACCG CCGATACGAA AGGTACATCC
2401 GATATTGCCT ACTCCTTCCG TAACGACATT TCAGGCACGG GCGGCCTGAT
2451 CAAAAAAGGC GGCAGCCAAC TGCAACTGCA CGGCAACAAC ACCTATACGG
2501 GCAAAACCAT TATCGAAGGC GGTTCGCTGG TGTTGTACGG CAACAACAAA
2551 TCGGATATGC GCGTCGAAAC CAAAGGTGCG CTGATTTATA ACGGGGCGGC
2601 ATCCGGCGGC AGCCTGAACA GCGACGGCAT TGTCTATCTG GCAGATACCG
2651 ACCAATCCGG CGCAAACGAA ACCOTACACA TCAAAGGCAG TCTGCAGCTG
2701 GAGGGCAAAG GTACGCTGTA CACACGWG GGCAAACTGC TGAAAGTGGA
2751 CGGTACGGCG ATTATCGGCG GCAAGCTGTA CATGTCGGCA CGCGGCAAGG
2801 GGGCAGGCTA TCTCAACAGT ACCGGACGAC GTGTTCCCTT CCTGAGTGCC
2851 GCCAAAATCG GGCAGGATTA TTCTTTCTTC ACAAACATCG AAACCGACGG
2901 CGGCCTGCTG GCTTCCCTCG ACAGCGTCGA AAAAACAGCG GGCAGTGAAG
2951 GCGACACGCT GTCTTATTAT GTCCGTCGCG GCAATGCGGC ACGGACTGCT
3001 TCGGCAGCGG CACATTCCGC GCCCGCCGGT CTGAAACACG CCGTAGAACA
3051 GGGCGGCAGC AATCTGGAAA ACCTGATGGT CGAACTGGAT GCCTCCGAAT
3101 CATCCGCAAC ACCCGAGACG GTTGAAACTG CGGCAGCCGA CCGCACAGAT
3151 ATGCCGGGCA TCCGCCCCTA CGGCGCAACT TTCCGCGCAG CGGCAGCCGT
3201 ACAGCATGCG AATGCCGCCG ACGGTGTACG CATCTTCAAC AGTCTCGCCG
3251 CTACCGTCTA TGCCGACAGT ACCGCCGCCC ATGCCGATAT GCAGGGACGC
3301 CGCCTGAACG CCGTATCGGA CGGGTTGGAC CACAACGGCA CGGGTCTGCG
3351 CGTCATCGCG CAAACCCAAC AGGACGGTGG AACGTGGGAA CAGGGCGGTG
```

-continued

3401 TTGAAGGCAA AATGCGCGGC AGTACCCAAA CCGTCGGCAT TGCCGCGAAA
3451 ACCGGCGAAA ATACGACAGC AGCCGCCACA CTGGGCATGG GACGCAGCAC
3501 ATGGAGCGAA AACAGTGCAA ATGCAAAAAC CGACAGCATT AGTCTGTTTG
3551 CAGGCATACG GCACGATGCG GGCGATATCG GCTATCTCAA AGGCCTGTTC
3601 TCCTACGGAC GCTACAAAAA CAGCATCAGC CGCAGCACCG GTGCGGACGA
3651 ACATGCGGAA GGCAGCGTCA ACGGCACGCT GATGCAQCTG GGCGCACTGG
3701 GCGGTGTCAA CGTTCCGCT GCCGCAACGG GAGATTTGAC GGTCGAAGGC
3751 GGTCTGCGCT ACGACCTGCT CAAACAGGAT GCATTCGCCG AAAAAGGCAG
3801 TGCTTTGGGC TGGAGCGGCA ACAGCCTCAC TGAAGGCACG CTGGTCGGAC
3851 TCGCGGGTCT GAAGCTGTCG CAACCCTTGA GCGATAAAGC CGTCCTGTTT
3901 GCAACGGCGG GCGTGGAACG CGACCTGAAC GGACGCGACT ACACGGTAAC
3951 GGGCGGCTTT ACCGGCGCGA CTGCAGCAAC CGGCAAGACG GGGGCACGCA
4001 ATATGCCGCA CACCCGTCTG GTTGCCGGCC TGGGCGCGGA TGTCGAATTC
4051 GGCAACGGCT GGAACGGCTT GGCACGTTAC AGCTACGCCG GTTCCAAACA
4101 GTACGGCAAC CACAGCGGAC GAGTCGGCGT AGGCTACCGG TTCCTCGAGC
4151 ACCACCACCA CCACCACTGA

1 MATNDDDVKK AATVAIAAAY NNGQEINGFK AGETIYDIDE DGTITKKDAT
51 AADVEADDFK GLGLXKVVTN LTKTVNENKQ NVDAKVKAAE SEIEKLTTKL
101 ADTDAALAflT DAALDATTNA LNKLGENITT PAEETKTNIV KIDEKI-
AEAVA
151 DTVDKHAEAF NDIADSIJDET NTKADEAVKT AEAKQTAEE TKQNVDAKVK
201 AAETAAGKAE AAAGTANTAA DKAEAVAARV TDIKADIATN XDNIAKKANS
251 ADVYTREESD SKFVRIDGLN ATTEKLDTRL ASAEKSIADH DTRLNGLDKT
301 VSDLRKETRQ GLAEQAALSG LFQPYNVGGS GGGGTSAPDF NAGGTGIGSN
351 SRATTAXSAA VSYAGIKNEM CKDRSMLCAG RDDVAVTDRD AKINAPPPNL
401 HTGDFPNPND AYKNLINLKP AIEAGYTGRG VEVGIVDTGE SVGSISFPEL
451 YGRKEEGYNE NYKNYTAYMR KEAPEDGGGK DIEASFDDEA VIETEAKPTD
501 IRHVKEIGHI DIJVSHHGGR SVDGRPAGGI APDATLHIMN TNDETKNEMM
551 VAAIRNAWVK LGERGVRIVN NSFGTTSRAG TADLFQIANS EEQYRQALLD
601 YSGGDKTDEG IRLMQQSDYG NLSYHIRNKN MLFIFSTGND AQAQPNTYAL
651 LPFYEDAQK GIITVAGVDR SGEKPKEEKY GEPGTEPLEY GSNHCGITAM
701 WCLSAPYEAS VRFTRTNPIQ IAGTSFSAPI VTGTAALLLQ KPWMSNDNL
751 RTTLLTTAQD IGAVUVDSKP GWGLLDAGKA MNGPASFPFG DFTADTKGTS
801 DIAYSFRNDI SGTGGLIKKG GSQLQLHGHNN TYTGKTIIEG GSLVLYGNNK
851 SDHRVETKGA LIYNGAASGG SLNSDGIVYD ADTDQSGANIE TVHIKGBLQL
901 DGKGTLYTPL GKIJLKVDGTA IIGGELYNSA RGKGAGYLNS TGERVPFLSA
951 AKIGQDYSPF TNIETDGGLL ASLDSVEKTA GSEGDTLSYY VRRGNAARTA
1001 SAAAHSAPAG LKHAVEQGGS NLBNIMVELD ASESSATPET VETAAADRTD
1051 MPGIRPYGAT FRAAAAVQHA NAADGVRIFN SLAATVYADS TAAEADMQGR
1101 RLKAVSDGLD HNGTGLRVIA QTQQDGGTWE QGGVEGKNRG STQTVGIAAK

-continued

1151 TGENTTAAAT LGMGRSTWSE NSANAKTDSI SLPAGIRHDA GDIGYLKGLF

1201 SYGRYKNSIS RSTGADEHAE GSVNGTIMQL GALGGVNVPP AATGDLTVEG

1251 GLRYDLLKQD AFAEKGSALG WSGNSLTEGT LVGLAGLKLS QPLSDRAVLF

1301 ATAGVERDLN GRDYTVTGGF TGATAATGKT GARNMPHTRL VAGLGADVEF

1351 GNGWNGLARY SYAGSKQYGN HSGRVGVGYR FLEHHHHHH*

961cL-ORF46.1
(SEQ ID NOS: 158 and 159)

1 ATGAAACACT TTCCATCCAA AGTACTGACC ACAGCCATCC TTGCCACTTT

51 CTGTAGCGGC GCACTGGCAG CCACAAACGA CGACGATGTT AAAAAAGCTG

101 CCAGTGTGGC CATTGCTGCT GCCTACAACA ATGGCCAAGA AATCAACGGT

151 TTCAAAGCTG GAGAGACCAT CTACGACATT GATGAAGACG GCACAATTAC

201 CAAAAAAGAC GCAACTGCAG CCGATGTTGA AGCCGACQAC TTTAAAGGTC

251 TGGGTCTGAA AAAAGTCGTG ACTAACCTGA CCAAAACCGT CAATGAAAAC

301 AAACAAAACG TCGATGCCAA AGTAAAAGCT GCAGAATCTG AAATAGAAAA

351 GTTAACAACC AAGTTAGCAG ACACTGATGC CGCTTTAGCA GATACTGATG

401 CCGCTCTGGA TGCAACCACC AACGCCTTGA ATAAATTGGG AGAAAATATA

451 ACGACATTTG CTGAAGAGAC TAAGACAAAT ATCGTAAAAA TTGATGAAAA

501 ATTAGAAGCC GTGGCTGATA CCGTCGACAA GCATGCCGAA GCATTCAACG

551 ATATCGCCGA TTCATTGGAT GAAACCAACA CTAAGGCAGA CGAAGCCGTC

601 AAAACCGCCA ATGAAGCCAA ACAGACGGCC GAAGAAACCA AACAAAACGT

651 CGATGCCAAA GTAAAAGCTG CAGAAACTGC AGCAGGCAAA GCCGAAGCTG

701 CCGCTGGCAC AGCTAATACT GCAGCCGACA AGGCCGAAGC TGTCGCTGCA

751 AAAGTTACCG ACATCAAAGC TGATATCGCT ACGAACAAAG ATAATATTGC

801 TAAAAAAGCA AACAGTGCCG ACGTGTACAC CAGAGAAGAG TCTGACAGCA

851 AATTTGTCAG AATTGATGGT CTGAACGCTA CTACCGAAAA ATTGGACACA

901 CGCTTGGCTT CTGCTGAAAA ATCCATTGCC GATCACGATA CTCGCCTGAA

951 CGGTTTGGAT AAAACAGTGT CAGACCTGCG CAAAGAAACC CGCCAAGGCC

1001 TTGCAGAACA AGCCGCGCTC TCCGGTCTGT TCCAACCTTA CAACGTGGGT

1051 GGATCCGGAG GAGGAGGATC AGATTTGGCA AACGATTCTT TTATCCGGCA

1101 GGTTCTCGAC CGTCAGCATT TCGAACCCGA CGGGAAATAC CACCTATTCG

1151 GCAGCAGGGG GGAACAGGCC GAGCGCAGCG GCCATATCGG ATTGGGAAAA

1201 ATACAAAGCC ATCAGTTGGG CAACCTGATG ATTCAACAGG CGGCCATTAA

1251 AGGAAATATC GGCTACATTG TCCGCTTTTC CQATCACGGG CACGAAGTCC

1301 ATTCCCCCTT CGACAACCAT GCCTCACATT CCGATTCTGA TGAAGCCGGT

1351 AGTCCCGTTG ACGGATTTAG CCTTTACCGC ATCCATTGGG ACGGATACGA

1401 ACACCATCCC GCCGACGGCT ATGACGGGCC ACAGGGCGGC GGCTATCCCG

1451 CTCCCAAAGG CGCGACGGAT ATATACAGCT ACGACATAAA AGGCGTTGCC

1501 CAAAATATCC GCCTCAACCT GACCGACAAC CGCAGCACCG GACAACGGCT

1551 TGCCGACCGT TTCCACAATG CCGGTAGTAT GCTGACGCAA GGACTAGGCG

1601 ACGGATTCAA ACGCGCCACC CGATACAGCC CCGAGCTGGA CAGATCGGGC

1651 AATGCCGCCG AAGCCTTCAA CGGCACTGCA GATATCGTTA AAAACATCAT

-continued

```
1701 CGGCGCGGCA GGAGAAATTG TCGGCGCAGG CGATGCCGTG CAGGGCATAA
1751 GCGAAGGCTC AAACATTGCT GTCATGCACG GCTTGGGTCT GCTTTCCACC
1801 GAAAACAAGA TGGCGCGCAT CAACGATTTG GCAGATATGG CGCAACTCAA
1851 AGACTATGCC GCAGCAGCCA TCCGCGATTG GGCAGTCCAA AACCCCAATG
1901 CCGCACAAOG CATAGAAGCC GTCAGCAATA TCTTTATGGC AGCCATCCCC
1951 ATCAAAGGGA TTGGAGCTGT TCGGGGAAAA TACGGCTTGG GCGGCATCAC
2001 GGCACATCCT ATCAAGCGGT CGCAGATGGG CGCGATCGCA TTGCCGAAAG
2051 GGAAATCCGC CGTCAGCGAC AATTTTGCCG ATGCGGCATA CGCCAAATAC
2101 CCGTCCCCTT ACCATTCCCG AAATATCCGT TCAAACTTGG AGCAGCGTTA
2151 CGGCAAAGAA AACATCACCT CCTCAACCGT GCCGCCGTCA AACGGCAAAA
2201 ATGTCAAACT GGCAGACCAA CGCCACCCGA AGACAGGCGT ACCGTTTGAC
2251 GGTAAAGGGT TTCCGAATTT TGAGAAGCAC GTGAAATATG ATACGTAACT
2301 CGAG

   1 MKHFPSKVLT TAILATFCSG ALAATNDDDV KKAATVAIAA AYNNGQEING
  51 FKAGBTIYDI DEDGTITKKD ATAADVBADD FKGLGLKKVV TNLTKTVNEN
 101 KQNVDAXVKA AESBIEILTT KLADTDAALA DTDAALDATT NALNKLGENI
 151 TTFAEETKTN IVKIDEKLEA VADTVDKHAE AFNDIADSLD ETNTKADEAV
 201 KTANEAKQTA EETKQNVDAK VKAAETAAGR AEAAAGTANT AADKAEAVAA
 251 KVTDIKADIA TNKDNIAKKA NSADVYTRBE SDSKFVRIDG LNATTEKIJDT
 301 RLASAEKSIA DHDTRLNGLD KWSDLRKRT RQGLAEQAAL SGLPQPYNVG
 351 GSGGOGSDLA NDSFIRQVLD RQHFEPDGKY HLFGSRGELA ERSGHIGLGK
 401 IQSHQLGNIM ZQQAAIKGNI GYIVRFSDHG HHVHSPFDNH ASHSDSDEAG
 451 SPVDGFSLYR IHWDGYEHHP ADGYDGPQGG GYPAPKGARD IYSYDIKGVA
 501 QNIRLNLTDN RSTGQRLADR FHNAGSMLTQ GVGDGFKRAT RYSPELDRSG
 551 NAAEAPNGTA DIVKNIIGAA GEIVGAGDAV QGISBGSNIA VMHGLGLLST
 601 ENKMARINDL ADNAQLKDYA AAIRDWAVQ NPNAAQGIEA VSNIFNAAIP
 651 IKGIGAVRGK YGLGGITAHP IKRSQMGAIA LPKGKSAVSD NFADAAYAKY
 701 PSPYHSRNIR SNLEQRYGK NITSSTVPPS NGKNVKLADQ RHPKTGVPFD
 751 GKGFPNFEKH VKYDT*
```

961cL-741
(SEQ ID NOS: 160 and 161)

```
   1 ATGAAACACT TTCCATCCAA AGTACTGACC ACAGCCATCC TTGCCACTTT
  51 CTGTAGCGGC GCACTGGCAG CCACAAACGA CGACGATGTT AAAAAAGCTG
 101 CCACTGTGGC CATTGCTGCT GCCTACAACA ATGGCCAACA AATCAACGGT
 151 TTCAAAGOTG GAGACACCAT CTACGACATT GATGAAGACG GCACAATTAC
 201 CAAAAAAGAC GCAACTGCAG CCGATGTTGA AGCCGACGAC TTTAAAGGTC
 251 TGGGTCTGAA AAAAGTCGTG ACTAACCTGA CCAAAACCGT CAATGAAAAC
 301 AAACAAAACG TCGATGCCAA AGTAAAAGCT GCAGAATCTG AAATAGAAAA
 351 GTTAACAACC AAGTTAGCAG ACACTGATGC CGCTTTAGCA GATACTGATG
 401 CCGCTCTGGA TGCAACCACC AACGCCTTGA ATAAATTGGG AGAAAATATA
 451 ACGACATTTG CTGAAGAGAC TAAGACAAAT ATCGTAAAAA TTGATGAAAA
```

-continued

```
 501 ATTAGAAGCC GTGGCTGATA CCGTCGACAA GCATGCCGAA GCATTCAACG
 551 ATATCGCCGA TTCATTGGAT GAAACCAACA CTAAGGCAGA CGAAGCCGTC
 601 AAAACCGCCA ATGAAGCCAA ACAGACGGCC GAAGAAACCA AACAAAACGT
 651 CGATGCCAAA GTAAAAGCTG CAGAAACTGC AGCAGGCAAk GCCGAAGCTG
 701 CCGCTGGCAC AGCTAATACT GCAGCCGACA ACGCCGAAGC TGTCGCTGCA
 751 AAAGTTACCG ACATCAAAGC TGATATCGCT ACGAACAAAG ATAATATPGC
 801 TAAAAAAGCA AACAGTGCCG ACGTGTACAC CAGAGAAGAG TCTGACAGCA
 851 AATTTGTCAG AATTGCTGGT CTGAACGCTA CTACCGAAAA ATTGGACACA
 901 CGCTTGGCTT CTGCTGAAAA ATCCATTGCC GATCACGATA CTCGCCTGAA
 951 CGGGTTGGAT AAAACAGTGT CACACCTGCG CAAAGAAACC CGCCAAGGCC
1001 TTGCAGAACA AGCCGCGCTC TCCGGTCTGT TCCAACCTTA CAACGTGGGT
1051 GGATCCGGAC GGGGTGGTGT CGCCGCCGkC ATCGGTGCGG GGCTTGCCGA
1101 TGCACTAACC GCACCGCTCG ACCATAAAGA CAAAGGTTTG CAGTCTTTGA
1151 CGCTGGATCA GTCCGTCAGG AAAAACGAGA AACTGAAGGT GGCGGCACAA
1201 GGTGCGGAAA AACTTATGG AAACGGTGAC AGCCTCAATA CGGGCAAATT
1251 GAAGAACGAC AAGGTCAGCC GTTTCGACTT TATCCGCCAA ATCGAAGTGG
1301 ACGGGCAGOT CATTACCTTG GAGAGTGGAG AGTTCCAAGT ATACAAACAA
1351 AGCCATTCCG CCTTAACCGC CTTTCAGACC GAGCAAATAC AAGATTCGGA
1401 GCATTCCGGG AAGATGGTTG CGAAACGCCA GTTCAGAATC GGCGACATAG
1451 CGGGCGAACA TACATCTTTT GACAAGCTTC CCGAAGGCGG CAGGGCGACA
1501 TATCGCGGGA CGGCGTTCGG TTCAGACGAT GCCGGCGGAA AACTGACCTA
1551 CACCATAGAT TTCGCCGCCA AGCAGGGAAA CGGCAAAATC GAACATTTGA
1601 AATCGCCAGA ACTCAATGTC GACCTGGCCG CCGCCGATAT CAAGCCGGAT
1651 GGAAAACGCC ATGCCGTCAT CAGCGGTTCC GTCCTTTACA ACCAAGCCGA
1701 GAAAGGCAGT TACTCCCTCG GTATCTTTGG CGGAAAAGCC CAGGAAGTTG
1751 CCGGCAGCGC GGAAGTGAAA ACCGTAAACG GCATACGCCA TATCGGCCTT
1801 GCCGCCAAGC AACTCGAGCA CCACCACCAC CACCACTGA

   1 MKHFPSKVLT TAILATFCSG ALAATNDDDV KKAATVAZAA AYNNGQEING
  51 FKAGETIYDI DEDGTITKKD ATAADVEADD FKGLGLKKVV TNLTKTVNEN
 101 KQNVDAKVKA AESEIEKLTT KLADTDAALA DTDAALDATT NALNKLGHNI
 151 TTFABETKTN IVKIDEKLEA VADTVDKAE AFNDIADSLD ETNTKADEAV
 201 KTANEAKQTA EBTKQNVDAK VKAAETAAGK AEAAAGTANT AADKAEAVAA
 251 KVTDIKADIA TNKDNIAXKA NSADVYTREB SDSKFVRIDG LNATTEKLDT
 301 ELASAEKSIA DHDTRLNGLD KTVSDLRXET RQGLAEQAAL SGLFQPYNVG
 351 GSGGGGVAAD IGAGLADALT APLDHKDKGL QSLTDDQSVR KNEKLKLAAQ
 401 GAEKTYGNGD SLNTGKLKND KVSRFDFIRQ IEVDGQLITL ESGEFQVYKQ
 451 SHSALTAFQT EQIQDSEHSG KMVAXRQFRI GDIAGEHTSF DKLPEGGRAT
 501 YRGTAFGSDD AGGKLTYTID FAAKQGNGKI EHLKSPELNV DLAAADIKPD
 551 GKRHAVZSGS VLYNQAEKGS YSLGIPGGKA QEVAGSAEVK TVNGIRHIGL
 601 AAKQLEHHHH HH*
```

-continued

961cL-983
(SEQ ID NOS: 162 and 163)

```
   1 ATGAAACACT TTCCATCCAA AGTACTGACC ACAGCCATCC TTGCCACTTT

  51 CTGTAGCGGC GCACTGGCAG CCACAAACGA CGACGATGTT AAAAAAGCTG

 101 CCACTGTGGC CATTGCTGCT GCCTACAACA ATGGCCAAGA AATCAACGGT

 151 TTCAAAGCTG GAGAGACCAT CTACGACATT GATGAAGACG GCACAATTAC

 201 CAAAAAAGAC GCAACTGCAG CCGATGTTGA AGCCGACGAC TTTAAAGGTC

 251 TGGGTCTGAA AAAAGTCGTG ACTAACCTGA CCAAAACCGT CAATGAAAAC

 301 AAACAAAACG TCGATGCCAA AGTAAAAGCT GCAGAATCTG AAATAGAAAA

 351 GTTAACAACC AAGTTAGCAG ACACTGATGC CGCTTTAGCA GATACTGATG

 401 CCGCTCTGGA TGCAACCACC AACGCCTTGA ATAAATTGGG AGAAAATATA

 451 ACGACATTTG CTGAAGAGAC TAAGACAAAT ATCGTAAAAA TTGATGAAAA

 501 ATTAGAAGCC GTGGCTGATA CCGTCGACAA GCATGCCGAA GCATTCAACG

 551 ATATCGCCGA TTCATTGGAT GAAACCAACA CTAAGGCAGA CGAAGCCGTC

 601 AAAACCGCCA ATGAAGCCAA ACAGACGGCC GAAGAAACCA AACAAAACGT

 651 CGATGCCAAA GTAAAAGCTG CAGAAACTGC AGCAGGCAAA GCCGAAGCTG

 701 CCGCTGGCAC AGCTAATACT GCAGCCGACA AGGCCGAAGC TGTCGCTGCA

 751 AAAGTTACCG ACATCAAAGC TGATATCGCT ACGAACAAAG ATAATATTGC

 801 TAAAAAAGCA AACAGTGCCG ACGTGTACAC CAGAGAAGAG TCTGACAGCA

 851 AATTTGTCAG AATTGATGGT CTGAACGCTA CTACCGAAAA ATTGGACACA

 901 CGCTTGGCTT CTGCTGAAAA ATCCATTGCC GATCACGATA CTCGCCTGAA

 951 CGGTTTGGAT AAAACAGTGT CAGACCTGCG CAAAGAAACC CGCCAAGGCC

1001 TPGCAGAACA AGCCGCGCTC TCCGGTCTGT TCCAACCTTA CAACGTGGGT

1051 GGATCCGGCG GAGGCGGCAC TTCTGCGCCC GACTTCAATG CAGGCGGTAC

1101 CGGTATCGGC AGCAACAGCA GAGCAACAAC AGCGAAATCA GCAGCAGTAT

1151 CTTACGCCGG TATCAAGAAC GAAATGTGCA AAGACAGAAG CATGCTCTGT

1201 GCCGGTCGGG ATGACGTTGC GGTTACAGAC AGGGATGCCA AAATCAATGC

1251 CCCCCCCCCG AATCTGCATA CCGGAGACTT TCCAAACCCA AATGACGCAT

1301 ACAAGAATTT GATCAACCTC AAACCTGCAA TTGAAGCAGG CTATACAGGA

1351 CGCGGGGTAG AGGTAGGTAT CGTCGACACA GGCGAATCCG TCGGCAGCAT

1401 ATCCTTTCCC GAACTGTATG GCAGAAAAGA ACACGGCTAT AACGAAAATT

1451 ACAAAAACTA TACGGCGTAT ATGCGGAAGG AAGCGCCTGA AGACGGAGGC

1501 GGTAAAGACA TTGAAGCTTC TTTCGACGAT GAGGCCGTTA TAGAGACTGA

1551 ACCAAAGCCG ACGGATATCC GCCACGTAAA AGAAATCGGA CACATCGATT

1601 TGGTCTCCCA TATTATTGGC GGGCGTTCCG TGGACGGCAG ACCTGCAGGC

1651 GGTATTGCGC CCGATGCGAC GCTACACATA ATGAATACGA ATGATGAAAC

1701 CAAGAACGAA ATGATGGTTG CAGCCATCCG CAATGGATGG GTCAAGCTGG

1751 GCGAACGTGG CGTGCGCATC GTCAATAACA GTTTTGGAAC AACATCGAGG

1801 GCAGGCACTG CCGACCTTTT CCAAATAGCC AATTCGGAGG AGCAGTACCG

1851 CCAAGCGTTG CTCGACTATT CCGGCGGTGA TAAAACAGAC GAGGGTATCC

1901 GCCTGATGCA ACAGAGCGAT TACGGCAACC TGTCCTACCA CATCCGTAAT
```

-continued

1951 AAAAACATGC TTTTCATCTT TTCGACAGGC AATGACGCAC AAGCTCAGCC

2001 CAACACATAT GCCCTATTGC CATTTTATGA AAAAGACGCT CAAAAAGGCA

2051 TTATCACAQT CGCAGGCGTA GACCGCAGTG GAGAAAAGTT CAAACGGGAA

2101 ATGTATGGAG AACCGGGTAC AGAACCGCC GAGTATGGCT CCAACCATTG

2151 CGGAATTACT GCCATGTGGT GCCTGTCGGC ACCCTATGAA GCAAGCGTCC

2201 GTTTCACCCG TACAAACCCG ATTCAAATTG CCGGAACATC CTTTTCCGCA

2251 CCCATCGTAA CCGGCACGGC GGCTCTGCTG CTGCAGAAAT ACCCGTGGAT

2301 GAGCAACGAC AACCTGCGTA CCACGTTGCT GACGACGGCT CACGACATCG

2351 GTGCAGTCGG CGTGGACAGC AAGTTCGGCT GGGGACTGCT GGATGCGGGT

2401 AAGGCCATGA ACGGACCCGC GTCCTTTCCG TTCGGCGACT TTACCGCCGA

2451 TACGAAAGGT ACATCCGATA TTGCCTACTC CTTCCGTAAC GACATTTCAG

2501 GCACGGGCGG CTTGATCAAA AAAGGCGGCA GCCAACTGCA ACTGCACGGC

2551 AACAACACCT ATACGGGCAA AACCATTATC GAAGGCGGCC CGCTGGTGTT

2601 GTACGGCAAC AACAAATCGG ATATGCGCGT CGAAACCAAA GGTGCGCTGA

2651 TTTATAACGG GGCGGCATCC GGCGGCAGCC TGAACAGCGA CGGCATTGTC

2701 TATCTGGCAG ATACCGCCA ATCCGGCGCA AACGAAACCG TACACATCAA

2751 AGGCAGTCTG CAGCTGGACG GCAAAGGTAC GCTGTACACA CGTTTGGGCA

2801 AACTGCTGAA AGTGGACGGT ACGGCGATTA TCGGCGGCAA GCTGTACATG

2851 TCGGCACGCG GCAAGGGGGC AGGCTATCTC AACAGTACCG GACGACGTGT

2901 TCCCTTCCTG AGTGCCGCCA AAATCGGGCA GGATTATTCT TTCTACACAA

2951 ACATCGAAAC CGACGGCGGC CTGCTGGCTT CCCTCGACAG CGTCGAAAAA

3001 ACAGCGGGCA GTGAAGGCGA CACGCTGTCC TATTATGTCC GTCGCGGCAA

3051 TGCGGCACGG ACTGCTTCGG CAGCGGCACA TTCCGCGCCC GCCGGTCTGA

3101 AACACGCCGT AGAACAGGGC GGCAGCAATC TGGAAAACCT GATGGTCGAA

3151 CTGGATGCCT CCGAATCATC CGCAACACCC GAGACGGTTG AAAGTGCGGC

3201 AGCCGACCGC ACAGATATOC CGGGCATCCG CCCCTACGGC GCAACTTTCC

3251 GCGCAGCGGC AGCCGTACAG CATGCGAATG CCGCCGACGG TGTACGCATC

3301 TTCAACAGTC TCGCCGCTAC CGTCTATGCC GACAGTACCG CCGCCCATGC

3351 CGATATGCAG GGACGCCGCC TGAAAGCCGT ATCGGACGGG TTGGAGCACA

3401 ACGGCACGGG TCTGCGCGTC ATCGCGCAAA CCCAACAGGA CGGTGGAACG

3451 TGGGAACAGG GCGGTGTDGA AGGCAAAATG CGCGGCAGTA CCCAAACCGT

3501 CGGCATTGCC GCGAAAACCG GCGAAAATAC GACAGCAGCC GCCACACTGG

3551 GCATGGGACG CAGCACATGG AGCGAAAACA GTGCAAATGC AAAAACCGAC

3601 AGCATTACTC TGTTTGCAGG CATACGGCAC GATGCGGGCG ATATCGGCTA

3651 TCTCAAAGGC CTGTTCTCCT ACGGACGCTA CAAAAACAGC ATCAQCCGCA

3701 GCACCGGTGC GGACGAACAT GCGGAAGGCA GCGTCAACGG CACGCTGATG

3751 CAGCTGGGCG CACTGGGCGG TGTCAACGTT CCGTTTGCCG CAACGGGAGA

3801 TTTGACGGTC GAAGGCGGTC TGCGCTACGA CCTGCTCAAA CAGGATGCAT

3851 TCGCCGAAAA AGGCAGTGCT TTGGGCTGGA GCGGCAACAG CCTCACTGAA

3901 GGCACGCTGG TCGGACTCGC GGGTCTGAAG CTGTCGCAAC CCTTGAGCQA

-continued

```
3951 TAAAGCCGTC CTGTTTGCAA CGGCGGGCGT GGAACGCGAC CTGAACGGAC

4001 GCGACTACAC GGTAACGGGC GGCTTTACCG GCGCGACTGC AGCAACCGGC

4051 AAQACGGGGG CACGCAATAT GCCGCACACC CGTCTGGTTG CCGGCCTGGG

4101 CGCGGATGTC GAATTCGGCA ACGGCTGGAA CGGCTTGGCA CGTTACAGCT

4151 ACGCCGGTTC CAAACAGTAC GGCAACCACA GCGGACQAGT CGGCGTAGGC

4201 TACCGGTTCT GACTCGAG

   1 MKHFPSKVLT TAILATFCSG ALAATNDDDV KKAATVAIAA AYNNQQEING

  51 FKAGETIYDI DHDGTITKKD ATAADVEADD FKGLGLKKVV TNLTKTVNEN

 101 KQNVDAKVKA AESEIEKLTT KLADTDAALA DTDAALDATT NMZNKLGENI

 151 TTFABETKTN IVKIDEKLEA VADTVDKNIAE AFNDIADSLD ETNTKADEAV

 201 KTANEARQTA EETKQNVDAR VKAAETAAGK AEAAAGTANT AADKAEAVAA

 251 KVTDIKADIA TNKDNIAKKA NSADVYTREB SDSKFVRIDG LNATTEKLDT

 301 RLASAEKEIA DIWTPLNGLD KTVSDLRKET RQGLAEQAAL SGLFQPYNVG

 351 GSGGGGTSAP DFNAGGTGIG SNSRATTAKS AAVSYAGIKN EMCKDRSMLC

 401 AGRDDVAVTD RDAKINAPPP NLHTGDFPNP NDAYKNLINL KPAIEAGYTG

 451 EGVEVGIVDT GESVGSISFP BLYGRKEEGY NENYKNYTAY HRKEAPEDGG

 501 GKDIEASFDD BAVIETEAKP TDIRHVKEIG HIDLVSHIIG GESVDGEPAG

 551 GIAPDATLHI MNTNDETKNE LDYSGGDKTD EGIRLMQQSD YRNLSYHIRN

 601 AGTADLFQIA NSEBQYEQAL LDYSGGDKTD EGIEIMQQSD YGNLSYHIRN

 651 KNMLPIFSTG NDAQAQPNTY ALLPFYEKDA QKGIITVAGV DRSGEKFKRE

 701 MYGEPGTBPL EYGSNHCGIT AMWCLSAPYE ASVRFTRTNP IQIAGTSPSA

 751 PIVTGTAALL LQKYOWNSBD NLRTTLLTTA QDIGAVGVDS KFGWGLLDAG

 801 KAMNGPABFP FGDFTADTKG TSDIAYSFRN DISGTGGLIK KGGSQLQLHG

 851 NNTYTGKTII EGGBLVLYGN NKSDMRVETK GALIYNGAAS GGSLNBDGIV

 901 YLADTDQSGA NBTVHIKGSL QLDGKGTLYT ELGKLLKVDG TAIIGGKLYM

 951 SARGKGAGYL NSTGRRVPPL SAAKIGQDYS FFTNIETDGG LLASLDSVEK

1001 TAGSRGDTLS YYVRRGNAAR TASAAAHSAP AGLKHAVEQG GSNLENLMVB

1051 LDASESSATP ETVETAAADR TDNPGIEPYG ATFRAAAAVQ HANAADGVRI

1101 FNSLAATVYA DSTAAHADMQ GRRLKAVSDG LDHNGTGLRV IAQTQQDGGT

1151 WEQGGVEGKH RGSTQTVGIA AKTGENTTAA ATLGHGRSTW SENSANAKTD

1201 SISLFAGIRH DAGDIGYLKG LFSYGRYKNS ISRSTGADBH AEGSVNGTLM

1251 QLGALGGVNV PFAATGDLTV EGGLRYDLLK QDAFAEKGBA LGWSGNSLTE

1301 GTLVGLAGLK LSQPLSDKAV LFATAGVERD LNGRDYTVTG GFTGATAATG

1351 KTGAPNMPHT RLVAGLGADV EFGNGWNGLA RYSYAGSKQY GNHSGRVGVG

1401 YRF*
```

It will be understood that the invention has been described by way of example only and modifications may be made whilst remaining within the scope and spirit of the invention. For instance, the use of proteins from other strains is envisaged [e.g. see WO00/66741 for polymorphic sequences forORF4, ORF40, ORF46, 225, 235, 287, 519, 726, 919 and 953].

Experimental Details

FPLC Protein Purification

The following table summarises the FPLC protein purification that was used:

| Protein | PI | Column | Buffer | pH | Protocol |
|---|---|---|---|---|---|
| 121.1$^{untagged}$ | 6.23 | Mono Q | Tris | 8.0 | A |
| 128.1$^{untagged}$ | 5.04 | Mono Q | Bis-Tris propane | 6.5 | A |
| 406.1L | 7.75 | Mono Q | Diethanolamine | 9.0 | B |
| 576.1L | 5.63 | Mono Q | Tris | 7.5 | B |
| 593$^{untagged}$ | 8.79 | Mono S | Hepes | 7.4 | A |
| 726$^{untagged}$ | 4.95 | Hi-trap S | Bis-Tris | 6.0 | A |
| 919$^{untagged}$ | 10.5(-leader) | Mono S | Bicine | 8.5 | C |
| 919Lorf4 | 10.4(-leader) | Mono S | Tris | 8.0 | B |
| 920L | 6.92(-leader) | Mono Q | Diethanolamine | 8.5 | A |
| 953L | 7.56(-leader) | Mono S | MES | 6.6 | D |
| 982$^{untagged}$ | 4.73 | Mono Q | Bis-Tris propane | 6.5 | A |
| 919-287 | 6.58 | Hi-trap Q | Tris | 8.0 | A |
| 953-287 | 4.92 | Mono Q | Bis-Tris propane | 6.2 | A |

Buffer solutions included 20-120 mM NaCl, 5.0 mg/ml CHAPS and 10% v/v glycerol. The dialysate was centrifuged at 13000 g for 20 min and applied to either a mono Q or mono S FPLC ion-change resin. Buffer and ion exchange resins were chosen according to the pI of the protein of interest and the recommendations of the FPLC protocol manual [Pharmacia: *FPLC Ion Exchange and Chromatofocussing; Principles and Methods*. Pharmacia Publication]. Proteins were eluted using a step-wise NaCl gradient. Purification was analysed by SDS-PAGE and protein concentration determined by the Bradford method.

The letter in the 'protocol' column refers to the following:

FPLC-A: Clones 121.1, 128.1, 593, 726, 982, periplasmic protein 920L and hybrid proteins 919-287, 953-287 were purified from the soluble fraction of *E.coli* obtained after disruption of the cells. Single colonies harbouring the plasmid of interest were grown overnight at 37° C. in 20 ml of LB/Amp (100 μg/ml) liquid culture. Bacteria were diluted 1:30 in 1.0 L of fresh medium and grown at either 30° C. or 37° C. until the $OD_{550}$ reached 0.6-08. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed on ice or at 4° C. For cytosolic proteins (121.1, 128.1, 593, 726 and 982) and periplasmic protein 920L, bacteria were resuspended in 25 ml of PBS containing complete protease inhibitor (Boehringer-Mannheim). Cells were lysed by by sonication using a Branson Sonifier 450. Disrupted cells were centrifuged at 8000 g for 30 min to sediment unbroken cells and inclusion bodies and the supernatant taken to 35% v/v saturation by the addition of 3.9 M $(NH_4)_2SO_4$. The precipitate was sedimented at 8000 g for 30 minutes. The supernatant was taken to 70% v/v saturation by the addition of 3.9 M $(NH_4)_2SO_4$ and the precipitate collected as above. Pellets containing the protein of interest were identified by SDS-PAGE and dialysed against the appropriate ion-exchange buffer (see below) for 6 hours or overnight. The periplasmic fraction from *E.coli* expressing 953L was prepared according to the protocol of Evans et. al. [*Infect. Immun.* (1974) 10:1010-1017] and dialysed against the appropriate ion-exchange buffer. Buffer and ion exchange resin were chosen according to the pI of the protein of interest and the recommendations of the FPLC protocol manual (Pharmacia). Buffer solutions included 20 mM NaCl, and 10% (v/v) glycerol. The dialysate was centrifuged at 13000 g for 20 min and applied to either a mono Q or mono S FPLC ion-exchange resin. Buffer and ion exchange resin were chosen according to the pI of the protein of interest and the recommendations of the FPLC protocol manual (Pharmacia). Proteins were eluted from the ion-exchange resin using either step-wise or continuous NaCl gradients. Purification was analysed by SDS-PAGE and protein concentration determined by Bradford method. Cleavage of the leader peptide of periplasmic proteins was demonstrated by sequencing the $NH_2$-terminus (see below).

FPLC-B: These proteins were purified from the membrane fraction of *E.coli*. Single colonies harbouring the plasmid of interest were grown overnight at 37° C. in 20 ml of LB/Amp (100 μg/ml) liquid culture. Bacteria were diluted 1:30 in 1.0 L of fresh medium. Clones 406.1L and 919LOrf4 were grown at 30° C. and Orf25L and 576.1L at 37° C. until the $OD_{550}$ reached 0.6-0.8. In the case of 919LOrf4, growth at 30° C. was essential since expression of recombinant protein at 37° C. resulted in lysis of the cells. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed at 4° C. Bacteria were resuspended in 25 ml of PBS containing complete protease inhibitor (Boehringer-Mannheim) and lysed by osmotic shock with 2-3 passages through a French Press. Unbroken cells were removed by centrifugation at 5000 g for 15 min and membranes precipitated by centrifugation at 100000 g (Beckman Ti50, 38000 rpm) for 45 minutes. A Dounce homogenizer was used to re-suspend the membrane pellet in 7.5 ml of 20 mM Tris-HCl (pH 8.0), 1.0 M NaCl and complete protease inhibitor. The suspension was mixed for 2-4 hours, centrifuged at 100000 g for 45 min and the pellet resuspended in 7.5 ml of 20 mM Tris-HCl (pH 8.0), 1.0M NaCl, 5.0 mg/ml CHAPS, 10% (v/v) glycerol and complete protease inhibitor. The solution was mixed overnight, centrifuged at 100000 g for 45 minutes and the supernatant dialysed for 6 hours against an appropriately selected buffer. In the case of Orf25.L, the pellet obtained after CHAPS extraction was found to contain the recombinant protein. This fraction, without further purification, was used to immunise mice.

FPLC-C: Identical to FPLC-A, but purification was from the soluble fraction obtained after permeabilising *E.coli* with polymyxin B, rather than after cell disruption.

FPLC-D: A single colony harbouring the plasmid of interest was grown overnight at 37° C. in 20 ml of LB/Amp (100 μg/ml) liquid culture. Bacteria were diluted 1:30 in 1.0 L of fresh medium and grown at 30° C. until the $OD_{550}$ reached 0.6-0.8. Expression of recombinant protein was induced with IPTG at a final concentration of 1.0 mM After incubation for 3 hours, bacteria were harvested by centrifugation at 8000 g for 15 minutes at 4° C. When necessary cells were stored at −20° C. All subsequent procedures were performed on ice or at 4° C. Cells were resuspended in 20 mM Bicine (pH 8.5), 20 mM NaCl, 10% (v/v) glycerol, complete protease inhibitor (Boehringer-Mannheim) and disrupted using a Branson Sonifier 450. The sonicate was centrifuged at 8000 g for 30 min to sediment unbroken cells and inclusion bodies. The recombinant protein was precipitated from solution between 35% v/v and 70% v/v saturation by the addition of 3.9M $(NH_4)_2SO_4$. The precipitate was sedimented at 8000 g for 30 minutes, resuspended in 20 mM Bicine (pH 8.5), 20 mM NaCl, 10% (v/v) glycerol and dialysed against this buffer for 6 hours or overnight. The dialysate was centrifuged at 13000 g for 20 min and applied to the FPLC resin. The protein was eluted from the column using a step-wise NaCl gradients. Purification was analysed by SDS-PAGE and protein concentration determined by Bradford method.

Cloning Strategy and Oligonucleotide Design

Genes coding for antigens of interest were amplified by PCR, using oligonucleotides designed on the basis of the genomic sequence of *N.meningitidis* B MC58. Genomic DNA from strain 2996 was always used as a template in PCR reactions, unless otherwise specified, and the amplified fragments were cloned in the expression vector pET21b+ (Novagen) to express the protein as C-terminal His-tagged product, or in pET-24b+(Novagen) to express the protein in 'untagged' form (e.g. ΔG 287K).

Where a protein was expressed without a fusion partner and with its own leader peptide (if present), amplification of the open reading frame (ATG to STOP codons) was performed.

Where a protein was expressed in 'untagged' form, the leader peptide was omitted by designing the 5'-end amplification primer downstream from the predicted leader sequence.

The melting temperature of the primers used in PCR depended on the number and type of hybridising nucleotides in the whole primer, and was determined using the formulae:

$$T_{m1}=4\ (G+C)+2\ (A+T) \quad \text{(tail excluded)}$$

$$T_{m2}=64.9+0.41\ (\%\ GC)-600/N \quad \text{(whole primer)}$$

The melting temperatures of the selected oligonucleotides were usually 65-70° C. for the whole oligo and 50-60° C. for the hybridising region alone.

Oligonucleotides were synthesised using a Perkin Elmer 394 DNA/RNA Synthesizer, eluted from the columns in 2.0 ml $NH_4OH$, and deprotected by 5 hours incubation at 56° C. The oligos were precipitated by addition of 0.3M Na-Acetate and 2 volumes ethanol. The samples were centrifuged and the pellets resuspended in water.

| | | Sequences | SEQ ID NO: | Restriction site |
|---|---|---|---|---|
| Orf1L | Fwd | CGCGGATCCGCTAGC-AAAACAACCGACAAACGG | 164 | NheI |
| | Rev | CCCGCTCGAG-TTACCAGCGGTAGCCTA | 165 | XhoI |
| Orf1 | Fwd | CTAGCTAGC-GGACACACTTATTTCGGCATC | 166 | NheI |
| | Rev | CCCGCTCGAG- TTACCAGCGGTAGCCTAATTTG | 167 | XhoI |
| Orf1LOmpA | Fwd | | | NdeI-(NheI) |
| | Rev | CCCGCTCGAG- | 168 | XhoI |
| Orf4L | Fwd | CGCGGATCCCATATG-AAAACCTTCTTCAAAACC | 169 | NdeI |
| | Rev | CCCGCTCGAG-TTATTTGGCTGCGCCTTC | 170 | XhoI |
| Orf7-1L | Fwd | GCGGCATTAAT-ATGTTGAGAAAATTGTTGAAATGG | 171 | AseI |
| | Rev | GCGGCCTCGAG-TTATTTTTTCAAAATATATTTGC | 172 | XhoI |
| Orf9-1L | Fwd | GCGGCCATATG-TTACCTAACCGTTTCAAAATGT | 173 | NdeI |
| | Rev | GCGGCCTCGAG-TTATTTCCGAGGTTTTCGGG | 174 | XhoI |
| Orf23L | Fwd | CGCGGATCCCATATG-ACACGCTTCAAATATTC | 175 | NdeI |
| | Rev | CCCGCTCGAG-TTATTTAAACCGATAGGTAAA | 176 | XhoI |
| Orf25-l His | Fwd | CGCGGATCCCATATG-GGCAGGGAAGAACCGC | 177 | NdeI |
| | Rev | GCCCAAGCTT-ATCGATGGAATAGCCGCG | 178 | HindIII |
| Orf29-1 b-His | Fwd | CGCGGATCCGCTAGC-AACGGTTTGGATGCCCG | 179 | NheI |
| (MC58) | Rev | CCCGCTCGAG-TTTGTCTAAGTTCCTGATAT | 180 | XhoI |
| | | CCCGCTCGAG-ATTCCCACCTGCCATC | 181 | |
| Orf29-1 b-L | Fwd | CGCGGATCCGCTAGC-ATGAATTTGCCTATTCAAAAAT | 182 | NheI |
| (MC58) | Rev | CCCGCTCGAG-TTAATTCCCACCTGCCATC | 183 | XhoI |
| Orf29-1 c-His | Fwd | CGCGGATCCGCTAGC-ATGAATTTGCCTATTCAAAAAT | 184 | NheI |
| (MC58) | Rev | CCCGCTCGAG-TTGGACGATGCCCGCGA | 185 | XhoI |
| Orf29-1 c-L | Fwd | CGCGGATCCGCTAGC-ATGAATTTGCCTATTCAAAAAT | 186 | NheI |
| (MC58) | Rev | CCCGCTCGAG-TTATTGGACGATGCCCGC | 187 | XhoI |
| Orf25L | Fwd | CGCGGATCCCATATG-TATCGCAAACTGATTGC | 188 | NdeI |
| | Rev | CCCGCTCGAG-CTAATCGATGGAATAGCC | 189 | XhoI |
| Orf37L | Fwd | CGCGGATCCCATATG-AAACAGACAGTCAAATG | 190 | NdeI |
| | Rev | CCCGCTCGAG-TCAATAACCCGCCTTCAG | 191 | XhoI |
| Orf38L | Fwd | CGCGGATCCCATATG-TTACGTTTGACTGCTTTAGCCGTATGCACC | 192 | NdeI |
| | Rev | CCCGCTCGAG-TTATTTTGCCGCGTTAAAAGCGTCGGCAAC | 193 | XhoI |
| Orf40L | Fwd | CGCGGATCCCATATG-AACAAAATATACCGCAT | 194 | NdeI |
| | Rev | CCCGCTCGAG-TTACCACTGATAACCGAC | 195 | XhoI |
| Orf40.2-His | Fwd | CGCGGATCCCATATG-ACCGATGACGACGATTTAT | 196 | NdeI |
| | Rev | GCCCAAGCTT-CCACTGATAACCGACAGA | 197 | HindIII |
| Orf40.2L | Fwd | CGCGGATCCCATATG-AACAAAATATACCGCAT | 198 | NdeI |
| | Rev | GCCCAAGCTT-TTACCACTGATAACCGAC | 199 | HindIII |
| Orf46-2L | Fwd | GGGAATTCCATATG-GGCATTTCCCGCAAAATATC | 200 | NdeI |
| | Rev | CCCGCTCGAG-TTATTTACTCCTATAACGAGGTCTCTTAAC | 201 | XhoI |
| Orf46-2 | Fwd | GGGAATTCCATATG-TCAGATTTGGCAAACGATTGTT | 202 | NdeI |
| | Rev | CCCGCTCGAG-TTATTTACTCCTATAACGAGGTCTCTTAAC | 203 | XhoI |

-continued

| | | Sequences | SEQ ID NO: | Restriction site |
|---|---|---|---|---|
| Orf46.1L | Fwd | GGGAATTCCATATG-GGCATTTCCCGCAAAATATC | 204 | NdeI |
| | Rev | CCCGCTCGAG-TTACGTATCATATTTCACGTGC | 205 | XhoI |
| orf46. (His-GST) | Fwd | GGGAATTCCATATGCACGTGAAATATGATACGAAG | 206 | BamHI-NdeI |
| | Rev | CCCGCTCGAGTTTACTCCTATAACGAGGTCTCTTAAC | 207 | XhoI |
| orf46.1-His | Fwd | GGGAATTCCATATGTCAGATTTGGCAAACGATTCTT | 208 | NdeI |
| | Rev | CCCGCTCGAGCGTATCATATTTCACGTGC | 209 | XhoI |
| orf46.2-His | Fwd | GGGAATTCCATATGTCAGATTTGGCAAACGATTCTT | 210 | NdeI |
| | Rev | CCCGCTCGAGTTTACTCCTATAACGAGGTCTCTTAAC | 211 | XhoI |
| Orf65-1-(His/GST) | Fwd | CGCGGATCCCATATG-CAAAATGCGTTCAAAATCCC | 212 | BamHI-NdeI |
| (MC58) | Rev | CGCGGATCCCATATG-AACAAAATATACCGCAT | 213 | XhoI |
| | | CCCGCTCGAG-TTTGCTTTTCGATAGAACGG | 214 | |
| Orf72-1L | Fwd | GCGGCCATATG-GTCATAAAATATACAAATTTGAA | 215 | NdeI |
| | Rev | GCGGCCTCGAG-TTAGCCTGAGACCTTTGCAAATT | 216 | XhoI |
| Orf76-1L | Fwd | GCGGCCATATG-AAACAGAAAAAAACCGCTG | 217 | NdeI |
| | Rev | GCGGCCTCGAG-TTACGGTTTGACACCGTTTTC | 218 | XhoI |
| Orf83.1L | Fwd | CGCGGATCCCATATG-AAAACCCTGCTCCTC | 219 | NdeI |
| | Rev | CCCGCTCGAG-TTATCCTCCTTTGCGGC | 220 | XhoI |
| Orf85-2L | Fwd | GCGGCCATATG-GCAAAAATGATGAAATGGG | 221 | NdeI |
| | Rev | GCGGCCTCGAG-TTATCGGCGCGGCGGGCC | 222 | XhoI |
| Orf91L (MC58) | Fwd | GCGGCCATATGAAAAAATCCTCCCTCATCA | 223 | NdeI |
| | Rev | GCGGCCTCGAGTTATTTGCCGCCGTTTTTGGC | 224 | XhoI |
| Orf91-His (MC58) | Fwd | GCGGCCATATGGCCCCTGCCGACGCGGTAAG | 225 | NdeI |
| | Rev | GCGGCCTCGAGTTTGCCGCCGTTTTTGGCTTTC | 226 | XhoI |
| Orf97-1L | Fwd | GCGGCCATATG-AAACACATACTCCCCCTGA | 227 | NdeI |
| | Rev | GCGGCCTCGAG-TTATTCGCCTACGGTTTTTTG | 228 | XhoI |
| Orf119L (MC58) | Fwd | GCGGCCATATGATTTACATCGTACTGTTTC | 229 | NdeI |
| | Rev | GCGGCCTCGAGTTAGGAGAACAGGCGCAATGC | 230 | XhoI |
| Orf119-His (MC58) | Fwd | GCGGCCATATGTACAACATGTATCAGGAAAAC | 231 | NdeI |
| | Rev | GCGGCCTCGAGGGAGAACAGGCGCAATGCGG | 232 | XhoI |
| Orf137.1 (His-GST) (MC58) | Fwd | CGCGGATCCGCTAGCTGCGGCACGGCGGG | 233 | BamHI-NheI |
| | Rev | CCCGCTCGAGATAACGGTATGCCGCCAG | 234 | XhoI |
| Orf143-1L | Fwd | CGCGGATCCCATATG-GAATCAACACTTTCAC | 235 | NdeI |
| | Rev | CCCGCTCGAG-TTACACGCGGTTGCTGT | 236 | XhoI |
| 008 | Fwd | CGCGGATCCCATATG-AACAACAGACATTTTG | 237 | NdeI |
| | Rev | CCCGCTCGAG-TTACCTGTCCGGTAAAAG | 238 | XhoI |
| 050-1 (48) | Fwd | CGCGGATCCGCTAGC-ACCGTCATCAAACAGGAA | 239 | NheI |
| | Rev | CCCGCTCGAG-TCAAGATTCGACGGGGA | 240 | XhoI |
| 105 | Fwd | CGCGGATCCCATATG-TCCGCAAACGAATACG | 241 | NdeI |
| | Rev | CCCGCTCGAG-TCAGTGTTCTGCCAGTTT | 242 | XhoI |
| 111L | Fwd | CGCGGATCCCATATG-CCGTCTGAAACACG | 243 | NdeI |
| | Rev | CCCGCTCGAG-TTAGCGGAGCAGTTTTTC | 244 | XhoI |
| 117-1 | Fwd | CGCGGATCCCATATG-ACCGCCATCAGCC | 245 | NdeI |
| | Rev | CCCGCTCGAG-TTAAAGCCGGGTAACGC | 246 | XhoI |
| 121-1 | Fwd | GCGGCCATATG-GAAACACAGCTTTACATCGG | 247 | NdeI |
| | Rev | GCGGCCTCGAG-TCAATAATAATATCCCGCG | 248 | XhoI |
| 122-1 | Fwd | GCGGCCATATG-ATTAAAATCCGCAATATCC | 249 | NdeI |
| | Rev | GCGGCCTCGAG-TTAAATCTTGGTAGATTGGATTTGG | 250 | XhoI |
| 128-1 | Fwd | GCGGCCATATG-ACTGACAACGCACTGCTCC | 251 | NdeI |
| | Rev | GCGGCCTCGAG-TCAGACCGCGTTGTCGAAAC | 252 | XhoI |
| 148 | Fwd | CGCGGATCCCATATG-GCGTTAAAAACATCAAA | 253 | NdeI |
| | Rev | CCCGCTCGAG-TCAGCCCTTCATACAGC | 254 | XhoI |
| 149.1L (MC58) | Fwd | GCGGCATTAATGGCACAAACTACACTCAAACC | 255 | AseI |
| | Rev | GCGGCCTCGAGTTAAAACTTCACGTTCACGCCG | 256 | XhoI |
| 149.1-His (MC58) | Fwd | GCGGCATTAATGCATGAAACTGAGCAATCGGTGG | 257 | AseI |
| | Rev | GCGGCCTCGAGAAACTTCACGTTCACGCCGCCGGTAAA | 258 | XhoI |
| 205 (His-GST) | Fwd | CGCGGATCCCATATGGGCAAATCCGAAAATACG | 259 | BamHI-NdeI |
| (MC58) | Rev | CCCGCTCGAGATAATGGCGGCGGCGG | 260 | XhoI |
| 206L | Fwd | CGCGGATCCCATATG-TTTCCCCCCGACAA | 261 | NdeI |
| | Rev | CCCGCTCGAG-TCATTCTGTAAAAAAAGTATG | 262 | XhoI |
| 214 (His-GST) | Fwd | CGCGGATCCCATATGCTTCAAAGCGACAGCAG | 263 | BamHI-NdeI |
| (MC58) | Rev | CCCGCTCGAGTTCGGATTTTTGCGTACTC | 264 | XhoI |
| 216 | Fwd | CGCGGATCCCATATG-GCAATGGCAGAAAACG | 265 | NdeI |
| | Rev | CCCGCTCGAG-CTATACAATCCGTGCCG | 266 | XhoI |
| 225-1L | Fwd | CGCGGATCCCATATG-GATTCTTTTTTCAAACC | 267 | NdeI |
| | Rev | CCCGCTCGAG-TCAGTTCAGAAAGCGGG | 268 | XhoI |
| 235L | Fwd | CGCGGATCCCATATG-AAACCTTTGATTTTAGG | 269 | NdeI |
| | Rev | CCCGCTCGAG-TTATTTGGGCTGCTCTTC | 270 | XhoI |
| 243 | Fwd | CGCGGATCCCATATG-GTAATCGTCTGGTTG | 271 | NdeI |
| | Rev | CCCGCTCGAG-CTACGACTTGGTTACCG | 272 | XhoI |
| 247-1L | Fwd | GCGGCCATATG-AGACGTAAAATGCTAAAGCTAC | 273 | NdeI |
| | Rev | GCGGCCTCGAG-TCAAAGTGTTCTGTTTGCGC | 274 | XhoI |
| 264-His | Fwd | GCCGCCATATG-TTGACTTTAACCCGAAAAA | 275 | NdeI |
| | Rev | GCCGCCTCGAG-GCCGGCGGTCAATACCGCCCGAA | 276 | XhoI |
| 270 (His-GST) | Fwd | CGCGGATCCCATATGGCGCAATGCGATTTGAG | 277 | BamHI-NdeI |
| (MC58) | Rev | CCCGCTCGAGTTCGGCGGTAAATGCCG | 278 | XhoI |

-continued

| | | Sequences | SEQ ID NO: | Restriction site |
|---|---|---|---|---|
| 274L | Fwd | GCGGCCATATG-GCGGGGCCGATTTTTGT | 279 | NdeI |
| | Rev | GCGGCCTCGAG-TTATTTGCTTTCAGTATTATTG | 280 | XhoI |
| 283L | Fwd | GCGGCCATATG-AACTTTGCTTTATCCGTCA | 281 | NdeI |
| | Rev | GCGGCCTCGAG-TTAACGGCAGTATTTGTTTAC | 282 | XhoI |
| 285-His | Fwd | CGCGGATCCCATATGGGTTTGCGCTTCGGGC | 283 | BamHI |
| | Rev | GCCCAAGCTTTTTTCCTTTGCCGTTTCCG | 284 | HindIII |
| 286-His | Fwd | CGCGGATCCCATATG-GCCGACCTTTCCGAAAA | 285 | NdeI |
| (MC58) | Rev | CCCGCTCGAG-GAAGCGCGTTCCCAAGC | 286 | XhoI |
| 286L | Fwd | CGCGGATCCCATATG-CACGACACCCGTAC | 287 | NdeI |
| (MC58) | Rev | CCCGCTCGAG-TTAGAAGCGCGTTCCCAA | 288 | XhoI |
| 287L | Fwd | CTAGCTAGC-TTTAAACGCAGCGTAATCGCAATGG | 289 | NdeI |
| | Rev | CCCGCTCGAG-TCAATCCTGCTCTTTTTTGCC | 290 | XhoI |
| 287 | Fwd | CTAGCTAGC-GGGGGCGGCGGTGGCG | 291 | NheI |
| | Rev | CCCGCTCGAG-TCAATCCTGCTCTTTTTTGCC | 292 | XhoI |
| 287LOrf4 | Fwd | CTAGCTAGCGCTCATCCTCGCCGCC-<br>TGCGGGGGCGGCGGT | 293 | NheI |
| | Rev | CCCGCTCGAG-TCAATCCTGCTCTTTTTTGCC | 294 | XhoI |
| 287-fu | Fwd | CGGGGATCC-GGGGGCGGCGGTGGCG | 295 | BamHI |
| | Rev | CCCGCTCGAG-TCAATCCTGCTCTTTTTTGCC | 296 | XhoI |
| 287-His | Fwd | CTAGCTAGC-GGGGGCGGCGGTGGCG | 297 | NheI |
| | Rev | CCCGCTCGAG-ATCCTGCTCTTTTTTGCC * | 298 | XhoI |
| 287-His (2996) | Fwd | CTAGCTAGC-TGCGGGGGCGGCGGTGGCG | 299 | NheI |
| | Rev | CCCGCTCGAG-ATCCTGCTCTTTTTTGCC | 300 | XhoI |
| Δl 287-His | Fwd | CGCGGATCCGCTAGC-CCCGATGTTAAATCGGC § | 301 | NheI |
| Δ2 287-His | Fwd | CGCGGATCCGCTAGC-CAAGATATGGCGGCAGT § | 302 | NheI |
| Δ3 287-His | Fwd | CGCGGATCCGCTAGC-GCCGAATCCGCAAATCA § | 303 | NheI |
| Δ4 287-His | Fwd | CGCGCTAGC-GGAAGGGTTGATTTGGCTAATGG § | 304 | NheI |
| Δ4 287MC58-His | Fwd | CGCGCTAGC-GGAAGGGTTGATTTGGCTAATGG § | 305 | NheI |
| 287a-His | Fwd | CGCCATATG-TTTAAACGCAGCGTAATCGC | 306 | NdeI |
| | Rev | CCCGCTCGAG-AAAATTGCTACCGCCATTCGCAGG | 307 | XhoI |
| 287b-His | Fwd | CGCCATATG-GGAAGGGTTGATTTGGCTAATGG | 308 | NdeI |
| 287b-2996-His | Rev | CCCGCTCGAG-CTTGTCTTTATAAATGATGACATATTTG | 309 | XhoI |
| 287b-MC58-His | Rev | CCCGCTCGAG-TTTATAAAAGATAATATATTGATTGATTCC | 310 | XhoI |
| 287c-2996-His | Fwd | CGCGCTAGC-ATGCCGCTGATTCCCGTCAATC § | 311 | NheI |
| ‘$287^{untagged}$’ (2996) | Fwd | CTAGCTAGC-GGGGGCGGCGGTGGCG | 312 | NheI |
| | Rev | CCCGCTCGAG-TCAATCCTGCTCTTTTTTGCC | 313 | XhoI |
| ΔG 287-His * | Fwd | CGCGGATCCGCTAGC-CCCGATGTTAAATCGGC | 314 | NheI |
| | Rev | CCCGCTCGAG-ATCCTGCTCTTTTTTGCC | 315 | XhoI |
| ΔG 287K (2996) | Fwd | CGCGGATCCGCTAGC-CCCGATGTTAAATCGGC | 316 | NheI |
| | Rev | CCCGCTCGAG-TCAATCCTGCTCTTTTTTGCC | 317 | XhoI |
| ΔG 287-L | Fwd | CGCGGATCCGCTAGC-<br>TTTGAACGCAGTGTGATTGCAATGGCTTGTATTTTTGCC<br>CTTTCAGCCTGT-TCGCCCGATGTTAAATCGGCG | 318 | NheI |
| | Rev | CCCGCTCGAG-TCAATCCTGCTCTTTTTTGCC | 319 | XhoI |
| ΔG 287-Orf4L | Fwd | CGCGGATCCGCTAGC-<br>AAAACCTTCTTCAAAACCCTTTCCGCCGCCGCACTCGCG<br>CTCATCCTCGCCGCCTGC-TCGCCCGATGTTAAATCG | 320 | NheI |
| | Rev | CCCGCTCGAG-TCAATCCTGCTCTTTTTTGCC | 321 | XhoI |
| 292L | Fwd | CGCGGATCCCATATG-AAAACCAAGTTAATCAAA | 322 | NdeI |
| | Rev | CCCGCTCGAG-TTATTGATTTTTGCGGATGA | 323 | XhoI |
| 308-1 | Fwd | CGCGGATCCCATATG-TTAAATCGGGTATTTTATC | 324 | NdeI |
| | Rev | CCCGCTCGAG-TTAATCCGCCATTCCCTG | 325 | XhoI |
| 401L | Fwd | GCGGCCATATG-AAATTACAACAATTGGCTG | 326 | NdeI |
| | Rev | GCGGCCTCGAG-TTACCTTACGTTTTTCAAAG | 327 | XhoI |
| 406L | Fwd | CGCGGATCCCATATG-CAAGCACGGCTGCT | 328 | NdeI |
| | Rev | CCCGCTCGAG-TCAAGGTTGTCCTTGTCTA | 329 | XhoI |
| 502-1L | Fwd | CGCGGATCCCATATG-ATGAAACCGCACAAC | 330 | NdeI |
| | Rev | CCCGCTCGAG-TCAGTTGCTCAACACGTC | 331 | XhoI |
| 502-A (His-GST) | Fwd | CGCGGATCCCATATGGTAGACGCGCTTAAGCA | 332 | BamHI-NdeI |
| | Rev | CCCGCTCGAGAGCTGCATGGCGGCG | 333 | XhoI |
| 503-1L | Fwd | CGCGGATCCCATATG-GCACGGTCGTTATAC | 334 | NdeI |
| | Rev | CCCGCTCGAG-CTACCGCGCATTCCTG | 335 | XhoI |
| 519-1L | Fwd | GCGGCCATATG-GAATTTTTCATTATCTTGTT | 336 | NdeI |
| | Rev | GCGGCCTCGAG-TTATTTGGCGGTTTTGCTGC | 337 | XhoI |
| 525-1L | Fwd | GCGGCCATATG-AAGTATGTCCGGTTATTTTTC | 338 | NdeI |
| | Rev | GCGGCCTCGAG-TTATCGGCTTGTGCAACGG | 339 | XhoI |
| 529-(His/GST) | Fwd | CGCGGATCCGCTAGC-TCCGGCAGCAAAACCGA | 340 | BamHI-NheI |
| (MC58) | Rev | GCCCAAGCTT-ACGCAGTTCGGAATGGAG | 341 | HindIII |
| 552L | Fwd | GCCGCCATATGTTGAATATTAAACTGAAAACCTTG | 342 | NdeI |
| | Rev | GCCGCCTCGAGTTATTTCTGATGCCTTTTCCC | 343 | XhoI |
| 556L | Fwd | GCCGCCATATGGACAATAAGACCAAACTG | 344 | NdeI |
| | Rev | GCCGCCTCGAGTTAACGGTGCGGACGTTTC | 345 | XhoI |
| 557L | Fwd | CGCGGATCCCATATG-AACAAACTGTTTCTTAC | 346 | NdeI |
| | Rev | CCCGCTCGAG-TCATTCCGCCTTCAGAAA | 347 | XhoI |

-continued

| | | Sequences | SEQ ID NO: | Restriction site |
|---|---|---|---|---|
| 564ab-(His/GST) (MC58) | Fwd | CGCGGATCCCATATG-CAAGGTATCGTTGCCGACAAATCCGCACCT | 348 | BamHI-NdeI |
| | Rev | CCCGCTCGAG-AGCTAATTGTGCTTGGTTTGCAGATAGGAGTT | 349 | XhoI |
| 564abL (MC58) | Fwd | CGCGGATCCCATATG-AACCGCACCCTGTACAAAGTTGTATTTAACAAACATC | 350 | NdeI |
| | Rev | CCCGCTCGAG-TTAAGCTAATTGTGCTTGGTTGCAGATAGGAGTT | 351 | XhoI |
| 564b-(His/GST) (MC58) | Fwd | CGCGGATCCCATATG-ACGGGAGAAAATCATGCGGTTTCACTTCATG | 352 | BamHI-NdeI |
| | Rev | CCCGCTCGAG-AGCTAATTGTGCTTGGTTTGCAGATAGGAGTT | 353 | XhoI |
| 564c-(His/GST) (MC58) | Fwd | CGCGGATCCCATATG-GTTTCAGACGGCCTATACAACCAACATGGTGAAATT | 354 | BamHI-NdeI |
| | Rev | CCCGCTCGAG-GCGGTAACTGCCGCTTGCACTGAATCCGTAA | 355 | XhoI |
| 564bc-(His/GST) (MC58) | Fwd | CGCGGAGGATCCCATATG-ACGGGAGAAAATCATGCGGTTTCACTTCATG | 356 | BamHI-NdeI |
| | Rev | CCCGCTCGAG-GCGGTAACTGCCGCTTGCACTGAATCCGTAA | 357 | XhoI |
| 564d-(His/GST) (MC58) | Fwd | CGCGGATCCCATATG-CAAAGCAAAGTCAAAGCAGACCATGCCTCCGTAA | 358 | BamHI-NdeI |
| | Rev | CCCGCTCGAG-TCTTTTCCTTTCAATTATAACTTTAGTAGGTTCAATTTTGGTCCCC | 359 | XhoI |
| 564cd-(His/GST) (MC58) | Fwd | CGCGGATCCCATATG-GTTCAGACGGCCTATACAACCAACATGGTGAAATT | 360 | BamHI-NdeI |
| | Rev | CCCGCTCGAG-TCTTTTCCTTTCAATTATAACTTTAGTAGGTTCAATTTTGGTCCCC | 361 | XhoI |
| 570L | Fwd | GCGGCCATATG-ACCCGTTTGACCCGCG | 362 | NdeI |
| | Rev | GCGGCCTCGAG-TCAGCGGGCGTTCATTTCTT | 363 | XhoI |
| 576-1L | Fwd | CGCGGATCCCATATG-AACACCATTTTCAAAATG | 364 | NdeI |
| | Rev | CCCGCTCGAG-TTAATTTACTTTTTTGATGTCG | 365 | XhoI |
| 580L | Fwd | GCGGCCATATG-GATTCGCCCAAGGTCGG | 366 | NdeI |
| | Rev | GCGGCCTCGAG-CTACACTTCCCCCGAAGTGG | 367 | XhoI |
| 583L | Fwd | CGCGGATCCCATATG-ATAGTTGACCAAAGCC | 368 | NdeI |
| | Rev | CCCGCTCGAG-TTATTTTTCCGATTTTTCGG | 369 | XhoI |
| 593 | Fwd | GCGGCCATATG-CTTGAACTGAACGGACT | 370 | NdeI |
| | Rev | GCGGCCTCGAG-TCAGCGGAAGCGGACGATT | 371 | XhoI |
| 650 (His-GST) | Fwd | CGCGGATCCCATATGTCCAAACTCAAAACCATCG | 372 | BamHI-NdeI |
| (MC58) | Rev | CCCGCTCGAGGCTTCCAATCAGTTTGACC | 373 | XhoI |
| 652 | Fwd | GCGGCCATATG-AGCGCAATCGTTGATATTTTC | 374 | NdeI |
| | Rev | GCGGCCTCGAG-TTATTTGCCCAGTTGGTAGAATG | 375 | XhoI |
| 664L | Fwd | GCGGCCATATG-GTGATACATCCGCACTACTTC | 376 | NdeI |
| | Rev | GCGGCCTCGAG-TCAAAATCGAGTTTTACACCA | 377 | XhoI |
| 726 | Fwd | GCGGCCATATG-ACCATCTATTTCAAAAACGG | 378 | NdeI |
| | Rev | GCGGCCTCGAG-TCAGCCGATGTTTAGCGTCCATT | 379 | XhoI |
| 741-His (MC58) | Fwd | CGCGGATCCCATATG-AGCAGCGGAGGGGGTG | 380 | NdeI |
| | Rev | CCCGCTCGAG-TTGCTTGGCGGCAAGGC | 381 | XhoI |
| ΔG741-His (MC58) | Fwd | CGCGGATCCCATATG-GTCGCCGCCGACATCG | 382 | NdeI |
| | Rev | CCCGCTCGAG-TTGCTTGGCGGCAAGGC | 383 | XhoI |
| 686-2-(His/GST) | Fwd | CGCGGATCCCATATG-GGCGGTTCGGAAGGCG | 384 | BamHI-NdeI |
| (MC58) | Rev | CCCGCTCGAG-TTGAACACTGATGTCTTTTCCGA | 385 | XhoI |
| 719-(His/GST) | Fwd | CGCGGATCCGCTAGC-AAACTGTCGTTGGTGTTAAC | 386 | BamHI-NheI |
| (MC58) | Rev | CCCGCTCGAG-TTGACCCGCTCCACGG | 387 | XhoI |
| 730-His (MC58) | Fwd | GCCGCCATATGGCGGACTTGGCGCAAGACCC | 388 | NdeI |
| | Rev | GCCGCCTCGAGATCTCCTAAACCTGTTTTAACAATGCCG | 389 | XhoI |
| 730A-His (MC58) | Fwd | GCCGCCATATGGCGGACTTGGCGCAAGACCC | 390 | NdeI |
| | Rev | GCGGCCTCGAGCTCCATGCTGTTGCCCCAGC | 391 | XhoI |
| 730B-His (MC58) | Fwd | GCCGCCATATGGCGGACTTGGCGCAAGACCC | 392 | NdeI |
| | Rev | GCGGCCTCGAGAAAATCCCCGCTAACCGCAG | 393 | XhoI |
| 741-His | Fwd | CGCGGATCCCATATG-AGCAGCGGAGGGGGTG | 394 | NdeI |
| (MC58) | Rev | CCCGCTCGAG-TTGCTTGGCGGCAAGGC | 395 | XhoI |
| ΔG741-His | Fwd | CGCGGATCCCATATG-GTCGCCGCCGACATCG | 396 | NdeI |
| (MC58) | Rev | CCCGCTCGAG-TTGCTTGGCGGCAAGGC | 397 | XhoI |
| 743 (His-GST) | Fwd | CGCGGATCCCATATGGACGGTGTTGTGCCTGTT | 398 | BamHI-NdeI |
| | Rev | CCCGCTCGAGCTTACGGATCAAATTGACG | 399 | XhoI |
| 757 (His-GST) | Fwd | CGCGGATCCCATATGGGCAGCCAATCTGAAGAA | 400 | BamHI-NdeI |
| (MC58) | Rev | CCCGCTCGAGCTCAGCTTTTGCCGTCAA | 401 | XhoI |
| 759-His/GST | Fwd | CGCGGATCCGCTAGC-TACTCATCCATTGTCCGC | 402 | BamHI-NheI |
| (MC58) | Rev | CCCGCTCGAG-CCAGTTGTAGCCTATTTTG | 403 | XhoI |
| 759L | Fwd | CGCGGATCCGCTAGC-ATGCGCTTCACACACAC | 404 | NheI |
| (MC58) | Rev | CCCGCTCGAG-TTACCAGTTGTAGCCTATTT | 405 | XhoI |
| 760-His | Fwd | GCCGCCATATGGCACAAACGGAAGGTTTGGAA | 406 | NdeI |
| | Rev | GCCGCCTCGAGAAAACTGTAACGCAGGTTTGCCGTC | 407 | XhoI |
| 769-His (MC58) | Fwd | GCGGCCATATGGAAGAAACACCGCGCGAACCG | 408 | NdeI |
| | Rev | GCGGCCTCGAGGAACGTTTTATTAAACTCGAC | 409 | XhoI |

-continued

| | | Sequences | SEQ ID NO: | Restriction site |
|---|---|---|---|---|
| 907L | Fwd | GCGGCCATATG-AGAAAACCGACCGATACCCTA | 410 | NdeI |
| | Rev | GCGGCCTCGAG-TCAACGCCACTGCCAGCGGTTG | 411 | XhoI |
| 911L | Fwd | CGCGGATCCCATATG-AAGAAGAACATATTGGAATTTTGGGTCGGACTG | 412 | NdeI |
| | Rev | CCCGCTCGAG-TTATTCGGCGGCTTTTTCCGCATTGCCG | 413 | XhoI |
| 911LOmpA | Fwd | GGGAATTCCATATGAAAAAGACAGCTATCGCGATTGCA GTGGCACTGGCTGGTTTCGCTACCGTAGCGCAGGCCGCTAGC-GCTTTCCGCGTGGCCGGCGGTGC | 414 | NdeI-(NheI) |
| | Rev | CCCGCTCGAG-TTATTCGGCGGCTTTTTCCGCATTGCCG | 415 | XhoI |
| 911LPelB | Fwd | CATGCCATGG-CTTTCCGCGTGGCCGGCGGTGC | 416 | NcoI |
| | Rev | CCCGCTCGAG-TTATTCGGCGGCTTTTTCCGCATTGCCG | 417 | XhoI |
| 913-His/GST | Fwd | CGCGGATCCCATATG-TTTGCCGAAACCCGCC | 418 | BamHI-NdeI |
| (MC58) | Rev | CCCGCTCGAG-AGGTTGTGTTCCAGGTTG | 419 | XhoI |
| 913L | Fwd | CGCGGATCCCATATG-AAAAAAACCGCCTATG | 420 | NdeI |
| (MC58) | Rev | CCCGCTCGAG-TTAAGGTTGTGTTCCAGG | 421 | XhoI |
| 919L | Fwd | CGCGGATCCCATATG-AAAAAATACCTATTCCGC | 422 | NdeI |
| | Rev | CCCGCTCGAG-TTACGGGCGGTATTCGG | 423 | XhoI |
| 919 | Fwd | CGCGGATCCCATATG-CAAAGCAAGAGCATCCAAA | 424 | NdeI |
| | Rev | CCCGCTCGAG-TTACGGGCGGTATTCGG | 425 | XhoI |
| 919L Orf4 | Fwd | GGGAATTCCATATGAAAACCTTCTTCAAAACCCTTTCCG CCGCCGCGCTAGCGCTCATCCTCGCCGCC-TGCCAAAGCAAGAGCATC | 426 | NdeI-(NheI) |
| | Rev | CCCGCTCGAG-TTACGGGCGGTATTCGGGCTTCATACCG | 427 | XhoI |
| (919)-287fusion | Fwd | CGCGGATCCGTCGAC-TGTGGGGGCGGCGGTGGC | 428 | SalI |
| | Rev | CCCGCTCGAG-TCAATCCTGCTCTTTTTTGCC | 429 | XhoI |
| 920-1L | Fwd | GCGGCCATATG-AAGAAAACATTGACACTGC | 430 | NdeI |
| | Rev | GCGGCCTCGAG-TTAATGGTGCGAATGACCGAT | 431 | XhoI |
| 925-His/GST | Fwd | ggggacaagtttgtacaaaaaagcaggctTGCGGCAAGGATGCCGG | 432 | attB1 |
| (MC58) GATE | Rev | ggggaccactttgtacaagaaagctgggtCTAAAGCAACAATGCCGG | 433 | attB2 |
| 926L | Fwd | CGCGGATCCCATATG-AAACACACCGTATCC | 434 | NdeI |
| | Rev | CCCGCTCGAG-TTATCTCGTGCGCGCC | 435 | XhoI |
| 927-2-(His/GST) | Fwd | CGCGGATCCCATATG-AGCCCCGCGCCGATT | 436 | BamHI-NdeI |
| (MC58) | Rev | CCCGCTCGAG-TTTTTGTGCGGTCAGGCG | 437 | XhoI |
| 932-His/GST (MC58) GATE | Fwd | ggggacaagtttgtacaaaaaagcaggctTGTTCGTTTGGGGGATTTAA ACCAAACCAAATC | 438 | attB1 |
| 935 (His-GST) | For | CGCGGATCCCATATGGCGGATGCGCCCGCG | 439 | BamHI-NdeI |
| (MC58) | Rev | CCCGCTCGAGAAACCGCCAATCCGCC | 440 | XhoI |
| 936-1L | Rev | ggggaccactttgtacaagaaagctgggtTCATTTTGTTTTTCCTTCTTC TCGAGGCCATT | 441 | attB2 |
| | Fwd | CGCGGATCCCATATG-AAACCCAAACCGCAC | 442 | NdeI |
| | Rev | CCCGCTCGAG-TCAGCGTTGGACGTAGT | 443 | XhoI |
| 953L | Fwd | GGGAATTCCATATG-AAAAAAATCATCTTCGCCG | 444 | NdeI |
| | Rev | CCCGCTCGAG-TTATTGTTTGGCTGCCTCGAT | 445 | XhoI |
| 953-fu | Fwd | GGGAATTCCATATG-GCCACCTACAAAGTGGACG | 446 | NdeI |
| | Rev | CGGGGATCC-TTGTTTGGCTGCCTCGATTTTG | 447 | BamHI |
| 954 (His-GST) | Fwd | CGCGGATCCCATATGCAAGAACAATCGCAGAAAG | 448 | BamHI-NdeI |
| (MC58) | Rev | CCCGCTCGAGTTTTTTCGGCAAATTGGCTT | 449 | XhoI |
| 958-His/GST | Fwd | ggggacaagtttgtacaaaaaagcaggctGCCGATGCCGTTGCGG | 450 | attB1 |
| (MC58) GATE | Rev | ggggaccactttgtacaagaaagctgggtTCAGGGTCGTTTGTTGCG | 451 | attB2 |
| 961L | Fwd | CGCGGATCCCATATG-AAACACTTTCCATCC | 452 | NdeI |
| | Rev | CCCGCTCGAG-TTACCACTCGTAATTGAC | 453 | XhoI |
| 961 | Fwd | CGCGGATCCCATATG-GCCACAAGCGACGAG | 454 | NdeI |
| | Rev | CCCGCTCGAG-TTACCACTCGTAATTGAC | 455 | XhoI |
| 961 c (His/GST) | Fwd | CGCGGATCCCATATG-GCCACAAACGACG | 456 | BamHI-NdeI |
| | Rev | CCCGCTCGAG-ACCCACGTTGTAAGGTTG | 457 | XhoI |
| 961 c-(His/GST) | Fwd | CGCGGATCCCATATG-GCCACAAGCGACGACGA | 458 | BamHI-NdeI |
| (MC58) | Rev | CCCGCTCGAG-ACCCACGTTGTAAGGTTG | 459 | XhoI |
| 961 c-L | Fwd | CGCGGATCCCATATG-ATGAAACACTTTCCATCC | 460 | NdeI |
| | Rev | CCCGCTCGAG-TTAACCCACGTTGTAAGGT | 461 | XhoI |
| 961 c-L | Fwd | CGCGGATCCCATATG-ATGAAACACTTTCCATCC | 462 | NdeI |
| (MC58) | Rev | CCCGCTCGAG-TTAACCCACGTTGTAAGGT | 463 | XhoI |
| 961 d (His/GST) | Fwd | CGCGGATCCCATATG-GCCACAAACGACG | 464 | BamHI-NdeI |
| | Rev | CCCGCTCGAG-GTCTGACACTGTTTTATCC | 465 | XhoI |
| 961 Δ1-L | Fwd | CGCGGATCCCATATG-ATGAAACACTTTCCATCC | 466 | NdeI |
| | Rev | CCCGCTCGAG-TTATGCTTTGGCGGCAAAG | 467 | XhoI |
| fu 961- . . . | Fwd | CGCGGATCCCATATG-GCCACAAACGACGAC | 468 | NdeI |
| | Rev | CGCGGATCC-CCACTCGTAATTGACGCC | 469 | BamHI |
| fu 961- . . . | Fwd | CGCGGATCCCATATG-GCCACAAGCGACGAC | 470 | NdeI |
| (MC58) | Rev | CGCGGATCC-CCACTCGTAATTGACGCC | 471 | BamhI |
| fu 961 c - . . . | Fwd | CGCGGATCCCATATG-GCCACAAACGACGAC | 472 | NdeI |
| | Rev | CGCGGATCC-ACCCACGTTGTAAGGTTG | 473 | BamHI |
| fu 961 c-L- . . . | Fwd | CGCGGATCCCATATG-ATGAAACACTTTCCATCC | 474 | NdeI |
| | Rev | CGCGGATCC-ACCCACGTTGTAAGGTTG | 475 | BamHI |
| fu (961)- | Fwd | CGCGGATCC-GGAGGGGGTGGTGTCG | 476 | BamHI |
| 741 (MC58)-His | Rev | CCCGCTCGAG-TTGCTTGGCGGCAAGGC | 477 | XhoI |

-continued

| | | Sequences | SEQ ID NO: | Restriction site |
|---|---|---|---|---|
| fu (961)-983-His | Fwd | CGCGGATCC-GGCGGAGGCGGCACTT | 478 | BamHI |
| | Rev | CCCGCTCGAG-GAACCGGTAGCCTACG | 479 | XhoI |
| fu (961)- Orf46.1-His | Fwd | CGCGGATCCGGTGGTGGTGGT-TCAGATTTGGCAAACGATTC | 480 | BamHI |
| | Rev | CCCGCTCGAG-CGTATCATATTTCACGTGC | 481 | XhoI |
| fu (961 c-L)- | Fwd | CGCGGATCC-GGAGGGGGTGGTGTCG | 482 | BamHI |
| 741(MC58) | Rev | CCCGCTCGAG-TTATTGCTTGGCGGCAAG | 483 | XhoI |
| fu (961 c-L)-983 | Fwd | CGCGGATCC-GGCGGAGGCGGCACTT | 484 | BamHI |
| | Rev | CCCGCTCGAG-TCAGAACCGGTAGCCTAC | 485 | XhoI |
| fu (961 c-L)-Orf46.1 | Fwd | CGCGGATCCGGTGGTGGTGGT-TCAGATTTGGCAAACGATTC | 486 | BamHI |
| | Rev | CCCGCTCGAG-TTACGTATCATATTTCACGTGC | 487 | XhoI |
| 961-(His/GST) | Fwd | CGCGGATCCCATATG-GCCACAAGCGACGACG | 488 | BamHI-NdeI |
| (MC58) | Rev | CCCGCTCGAG-CCACTCGTAATTGACGCC | 489 | XhoI |
| 961 Δl-His | Fwd | CGCGGATCCCATATG-GCCACAAACGACGAC | 490 | NdeI |
| | Rev | CCCGCTCGAG-TGCTTTGGCGGCAAAGTT | 491 | XhoI |
| 961 a-(His/GST) | Fwd | CGCGGATCCCATATG-GCCACAAACGACGAC | 492 | BamHI-NdeI |
| | Rev | CCCGCTCGAG-TTTAGCAATATTATCTTTGTTCGTAGC | 493 | XhoI |
| 961b-(His/GST) | Fwd | CGCGGATCCCATATG-AAAGCAAACCGTGCCGA | 494 | BamHI-NdeI |
| | Rev | CCCGCTCGAG-CCACTCGTAATTGACGCC | 495 | XhoI |
| 961-His/GST $^{GATE}$ | Fwd | ggggacaagtttgtacaaaaaagcaggctGCAGCCACAAACGACGACGA TGTTAAAAAAGC | 496 | attB1 |
| | Rev | ggggaccactttgtacaagaaagctgggtTTACCACTCGTAATTGACGC CGACATGGTAGG | 497 | attB2 |
| 982 | Fwd | GCGGCCATATG-GCAGCAAAAGACGTACAGTT | 498 | NdeI |
| | Rev | GCGGCCTCGAG-TTACATCATGCCGCCCATACCA | 499 | XhoI |
| 983-His (2996) | Fwd | CGCGGATCCGCTAGC-TTAGGCGGCGGCGGAG | 500 | NheI |
| | Rev | CCCGCTCGAG-GAACCGGTAGCCTACG | 501 | XhoI |
| ΔG983-His (2996) | Fwd | CCCCTAGCTAGC-ACTTCTGCGCCCGACTT | 502 | NheI |
| | Rev | CCCGCTCGAG-GAACCGGTAGCCTACG | 503 | XhoI |
| 983-His | Fwd | CGCGGATCCGCTAGC-TTAGGCGGCGGCGGAG | 504 | NheI |
| | Rev | CCCGCTCGAG-GAACCGGTAGCCTACG | 505 | XhoI |
| ΔG983-His | Fwd | CGCGGATCCGCTAGC-ACTTCTGCGCCCGACTT | 506 | NheI |
| | Rev | CCCGCTCGAG-GAACCGGTAGCCTACG | 507 | XhoI |
| 983L | Fwd | CGCGGATCCGCTAGC-CGAACGACCCCAACCTTCCCTACAAAAACTTTCAA | 508 | NheI |
| | Rev | CCCGCTCGAG-TCAGAACCGACGTGCCAAGCCGTTC | 509 | XhoI |
| 987-His (MC58) | Fwd | GCCGCCATATGCCCCCACTGGAAGAACGGACG | 510 | NdeI |
| | Rev | GCCGCCTCGAGTAATAAACCTTCTATGGGCAGCAG | 511 | XhoI |
| 989-(His/GST) | Fwd | CGCGGATCCCATATG-TCCGTCCACGCATCCG | 512 | BamHI-NdeI |
| (MC58) | Rev | CCCGCTCGAG-TTTGAATTTGTAGGTGTATTG | 513 | XhoI |
| 989L | Fwd | CGCGGATCCCATATG-ACCCCTTCCGCACT | 514 | NdeI |
| (MC58) | Rev | CCCGCTCGAG-TTATTTGAATTTGTAGGTGTAT | 515 | XhoI |
| CrgA-His | Fwd | CGCGGATCCCATATG-AAAACCAATTCAGAAGAA | 516 | NdeI |
| (MC58) | Rev | CCCGCTCGAG-TCCACAGAGATTGTTTCC | 517 | XhoI |
| PilC1-ES | Fwd | GATGCCCGAAGGGCGGC | 518 | |
| (MC58) | Rev | GCCCAAGCTT-TCAGAAGAAGACTTCAGGC | 519 | |
| PilC1-His | Fwd | CGCGGATCCCATATG-CAAACCCATAAATACGCTATT | 520 | NdeI |
| (MC58) | Rev | GCCCAAGCTT-GAAGAAGACTTCACGCCAG | 521 | HindIII |
| Δ1PilC1-His | Fwd | CGCGGATCCCATATG-GTCTTTTTCGACAATACCGA | 522 | NdeI |
| (MC58) | Rev | GCCCAAGCTT- | 523 | HindIII |
| PilC1L | Fwd | CGCGGATCCCATATG-AATAAAACTTTAAAAAGGCGG | 524 | NdeI |
| (MC58) | Rev | GCCCAAGCTT-TCAGAAGAAGACTTCACGC | 525 | HindIII |
| ΔGTbp2-His | Fwd | CGCGAATCCCATATG-TTCGATCTTGATTCTGTCGA | 526 | NdeI |
| (MC58) | Rev | CCCGCTCGAG-TCGCACAGGCTGTTGGCG | 527 | XhoI |
| Tbp2-His | Fwd | CGCGAATCCCATATG-TTGGGCGGAGGCGGCAG | 528 | NdeI |
| (MC58) | Rev | CCCGCTCGAG-TCGCACAGGCTGTTGGCG | 529 | XhoI |
| Tbp2-His (MC58) | Fwd | CGCGAATCCCATATG-TTGGGCGGAGGCGGCAG | 530 | NdeI |
| | Rev | CCCGCTCGAG-TCGCACAGGCTGTTGGCG | 531 | XhoI |
| NMB0109- | Fwd | CGCGGATCCCATATG-GCAAATTTGGAGGTGCGC | 532 | BamHI-NdeI |
| (His/GST) (MC58) | Rev | CCCGCTCGAG-TTCGGAGCGGTTGAAGC | 533 | XhoI |
| NMB0109L | Fwd | CGCGGATCCCATATG-CAACGTCGTATTATAACCC | 534 | NdeI |
| (MC58) | Rev | CCCGCTCGAG-TTATTCGGAGCGGTTGAAG | 535 | XhoI |
| NMB0207-(His/GST) | Fwd | CGCGGATCCCATATG-GGCATCAAAGTCGCCATCAACGGCTAC | 536 | BamHI-NdeI |
| (MC58) | Rev | CCCGCTCGAG-TTTGAGCGGGCGCACTTCAAGTCCG | 537 | XhoI |
| NMB0462- | Fwd | CGCGGATCCCATATG-GGCGGCAGCGAAAAAAAC | 538 | BamHI-NdeI |
| (His/GST) (MC58) | Rev | CCCGCTCGAG-GTTGGTGCCGACTTTGAT | 539 | XhoI |
| NMB0623- | Fwd | CGCGGATCCCATATG-GGCGGCGGAAGCGATA | 540 | BamHI-NdeI |
| (His/GST) (MC58) | Rev | CCCGCTCGAG-TTTGCCCGCTTTGAGCC | 541 | XhoI |
| NMB0625 (His- | Fwd | CGCGGATCCCATATGGGCAAATCCGAAAATACG | 542 | BamHI-NdeI |
| GST) (MC58) | Rev | CCCGCTCGAGCATCCCGTACTGTTTCG | 543 | XhoI |
| NMB0634 | Fwd | ggggacaagtttgtacaaaaaagcaggctCCGACATTACCGTGTACAAC | 544 | attBl |

-continued

| | | Sequences | SEQ ID NO: | Restriction site |
|---|---|---|---|---|
| (His/GST) (MC58) | | GGCCAACAAAGAA | | |
| | Rev | ggggaccactttgtacaagaaagctgggtCTTATTTCATACCGGCTTGCT | 545 | attB2 |
| | | CAAGCAGCCGG | | |
| NMB0776- | Fwd | ggggacaagtttgtacaaaaaagcaggctGATACGGTGTTTTCCTGTAA | 546 | attB1 |
| (His/GST) | | AACGGACAACAA | | |
| (MC58) $^{GATE}$ | Rev | ggggaccactttgtacaagaaagctgggtCTAGGAAAAATCGTCATCGT | 547 | attB2 |
| | | TGAAATTCGCC | | |
| NMB1115- | Fwd | ggggacaagtttgtacaaaaaagcaggctATGCACCCCATCGAAACC | 548 | attBl |
| His/GST | Rev | ggggaccactttgtacaagaaagctgggtCTAGTCTTGCAGTGCCTC | 549 | attB2 |
| (MC58) $^{GATE}$ | | | | |
| NMB1343- | Fwd | CGCGGATCCCATATG-GGAAATTTCTATATAGAGGCATTAG | 550 | BamHI-NdeI |
| (His/GST) | | | | |
| (MC58) | Rev | CCCGCTCGAG-GTTAATTTCTATCAACTCTTTAGCAATAAT | 551 | XhoI |
| NMB1369 (His- | Fwd | CGCGGATCCCATATGGCCTGCCAAGACGACA | 552 | BamHI-NdeI |
| GST (MC58) | Rev | CCCGCTCGAGCCGCCTCCTGCCGAAA | 553 | XhoI |
| NMB1551 (His- | Fwd | CGCGGATCCCATATGGCAGAGATCTGTTTGATAA | 554 | BamHI-NdeI |
| GST)(MC58) | Rev | CCCGCTCGAGCGGTTTTCCGCCCAATG | 555 | XhoI |
| NMB1899 (His- | Fwd | CGCGGATCCCATATGCAGCCGGATACGGTC | 556 | BamHI-NdeI |
| GST) (MC58) | Rev | CCCGCTCGAGAATCACTTCCAACACAAAAT | 557 | XhoI |
| NMB2050- | Fwd | CGCGGATCCCATATG-TGGTTGCTGATGAAGGGC | 558 | BamHI-NdeI |
| (His/GST) | Rev | CCCGCTCGAG-GACTGCTTCATCTTCTGC | 559 | XhoI |
| (MC58) | | | | |
| NMB2050L | Fwd | CGCGGATCCCATATG-GAACTGATGACTGTTTTGC | 560 | NdeI |
| (MC58) | Rev | CCCGCTCGAG-TCAGACTGCTTCATCTTCT | 561 | XhoI |
| NMB2159- | Fwd | CGCGGATCCCATATG- | 562 | BamHI-NdeI |
| (His/GST) | | AGCATTAAAGTAGCGATTAACGGTTTCGGC | | |
| (MC58) | Rev | CCCGCTCGAG-GATTTTGCCTGCGAAGTATTCCAAAGTGCG | 563 | XhoI |
| fu-ΔG287. . .-His | Fwd | CGCGGATCCGCTAGC-CCCGATGTTAAATCGGC | 564 | NheI |
| | Rev | CGGGGATCC-ATCCTGCTCTTTTTTGCCGG | 565 | BamHI |
| fu-(ΔG287)-919- | Fwd | CGCGGATCCGGTGGTGGTGGT-CAAAGCAAGAGCATCCAAACC | 566 | BamHI |
| His | Rev | CCCAAGCTT-TTCGGGCGGTATTCGGGCTTC | 567 | HindIII |
| fu-(ΔG287)-953- | Fwd | CGCGGATCCGGTGGTGGTGGT-GCCACCTACAAAGTGGAC | 568 | BamHI |
| His | Rev | GCCCAAGCTT-TTGTTTGGCTGCCTCGAT | 569 | HindIII |
| fu-(ΔG287)-961- | Fwd | CGCGGATCCGGTGGTGGTGGT-ACAAGCGACGACG | 570 | BamHI |
| His | Rev | GCCCAAGCTT-CCACTCGTAATTGACGCC | 571 | HindIII |
| fu-(ΔG287)- | Fwd | CGCGGATCCGGTGGTGGTGGT-TCAGATTTGGCAAACGATTC | 572 | BamHI |
| Orf46.1-His | Rev | CCCAAGCTT-CGTATCATATTTCACGTGC | 573 | HindIII |
| fu-(ΔG287-919)- | Fwd | CCCAAGCTTGGTGGTGGTGGTGGT- | 574 | HindIII |
| Orf46.1-His | | TCAGATTTGGCAAACGATTC | | |
| | Rev | CCCGCTCGAG-CGTATCATATTTCACGTGC | 575 | XhoI |
| fu-(ΔG287- | Fwd | CCCAAGCTTGGTGGTGGTGGTGGT- | 576 | HindIII |
| Orf46.1)-919-His | | CAAAGCAAGAGCATCCAAACC | | |
| | Rev | CCCGCTCGAG-CGGGCGGTATTCGGGCTT | 577 | XhoI |
| fu ΔG287(394.98)- | Fwd | CGCGGATCCGCTAGC-CCCGATGTTAAATCGGC | 578 | NheI |
| . . . | Rev | CGGGGATCC-ATCCTGCTCTTTTTTGCCGG | 579 | BamHI |
| fu Orf1-(Orf46.1)- | Fwd | CGCGGATCCGCTAGC-GGACACACTTATTTCGGCATC | 580 | NheI |
| His | Rev | CGCGGATCC-CCAGCGGTAGCCTAATTTGAT | 581 | |
| fu (Orf1)-Orf46.1- | Fwd | CGCGGATCCGGTGGTGGTGGT-TCAGATTTGGCAAACGATTC | 582 | BamHI |
| His | Rev | CCCAAGCTT-CGTATCATATTTCACGTGC | 583 | HindIII |
| fu (919)-Orf46.1- | Fwd1 | GCGGCGTCGACGGTGGCGGAGGCACTGGATCCTCAG | 584 | SalI |
| His | Fwd2 | GGAGGCACTGGATCCTCAGATTTGGCAAACGATTC | 585 | |
| | Rev | CCCGCTCGAG-CGTATCATATTTCACGTGC | 586 | XhoI |
| Fu orf46- . . . | Fwd | GGAATTCCATATGTCAGATTTGGCAAACGATTC | 587 | NdeI |
| | Rev | CGCGGATCCCGTATCATATTTCACGTGC | 588 | BamHI |
| Fu (orf46)-287-His | Fwd | CGGGGATCCGGGGGCGGCGGTGGCG | 589 | BamHI |
| | Rev | CCCAAGCTTATCCTGCTCTTTTTTGCCGGC | 590 | HindIII |
| Fu (orf46)-919-His | Fwd | CGCGGATCCGGTGGTGGTGGTCAAAGCAAGAGCATCCAAACC | 591 | BamHI |
| | Rev | CCCAAGCTTCGGGCGGTATTCGGGCTTC | 592 | HindIII |
| Fu (orf46-919)- | Fwd | CCCCAAGCTTGGGGGCGGCGGTGGCG | 593 | HindIII |
| 287-His | Rev | CCCGCTCGAGATCCTGCTCTTTTTTGCCGGC | 594 | XhoI |
| Fu (orf46-287)- | Fwd | CCCAAGCTTGGTGGTGGTGGTGGTCAAAGCAAGAGCAT | 595 | HindII |
| 919-His | | CCAAACC | | |
| | Rev | CCCGCTCGAGCGGGCGGTATTCGGGCTT | 596 | XhoI |
| (ΔG741 )-961c-His | Fwd1 | GGAGGCACTGGATCCGCAGCCACAAACGACGACGA | 597 | XhoI |
| | Fwd2 | GCGGCCTCGAG-GGTGGCGGAGGCACTGGATCCGCAG | 598 | |
| | Rev | CCCGCTCGAG-ACCCAGCTTGTAAGGTTG | 599 | XhoI |
| (ΔG741 )-961-His | Fwd1 | GGAGGCACTGGATCCGCAGCCACAAACGACGACGA | 600 | XhoI |
| | Fwd2 | GCGGCCTCGAG-GGTGGCGGAGGCACTGGATCCGCAG | 601 | |
| | Rev | CCCGCTCGAG-CCACTCGTAATTGACGCC | 602 | XhoI |
| (ΔG741 )-983-His | Fwd | GCGGCCTCGAG-GGATCCGGCGGAGGCGGCACTTCTGCG | 603 | XhoI |
| | Rev | CCCGCTCGAG-GAACCGGTAGCCTACG | 604 | XhoI |
| (ΔG741)-orf46.1- | Fwd1 | GGAGGCACTGGATCCTCAGATTTGGCAAACGATTC | 605 | SalI |
| His | Fwd2 | GCGGCGTCGACGGTGGCGGAGGCACTGGATCCTCAGA | 606 | |
| | Rev | CCCGCTCGAG-CGTATCATATTTCACGTGC | 607 | XhoI |
| (ΔG983)- | Fwd | GCGGCCTCGAG-GGATCCGGAGGGGGTGGTGTCGCC | 608 | XhoI |
| 741 (MC58) -His | Rev | CCCGCTCGAG-TTGCTTGGCGGCAAG | 609 | XhoI |

-continued

| | | Sequences | SEQ ID NO: | Restriction site |
|---|---|---|---|---|
| (ΔG983)-961c-His | Fwd1 | GGAGGCACTGGATCCGCAGCCACAAACGACGACGA | 610 | XhoI |
| | Fwd2 | GCGGCCTCGAG-GGTGGCGGAGGCACTGGATCCGCAG | 611 | |
| | Rev | CCCGCTCGAG-ACCCAGCTTGTAAGGTTG | 612 | XhoI |
| (ΔG983)-961-His | Fwd1 | GGAGGCACTGGATCCGCAGCCACAAACGACGACGA | 613 | XhoI |
| | Fwd2 | GCGGCCTCGAG-GGTGGCGGAGGCACTGGATCCGCAG | 614 | |
| | Rev | CCCGCTCGAG-CCACTCGTAATTGACGCC | 615 | XhoI |
| (ΔG983)-Orf46.1-His | Fwd1 | GGAGGCACTGGATCCTCAGATTTGGCAAACGATTC | 616 | SalI |
| | Fwd2 | GCGGCGTCGACGGTGGCGGAGGCACTGGATCCTCAGA | 617 | |
| | Rev | CCCGCTCGAG-CGTATCATATTTCACGTGC | 618 | XhoI |

* This primer was used as a Reverse primer for all the C terminal fusions of 287 to the His-tag.
§Forward primers used in combination with the 287-His Reverse primer.
NB - All PCR reactions use strain 2996 unless otherwise specified (e.g. strain MC58)

In all constructs starting with an ATG not followed by a unique NheI site, the ATG codon is part of the NdeI site used for cloning. The constructs made using NheI as a cloning site at the 5' end (e.g. all those containing 287 at the N-terminus) have two additional codons (GCT AGC) fused to the coding sequence of the antigen.

Preparation of Chromosomal DNA Templates

*N.meningitidis* strains 2996, MC58, 394.98, 1000 and BZ232 (and others) were grown to exponential phase in 100 ml of GC medium, harvested by centrifugation, and resuspended in 5 ml buffer (20% w/v sucrose, 50 mM Tris-HCl, 50 mM EDTA, pH8). After 10 minutes incubation on ice, the bacteria were lysed by adding 10 ml of lysis solution (50 mM NaCl, 1% Na-Sarkosyl, 50 μg/ml Proteinase K), and the suspension incubated at 37° C. for 2 hours. Two phenol extractions (equilibrated to pH 8) and one $CHCl_3$/isoamylalcohol (24:1) extraction were performed. DNA was precipitated by addition of 0.3M sodium acetate and 2 volumes of ethanol, and collected by centrifugation. The pellet was washed once with 70% (v/v) ethanol and redissolved in 4.0 ml TE buffer (10 mM Tris-HCl, 1 mM EDTA, pH 8.0). The DNA concentration was measured by reading $OD_{260}$.

PCR Amplification

The standard PCR protocol was as follows: 200 ng of genomic DNA from 2996, MC581000, or BZ232 strains or 10 ng of plasmid DNA preparation of recombinant clones were used as template in the presence of 40 μg of each oligonucleotide primer 400-800 μM d NTPs solution, 1×PCR buffer (including 1.5 mM $MgCl_2$), 2.5 units TaqI DNA polymerase (using Perkin-Elmer AmpliTaq® DNA Polymerase kit, Boerhingher Mannheim Expand™ Long Template kit).

After a preliminary 3 minute incubation of the whole mix at 95° C., each sample underwent a two-step amplification: the first 5 cycles were performed using the hybridisation temperature that excluded the restriction enzyme tail of the primer ($T_{m1}$). This was followed by 30 cycles according to the hybridisation temperature calculated for the whole length oligos ($T_{m2}$). Elongation times, performed at 68° C., or 72° C., varied according to the length of the Orf to be amplified. In the case of Orf1 the elongation time, starting from 3 minutes, was increased by 15 seconds each cycle. The cycles were completed with a 10 minute extension step at 72° C.

The amplified DNA was either loaded directly on a 1% agarose gel. The DNA fragment corresponding to the band of correct size was purified from the gel using the Qiagen Gel Extraction Kit, following the manufacturer's protocol.

Digestion of PCR Fragments and of the Cloning Vectors

The purified DNA corresponding to the amplified fragment was digested with the appropriate restriction enzymes for cloning into pET-21b+, pET22b+ or pET-24b+. Digested fragments were purified using the QIAquick PCR purification kit (following the manufacturer's instructions) and eluted with either $H_2O$ or 10 mM Tris, pH 8.5. Plasmid vectors were digested with the appropriate restriction enzymes, loaded onto a 1.0% agarose gel and the band corresponding to the digested vector purified using the Qiagen QIAquick Gel Extraction Kit.

Cloning

The fragments corresponding to each gene, previously digested and purified, were ligated into pET21b+, pET22b+ or pET-24b+. A molar ratio of 3:1 fragment/vector was used with T4 DNA ligase in the ligation buffer supplied by the manufacturer.

Recombinant plasmid was transformed into competent *E.coli* DH5 or HB101 by incubating the ligase reaction solution and bacteria for 40 minutes on ice, then at 37° C. for 3 minutes.

This was followed by the addition of 800 μl LB broth and incubation at 37° C. for 20 minutes. The cells were centrifuged at maximum speed in an Eppendorf microfuge, resuspended in approximately 200 μl of the supernatant and plated onto LB ampicillin (10 mg/ml) agar.

Screening for recombinant clones was performed by growing randomly selected colonies overnight at 37° C. in 4.0 ml of LB broth+100 μg/ml ampicillin. Cells were pelleted and plasmid DNA extracted using the Qiagen QIAprep Spin Miniprep Kit, following the manufacturer's instructions. Approximately 1 μg of each individual miniprep was digested with the appropriate restriction enzymes and the digest loaded onto a 1-1.5% agarose gel (depending on the expected insert size), in parallel with the molecular weight marker (1 kb DNA Ladder, GIBCO). Positive clones were selected on the basis of the size of insert.

Expression

After cloning each gene into the expression vector, recombinant plasmids were transformed into *E.coli* strains suitable for expression of the recombinant protein. 1 μl of each construct was used to transform *E.coli* BL21-DE3 as described above. Single recombinant colonies were inoculated into 2 ml LB+Amp (100 μg/ml), incubated at 37° C. overnight, then diluted 1:30 in 20 ml of LB+Amp (100 μg/ml) in 100 ml flasks, to give an $OD_{600}$ between 0.1 and 0.2. The flasks were incubated at 30° C. or at 37° C. in a gyratory water bath shaker until $OD_{600}$ indicated exponential growth suitable for induction of expression (0.4-0.8 OD). Protein expression was induced by addition of 1.0 mM IPTG. After 3 hours incubation at 30° C. or 37° C. the $OD_{600}$ was measured and expression examined. 1.0 ml of each sample was centrifuged in a microfuge, the pellet resuspended in PBS and analysed by SDS-PAGE and Coomassie Blue staining.

Gateway Cloning and Expression

Sequences labelled GATE were cloned and expressed using the GATEWAY Cloning Technology (GIBCO-BRL). Recombinational cloning (RC) is based on the recombination reactions that mediate the integration and excision of phage into and from the *E.coli* genome, respectively. The integration involves recombination of the attP site of the phage DNA within the attB site located in the bacterial genome (BP reaction) and generates an integrated phage genome flanked by attL and attR sites. The excision recombines attL and attR sites back to attP and attB sites (LR reaction). The integration reaction requires two enzymes [the phage protein Integrase (Int) and the bacterial protein integration host factor (IHF] (BP clonase). The excision reaction requires Int, IHF, and an additional phage enzyme, Excisionase (Xis) (LR clonase). Artificial derivatives of the 25-bp bacterial attB recombination site, referred to as B1 and B2, were added to the 5' end of the primers used in PCR reactions to amplify Neisserial ORFs. The resulting products were BP cloned into a "Donor vector" containing complementary derivatives of the phage attP recombination site (P1 and P2) using BP clonase. The resulting "Entry clones" contain ORFs flanked by derivatives of the attL site (L1 and L2) and were subcloned into expression "destination vectors" which contain derivatives of the attL-compatible attR sites (R1 and R2) using LR clonase. This resulted in "expression clones" in which ORFs are flanked by B1 and B2 and fused in frame to the GST or His N terminal tags.

The *E. coli* strain used for GATEWAY expression is BL21-SI. Cells of this strain are induced for expression of the T7 RNA polymerase by growth in medium containing salt (0.3 M NaCl).

Note that this system gives N-terminus His tags.

Preparation of Membrane Proteins.

Fractions composed principally of either inner, outer or total membrane were isolated in order to obtain recombinant proteins expressed with membrane-localisation leader sequences. The method for preparation of membrane fractions, enriched for recombinant proteins, was adapted from Filip et. al. [*J. Bact.* (1973) 115:717-722] and Davies et. al. [*J. Immunol. Meth.* (1990) 143:215-225]. Single colonies harbouring the plasmid of interest were grown overnight at 37° C. in 20 ml of LB/Amp (100 μg/ml) liquid culture. Bacteria were diluted 1:30 in 1.0 L of fresh medium and grown at either 30° C. or 37° C. until the $OD_{550}$ reached 0.6-0.8. Expression of recombinant protein was induced with IPTG at a final concentration of 1.0 mM. After incubation for 3 hours, bacteria were harvested by centrifugation at 8000 g for 15 minutes at 4° C. and resuspended in 20 ml of 20 mM Tris-HCl (pH 7.5) and complete protease inhibitors (Boehringer-Mannheim). All subsequent procedures were performed at 4° C. or on ice.

Cells were disrupted by sonication using a Branson Sonifier 450 and centrifuged at 5000 g for 20 min to sediment unbroken cells and inclusion bodies. The supernatant, containing membranes and cellular debris, was centrifuged at 50000 g (Beckman Ti50, 29000 rpm) for 75 min, washed with 20 mM Bis-tris propane (pH 6.5), 1.0 M NaCl, 10% (v/v) glycerol and sedimented again at 50000 g for 75 minutes. The pellet was resuspended in 20 mM Tris-HCl (pH 7.5), 2.0% (v/v) Sarkosyl, complete protease inhibitor (1.0 mM EDTA, final concentration) and incubated for 20 minutes to dissolve inner membrane. Cellular debris was pelleted by centrifugation at 5000 g for 10 min and the supernatant centrifuged at 75000 g for 75 minutes (Beckman Ti50, 33000 rpm). Proteins 008L and 519L were found in the supernatant suggesting inner membrane localisation. For these proteins both inner and total membrane fractions (washed with NaCl as above) were used to immunise mice. Outer membrane vesicles obtained from the 75000 g pellet were washed with 20 mM Tris-HCl (pH 7.5) and centrifuged at 75000 g for 75 minutes or overnight. The OMV was finally resuspended in 500 μl of 20 mM Tris-HCl (pH 7.5), 10% v/v glycerol. Orf1L and Orf40L were both localised and enriched in the outer membrane fraction which was used to immunise mice. Protein concentration was estimated by standard Bradford Assay (Bio-Rad), while protein concentration of inner membrane fraction was determined with the DC protein assay (Bio-Rad). Various fractions from the isolation procedure were assayed by SDS-PAGE.

Purification of His-Tagged Proteins

Various forms of 287 were cloned from strains 2996 and MC58. They were constructed with a C-terminus His-tagged fusion and included a mature form (aa 18-427), constructs with deletions (Δ, Δ2, Δ3 and Δ4) and clones composed of either B or C domains. For each clone purified as a His-fusion, a single colony was streaked and grown overnight at 37° C. on a LB/Amp (100 μg/ml) agar plate. An isolated colony from this plate was inoculated into 20 ml of LB/Amp (100 μg/ml) liquid medium and grown overnight at 37° C. with shaking. The overnight culture was diluted 1:30 into 1.0 L LB/Amp (100 μg/ml) liquid medium and allowed to grow at the optimal temperature (30 or 37° C.) until the $OD_{550}$ reached 0.6-0.8. Expression of recombinant protein was induced by addition of IPTG (final concentration 1.0 mM) and the culture incubated for a further 3 hours. Bacteria were harvested by centrifugation at 8000 g for 15 min at 4° C. The bacterial pellet was resuspended in 7.5 ml of either (i) cold buffer A (300 mM NaCl, 50 mM phosphate buffer, 10 mM imidazole, pH 8.0) for soluble proteins or (ii) buffer B (10 mM Tris-HCl, 100 mM phosphate buffer, pH 8.8 and, optionally, 8M urea) for insoluble proteins. Proteins purified in a soluble form included 287-His, Δ1, Δ2, Δ3 and Δ4287-His, Δ4287MC58-His, 287c-His and 287cMC58-His. Protein 287bMC58-His was insoluble and purified accordingly. Cells were disrupted by sonication on ice four times for 30 sec at 40 W using a Branson sonifier 450 and centrifuged at 13000×g for 30 min at 4° C. For insoluble proteins, pellets were resuspended in 2.0 ml buffer C (6 M guanidine hydrochloride, 100 mM phosphate buffer, 10 mM Tris-HCl, pH 7.5 and treated with 10 passes of a Dounce homogenizer. The homogenate was centrifuged at 13000 g for 30 min and the supernatant retained. Supernatants for both soluble and insoluble preparations were mixed with 150 μl $Ni^{2+}$-resin (previously equilibrated with either buffer A or buffer B, as appropriate) and incubated at room temperature with gentle agitation for 30 min. The resin was Chelating Sepharose Fast Flow (Pharmacia), prepared according to the manufacturer's protocol. The batch-wise preparation was centrifuged at 700 g for 5 min at 4° C. and the supernatant discarded. The resin was washed twice (batch-wise) with 10 ml buffer A or B for 10 min, resuspended in 1.0 ml buffer A or B and loaded onto a disposable column. The resin continued to be washed with either (i) buffer A at 4° C. or (ii) buffer B at room temperature, until the $OD_{280}$ of the flow-through reached 0.02-0.01. The resin was further washed with either (i) cold buffer C (300 mM NaCl, 50 mM phosphate buffer, 20 mM imidazole, pH 8.0) or (ii) buffer D (10 mM Tris-HCl, 100 mM phosphate buffer, pH 6.3 and, optionally, 8M urea) until $OD_{280}$ of the flow-through reached 0.02-0.01. The His-fusion protein was eluted by addition of 700 μl of either (i) cold elution buffer A (300 mM NaCl, 50 mM phosphate buffer, 250 mM imidazole, pH 8.0) or (ii) elution buffer B (10 mM Tris-HCl, 100 mM phosphate buffer, pH 4.5 and, optionally, 8M urea) and fractions collected until the $OD_{280}$ indicated all the recombinant protein was obtained. 20 μl aliquots of each elution fraction were analysed by SDS-PAGE. Protein concentrations were estimated using the Bradford assay.

Renaturation of Denatured His-Fusion Proteins.

Denaturation was required to solubilize 287bMC8, so a renaturation step was employed prior to immunisation. Glycerol was added to the denatured fractions obtained above to give a final concentration of 10% v/v. The proteins were diluted to 200 μg/ml using dialysis buffer I (10% v/v glycerol, 0.5M arginine, 50 mM phosphate buffer, 5.0 mM reduced glutathione, 0.5 mM oxidised glutathione, 2.0M urea, pH 8.8) and dialysed against the same buffer for 12-14 hours at 4° C. Further dialysis was performed with buffer II (10% v/v glycerol, 0.5M arginine, 50 mM phosphate buffer, 5.0 mM reduced glutathione, 0.5 mM oxidised glutathione, pH 8.8) for 12-14 hours at 4° C. Protein concentration was estimated using the formula:

$$\text{Protein (mg/ml)}=(1.55\times OD_{280})-(0.76\times OD_{260})$$

Amino Acid Sequence Analysis.

Automated sequence analysis of the $NH_2$-terminus of proteins was performed on a Beckman sequencer (LF 3000) equipped with an on-line phenylthiohydantoin-amino acid analyser (System Gold) according to the manufacturer's recommendations.

Immunization

Balb/C mice were immunized with antigens on days 0, 21 and 35 and sera analyzed at day 49.

Sera Analysis—ELISA

The acapsulated MenB M7 and the capsulated strains were plated on chocolate agar plates and incubated overnight at 37° C. with 5% $CO_2$. Bacterial colonies were collected from the agar plates using a sterile dracon swab and inoculated into Mueller-Hinton Broth (Difco) containing 0.25% glucose. Bacterial growth was monitored every 30 minutes by following $OD_{620}$. The bacteria were let to grow until the OD reached the value of 0.4-0.5. The culture was centrifuged for 10 minutes at 400 rpm. The supernatant was discarded and bacteria were washed twice with PBS, resuspended in PBS containing 0.025% formaldehyde, and incubated for 1 hour at 37° C. and then overnight at 4° C. with stirring. 100 μl bacterial cells were added to each well of a 96 well Greiner plate and incubated overnight at 4° C. The wells were then washed three times with PBT washing buffer (0.1% Tween-20 in PBS). 200 μl of saturation buffer (2.7% polyvinylpyrrolidone 10 in water) was added to each well and the plates incubated for 2 hours at 37° C. Wells were washed three times with PBT. 200 μl of diluted sera (Dilution buffer: 1% BSA, 0.1% Tween-20, 0.1% $NaN_3$ in PBS) were added to each well and the plates incubated for 2 hours at 37° C. Wells were washed three times with PBT. 100 μl of HRP-conjugated rabbit anti-mouse (Dako) serum diluted 1:2000 in dilution buffer were added to each well and the plates were incubated for 90 minutes at 37° C. Wells were washed three times with PBT buffer. 100 μl of substrate buffer for HRP (25 ml of citrate buffer pH5, 10 mg of O-phenildiamine and 10 μl of $H_2O_2$) were added to each well and the plates were left at room temperature for 20 minutes. 100 μl 12.5% $H_2SO_4$ was added to each well and $OD_{490}$ was followed. The ELISA titers were calculated abitrarely as the dilution of sera which gave an $OD_{490}$ value of 0.4 above the level of preimmune sera The ELISA was considered positive when the dilution of sera with $OD_{490}$ of 0.4 was higher than 1:400.

Sera Analysis—FACS Scan Bacteria Binding Assay

The acapsulated MenB M7 strain was plated on chocolate agar plates and incubated overnight at 37° C. with 5% $CO_2$. Bacterial colonies were collected from the agar plates using a sterile dracon swab and inoculated into 4 tubes containing 8 ml each Mueller-Hinton Broth (Difco) containing 0.25% glucose. Bacterial growth was monitored every 30 minutes by following $OD_{620}$. The bacteria were let to grow until the OD reached the value of 0.35-0.5. The culture was centrifuged for 10 minutes at 400 rpm. The supernatant was discarded and the pellet was resuspended in blocking buffer (1% BSA in PBS, 0.4% $NaN_3$) and centrifuged for 5 minutes at 4000 rpm. Cells were resuspended in blocking buffer to reach $OD_{620}$ of 0.05. 100 μl bacterial cells were added to each well of a Costar 96 well plate. 100 μl of diluted (1:100, 1:200, 1:400) sera (in blocking buffer) were added to each well and plates incubated for 2 hours at 4° C. Cells, were centrifuged for 5 minutes at 4000 rpm, the supernatant aspirated and cells washed by addition of 200 μl/well of blocking buffer in each well. 100 μl of R-Phicoerytrin conjugated $F(ab)_2$ goat anti-mouse, diluted 1:100, was added to each well and plates incubated for 1 hour at 4° C. Cells were spun down by centrifugation at 400 rpm for 5 minutes and washed by addition of 200 μl/well of blocking buffer. The supernatant was aspirated and cells resuspended in 200 μl/well of PBS, 0.25% formaldehyde. Samples were transferred to FACScan tubes and read. The condition for FACScan (Laser Power 15 mW) setting were: FL2 on; FSC-H threshold: 92; FSC PMT Voltage: E 01; SSC PMT: 474; Amp. Gains 6.1; FL-2 PMT: 586; compensation values: 0.

Sera Analysis—Bactericidal Assay

*N.meningitidis* strain 2996 was grown overnight at 37° C. on chocolate agar plates (starting from a frozen stock) with 5% $CO_2$. Colonies were collected and used to inoculate 7 ml Mueller-Hinton broth, containing 0.25% glucose to reach an $OD_{620}$ of 0.05-0.08. The culture was incubated for approximately 1.5 hours at 37 degrees with shacking until the $OD_{620}$ reached the value of 0.23-0.24. Bacteria were diluted in 50 mM Phosphate buffer pH 7.2 containing 10 mM $MgCl_2$, 10 mM $CaCl_2$ and 0.5% (w/v) BSA (assay buffer) at the working dilution of $10^5$ CFU/ml. The total volume of the final reaction mixture was 50 μl with 25 μl of serial two fold dilution of test serum, 12.5 μl of bacteria at the working dilution, 12.5 μl of baby rabbit complement (final concentration 25%).

Controls included bacteria incubated with complement serum, immune sera incubated with bacteria and with complement inactivated by heating at 56° C. for 30'. Immediately after the addition of the baby rabbit complement, 10 μl of the controls were plated on Mueller-Hinton agar plates using the tilt method (time 0). The 96-wells plate was incubated for 1 hour at 37° C. with rotation. 7 μl of each sample were plated on Mueller-Hinton agar plates as spots, whereas 10 μl of the controls were plated on Mueller-Hinton agar plates using the tilt method (time 1). Agar plates were incubated for 18 hours at 37 degrees and the colonies corresponding to time 0 and time 1 were counted.

Sera Analysis—Western Blots

Purified proteins (500 ng/lane), outer membrane vesicles (5 μg) and total cell extracts (25 μg) derived from MenB strain 2996 were loaded onto a 12% SDS-polyacrylamide gel and transferred to a nitrocellulose membrane. The transfer was performed for 2 hours at 150 mA at 4° C., using transfer buffer (0.3% Tris base, 1.44% glycine, 20% (v/v) methanol). The membrane was saturated by overnight incubation at 4° C. in saturation buffer (10% skimmed milk, 0.1% Triton X100 in PBS). The membrane was washed twice with washing buffer (3% skimmed milk, 0.1% Triton X100 in PBS) and incubated for 2 hours at 37° C. with mice sera diluted 1:200 in washing buffer. The membrane was washed twice and incubated for 90 minutes with a 1:2000 dilution of horseradish peroxidase labelled anti-mouse Ig. The membrane was washed twice with 0.1% Triton X100 in PBS and developed with the Opti-4CN Substrate Kit (Bio-Rad). The reaction was stopped by adding water.

The OMVs were prepared as follows: *N.meningitidis* strain 2996 was grown overnight at 37 degrees with 5% $CO_2$ on 5 GC plates, harvested with a loop and resuspended in 10 ml of 20 mM Tris-HCl pH 7.5, 2 mM EDTA. Heat inactivation was performed at 56° C. for 45 minutes and the bacteria disrupted by sonication for 5 minutes on ice (50% duty cycle, 50% output, Branson sonifier 3 mm microtip). Unbroken cells were removed by centrifugation at 5000 g for 10 minutes, the supernatant containing the total cell envelope fraction recovered and further centrifuged overnight at 50000 g at the temperature of 4° C. The pellet containing the membranes was resuspended in 2% sarkosyl, 20 mM Tris-HCl pH 7.5, 2 mM EDTA and incubated at room temperature for 20 minutes to solubilise the inner membranes. The suspension was centrifuged at 10000 g for 10 minutes to remove aggregates, the supernatant was further centrifuged at 50000 g for 3 hours. The pellet, containing the outer membranes was washed in PBS and resuspended in the same buffer. Protein concentration was measured by the D.C. Bio-Rad Protein assay (Modified Lowry method), using BSA as a standard.

Total cell extracts were prepared as follows: *N.meningitidis* strain 2996 was grown overnight on a GC plate, harvested with a loop and resuspended in 1 ml of 20 mM Tris-HCl. Heat inactivation was performed at 56° C. for 30 minutes.

961 Domain Studies

Cellular fractions preparation Total lysate, periplasm, supernatant and OMV of *E.coli* clones expressing different domains of 961 were prepared using bacteria from over-night cultures or after 3 hours induction with IPTG. Briefly, the periplasm were obtained suspending bacteria in saccarose 25% and Tris. 50 mM (pH 8) with polimixine 100 μg/ml. After 1 hr at room temperature bacteria were centrifuged at 13000 rpm for 15 min and the supernatant were collected. The culture supernatant were filtered with 0.2 μm and precipitated with TCA 50% in ice for two hours. After centrifugation (30 min at 13000 rp) pellets were rinsed twice with ethanol 70% and suspended in PBS. The OMV preparation was performed as previously described. Each cellular fraction were analyzed in SDS-PAGE or in Western Blot using the polyclonal anti-serum raised against GST-961.

Adhesion assay Chang epithelial cells (Wong-Kilbourne derivative, clone 1-5c-4, human conjunctiva) were maintained in DMEM (Gibco) supplemented with 10% heat-inactivated FCS, 15 mM 1-glutamine and antibiotics.

For the adherence assay, sub-confluent culture of Chang epithelial cells were rinsed with PBS and treated with trypsin-EDTA (Gibco), to release them from the plastic support. The cells were then suspended in PBS, counted and dilute in PBS to $5\times10^5$ cells/ml.

Bacteria from over-night cultures or after induction with IPTG, were pelleted and washed twice with PBS by centrifuging at 13000 for 5 min. Approximately 2-$3\times10^8$ (cfu) were incubated with 0.5 mg/ml FITC (Sigma) in 1 ml buffer containing 50 mM $NaHCO_3$ and 100 mM NaCl pH 8, for 30 min at room temperature in the dark. FITC-labeled bacteria were wash 2-3 times and suspended in PBS at 1-$1.5\times10^9$/ml. 200 μl of this suspension (2-$3\times10^8$) were incubated with 2000 rpm ($1\times10^5$) epithelial cells for 30 min a 37° C. Cells were than centrifuged at 200 rpm for 5 min to remove non-adherent bacteria, suspended in 200 μl of PBS, transferred to FACScan tubes and read

The invention claimed is:

1. A method for producing an immunogenic protein comprising expressing in a heterologous host a protein comprising a sequence having greater than 90% sequence identity to SEQ ID NO: 78, in which at least one domain in the protein is deleted, wherein the at least one domain is selected from the group comprising amino acids 24-268 of SEQ ID NO: 78, amino acids 269-307 of SEQ ID NO: 78, and amino acids 308-364 of SEQ ID NO: 78; and purifying the protein.

2. The method of claim 1, in which the N-terminal domain of the protein is mutated.

3. The method of claim 1, in which the heterologous host is an *E. coli* host.

4. The method of claim 1, wherein the protein includes a C-terminal His-tag.

5. The method of claim 1, wherein the protein includes a N-terminal GST.

6. The method of claim 1, wherein the protein '961' is at the N-terminus of a hybrid protein.

7. The method of claim 1, wherein the protein comprises a sequence having greater than 95% sequence identity to a sequence represented by SEQ ID NO: 78.

8. A protein expressed by the method of claim 1.

* * * * *

SEQUENCE LISTING

```
<160> NUMBER OF SEQ ID NOS: 633

<210> SEQ ID NO 1
<211> LENGTH: 441
<212> TYPE: PRT
<213> ORGANISM: Neisseria meningitidis

<400> SEQUENCE: 1

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95
```

-continued

```
Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ala Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440
```

<210> SEQ ID NO 2
<211> LENGTH: 420
<212> TYPE: PRT
<213> ORGANISM: Neisseria meningitidis

<400> SEQUENCE: 2

```
Gln Ser Lys Ser Ile Gln Thr Phe Pro Gln Pro Asp Thr Ser Val Ile
1               5                   10                  15

Asn Gly Pro Asp Arg Pro Val Gly Ile Pro Asp Pro Ala Gly Thr Thr
            20                  25                  30
```

-continued

```
Val Gly Gly Gly Gly Ala Val Tyr Thr Val Val Pro His Leu Ser Leu
        35                  40                  45

Pro His Trp Ala Ala Gln Asp Phe Ala Lys Ser Leu Gln Ser Phe Arg
    50                  55                  60

Leu Gly Cys Ala Asn Leu Lys Asn Arg Gln Gly Trp Gln Asp Val Cys
65                  70                  75                  80

Ala Gln Ala Phe Gln Thr Pro Val His Ser Phe Gln Ala Lys Gln Phe
                85                  90                  95

Phe Glu Arg Tyr Phe Thr Pro Trp Gln Val Ala Gly Asn Gly Ser Leu
            100                 105                 110

Ala Gly Thr Val Thr Gly Tyr Tyr Glu Pro Val Leu Lys Gly Asp Asp
        115                 120                 125

Arg Arg Thr Ala Gln Ala Arg Phe Pro Ile Tyr Gly Ile Pro Asp Asp
    130                 135                 140

Phe Ile Ser Val Pro Leu Pro Ala Gly Leu Arg Ser Gly Lys Ala Leu
145                 150                 155                 160

Val Arg Ile Arg Gln Thr Gly Lys Asn Ser Gly Thr Ile Asp Asn Thr
                165                 170                 175

Gly Gly Thr His Thr Ala Asp Leu Ser Arg Phe Pro Ile Thr Ala Arg
            180                 185                 190

Thr Thr Ala Ile Lys Gly Arg Phe Glu Gly Ser Arg Phe Leu Pro Tyr
        195                 200                 205

His Thr Arg Asn Gln Ile Asn Gly Gly Ala Leu Asp Gly Lys Ala Pro
    210                 215                 220

Ile Leu Gly Tyr Ala Glu Asp Pro Val Glu Leu Phe Phe Met His Ile
225                 230                 235                 240

Gln Gly Ser Gly Arg Leu Lys Thr Pro Ser Gly Lys Tyr Ile Arg Ile
                245                 250                 255

Gly Tyr Ala Asp Lys Asn Glu His Pro Tyr Val Ser Ile Gly Arg Tyr
            260                 265                 270

Met Ala Asp Lys Gly Tyr Leu Lys Leu Gly Gln Thr Ser Met Gln Gly
        275                 280                 285

Ile Lys Ala Tyr Met Arg Gln Asn Pro Gln Arg Leu Ala Glu Val Leu
    290                 295                 300

Gly Gln Asn Pro Ser Tyr Ile Phe Phe Arg Glu Leu Ala Gly Ser Ser
305                 310                 315                 320

Asn Asp Gly Pro Val Gly Ala Leu Gly Thr Pro Leu Met Gly Glu Tyr
                325                 330                 335

Ala Gly Ala Val Asp Arg His Tyr Ile Thr Leu Gly Ala Pro Leu Phe
            340                 345                 350

Val Ala Thr Ala His Pro Val Thr Arg Lys Ala Leu Asn Arg Leu Ile
        355                 360                 365

Met Ala Gln Asp Thr Gly Ser Ala Ile Lys Gly Ala Val Arg Val Asp
    370                 375                 380

Tyr Phe Trp Gly Tyr Gly Asp Glu Ala Gly Glu Leu Ala Gly Lys Gln
385                 390                 395                 400

Lys Thr Thr Gly Tyr Val Trp Gln Leu Leu Pro Asn Gly Met Lys Pro
                405                 410                 415

Glu Tyr Arg Pro
            420

<210> SEQ ID NO 3
<211> LENGTH: 440
```

-continued

<212> TYPE: PRT
<213> ORGANISM: Artificial Sequence
<220> FEATURE:
<223> OTHER INFORMATION: 919

<400> SEQUENCE: 3

```
Met Lys Thr Phe Phe Lys Thr Leu Ser Ala Ala Ala Leu Ala Leu Ile
1               5                   10                  15

Leu Ala Ala Cys Gln Ser Lys Ser Ile Gln Thr Phe Pro Gln Pro Asp
            20                  25                  30

Thr Ser Val Ile Asn Gly Pro Asp Arg Pro Val Gly Ile Pro Asp Pro
        35                  40                  45

Ala Gly Thr Thr Val Gly Gly Gly Gly Ala Val Tyr Thr Val Val Pro
    50                  55                  60

His Leu Ser Leu Pro His Trp Ala Ala Gln Asp Phe Ala Lys Ser Leu
65                  70                  75                  80

Gln Ser Phe Arg Leu Gly Cys Ala Asn Leu Lys Asn Arg Gln Gly Trp
                85                  90                  95

Gln Asp Val Cys Ala Gln Ala Phe Gln Thr Pro Val His Ser Phe Gln
            100                 105                 110

Ala Lys Gln Phe Phe Glu Arg Tyr Phe Thr Pro Trp Gln Val Ala Gly
        115                 120                 125

Asn Gly Ser Leu Ala Gly Thr Val Thr Gly Tyr Tyr Glu Pro Val Leu
    130                 135                 140

Lys Gly Asp Asp Arg Arg Thr Ala Gln Ala Arg Phe Pro Ile Tyr Gly
145                 150                 155                 160

Ile Pro Asp Asp Phe Ile Ser Val Pro Leu Pro Ala Gly Leu Arg Ser
                165                 170                 175

Gly Lys Ala Leu Val Arg Ile Arg Gln Thr Gly Lys Asn Ser Gly Thr
            180                 185                 190

Ile Asp Asn Thr Gly Gly Thr His Thr Ala Asp Leu Ser Arg Phe Pro
        195                 200                 205

Ile Thr Ala Arg Thr Thr Ala Ile Lys Gly Arg Phe Glu Gly Ser Arg
    210                 215                 220

Phe Leu Pro Tyr His Thr Arg Asn Gln Ile Asn Gly Gly Ala Leu Asp
225                 230                 235                 240

Gly Lys Ala Pro Ile Leu Gly Tyr Ala Glu Asp Pro Val Glu Leu Phe
                245                 250                 255

Phe Met His Ile Gln Gly Ser Gly Arg Leu Lys Thr Pro Ser Gly Lys
            260                 265                 270

Tyr Ile Arg Ile Gly Tyr Ala Asp Lys Asn Glu His Pro Tyr Val Ser
        275                 280                 285

Ile Gly Arg Tyr Met Ala Asp Lys Gly Tyr Leu Lys Leu Gly Gln Thr
    290                 295                 300

Ser Met Gln Gly Ile Lys Ser Tyr Met Arg Gln Asn Pro Gln Arg Leu
305                 310                 315                 320

Ala Glu Val Leu Gly Gln Asn Pro Ser Tyr Ile Phe Phe Arg Glu Leu
                325                 330                 335

Ala Gly Ser Ser Asn Asp Gly Pro Val Gly Ala Leu Gly Thr Pro Leu
            340                 345                 350

Met Gly Glu Tyr Ala Gly Ala Val Asp Arg His Tyr Ile Thr Leu Gly
        355                 360                 365

Ala Pro Leu Phe Val Ala Thr Ala His Pro Val Thr Arg Lys Ala Leu
    370                 375                 380
```

-continued

Asn Arg Leu Ile Met Ala Gln Asp Thr Gly Ser Ala Ile Lys Gly Ala
385 390 395 400

Val Arg Val Asp Tyr Phe Trp Gly Tyr Gly Asp Glu Ala Gly Glu Leu
405 410 415

Ala Gly Lys Gln Lys Thr Thr Gly Tyr Val Trp Gln Leu Leu Pro Asn
420 425 430

Gly Met Lys Pro Glu Tyr Arg Pro
435 440

<210> SEQ ID NO 4
<211> LENGTH: 58
<212> TYPE: PRT
<213> ORGANISM: Artificial Sequence
<220> FEATURE:
<223> OTHER INFORMATION: 907-2.pep

<400> SEQUENCE: 4

Glu Arg Arg Arg Leu Leu Val Asn Ile Gln Tyr Glu Ser Ser Arg Ala
1 5 10 15

Gly Leu Asp Thr Gln Ile Val Leu Gly Leu Ile Glu Val Glu Ser Ala
20 25 30

Phe Arg Gln Tyr Ala Ile Ser Gly Val Gly Ala Arg Gly Leu Met Gln
35 40 45

Val Met Pro Phe Trp Lys Asn Tyr Ile Gly
50 55

<210> SEQ ID NO 5
<211> LENGTH: 60
<212> TYPE: PRT
<213> ORGANISM: Artificial Sequence
<220> FEATURE:
<223> OTHER INFORMATION: Escherichia coli

<400> SEQUENCE: 5

Glu Arg Phe Pro Leu Ala Tyr Asn Asp Leu Phe Lys Arg Tyr Thr Ser
1 5 10 15

Gly Lys Glu Ile Pro Gln Ser Tyr Ala Met Ala Ile Ala Arg Gln Glu
20 25 30

Ser Ala Trp Asn Pro Lys Val Lys Ser Pro Val Gly Ala Ser Gly Leu
35 40 45

Met Gln Ile Met Pro Gly Thr Ala Thr His Thr Val
50 55 60

<210> SEQ ID NO 6
<211> LENGTH: 120
<212> TYPE: PRT
<213> ORGANISM: Artificial Sequence
<220> FEATURE:
<223> OTHER INFORMATION: 922.pep

<400> SEQUENCE: 6

Val Ala Gln Lys Tyr Gly Val Pro Ala Glu Leu Ile Val Ala Val Ile
1 5 10 15

Gly Ile Glu Thr Asn Tyr Gly Lys Asn Thr Gly Ser Phe Arg Val Ala
20 25 30

Asp Ala Leu Ala Thr Leu Gly Phe Asp Tyr Pro Arg Arg Ala Gly Phe
35 40 45

Phe Gln Lys Glu Leu Val Glu Leu Leu Lys Leu Ala Lys Glu Glu Gly
50 55 60

Gly Asp Val Phe Ala Phe Lys Gly Ser Tyr Ala Gly Ala Met Gly Met

-continued

```
65                  70                  75                  80

Pro Gln Phe Met Pro Ser Ser Tyr Arg Lys Trp Ala Val Asp Tyr Asp
                85                  90                  95

Gly Asp Gly His Arg Asp Ile Trp Gly Asn Val Gly Asp Val Ala Ala
            100                 105                 110

Ser Val Ala Asn Tyr Met Lys Gln
        115                 120


<210> SEQ ID NO 7
<211> LENGTH: 119
<212> TYPE: PRT
<213> ORGANISM: Artificial Sequence
<220> FEATURE:
<223> OTHER INFORMATION: Escherichia coli

<400> SEQUENCE: 7

Ala Trp Gln Val Tyr Gly Val Pro Pro Glu Ile Ile Val Gly Ile Ile
1               5                   10                  15

Gly Val Glu Thr Arg Trp Gly Arg Val Met Gly Lys Thr Arg Ile Leu
            20                  25                  30

Asp Ala Leu Ala Thr Leu Ser Phe Asn Tyr Pro Arg Arg Ala Glu Tyr
        35                  40                  45

Phe Ser Gly Glu Leu Glu Thr Phe Leu Leu Met Ala Arg Asp Glu Gln
    50                  55                  60

Asp Asp Pro Leu Asn Leu Lys Gly Ser Phe Ala Gly Ala Met Gly Tyr
65                  70                  75                  80

Gly Gln Phe Met Pro Ser Ser Tyr Lys Gln Tyr Ala Val Asp Phe Ser
                85                  90                  95

Gly Asp Gly His Ile Asn Leu Trp Asp Pro Val Asp Ala Ile Gly Ser
            100                 105                 110

Val Ala Asn Tyr Phe Lys Ala
        115


<210> SEQ ID NO 8
<211> LENGTH: 194
<212> TYPE: PRT
<213> ORGANISM: Artificial Sequence
<220> FEATURE:
<223> OTHER INFORMATION: 919.pep

<400> SEQUENCE: 8

Ala Leu Asp Gly Lys Ala Pro Ile Leu Gly Tyr Ala Glu Asp Pro Val
1               5                   10                  15

Glu Leu Phe Phe Met His Ile Gln Gly Ser Gly Arg Leu Lys Thr Pro
            20                  25                  30

Ser Gly Lys Tyr Ile Arg Ile Gly Tyr Ala Asp Lys Asn Glu His Pro
        35                  40                  45

Tyr Val Ser Ile Gly Arg Tyr Met Ala Asp Lys Gly Tyr Leu Lys Leu
    50                  55                  60

Gly Gln Thr Ser Met Gln Gly Ile Lys Ser Tyr Met Arg Gln Asn Pro
65                  70                  75                  80

Gln Arg Leu Ala Glu Val Leu Gly Gln Asn Pro Ser Tyr Ile Phe Phe
                85                  90                  95

Arg Glu Leu Ala Gly Ser Ser Asn Asp Gly Pro Val Gly Ala Leu Gly
            100                 105                 110

Thr Pro Leu Met Gly Glu Tyr Ala Gly Ala Val Asp Arg His Tyr Ile
        115                 120                 125
```

-continued

```
Thr Leu Gly Ala Pro Leu Phe Val Ala Thr Ala His Pro Val Thr Arg
    130                 135                 140

Lys Ala Leu Asn Arg Leu Ile Met Ala Gln Asp Thr Gly Ser Ala Ile
145                 150                 155                 160

Lys Gly Ala Val Arg Val Asp Tyr Phe Trp Gly Tyr Gly Asp Glu Ala
                165                 170                 175

Gly Glu Leu Ala Gly Lys Gln Lys Thr Thr Gly Tyr Val Trp Gln Leu
            180                 185                 190

Leu Pro


<210> SEQ ID NO 9
<211> LENGTH: 196
<212> TYPE: PRT
<213> ORGANISM: Escherichia coli

<400> SEQUENCE: 9

Ala Leu Ser Asp Lys Tyr Ile Leu Ala Tyr Ser Asn Ser Leu Met Asp
1               5                   10                  15

Asn Phe Ile Met Asp Val Gln Gly Ser Gly Tyr Ile Asp Phe Gly Asp
            20                  25                  30

Gly Ser Pro Leu Asn Phe Phe Ser Tyr Ala Gly Lys Asn Gly His Ala
        35                  40                  45

Tyr Arg Ser Ile Gly Lys Val Leu Ile Asp Arg Gly Glu Val Lys Lys
    50                  55                  60

Glu Asp Met Ser Met Gln Ala Ile Arg His Trp Gly Glu Thr His Ser
65                  70                  75                  80

Glu Ala Glu Val Arg Glu Leu Leu Glu Gln Asn Pro Ser Phe Val Phe
                85                  90                  95

Phe Lys Pro Gln Ser Phe Ala Pro Val Lys Gly Ala Ser Ala Val Pro
            100                 105                 110

Leu Val Gly Arg Ala Ser Val Ala Ser Asp Arg Ser Ile Ile Pro Pro
        115                 120                 125

Gly Thr Thr Leu Leu Ala Glu Val Pro Leu Leu Asp Asn Asn Gly Lys
    130                 135                 140

Phe Asn Gly Gln Tyr Glu Leu Arg Leu Met Val Ala Leu Asp Val Gly
145                 150                 155                 160

Gly Ala Ile Lys Gly Gln His Phe Asp Ile Tyr Gln Gly Ile Gly Pro
                165                 170                 175

Glu Ala Gly His Arg Ala Gly Trp Tyr Asn His Tyr Gly Arg Val Trp
            180                 185                 190

Val Leu Lys Thr
        195


<210> SEQ ID NO 10
<211> LENGTH: 28
<212> TYPE: DNA
<213> ORGANISM: Artificial Sequence
<220> FEATURE:
<223> OTHER INFORMATION: Oligonucleotide

<400> SEQUENCE: 10

cgaagacccc gtcggtcttt tttttatg                                        28


<210> SEQ ID NO 11
<211> LENGTH: 28
<212> TYPE: DNA
<213> ORGANISM: Artificial Sequence
<220> FEATURE:
```

-continued

<223> OTHER INFORMATION: Oligonucleotide

<400> SEQUENCE: 11
gtgcataaaa aaaagaccga cggggtct 28

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide

<400> SEQUENCE: 12
aacgcctcgc cggtgttttg ggtca 25

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide

<400> SEQUENCE: 13
tttgacccaa aacaccggcg aggcg 25

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide

<400> SEQUENCE: 14
tgccggcgca gtcggtcggc actaca 26

<210> SEQ ID NO 15
<211> LENGTH: 26
<212> TYPE: DNA
<213> ORGANISM: Artificial Sequence
<220> FEATURE:
<223> OTHER INFORMATION: Oligonucleotide

<400> SEQUENCE: 15
taatgtagtg ccgaccgact gcgccg 26

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide

<400> SEQUENCE: 16
tgattgaggt gggtagcgcg ttccg 25

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide

<400> SEQUENCE: 17
ggcggaacgc gctacccacc tcaat 25

-continued

<210> SEQ ID NO 18
<211> LENGTH: 34
<212> TYPE: DNA
<213> ORGANISM: Artificial Sequence
<220> FEATURE:
<223> OTHER INFORMATION: Oligonucleotide

<400> SEQUENCE: 18
ccggaattct tatgaaaaaa atcatcttcg ccgc 34

<210> SEQ ID NO 19
<211> LENGTH: 32
<212> TYPE: DNA
<213> ORGANISM: Artificial Sequence
<220> FEATURE:
<223> OTHER INFORMATION: Oligonucleotide

<400> SEQUENCE: 19
gcccaagctt ttattgtttg gctgcctcga tt 32

<210> SEQ ID NO 20
<211> LENGTH: 37
<212> TYPE: DNA
<213> ORGANISM: Artificial Sequence
<220> FEATURE:
<223> OTHER INFORMATION: Oligonucleotide

<400> SEQUENCE: 20
ccggaattct tatgtcgccc gatgttaaat cggcgga 37

<210> SEQ ID NO 21
<211> LENGTH: 32
<212> TYPE: DNA
<213> ORGANISM: Artificial Sequence
<220> FEATURE:
<223> OTHER INFORMATION: Oligonucleotide

<400> SEQUENCE: 21
gcccaagctt tcaatcctgc tctttttgc cg 32

<210> SEQ ID NO 22
<211> LENGTH: 34
<212> TYPE: DNA
<213> ORGANISM: Artificial Sequence
<220> FEATURE:
<223> OTHER INFORMATION: Oligonucleotide

<400> SEQUENCE: 22
ccggaattct tatgagccaa gatatggcgg cagt 34

<210> SEQ ID NO 23
<211> LENGTH: 32
<212> TYPE: DNA
<213> ORGANISM: Artificial Sequence
<220> FEATURE:
<223> OTHER INFORMATION: Oligonucleotide

<400> SEQUENCE: 23
gcccaagctt tcaatcctgc tctttttgc cg 32

<210> SEQ ID NO 24
<211> LENGTH: 34
<212> TYPE: DNA
<213> ORGANISM: Artificial Sequence
<220> FEATURE:
<223> OTHER INFORMATION: Oligonucleotide

```
<400> SEQUENCE: 24

ccggaattct tatgtccgcc gaatccgcaa atca                          34

<210> SEQ ID NO 25
<211> LENGTH: 32
<212> TYPE: DNA
<213> ORGANISM: Artificial Sequence
<220> FEATURE:
<223> OTHER INFORMATION: Oligonucleotide

<400> SEQUENCE: 25

gcccaagctt tcaatcctgc tcttttttgc cg                            32

<210> SEQ ID NO 26
<211> LENGTH: 36
<212> TYPE: DNA
<213> ORGANISM: Artificial Sequence
<220> FEATURE:
<223> OTHER INFORMATION: Oligonucleotide

<400> SEQUENCE: 26

ccggaattct tatgggaagg gttgatttgg ctaatg                        36

<210> SEQ ID NO 27
<211> LENGTH: 32
<212> TYPE: DNA
<213> ORGANISM: Artificial Sequence
<220> FEATURE:
<223> OTHER INFORMATION: Oligonucleotide

<400> SEQUENCE: 27

gcccaagctt tcaatcctgc tcttttttgc cg                            32

<210> SEQ ID NO 28
<211> LENGTH: 36
<212> TYPE: DNA
<213> ORGANISM: Artificial Sequence
<220> FEATURE:
<223> OTHER INFORMATION: Oligonucleotide

<400> SEQUENCE: 28

ccggaattct tatgtcagat ttggcaaacg attctt                        36

<210> SEQ ID NO 29
<211> LENGTH: 35
<212> TYPE: DNA
<213> ORGANISM: Artificial Sequence
<220> FEATURE:
<223> OTHER INFORMATION: Oligonucleotide

<400> SEQUENCE: 29

gcccaagctt ttacgtatca tatttcacgt gcttc                         35

<210> SEQ ID NO 30
<211> LENGTH: 37
<212> TYPE: DNA
<213> ORGANISM: Artificial Sequence
<220> FEATURE:
<223> OTHER INFORMATION: Oligonucleotide

<400> SEQUENCE: 30

ccggaattct tatgtcgccc gatgttaaat cggcgga                       37

<210> SEQ ID NO 31
<211> LENGTH: 35
```

-continued

<212> TYPE: DNA
<213> ORGANISM: Artificial Sequence
<220> FEATURE:
<223> OTHER INFORMATION: Oligonucleotide

<400> SEQUENCE: 31
gcccaagctt ttacgtatca tatttcacgt gcttc 35

<210> SEQ ID NO 32
<211> LENGTH: 36
<212> TYPE: DNA
<213> ORGANISM: Artificial Sequence
<220> FEATURE:
<223> OTHER INFORMATION: Oligonucleotide

<400> SEQUENCE: 32
ccggaattct tatgcaaagc aagagcatcc aaacct 36

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide

<400> SEQUENCE: 33
gcccaagctt ttacgggcgg tattcgggct 30

<210> SEQ ID NO 34
<211> LENGTH: 29
<212> TYPE: DNA
<213> ORGANISM: Artificial Sequence
<220> FEATURE:
<223> OTHER INFORMATION: Oligonucleotide

<400> SEQUENCE: 34
ccggaattca tatgaaacac tttccatcc 29

<210> SEQ ID NO 35
<211> LENGTH: 28
<212> TYPE: DNA
<213> ORGANISM: Artificial Sequence
<220> FEATURE:
<223> OTHER INFORMATION: Oligonucleotide

<400> SEQUENCE: 35
gcccaagctt ttaccactcg taattgac 28

<210> SEQ ID NO 36
<211> LENGTH: 29
<212> TYPE: DNA
<213> ORGANISM: Artificial Sequence
<220> FEATURE:
<223> OTHER INFORMATION: Oligonucleotide

<400> SEQUENCE: 36
ccggaattca tatggccaca agcgacgac 29

<210> SEQ ID NO 37
<211> LENGTH: 28
<212> TYPE: DNA
<213> ORGANISM: Artificial Sequence
<220> FEATURE:
<223> OTHER INFORMATION: Oligonucleotide

<400> SEQUENCE: 37

-continued gcccaagctt ttaccactcg taattgac 28

<210> SEQ ID NO 38
<211> LENGTH: 29
<212> TYPE: DNA
<213> ORGANISM: Artificial Sequence
<220> FEATURE:
<223> OTHER INFORMATION: Oligonucleotide

<400> SEQUENCE: 38
ccggaattct tatgaaacac tttccatcc 29

<210> SEQ ID NO 39
<211> LENGTH: 31
<212> TYPE: DNA
<213> ORGANISM: Artificial Sequence
<220> FEATURE:
<223> OTHER INFORMATION: Oligonucleotide

<400> SEQUENCE: 39
gcccaagctt tcaacccacg ttgtaaggtt g 31

<210> SEQ ID NO 40
<211> LENGTH: 30
<212> TYPE: DNA
<213> ORGANISM: Artificial Sequence
<220> FEATURE:
<223> OTHER INFORMATION: Oligonucleotide

<400> SEQUENCE: 40
ccggaattct tatggccaca aacgacgacg 30

<210> SEQ ID NO 41
<211> LENGTH: 31
<212> TYPE: DNA
<213> ORGANISM: Artificial Sequence
<220> FEATURE:
<223> OTHER INFORMATION: Oligonucleotide

<400> SEQUENCE: 41
gcccaagctt tcaacccacg ttgtaaggtt g 31

<210> SEQ ID NO 42
<211> LENGTH: 34
<212> TYPE: DNA
<213> ORGANISM: Artificial Sequence
<220> FEATURE:
<223> OTHER INFORMATION: Oligonucleotide

<400> SEQUENCE: 42
ccggaattct tatggccacc tacaaagtgg acga 34

<210> SEQ ID NO 43
<211> LENGTH: 32
<212> TYPE: DNA
<213> ORGANISM: Artificial Sequence
<220> FEATURE:
<223> OTHER INFORMATION: Oligonucleotide

<400> SEQUENCE: 43
gcccaagctt ttattgtttg gctgcctcga tt 32

<210> SEQ ID NO 44
<211> LENGTH: 32
<212> TYPE: DNA
<213> ORGANISM: Artificial Sequence -continued
<220> FEATURE:
<223> OTHER INFORMATION: Oligonucleotide

<400> SEQUENCE: 44
cgcggatccg ctagccccga tgttaaatcg gc 32

<210> SEQ ID NO 45
<211> LENGTH: 31
<212> TYPE: DNA
<213> ORGANISM: Artificial Sequence
<220> FEATURE:
<223> OTHER INFORMATION: Oligonucleotide

<400> SEQUENCE: 45
cccgctcgag tcaatcctgc tcttttttgc c 31

<210> SEQ ID NO 46
<211> LENGTH: 32
<212> TYPE: DNA
<213> ORGANISM: Artificial Sequence
<220> FEATURE:
<223> OTHER INFORMATION: Oligonucleotide

<400> SEQUENCE: 46
cgcggatccg ctagccaaga tatggcggca gt 32

<210> SEQ ID NO 47
<211> LENGTH: 32
<212> TYPE: DNA
<213> ORGANISM: Artificial Sequence
<220> FEATURE:
<223> OTHER INFORMATION: Oligonucleotide

<400> SEQUENCE: 47
cgcggatccg ctagcgccga atccgcaaat ca 32

<210> SEQ ID NO 48
<211> LENGTH: 32
<212> TYPE: DNA
<213> ORGANISM: Artificial Sequence
<220> FEATURE:
<223> OTHER INFORMATION: Oligonucleotide

<400> SEQUENCE: 48
cgcgctagcg gaagggttga tttggctaat gg 32

<210> SEQ ID NO 49
<211> LENGTH: 34
<212> TYPE: DNA
<213> ORGANISM: Artificial Sequence
<220> FEATURE:
<223> OTHER INFORMATION: Oligonucleotide

<400> SEQUENCE: 49
gggaattcca tatgggcatt tcccgcaaaa tatc 34

<210> SEQ ID NO 50
<211> LENGTH: 32
<212> TYPE: DNA
<213> ORGANISM: Artificial Sequence
<220> FEATURE:
<223> OTHER INFORMATION: Oligonucleotide

<400> SEQUENCE: 50
cccgctcgag ttacgtatca tatttcacgt gc 32

-continued

<210> SEQ ID NO 51
<211> LENGTH: 34
<212> TYPE: DNA
<213> ORGANISM: Artificial Sequence
<220> FEATURE:
<223> OTHER INFORMATION: Oligonucleotide

<400> SEQUENCE: 51
gggaattcca tatgggcatt tcccgcaaaa tatc 34

<210> SEQ ID NO 52
<211> LENGTH: 33
<212> TYPE: DNA
<213> ORGANISM: Artificial Sequence
<220> FEATURE:
<223> OTHER INFORMATION: Oligonucleotide

<400> SEQUENCE: 52
cccgctcgag ttattctatg ccttgtgcgg cat 33

<210> SEQ ID NO 53
<211> LENGTH: 32
<212> TYPE: DNA
<213> ORGANISM: Artificial Sequence
<220> FEATURE:
<223> OTHER INFORMATION: Oligonucleotide

<400> SEQUENCE: 53
cgcggatccc atatggccac aagcgacgac ga 32

<210> SEQ ID NO 54
<211> LENGTH: 28
<212> TYPE: DNA
<213> ORGANISM: Artificial Sequence
<220> FEATURE:
<223> OTHER INFORMATION: Oligonucleotide

<400> SEQUENCE: 54
cccgctcgag ttaccactcg taattgac 28

<210> SEQ ID NO 55
<211> LENGTH: 28
<212> TYPE: DNA
<213> ORGANISM: Artificial Sequence
<220> FEATURE:
<223> OTHER INFORMATION: Oligonucleotide

<400> SEQUENCE: 55
cgcggatccc atatggccac aaacgacg 28

<210> SEQ ID NO 56
<211> LENGTH: 35
<212> TYPE: DNA
<213> ORGANISM: Artificial Sequence
<220> FEATURE:
<223> OTHER INFORMATION: Oligonucleotide

<400> SEQUENCE: 56
cccgctcgag tcatttagca atattatctt tgttc 35

<210> SEQ ID NO 57
<211> LENGTH: 33
<212> TYPE: DNA
<213> ORGANISM: Artificial Sequence
<220> FEATURE:
<223> OTHER INFORMATION: Oligonucleotide -continued

<400> SEQUENCE: 57
cgcggatccc atatgaaagc aaacagtgcc gac 33

<210> SEQ ID NO 58
<211> LENGTH: 28
<212> TYPE: DNA
<213> ORGANISM: Artificial Sequence
<220> FEATURE:
<223> OTHER INFORMATION: Oligonucleotide

<400> SEQUENCE: 58
cccgctcgag ttaccactcg taattgac 28

<210> SEQ ID NO 59
<211> LENGTH: 28
<212> TYPE: DNA
<213> ORGANISM: Artificial Sequence
<220> FEATURE:
<223> OTHER INFORMATION: Oligonucleotide

<400> SEQUENCE: 59
cgcggatccc atatggccac aaacgacg 28

<210> SEQ ID NO 60
<211> LENGTH: 29
<212> TYPE: DNA
<213> ORGANISM: Artificial Sequence
<220> FEATURE:
<223> OTHER INFORMATION: Oligonucleotide

<400> SEQUENCE: 60
cccgctcgag ttaacccacg ttgtaaggt 29

<210> SEQ ID NO 61
<211> LENGTH: 33
<212> TYPE: DNA
<213> ORGANISM: Artificial Sequence
<220> FEATURE:
<223> OTHER INFORMATION: Oligonucleotide

<400> SEQUENCE: 61
cgcggatccc atatgatgaa acactttcca tcc 33

<210> SEQ ID NO 62
<211> LENGTH: 29
<212> TYPE: DNA
<213> ORGANISM: Artificial Sequence
<220> FEATURE:
<223> OTHER INFORMATION: Oligonucleotide

<400> SEQUENCE: 62
cccgctcgag ttaacccacg ttgtaaggt 29

<210> SEQ ID NO 63
<211> LENGTH: 28
<212> TYPE: DNA
<213> ORGANISM: Artificial Sequence
<220> FEATURE:
<223> OTHER INFORMATION: Oligonucleotide

<400> SEQUENCE: 63
cgcggatccc atatggccac aaacgacg 28

<210> SEQ ID NO 64

-continued

<211> LENGTH: 32
<212> TYPE: DNA
<213> ORGANISM: Artificial Sequence
<220> FEATURE:
<223> OTHER INFORMATION: Oligonucleotide

<400> SEQUENCE: 64
cccgctcgag tcagtctgac actgttttat cc 32

<210> SEQ ID NO 65
<211> LENGTH: 32
<212> TYPE: DNA
<213> ORGANISM: Artificial Sequence
<220> FEATURE:
<223> OTHER INFORMATION: Oligonucleotide

<400> SEQUENCE: 65
cgcggatccg ctagccccga tgttaaatcg gc 32

<210> SEQ ID NO 66
<211> LENGTH: 27
<212> TYPE: DNA
<213> ORGANISM: Artificial Sequence
<220> FEATURE:
<223> OTHER INFORMATION: Oligonucleotide

<400> SEQUENCE: 66
cccgctcgag ttacgggcgg tattcgg 27

<210> SEQ ID NO 67
<211> LENGTH: 32
<212> TYPE: DNA
<213> ORGANISM: Artificial Sequence
<220> FEATURE:
<223> OTHER INFORMATION: Oligonucleotide

<400> SEQUENCE: 67
cgcggatccg ctagccccga tgttaaatcg gc 32

<210> SEQ ID NO 68
<211> LENGTH: 32
<212> TYPE: DNA
<213> ORGANISM: Artificial Sequence
<220> FEATURE:
<223> OTHER INFORMATION: Oligonucleotide

<400> SEQUENCE: 68
cccgctcgag ttacgtatca tatttcacgt gc 32

<210> SEQ ID NO 69
<211> LENGTH: 32
<212> TYPE: DNA
<213> ORGANISM: Artificial Sequence
<220> FEATURE:
<223> OTHER INFORMATION: Oligonucleotide

<400> SEQUENCE: 69
cgcggatccg ctagccccga tgttaaatcg gc 32

<210> SEQ ID NO 70
<211> LENGTH: 28
<212> TYPE: DNA
<213> ORGANISM: Artificial Sequence
<220> FEATURE:
<223> OTHER INFORMATION: Oligonucleotide

<400> SEQUENCE: 70

-continued cccgctcgag ttaccactcg taattgac 28

<210> SEQ ID NO 71
<211> LENGTH: 1457
<212> TYPE: PRT
<213> ORGANISM: Neisseria meningitidis

<400> SEQUENCE: 71

```
Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
    210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365
```

-continued

```
Glu Thr Ala Arg Glu Pro Val Tyr His Ala Ala Gly Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Val Val Ser Arg Asn Val Ala Lys Val Lys Gly Asp
    690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
        755                 760                 765

Asn Leu Thr Gly Leu Ala Thr Leu Asn Gly Asn Leu Ser Ala Asn Gly
    770                 775                 780
```

-continued

```
Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
        835                 840                 845

Val Ser His Ser Ala Leu Asn Gly Asn Val Ser Leu Ala Asp Lys Ala
    850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
        915                 920                 925

Thr Asp Ala Pro Arg Arg Arg Ser Arg Arg Ser Arg Arg Ser Leu Leu
    930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
            980                 985                 990

Gly Thr Tyr Thr Leu Ala Val Asn Asn Thr Gly Asn Glu Pro Ala Ser
        995                 1000                1005

Leu Glu Gln Leu Thr Val Val Glu Gly Lys Asp Asn Lys Pro Leu Ser
    1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
                1045                1050                1055

Pro Val Lys Glu Gln Glu Leu Ser Asp Lys Leu Gly Lys Ala Glu Ala
            1060                1065                1070

Lys Lys Gln Ala Glu Lys Asp Asn Ala Gln Ser Leu Asp Ala Leu Ile
        1075                1080                1085

Ala Ala Gly Arg Asp Ala Val Glu Lys Thr Glu Ser Val Ala Glu Pro
    1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
                1125                1130                1135

Arg Glu Ala Glu Thr Arg Pro Ala Thr Thr Ala Phe Pro Arg Ala Arg
            1140                1145                1150

Arg Ala Arg Arg Asp Leu Pro Gln Leu Gln Pro Gln Pro Gln Pro Gln
        1155                1160                1165

Pro Gln Arg Asp Leu Ile Ser Arg Tyr Ala Asn Ser Gly Leu Ser Glu
    1170                1175                1180

Phe Ser Ala Thr Leu Asn Ser Val Phe Ala Val Gln Asp Glu Leu Asp
1185                1190                1195                1200

Arg Val Phe Ala Glu Asp Arg Arg Asn Ala Val Trp Thr Ser Gly Ile
```

-continued

```
                1205                1210                1215

Arg Asp Thr Lys His Tyr Arg Ser Gln Asp Phe Arg Ala Tyr Arg Gln
            1220                1225                1230

Gln Thr Asp Leu Arg Gln Ile Gly Met Gln Lys Asn Leu Gly Ser Gly
        1235                1240                1245

Arg Val Gly Ile Leu Phe Ser His Asn Arg Thr Glu Asn Thr Phe Asp
    1250                1255                1260

Asp Gly Ile Gly Asn Ser Ala Arg Leu Ala His Gly Ala Val Phe Gly
1265                1270                1275                1280

Gln Tyr Gly Ile Asp Arg Phe Tyr Ile Gly Ile Ser Ala Gly Ala Gly
                1285                1290                1295

Phe Ser Ser Gly Ser Leu Ser Asp Gly Ile Gly Gly Lys Ile Arg Arg
            1300                1305                1310

Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
    1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
                1365                1370                1375

Pro Ala Gln His Ile Ser Ile Thr Pro Tyr Leu Ser Leu Ser Tyr Thr
            1380                1385                1390

Asp Ala Ala Ser Gly Lys Val Arg Thr Arg Val Asn Thr Ala Val Leu
        1395                1400                1405

Ala Gln Asp Phe Gly Lys Thr Arg Ser Ala Glu Trp Gly Val Asn Ala
    1410                1415                1420

Glu Ile Lys Gly Phe Thr Leu Ser Leu His Ala Ala Ala Ala Lys Gly
1425                1430                1435                1440

Pro Gln Leu Glu Ala Gln His Ser Ala Gly Ile Lys Leu Gly Tyr Arg
                1445                1450                1455

Trp


<210> SEQ ID NO 72
<211> LENGTH: 21
<212> TYPE: PRT
<213> ORGANISM: Escherichia coli

<400> SEQUENCE: 72

Met Lys Lys Thr Ala Ile Ala Ile Ala Val Ala Leu Ala Gly Phe Ala
1               5                   10                  15

Thr Val Ala Gln Ala
            20


<210> SEQ ID NO 73
<211> LENGTH: 1439
<212> TYPE: PRT
<213> ORGANISM: Neisseria meningitidis

<400> SEQUENCE: 73

Met Lys Lys Thr Ala Ile Ala Ile Ala Val Ala Leu Ala Gly Phe Ala
1               5                   10                  15

Thr Val Ala Gln Ala Ala Ser Ala Gly His Thr Tyr Phe Gly Ile Asn
            20                  25                  30

Tyr Gln Tyr Tyr Arg Asp Phe Ala Glu Asn Lys Gly Lys Phe Ala Val
        35                  40                  45
```

-continued

```
Gly Ala Lys Asp Ile Glu Val Tyr Asn Lys Lys Gly Glu Leu Val Gly
    50                  55                  60

Lys Ser Met Thr Lys Ala Pro Met Ile Asp Phe Ser Val Val Ser Arg
65                  70                  75                  80

Asn Gly Val Ala Ala Leu Val Gly Asp Gln Tyr Ile Val Ser Val Ala
                85                  90                  95

His Asn Gly Gly Tyr Asn Asn Val Asp Phe Gly Ala Glu Gly Arg Asn
            100                 105                 110

Pro Asp Gln His Arg Phe Thr Tyr Lys Ile Val Lys Arg Asn Asn Tyr
        115                 120                 125

Lys Ala Gly Thr Lys Gly His Pro Tyr Gly Gly Asp Tyr His Met Pro
    130                 135                 140

Arg Leu His Lys Phe Val Thr Asp Ala Glu Pro Val Glu Met Thr Ser
145                 150                 155                 160

Tyr Met Asp Gly Arg Lys Tyr Ile Asp Gln Asn Asn Tyr Pro Asp Arg
                165                 170                 175

Val Arg Ile Gly Ala Gly Arg Gln Tyr Trp Arg Ser Asp Glu Asp Glu
            180                 185                 190

Pro Asn Asn Arg Glu Ser Ser Tyr His Ile Ala Ser Ala Tyr Ser Trp
        195                 200                 205

Leu Val Gly Gly Asn Thr Phe Ala Gln Asn Gly Ser Gly Gly Gly Thr
    210                 215                 220

Val Asn Leu Gly Ser Glu Lys Ile Lys His Ser Pro Tyr Gly Phe Leu
225                 230                 235                 240

Pro Thr Gly Gly Ser Phe Gly Asp Ser Gly Ser Pro Met Phe Ile Tyr
                245                 250                 255

Asp Ala Gln Lys Gln Lys Trp Leu Ile Asn Gly Val Leu Gln Thr Gly
            260                 265                 270

Asn Pro Tyr Ile Gly Lys Ser Asn Gly Phe Gln Leu Val Arg Lys Asp
        275                 280                 285

Trp Phe Tyr Asp Glu Ile Phe Ala Gly Asp Thr His Ser Val Phe Tyr
    290                 295                 300

Glu Pro Arg Gln Asn Gly Lys Tyr Ser Phe Asn Asp Asp Asn Asn Gly
305                 310                 315                 320

Thr Gly Lys Ile Asn Ala Lys His Glu His Asn Ser Leu Pro Asn Arg
                325                 330                 335

Leu Lys Thr Arg Thr Val Gln Leu Phe Asn Val Ser Leu Ser Glu Thr
            340                 345                 350

Ala Arg Glu Pro Val Tyr His Ala Ala Gly Gly Val Asn Ser Tyr Arg
        355                 360                 365

Pro Arg Leu Asn Asn Gly Glu Asn Ile Ser Phe Ile Asp Glu Gly Lys
    370                 375                 380

Gly Glu Leu Ile Leu Thr Ser Asn Ile Asn Gln Gly Ala Gly Gly Leu
385                 390                 395                 400

Tyr Phe Gln Gly Asp Phe Thr Val Ser Pro Glu Asn Asn Glu Thr Trp
                405                 410                 415

Gln Gly Ala Gly Val His Ile Ser Glu Asp Ser Thr Val Thr Trp Lys
            420                 425                 430

Val Asn Gly Val Ala Asn Asp Arg Leu Ser Lys Ile Gly Lys Gly Thr
        435                 440                 445

Leu His Val Gln Ala Lys Gly Glu Asn Gln Gly Ser Ile Ser Val Gly
    450                 455                 460
```

-continued

```
Asp Gly Thr Val Ile Leu Asp Gln Gln Ala Asp Asp Lys Gly Lys Lys
465                 470                 475                 480

Gln Ala Phe Ser Glu Ile Gly Leu Val Ser Gly Arg Gly Thr Val Gln
                485                 490                 495

Leu Asn Ala Asp Asn Gln Phe Asn Pro Asp Lys Leu Tyr Phe Gly Phe
            500                 505                 510

Arg Gly Gly Arg Leu Asp Leu Asn Gly His Ser Leu Ser Phe His Arg
        515                 520                 525

Ile Gln Asn Thr Asp Glu Gly Ala Met Ile Val Asn His Asn Gln Asp
    530                 535                 540

Lys Glu Ser Thr Val Thr Ile Thr Gly Asn Lys Asp Ile Ala Thr Thr
545                 550                 555                 560

Gly Asn Asn Asn Ser Leu Asp Ser Lys Lys Glu Ile Ala Tyr Asn Gly
                565                 570                 575

Trp Phe Gly Glu Lys Asp Thr Thr Lys Thr Asn Gly Arg Leu Asn Leu
            580                 585                 590

Val Tyr Gln Pro Ala Ala Glu Asp Arg Thr Leu Leu Leu Ser Gly Gly
        595                 600                 605

Thr Asn Leu Asn Gly Asn Ile Thr Gln Thr Asn Gly Lys Leu Phe Phe
    610                 615                 620

Ser Gly Arg Pro Thr Pro His Ala Tyr Asn His Leu Asn Asp His Trp
625                 630                 635                 640

Ser Gln Lys Glu Gly Ile Pro Arg Gly Glu Ile Val Trp Asp Asn Asp
                645                 650                 655

Trp Ile Asn Arg Thr Phe Lys Ala Glu Asn Phe Gln Ile Lys Gly Gly
            660                 665                 670

Gln Ala Val Val Ser Arg Asn Val Ala Lys Val Lys Gly Asp Trp His
        675                 680                 685

Leu Ser Asn His Ala Gln Ala Val Phe Gly Val Ala Pro His Gln Ser
    690                 695                 700

His Thr Ile Cys Thr Arg Ser Asp Trp Thr Gly Leu Thr Asn Cys Val
705                 710                 715                 720

Glu Lys Thr Ile Thr Asp Asp Lys Val Ile Ala Ser Leu Thr Lys Thr
                725                 730                 735

Asp Ile Ser Gly Asn Val Asp Leu Ala Asp His Ala His Leu Asn Leu
            740                 745                 750

Thr Gly Leu Ala Thr Leu Asn Gly Asn Leu Ser Ala Asn Gly Asp Thr
        755                 760                 765

Arg Tyr Thr Val Ser His Asn Ala Thr Gln Asn Gly Asn Leu Ser Leu
    770                 775                 780

Val Gly Asn Ala Gln Ala Thr Phe Asn Gln Ala Thr Leu Asn Gly Asn
785                 790                 795                 800

Thr Ser Ala Ser Gly Asn Ala Ser Phe Asn Leu Ser Asp His Ala Val
                805                 810                 815

Gln Asn Gly Ser Leu Thr Leu Ser Gly Asn Ala Lys Ala Asn Val Ser
            820                 825                 830

His Ser Ala Leu Asn Gly Asn Val Ser Leu Ala Asp Lys Ala Val Phe
        835                 840                 845

His Phe Glu Ser Ser Arg Phe Thr Gly Gln Ile Ser Gly Gly Lys Asp
    850                 855                 860

Thr Ala Leu His Leu Lys Asp Ser Glu Trp Thr Leu Pro Ser Gly Thr
865                 870                 875                 880

Glu Leu Gly Asn Leu Asn Leu Asp Asn Ala Thr Ile Thr Leu Asn Ser
```

-continued

```
                885                 890                 895

Ala Tyr Arg His Asp Ala Ala Gly Ala Gln Thr Gly Ser Ala Thr Asp
            900                 905                 910

Ala Pro Arg Arg Arg Ser Arg Arg Ser Arg Arg Ser Leu Leu Ser Val
        915                 920                 925

Thr Pro Pro Thr Ser Val Glu Ser Arg Phe Asn Thr Leu Thr Val Asn
    930                 935                 940

Gly Lys Leu Asn Gly Gln Gly Thr Phe Arg Phe Met Ser Glu Leu Phe
945                 950                 955                 960

Gly Tyr Arg Ser Asp Lys Leu Lys Leu Ala Glu Ser Ser Glu Gly Thr
                965                 970                 975

Tyr Thr Leu Ala Val Asn Asn Thr Gly Asn Glu Pro Ala Ser Leu Glu
            980                 985                 990

Gln Leu Thr Val Val Glu Gly Lys Asp Asn Lys Pro Leu Ser Glu Asn
        995                 1000                1005

Leu Asn Phe Thr Leu Gln Asn Glu His Val Asp Ala Gly Ala Trp Arg
    1010                1015                1020

Tyr Gln Leu Ile Arg Lys Asp Gly Glu Phe Arg Leu His Asn Pro Val
1025                1030                1035                1040

Lys Glu Gln Glu Leu Ser Asp Lys Leu Gly Lys Ala Glu Ala Lys Lys
                1045                1050                1055

Gln Ala Glu Lys Asp Asn Ala Gln Ser Leu Asp Ala Leu Ile Ala Ala
            1060                1065                1070

Gly Arg Asp Ala Val Glu Lys Thr Glu Ser Val Ala Glu Pro Ala Arg
        1075                1080                1085

Gln Ala Gly Gly Glu Asn Val Gly Ile Met Gln Ala Glu Glu Glu Lys
    1090                1095                1100

Lys Arg Val Gln Ala Asp Lys Asp Thr Ala Leu Ala Lys Gln Arg Glu
1105                1110                1115                1120

Ala Glu Thr Arg Pro Ala Thr Thr Ala Phe Pro Arg Ala Arg Arg Ala
                1125                1130                1135

Arg Arg Asp Leu Pro Gln Leu Gln Pro Gln Pro Gln Pro Gln Pro Gln
            1140                1145                1150

Arg Asp Leu Ile Ser Arg Tyr Ala Asn Ser Gly Leu Ser Glu Phe Ser
        1155                1160                1165

Ala Thr Leu Asn Ser Val Phe Ala Val Gln Asp Glu Leu Asp Arg Val
    1170                1175                1180

Phe Ala Glu Asp Arg Arg Asn Ala Val Trp Thr Ser Gly Ile Arg Asp
1185                1190                1195                1200

Thr Lys His Tyr Arg Ser Gln Asp Phe Arg Ala Tyr Arg Gln Gln Thr
                1205                1210                1215

Asp Leu Arg Gln Ile Gly Met Gln Lys Asn Leu Gly Ser Gly Arg Val
            1220                1225                1230

Gly Ile Leu Phe Ser His Asn Arg Thr Glu Asn Thr Phe Asp Asp Gly
        1235                1240                1245

Ile Gly Asn Ser Ala Arg Leu Ala His Gly Ala Val Phe Gly Gln Tyr
    1250                1255                1260

Gly Ile Asp Arg Phe Tyr Ile Gly Ile Ser Ala Gly Ala Gly Phe Ser
1265                1270                1275                1280

Ser Gly Ser Leu Ser Asp Gly Ile Gly Gly Lys Ile Arg Arg Arg Val
                1285                1290                1295

Leu His Tyr Gly Ile Gln Ala Arg Tyr Arg Ala Gly Phe Gly Gly Phe
            1300                1305                1310
```

-continued

```
Gly Ile Glu Pro His Ile Gly Ala Thr Arg Tyr Phe Val Gln Lys Ala
        1315                1320                1325

Asp Tyr Arg Tyr Glu Asn Val Asn Ile Ala Thr Pro Gly Leu Ala Phe
    1330                1335                1340

Asn Arg Tyr Arg Ala Gly Ile Lys Ala Asp Tyr Ser Phe Lys Pro Ala
1345                1350                1355                1360

Gln His Ile Ser Ile Thr Pro Tyr Leu Ser Leu Ser Tyr Thr Asp Ala
                1365                1370                1375

Ala Ser Gly Lys Val Arg Thr Arg Val Asn Thr Ala Val Leu Ala Gln
            1380                1385                1390

Asp Phe Gly Lys Thr Arg Ser Ala Glu Trp Gly Val Asn Ala Glu Ile
        1395                1400                1405

Lys Gly Phe Thr Leu Ser Leu His Ala Ala Ala Ala Lys Gly Pro Gln
    1410                1415                1420

Leu Glu Ala Gln His Ser Ala Gly Ile Lys Leu Gly Tyr Arg Trp
1425                1430                1435
```

<210> SEQ ID NO 74
<211> LENGTH: 164
<212> TYPE: PRT
<213> ORGANISM: Neisseria meningitidis

<400> SEQUENCE: 74

```
Met Lys Lys Asn Ile Leu Glu Phe Trp Val Gly Leu Phe Val Leu Ile
1               5                   10                  15

Gly Ala Ala Ala Val Ala Phe Leu Ala Phe Arg Val Ala Gly Gly Ala
            20                  25                  30

Ala Phe Gly Gly Ser Asp Lys Thr Tyr Ala Val Tyr Ala Asp Phe Gly
        35                  40                  45

Asp Ile Gly Gly Leu Lys Val Asn Ala Pro Val Lys Ser Ala Gly Val
    50                  55                  60

Leu Val Gly Arg Val Gly Ala Ile Gly Leu Asp Pro Lys Ser Tyr Gln
65                  70                  75                  80

Ala Arg Val Arg Leu Asp Leu Asp Gly Lys Tyr Gln Phe Ser Ser Asp
                85                  90                  95

Val Ser Ala Gln Ile Leu Thr Ser Gly Leu Leu Gly Glu Gln Tyr Ile
            100                 105                 110

Gly Leu Gln Gln Gly Gly Asp Thr Glu Asn Leu Ala Ala Gly Asp Thr
        115                 120                 125

Ile Ser Val Thr Ser Ser Ala Met Val Leu Glu Asn Leu Ile Gly Lys
    130                 135                 140

Phe Met Thr Ser Phe Ala Glu Lys Asn Ala Asp Gly Gly Asn Ala Glu
145                 150                 155                 160

Lys Ala Ala Glu
```

<210> SEQ ID NO 75
<211> LENGTH: 21
<212> TYPE: PRT
<213> ORGANISM: Erwinia carotovora

<400> SEQUENCE: 75

```
Met Lys Tyr Leu Leu Pro Thr Ala Ala Ala Gly Leu Leu Leu Ala Ala
1               5                   10                  15

Gln Pro Ala Met Ala
            20
```

<210> SEQ ID NO 76
<211> LENGTH: 608
<212> TYPE: PRT
<213> ORGANISM: Neisseria meningitidis ORF46

<400> SEQUENCE: 76

Leu Gly Ile Ser Arg Lys Ile Ser Leu Ile Leu Ser Ile Leu Ala Val
1 5 10 15

Cys Leu Pro Met His Ala His Ala Ser Asp Leu Ala Asn Asp Ser Phe
20 25 30

Ile Arg Gln Val Leu Asp Arg Gln His Phe Glu Pro Asp Gly Lys Tyr
35 40 45

His Leu Phe Gly Ser Arg Gly Glu Leu Ala Glu Arg Ser Gly His Ile
50 55 60

Gly Leu Gly Lys Ile Gln Ser His Gln Leu Gly Asn Leu Met Ile Gln
65 70 75 80

Gln Ala Ala Ile Lys Gly Asn Ile Gly Tyr Ile Val Arg Phe Ser Asp
85 90 95

His Gly His Glu Val His Ser Pro Phe Asp Asn His Ala Ser His Ser
100 105 110

Asp Ser Asp Glu Ala Gly Ser Pro Val Asp Gly Phe Ser Leu Tyr Arg
115 120 125

Ile His Trp Asp Gly Tyr Glu His His Pro Ala Asp Gly Tyr Asp Gly
130 135 140

Pro Gln Gly Gly Gly Tyr Pro Ala Pro Lys Gly Ala Arg Asp Ile Tyr
145 150 155 160

Ser Tyr Asp Ile Lys Gly Val Ala Gln Asn Ile Arg Leu Asn Leu Thr
165 170 175

Asp Asn Arg Ser Thr Gly Gln Arg Leu Ala Asp Arg Phe His Asn Ala
180 185 190

Gly Ser Met Leu Thr Gln Gly Val Gly Asp Gly Phe Lys Arg Ala Thr
195 200 205

Arg Tyr Ser Pro Glu Leu Asp Arg Ser Gly Asn Ala Ala Glu Ala Phe
210 215 220

Asn Gly Thr Ala Asp Ile Val Lys Asn Ile Ile Gly Ala Ala Gly Glu
225 230 235 240

Ile Val Gly Ala Gly Asp Ala Val Gln Gly Ile Ser Glu Gly Ser Asn
245 250 255

Ile Ala Val Met His Gly Leu Gly Leu Leu Ser Thr Glu Asn Lys Met
260 265 270

Ala Arg Ile Asn Asp Leu Ala Asp Met Ala Gln Leu Lys Asp Tyr Ala
275 280 285

Ala Ala Ala Ile Arg Asp Trp Ala Val Gln Asn Pro Asn Ala Ala Gln
290 295 300

Gly Ile Glu Ala Val Ser Asn Ile Phe Met Ala Ala Ile Pro Ile Lys
305 310 315 320

Gly Ile Gly Ala Val Arg Gly Lys Tyr Gly Leu Gly Gly Ile Thr Ala
325 330 335

His Pro Ile Lys Arg Ser Gln Met Gly Ala Ile Ala Leu Pro Lys Gly
340 345 350

Lys Ser Ala Val Ser Asp Asn Phe Ala Asp Ala Ala Tyr Ala Lys Tyr
355 360 365

Pro Ser Pro Tyr His Ser Arg Asn Ile Arg Ser Asn Leu Glu Gln Arg
370 375 380

Tyr Gly Lys Glu Asn Ile Thr Ser Ser Thr Val Pro Pro Ser Asn Gly
385 390 395 400

Lys Asn Val Lys Leu Ala Asp Gln Arg His Pro Lys Thr Gly Val Pro
405 410 415

Phe Asp Gly Lys Gly Phe Pro Asn Phe Glu Lys His Val Lys Tyr Asp
420 425 430

Thr Lys Leu Asp Ile Gln Glu Leu Ser Gly Gly Gly Ile Pro Lys Ala
435 440 445

Lys Pro Val Ser Asp Ala Lys Pro Arg Trp Glu Val Asp Arg Lys Leu
450 455 460

Asn Lys Leu Thr Thr Arg Glu Gln Val Glu Lys Asn Val Gln Glu Ile
465 470 475 480

Arg Asn Gly Asn Lys Asn Ser Asn Phe Ser Gln His Ala Gln Leu Glu
485 490 495

Arg Glu Ile Asn Lys Leu Lys Ser Ala Asp Glu Ile Asn Phe Ala Asp
500 505 510

Gly Met Gly Lys Phe Thr Asp Ser Met Asn Asp Lys Ala Phe Ser Arg
515 520 525

Leu Val Lys Ser Val Lys Glu Asn Gly Phe Thr Asn Pro Val Val Glu
530 535 540

Tyr Val Glu Ile Asn Gly Lys Ala Tyr Ile Val Arg Gly Asn Asn Arg
545 550 555 560

Val Phe Ala Ala Glu Tyr Leu Gly Arg Ile His Glu Leu Lys Phe Lys
565 570 575

Lys Val Asp Phe Pro Val Pro Asn Thr Ser Trp Lys Asn Pro Thr Asp
580 585 590

Val Leu Asn Glu Ser Gly Asn Val Lys Arg Pro Arg Tyr Arg Ser Lys
595 600 605

<210> SEQ ID NO 77
<211> LENGTH: 584
<212> TYPE: PRT
<213> ORGANISM: Artificial Sequence
<220> FEATURE:
<223> OTHER INFORMATION: ORF46-2

<400> SEQUENCE: 77

Ser Asp Leu Ala Asn Asp Ser Phe Ile Arg Gln Val Leu Asp Arg Gln
1 5 10 15

His Phe Glu Pro Asp Gly Lys Tyr His Leu Phe Gly Ser Arg Gly Glu
20 25 30

Leu Ala Glu Arg Ser Gly His Ile Gly Leu Gly Lys Ile Gln Ser His
35 40 45

Gln Leu Gly Asn Leu Met Ile Gln Gln Ala Ala Ile Lys Gly Asn Ile
50 55 60

Gly Tyr Ile Val Arg Phe Ser Asp His Gly His Glu Val His Ser Pro
65 70 75 80

Phe Asp Asn His Ala Ser His Ser Asp Ser Asp Glu Ala Gly Ser Pro
85 90 95

Val Asp Gly Phe Ser Leu Tyr Arg Ile His Trp Asp Gly Tyr Glu His
100 105 110

His Pro Ala Asp Gly Tyr Asp Gly Pro Gln Gly Gly Gly Tyr Pro Ala
115 120 125

Pro Lys Gly Ala Arg Asp Ile Tyr Ser Tyr Asp Ile Lys Gly Val Ala
130 135 140

-continued

```
Gln Asn Ile Arg Leu Asn Leu Thr Asp Asn Arg Ser Thr Gly Gln Arg
145                 150                 155                 160

Leu Ala Asp Arg Phe His Asn Ala Gly Ser Met Leu Thr Gln Gly Val
                165                 170                 175

Gly Asp Gly Phe Lys Arg Ala Thr Arg Tyr Ser Pro Glu Leu Asp Arg
            180                 185                 190

Ser Gly Asn Ala Ala Glu Ala Phe Asn Gly Thr Ala Asp Ile Val Lys
        195                 200                 205

Asn Ile Ile Gly Ala Ala Gly Glu Ile Val Gly Ala Gly Asp Ala Val
    210                 215                 220

Gln Gly Ile Ser Glu Gly Ser Asn Ile Ala Val Met His Gly Leu Gly
225                 230                 235                 240

Leu Leu Ser Thr Glu Asn Lys Met Ala Arg Ile Asn Asp Leu Ala Asp
                245                 250                 255

Met Ala Gln Leu Lys Asp Tyr Ala Ala Ala Ala Ile Arg Asp Trp Ala
            260                 265                 270

Val Gln Asn Pro Asn Ala Ala Gln Gly Ile Glu Ala Val Ser Asn Ile
        275                 280                 285

Phe Met Ala Ala Ile Pro Ile Lys Gly Ile Gly Ala Val Arg Gly Lys
    290                 295                 300

Tyr Gly Leu Gly Gly Ile Thr Ala His Pro Ile Lys Arg Ser Gln Met
305                 310                 315                 320

Gly Ala Ile Ala Leu Pro Lys Gly Lys Ser Ala Val Ser Asp Asn Phe
                325                 330                 335

Ala Asp Ala Ala Tyr Ala Lys Tyr Pro Ser Pro Tyr His Ser Arg Asn
            340                 345                 350

Ile Arg Ser Asn Leu Glu Gln Arg Tyr Gly Lys Glu Asn Ile Thr Ser
        355                 360                 365

Ser Thr Val Pro Pro Ser Asn Gly Lys Asn Val Lys Leu Ala Asp Gln
    370                 375                 380

Arg His Pro Lys Thr Gly Val Pro Phe Asp Gly Lys Gly Phe Pro Asn
385                 390                 395                 400

Phe Glu Lys His Val Lys Tyr Asp Thr Lys Leu Asp Ile Gln Glu Leu
                405                 410                 415

Ser Gly Gly Gly Ile Pro Lys Ala Lys Pro Val Ser Asp Ala Lys Pro
            420                 425                 430

Arg Trp Glu Val Asp Arg Lys Leu Asn Lys Leu Thr Thr Arg Glu Gln
        435                 440                 445

Val Glu Lys Asn Val Gln Glu Ile Arg Asn Gly Asn Lys Asn Ser Asn
    450                 455                 460

Phe Ser Gln His Ala Gln Leu Glu Arg Glu Ile Asn Lys Leu Lys Ser
465                 470                 475                 480

Ala Asp Glu Ile Asn Phe Ala Asp Gly Met Gly Lys Phe Thr Asp Ser
                485                 490                 495

Met Asn Asp Lys Ala Phe Ser Arg Leu Val Lys Ser Val Lys Glu Asn
            500                 505                 510

Gly Phe Thr Asn Pro Val Val Glu Tyr Val Glu Ile Asn Gly Lys Ala
        515                 520                 525

Tyr Ile Val Arg Gly Asn Asn Arg Val Phe Ala Ala Glu Tyr Leu Gly
    530                 535                 540

Arg Ile His Glu Leu Lys Phe Lys Lys Val Asp Phe Pro Val Pro Asn
545                 550                 555                 560
```

-continued

Thr Ser Trp Lys Asn Pro Thr Asp Val Leu Asn Glu Ser Gly Asn Val
565 570 575

Lys Arg Pro Arg Tyr Arg Ser Lys
580

<210> SEQ ID NO 78
<211> LENGTH: 364
<212> TYPE: PRT
<213> ORGANISM: Neisseria meningitidis

<400> SEQUENCE: 78

Met Ser Met Lys His Phe Pro Ala Lys Val Leu Thr Thr Ala Ile Leu
1 5 10 15

Ala Thr Phe Cys Ser Gly Ala Leu Ala Ala Thr Ser Asp Asp Asp Val
20 25 30

Lys Lys Ala Ala Thr Val Ala Ile Val Ala Ala Tyr Asn Asn Gly Gln
35 40 45

Glu Ile Asn Gly Phe Lys Ala Gly Glu Thr Ile Tyr Asp Ile Gly Glu
50 55 60

Asp Gly Thr Ile Thr Gln Lys Asp Ala Thr Ala Ala Asp Val Glu Ala
65 70 75 80

Asp Asp Phe Lys Gly Leu Gly Leu Lys Lys Val Val Thr Asn Leu Thr
85 90 95

Lys Thr Val Asn Glu Asn Lys Gln Asn Val Asp Ala Lys Val Lys Ala
100 105 110

Ala Glu Ser Glu Ile Glu Lys Leu Thr Thr Lys Leu Ala Asp Thr Asp
115 120 125

Ala Ala Leu Ala Asp Thr Asp Ala Ala Leu Asp Glu Thr Thr Asn Ala
130 135 140

Leu Asn Lys Leu Gly Glu Asn Ile Thr Thr Phe Ala Glu Glu Thr Lys
145 150 155 160

Thr Asn Ile Val Lys Ile Asp Glu Lys Leu Glu Ala Val Ala Asp Thr
165 170 175

Val Asp Lys His Ala Glu Ala Phe Asn Asp Ile Ala Asp Ser Leu Asp
180 185 190

Glu Thr Asn Thr Lys Ala Asp Glu Ala Val Lys Thr Ala Asn Glu Ala
195 200 205

Lys Gln Thr Ala Glu Glu Thr Lys Gln Asn Val Asp Ala Lys Val Lys
210 215 220

Ala Ala Glu Thr Ala Ala Gly Lys Ala Glu Ala Ala Ala Gly Thr Ala
225 230 235 240

Asn Thr Ala Ala Asp Lys Ala Glu Ala Val Ala Ala Lys Val Thr Asp
245 250 255

Ile Lys Ala Asp Ile Ala Thr Asn Lys Ala Asp Ile Ala Lys Asn Ser
260 265 270

Ala Arg Ile Asp Ser Leu Asp Lys Asn Val Ala Asn Leu Arg Lys Glu
275 280 285

Thr Arg Gln Gly Leu Ala Glu Gln Ala Ala Leu Ser Gly Leu Phe Gln
290 295 300

Pro Tyr Asn Val Gly Arg Phe Asn Val Thr Ala Ala Val Gly Gly Tyr
305 310 315 320

Lys Ser Glu Ser Ala Val Ala Ile Gly Thr Gly Phe Arg Phe Thr Glu
325 330 335

Asn Phe Ala Ala Lys Ala Gly Val Ala Val Gly Thr Ser Ser Gly Ser
340 345 350

-continued

Ser Ala Ala Tyr His Val Gly Val Asn Tyr Glu Trp
        355                 360

<210> SEQ ID NO 79
<211> LENGTH: 427
<212> TYPE: PRT
<213> ORGANISM: Neisseria meningitidis

<400> SEQUENCE: 79

```
Met Phe Glu Arg Ser Val Ile Ala Met Ala Cys Ile Phe Ala Leu Ser
1               5                   10                  15

Ala Cys Gly Gly Gly Gly Gly Gly Ser Pro Asp Val Lys Ser Ala Asp
            20                  25                  30

Thr Leu Ser Lys Pro Ala Ala Pro Val Val Ala Glu Lys Glu Thr Glu
        35                  40                  45

Val Lys Glu Asp Ala Pro Gln Ala Gly Ser Gln Gly Gln Gly Ala Pro
    50                  55                  60

Ser Thr Gln Gly Ser Gln Asp Met Ala Ala Val Ser Ala Glu Asn Thr
65                  70                  75                  80

Gly Asn Gly Gly Ala Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110

Thr Gly Asn Asn Gln Pro Ala Asp Ser Ser Asp Ser Ala Pro Ala Ser
        115                 120                 125

Asn Pro Ala Pro Ala Asn Gly Gly Ser Asn Phe Gly Arg Val Asp Leu
    130                 135                 140

Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
        195                 200                 205

Ala Thr Ala Val Gln Ala Asn Gly Thr Asn Lys Tyr Val Ile Ile Tyr
    210                 215                 220

Lys Asp Lys Ser Ala Ser Ser Ser Ser Ala Arg Phe Arg Arg Ser Ala
225                 230                 235                 240

Arg Ser Arg Arg Ser Leu Pro Ala Glu Met Pro Leu Ile Pro Val Asn
                245                 250                 255

Gln Ala Asp Thr Leu Ile Val Asp Gly Glu Ala Val Ser Leu Thr Gly
            260                 265                 270

His Ser Gly Asn Ile Phe Ala Pro Glu Gly Asn Tyr Arg Tyr Leu Thr
        275                 280                 285

Tyr Gly Ala Glu Lys Leu Pro Gly Gly Ser Tyr Ala Leu Arg Val Gln
    290                 295                 300

Gly Glu Pro Ala Lys Gly Glu Met Leu Ala Gly Thr Ala Val Tyr Asn
305                 310                 315                 320

Gly Glu Val Leu His Phe His Thr Glu Asn Gly Arg Pro Tyr Pro Thr
                325                 330                 335

Arg Gly Arg Phe Ala Ala Lys Val Asp Phe Gly Ser Lys Ser Val Asp
            340                 345                 350

Gly Ile Ile Asp Ser Gly Asp Asp Leu His Met Gly Thr Gln Lys Phe
```

-continued

```
        355                 360                 365

Lys Ala Ala Ile Asp Gly Asn Gly Phe Lys Gly Thr Trp Thr Glu Asn
    370                 375                 380

Gly Gly Gly Asp Val Ser Gly Arg Phe Tyr Gly Pro Ala Gly Glu Glu
385                 390                 395                 400

Val Ala Gly Lys Tyr Ser Tyr Arg Pro Thr Asp Ala Glu Lys Gly Gly
                405                 410                 415

Phe Gly Val Phe Ala Gly Lys Lys Glu Gln Asp
            420                 425


<210> SEQ ID NO 80
<211> LENGTH: 410
<212> TYPE: PRT
<213> ORGANISM: Artificial Sequence
<220> FEATURE:
<223> OTHER INFORMATION: 287untagged

<400> SEQUENCE: 80

Cys Gly Gly Gly Gly Gly Gly Ser Pro Asp Val Lys Ser Ala Asp Thr
1               5                   10                  15

Leu Ser Lys Pro Ala Ala Pro Val Val Ala Glu Lys Glu Thr Glu Val
            20                  25                  30

Lys Glu Asp Ala Pro Gln Ala Gly Ser Gln Gly Gln Gly Ala Pro Ser
        35                  40                  45

Thr Gln Gly Ser Gln Asp Met Ala Ala Val Ser Ala Glu Asn Thr Gly
    50                  55                  60

Asn Gly Gly Ala Ala Thr Thr Asp Lys Pro Lys Asn Glu Asp Glu Gly
65                  70                  75                  80

Pro Gln Asn Asp Met Pro Gln Asn Ser Ala Glu Ser Ala Asn Gln Thr
                85                  90                  95

Gly Asn Asn Gln Pro Ala Asp Ser Ser Asp Ser Ala Pro Ala Ser Asn
            100                 105                 110

Pro Ala Pro Ala Asn Gly Gly Ser Asn Phe Gly Arg Val Asp Leu Ala
        115                 120                 125

Asn Gly Val Leu Ile Asp Gly Pro Ser Gln Asn Ile Thr Leu Thr His
    130                 135                 140

Cys Lys Gly Asp Ser Cys Asn Gly Asp Asn Leu Leu Asp Glu Glu Ala
145                 150                 155                 160

Pro Ser Lys Ser Glu Phe Glu Asn Leu Asn Glu Ser Glu Arg Ile Glu
                165                 170                 175

Lys Tyr Lys Lys Asp Gly Lys Ser Asp Lys Phe Thr Asn Leu Val Ala
            180                 185                 190

Thr Ala Val Gln Ala Asn Gly Thr Asn Lys Tyr Val Ile Ile Tyr Lys
        195                 200                 205

Asp Lys Ser Ala Ser Ser Ser Ser Ala Arg Phe Arg Arg Ser Ala Arg
    210                 215                 220

Ser Arg Arg Ser Leu Pro Ala Glu Met Pro Leu Ile Pro Val Asn Gln
225                 230                 235                 240

Ala Asp Thr Leu Ile Val Asp Gly Glu Ala Val Ser Leu Thr Gly His
                245                 250                 255

Ser Gly Asn Ile Phe Ala Pro Glu Gly Asn Tyr Arg Tyr Leu Thr Tyr
            260                 265                 270

Gly Ala Glu Lys Leu Pro Gly Gly Ser Tyr Ala Leu Arg Val Gln Gly
        275                 280                 285

Glu Pro Ala Lys Gly Glu Met Leu Ala Gly Thr Ala Val Tyr Asn Gly
```

-continued

```
    290                 295                 300

Glu Val Leu His Phe His Thr Glu Asn Gly Arg Pro Tyr Pro Thr Arg
305                 310                 315                 320

Gly Arg Phe Ala Ala Lys Val Asp Phe Gly Ser Lys Ser Val Asp Gly
                325                 330                 335

Ile Ile Asp Ser Gly Asp Asp Leu His Met Gly Thr Gln Lys Phe Lys
            340                 345                 350

Ala Ala Ile Asp Gly Asn Gly Phe Lys Gly Thr Trp Thr Glu Asn Gly
        355                 360                 365

Gly Gly Asp Val Ser Gly Arg Phe Tyr Gly Pro Ala Gly Glu Glu Val
    370                 375                 380

Ala Gly Lys Tyr Ser Tyr Arg Pro Thr Asp Ala Glu Lys Gly Gly Phe
385                 390                 395                 400

Gly Val Phe Ala Gly Lys Lys Glu Gln Asp
                405                 410


<210> SEQ ID NO 81
<211> LENGTH: 9
<212> TYPE: PRT
<213> ORGANISM: Artificial Sequence
<220> FEATURE:
<223> OTHER INFORMATION: 920L N-terminal

<400> SEQUENCE: 81

His Arg Val Trp Val Glu Thr Ala His
1               5


<210> SEQ ID NO 82
<211> LENGTH: 16
<212> TYPE: PRT
<213> ORGANISM: Artificial Sequence
<220> FEATURE:
<223> OTHER INFORMATION: 953L N-terminal

<400> SEQUENCE: 82

Ala Thr Tyr Lys Val Asp Glu Tyr His Ala Asn Ala Arg Phe Ala Phe
1               5                   10                  15


<210> SEQ ID NO 83
<211> LENGTH: 9
<212> TYPE: PRT
<213> ORGANISM: Artificial Sequence
<220> FEATURE:
<223> OTHER INFORMATION: 519.1L N-terminal

<400> SEQUENCE: 83

Met Glu Phe Phe Ile Ile Leu Leu Ala
1               5


<210> SEQ ID NO 84
<211> LENGTH: 488
<212> TYPE: PRT
<213> ORGANISM: Artificial Sequence
<220> FEATURE:
<223> OTHER INFORMATION: deltaG287

<400> SEQUENCE: 84

Met Phe Lys Arg Ser Val Ile Ala Met Ala Cys Ile Phe Ala Leu Ser
1               5                   10                  15

Ala Cys Gly Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
```

-continued

```
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
    450                 455                 460
```

-continued

Lys Tyr Ser Tyr Arg Pro Thr Asp Ala Glu Lys Gly Gly Phe Gly Val
465 470 475 480

Phe Ala Gly Lys Lys Glu Gln Asp
485

<210> SEQ ID NO 85
<211> LENGTH: 712
<212> TYPE: PRT
<213> ORGANISM: Artificial Sequence
<220> FEATURE:
<223> OTHER INFORMATION: TBP2

<400> SEQUENCE: 85

Met Asn Asn Pro Leu Val Asn Gln Ala Ala Met Val Leu Pro Val Phe
1 5 10 15

Leu Leu Ser Ala Cys Leu Gly Gly Gly Gly Ser Phe Asp Leu Asp Ser
20 25 30

Val Asp Thr Glu Ala Pro Arg Pro Ala Pro Lys Tyr Gln Asp Val Phe
35 40 45

Ser Glu Lys Pro Gln Ala Gln Lys Asp Gln Gly Gly Tyr Gly Phe Ala
50 55 60

Met Arg Leu Lys Arg Arg Asn Trp Tyr Pro Gln Ala Lys Glu Asp Glu
65 70 75 80

Val Lys Leu Asp Glu Ser Asp Trp Glu Ala Thr Gly Leu Pro Asp Glu
85 90 95

Pro Lys Glu Leu Pro Lys Arg Gln Lys Ser Val Ile Glu Lys Val Glu
100 105 110

Thr Asp Ser Asp Asn Asn Ile Tyr Ser Ser Pro Tyr Leu Lys Pro Ser
115 120 125

Asn His Gln Asn Gly Asn Thr Gly Asn Gly Ile Asn Gln Pro Lys Asn
130 135 140

Gln Ala Lys Asp Tyr Glu Asn Phe Lys Tyr Val Tyr Ser Gly Trp Phe
145 150 155 160

Tyr Lys His Ala Lys Arg Glu Phe Asn Leu Lys Val Glu Pro Lys Ser
165 170 175

Ala Lys Asn Gly Asp Asp Gly Tyr Ile Phe Tyr His Gly Lys Glu Pro
180 185 190

Ser Arg Gln Leu Pro Ala Ser Gly Lys Ile Thr Tyr Lys Gly Val Trp
195 200 205

His Phe Ala Thr Asp Thr Lys Lys Gly Gln Lys Phe Arg Glu Ile Ile
210 215 220

Gln Pro Ser Lys Ser Gln Gly Asp Arg Tyr Ser Gly Phe Ser Gly Asp
225 230 235 240

Asp Gly Glu Glu Tyr Ser Asn Lys Asn Lys Ser Thr Leu Thr Asp Gly
245 250 255

Gln Glu Gly Tyr Gly Phe Thr Ser Asn Leu Glu Val Asp Phe His Asn
260 265 270

Lys Lys Leu Thr Gly Lys Leu Ile Arg Asn Asn Ala Asn Thr Asp Asn
275 280 285

Asn Gln Ala Thr Thr Thr Gln Tyr Tyr Ser Leu Glu Ala Gln Val Thr
290 295 300

Gly Asn Arg Phe Asn Gly Lys Ala Thr Ala Thr Asp Lys Pro Gln Gln
305 310 315 320

Asn Ser Glu Thr Lys Glu His Pro Phe Val Ser Asp Ser Ser Ser Leu
325 330 335

-continued

```
Ser Gly Gly Phe Phe Gly Pro Gln Gly Glu Glu Leu Gly Phe Arg Phe
            340                 345                 350

Leu Ser Asp Asp Gln Lys Val Ala Val Val Gly Ser Ala Lys Thr Lys
        355                 360                 365

Asp Lys Pro Ala Asn Gly Asn Thr Ala Ala Ala Ser Gly Gly Thr Asp
    370                 375                 380

Ala Ala Ala Ser Asn Gly Ala Ala Gly Thr Ser Ser Glu Asn Gly Lys
385                 390                 395                 400

Leu Thr Thr Val Leu Asp Ala Val Glu Leu Lys Leu Gly Asp Lys Glu
                405                 410                 415

Val Gln Lys Leu Asp Asn Phe Ser Asn Ala Ala Gln Leu Val Val Asp
            420                 425                 430

Gly Ile Met Ile Pro Leu Leu Pro Glu Ala Ser Glu Ser Gly Asn Asn
        435                 440                 445

Gln Ala Asn Gln Gly Thr Asn Gly Gly Thr Ala Phe Thr Arg Lys Phe
    450                 455                 460

Asp His Thr Pro Glu Ser Asp Lys Lys Asp Ala Gln Ala Gly Thr Gln
465                 470                 475                 480

Thr Asn Gly Ala Gln Thr Ala Ser Asn Thr Ala Gly Asp Thr Asn Gly
                485                 490                 495

Lys Thr Lys Thr Tyr Glu Val Glu Val Cys Cys Ser Asn Leu Asn Tyr
            500                 505                 510

Leu Lys Tyr Gly Met Leu Thr Arg Lys Asn Ser Lys Ser Ala Met Gln
        515                 520                 525

Ala Gly Glu Ser Ser Ser Gln Ala Asp Ala Lys Thr Glu Gln Val Glu
    530                 535                 540

Gln Ser Met Phe Leu Gln Gly Glu Arg Thr Asp Glu Lys Glu Ile Pro
545                 550                 555                 560

Ser Glu Gln Asn Ile Val Tyr Arg Gly Ser Trp Tyr Gly Tyr Ile Ala
                565                 570                 575

Asn Asp Lys Ser Thr Ser Trp Ser Gly Asn Ala Ser Asn Ala Thr Ser
            580                 585                 590

Gly Asn Arg Ala Glu Phe Thr Val Asn Phe Ala Asp Lys Lys Ile Thr
        595                 600                 605

Gly Thr Leu Thr Ala Asp Asn Arg Gln Glu Ala Thr Phe Thr Ile Asp
    610                 615                 620

Gly Asn Ile Lys Asp Asn Gly Phe Glu Gly Thr Ala Lys Thr Ala Glu
625                 630                 635                 640

Ser Gly Phe Asp Leu Asp Gln Ser Asn Thr Thr Arg Thr Pro Lys Ala
                645                 650                 655

Tyr Ile Thr Asp Ala Lys Val Gln Gly Gly Phe Tyr Gly Pro Lys Ala
            660                 665                 670

Glu Glu Leu Gly Gly Trp Phe Ala Tyr Pro Gly Asp Lys Gln Thr Lys
        675                 680                 685

Asn Ala Thr Asn Ala Ser Gly Asn Ser Ser Ala Thr Val Val Phe Gly
    690                 695                 700

Ala Lys Arg Gln Gln Pro Val Arg
705                 710
```

<210> SEQ ID NO 86
<211> LENGTH: 274
<212> TYPE: PRT
<213> ORGANISM: Artificial Sequence
<220> FEATURE:

-continued

<223> OTHER INFORMATION: 741

<400> SEQUENCE: 86

Val Asn Arg Thr Ala Phe Cys Cys Leu Ser Leu Thr Thr Ala Leu Ile
1 5 10 15

Leu Thr Ala Cys Ser Ser Gly Gly Gly Gly Val Ala Ala Asp Ile Gly
20 25 30

Ala Gly Leu Ala Asp Ala Leu Thr Ala Pro Leu Asp His Lys Asp Lys
35 40 45

Gly Leu Gln Ser Leu Thr Leu Asp Gln Ser Val Arg Lys Asn Glu Lys
50 55 60

Leu Lys Leu Ala Ala Gln Gly Ala Glu Lys Thr Tyr Gly Asn Gly Asp
65 70 75 80

Ser Leu Asn Thr Gly Lys Leu Lys Asn Asp Lys Val Ser Arg Phe Asp
85 90 95

Phe Ile Arg Gln Ile Glu Val Asp Gly Gln Leu Ile Thr Leu Glu Ser
100 105 110

Gly Glu Phe Gln Val Tyr Lys Gln Ser His Ser Ala Leu Thr Ala Phe
115 120 125

Gln Thr Glu Gln Ile Gln Asp Ser Glu His Ser Gly Lys Met Val Ala
130 135 140

Lys Arg Gln Phe Arg Ile Gly Asp Ile Ala Gly Glu His Thr Ser Phe
145 150 155 160

Asp Lys Leu Pro Glu Gly Gly Arg Ala Thr Tyr Arg Gly Thr Ala Phe
165 170 175

Gly Ser Asp Asp Ala Gly Gly Lys Leu Thr Tyr Thr Ile Asp Phe Ala
180 185 190

Ala Lys Gln Gly Asn Gly Lys Ile Glu His Leu Lys Ser Pro Glu Leu
195 200 205

Asn Val Asp Leu Ala Ala Ala Asp Ile Lys Pro Asp Gly Lys Arg His
210 215 220

Ala Val Ile Ser Gly Ser Val Leu Tyr Asn Gln Ala Glu Lys Gly Ser
225 230 235 240

Tyr Ser Leu Gly Ile Phe Gly Gly Lys Ala Gln Glu Val Ala Gly Ser
245 250 255

Ala Glu Val Lys Thr Val Asn Gly Ile Arg His Ile Gly Leu Ala Ala
260 265 270

Lys Gln

<210> SEQ ID NO 87
<211> LENGTH: 1082
<212> TYPE: PRT
<213> ORGANISM: Artificial Sequence
<220> FEATURE:
<223> OTHER INFORMATION: 983

<400> SEQUENCE: 87

Met Arg Thr Thr Pro Thr Phe Pro Thr Lys Thr Phe Lys Pro Thr Ala
1 5 10 15

Met Ala Leu Ala Val Ala Thr Thr Leu Ser Ala Cys Leu Gly Gly Gly
20 25 30

Gly Gly Gly Thr Ser Ala Pro Asp Phe Asn Ala Gly Gly Thr Gly Ile
35 40 45

Gly Ser Asn Ser Arg Ala Thr Thr Ala Lys Ser Ala Ala Val Ser Tyr
50 55 60

-continued

```
Ala Gly Ile Lys Asn Glu Met Cys Lys Asp Arg Ser Met Leu Cys Ala
65                  70                  75                  80

Gly Arg Asp Asp Val Ala Val Thr Asp Arg Asp Ala Lys Ile Asn Ala
                85                  90                  95

Pro Pro Pro Asn Leu His Thr Gly Asp Phe Pro Asn Pro Asn Asp Ala
            100                 105                 110

Tyr Lys Asn Leu Ile Asn Leu Lys Pro Ala Ile Glu Ala Gly Tyr Thr
        115                 120                 125

Gly Arg Gly Val Glu Val Gly Ile Val Asp Thr Gly Glu Ser Val Gly
    130                 135                 140

Ser Ile Ser Phe Pro Glu Leu Tyr Gly Arg Lys Glu His Gly Tyr Asn
145                 150                 155                 160

Glu Asn Tyr Lys Asn Tyr Thr Ala Tyr Met Arg Lys Glu Ala Pro Glu
                165                 170                 175

Asp Gly Gly Gly Lys Asp Ile Glu Ala Ser Phe Asp Asp Glu Ala Val
            180                 185                 190

Ile Glu Thr Glu Ala Lys Pro Thr Asp Ile Arg His Val Lys Glu Ile
        195                 200                 205

Gly His Ile Asp Leu Val Ser His Ile Ile Gly Gly Arg Ser Val Asp
    210                 215                 220

Gly Arg Pro Ala Gly Gly Ile Ala Pro Asp Ala Thr Leu His Ile Met
225                 230                 235                 240

Asn Thr Asn Asp Glu Thr Lys Asn Glu Met Met Val Ala Ala Ile Arg
                245                 250                 255

Asn Ala Trp Val Lys Leu Gly Glu Arg Gly Val Arg Ile Val Asn Asn
            260                 265                 270

Ser Phe Gly Thr Thr Ser Arg Ala Gly Thr Ala Asp Leu Phe Gln Ile
        275                 280                 285

Ala Asn Ser Glu Glu Gln Tyr Arg Gln Ala Leu Leu Asp Tyr Ser Gly
    290                 295                 300

Gly Asp Lys Thr Asp Glu Gly Ile Arg Leu Met Gln Gln Ser Asp Tyr
305                 310                 315                 320

Gly Asn Leu Ser Tyr His Ile Arg Asn Lys Asn Met Leu Phe Ile Phe
                325                 330                 335

Ser Thr Gly Asn Asp Ala Gln Ala Gln Pro Asn Thr Tyr Ala Leu Leu
            340                 345                 350

Pro Phe Tyr Glu Lys Asp Ala Gln Lys Gly Ile Ile Thr Val Ala Gly
        355                 360                 365

Val Asp Arg Ser Gly Glu Lys Phe Lys Arg Glu Met Tyr Gly Glu Pro
    370                 375                 380

Gly Thr Glu Pro Leu Glu Tyr Gly Ser Asn His Cys Gly Ile Thr Ala
385                 390                 395                 400

Met Trp Cys Leu Ser Ala Pro Tyr Glu Ala Ser Val Arg Phe Thr Arg
                405                 410                 415

Thr Asn Pro Ile Gln Ile Ala Gly Thr Ser Phe Ser Ala Pro Ile Val
            420                 425                 430

Thr Gly Thr Ala Ala Leu Leu Leu Gln Lys Tyr Pro Trp Met Ser Asn
        435                 440                 445

Asp Asn Leu Arg Thr Thr Leu Leu Thr Thr Ala Gln Asp Ile Gly Ala
    450                 455                 460

Val Gly Val Asp Ser Lys Phe Gly Trp Gly Leu Leu Asp Ala Gly Lys
465                 470                 475                 480

Ala Met Asn Gly Pro Ala Ser Phe Pro Phe Gly Asp Phe Thr Ala Asp
```

-continued

```
                485                 490                 495

Thr Lys Gly Thr Ser Asp Ile Ala Tyr Ser Phe Arg Asn Asp Ile Ser
            500                 505                 510

Gly Thr Gly Gly Leu Ile Lys Lys Gly Gly Ser Gln Leu Gln Leu His
        515                 520                 525

Gly Asn Asn Thr Tyr Thr Gly Lys Thr Ile Ile Glu Gly Gly Ser Leu
    530                 535                 540

Val Leu Tyr Gly Asn Asn Lys Ser Asp Met Arg Val Glu Thr Lys Gly
545                 550                 555                 560

Ala Leu Ile Tyr Asn Gly Ala Ala Ser Gly Gly Ser Leu Asn Ser Asp
                565                 570                 575

Gly Ile Val Tyr Leu Ala Asp Thr Asp Gln Ser Gly Ala Asn Glu Thr
            580                 585                 590

Val His Ile Lys Gly Ser Leu Gln Leu Asp Gly Lys Gly Thr Leu Tyr
        595                 600                 605

Thr Arg Leu Gly Lys Leu Leu Lys Val Asp Gly Thr Ala Ile Ile Gly
    610                 615                 620

Gly Lys Leu Tyr Met Ser Ala Arg Gly Lys Gly Ala Gly Tyr Leu Asn
625                 630                 635                 640

Ser Thr Gly Arg Arg Val Pro Phe Leu Ser Ala Ala Lys Ile Gly Gln
                645                 650                 655

Asp Tyr Ser Phe Phe Thr Asn Ile Glu Thr Asp Gly Gly Leu Leu Ala
            660                 665                 670

Ser Leu Asp Ser Val Glu Lys Thr Ala Gly Ser Glu Gly Asp Thr Leu
        675                 680                 685

Ser Tyr Tyr Val Arg Arg Gly Asn Ala Ala Arg Thr Ala Ser Ala Ala
    690                 695                 700

Ala His Ser Ala Pro Ala Gly Leu Lys His Ala Val Glu Gln Gly Gly
705                 710                 715                 720

Ser Asn Leu Glu Asn Leu Met Val Glu Leu Asp Ala Ser Glu Ser Ser
                725                 730                 735

Ala Thr Pro Glu Thr Val Glu Thr Ala Ala Ala Asp Arg Thr Asp Met
            740                 745                 750

Pro Gly Ile Arg Pro Tyr Gly Ala Thr Phe Arg Ala Ala Ala Ala Val
        755                 760                 765

Gln His Ala Asn Ala Ala Asp Gly Val Arg Ile Phe Asn Ser Leu Ala
    770                 775                 780

Ala Thr Val Tyr Ala Asp Ser Thr Ala Ala His Ala Asp Met Gln Gly
785                 790                 795                 800

Arg Arg Leu Lys Ala Val Ser Asp Gly Leu Asp His Asn Gly Thr Gly
                805                 810                 815

Leu Arg Val Ile Ala Gln Thr Gln Gln Asp Gly Gly Thr Trp Glu Gln
            820                 825                 830

Gly Gly Val Glu Gly Lys Met Arg Gly Ser Thr Gln Thr Val Gly Ile
        835                 840                 845

Ala Ala Lys Thr Gly Glu Asn Thr Thr Ala Ala Ala Thr Leu Gly Met
    850                 855                 860

Gly Arg Ser Thr Trp Ser Glu Asn Ser Ala Asn Ala Lys Thr Asp Ser
865                 870                 875                 880

Ile Ser Leu Phe Ala Gly Ile Arg His Asp Ala Gly Asp Ile Gly Tyr
                885                 890                 895

Leu Lys Gly Leu Phe Ser Tyr Gly Arg Tyr Lys Asn Ser Ile Ser Arg
            900                 905                 910
```

-continued

```
Ser Thr Gly Ala Asp Glu His Ala Glu Gly Ser Val Asn Gly Thr Leu
        915                 920                 925

Met Gln Leu Gly Ala Leu Gly Gly Val Asn Val Pro Phe Ala Ala Thr
    930                 935                 940

Gly Asp Leu Thr Val Glu Gly Gly Leu Arg Tyr Asp Leu Leu Lys Gln
945                 950                 955                 960

Asp Ala Phe Ala Glu Lys Gly Ser Ala Leu Gly Trp Ser Gly Asn Ser
                965                 970                 975

Leu Thr Glu Gly Thr Leu Val Gly Leu Ala Gly Leu Lys Leu Ser Gln
            980                 985                 990

Pro Leu Ser Asp Lys Ala Val Leu Phe Ala Thr Ala Gly Val Glu Arg
        995                 1000                1005

Asp Leu Asn Gly Arg Asp Tyr Thr Val Thr Gly Gly Phe Thr Gly Ala
    1010                1015                1020

Thr Ala Ala Thr Gly Lys Thr Gly Ala Arg Asn Met Pro His Thr Arg
1025                1030                1035                1040

Leu Val Ala Gly Leu Gly Ala Asp Val Glu Phe Gly Asn Gly Trp Asn
                1045                1050                1055

Gly Leu Ala Arg Tyr Ser Tyr Ala Gly Ser Lys Gln Tyr Gly Asn His
            1060                1065                1070

Ser Gly Arg Val Gly Val Gly Tyr Arg Phe
        1075                1080
```

<210> SEQ ID NO 88
<211> LENGTH: 2505
<212> TYPE: DNA
<213> ORGANISM: Artificial Sequence
<220> FEATURE:
<223> OTHER INFORMATION: deltaG287-919

<400> SEQUENCE: 88

```
atggctagcc ccgatgttaa atcggcggac acgctgtcaa aaccggccgc tcctgttgtt      60

gctgaaaaag agacagaggt aaaagaagat gcgccacagg caggttctca aggacagggc     120

gcgccatcca cacaaggcag ccaagatatg gcggcagttt cggcagaaaa tacaggcaat     180

ggcggtgcgg caacaacgga caaacccaaa aatgaagacg agggaccgca aaatgatatg     240

ccgcaaaatt ccgccgaatc cgcaaatcaa acagggaaca accaacccgc cgattcttca     300

gattccgccc ccgcgtcaaa ccctgcacct gcgaatggcg gtagcaattt tggaagggtt     360

gatttggcta atggcgtttt gattgatggg ccgtcgcaaa atataacgtt gacccactgt     420

aaaggcgatt cttgtaatgg tgataattta ttggatgaag aagcaccgtc aaaatcagaa     480

tttgaaaatt taaatgagtc tgaacgaatt gagaaatata agaaagatgg gaaaagcgat     540

aaatttacta atttggttgc gacagcagtt caagctaatg gaactaacaa atatgtcatc     600

atttataaag acaagtccgc ttcatcttca tctgcgcgat tcaggcgttc tgcacggtcg     660

aggaggtcgc ttcctgccga gatgccgcta atccccgtca atcaggcgga tacgctgatt     720

gtcgatgggg aagcggtcag cctgacgggg cattccggca atatcttcgc gcccgaaggg     780

aattaccggt atctgactta cggggcggaa aaattgcccg gcggatcgta tgccctccgt     840

gtgcaaggcg aaccggcaaa aggcgaaatg cttgctggca cggccgtgta caacggcgaa     900

gtgctgcatt ttcatacgga aaacggccgt ccgtacccga ctagaggcag gtttgccgca     960

aaagtcgatt tcggcagcaa atctgtggac ggcattatcg acagcggcga tgatttgcat    1020

atgggtacgc aaaaattcaa agccgccatc gatggaaacg gctttaaggg gacttggacg    1080
```

-continued gaaaatggcg gcggggatgt ttccggaagg ttttacggcc cggccggcga ggaagtggcg 1140
ggaaaataca gctatcgccc gacagatgcg gaaaagggcg gattcggcgt gtttgccggc 1200
aaaaaagagc aggatggatc cggaggagga ggatgccaaa gcaagagcat ccaaaccttt 1260
ccgcaacccg acacatccgt catcaacggc ccggaccggc cggtcggcat ccccgacccc 1320
gccggaacga cggtcggcgg cggcggggcc gtctataccg ttgtaccgca cctgtccctg 1380
ccccactggg cggcgcagga tttcgccaaa agcctgcaat ccttccgcct cggctgcgcc 1440
aatttgaaaa accgccaagg ctggcaggat gtgtgcgccc aagcctttca aaccccccgtc 1500 cattcctttc aggcaaaaca gtttttgaa cgctatttca cgccgtggca ggttgcaggc 1560
aacggaagcc ttgccggtac ggttaccggc tattacgagc cggtgctgaa gggcgacgac 1620
aggcggacgg cacaagcccg cttcccgatt tacggtattc ccgacgattt tatctccgtc 1680
cccctgcctg ccggtttgcg gagcggaaaa gcccttgtcc gcatcaggca gacgggaaaa 1740
aacagcggca caatcgacaa taccggcggc acacataccg ccgacctctc ccgattcccc 1800
atcaccgcgc gcacaacggc aatcaaaggc aggtttgaag gaagccgctt cctcccctac 1860
cacacgcgca accaaatcaa cggcggcgcg cttgacggca aagccccgat actcggttac 1920
gccgaagacc ccgtcgaact ttttttatg cacatccaag gctcgggccg tctgaaaacc 1980
ccgtccggca aatacatccg catcggctat gccgacaaaa acgaacatcc ctacgtttcc 2040
atcggacgct atatggcgga caaaggctac ctcaagctcg ggcagacctc gatgcagggc 2100
atcaaagcct atatgcggca aaatccgcaa cgcctcgccg aagttttggg tcaaaacccc 2160
agctatatct tttccgcgga gcttgccgga agcagcaatg acggtcccgt cggcgcactg 2220
ggcacgccgt tgatgggga atatgccggc gcagtcgacc ggcactacat taccttgggc 2280
gcgcccttat ttgtcgccac cgcccatccg gttacccgca aagccctcaa ccgcctgatt 2340
atggcgcagg ataccggcag cgcgattaaa ggcgcggtgc gcgtggatta tttttgggga 2400
tacggcgacg aagccggcga acttgccggc aaacagaaaa ccacgggtta cgtctggcag 2460
ctcctaccca acggtatgaa gcccgaatac cgcccgtaac tcgag 2505

<210> SEQ ID NO 89
<211> LENGTH: 832
<212> TYPE: PRT
<213> ORGANISM: Artificial Sequence
<220> FEATURE:
<223> OTHER INFORMATION: deltaG287-919

<400> SEQUENCE: 89

Met Ala Ser Pro Asp Val Lys Ser Ala Asp Thr Leu Ser Lys Pro Ala
1 5 10 15

Ala Pro Val Val Ala Glu Lys Glu Thr Glu Val Lys Glu Asp Ala Pro
20 25 30

Gln Ala Gly Ser Gln Gly Gln Gly Ala Pro Ser Thr Gln Gly Ser Gln
35 40 45

Asp Met Ala Ala Val Ser Ala Glu Asn Thr Gly Asn Gly Gly Ala Ala
50 55 60

Thr Thr Asp Lys Pro Lys Asn Glu Asp Glu Gly Pro Gln Asn Asp Met
65 70 75 80

Pro Gln Asn Ser Ala Glu Ser Ala Asn Gln Thr Gly Asn Asn Gln Pro
85 90 95

Ala Asp Ser Ser Asp Ser Ala Pro Ala Ser Asn Pro Ala Pro Ala Asn
100 105 110

-continued

```
Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
            340                 345                 350

Asn Gly Phe Lys Gly Thr Trp Thr Glu Asn Gly Gly Gly Asp Val Ser
        355                 360                 365

Gly Arg Phe Tyr Gly Pro Ala Gly Glu Glu Val Ala Gly Lys Tyr Ser
    370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Gly Cys Gln Ser Lys Ser
                405                 410                 415

Ile Gln Thr Phe Pro Gln Pro Asp Thr Ser Val Ile Asn Gly Pro Asp
            420                 425                 430

Arg Pro Val Gly Ile Pro Asp Pro Ala Gly Thr Thr Val Gly Gly Gly
        435                 440                 445

Gly Ala Val Tyr Thr Val Val Pro His Leu Ser Leu Pro His Trp Ala
    450                 455                 460

Ala Gln Asp Phe Ala Lys Ser Leu Gln Ser Phe Arg Leu Gly Cys Ala
465                 470                 475                 480

Asn Leu Lys Asn Arg Gln Gly Trp Gln Asp Val Cys Ala Gln Ala Phe
                485                 490                 495

Gln Thr Pro Val His Ser Phe Gln Ala Lys Gln Phe Phe Glu Arg Tyr
            500                 505                 510

Phe Thr Pro Trp Gln Val Ala Gly Asn Gly Ser Leu Ala Gly Thr Val
        515                 520                 525
```

-continued

```
Thr Gly Tyr Tyr Glu Pro Val Leu Lys Gly Asp Asp Arg Arg Thr Ala
    530                 535                 540

Gln Ala Arg Phe Pro Ile Tyr Gly Ile Pro Asp Asp Phe Ile Ser Val
545                 550                 555                 560

Pro Leu Pro Ala Gly Leu Arg Ser Gly Lys Ala Leu Val Arg Ile Arg
                565                 570                 575

Gln Thr Gly Lys Asn Ser Gly Thr Ile Asp Asn Thr Gly Gly Thr His
            580                 585                 590

Thr Ala Asp Leu Ser Arg Phe Pro Ile Thr Ala Arg Thr Thr Ala Ile
        595                 600                 605

Lys Gly Arg Phe Glu Gly Ser Arg Phe Leu Pro Tyr His Thr Arg Asn
    610                 615                 620

Gln Ile Asn Gly Gly Ala Leu Asp Gly Lys Ala Pro Ile Leu Gly Tyr
625                 630                 635                 640

Ala Glu Asp Pro Val Glu Leu Phe Phe Met His Ile Gln Gly Ser Gly
                645                 650                 655

Arg Leu Lys Thr Pro Ser Gly Lys Tyr Ile Arg Ile Gly Tyr Ala Asp
            660                 665                 670

Lys Asn Glu His Pro Tyr Val Ser Ile Gly Arg Tyr Met Ala Asp Lys
        675                 680                 685

Gly Tyr Leu Lys Leu Gly Gln Thr Ser Met Gln Gly Ile Lys Ala Tyr
    690                 695                 700

Met Arg Gln Asn Pro Gln Arg Leu Ala Glu Val Leu Gly Gln Asn Pro
705                 710                 715                 720

Ser Tyr Ile Phe Phe Arg Glu Leu Ala Gly Ser Ser Asn Asp Gly Pro
                725                 730                 735

Val Gly Ala Leu Gly Thr Pro Leu Met Gly Glu Tyr Ala Gly Ala Val
            740                 745                 750

Asp Arg His Tyr Ile Thr Leu Gly Ala Pro Leu Phe Val Ala Thr Ala
        755                 760                 765

His Pro Val Thr Arg Lys Ala Leu Asn Arg Leu Ile Met Ala Gln Asp
    770                 775                 780

Thr Gly Ser Ala Ile Lys Gly Ala Val Arg Val Asp Tyr Phe Trp Gly
785                 790                 795                 800

Tyr Gly Asp Glu Ala Gly Glu Leu Ala Gly Lys Gln Lys Thr Thr Gly
                805                 810                 815

Tyr Val Trp Gln Leu Leu Pro Asn Gly Met Lys Pro Glu Tyr Arg Pro
            820                 825                 830
```

<210> SEQ ID NO 90
<211> LENGTH: 1746
<212> TYPE: DNA
<213> ORGANISM: Artificial Sequence
<220> FEATURE:
<223> OTHER INFORMATION: deltaG287-953

<400> SEQUENCE: 90

```
atggctagcc ccgatgttaa atcggcggac acgctgtcaa aaccggccgc tcctgttgtt      60

gctgaaaaag agacagaggt aaaagaagat gcgccacagg caggttctca aggacagggc     120

gcgccatcca cacaaggcag ccaagatatg gcggcagttt cggcagaaaa tacaggcaat     180

ggcggtgcgg caacaacgga caaacccaaa aatgaagacg agggaccgca aaatgatatg     240

ccgcaaaatt ccgccgaatc cgcaaatcaa acagggaaca accaacccgc cgattcttca     300

gattccgccc ccgcgtcaaa ccctgcacct gcgaatggcg gtagcaattt tggaagggtt     360
```

-continued

```
gatttggcta atggcgtttt gattgatggg ccgtcgcaaa atataacgtt gacccactgt     420

aaaggcgatt cttgtaatgg tgataattta ttggatgaag aagcaccgtc aaaatcagaa     480

tttgaaaatt taaatgagtc tgaacgaatt gagaaatata agaaagatgg gaaaagcgat     540

aaatttacta atttggttgc gacagcagtt caagctaatg gaactaacaa atatgtcatc     600

atttataaag acaagtccgc ttcatcttca tctgcgcgat tcaggcgttc tgcacggtcg     660

aggaggtcgc ttcctgccga gatgccgcta atccccgtca atcaggcgga tacgctgatt     720

gtcgatgggg aagcggtcag cctgacgggg cattccggca atatcttcgc gcccgaaggg     780

aattaccggt atctgactta cggggcggaa aaattgcccg gcggatcgta tgccctccgt     840

gtgcaaggcg aaccggcaaa aggcgaaatg cttgctggca cggccgtgta caacggcgaa     900

gtgctgcatt ttcatacgga aaacggccgt ccgtacccga ctagaggcag gtttgccgca     960

aaagtcgatt tcggcagcaa atctgtggac ggcattatcg acagcggcga tgatttgcat    1020

atgggtacgc aaaaattcaa agccgccatc gatggaaacg gctttaaggg gacttggacg    1080

gaaaatggcg gcggggatgt ttccggaagg ttttacggcc cggccggcga ggaagtggcg    1140

ggaaaataca gctatcgccc gacagatgcg gaaaagggcg gattcggcgt gtttgccggc    1200

aaaaaagagc aggatggatc cggaggagga ggagccacct acaaagtgga cgaatatcac    1260

gccaacgccc gtttcgccat cgaccatttc aacaccagca ccaacgtcgg cggtttttac    1320

ggtctgaccg gttccgtcga gttcgaccaa gcaaaacgcg acggtaaaat cgacatcacc    1380

atccccgttg ccaacctgca aagcggttcg caacacttta ccgaccacct gaaatcagcc    1440

gacatcttcg atgccgccca atatccggac atccgctttg tttccaccaa attcaacttc    1500

aacggcaaaa aactggtttc cgttgacggc aacctgacca tgcacggcaa aaccgccccc    1560

gtcaaactca aagccgaaaa attcaactgc taccaaagcc cgatggcgaa aaccgaagtt    1620

tgcggcggcg acttcagcac caccatcgac cgcaccaaat ggggcgtgga ctacctcgtt    1680

aacgttggta tgaccaaaag cgtccgcatc gacatccaaa tcgaggcagc caaacaataa    1740

ctcgag                                                                1746
```

<210> SEQ ID NO 91
<211> LENGTH: 579
<212> TYPE: PRT
<213> ORGANISM: Artificial Sequence
<220> FEATURE:
<223> OTHER INFORMATION: deltaG287-953

<400> SEQUENCE: 91

```
Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
            20                  25                  30

Gln Ala Gly Ser Gln Gly Gln Gly Ala Pro Ser Thr Gln Gly Ser Gln
        35                  40                  45

Asp Met Ala Ala Val Ser Ala Glu Asn Thr Gly Asn Gly Gly Ala Ala
    50                  55                  60

Thr Thr Asp Lys Pro Lys Asn Glu Asp Glu Gly Pro Gln Asn Asp Met
65                  70                  75                  80

Pro Gln Asn Ser Ala Glu Ser Ala Asn Gln Thr Gly Asn Asn Gln Pro
                85                  90                  95

Ala Asp Ser Ser Asp Ser Ala Pro Ala Ser Asn Pro Ala Pro Ala Asn
            100                 105                 110
```

-continued

```
Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
            340                 345                 350

Asn Gly Phe Lys Gly Thr Trp Thr Glu Asn Gly Gly Gly Asp Val Ser
        355                 360                 365

Gly Arg Phe Tyr Gly Pro Ala Gly Glu Glu Val Ala Gly Lys Tyr Ser
    370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Gly Ala Thr Tyr Lys Val
                405                 410                 415

Asp Glu Tyr His Ala Asn Ala Arg Phe Ala Ile Asp His Phe Asn Thr
            420                 425                 430

Ser Thr Asn Val Gly Gly Phe Tyr Gly Leu Thr Gly Ser Val Glu Phe
        435                 440                 445

Asp Gln Ala Lys Arg Asp Gly Lys Ile Asp Ile Thr Ile Pro Val Ala
    450                 455                 460

Asn Leu Gln Ser Gly Ser Gln His Phe Thr Asp His Leu Lys Ser Ala
465                 470                 475                 480

Asp Ile Phe Asp Ala Ala Gln Tyr Pro Asp Ile Arg Phe Val Ser Thr
                485                 490                 495

Lys Phe Asn Phe Asn Gly Lys Lys Leu Val Ser Val Asp Gly Asn Leu
            500                 505                 510

Thr Met His Gly Lys Thr Ala Pro Val Lys Leu Lys Ala Glu Lys Phe
        515                 520                 525

Asn Cys Tyr Gln Ser Pro Met Ala Lys Thr Glu Val Cys Gly Gly Asp
```

-continued

```
    530                 535                 540

Phe Ser Thr Thr Ile Asp Arg Thr Lys Trp Gly Val Asp Tyr Leu Val
545                 550                 555                 560

Asn Val Gly Met Thr Lys Ser Val Arg Ile Asp Ile Gln Ile Glu Ala
                565                 570                 575

Ala Lys Gln


<210> SEQ ID NO 92
<211> LENGTH: 2388
<212> TYPE: DNA
<213> ORGANISM: Artificial Sequence
<220> FEATURE:
<223> OTHER INFORMATION: deltaG287-961

<400> SEQUENCE: 92

atggctagcc ccgatgttaa atcggcggac acgctgtcaa aaccggccgc tcctgttgtt      60

gctgaaaaag agacagaggt aaaagaagat gcgccacagg caggttctca aggacagggc     120

gcgccatcca cacaaggcag ccaagatatg gcggcagttt cggcagaaaa tacaggcaat     180

ggcggtgcgg caacaacgga caaacccaaa aatgaagacg agggaccgca aaatgatatg     240

ccgcaaaatt ccgccgaatc cgcaaatcaa acagggaaca accaacccgc cgattcttca     300

gattccgccc ccgcgtcaaa ccctgcacct gcgaatggcg gtagcaattt tggaagggtt     360

gatttggcta atggcgtttt gattgatggg ccgtcgcaaa atataacgtt gacccactgt     420

aaaggcgatt cttgtaatgg tgataattta ttggatgaag aagcaccgtc aaaatcagaa     480

tttgaaaatt taaatgagtc tgaacgaatt gagaaatata agaaagatgg gaaaagcgat     540

aaatttacta atttggttgc gacagcagtt caagctaatg gaactaacaa atatgtcatc     600

atttataaag acaagtccgc ttcatcttca tctgcgcgat tcaggcgttc tgcacggtcg     660

aggaggtcgc ttcctgccga gatgccgcta atccccgtca atcaggcgga tacgctgatt     720

gtcgatgggg aagcggtcag cctgacgggg cattccggca atatcttcgc gcccgaaggg     780

aattaccggt atctgactta cggggcggaa aaattgcccg gcggatcgta tgccctccgt     840

gtgcaaggcg aaccggcaaa aggcgaaatg cttgctggca cggccgtgta caacggcgaa     900

gtgctgcatt ttcatacgga aaacggccgt ccgtacccga ctagaggcag gtttgccgca     960

aaagtcgatt tcggcagcaa atctgtggac ggcattatcg acagcggcga tgatttgcat    1020

atgggtacgc aaaaattcaa agccgccatc gatggaaacg gctttaaggg gacttggacg    1080

gaaaatggcg gcggggatgt ttccggaagg ttttacggcc cggccggcga ggaagtggcg    1140

ggaaaataca gctatcgccc gacagatgcg gaaaagggcg gattcggcgt gtttgccggc    1200

aaaaaagagc aggatggatc cggaggagga ggagccacaa acgacgacga tgttaaaaaa    1260

gctgccactg tggccattgc tgctgcctac aacaatggcc aagaaatcaa cggtttcaaa    1320

gctggagaga ccatctacga cattgatgaa gacggcacaa ttaccaaaaa agacgcaact    1380

gcagccgatg ttgaagccga cgactttaaa ggtctgggtc tgaaaaaagt cgtgactaac    1440

ctgaccaaaa ccgtcaatga aaacaaacaa aacgtcgatg ccaaagtaaa agctgcagaa    1500

tctgaaatag aaaagttaac aaccaagtta gcagacactg atgccgcttt agcagatact    1560

gatgccgctc tggatgcaac caccaacgcc ttgaataaat tgggagaaaa tataacgaca    1620

tttgctgaag agactaagac aaatatcgta aaaattgatg aaaaattaga agccgtggct    1680

gataccgtcg acaagcatgc cgaagcattc aacgatatcg ccgattcatt ggatgaaacc    1740

aacactaagg cagacgaagc cgtcaaaacc gccaatgaag ccaaacagac ggccgaagaa    1800
```

```
accaaacaaa acgtcgatgc caaagtaaaa gctgcagaaa ctgcagcagg caaagccgaa   1860

gctgccgctg gcacagctaa tactgcagcc gacaaggccg aagctgtcgc tgcaaaagtt   1920

accgacatca aagctgatat cgctacgaac aaagataata ttgctaaaaa agcaaacagt   1980

gccgacgtgt acaccagaga agagtctgac agcaaatttg tcagaattga tggtctgaac   2040

gctactaccg aaaaattgga cacacgcttg gcttctgctg aaaaatccat tgccgatcac   2100

gatactcgcc tgaacggttt ggataaaaca gtgtcagacc tgcgcaaaga aacccgccaa   2160

ggccttgcag aacaagccgc gctctccggt ctgttccaac cttacaacgt gggtcggttc   2220

aatgtaacgg ctgcagtcgg cggctacaaa tccgaatcgg cagtcgccat cggtaccggc   2280

ttccgcttta ccgaaaactt tgccgccaaa gcaggcgtgg cagtcggcac ttcgtccggt   2340

tcttccgcag cctaccatgt cggcgtcaat tacgagtggt aactcgag                2388
```

```
<210> SEQ ID NO 93
<211> LENGTH: 793
<212> TYPE: PRT
<213> ORGANISM: Artificial Sequence
<220> FEATURE:
<223> OTHER INFORMATION: deltaG287-961

<400> SEQUENCE: 93

Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
            20                  25                  30

Gln Ala Gly Ser Gln Gly Gln Gly Ala Pro Ser Thr Gln Gly Ser Gln
        35                  40                  45

Asp Met Ala Ala Val Ser Ala Glu Asn Thr Gly Asn Gly Gly Ala Ala
    50                  55                  60

Thr Thr Asp Lys Pro Lys Asn Glu Asp Glu Gly Pro Gln Asn Asp Met
65                  70                  75                  80

Pro Gln Asn Ser Ala Glu Ser Ala Asn Gln Thr Gly Asn Asn Gln Pro
                85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255
```

-continued

```
Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
            340                 345                 350

Asn Gly Phe Lys Gly Thr Trp Thr Glu Asn Gly Gly Gly Asp Val Ser
        355                 360                 365

Gly Arg Phe Tyr Gly Pro Ala Gly Glu Glu Val Ala Gly Lys Tyr Ser
    370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Gly Ala Thr Asn Asp Asp
                405                 410                 415

Asp Val Lys Lys Ala Ala Thr Val Ala Ile Ala Ala Ala Tyr Asn Asn
            420                 425                 430

Gly Gln Glu Ile Asn Gly Phe Lys Ala Gly Glu Thr Ile Tyr Asp Ile
        435                 440                 445

Asp Glu Asp Gly Thr Ile Thr Lys Lys Asp Ala Thr Ala Ala Asp Val
    450                 455                 460

Glu Ala Asp Asp Phe Lys Gly Leu Gly Leu Lys Lys Val Val Thr Asn
465                 470                 475                 480

Leu Thr Lys Thr Val Asn Glu Asn Lys Gln Asn Val Asp Ala Lys Val
                485                 490                 495

Lys Ala Ala Glu Ser Glu Ile Glu Lys Leu Thr Thr Lys Leu Ala Asp
            500                 505                 510

Thr Asp Ala Ala Leu Ala Asp Thr Asp Ala Ala Leu Asp Ala Thr Thr
        515                 520                 525

Asn Ala Leu Asn Lys Leu Gly Glu Asn Ile Thr Thr Phe Ala Glu Glu
    530                 535                 540

Thr Lys Thr Asn Ile Val Lys Ile Asp Glu Lys Leu Glu Ala Val Ala
545                 550                 555                 560

Asp Thr Val Asp Lys His Ala Glu Ala Phe Asn Asp Ile Ala Asp Ser
                565                 570                 575

Leu Asp Glu Thr Asn Thr Lys Ala Asp Glu Ala Val Lys Thr Ala Asn
            580                 585                 590

Glu Ala Lys Gln Thr Ala Glu Glu Thr Lys Gln Asn Val Asp Ala Lys
        595                 600                 605

Val Lys Ala Ala Glu Thr Ala Ala Gly Lys Ala Glu Ala Ala Ala Gly
    610                 615                 620

Thr Ala Asn Thr Ala Ala Asp Lys Ala Glu Ala Val Ala Ala Lys Val
625                 630                 635                 640

Thr Asp Ile Lys Ala Asp Ile Ala Thr Asn Lys Asp Asn Ile Ala Lys
                645                 650                 655

Lys Ala Asn Ser Ala Asp Val Tyr Thr Arg Glu Glu Ser Asp Ser Lys
            660                 665                 670

Phe Val Arg Ile Asp Gly Leu Asn Ala Thr Thr Glu Lys Leu Asp Thr
```

-continued

```
        675                 680                 685

Arg Leu Ala Ser Ala Glu Lys Ser Ile Ala Asp His Asp Thr Arg Leu
    690                 695                 700

Asn Gly Leu Asp Lys Thr Val Ser Asp Leu Arg Lys Glu Thr Arg Gln
705                 710                 715                 720

Gly Leu Ala Glu Gln Ala Ala Leu Ser Gly Leu Phe Gln Pro Tyr Asn
                725                 730                 735

Val Gly Arg Phe Asn Val Thr Ala Ala Val Gly Gly Tyr Lys Ser Glu
            740                 745                 750

Ser Ala Val Ala Ile Gly Thr Gly Phe Arg Phe Thr Glu Asn Phe Ala
        755                 760                 765

Ala Lys Ala Gly Val Ala Val Gly Thr Ser Ser Gly Ser Ser Ala Ala
    770                 775                 780

Tyr His Val Gly Val Asn Tyr Glu Trp
785                 790


<210> SEQ ID NO 94
<211> LENGTH: 2700
<212> TYPE: DNA
<213> ORGANISM: Artificial Sequence
<220> FEATURE:
<223> OTHER INFORMATION: deltaG287NZ-919

<400> SEQUENCE: 94

atggctagcc ccgatgtcaa gtcggcggac acgctgtcaa aacctgccgc ccctgttgtt      60

tctgaaaaag agacagaggc aaaggaagat gcgccacagg caggttctca aggacagggc     120

gcgccatccg cacaaggcgg tcaagatatg gcggcggttt cggaagaaaa tacaggcaat     180

ggcggtgcgg cagcaacgga caaacccaaa aatgaagacg agggggcgca aaatgatatg     240

ccgcaaaatg ccgccgatac agatagtttg acaccgaatc acaccccggc ttcgaatatg     300

ccggccggaa atatggaaaa ccaagcaccg gatgccgggg aatcggagca gccggcaaac     360

caaccggata tggcaaatac ggcggacgga atgcagggtg acgatccgtc ggcaggcggg     420

gaaaatgccg gcaatacggc tgcccaaggt acaaatcaag ccgaaaacaa tcaaaccgcc     480

ggttctcaaa atcctgcctc ttcaaccaat cctagcgcca cgaatagcgg tggtgatttt     540

ggaaggacga acgtgggcaa ttctgttgtg attgacgggc cgtcgcaaaa tataacgttg     600

acccactgta aaggcgattc ttgtagtggc aataatttct tggatgaaga agtacagcta     660

aaatcagaat ttgaaaaatt aagtgatgca gacaaaataa gtaattacaa gaaagatggg     720

aagaatgacg ggaagaatga taaatttgtc ggtttggttg ccgatagtgt gcagatgaag     780

ggaatcaatc aatatattat cttttataaa cctaaaccca cttcatttgc gcgatttagg     840

cgttctgcac ggtcgaggcg gtcgcttccg gccgagatgc cgctgattcc cgtcaatcag     900

gcggatacgc tgattgtcga tggggaagcg gtcagcctga cggggcattc cggcaatatc     960

ttcgcgcccg aagggaatta ccggtatctg acttacgggg cggaaaaatt gcccggcgga    1020

tcgtatgccc tccgtgttca aggcgaacct tcaaaaggcg aaatgctcgc gggcacggca    1080

gtgtacaacg gcgaagtgct gcattttcat acggaaaacg gccgtccgtc cccgtccaga    1140

ggcaggtttg ccgcaaaagt cgatttcggc agcaaatctg tggacggcat tatcgacagc    1200

ggcgatggtt tgcatatggg tacgcaaaaa ttcaaagccg ccatcgatgg aaacggcttt    1260

aaggggactt ggacggaaaa tggcggcggg gatgtttccg gaaagtttta cggcccggcc    1320

ggcgaggaag tggcgggaaa atacagctat cgcccaacag atgcggaaaa gggcggattc    1380
```

-continued

```
ggcgtgtttg ccggcaaaaa agagcaggat ggatccggag gaggaggatg ccaaagcaag   1440

agcatccaaa cctttccgca acccgacaca tccgtcatca acggcccgga ccggccggtc   1500

ggcatccccg accccgccgg aacgacggtc ggcggcggcg gggccgtcta taccgttgta   1560

ccgcacctgt ccctgcccca ctgggcggcg caggatttcg ccaaaagcct gcaatccttc   1620

cgcctcggct gcgccaattt gaaaaaccgc caaggctggc aggatgtgtg cgcccaagcc   1680

tttcaaaccc ccgtccattc ctttcaggca aaacagtttt ttgaacgcta tttcacgccg   1740

tggcaggttg caggcaacgg aagccttgcc ggtacggtta ccggctatta cgagccggtg   1800

ctgaagggcg acgacaggcg gacggcacaa gcccgcttcc cgatttacgg tattcccgac   1860

gattttatct ccgtccccct gcctgccggt ttgcggagcg gaaaagccct tgtccgcatc   1920

aggcagacgg gaaaaaacag cggcacaatc gacaataccg gcggcacaca taccgccgac   1980

ctctcccgat tccccatcac cgcgcgcaca acggcaatca aaggcaggtt tgaaggaagc   2040

cgcttcctcc cctaccacac gcgcaaccaa atcaacggcg gcgcgcttga cggcaaagcc   2100

ccgatactcg gttacgccga agaccccgtc gaactttttt ttatgcacat ccaaggctcg   2160

ggccgtctga aaaccccgtc cggcaaatac atccgcatcg gctatgccga caaaaacgaa   2220

catccctacg tttccatcgg acgctatatg gcggacaaag gctacctcaa gctcgggcag   2280

acctcgatgc agggcatcaa agcctatatg cggcaaaatc cgcaacgcct cgccgaagtt   2340

ttgggtcaaa accccagcta tatctttttc cgcgagcttg ccggaagcag caatgacggt   2400

cccgtcggcg cactgggcac gccgttgatg ggggaatatg ccggcgcagt cgaccggcac   2460

tacattacct tgggcgcgcc cttatttgtc gccaccgccc atccggttac ccgcaaagcc   2520

ctcaaccgcc tgattatggc gcaggatacc ggcagcgcga ttaaaggcgc ggtgcgcgtg   2580

gattattttt ggggatacgg cgacgaagcc ggcgaacttg ccggcaaaca gaaaaccacg   2640

ggttacgtct ggcagctcct acccaacggt atgaagcccg aataccgccc gtaaaagctt   2700
```

```
<210> SEQ ID NO 95
<211> LENGTH: 897
<212> TYPE: PRT
<213> ORGANISM: Artificial Sequence
<220> FEATURE:
<223> OTHER INFORMATION: deltaG287NZ-919

<400> SEQUENCE: 95

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
```

-continued

```
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Gly Cys Gln Ser Lys
465                 470                 475                 480

Ser Ile Gln Thr Phe Pro Gln Pro Asp Thr Ser Val Ile Asn Gly Pro
                485                 490                 495

Asp Arg Pro Val Gly Ile Pro Asp Pro Ala Gly Thr Thr Val Gly Gly
            500                 505                 510

Gly Gly Ala Val Tyr Thr Val Val Pro His Leu Ser Leu Pro His Trp
        515                 520                 525

Ala Ala Gln Asp Phe Ala Lys Ser Leu Gln Ser Phe Arg Leu Gly Cys
    530                 535                 540

Ala Asn Leu Lys Asn Arg Gln Gly Trp Gln Asp Val Cys Ala Gln Ala
545                 550                 555                 560
```

-continued

```
Phe Gln Thr Pro Val His Ser Phe Gln Ala Lys Gln Phe Phe Glu Arg
                565                 570                 575

Tyr Phe Thr Pro Trp Gln Val Ala Gly Asn Gly Ser Leu Ala Gly Thr
            580                 585                 590

Val Thr Gly Tyr Tyr Glu Pro Val Leu Lys Gly Asp Asp Arg Arg Thr
        595                 600                 605

Ala Gln Ala Arg Phe Pro Ile Tyr Gly Ile Pro Asp Asp Phe Ile Ser
    610                 615                 620

Val Pro Leu Pro Ala Gly Leu Arg Ser Gly Lys Ala Leu Val Arg Ile
625                 630                 635                 640

Arg Gln Thr Gly Lys Asn Ser Gly Thr Ile Asp Asn Thr Gly Gly Thr
                645                 650                 655

His Thr Ala Asp Leu Ser Arg Phe Pro Ile Thr Ala Arg Thr Thr Ala
            660                 665                 670

Ile Lys Gly Arg Phe Glu Gly Ser Arg Phe Leu Pro Tyr His Thr Arg
        675                 680                 685

Asn Gln Ile Asn Gly Gly Ala Leu Asp Gly Lys Ala Pro Ile Leu Gly
    690                 695                 700

Tyr Ala Glu Asp Pro Val Glu Leu Phe Phe Met His Ile Gln Gly Ser
705                 710                 715                 720

Gly Arg Leu Lys Thr Pro Ser Gly Lys Tyr Ile Arg Ile Gly Tyr Ala
                725                 730                 735

Asp Lys Asn Glu His Pro Tyr Val Ser Ile Gly Arg Tyr Met Ala Asp
            740                 745                 750

Lys Gly Tyr Leu Lys Leu Gly Gln Thr Ser Met Gln Gly Ile Lys Ala
        755                 760                 765

Tyr Met Arg Gln Asn Pro Gln Arg Leu Ala Glu Val Leu Gly Gln Asn
    770                 775                 780

Pro Ser Tyr Ile Phe Phe Arg Glu Leu Ala Gly Ser Ser Asn Asp Gly
785                 790                 795                 800

Pro Val Gly Ala Leu Gly Thr Pro Leu Met Gly Glu Tyr Ala Gly Ala
                805                 810                 815

Val Asp Arg His Tyr Ile Thr Leu Gly Ala Pro Leu Phe Val Ala Thr
            820                 825                 830

Ala His Pro Val Thr Arg Lys Ala Leu Asn Arg Leu Ile Met Ala Gln
        835                 840                 845

Asp Thr Gly Ser Ala Ile Lys Gly Ala Val Arg Val Asp Tyr Phe Trp
    850                 855                 860

Gly Tyr Gly Asp Glu Ala Gly Glu Leu Ala Gly Lys Gln Lys Thr Thr
865                 870                 875                 880

Gly Tyr Val Trp Gln Leu Leu Pro Asn Gly Met Lys Pro Glu Tyr Arg
                885                 890                 895

Pro
```

<210> SEQ ID NO 96
<211> LENGTH: 1941
<212> TYPE: DNA
<213> ORGANISM: Artificial Sequence
<220> FEATURE:
<223> OTHER INFORMATION: deltaG287NZ-953

<400> SEQUENCE: 96

```
atggctagcc ccgatgtcaa gtcggcggac acgctgtcaa aacctgccgc ccctgttgtt      60

tctgaaaaag agacagaggc aaaggaagat gcgccacagg caggttctca aggacagggc     120
```

-continued

```
gcgccatccg cacaaggcgg tcaagatatg gcggcggttt cggaagaaaa tacaggcaat    180

ggcggtgcgg cagcaacgga caaacccaaa aatgaagacg agggggcgca aaatgatatg    240

ccgcaaaatg ccgccgatac agatagtttg acaccgaatc acaccccggc ttcgaatatg    300

ccggccggaa atatggaaaa ccaagcaccg gatgccgggg aatcggagca gccggcaaac    360

caaccggata tggcaaatac ggcggacgga atgcagggtg acgatccgtc ggcaggcggg    420

gaaaatgccg gcaatacggc tgcccaaggt acaaatcaag ccgaaaacaa tcaaaccgcc    480

ggttctcaaa atcctgcctc ttcaaccaat cctagcgcca cgaatagcgg tggtgatttt    540

ggaaggacga acgtgggcaa ttctgttgtg attgacgggc cgtcgcaaaa tataacgttg    600

acccactgta aaggcgattc ttgtagtggc aataatttct tggatgaaga agtacagcta    660

aaatcagaat ttgaaaaatt aagtgatgca gacaaaataa gtaattacaa gaaagatggg    720

aagaatgacg ggaagaatga taaatttgtc ggtttggttg ccgatagtgt gcagatgaag    780

ggaatcaatc aatatattat cttttataaa cctaaaccca cttcatttgc gcgatttagg    840

cgttctgcac ggtcgaggcg gtcgcttccg gccgagatgc cgctgattcc cgtcaatcag    900

gcggatacgc tgattgtcga tggggaagcg gtcagcctga cggggcattc cggcaatatc    960

ttcgcgcccg aagggaatta ccggtatctg acttacgggg cggaaaaatt gcccggcgga   1020

tcgtatgccc tccgtgttca aggcgaacct tcaaaaggcg aaatgctcgc gggcacggca   1080

gtgtacaacg gcgaagtgct gcattttcat acggaaaacg gccgtccgtc cccgtccaga   1140

ggcaggtttg ccgcaaaagt cgatttcggc agcaaatctg tggacggcat tatcgacagc   1200

ggcgatggtt tgcatatggg tacgcaaaaa ttcaaagccg ccatcgatgg aaacggcttt   1260

aaggggactt ggacggaaaa tggcggcggg gatgtttccg gaaagtttta cggcccggcc   1320

ggcgaggaag tggcgggaaa atacagctat cgcccaacag atgcggaaaa gggcggattc   1380

ggcgtgtttg ccggcaaaaa agagcaggat ggatccggag gaggaggagc cacctacaaa   1440

gtggacgaat atcacgccaa cgcccgtttc gccatcgacc atttcaacac cagcaccaac   1500

gtcggcggtt tttacggtct gaccggttcc gtcgagttcg accaagcaaa acgcgacggt   1560

aaaatcgaca tcaccatccc cgttgccaac ctgcaaagcg gttcgcaaca ctttaccgac   1620

cacctgaaat cagccgacat cttcgatgcc gcccaatatc cggacatccg ctttgtttcc   1680

accaaattca acttcaacgg caaaaaactg gtttccgttg acggcaacct gaccatgcac   1740

ggcaaaaccg cccccgtcaa actcaaagcc gaaaaattca actgctacca aagcccgatg   1800

gcgaaaaccg aagtttgcgg cggcgacttc agcaccacca tcgaccgcac caaatggggc   1860

gtggactacc tcgttaacgt tggtatgacc aaaagcgtcc gcatcgacat ccaaatcgag   1920

gcagccaaac aataaaagct t                                             1941
```

<210> SEQ ID NO 97
<211> LENGTH: 644
<212> TYPE: PRT
<213> ORGANISM: Artificial Sequence
<220> FEATURE:
<223> OTHER INFORMATION: deltaG287NZ-953

<400> SEQUENCE: 97

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30
```

-continued

```
Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
```

-continued

```
    450                 455                 460

Gly Lys Lys Glu Gln Asp Gly Ser Gly Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
    530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
    610                 615                 620

Val Asn Val Gly Met Thr Lys Ser Val Arg Ile Asp Ile Gln Ile Glu
625                 630                 635                 640

Ala Ala Lys Gln


<210> SEQ ID NO 98
<211> LENGTH: 2583
<212> TYPE: DNA
<213> ORGANISM: Artificial Sequence
<220> FEATURE:
<223> OTHER INFORMATION: deltaG287NZ-961

<400> SEQUENCE: 98

atggctagcc ccgatgtcaa gtcggcggac acgctgtcaa aacctgccgc ccctgttgtt      60

tctgaaaaag agacagaggc aaaggaagat gcgccacagg caggttctca aggacagggc     120

gcgccatccg cacaaggcgg tcaagatatg gcggcggttt cggaagaaaa tacaggcaat     180

ggcggtgcgg cagcaacgga caaacccaaa aatgaagacg aggggggcgca aaatgatatg     240

ccgcaaaatg ccgccgatac agatagtttg acaccgaatc acaccccggc ttcgaatatg     300

ccggccggaa atatggaaaa ccaagcaccg gatgccgggg aatcggagca gccggcaaac     360

caaccggata tggcaaatac ggcggacgga atgcagggtg acgatccgtc ggcaggcggg     420

gaaaatgccg gcaatacggc tgcccaaggt acaaatcaag ccgaaaacaa tcaaaccgcc     480

ggttctcaaa atcctgcctc ttcaaccaat cctagcgcca cgaatagcgg tggtgatttt     540

ggaaggacga acgtgggcaa ttctgttgtg attgacgggc cgtcgcaaaa tataacgttg     600

acccactgta aaggcgattc ttgtagtggc aataatttct tggatgaaga agtacagcta     660

aaatcagaat ttgaaaaatt aagtgatgca gacaaaataa gtaattacaa gaaagatggg     720

aagaatgacg ggaagaatga taaatttgtc ggtttggttg ccgatagtgt gcagatgaag     780

ggaatcaatc aatatattat cttttataaa cctaaaccca cttcatttgc gcgatttagg     840

cgttctgcac ggtcgaggcg gtcgcttccg gccgagatgc cgctgattcc cgtcaatcag     900

gcggatacgc tgattgtcga tggggaagcg gtcagcctga cggggcattc cggcaatatc     960
```

-continued ttcgcgcccg aagggaatta ccggtatctg acttacgggg cggaaaaatt gcccggcgga 1020
tcgtatgccc tccgtgttca aggcgaacct tcaaaaggcg aaatgctcgc gggcacggca 1080
gtgtacaacg gcgaagtgct gcattttcat acggaaaacg gccgtccgtc cccgtccaga 1140
ggcaggtttg ccgcaaaagt cgatttcggc agcaaatctg tggacggcat tatcgacagc 1200
ggcgatggtt tgcatatggg tacgcaaaaa ttcaaagccg ccatcgatgg aaacggcttt 1260
aaggggactt ggacggaaaa tggcggcggg gatgtttccg gaaagtttta cggcccggcc 1320
ggcgaggaag tggcgggaaa atacagctat cgcccaacag atgcggaaaa gggcggattc 1380
ggcgtgtttg ccggcaaaaa agagcaggat ggatccggag gaggaggagc cacaaacgac 1440
gacgatgtta aaaaagctgc cactgtggcc attgctgctg cctacaacaa tggccaagaa 1500
atcaacggtt tcaaagctgg agagaccatc tacgacattg atgaagacgg cacaattacc 1560
aaaaaagacg caactgcagc cgatgttgaa gccgacgact ttaaaggtct gggtctgaaa 1620
aaagtcgtga ctaacctgac caaaaccgtc aatgaaaaca aacaaaacgt cgatgccaaa 1680
gtaaaagctg cagaatctga aatagaaaag ttaacaacca agttagcaga cactgatgcc 1740
gctttagcag atactgatgc cgctctggat gcaaccacca acgccttgaa taaattggga 1800
gaaaatataa cgacatttgc tgaagagact aagacaaata tcgtaaaaat tgatgaaaaa 1860
ttagaagccg tggctgatac cgtcgacaag catgccgaag cattcaacga tatcgccgat 1920
tcattggatg aaaccaacac taaggcagac gaagccgtca aaaccgccaa tgaagccaaa 1980
cagacggccg aagaaaccaa acaaaacgtc gatgccaaag taaaagctgc agaaactgca 2040
gcaggcaaag ccgaagctgc cgctggcaca gctaatactg cagccgacaa ggccgaagct 2100
gtcgctgcaa aagttaccga catcaaagct gatatcgcta cgaacaaaga taatattgct 2160
aaaaaagcaa acagtgccga cgtgtacacc agagaagagt ctgacagcaa atttgtcaga 2220
attgatggtc tgaacgctac taccgaaaaa ttggacacac gcttggcttc tgctgaaaaa 2280
tccattgccg atcacgatac tcgcctgaac ggtttggata aaacagtgtc agacctgcgc 2340
aaagaaaccc gccaaggcct tgcagaacaa gccgcgctct ccggtctgtt ccaaccttac 2400
aacgtgggtc ggttcaatgt aacggctgca gtcggcggct acaaatccga atcggcagtc 2460
gccatcggta ccggcttccg ctttaccgaa aactttgccg ccaaagcagg cgtggcagtc 2520
ggcacttcgt ccggttcttc cgcagcctac catgtcggcg tcaattacga gtggtaaaag 2580
ctt 2583

<210> SEQ ID NO 99
<211> LENGTH: 858
<212> TYPE: PRT
<213> ORGANISM: Artificial Sequence
<220> FEATURE:
<223> OTHER INFORMATION: deltaG287NZ-961

<400> SEQUENCE: 99

Met Ala Ser Pro Asp Val Lys Ser Ala Asp Thr Leu Ser Lys Pro Ala
1 5 10 15

Ala Pro Val Val Ser Glu Lys Glu Thr Glu Ala Lys Glu Asp Ala Pro
20 25 30

Gln Ala Gly Ser Gln Gly Gln Gly Ala Pro Ser Ala Gln Gly Gly Gln
35 40 45

Asp Met Ala Ala Val Ser Glu Glu Asn Thr Gly Asn Gly Gly Ala Ala
50 55 60

Ala Thr Asp Lys Pro Lys Asn Glu Asp Glu Gly Ala Gln Asn Asp Met

-continued

```
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Gly Ala Thr Asn Asp
465                 470                 475                 480

Asp Asp Val Lys Lys Ala Ala Thr Val Ala Ile Ala Ala Ala Tyr Asn
                485                 490                 495
```

-continued

```
Asn Gly Gln Glu Ile Asn Gly Phe Lys Ala Gly Glu Thr Ile Tyr Asp
            500                 505                 510

Ile Asp Glu Asp Gly Thr Ile Thr Lys Lys Asp Ala Thr Ala Ala Asp
        515                 520                 525

Val Glu Ala Asp Asp Phe Lys Gly Leu Gly Leu Lys Lys Val Val Thr
    530                 535                 540

Asn Leu Thr Lys Thr Val Asn Glu Asn Lys Gln Asn Val Asp Ala Lys
545                 550                 555                 560

Val Lys Ala Ala Glu Ser Glu Ile Glu Lys Leu Thr Thr Lys Leu Ala
                565                 570                 575

Asp Thr Asp Ala Ala Leu Ala Asp Thr Asp Ala Ala Leu Asp Ala Thr
            580                 585                 590

Thr Asn Ala Leu Asn Lys Leu Gly Glu Asn Ile Thr Thr Phe Ala Glu
        595                 600                 605

Glu Thr Lys Thr Asn Ile Val Lys Ile Asp Glu Lys Leu Glu Ala Val
    610                 615                 620

Ala Asp Thr Val Asp Lys His Ala Glu Ala Phe Asn Asp Ile Ala Asp
625                 630                 635                 640

Ser Leu Asp Glu Thr Asn Thr Lys Ala Asp Glu Ala Val Lys Thr Ala
                645                 650                 655

Asn Glu Ala Lys Gln Thr Ala Glu Glu Thr Lys Gln Asn Val Asp Ala
            660                 665                 670

Lys Val Lys Ala Ala Glu Thr Ala Ala Gly Lys Ala Glu Ala Ala Ala
        675                 680                 685

Gly Thr Ala Asn Thr Ala Ala Asp Lys Ala Glu Ala Val Ala Ala Lys
    690                 695                 700

Val Thr Asp Ile Lys Ala Asp Ile Ala Thr Asn Lys Asp Asn Ile Ala
705                 710                 715                 720

Lys Lys Ala Asn Ser Ala Asp Val Tyr Thr Arg Glu Glu Ser Asp Ser
                725                 730                 735

Lys Phe Val Arg Ile Asp Gly Leu Asn Ala Thr Thr Glu Lys Leu Asp
            740                 745                 750

Thr Arg Leu Ala Ser Ala Glu Lys Ser Ile Ala Asp His Asp Thr Arg
        755                 760                 765

Leu Asn Gly Leu Asp Lys Thr Val Ser Asp Leu Arg Lys Glu Thr Arg
    770                 775                 780

Gln Gly Leu Ala Glu Gln Ala Ala Leu Ser Gly Leu Phe Gln Pro Tyr
785                 790                 795                 800

Asn Val Gly Arg Phe Asn Val Thr Ala Ala Val Gly Gly Tyr Lys Ser
                805                 810                 815

Glu Ser Ala Val Ala Ile Gly Thr Gly Phe Arg Phe Thr Glu Asn Phe
            820                 825                 830

Ala Ala Lys Ala Gly Val Ala Val Gly Thr Ser Ser Gly Ser Ser Ala
        835                 840                 845

Ala Tyr His Val Gly Val Asn Tyr Glu Trp
    850                 855
```

<210> SEQ ID NO 100
<211> LENGTH: 4425
<212> TYPE: DNA
<213> ORGANISM: Artificial Sequence
<220> FEATURE:
<223> OTHER INFORMATION: deltaG983-ORF46.1

<400> SEQUENCE: 100

-continued

```
atgacttctg cgcccgactt caatgcaggc ggtaccggta tcggcagcaa cagcagagca     60
acaacagcga aatcagcagc agtatcttac gccggtatca agaacgaaat gtgcaaagac    120
agaagcatgc tctgtgccgg tcgggatgac gttgcggtta cagacaggga tgccaaaatc    180
aatgcccccc ccccgaatct gcataccgga gactttccaa acccaaatga cgcatacaag    240
aatttgatca acctcaaacc tgcaattgaa gcaggctata caggacgcgg ggtagaggta    300
ggtatcgtcg acacaggcga atccgtcggc agcatatcct ttcccgaact gtatggcaga    360
aaagaacacg gctataacga aaattacaaa aactatacgg cgtatatgcg gaaggaagcg    420
cctgaagacg gaggcggtaa agacattgaa gcttctttcg acgatgaggc cgttatagag    480
actgaagcaa agccgacgga tatccgccac gtaaaagaaa tcggacacat cgatttggtc    540
tcccatatta ttggcgggcg ttccgtggac ggcagacctg caggcggtat tgcgcccgat    600
gcgacgctac acataatgaa tacgaatgat gaaaccaaga acgaaatgat ggttgcagcc    660
atccgcaatg catgggtcaa gctgggcgaa cgtggcgtgc gcatcgtcaa taacagtttt    720
ggaacaacat cgagggcagg cactgccgac cttttccaaa tagccaattc ggaggagcag    780
taccgccaag cgttgctcga ctattccggc ggtgataaaa cagacgaggg tatccgcctg    840
atgcaacaga gcgattacgg caacctgtcc taccacatcc gtaataaaaa catgcttttc    900
atcttttcga caggcaatga cgcacaagct cagcccaaca catatgccct attgccattt    960
tatgaaaaag acgctcaaaa aggcattatc acagtcgcag gcgtagaccg cagtggagaa   1020
aagttcaaac gggaaatgta tggagaaccg ggtacagaac cgcttgagta tggctccaac   1080
cattgcggaa ttactgccat gtggtgcctg tcggcaccct atgaagcaag cgtccgtttc   1140
acccgtacaa acccgattca aattgccgga acatcctttt ccgcacccat cgtaaccggc   1200
acggcggctc tgctgctgca gaaatacccg tggatgagca acgacaacct gcgtaccacg   1260
ttgctgacga cggctcagga catcggtgca gtcggcgtgg acagcaagtt cggctgggga   1320
ctgctggatg cgggtaaggc catgaacgga cccgcgtcct ttccgttcgg cgactttacc   1380
gccgatacga aaggtacatc cgatattgcc tactccttcc gtaacgacat ttcaggcacg   1440
ggcggcctga tcaaaaaagg cggcagccaa ctgcaactgc acggcaacaa cacctatacg   1500
ggcaaaacca ttatcgaagg cggttcgctg gtgttgtacg gcaacaacaa atcggatatg   1560
cgcgtcgaaa ccaaaggtgc gctgatttat aacggggcgg catccggcgg cagcctgaac   1620
agcgacggca ttgtctatct ggcagatacc gaccaatccg gcgcaaacga aaccgtacac   1680
atcaaaggca gtctgcagct ggacggcaaa ggtacgctgt acacacgttt gggcaaactg   1740
ctgaaagtgg acggtacggc gattatcggc ggcaagctgt acatgtcggc acgcggcaag   1800
ggggcaggct atctcaacag taccggacga cgtgttccct tcctgagtgc cgccaaaatc   1860
gggcaggatt attctttctt cacaaacatc gaaaccgacg gcggcctgct ggcttccctc   1920
gacagcgtcg aaaaaacagc gggcagtgaa ggcgacacgc tgtcctatta tgtccgtcgc   1980
ggcaatgcgg cacggactgc ttcggcagcg gcacattccg cgcccgccgg tctgaaacac   2040
gccgtagaac agggcggcag caatctggaa aacctgatgg tcgaactgga tgcctccgaa   2100
tcatccgcaa cacccgagac ggttgaaact gcggcagccg accgcacaga tatgccgggc   2160
atccgcccct acggcgcaac tttccgcgca gcggcagccg tacagcatgc gaatgccgcc   2220
gacggtgtac gcatcttcaa cagtctcgcc gctaccgtct atgccgacag taccgccgcc   2280
catgccgata tgcagggacg ccgcctgaaa gccgtatcgg acgggttgga ccacaacggc   2340
```

-continued

```
acgggtctgc gcgtcatcgc gcaaacccaa caggacggtg gaacgtggga acagggcggt   2400

gttgaaggca aaatgcgcgg cagtacccaa accgtcggca ttgccgcgaa aaccggcgaa   2460

aatacgacag cagccgccac actgggcatg ggacgcagca catggagcga aaacagtgca   2520

aatgcaaaaa ccgacagcat tagtctgttt gcaggcatac ggcacgatgc gggcgatatc   2580

ggctatctca aaggcctgtt ctcctacgga cgctacaaaa acagcatcag ccgcagcacc   2640

ggtgcggacg aacatgcgga aggcagcgtc aacggcacgc tgatgcagct gggcgcactg   2700

ggcggtgtca acgttccgtt tgccgcaacg ggagatttga cggtcgaagg cggtctgcgc   2760

tacgacctgc tcaaacagga tgcattcgcc gaaaaaggca gtgctttggg ctggagcggc   2820

aacagcctca ctgaaggcac gctggtcgga ctcgcgggtc tgaagctgtc gcaacccttg   2880

agcgataaag ccgtcctgtt tgcaacggcg ggcgtggaac gcgacctgaa cggacgcgac   2940

tacacggtaa cgggcggctt taccggcgcg actgcagcaa ccggcaagac gggggcacgc   3000

aatatgccgc acacccgtct ggttgccggc ctgggcgcgg atgtcgaatt cggcaacggc   3060

tggaacggct tggcacgtta cagctacgcc ggttccaaac agtacggcaa ccacagcgga   3120

cgagtcggcg taggctaccg gttcctcgac ggtggcggag gcactggatc ctcagatttg   3180

gcaaacgatt cttttatccg gcaggttctc gaccgtcagc atttcgaacc cgacgggaaa   3240

taccacctat tcggcagcag gggggaactt gccgagcgca gcggccatat cggattggga   3300

aaaatacaaa gccatcagtt gggcaacctg atgattcaac aggcggccat taaaggaaat   3360

atcggctaca ttgtccgctt ttccgatcac gggcacgaag tccattcccc cttcgacaac   3420

catgcctcac attccgattc tgatgaagcc ggtagtcccg ttgacggatt tagcctttac   3480

cgcatccatt gggacggata cgaacaccat cccgccgacg gctatgacgg gccacagggc   3540

ggcggctatc ccgctcccaa aggcgcgagg gatatataca gctacgacat aaaaggcgtt   3600

gcccaaaata tccgcctcaa cctgaccgac aaccgcagca ccggacaacg gcttgccgac   3660

cgtttccaca atgccggtag tatgctgacg caaggagtag gcgacggatt caaacgcgcc   3720

acccgataca gccccgagct ggacagatcg ggcaatgccg ccgaagcctt caacggcact   3780

gcagatatcg ttaaaaacat catcggcgcg gcaggagaaa ttgtcggcgc aggcgatgcc   3840

gtgcagggca taagcgaagg ctcaaacatt gctgtcatgc acggcttggg tctgctttcc   3900

accgaaaaca agatggcgcg catcaacgat ttggcagata tggcgcaact caaagactat   3960

gccgcagcag ccatccgcga ttgggcagtc caaaaacccca atgccgcaca aggcatagaa   4020

gccgtcagca atatctttat ggcagccatc cccatcaaag ggattggagc tgttcgggga   4080

aaatacggct tgggcggcat cacggcacat cctatcaagc ggtcgcagat gggcgcgatc   4140

gcattgccga aagggaaatc cgccgtcagc gacaattttg ccgatgcggc atacgccaaa   4200

tacccgtccc cttaccattc ccgaaatatc cgttcaaact tggagcagcg ttacggcaaa   4260

gaaaacatca cctcctcaac cgtgccgccg tcaaacggca aaaatgtcaa actggcagac   4320

caacgccacc cgaagacagg cgtaccgttt gacggtaaag ggtttccgaa ttttgagaag   4380

cacgtgaaat atgatacgct cgagcaccac caccaccacc actga                  4425
```

<210> SEQ ID NO 101
<211> LENGTH: 1474
<212> TYPE: PRT
<213> ORGANISM: Artificial Sequence
<220> FEATURE:
<223> OTHER INFORMATION: deltaG983-ORF46.1

<400> SEQUENCE: 101

-continued

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415
```

-continued

```
Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
    610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
    690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Ala Val Gln His
                725                 730                 735

Ala Asn Ala Ala Asp Gly Val Arg Ile Phe Asn Ser Leu Ala Ala Thr
            740                 745                 750

Val Tyr Ala Asp Ser Thr Ala Ala His Ala Asp Met Gln Gly Arg Arg
        755                 760                 765

Leu Lys Ala Val Ser Asp Gly Leu Asp His Asn Gly Thr Gly Leu Arg
    770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Ala Thr Leu Gly Met Gly Arg
            820                 825                 830

Ser Thr Trp Ser Glu Asn Ser Ala Asn Ala Lys Thr Asp Ser Ile Ser
```

-continued

```
        835                 840                 845

Leu Phe Ala Gly Ile Arg His Asp Ala Gly Asp Ile Gly Tyr Leu Lys
    850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
        915                 920                 925

Phe Ala Glu Lys Gly Ser Ala Leu Gly Trp Ser Gly Asn Ser Leu Thr
    930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
            980                 985                 990

Ala Thr Gly Lys Thr Gly Ala Arg Asn Met Pro His Thr Arg Leu Val
        995                 1000                1005

Ala Gly Leu Gly Ala Asp Val Glu Phe Gly Asn Gly Trp Asn Gly Leu
    1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Asp Gly Gly Gly Gly Thr Gly
                1045                1050                1055

Ser Ser Asp Leu Ala Asn Asp Ser Phe Ile Arg Gln Val Leu Asp Arg
            1060                1065                1070

Gln His Phe Glu Pro Asp Gly Lys Tyr His Leu Phe Gly Ser Arg Gly
        1075                1080                1085

Glu Leu Ala Glu Arg Ser Gly His Ile Gly Leu Gly Lys Ile Gln Ser
    1090                1095                1100

His Gln Leu Gly Asn Leu Met Ile Gln Gln Ala Ala Ile Lys Gly Asn
1105                1110                1115                1120

Ile Gly Tyr Ile Val Arg Phe Ser Asp His Gly His Glu Val His Ser
                1125                1130                1135

Pro Phe Asp Asn His Ala Ser His Ser Asp Ser Asp Glu Ala Gly Ser
            1140                1145                1150

Pro Val Asp Gly Phe Ser Leu Tyr Arg Ile His Trp Asp Gly Tyr Glu
        1155                1160                1165

His His Pro Ala Asp Gly Tyr Asp Gly Pro Gln Gly Gly Gly Tyr Pro
    1170                1175                1180

Ala Pro Lys Gly Ala Arg Asp Ile Tyr Ser Tyr Asp Ile Lys Gly Val
1185                1190                1195                1200

Ala Gln Asn Ile Arg Leu Asn Leu Thr Asp Asn Arg Ser Thr Gly Gln
                1205                1210                1215

Arg Leu Ala Asp Arg Phe His Asn Ala Gly Ser Met Leu Thr Gln Gly
            1220                1225                1230

Val Gly Asp Gly Phe Lys Arg Ala Thr Arg Tyr Ser Pro Glu Leu Asp
        1235                1240                1245

Arg Ser Gly Asn Ala Ala Glu Ala Phe Asn Gly Thr Ala Asp Ile Val
    1250                1255                1260
```

-continued

```
Lys Asn Ile Ile Gly Ala Ala Gly Glu Ile Val Gly Ala Gly Asp Ala
1265                1270                1275                1280

Val Gln Gly Ile Ser Glu Gly Ser Asn Ile Ala Val Met His Gly Leu
                1285                1290                1295

Gly Leu Leu Ser Thr Glu Asn Lys Met Ala Arg Ile Asn Asp Leu Ala
            1300                1305                1310

Asp Met Ala Gln Leu Lys Asp Tyr Ala Ala Ala Ala Ile Arg Asp Trp
        1315                1320                1325

Ala Val Gln Asn Pro Asn Ala Ala Gln Gly Ile Glu Ala Val Ser Asn
    1330                1335                1340

Ile Phe Met Ala Ala Ile Pro Ile Lys Gly Ile Gly Ala Val Arg Gly
1345                1350                1355                1360

Lys Tyr Gly Leu Gly Gly Ile Thr Ala His Pro Ile Lys Arg Ser Gln
                1365                1370                1375

Met Gly Ala Ile Ala Leu Pro Lys Gly Lys Ser Ala Val Ser Asp Asn
            1380                1385                1390

Phe Ala Asp Ala Ala Tyr Ala Lys Tyr Pro Ser Pro Tyr His Ser Arg
        1395                1400                1405

Asn Ile Arg Ser Asn Leu Glu Gln Arg Tyr Gly Lys Glu Asn Ile Thr
    1410                1415                1420

Ser Ser Thr Val Pro Pro Ser Asn Gly Lys Asn Val Lys Leu Ala Asp
1425                1430                1435                1440

Gln Arg His Pro Lys Thr Gly Val Pro Phe Asp Gly Lys Gly Phe Pro
                1445                1450                1455

Asn Phe Glu Lys His Val Lys Tyr Asp Thr Leu Glu His His His His
            1460                1465                1470

His His
```

<210> SEQ ID NO 102
<211> LENGTH: 3939
<212> TYPE: DNA
<213> ORGANISM: Artificial Sequence
<220> FEATURE:
<223> OTHER INFORMATION: deltaG983-741

<400> SEQUENCE: 102

```
atgacttctg cgcccgactt caatgcaggc ggtaccggta tcggcagcaa cagcagagca     60

acaacagcga aatcagcagc agtatcttac gccggtatca agaacgaaat gtgcaaagac    120

agaagcatgc tctgtgccgg tcgggatgac gttgcggtta cagacaggga tgccaaaatc    180

aatgcccccc ccccgaatct gcataccgga gactttccaa acccaaatga cgcatacaag    240

aatttgatca acctcaaacc tgcaattgaa gcaggctata caggacgcgg ggtagaggta    300

ggtatcgtcg acacaggcga atccgtcggc agcatatcct ttcccgaact gtatggcaga    360

aaagaacacg gctataacga aaattacaaa aactatacgg cgtatatgcg gaaggaagcg    420

cctgaagacg gaggcggtaa agacattgaa gcttctttcg acgatgaggc cgttatagag    480

actgaagcaa agccgacgga tatccgccac gtaaaagaaa tcggacacat cgatttggtc    540

tcccatatta ttggcgggcg ttccgtggac ggcagacctg caggcggtat tgcgcccgat    600

gcgacgctac acataatgaa tacgaatgat gaaaccaaga acgaaatgat ggttgcagcc    660

atccgcaatg catgggtcaa gctgggcgaa cgtggcgtgc gcatcgtcaa taacagtttt    720

ggaacaacat cgagggcagg cactgccgac cttttccaaa tagccaattc ggaggagcag    780

taccgccaag cgttgctcga ctattccggc ggtgataaaa cagacgaggg tatccgcctg    840
```

-continued

```
atgcaacaga gcgattacgg caacctgtcc taccacatcc gtaataaaaa catgcttttc    900
atcttttcga caggcaatga cgcacaagct cagcccaaca catatgccct attgccattt    960
tatgaaaaag acgctcaaaa aggcattatc acagtcgcag gcgtagaccg cagtggagaa   1020
aagttcaaac gggaaatgta tggagaaccg ggtacagaac cgcttgagta tggctccaac   1080
cattgcggaa ttactgccat gtggtgcctg tcggcaccct atgaagcaag cgtccgtttc   1140
acccgtacaa acccgattca aattgccgga acatcctttt ccgcacccat cgtaaccggc   1200
acggcggctc tgctgctgca gaaataccccg tggatgagca acgacaacct gcgtaccacg   1260
ttgctgacga cggctcagga catcggtgca gtcggcgtgg acagcaagtt cggctgggga   1320
ctgctggatg cgggtaaggc catgaacgga cccgcgtcct ttccgttcgg cgactttacc   1380
gccgatacga aaggtacatc cgatattgcc tactccttcc gtaacgacat ttcaggcacg   1440
ggcggcctga tcaaaaaagg cggcagccaa ctgcaactgc acggcaacaa cacctatacg   1500
ggcaaaacca ttatcgaagg cggttcgctg gtgttgtacg gcaacaacaa atcggatatg   1560
cgcgtcgaaa ccaaaggtgc gctgatttat aacggggcgg catccggcgg cagcctgaac   1620
agcgacggca ttgtctatct ggcagatacc gaccaatccg gcgcaaacga aaccgtacac   1680
atcaaaggca gtctgcagct ggacggcaaa ggtacgctgt acacacgttt gggcaaactg   1740
ctgaaagtgg acggtacggc gattatcggc ggcaagctgt acatgtcggc acgcggcaag   1800
ggggcaggct atctcaacag taccggacga cgtgttccct tcctgagtgc cgccaaaatc   1860
gggcaggatt attctttctt cacaaacatc gaaaccgacg gcggcctgct ggcttccctc   1920
gacagcgtcg aaaaaacagc gggcagtgaa ggcgacacgc tgtcctatta tgtccgtcgc   1980
ggcaatgcgg cacggactgc ttcggcagcg gcacattccg cgcccgccgg tctgaaacac   2040
gccgtagaac agggcggcag caatctggaa aacctgatgg tcgaactgga tgcctccgaa   2100
tcatccgcaa cacccgagac ggttgaaact gcggcagccg accgcacaga tatgccgggc   2160
atccgcccct acggcgcaac tttccgcgca gcggcagccg tacagcatgc gaatgccgcc   2220
gacggtgtac gcatcttcaa cagtctcgcc gctaccgtct atgccgacag taccgccgcc   2280
catgccgata tgcagggacg ccgcctgaaa gccgtatcgg acgggttgga ccacaacggc   2340
acgggtctgc gcgtcatcgc gcaaacccaa caggacggtg gaacgtggga acagggcggt   2400
gttgaaggca aaatgcgcgg cagtacccaa accgtcggca ttgccgcgaa aaccggcgaa   2460
aatacgacag cagccgccac actgggcatg ggacgcagca catggagcga aaacagtgca   2520
aatgcaaaaa ccgacagcat tagtctgttt gcaggcatac ggcacgatgc gggcgatatc   2580
ggctatctca aaggcctgtt ctcctacgga cgctacaaaa acagcatcag ccgcagcacc   2640
ggtgcggacg aacatgcgga aggcagcgtc aacggcacgc tgatgcagct gggcgcactg   2700
ggcggtgtca acgttccgtt tgccgcaacg ggagatttga cggtcgaagg cggtctgcgc   2760
tacgacctgc tcaaacagga tgcattcgcc gaaaaaggca gtgctttggg ctggagcggc   2820
aacagcctca ctgaaggcac gctggtcgga ctcgcgggtc tgaagctgtc gcaacccttg   2880
agcgataaag ccgtcctgtt tgcaacggcg ggcgtggaac gcgacctgaa cggacgcgac   2940
tacacggtaa cgggcggctt taccggcgcg actgcagcaa ccggcaagac gggggcacgc   3000
aatatgccgc acacccgtct ggttgccggc ctgggcgcgg atgtcgaatt cggcaacggc   3060
tggaacggct tggcacgtta cagctacgcc ggttccaaac agtacggcaa ccacagcgga   3120
cgagtcggcg taggctaccg gttcctcgag ggatccggag ggggtggtgt cgccgccgac   3180
```

-continued

```
atcggtgcgg ggcttgccga tgcactaacc gcaccgctcg accataaaga caaaggtttg   3240

cagtctttga cgctggatca gtccgtcagg aaaaacgaga aactgaagct ggcggcacaa   3300

ggtgcggaaa aaacttatgg aaacggtgac agcctcaata cgggcaaatt gaagaacgac   3360

aaggtcagcc gtttcgactt tatccgccaa atcgaagtgg acgggcagct cattaccttg   3420

gagagtggag agttccaagt atacaaacaa agccattccg ccttaaccgc ctttcagacc   3480

gagcaaatac aagattcgga gcattccggg aagatggttg cgaaacgcca gttcagaatc   3540

ggcgacatag cgggcgaaca tacatctttt gacaagcttc ccgaaggcgg cagggcgaca   3600

tatcgcggga cggcgttcgg ttcagacgat gccggcggaa aactgaccta caccatagat   3660

ttcgccgcca agcagggaaa cggcaaaatc gaacatttga aatcgccaga actcaatgtc   3720

gacctggccg ccgccgatat caagccggat ggaaaacgcc atgccgtcat cagcggttcc   3780

gtcctttaca accaagccga gaaaggcagt tactccctcg gtatctttgg cggaaaagcc   3840

caggaagttg ccggcagcgc ggaagtgaaa accgtaaacg gcatacgcca tatcggcctt   3900

gccgccaagc aactcgagca ccaccaccac caccactga                          3939
```

<210> SEQ ID NO 103
<211> LENGTH: 1312
<212> TYPE: PRT
<213> ORGANISM: Artificial Sequence
<220> FEATURE:
<223> OTHER INFORMATION: deltaG983-741

<400> SEQUENCE: 103

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
```

-continued

```
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
    610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655
```

-continued

```
Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
    690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Ala Val Gln His
                725                 730                 735

Ala Asn Ala Ala Asp Gly Val Arg Ile Phe Asn Ser Leu Ala Ala Thr
            740                 745                 750

Val Tyr Ala Asp Ser Thr Ala Ala His Ala Asp Met Gln Gly Arg Arg
        755                 760                 765

Leu Lys Ala Val Ser Asp Gly Leu Asp His Asn Gly Thr Gly Leu Arg
    770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Ala Thr Leu Gly Met Gly Arg
            820                 825                 830

Ser Thr Trp Ser Glu Asn Ser Ala Asn Ala Lys Thr Asp Ser Ile Ser
        835                 840                 845

Leu Phe Ala Gly Ile Arg His Asp Ala Gly Asp Ile Gly Tyr Leu Lys
    850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
        915                 920                 925

Phe Ala Glu Lys Gly Ser Ala Leu Gly Trp Ser Gly Asn Ser Leu Thr
    930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
            980                 985                 990

Ala Thr Gly Lys Thr Gly Ala Arg Asn Met Pro His Thr Arg Leu Val
        995                 1000                1005

Ala Gly Leu Gly Ala Asp Val Glu Phe Gly Asn Gly Trp Asn Gly Leu
    1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Ser Gly Gly Gly Gly
                1045                1050                1055

Val Ala Ala Asp Ile Gly Ala Gly Leu Ala Asp Ala Leu Thr Ala Pro
            1060                1065                1070
```

-continued

```
Leu Asp His Lys Asp Lys Gly Leu Gln Ser Leu Thr Leu Asp Gln Ser
        1075                1080                1085

Val Arg Lys Asn Glu Lys Leu Lys Leu Ala Ala Gln Gly Ala Glu Lys
    1090                1095                1100

Thr Tyr Gly Asn Gly Asp Ser Leu Asn Thr Gly Lys Leu Lys Asn Asp
1105                1110                1115                1120

Lys Val Ser Arg Phe Asp Phe Ile Arg Gln Ile Glu Val Asp Gly Gln
                1125                1130                1135

Leu Ile Thr Leu Glu Ser Gly Glu Phe Gln Val Tyr Lys Gln Ser His
            1140                1145                1150

Ser Ala Leu Thr Ala Phe Gln Thr Glu Gln Ile Gln Asp Ser Glu His
        1155                1160                1165

Ser Gly Lys Met Val Ala Lys Arg Gln Phe Arg Ile Gly Asp Ile Ala
    1170                1175                1180

Gly Glu His Thr Ser Phe Asp Lys Leu Pro Glu Gly Gly Arg Ala Thr
1185                1190                1195                1200

Tyr Arg Gly Thr Ala Phe Gly Ser Asp Asp Ala Gly Gly Lys Leu Thr
                1205                1210                1215

Tyr Thr Ile Asp Phe Ala Ala Lys Gln Gly Asn Gly Lys Ile Glu His
            1220                1225                1230

Leu Lys Ser Pro Glu Leu Asn Val Asp Leu Ala Ala Ala Asp Ile Lys
        1235                1240                1245

Pro Asp Gly Lys Arg His Ala Val Ile Ser Gly Ser Val Leu Tyr Asn
    1250                1255                1260

Gln Ala Glu Lys Gly Ser Tyr Ser Leu Gly Ile Phe Gly Gly Lys Ala
1265                1270                1275                1280

Gln Glu Val Ala Gly Ser Ala Glu Val Lys Thr Val Asn Gly Ile Arg
                1285                1290                1295

His Ile Gly Leu Ala Ala Lys Gln Leu Glu His His His His His His
            1300                1305                1310


<210> SEQ ID NO 104
<211> LENGTH: 4344
<212> TYPE: DNA
<213> ORGANISM: Artificial Sequence
<220> FEATURE:
<223> OTHER INFORMATION: deltaG983-961

<400> SEQUENCE: 104

atgacttctg cgcccgactt caatgcaggc ggtaccggta tcggcagcaa cagcagagca     60

acaacagcga aatcagcagc agtatcttac gccggtatca agaacgaaat gtgcaaagac    120

agaagcatgc tctgtgccgg tcgggatgac gttgcggtta cagacaggga tgccaaaatc    180

aatgcccccc ccccgaatct gcataccgga gactttccaa acccaaatga cgcatacaag    240

aatttgatca acctcaaacc tgcaattgaa gcaggctata caggacgcgg ggtagaggta    300

ggtatcgtcg acacaggcga atccgtcggc agcatatcct ttcccgaact gtatggcaga    360

aaagaacacg gctataacga aaattacaaa aactatacgg cgtatatgcg gaaggaagcg    420

cctgaagacg gaggcggtaa agacattgaa gcttctttcg acgatgaggc cgttatagag    480

actgaagcaa agccgacgga tatccgccac gtaaaagaaa tcggacacat cgatttggtc    540

tcccatatta ttggcgggcg ttccgtggac ggcagacctg caggcggtat tgcgcccgat    600

gcgacgctac acataatgaa tacgaatgat gaaaccaaga acgaaatgat ggttgcagcc    660

atccgcaatg catgggtcaa gctgggcgaa cgtggcgtgc gcatcgtcaa taacagtttt    720
```

-continued

```
ggaacaacat cgagggcagg cactgccgac cttttccaaa tagccaattc ggaggagcag    780
taccgccaag cgttgctcga ctattccggc ggtgataaaa cagacgaggg tatccgcctg    840
atgcaacaga gcgattacgg caacctgtcc taccacatcc gtaataaaaa catgcttttc    900
atcttttcga caggcaatga cgcacaagct cagcccaaca catatgccct attgccattt    960
tatgaaaaag acgctcaaaa aggcattatc acagtcgcag gcgtagaccg cagtggagaa   1020
aagttcaaac gggaaatgta tggagaaccg ggtacagaac cgcttgagta tggctccaac   1080
cattgcggaa ttactgccat gtggtgcctg tcggcaccct atgaagcaag cgtccgtttc   1140
acccgtacaa acccgattca aattgccgga acatcctttt ccgcacccat cgtaaccggc   1200
acggcggctc tgctgctgca gaaataccg  tggatgagca acgacaacct gcgtaccacg   1260
ttgctgacga cggctcagga catcggtgca gtcggcgtgg acagcaagtt cggctgggga   1320
ctgctggatg cgggtaaggc catgaacgga cccgcgtcct ttccgttcgg cgactttacc   1380
gccgatacga aaggtacatc cgatattgcc tactccttcc gtaacgacat ttcaggcacg   1440
ggcggcctga tcaaaaaagg cggcagccaa ctgcaactgc acggcaacaa cacctatacg   1500
ggcaaaacca ttatcgaagg cggttcgctg gtgttgtacg gcaacaacaa atcggatatg   1560
cgcgtcgaaa ccaaaggtgc gctgatttat aacggggcgg catccggcgg cagcctgaac   1620
agcgacggca ttgtctatct ggcagatacc gaccaatccg gcgcaaacga aaccgtacac   1680
atcaaaggca gtctgcagct ggacggcaaa ggtacgctgt acacacgttt gggcaaactg   1740
ctgaaagtgg acggtacggc gattatcggc ggcaagctgt acatgtcggc acgcggcaag   1800
ggggcaggct atctcaacag taccggacga cgtgttccct tcctgagtgc cgccaaaatc   1860
gggcaggatt attctttctt cacaaacatc gaaaccgacg gcggcctgct ggcttccctc   1920
gacagcgtcg aaaaaacagc gggcagtgaa ggcgacacgc tgtcctatta tgtccgtcgc   1980
ggcaatgcgg cacggactgc ttcggcagcg gcacattccg cgcccgccgg tctgaaacac   2040
gccgtagaac agggcggcag caatctggaa aacctgatgg tcgaactgga tgcctccgaa   2100
tcatccgcaa cacccgagac ggttgaaact gcggcagccg accgcacaga tatgccgggc   2160
atccgcccct acggcgcaac tttccgcgca gcggcagccg tacagcatgc gaatgccgcc   2220
gacggtgtac gcatcttcaa cagtctcgcc gctaccgtct atgccgacag taccgccgcc   2280
catgccgata tgcagggacg ccgcctgaaa gccgtatcgg acgggttgga ccacaacggc   2340
acgggtctgc gcgtcatcgc gcaaacccaa caggacggtg gaacgtggga acagggcggt   2400
gttgaaggca aaatgcgcgg cagtacccaa accgtcggca ttgccgcgaa aaccggcgaa   2460
aatacgacag cagccgccac actgggcatg ggacgcagca catggagcga aaacagtgca   2520
aatgcaaaaa ccgacagcat tagtctgttt gcaggcatac ggcacgatgc gggcgatatc   2580
ggctatctca aaggcctgtt ctcctacgga cgctacaaaa acagcatcag ccgcagcacc   2640
ggtgcggacg aacatgcgga aggcagcgtc aacggcacgc tgatgcagct gggcgcactg   2700
ggcggtgtca acgttccgtt tgccgcaacg ggagatttga cggtcgaagg cggtctgcgc   2760
tacgacctgc tcaaacagga tgcattcgcc gaaaaaggca gtgctttggg ctggagcggc   2820
aacagcctca ctgaaggcac gctggtcgga ctcgcgggtc tgaagctgtc gcaacccttg   2880
agcgataaag ccgtcctgtt tgcaacggcg ggcgtggaac gcgacctgaa cggacgcgac   2940
tacacggtaa cgggcggctt taccggcgcg actgcagcaa ccggcaagac gggggcacgc   3000
aatatgccgc acacccgtct ggttgccggc ctgggcgcgg atgtcgaatt cggcaacggc   3060
tggaacggct tggcacgtta cagctacgcc ggttccaaac agtacggcaa ccacagcgga   3120
```

-continued

```
cgagtcggcg taggctaccg gttcctcgag ggtggcggag gcactggatc cgccacaaac   3180
gacgacgatg ttaaaaaagc tgccactgtg gccattgctg ctgcctacaa caatggccaa   3240
gaaatcaacg gtttcaaagc tggagagacc atctacgaca ttgatgaaga cggcacaatt   3300
accaaaaaag acgcaactgc agccgatgtt gaagccgacg actttaaagg tctgggtctg   3360
aaaaaagtcg tgactaacct gaccaaaacc gtcaatgaaa acaaacaaaa cgtcgatgcc   3420
aaagtaaaag ctgcagaatc tgaaatagaa aagttaacaa ccaagttagc agacactgat   3480
gccgctttag cagatactga tgccgctctg gatgcaacca ccaacgcctt gaataaattg   3540
ggagaaaata taacgacatt tgctgaagag actaagacaa atatcgtaaa aattgatgaa   3600
aaattagaag ccgtggctga taccgtcgac aagcatgccg aagcattcaa cgatatcgcc   3660
gattcattgg atgaaaccaa cactaaggca gacgaagccg tcaaaaccgc caatgaagcc   3720
aaacagacgg ccgaagaaac caaacaaaac gtcgatgcca aagtaaaagc tgcagaaact   3780
gcagcaggca aagccgaagc tgccgctggc acagctaata ctgcagccga caaggccgaa   3840
gctgtcgctg caaaagttac cgacatcaaa gctgatatcg ctacgaacaa agataatatt   3900
gctaaaaaag caaacagtgc cgacgtgtac accagagaag agtctgacag caaatttgtc   3960
agaattgatg gtctgaacgc tactaccgaa aaattggaca cacgcttggc ttctgctgaa   4020
aaatccattg ccgatcacga tactcgcctg aacggtttgg ataaaacagt gtcagacctg   4080
cgcaaagaaa cccgccaagg ccttgcagaa caagccgcgc tctccggtct gttccaacct   4140
tacaacgtgg gtcggttcaa tgtaacggct gcagtcggcg gctacaaatc cgaatcggca   4200
gtcgccatcg gtaccggctt ccgctttacc gaaaactttg ccgccaaagc aggcgtggca   4260
gtcggcactt cgtccggttc ttccgcagcc taccatgtcg gcgtcaatta cgagtggctc   4320
gagcaccacc accaccacca ctga                                          4344
```

<210> SEQ ID NO 105
<211> LENGTH: 1447
<212> TYPE: PRT
<213> ORGANISM: Artificial Sequence
<220> FEATURE:
<223> OTHER INFORMATION: deltaG983-961

<400> SEQUENCE: 105

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140
```

-continued

```
Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560
```

-continued

```
Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
    610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
    690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Ala Val Gln His
                725                 730                 735

Ala Asn Ala Ala Asp Gly Val Arg Ile Phe Asn Ser Leu Ala Ala Thr
            740                 745                 750

Val Tyr Ala Asp Ser Thr Ala Ala His Ala Asp Met Gln Gly Arg Arg
        755                 760                 765

Leu Lys Ala Val Ser Asp Gly Leu Asp His Asn Gly Thr Gly Leu Arg
    770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Ala Thr Leu Gly Met Gly Arg
            820                 825                 830

Ser Thr Trp Ser Glu Asn Ser Ala Asn Ala Lys Thr Asp Ser Ile Ser
        835                 840                 845

Leu Phe Ala Gly Ile Arg His Asp Ala Gly Asp Ile Gly Tyr Leu Lys
    850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
        915                 920                 925

Phe Ala Glu Lys Gly Ser Ala Leu Gly Trp Ser Gly Asn Ser Leu Thr
    930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
```

-continued

```
            980                 985                 990

Ala Thr Gly Lys Thr Gly Ala Arg Asn Met Pro His Thr Arg Leu Val
        995                 1000                1005

Ala Gly Leu Gly Ala Asp Val Glu Phe Gly Asn Gly Trp Asn Gly Leu
    1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Gly Gly Gly Thr Gly
                1045                1050                1055

Ser Ala Thr Asn Asp Asp Asp Val Lys Lys Ala Ala Thr Val Ala Ile
            1060                1065                1070

Ala Ala Ala Tyr Asn Asn Gly Gln Glu Ile Asn Gly Phe Lys Ala Gly
        1075                1080                1085

Glu Thr Ile Tyr Asp Ile Asp Glu Asp Gly Thr Ile Thr Lys Lys Asp
    1090                1095                1100

Ala Thr Ala Ala Asp Val Glu Ala Asp Asp Phe Lys Gly Leu Gly Leu
1105                1110                1115                1120

Lys Lys Val Val Thr Asn Leu Thr Lys Thr Val Asn Glu Asn Lys Gln
                1125                1130                1135

Asn Val Asp Ala Lys Val Lys Ala Ala Glu Ser Glu Ile Glu Lys Leu
            1140                1145                1150

Thr Thr Lys Leu Ala Asp Thr Asp Ala Ala Leu Ala Asp Thr Asp Ala
        1155                1160                1165

Ala Leu Asp Ala Thr Thr Asn Ala Leu Asn Lys Leu Gly Glu Asn Ile
    1170                1175                1180

Thr Thr Phe Ala Glu Glu Thr Lys Thr Asn Ile Val Lys Ile Asp Glu
1185                1190                1195                1200

Lys Leu Glu Ala Val Ala Asp Thr Val Asp Lys His Ala Glu Ala Phe
                1205                1210                1215

Asn Asp Ile Ala Asp Ser Leu Asp Glu Thr Asn Thr Lys Ala Asp Glu
            1220                1225                1230

Ala Val Lys Thr Ala Asn Glu Ala Lys Gln Thr Ala Glu Glu Thr Lys
        1235                1240                1245

Gln Asn Val Asp Ala Lys Val Lys Ala Ala Glu Thr Ala Ala Gly Lys
    1250                1255                1260

Ala Glu Ala Ala Ala Gly Thr Ala Asn Thr Ala Ala Asp Lys Ala Glu
1265                1270                1275                1280

Ala Val Ala Ala Lys Val Thr Asp Ile Lys Ala Asp Ile Ala Thr Asn
                1285                1290                1295

Lys Asp Asn Ile Ala Lys Lys Ala Asn Ser Ala Asp Val Tyr Thr Arg
            1300                1305                1310

Glu Glu Ser Asp Ser Lys Phe Val Arg Ile Asp Gly Leu Asn Ala Thr
        1315                1320                1325

Thr Glu Lys Leu Asp Thr Arg Leu Ala Ser Ala Glu Lys Ser Ile Ala
    1330                1335                1340

Asp His Asp Thr Arg Leu Asn Gly Leu Asp Lys Thr Val Ser Asp Leu
1345                1350                1355                1360

Arg Lys Glu Thr Arg Gln Gly Leu Ala Glu Gln Ala Ala Leu Ser Gly
                1365                1370                1375

Leu Phe Gln Pro Tyr Asn Val Gly Arg Phe Asn Val Thr Ala Ala Val
            1380                1385                1390

Gly Gly Tyr Lys Ser Glu Ser Ala Val Ala Ile Gly Thr Gly Phe Arg
        1395                1400                1405
```

-continued

Phe Thr Glu Asn Phe Ala Ala Lys Ala Gly Val Ala Val Gly Thr Ser
    1410                1415                1420

Ser Gly Ser Ser Ala Ala Tyr His Val Gly Val Asn Tyr Glu Trp Leu
1425                1430                1435                1440

Glu His His His His His His
                1445

<210> SEQ ID NO 106
<211> LENGTH: 4179
<212> TYPE: DNA
<213> ORGANISM: Artificial Sequence
<220> FEATURE:
<223> OTHER INFORMATION: deltaG983-961c

<400> SEQUENCE: 106
atgacttctg cgcccgactt caatgcaggc ggtaccggta tcggcagcaa cagcagagca 60
acaacagcga aatcagcagc agtatcttac gccggtatca agaacgaaat gtgcaaagac 120
agaagcatgc tctgtgccgg tcgggatgac gttgcggtta cagacaggga tgccaaaatc 180
aatgcccccc ccccgaatct gcataccgga gactttccaa acccaaatga cgcatacaag 240
aatttgatca acctcaaacc tgcaattgaa gcaggctata caggacgcgg ggtagaggta 300
ggtatcgtcg acacaggcga atccgtcggc agcatatcct ttcccgaact gtatggcaga 360
aaagaacacg gctataacga aaattacaaa aactatacgg cgtatatgcg gaaggaagcg 420
cctgaagacg gaggcggtaa agacattgaa gcttctttcg acgatgaggc cgttatagag 480
actgaagcaa agccgacgga tatccgccac gtaaaagaaa tcggacacat cgatttggtc 540
tcccatatta ttggcgggcg ttccgtggac ggcagacctg caggcggtat tgcgcccgat 600
gcgacgctac acataatgaa tacgaatgat gaaaccaaga acgaaatgat ggttgcagcc 660
atccgcaatg catgggtcaa gctgggcgaa cgtggcgtgc gcatcgtcaa taacagtttt 720
ggaacaacat cgagggcagg cactgccgac cttttccaaa tagccaattc ggaggagcag 780
taccgccaag cgttgctcga ctattccggc ggtgataaaa cagacgaggg tatccgcctg 840
atgcaacaga gcgattacgg caacctgtcc taccacatcc gtaataaaaa catgcttttc 900
atcttttcga caggcaatga cgcacaagct cagcccaaca catatgccct attgccattt 960
tatgaaaaag acgctcaaaa aggcattatc acagtcgcag gcgtagaccg cagtggagaa 1020
aagttcaaac gggaaatgta tggagaaccg ggtacagaac cgcttgagta tggctccaac 1080
cattgcggaa ttactgccat gtggtgcctg tcggcaccct atgaagcaag cgtccgtttc 1140
acccgtacaa acccgattca aattgccgga acatcctttt ccgcacccat cgtaaccggc 1200
acggcggctc tgctgctgca gaaataccgg tggatgagca acgacaacct gcgtaccacg 1260
ttgctgacga cggctcagga catcggtgca gtcggcgtgg acagcaagtt cggctgggga 1320
ctgctggatg cgggtaaggc catgaacgga cccgcgtcct ttccgttcgg cgactttacc 1380
gccgatacga aaggtacatc cgatattgcc tactccttcc gtaacgacat ttcaggcacg 1440
ggcggcctga tcaaaaaagg cggcagccaa ctgcaactgc acggcaacaa cacctatacg 1500
ggcaaaacca ttatcgaagg cggttcgctg gtgttgtacg gcaacaacaa atcggatatg 1560
cgcgtcgaaa ccaaaggtgc gctgatttat aacggggcgg catccggcgg cagcctgaac 1620
agcgacggca ttgtctatct ggcagatacc gaccaatccg gcgcaaacga aaccgtacac 1680
atcaaaggca gtctgcagct ggacggcaaa ggtacgctgt acacacgttt gggcaaactg 1740
ctgaaagtgg acggtacggc gattatcggc ggcaagctgt acatgtcggc acgcggcaag 1800

-continued

```
ggggcaggct atctcaacag taccggacga cgtgttccct tcctgagtgc cgccaaaatc   1860
gggcaggatt attctttctt cacaaacatc gaaaccgacg gcggcctgct ggcttccctc   1920
gacagcgtcg aaaaaacagc gggcagtgaa ggcgacacgc tgtcctatta tgtccgtcgc   1980
ggcaatgcgg cacggactgc ttcggcagcg gcacattccg cgcccgccgg tctgaaacac   2040
gccgtagaac agggcggcag caatctggaa aacctgatgg tcgaactgga tgcctccgaa   2100
tcatccgcaa cacccgagac ggttgaaact gcggcagccg accgcacaga tatgccgggc   2160
atccgcccct acggcgcaac tttccgcgca gcggcagccg tacagcatgc gaatgccgcc   2220
gacggtgtac gcatcttcaa cagtctcgcc gctaccgtct atgccgacag taccgccgcc   2280
catgccgata tgcagggacg ccgcctgaaa gccgtatcgg acgggttgga ccacaacggc   2340
acgggtctgc gcgtcatcgc gcaaacccaa caggacggtg gaacgtggga acagggcggt   2400
gttgaaggca aaatgcgcgg cagtacccaa accgtcggca ttgccgcgaa aaccggcgaa   2460
aatacgacag cagccgccac actgggcatg ggacgcagca catggagcga aaacagtgca   2520
aatgcaaaaa ccgacagcat tagtctgttt gcaggcatac ggcacgatgc gggcgatatc   2580
ggctatctca aaggcctgtt ctcctacgga cgctacaaaa acagcatcag ccgcagcacc   2640
ggtgcggacg aacatgcgga aggcagcgtc aacggcacgc tgatgcagct gggcgcactg   2700
ggcggtgtca acgttccgtt tgccgcaacg ggagatttga cggtcgaagg cggtctgcgc   2760
tacgacctgc tcaaacagga tgcattcgcc gaaaaaggca gtgctttggg ctggagcggc   2820
aacagcctca ctgaaggcac gctggtcgga ctcgcgggtc tgaagctgtc gcaaccttg    2880
agcgataaag ccgtcctgtt tgcaacggcg ggcgtggaac gcgacctgaa cggacgcgac   2940
tacacggtaa cgggcggctt taccggcgcg actgcagcaa ccggcaagac gggggcacgc   3000
aatatgccgc acacccgtct ggttgccggc ctgggcgcgg atgtcgaatt cggcaacggc   3060
tggaacggct tggcacgtta cagctacgcc ggttccaaac agtacggcaa ccacagcgga   3120
cgagtcggcg taggctaccg gttcctcgag ggtggcggag gcactggatc cgccacaaac   3180
gacgacgatg ttaaaaaagc tgccactgtg gccattgctg ctgcctacaa caatggccaa   3240
gaaatcaacg gtttcaaagc tggagagacc atctacgaca ttgatgaaga cggcacaatt   3300
accaaaaaag acgcaactgc agccgatgtt gaagccgacg actttaaagg tctgggtctg   3360
aaaaaagtcg tgactaacct gaccaaaacc gtcaatgaaa acaaacaaaa cgtcgatgcc   3420
aaagtaaaag ctgcagaatc tgaaatagaa aagttaacaa ccaagttagc agacactgat   3480
gccgctttag cagatactga tgccgctctg gatgcaacca ccaacgcctt gaataaattg   3540
ggagaaaata taacgacatt tgctgaagag actaagacaa atatcgtaaa aattgatgaa   3600
aaattagaag ccgtggctga taccgtcgac aagcatgccg aagcattcaa cgatatcgcc   3660
gattcattgg atgaaaccaa cactaaggca gacgaagccg tcaaaaccgc caatgaagcc   3720
aaacagacgg ccgaagaaac caaacaaaac gtcgatgcca aagtaaaagc tgcagaaact   3780
gcagcaggca aagccgaagc tgccgctggc acagctaata ctgcagccga caaggccgaa   3840
gctgtcgctg caaaagttac cgacatcaaa gctgatatcg ctacgaacaa agataatatt   3900
gctaaaaaag caaacagtgc cgacgtgtac accagagaag agtctgacag caaatttgtc   3960
agaattgatg gtctgaacgc tactaccgaa aaattggaca cacgcttggc ttctgctgaa   4020
aaatccattg ccgatcacga tactcgcctg aacggtttgg ataaaacagt gtcagacctg   4080
cgcaaagaaa cccgccaagg ccttgcagaa caagccgcgc tctccggtct gttccaacct   4140
```

-continued tacaacgtgg gtctcgagca ccaccaccac caccactga 4179

<210> SEQ ID NO 107
<211> LENGTH: 1392
<212> TYPE: PRT
<213> ORGANISM: Artificial Sequence
<220> FEATURE:
<223> OTHER INFORMATION: deltaG983-961c

<400> SEQUENCE: 107

Met Thr Ser Ala Pro Asp Phe Asn Ala Gly Gly Thr Gly Ile Gly Ser
1 5 10 15

Asn Ser Arg Ala Thr Thr Ala Lys Ser Ala Ala Val Ser Tyr Ala Gly
20 25 30

Ile Lys Asn Glu Met Cys Lys Asp Arg Ser Met Leu Cys Ala Gly Arg
35 40 45

Asp Asp Val Ala Val Thr Asp Arg Asp Ala Lys Ile Asn Ala Pro Pro
50 55 60

Pro Asn Leu His Thr Gly Asp Phe Pro Asn Pro Asn Asp Ala Tyr Lys
65 70 75 80

Asn Leu Ile Asn Leu Lys Pro Ala Ile Glu Ala Gly Tyr Thr Gly Arg
85 90 95

Gly Val Glu Val Gly Ile Val Asp Thr Gly Glu Ser Val Gly Ser Ile
100 105 110

Ser Phe Pro Glu Leu Tyr Gly Arg Lys Glu His Gly Tyr Asn Glu Asn
115 120 125

Tyr Lys Asn Tyr Thr Ala Tyr Met Arg Lys Glu Ala Pro Glu Asp Gly
130 135 140

Gly Gly Lys Asp Ile Glu Ala Ser Phe Asp Asp Glu Ala Val Ile Glu
145 150 155 160

Thr Glu Ala Lys Pro Thr Asp Ile Arg His Val Lys Glu Ile Gly His
165 170 175

Ile Asp Leu Val Ser His Ile Ile Gly Gly Arg Ser Val Asp Gly Arg
180 185 190

Pro Ala Gly Gly Ile Ala Pro Asp Ala Thr Leu His Ile Met Asn Thr
195 200 205

Asn Asp Glu Thr Lys Asn Glu Met Met Val Ala Ala Ile Arg Asn Ala
210 215 220

Trp Val Lys Leu Gly Glu Arg Gly Val Arg Ile Val Asn Asn Ser Phe
225 230 235 240

Gly Thr Thr Ser Arg Ala Gly Thr Ala Asp Leu Phe Gln Ile Ala Asn
245 250 255

Ser Glu Glu Gln Tyr Arg Gln Ala Leu Leu Asp Tyr Ser Gly Gly Asp
260 265 270

Lys Thr Asp Glu Gly Ile Arg Leu Met Gln Gln Ser Asp Tyr Gly Asn
275 280 285

Leu Ser Tyr His Ile Arg Asn Lys Asn Met Leu Phe Ile Phe Ser Thr
290 295 300

Gly Asn Asp Ala Gln Ala Gln Pro Asn Thr Tyr Ala Leu Leu Pro Phe
305 310 315 320

Tyr Glu Lys Asp Ala Gln Lys Gly Ile Ile Thr Val Ala Gly Val Asp
325 330 335

Arg Ser Gly Glu Lys Phe Lys Arg Glu Met Tyr Gly Glu Pro Gly Thr
340 345 350

Glu Pro Leu Glu Tyr Gly Ser Asn His Cys Gly Ile Thr Ala Met Trp

-continued

```
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
    610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
    690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Ala Val Gln His
                725                 730                 735

Ala Asn Ala Ala Asp Gly Val Arg Ile Phe Asn Ser Leu Ala Ala Thr
            740                 745                 750

Val Tyr Ala Asp Ser Thr Ala Ala His Ala Asp Met Gln Gly Arg Arg
        755                 760                 765

Leu Lys Ala Val Ser Asp Gly Leu Asp His Asn Gly Thr Gly Leu Arg
    770                 775                 780
```

-continued

```
Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Ala Thr Leu Gly Met Gly Arg
            820                 825                 830

Ser Thr Trp Ser Glu Asn Ser Ala Asn Ala Lys Thr Asp Ser Ile Ser
        835                 840                 845

Leu Phe Ala Gly Ile Arg His Asp Ala Gly Asp Ile Gly Tyr Leu Lys
    850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
        915                 920                 925

Phe Ala Glu Lys Gly Ser Ala Leu Gly Trp Ser Gly Asn Ser Leu Thr
    930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
            980                 985                 990

Ala Thr Gly Lys Thr Gly Ala Arg Asn Met Pro His Thr Arg Leu Val
        995                 1000                1005

Ala Gly Leu Gly Ala Asp Val Glu Phe Gly Asn Gly Trp Asn Gly Leu
    1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Gly Gly Gly Thr Gly
                1045                1050                1055

Ser Ala Thr Asn Asp Asp Asp Val Lys Lys Ala Ala Thr Val Ala Ile
            1060                1065                1070

Ala Ala Ala Tyr Asn Asn Gly Gln Glu Ile Asn Gly Phe Lys Ala Gly
        1075                1080                1085

Glu Thr Ile Tyr Asp Ile Asp Glu Asp Gly Thr Ile Thr Lys Lys Asp
    1090                1095                1100

Ala Thr Ala Ala Asp Val Glu Ala Asp Asp Phe Lys Gly Leu Gly Leu
1105                1110                1115                1120

Lys Lys Val Val Thr Asn Leu Thr Lys Thr Val Asn Glu Asn Lys Gln
                1125                1130                1135

Asn Val Asp Ala Lys Val Lys Ala Ala Glu Ser Glu Ile Glu Lys Leu
            1140                1145                1150

Thr Thr Lys Leu Ala Asp Thr Asp Ala Ala Leu Ala Asp Thr Asp Ala
        1155                1160                1165

Ala Leu Asp Ala Thr Thr Asn Ala Leu Asn Lys Leu Gly Glu Asn Ile
    1170                1175                1180

Thr Thr Phe Ala Glu Glu Thr Lys Thr Asn Ile Val Lys Ile Asp Glu
1185                1190                1195                1200
```

-continued

```
Lys Leu Glu Ala Val Ala Asp Thr Val Asp Lys His Ala Glu Ala Phe
                1205                1210                1215

Asn Asp Ile Ala Asp Ser Leu Asp Glu Thr Asn Thr Lys Ala Asp Glu
            1220                1225                1230

Ala Val Lys Thr Ala Asn Glu Ala Lys Gln Thr Ala Glu Glu Thr Lys
        1235                1240                1245

Gln Asn Val Asp Ala Lys Val Lys Ala Ala Glu Thr Ala Ala Gly Lys
    1250                1255                1260

Ala Glu Ala Ala Ala Gly Thr Ala Asn Thr Ala Ala Asp Lys Ala Glu
1265                1270                1275                1280

Ala Val Ala Ala Lys Val Thr Asp Ile Lys Ala Asp Ile Ala Thr Asn
                1285                1290                1295

Lys Asp Asn Ile Ala Lys Lys Ala Asn Ser Ala Asp Val Tyr Thr Arg
            1300                1305                1310

Glu Glu Ser Asp Ser Lys Phe Val Arg Ile Asp Gly Leu Asn Ala Thr
        1315                1320                1325

Thr Glu Lys Leu Asp Thr Arg Leu Ala Ser Ala Glu Lys Ser Ile Ala
    1330                1335                1340

Asp His Asp Thr Arg Leu Asn Gly Leu Asp Lys Thr Val Ser Asp Leu
1345                1350                1355                1360

Arg Lys Glu Thr Arg Gln Gly Leu Ala Glu Gln Ala Ala Leu Ser Gly
                1365                1370                1375

Leu Phe Gln Pro Tyr Asn Val Gly Leu Glu His His His His His His
            1380                1385                1390
```

<210> SEQ ID NO 108
<211> LENGTH: 1947
<212> TYPE: DNA
<213> ORGANISM: Artificial Sequence
<220> FEATURE:
<223> OTHER INFORMATION: deltaG741-961

<400> SEQUENCE: 108

```
atggtcgccg ccgacatcgg tgcggggctt gccgatgcac taaccgcacc gctcgaccat     60

aaagacaaag gtttgcagtc tttgacgctg gatcagtccg tcaggaaaaa cgagaaactg    120

aagctggcgg cacaaggtgc ggaaaaaact tatggaaacg gtgacagcct caatacgggc    180

aaattgaaga acgacaaggt cagccgtttc gactttatcc gccaaatcga agtggacggg    240

cagctcatta ccttggagag tggagagttc caagtataca aacaaagcca ttccgcctta    300

accgcctttc agaccgagca aatacaagat tcggagcatt ccgggaagat ggttgcgaaa    360

cgccagttca gaatcggcga catagcgggc gaacatacat cttttgacaa gcttcccgaa    420

ggcggcaggg cgacatatcg cgggacggcg ttcggttcag acgatgccgg cggaaaactg    480

acctacacca tagatttcgc cgccaagcag ggaaacggca aaatcgaaca tttgaaatcg    540

ccagaactca atgtcgacct ggccgccgcc gatatcaagc cggatggaaa acgccatgcc    600

gtcatcagcg gttccgtcct ttacaaccaa gccgagaaag gcagttactc cctcggtatc    660

tttggcggaa aagcccagga agttgccggc agcgcggaag tgaaaaccgt aaacggcata    720

cgccatatcg gccttgccgc caagcaactc gagggtggcg gaggcactgg atccgccaca    780

aacgacgacg atgttaaaaa agctgccact gtggccattg ctgctgccta caacaatggc    840

caagaaatca acggtttcaa agctggagag accatctacg acattgatga agacggcaca    900

attaccaaaa aagacgcaac tgcagccgat gttgaagccg acgactttaa aggtctgggt    960

ctgaaaaaag tcgtgactaa cctgaccaaa accgtcaatg aaaacaaaca aaacgtcgat   1020
```

-continued

```
gccaaagtaa aagctgcaga atctgaaata gaaaagttaa caaccaagtt agcagacact   1080
gatgccgctt tagcagatac tgatgccgct ctggatgcaa ccaccaacgc cttgaataaa   1140
ttgggagaaa atataacgac atttgctgaa gagactaaga caaatatcgt aaaaattgat   1200
gaaaaattag aagccgtggc tgataccgtc gacaagcatg ccgaagcatt caacgatatc   1260
gccgattcat tggatgaaac caacactaag gcagacgaag ccgtcaaaac cgccaatgaa   1320
gccaaacaga cggccgaaga aaccaaacaa aacgtcgatg ccaaagtaaa agctgcagaa   1380
actgcagcag gcaaagccga agctgccgct ggcacagcta atactgcagc cgacaaggcc   1440
gaagctgtcg ctgcaaaagt taccgacatc aaagctgata tcgctacgaa caaagataat   1500
attgctaaaa aagcaaacag tgccgacgtg tacaccagag aagagtctga cagcaaattt   1560
gtcagaattg atggtctgaa cgctactacc gaaaaattgg acacacgctt ggcttctgct   1620
gaaaaatcca ttgccgatca cgatactcgc ctgaacggtt tggataaaac agtgtcagac   1680
ctgcgcaaag aaacccgcca aggccttgca gaacaagccg cgctctccgg tctgttccaa   1740
ccttacaacg tgggtcggtt caatgtaacg gctgcagtcg gcggctacaa atccgaatcg   1800
gcagtcgcca tcggtaccgg cttccgcttt accgaaaact ttgccgccaa agcaggcgtg   1860
gcagtcggca cttcgtccgg ttcttccgca gcctaccatg tcggcgtcaa ttacgagtgg   1920
ctcgagcacc accaccacca ccactga                                       1947
```

<210> SEQ ID NO 109
<211> LENGTH: 648
<212> TYPE: PRT
<213> ORGANISM: Artificial Sequence
<220> FEATURE:
<223> OTHER INFORMATION: deltaG741-961

<400> SEQUENCE: 109

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190
```

-continued

```
Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Gly Gly Gly Thr
                245                 250                 255

Gly Ser Ala Thr Asn Asp Asp Asp Val Lys Lys Ala Ala Thr Val Ala
            260                 265                 270

Ile Ala Ala Ala Tyr Asn Asn Gly Gln Glu Ile Asn Gly Phe Lys Ala
        275                 280                 285

Gly Glu Thr Ile Tyr Asp Ile Asp Glu Asp Gly Thr Ile Thr Lys Lys
    290                 295                 300

Asp Ala Thr Ala Ala Asp Val Glu Ala Asp Asp Phe Lys Gly Leu Gly
305                 310                 315                 320

Leu Lys Lys Val Val Thr Asn Leu Thr Lys Thr Val Asn Glu Asn Lys
                325                 330                 335

Gln Asn Val Asp Ala Lys Val Lys Ala Ala Glu Ser Glu Ile Glu Lys
            340                 345                 350

Leu Thr Thr Lys Leu Ala Asp Thr Asp Ala Ala Leu Ala Asp Thr Asp
        355                 360                 365

Ala Ala Leu Asp Ala Thr Thr Asn Ala Leu Asn Lys Leu Gly Glu Asn
    370                 375                 380

Ile Thr Thr Phe Ala Glu Glu Thr Lys Thr Asn Ile Val Lys Ile Asp
385                 390                 395                 400

Glu Lys Leu Glu Ala Val Ala Asp Thr Val Asp Lys His Ala Glu Ala
                405                 410                 415

Phe Asn Asp Ile Ala Asp Ser Leu Asp Glu Thr Asn Thr Lys Ala Asp
            420                 425                 430

Glu Ala Val Lys Thr Ala Asn Glu Ala Lys Gln Thr Ala Glu Glu Thr
        435                 440                 445

Lys Gln Asn Val Asp Ala Lys Val Lys Ala Ala Glu Thr Ala Ala Gly
    450                 455                 460

Lys Ala Glu Ala Ala Ala Gly Thr Ala Asn Thr Ala Ala Asp Lys Ala
465                 470                 475                 480

Glu Ala Val Ala Ala Lys Val Thr Asp Ile Lys Ala Asp Ile Ala Thr
                485                 490                 495

Asn Lys Asp Asn Ile Ala Lys Lys Ala Asn Ser Ala Asp Val Tyr Thr
            500                 505                 510

Arg Glu Glu Ser Asp Ser Lys Phe Val Arg Ile Asp Gly Leu Asn Ala
        515                 520                 525

Thr Thr Glu Lys Leu Asp Thr Arg Leu Ala Ser Ala Glu Lys Ser Ile
    530                 535                 540

Ala Asp His Asp Thr Arg Leu Asn Gly Leu Asp Lys Thr Val Ser Asp
545                 550                 555                 560

Leu Arg Lys Glu Thr Arg Gln Gly Leu Ala Glu Gln Ala Ala Leu Ser
                565                 570                 575

Gly Leu Phe Gln Pro Tyr Asn Val Gly Arg Phe Asn Val Thr Ala Ala
            580                 585                 590

Val Gly Gly Tyr Lys Ser Glu Ser Ala Val Ala Ile Gly Thr Gly Phe
        595                 600                 605

Arg Phe Thr Glu Asn Phe Ala Ala Lys Ala Gly Val Ala Val Gly Thr
```

-continued

```
    610                 615                 620

Ser Ser Gly Ser Ser Ala Ala Tyr His Val Gly Val Asn Tyr Glu Trp
625                 630                 635                 640

Leu Glu His His His His His His
                645


<210> SEQ ID NO 110
<211> LENGTH: 1782
<212> TYPE: DNA
<213> ORGANISM: Artificial Sequence
<220> FEATURE:
<223> OTHER INFORMATION: deltaG741-961c

<400> SEQUENCE: 110

atggtcgccg ccgacatcgg tgcggggctt gccgatgcac taaccgcacc gctcgaccat     60

aaagacaaag gtttgcagtc tttgacgctg gatcagtccg tcaggaaaaa cgagaaactg    120

aagctggcgg cacaaggtgc ggaaaaaact tatggaaacg gtgacagcct caatacgggc    180

aaattgaaga acgacaaggt cagccgtttc gactttatcc gccaaatcga agtggacggg    240

cagctcatta ccttggagag tggagagttc caagtataca aacaaagcca ttccgcctta    300

accgcctttc agaccgagca aatacaagat tcggagcatt ccgggaagat ggttgcgaaa    360

cgccagttca gaatcggcga catagcgggc gaacatacat cttttgacaa gcttcccgaa    420

ggcggcaggg cgacatatcg cgggacggcg ttcggttcag acgatgccgg cggaaaactg    480

acctacacca tagatttcgc cgccaagcag ggaaacggca aaatcgaaca tttgaaatcg    540

ccagaactca atgtcgacct ggccgccgcc gatatcaagc cggatggaaa acgccatgcc    600

gtcatcagcg gttccgtcct ttacaaccaa gccgagaaag gcagttactc cctcggtatc    660

tttggcggaa aagcccagga agttgccggc agcgcggaag tgaaaaccgt aaacggcata    720

cgccatatcg gccttgccgc caagcaactc gagggtggcg gaggcactgg atccgccaca    780

aacgacgacg atgttaaaaa agctgccact gtggccattg ctgctgccta caacaatggc    840

caagaaatca acggtttcaa agctggagag accatctacg acattgatga agacggcaca    900

attaccaaaa aagacgcaac tgcagccgat gttgaagccg acgactttaa aggtctgggt    960

ctgaaaaaag tcgtgactaa cctgaccaaa accgtcaatg aaaacaaaca aaacgtcgat   1020

gccaaagtaa aagctgcaga atctgaaata gaaaagttaa caaccaagtt agcagacact   1080

gatgccgctt tagcagatac tgatgccgct ctggatgcaa ccaccaacgc cttgaataaa   1140

ttgggagaaa atataacgac atttgctgaa gagactaaga caaatatcgt aaaaattgat   1200

gaaaaattag aagccgtggc tgataccgtc gacaagcatg ccgaagcatt caacgatatc   1260

gccgattcat tggatgaaac caacactaag gcagacgaag ccgtcaaaac cgccaatgaa   1320

gccaaacaga cggccgaaga aaccaaacaa aacgtcgatg ccaaagtaaa agctgcagaa   1380

actgcagcag gcaaagccga agctgccgct ggcacagcta atactgcagc cgacaaggcc   1440

gaagctgtcg ctgcaaaagt taccgacatc aaagctgata tcgctacgaa caaagataat   1500

attgctaaaa aagcaaacag tgccgacgtg tacaccagag aagagtctga cagcaaattt   1560

gtcagaattg atggtctgaa cgctactacc gaaaaattgg acacacgctt ggcttctgct   1620

gaaaaatcca ttgccgatca cgatactcgc ctgaacggtt tggataaaac agtgtcagac   1680

ctgcgcaaag aaacccgcca aggccttgca gaacaagccg cgctctccgg tctgttccaa   1740

ccttacaacg tgggtctcga gcaccaccac caccaccact ga                       1782
```

<210> SEQ ID NO 111
<211> LENGTH: 593
<212> TYPE: PRT
<213> ORGANISM: Artificial Sequence
<220> FEATURE:
<223> OTHER INFORMATION: deltaG741-961c

<400> SEQUENCE: 111

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Gly Gly Gly Thr
                245                 250                 255

Gly Ser Ala Thr Asn Asp Asp Asp Val Lys Lys Ala Ala Thr Val Ala
            260                 265                 270

Ile Ala Ala Ala Tyr Asn Asn Gly Gln Glu Ile Asn Gly Phe Lys Ala
        275                 280                 285

Gly Glu Thr Ile Tyr Asp Ile Asp Glu Asp Gly Thr Ile Thr Lys Lys
    290                 295                 300

Asp Ala Thr Ala Ala Asp Val Glu Ala Asp Asp Phe Lys Gly Leu Gly
305                 310                 315                 320

Leu Lys Lys Val Val Thr Asn Leu Thr Lys Thr Val Asn Glu Asn Lys
                325                 330                 335

Gln Asn Val Asp Ala Lys Val Lys Ala Ala Glu Ser Glu Ile Glu Lys
            340                 345                 350

Leu Thr Thr Lys Leu Ala Asp Thr Asp Ala Ala Leu Ala Asp Thr Asp
        355                 360                 365

Ala Ala Leu Asp Ala Thr Thr Asn Ala Leu Asn Lys Leu Gly Glu Asn
```

-continued

```
    370                 375                 380

Ile Thr Thr Phe Ala Glu Glu Thr Lys Thr Asn Ile Val Lys Ile Asp
385                 390                 395                 400

Glu Lys Leu Glu Ala Val Ala Asp Thr Val Asp Lys His Ala Glu Ala
                405                 410                 415

Phe Asn Asp Ile Ala Asp Ser Leu Asp Glu Thr Asn Thr Lys Ala Asp
            420                 425                 430

Glu Ala Val Lys Thr Ala Asn Glu Ala Lys Gln Thr Ala Glu Glu Thr
        435                 440                 445

Lys Gln Asn Val Asp Ala Lys Val Lys Ala Ala Glu Thr Ala Ala Gly
    450                 455                 460

Lys Ala Glu Ala Ala Ala Gly Thr Ala Asn Thr Ala Ala Asp Lys Ala
465                 470                 475                 480

Glu Ala Val Ala Ala Lys Val Thr Asp Ile Lys Ala Asp Ile Ala Thr
                485                 490                 495

Asn Lys Asp Asn Ile Ala Lys Lys Ala Asn Ser Ala Asp Val Tyr Thr
            500                 505                 510

Arg Glu Glu Ser Asp Ser Lys Phe Val Arg Ile Asp Gly Leu Asn Ala
        515                 520                 525

Thr Thr Glu Lys Leu Asp Thr Arg Leu Ala Ser Ala Glu Lys Ser Ile
    530                 535                 540

Ala Asp His Asp Thr Arg Leu Asn Gly Leu Asp Lys Thr Val Ser Asp
545                 550                 555                 560

Leu Arg Lys Glu Thr Arg Gln Gly Leu Ala Glu Gln Ala Ala Leu Ser
                565                 570                 575

Gly Leu Phe Gln Pro Tyr Asn Val Gly Leu Glu His His His His His
            580                 585                 590

His
```

<210> SEQ ID NO 112
<211> LENGTH: 3939
<212> TYPE: DNA
<213> ORGANISM: Artificial Sequence
<220> FEATURE:
<223> OTHER INFORMATION: deltaG741-983

<400> SEQUENCE: 112

```
atggtcgccg ccgacatcgg tgcggggctt gccgatgcac taaccgcacc gctcgaccat     60

aaagacaaag gtttgcagtc tttgacgctg gatcagtccg tcaggaaaaa cgagaaactg    120

aagctggcgg cacaaggtgc ggaaaaaact tatggaaacg gtgacagcct caatacgggc    180

aaattgaaga acgacaaggt cagccgtttc gactttatcc gccaaatcga agtggacggg    240

cagctcatta ccttggagag tggagagttc caagtataca aacaaagcca ttccgcctta    300

accgcctttc agaccgagca aatacaagat tcggagcatt ccgggaagat ggttgcgaaa    360

cgccagttca gaatcggcga catagcgggc gaacatacat cttttgacaa gcttcccgaa    420

ggcggcaggg cgacatatcg cgggacggcg ttcggttcag acgatgccgg cggaaaactg    480

acctacacca tagatttcgc cgccaagcag ggaaacggca aaatcgaaca tttgaaatcg    540

ccagaactca atgtcgacct ggccgccgcc gatatcaagc cggatggaaa acgccatgcc    600

gtcatcagcg gttccgtcct ttacaaccaa gccgagaaag gcagttactc cctcggtatc    660

tttggcggaa aagcccagga agttgccggc agcgcggaag tgaaaaccgt aaacggcata    720

cgccatatcg gccttgccgc caagcaactc gagggatccg gcggaggcgg cacttctgcg    780
```

-continued

```
cccgacttca atgcaggcgg taccggtatc ggcagcaaca gcagagcaac aacagcgaaa    840
tcagcagcag tatcttacgc cggtatcaag aacgaaatgt gcaaagacag aagcatgctc    900
tgtgccggtc gggatgacgt tgcggttaca gacagggatg ccaaaatcaa tgcccccccc    960
ccgaatctgc ataccggaga ctttccaaac ccaaatgacg catacaagaa tttgatcaac   1020
ctcaaacctg caattgaagc aggctataca ggacgcgggg tagaggtagg tatcgtcgac   1080
acaggcgaat ccgtcggcag catatccttt cccgaactgt atggcagaaa agaacacggc   1140
tataacgaaa attacaaaaa ctatacggcg tatatgcgga aggaagcgcc tgaagacgga   1200
ggcggtaaag acattgaagc ttctttcgac gatgaggccg ttatagagac tgaagcaaag   1260
ccgacggata tccgccacgt aaaagaaatc ggacacatcg atttggtctc ccatattatt   1320
ggcgggcgtt ccgtggacgg cagacctgca ggcggtattg cgcccgatgc gacgctacac   1380
ataatgaata cgaatgatga aaccaagaac gaaatgatgg ttgcagccat ccgcaatgca   1440
tgggtcaagc tgggcgaacg tggcgtgcgc atcgtcaata acagttttgg aacaacatcg   1500
agggcaggca ctgccgacct tttccaaata gccaattcgg aggagcagta ccgccaagcg   1560
ttgctcgact attccggcgg tgataaaaca gacgagggta tccgcctgat gcaacagagc   1620
gattacggca acctgtccta ccacatccgt aataaaaaca tgcttttcat cttttcgaca   1680
ggcaatgacg cacaagctca gcccaacaca tatgccctat tgccatttta tgaaaaagac   1740
gctcaaaaag gcattatcac agtcgcaggc gtagaccgca gtggagaaaa gttcaaacgg   1800
gaaatgtatg gagaaccggg tacagaaccg cttgagtatg gctccaacca ttgcggaatt   1860
actgccatgt ggtgcctgtc ggcaccctat gaagcaagcg tccgtttcac ccgtacaaac   1920
ccgattcaaa ttgccggaac atccttttcc gcacccatcg taaccggcac ggcggctctg   1980
ctgctgcaga aatacccgtg gatgagcaac gacaacctgc gtaccacgtt gctgacgacg   2040
gctcaggaca tcggtgcagt cggcgtggac agcaagttcg gctggggact gctggatgcg   2100
ggtaaggcca tgaacggacc cgcgtccttt ccgttcggcg actttaccgc cgatacgaaa   2160
ggtacatccg atattgccta ctccttccgt aacgacattt caggcacggg cggcctgatc   2220
aaaaaaggcg gcagccaact gcaactgcac ggcaacaaca cctatacggg caaaaccatt   2280
atcgaaggcg gttcgctggt gttgtacggc aacaacaaat cggatatgcg cgtcgaaacc   2340
aaaggtgcgc tgatttataa cggggcggca tccggcggca gcctgaacag cgacggcatt   2400
gtctatctgg cagataccga ccaatccggc gcaaacgaaa ccgtacacat caaaggcagt   2460
ctgcagctgg acggcaaagg tacgctgtac acacgtttgg gcaaactgct gaaagtggac   2520
ggtacggcga ttatcggcgg caagctgtac atgtcggcac gcggcaaggg ggcaggctat   2580
ctcaacagta ccggacgacg tgttcccttc ctgagtgccg ccaaaatcgg gcaggattat   2640
tctttcttca caaacatcga aaccgacggc ggcctgctgg cttccctcga cagcgtcgaa   2700
aaaacagcgg gcagtgaagg cgacacgctg tcctattatg tccgtcgcgg caatgcggca   2760
cggactgctt cggcagcggc acattccgcg cccgccggtc tgaaacacgc cgtagaacag   2820
ggcggcagca atctggaaaa cctgatggtc gaactggatg cctccgaatc atccgcaaca   2880
cccgagacgg ttgaaactgc ggcagccgac cgcacagata tgccgggcat ccgcccctac   2940
ggcgcaactt tccgcgcagc ggcagccgta cagcatgcga atgccgccga cggtgtacgc   3000
atcttcaaca gtctcgccgc taccgtctat gccgacagta ccgccgccca tgccgatatg   3060
cagggacgcc gcctgaaagc cgtatcggac gggttggacc acaacggcac gggtctgcgc   3120
gtcatcgcgc aaacccaaca ggacggtgga acgtgggaac agggcggtgt tgaaggcaaa   3180
```

-continued

```
atgcgcggca gtacccaaac cgtcggcatt gccgcgaaaa ccggcgaaaa tacgacagca   3240

gccgccacac tgggcatggg acgcagcaca tggagcgaaa acagtgcaaa tgcaaaaacc   3300

gacagcatta gtctgtttgc aggcatacgg cacgatgcgg gcgatatcgg ctatctcaaa   3360

ggcctgttct cctacggacg ctacaaaaac agcatcagcc gcagcaccgg tgcggacgaa   3420

catgcggaag gcagcgtcaa cggcacgctg atgcagctgg gcgcactggg cggtgtcaac   3480

gttccgtttg ccgcaacggg agatttgacg gtcgaaggcg gtctgcgcta cgacctgctc   3540

aaacaggatg cattcgccga aaaaggcagt gctttgggct ggagcggcaa cagcctcact   3600

gaaggcacgc tggtcggact cgcgggtctg aagctgtcgc aacccttgag cgataaagcc   3660

gtcctgtttg caacggcggg cgtggaacgc gacctgaacg gacgcgacta cacggtaacg   3720

ggcggcttta ccggcgcgac tgcagcaacc ggcaagacgg gggcacgcaa tatgccgcac   3780

acccgtctgg ttgccggcct gggcgcggat gtcgaattcg gcaacggctg gaacggcttg   3840

gcacgttaca gctacgccgg ttccaaacag tacggcaacc acagcggacg agtcggcgta   3900

ggctaccggt tcctcgagca ccaccaccac caccactga                          3939
```

```
<210> SEQ ID NO 113
<211> LENGTH: 1312
<212> TYPE: PRT
<213> ORGANISM: Artificial Sequence
<220> FEATURE:
<223> OTHER INFORMATION: deltaG741-983

<400> SEQUENCE: 113

Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220
```

-continued

```
Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Ser Gly Gly Gly
                245                 250                 255

Gly Thr Ser Ala Pro Asp Phe Asn Ala Gly Gly Thr Gly Ile Gly Ser
            260                 265                 270

Asn Ser Arg Ala Thr Thr Ala Lys Ser Ala Ala Val Ser Tyr Ala Gly
        275                 280                 285

Ile Lys Asn Glu Met Cys Lys Asp Arg Ser Met Leu Cys Ala Gly Arg
    290                 295                 300

Asp Asp Val Ala Val Thr Asp Arg Asp Ala Lys Ile Asn Ala Pro Pro
305                 310                 315                 320

Pro Asn Leu His Thr Gly Asp Phe Pro Asn Pro Asn Asp Ala Tyr Lys
                325                 330                 335

Asn Leu Ile Asn Leu Lys Pro Ala Ile Glu Ala Gly Tyr Thr Gly Arg
            340                 345                 350

Gly Val Glu Val Gly Ile Val Asp Thr Gly Glu Ser Val Gly Ser Ile
        355                 360                 365

Ser Phe Pro Glu Leu Tyr Gly Arg Lys Glu His Gly Tyr Asn Glu Asn
    370                 375                 380

Tyr Lys Asn Tyr Thr Ala Tyr Met Arg Lys Glu Ala Pro Glu Asp Gly
385                 390                 395                 400

Gly Gly Lys Asp Ile Glu Ala Ser Phe Asp Asp Glu Ala Val Ile Glu
                405                 410                 415

Thr Glu Ala Lys Pro Thr Asp Ile Arg His Val Lys Glu Ile Gly His
            420                 425                 430

Ile Asp Leu Val Ser His Ile Ile Gly Gly Arg Ser Val Asp Gly Arg
        435                 440                 445

Pro Ala Gly Gly Ile Ala Pro Asp Ala Thr Leu His Ile Met Asn Thr
    450                 455                 460

Asn Asp Glu Thr Lys Asn Glu Met Met Val Ala Ala Ile Arg Asn Ala
465                 470                 475                 480

Trp Val Lys Leu Gly Glu Arg Gly Val Arg Ile Val Asn Asn Ser Phe
                485                 490                 495

Gly Thr Thr Ser Arg Ala Gly Thr Ala Asp Leu Phe Gln Ile Ala Asn
            500                 505                 510

Ser Glu Glu Gln Tyr Arg Gln Ala Leu Leu Asp Tyr Ser Gly Gly Asp
        515                 520                 525

Lys Thr Asp Glu Gly Ile Arg Leu Met Gln Gln Ser Asp Tyr Gly Asn
    530                 535                 540

Leu Ser Tyr His Ile Arg Asn Lys Asn Met Leu Phe Ile Phe Ser Thr
545                 550                 555                 560

Gly Asn Asp Ala Gln Ala Gln Pro Asn Thr Tyr Ala Leu Leu Pro Phe
                565                 570                 575

Tyr Glu Lys Asp Ala Gln Lys Gly Ile Ile Thr Val Ala Gly Val Asp
            580                 585                 590

Arg Ser Gly Glu Lys Phe Lys Arg Glu Met Tyr Gly Glu Pro Gly Thr
        595                 600                 605

Glu Pro Leu Glu Tyr Gly Ser Asn His Cys Gly Ile Thr Ala Met Trp
    610                 615                 620

Cys Leu Ser Ala Pro Tyr Glu Ala Ser Val Arg Phe Thr Arg Thr Asn
625                 630                 635                 640

Pro Ile Gln Ile Ala Gly Thr Ser Phe Ser Ala Pro Ile Val Thr Gly
```

-continued

```
                645                 650                 655

Thr Ala Ala Leu Leu Leu Gln Lys Tyr Pro Trp Met Ser Asn Asp Asn
            660                 665                 670

Leu Arg Thr Thr Leu Leu Thr Thr Ala Gln Asp Ile Gly Ala Val Gly
        675                 680                 685

Val Asp Ser Lys Phe Gly Trp Gly Leu Leu Asp Ala Gly Lys Ala Met
    690                 695                 700

Asn Gly Pro Ala Ser Phe Pro Phe Gly Asp Phe Thr Ala Asp Thr Lys
705                 710                 715                 720

Gly Thr Ser Asp Ile Ala Tyr Ser Phe Arg Asn Asp Ile Ser Gly Thr
                725                 730                 735

Gly Gly Leu Ile Lys Lys Gly Gly Ser Gln Leu Gln Leu His Gly Asn
            740                 745                 750

Asn Thr Tyr Thr Gly Lys Thr Ile Ile Glu Gly Gly Ser Leu Val Leu
        755                 760                 765

Tyr Gly Asn Asn Lys Ser Asp Met Arg Val Glu Thr Lys Gly Ala Leu
    770                 775                 780

Ile Tyr Asn Gly Ala Ala Ser Gly Gly Ser Leu Asn Ser Asp Gly Ile
785                 790                 795                 800

Val Tyr Leu Ala Asp Thr Asp Gln Ser Gly Ala Asn Glu Thr Val His
                805                 810                 815

Ile Lys Gly Ser Leu Gln Leu Asp Gly Lys Gly Thr Leu Tyr Thr Arg
            820                 825                 830

Leu Gly Lys Leu Leu Lys Val Asp Gly Thr Ala Ile Ile Gly Gly Lys
        835                 840                 845

Leu Tyr Met Ser Ala Arg Gly Lys Gly Ala Gly Tyr Leu Asn Ser Thr
    850                 855                 860

Gly Arg Arg Val Pro Phe Leu Ser Ala Ala Lys Ile Gly Gln Asp Tyr
865                 870                 875                 880

Ser Phe Phe Thr Asn Ile Glu Thr Asp Gly Gly Leu Leu Ala Ser Leu
                885                 890                 895

Asp Ser Val Glu Lys Thr Ala Gly Ser Glu Gly Asp Thr Leu Ser Tyr
            900                 905                 910

Tyr Val Arg Arg Gly Asn Ala Ala Arg Thr Ala Ser Ala Ala Ala His
        915                 920                 925

Ser Ala Pro Ala Gly Leu Lys His Ala Val Glu Gln Gly Gly Ser Asn
    930                 935                 940

Leu Glu Asn Leu Met Val Glu Leu Asp Ala Ser Glu Ser Ser Ala Thr
945                 950                 955                 960

Pro Glu Thr Val Glu Thr Ala Ala Ala Asp Arg Thr Asp Met Pro Gly
                965                 970                 975

Ile Arg Pro Tyr Gly Ala Thr Phe Arg Ala Ala Ala Ala Val Gln His
            980                 985                 990

Ala Asn Ala Ala Asp Gly Val Arg Ile Phe Asn Ser Leu Ala Ala Thr
        995                 1000                1005

Val Tyr Ala Asp Ser Thr Ala Ala His Ala Asp Met Gln Gly Arg Arg
    1010                1015                1020

Leu Lys Ala Val Ser Asp Gly Leu Asp His Asn Gly Thr Gly Leu Arg
1025                1030                1035                1040

Val Ile Ala Gln Thr Gln Gln Asp Gly Gly Thr Trp Glu Gln Gly Gly
                1045                1050                1055

Val Glu Gly Lys Met Arg Gly Ser Thr Gln Thr Val Gly Ile Ala Ala
            1060                1065                1070
```

-continued

```
Lys Thr Gly Glu Asn Thr Thr Ala Ala Ala Thr Leu Gly Met Gly Arg
        1075                1080                1085

Ser Thr Trp Ser Glu Asn Ser Ala Asn Ala Lys Thr Asp Ser Ile Ser
    1090                1095                1100

Leu Phe Ala Gly Ile Arg His Asp Ala Gly Asp Ile Gly Tyr Leu Lys
1105                1110                1115                1120

Gly Leu Phe Ser Tyr Gly Arg Tyr Lys Asn Ser Ile Ser Arg Ser Thr
                1125                1130                1135

Gly Ala Asp Glu His Ala Glu Gly Ser Val Asn Gly Thr Leu Met Gln
            1140                1145                1150

Leu Gly Ala Leu Gly Gly Val Asn Val Pro Phe Ala Ala Thr Gly Asp
        1155                1160                1165

Leu Thr Val Glu Gly Gly Leu Arg Tyr Asp Leu Leu Lys Gln Asp Ala
    1170                1175                1180

Phe Ala Glu Lys Gly Ser Ala Leu Gly Trp Ser Gly Asn Ser Leu Thr
1185                1190                1195                1200

Glu Gly Thr Leu Val Gly Leu Ala Gly Leu Lys Leu Ser Gln Pro Leu
                1205                1210                1215

Ser Asp Lys Ala Val Leu Phe Ala Thr Ala Gly Val Glu Arg Asp Leu
            1220                1225                1230

Asn Gly Arg Asp Tyr Thr Val Thr Gly Gly Phe Thr Gly Ala Thr Ala
        1235                1240                1245

Ala Thr Gly Lys Thr Gly Ala Arg Asn Met Pro His Thr Arg Leu Val
    1250                1255                1260

Ala Gly Leu Gly Ala Asp Val Glu Phe Gly Asn Gly Trp Asn Gly Leu
1265                1270                1275                1280

Ala Arg Tyr Ser Tyr Ala Gly Ser Lys Gln Tyr Gly Asn His Ser Gly
                1285                1290                1295

Arg Val Gly Val Gly Tyr Arg Phe Leu Glu His His His His His His
            1300                1305                1310
```

<210> SEQ ID NO 114
<211> LENGTH: 2028
<212> TYPE: DNA
<213> ORGANISM: Artificial Sequence
<220> FEATURE:
<223> OTHER INFORMATION: deltaG741-ORF46.1

<400> SEQUENCE: 114

```
atggtcgccg ccgacatcgg tgcggggctt gccgatgcac taaccgcacc gctcgaccat     60

aaagacaaag gtttgcagtc tttgacgctg gatcagtccg tcaggaaaaa cgagaaactg    120

aagctggcgg cacaaggtgc ggaaaaaact tatggaaacg gtgacagcct caatacgggc    180

aaattgaaga acgacaaggt cagccgtttc gactttatcc gccaaatcga agtggacggg    240

cagctcatta ccttggagag tggagagttc caagtataca aacaaagcca ttccgcctta    300

accgcctttc agaccgagca aatacaagat tcggagcatt ccgggaagat ggttgcgaaa    360

cgccagttca gaatcggcga catagcgggc gaacatacat cttttgacaa gcttcccgaa    420

ggcggcaggg cgacatatcg cgggacggcg ttcggttcag acgatgccgg cggaaaactg    480

acctacacca tagatttcgc cgccaagcag ggaaacggca aaatcgaaca tttgaaatcg    540

ccagaactca atgtcgacct ggccgccgcc gatatcaagc cggatggaaa acgccatgcc    600

gtcatcagcg gttccgtcct ttacaaccaa gccgagaaag gcagttactc cctcggtatc    660

tttggcggaa aagcccagga agttgccggc agcgcggaag tgaaaaccgt aaacggcata    720
```

-continued

```
cgccatatcg gccttgccgc caagcaactc gacggtggcg gaggcactgg atcctcagat    780

ttggcaaacg attcttttat ccggcaggtt ctcgaccgtc agcatttcga acccgacggg    840

aaataccacc tattcggcag caggggggaa cttgccgagc gcagcggcca tatcggattg    900

ggaaaaatac aaagccatca gttgggcaac ctgatgattc aacaggcggc cattaaagga    960

aatatcggct acattgtccg cttttccgat cacgggcacg aagtccattc cccottcgac   1020

aaccatgcct cacattccga ttctgatgaa gccggtagtc ccgttgacgg atttagcctt   1080

taccgcatcc attgggacgg atacgaacac catcccgccg acggctatga cgggccacag   1140

ggcggcggct atcccgctcc caaaggcgcg agggatatat acagctacga cataaaaggc   1200

gttgcccaaa atatccgcct caacctgacc gacaaccgca gcaccggaca acggcttgcc   1260

gaccgtttcc acaatgccgg tagtatgctg acgcaaggag taggcgacgg attcaaacgc   1320

gccacccgat acagccccga gctggacaga tcgggcaatg ccgccgaagc cttcaacggc   1380

actgcagata tcgttaaaaa catcatcggc gcggcaggag aaattgtcgg cgcaggcgat   1440

gccgtgcagg gcataagcga aggctcaaac attgctgtca tgcacggctt gggtctgctt   1500

tccaccgaaa acaagatggc gcgcatcaac gatttggcag atatggcgca actcaaagac   1560

tatgccgcag cagccatccg cgattgggca gtccaaaacc ccaatgccgc acaaggcata   1620

gaagccgtca gcaatatctt tatggcagcc atccccatca aagggattgg agctgttcgg   1680

ggaaaatacg gcttgggcgg catcacggca catcctatca agcggtcgca gatgggcgcg   1740

atcgcattgc cgaaagggaa atccgccgtc agcgacaatt ttgccgatgc ggcatacgcc   1800

aaatacccgt ccccttacca ttcccgaaat atccgttcaa acttggagca gcgttacggc   1860

aaagaaaaca tcacctcctc aaccgtgccg ccgtcaaacg gcaaaaatgt caaactggca   1920

gaccaacgcc acccgaagac aggcgtaccg tttgacggta aagggtttcc gaattttgag   1980

aagcacgtga aatatgatac gctcgagcac caccaccacc accactga                2028
```

<210> SEQ ID NO 115
<211> LENGTH: 675
<212> TYPE: PRT
<213> ORGANISM: Artificial Sequence
<220> FEATURE:
<223> OTHER INFORMATION: deltaG741-ORF46.1

<400> SEQUENCE: 115

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125
```

-continued

```
Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Asp Gly Gly Gly Gly Thr
                245                 250                 255

Gly Ser Ser Asp Leu Ala Asn Asp Ser Phe Ile Arg Gln Val Leu Asp
            260                 265                 270

Arg Gln His Phe Glu Pro Asp Gly Lys Tyr His Leu Phe Gly Ser Arg
        275                 280                 285

Gly Glu Leu Ala Glu Arg Ser Gly His Ile Gly Leu Gly Lys Ile Gln
    290                 295                 300

Ser His Gln Leu Gly Asn Leu Met Ile Gln Gln Ala Ala Ile Lys Gly
305                 310                 315                 320

Asn Ile Gly Tyr Ile Val Arg Phe Ser Asp His Gly His Glu Val His
                325                 330                 335

Ser Pro Phe Asp Asn His Ala Ser His Ser Asp Ser Asp Glu Ala Gly
            340                 345                 350

Ser Pro Val Asp Gly Phe Ser Leu Tyr Arg Ile His Trp Asp Gly Tyr
        355                 360                 365

Glu His His Pro Ala Asp Gly Tyr Asp Gly Pro Gln Gly Gly Gly Tyr
    370                 375                 380

Pro Ala Pro Lys Gly Ala Arg Asp Ile Tyr Ser Tyr Asp Ile Lys Gly
385                 390                 395                 400

Val Ala Gln Asn Ile Arg Leu Asn Leu Thr Asp Asn Arg Ser Thr Gly
                405                 410                 415

Gln Arg Leu Ala Asp Arg Phe His Asn Ala Gly Ser Met Leu Thr Gln
            420                 425                 430

Gly Val Gly Asp Gly Phe Lys Arg Ala Thr Arg Tyr Ser Pro Glu Leu
        435                 440                 445

Asp Arg Ser Gly Asn Ala Ala Glu Ala Phe Asn Gly Thr Ala Asp Ile
    450                 455                 460

Val Lys Asn Ile Ile Gly Ala Ala Gly Glu Ile Val Gly Ala Gly Asp
465                 470                 475                 480

Ala Val Gln Gly Ile Ser Glu Gly Ser Asn Ile Ala Val Met His Gly
                485                 490                 495

Leu Gly Leu Leu Ser Thr Glu Asn Lys Met Ala Arg Ile Asn Asp Leu
            500                 505                 510

Ala Asp Met Ala Gln Leu Lys Asp Tyr Ala Ala Ala Ala Ile Arg Asp
        515                 520                 525

Trp Ala Val Gln Asn Pro Asn Ala Ala Gln Gly Ile Glu Ala Val Ser
    530                 535                 540

Asn Ile Phe Met Ala Ala Ile Pro Ile Lys Gly Ile Gly Ala Val Arg
```

-continued 545 550 555 560

Gly Lys Tyr Gly Leu Gly Gly Ile Thr Ala His Pro Ile Lys Arg Ser
565 570 575

Gln Met Gly Ala Ile Ala Leu Pro Lys Gly Lys Ser Ala Val Ser Asp
580 585 590

Asn Phe Ala Asp Ala Ala Tyr Ala Lys Tyr Pro Ser Pro Tyr His Ser
595 600 605

Arg Asn Ile Arg Ser Asn Leu Glu Gln Arg Tyr Gly Lys Glu Asn Ile
610 615 620

Thr Ser Ser Thr Val Pro Pro Ser Asn Gly Lys Asn Val Lys Leu Ala
625 630 635 640

Asp Gln Arg His Pro Lys Thr Gly Val Pro Phe Asp Gly Lys Gly Phe
645 650 655

Pro Asn Phe Glu Lys His Val Lys Tyr Asp Thr Leu Glu His His His
660 665 670

His His His
675

<210> SEQ ID NO 116
<211> LENGTH: 249
<212> TYPE: PRT
<213> ORGANISM: Artificial Sequence
<220> FEATURE:
<223> OTHER INFORMATION: Novel protein

<400> SEQUENCE: 116

Met Lys Lys Tyr Leu Phe Arg Ala Ala Leu Tyr Gly Ile Ala Ala Ala
1 5 10 15

Ile Leu Ala Ala Ala Ile Pro Ala Gly Asn Asp Ala Thr Thr Lys Pro
20 25 30

Asp Leu Tyr Tyr Leu Lys Asn Glu Gln Ala Ile Asp Ser Leu Lys Leu
35 40 45

Leu Pro Pro Pro Pro Glu Val Gly Ser Ile Gln Phe Leu Asn Asp Gln
50 55 60

Ala Met Tyr Glu Lys Gly Arg Met Leu Arg Asn Thr Glu Arg Gly Lys
65 70 75 80

Gln Ala Gln Ala Asp Ala Asp Leu Ala Ala Gly Gly Val Ala Thr Ala
85 90 95

Phe Ser Gly Ala Phe Gly Tyr Pro Ile Thr Glu Lys Asp Ser Pro Glu
100 105 110

Leu Tyr Lys Leu Leu Thr Asn Met Ile Glu Asp Ala Gly Asp Leu Ala
115 120 125

Thr Arg Ser Ala Lys Glu His Tyr Met Arg Ile Arg Pro Phe Ala Phe
130 135 140

Tyr Gly Thr Glu Thr Cys Asn Thr Lys Asp Gln Lys Lys Leu Ser Thr
145 150 155 160

Asn Gly Ser Tyr Pro Ser Gly His Thr Ser Ile Gly Trp Ala Thr Ala
165 170 175

Leu Val Leu Ala Glu Val Asn Pro Ala Asn Gln Asp Ala Ile Leu Glu
180 185 190

Arg Gly Tyr Gln Leu Gly Gln Ser Arg Val Ile Cys Gly Tyr His Trp
195 200 205

Gln Ser Asp Val Asp Ala Ala Arg Ile Val Gly Ser Ala Ala Val Ala
210 215 220

Thr Leu His Ser Asp Pro Ala Phe Gln Ala Gln Leu Ala Lys Ala Lys

-continued

```
225                 230                 235                 240

Gln Glu Phe Ala Gln Lys Ser Gln Lys
                245


<210> SEQ ID NO 117
<211> LENGTH: 66
<212> TYPE: DNA
<213> ORGANISM: Artificial Sequence
<220> FEATURE:
<223> OTHER INFORMATION: L1 linker
<220> FEATURE:
<221> NAME/KEY: N
<222> LOCATION: 13
<223> OTHER INFORMATION: A, T/U, G or C

<400> SEQUENCE: 117

tatgaartay ytnttymgcg ccgccctgta cggcatcgcc gccgccatcc tcgccgccgc     60

gatccc                                                                66


<210> SEQ ID NO 118
<211> LENGTH: 69
<212> TYPE: DNA
<213> ORGANISM: Artificial Sequence
<220> FEATURE:
<223> OTHER INFORMATION: S1 linker
<220> FEATURE:
<221> NAME/KEY: N
<222> LOCATION: 25, 28
<223> OTHER INFORMATION: A, T/U, G or C

<400> SEQUENCE: 118

tatgaaaaaa tacctattcc grgcngcnyt rtayggsatc gccgccgcca tcctcgccgc     60

cgcgatccc                                                             69


<210> SEQ ID NO 119
<211> LENGTH: 27
<212> TYPE: DNA
<213> ORGANISM: Artificial Sequence
<220> FEATURE:
<223> OTHER INFORMATION: 9L1-a

<400> SEQUENCE: 119

atgaagaagt accttttcag cgccgcc                                         27


<210> SEQ ID NO 120
<211> LENGTH: 27
<212> TYPE: DNA
<213> ORGANISM: Artificial Sequence
<220> FEATURE:
<223> OTHER INFORMATION: 9L1-e

<400> SEQUENCE: 120

atgaaaaaat actttttccg cgccgcc                                         27


<210> SEQ ID NO 121
<211> LENGTH: 27
<212> TYPE: DNA
<213> ORGANISM: Artificial Sequence
<220> FEATURE:
<223> OTHER INFORMATION: 9L1-d

<400> SEQUENCE: 121

atgaaaaaat actttttccg cgccgcc                                         27


<210> SEQ ID NO 122
```

-continued

<211> LENGTH: 60
<212> TYPE: DNA
<213> ORGANISM: Artificial Sequence
<220> FEATURE:
<223> OTHER INFORMATION: 9L1-f

<400> SEQUENCE: 122
atgaaaaaat atctctttag cgccgccctg tacggcatcg ccgccgccat cctcgccgcc 60

<210> SEQ ID NO 123
<211> LENGTH: 60
<212> TYPE: DNA
<213> ORGANISM: Artificial Sequence
<220> FEATURE:
<223> OTHER INFORMATION: 919sp

<400> SEQUENCE: 123
atgaaaaaat acctattccg cgccgccctg tacggcatcg ccgccgccat cctcgccgcc 60

<210> SEQ ID NO 124
<211> LENGTH: 9
<212> TYPE: PRT
<213> ORGANISM: Artificial Sequence
<220> FEATURE:
<223> OTHER INFORMATION: 9L1a

<400> SEQUENCE: 124

Met Lys Lys Tyr Leu Phe Ser Ala Ala
1 5

<210> SEQ ID NO 125
<211> LENGTH: 9
<212> TYPE: PRT
<213> ORGANISM: Artificial Sequence
<220> FEATURE:
<223> OTHER INFORMATION: 9L1e

<400> SEQUENCE: 125

Met Lys Lys Tyr Phe Phe Arg Ala Ala
1 5

<210> SEQ ID NO 126
<211> LENGTH: 9
<212> TYPE: PRT
<213> ORGANISM: Artificial Sequence
<220> FEATURE:
<223> OTHER INFORMATION: 9L1d

<400> SEQUENCE: 126

Met Lys Lys Tyr Phe Phe Arg Ala Ala
1 5

<210> SEQ ID NO 127
<211> LENGTH: 20
<212> TYPE: PRT
<213> ORGANISM: Artificial Sequence
<220> FEATURE:
<223> OTHER INFORMATION: 9L1f

<400> SEQUENCE: 127

Met Lys Lys Tyr Leu Phe Ser Ala Ala Leu Tyr Gly Ile Ala Ala Ala
1 5 10 15

Ile Leu Ala Ala
20

<210> SEQ ID NO 128

-continued

<211> LENGTH: 20
<212> TYPE: PRT
<213> ORGANISM: Artificial Sequence
<220> FEATURE:
<223> OTHER INFORMATION: 9L1sp

<400> SEQUENCE: 128

Met Lys Lys Tyr Leu Phe Arg Ala Ala Leu Tyr Gly Ile Ala Ala Ala
1               5                   10                  15

Ile Leu Ala Ala
            20

<210> SEQ ID NO 129
<211> LENGTH: 42
<212> TYPE: DNA
<213> ORGANISM: Artificial Sequence
<220> FEATURE:
<223> OTHER INFORMATION: 9S1-e

<400> SEQUENCE: 129
atgaaaaaat acctattcat cgccgccgcc atcctcgccg cc 42

<210> SEQ ID NO 130
<211> LENGTH: 60
<212> TYPE: DNA
<213> ORGANISM: Artificial Sequence
<220> FEATURE:
<223> OTHER INFORMATION: 9S1-c

<400> SEQUENCE: 130
atgaaaaaat acctattccg agctgcccaa tacggcatcg ccgccgccat cctcgccgcc 60

<210> SEQ ID NO 131
<211> LENGTH: 60
<212> TYPE: DNA
<213> ORGANISM: Artificial Sequence
<220> FEATURE:
<223> OTHER INFORMATION: 9S1-b

<400> SEQUENCE: 131
atgaaaaaat acctattccg ggccgcccaa tacggcatcg ccgccgccat cctcgccgcc 60

<210> SEQ ID NO 132
<211> LENGTH: 60
<212> TYPE: DNA
<213> ORGANISM: Artificial Sequence
<220> FEATURE:
<223> OTHER INFORMATION: 9S1-i

<400> SEQUENCE: 132
atgaaaaaat acctattccg ggcggctttg tacgggatcg ccgccgccat cctcgccgcc 60

<210> SEQ ID NO 133
<211> LENGTH: 14
<212> TYPE: PRT
<213> ORGANISM: Artificial Sequence
<220> FEATURE:
<223> OTHER INFORMATION: 9S1e

<400> SEQUENCE: 133

Met Lys Lys Tyr Leu Phe Ile Ala Ala Ala Ile Leu Ala Ala
1               5                   10

<210> SEQ ID NO 134
<211> LENGTH: 20
<212> TYPE: PRT

-continued

<213> ORGANISM: Artificial Sequence
<220> FEATURE:
<223> OTHER INFORMATION: 9S1c

<400> SEQUENCE: 134

Met Lys Lys Tyr Leu Phe Arg Ala Ala Gln Tyr Gly Ile Ala Ala Ala
1 5 10 15

Ile Leu Ala Ala
20

<210> SEQ ID NO 135
<211> LENGTH: 20
<212> TYPE: PRT
<213> ORGANISM: Artificial Sequence
<220> FEATURE:
<223> OTHER INFORMATION: 9S1b

<400> SEQUENCE: 135

Met Lys Lys Tyr Leu Phe Arg Ala Ala Gln Tyr Gly Ile Ala Ala Ala
1 5 10 15

Ile Leu Ala Ala
20

<210> SEQ ID NO 136
<211> LENGTH: 20
<212> TYPE: PRT
<213> ORGANISM: Artificial Sequence
<220> FEATURE:
<223> OTHER INFORMATION: 9S1i

<400> SEQUENCE: 136

Met Lys Lys Tyr Leu Phe Arg Ala Ala Leu Tyr Gly Ile Ala Ala Ala
1 5 10 15

Ile Leu Ala Ala
20

<210> SEQ ID NO 137
<211> LENGTH: 467
<212> TYPE: PRT
<213> ORGANISM: Artificial Sequence
<220> FEATURE:
<223> OTHER INFORMATION: 730

<400> SEQUENCE: 137

Val Lys Pro Leu Arg Arg Leu Thr Asn Leu Leu Ala Ala Cys Ala Val
1 5 10 15

Ala Ala Ala Ala Leu Ile Gln Pro Ala Leu Ala Ala Asp Leu Ala Gln
20 25 30

Asp Pro Phe Ile Thr Asp Asn Ala Gln Arg Gln His Tyr Glu Pro Gly
35 40 45

Gly Lys Tyr His Leu Phe Gly Asp Pro Arg Gly Ser Val Ser Asp Arg
50 55 60

Thr Gly Lys Ile Asn Val Ile Gln Asp Tyr Thr His Gln Met Gly Asn
65 70 75 80

Leu Leu Ile Gln Gln Ala Asn Ile Asn Gly Thr Ile Gly Tyr His Thr
85 90 95

Arg Phe Ser Gly His Gly His Glu Glu His Ala Pro Phe Asp Asn His
100 105 110

Ala Ala Asp Ser Ala Ser Glu Glu Lys Gly Asn Val Asp Glu Gly Phe
115 120 125

Thr Val Tyr Arg Leu Asn Trp Glu Gly His Glu His His Pro Ala Asp

-continued

```
    130                 135                 140

Ala Tyr Asp Gly Pro Lys Gly Gly Asn Tyr Pro Lys Pro Thr Gly Ala
145                 150                 155                 160

Arg Asp Glu Tyr Thr Tyr His Val Asn Gly Thr Ala Arg Ser Ile Lys
                165                 170                 175

Leu Asn Pro Thr Asp Thr Arg Ser Ile Arg Gln Arg Ile Ser Asp Asn
            180                 185                 190

Tyr Ser Asn Leu Gly Ser Asn Phe Ser Asp Arg Ala Asp Glu Ala Asn
        195                 200                 205

Arg Lys Met Phe Glu His Asn Ala Lys Leu Asp Arg Trp Gly Asn Ser
    210                 215                 220

Met Glu Phe Ile Asn Gly Val Ala Ala Gly Ala Leu Asn Pro Phe Ile
225                 230                 235                 240

Ser Ala Gly Glu Ala Leu Gly Ile Gly Asp Ile Leu Tyr Gly Thr Arg
                245                 250                 255

Tyr Ala Ile Asp Lys Ala Ala Met Arg Asn Ile Ala Pro Leu Pro Ala
            260                 265                 270

Glu Gly Lys Phe Ala Val Ile Gly Gly Leu Gly Ser Val Ala Gly Phe
        275                 280                 285

Glu Lys Asn Thr Arg Glu Ala Val Asp Arg Trp Ile Gln Glu Asn Pro
    290                 295                 300

Asn Ala Ala Glu Thr Val Glu Ala Val Phe Asn Val Ala Ala Ala Ala
305                 310                 315                 320

Lys Val Ala Lys Leu Ala Lys Ala Ala Lys Pro Gly Lys Ala Ala Val
                325                 330                 335

Ser Gly Asp Phe Ala Asp Ser Tyr Lys Lys Lys Leu Ala Leu Ser Asp
            340                 345                 350

Ser Ala Arg Gln Leu Tyr Gln Asn Ala Lys Tyr Arg Glu Ala Leu Asp
        355                 360                 365

Ile His Tyr Glu Asp Leu Ile Arg Arg Lys Thr Asp Gly Ser Ser Lys
    370                 375                 380

Phe Ile Asn Gly Arg Glu Ile Asp Ala Val Thr Asn Asp Ala Leu Ile
385                 390                 395                 400

Gln Ala Lys Arg Thr Ile Ser Ala Ile Asp Lys Pro Lys Asn Phe Leu
                405                 410                 415

Asn Gln Lys Asn Arg Lys Gln Ile Lys Ala Thr Ile Glu Ala Ala Asn
            420                 425                 430

Gln Gln Gly Lys Arg Ala Glu Phe Trp Phe Lys Tyr Gly Val His Ser
        435                 440                 445

Gln Val Lys Ser Tyr Ile Glu Ser Lys Gly Gly Ile Val Lys Thr Gly
    450                 455                 460

Leu Gly Asp
465


<210> SEQ ID NO 138
<211> LENGTH: 377
<212> TYPE: PRT
<213> ORGANISM: Artificial Sequence
<220> FEATURE:
<223> OTHER INFORMATION: 730-C1

<400> SEQUENCE: 138

Met Ala Asp Leu Ala Gln Asp Pro Phe Ile Thr Asp Asn Ala Gln Arg
1               5                   10                  15

Gln His Tyr Glu Pro Gly Gly Lys Tyr His Leu Phe Gly Asp Pro Arg
```

-continued

```
            20                  25                  30

Gly Ser Val Ser Asp Arg Thr Gly Lys Ile Asn Val Ile Gln Asp Tyr
        35                  40                  45

Thr His Gln Met Gly Asn Leu Leu Ile Gln Gln Ala Asn Ile Asn Gly
    50                  55                  60

Thr Ile Gly Tyr His Thr Arg Phe Ser Gly His Gly His Glu Glu His
65                  70                  75                  80

Ala Pro Phe Asp Asn His Ala Ala Asp Ser Ala Ser Glu Glu Lys Gly
                85                  90                  95

Asn Val Asp Glu Gly Phe Thr Val Tyr Arg Leu Asn Trp Glu Gly His
            100                 105                 110

Glu His His Pro Ala Asp Ala Tyr Asp Gly Pro Lys Gly Gly Asn Tyr
        115                 120                 125

Pro Lys Pro Thr Gly Ala Arg Asp Glu Tyr Thr Tyr His Val Asn Gly
    130                 135                 140

Thr Ala Arg Ser Ile Lys Leu Asn Pro Thr Asp Thr Arg Ser Ile Arg
145                 150                 155                 160

Gln Arg Ile Ser Asp Asn Tyr Ser Asn Leu Gly Ser Asn Phe Ser Asp
                165                 170                 175

Arg Ala Asp Glu Ala Asn Arg Lys Met Phe Glu His Asn Ala Lys Leu
            180                 185                 190

Asp Arg Trp Gly Asn Ser Met Glu Phe Ile Asn Gly Val Ala Ala Gly
        195                 200                 205

Ala Leu Asn Pro Phe Ile Ser Ala Gly Glu Ala Leu Gly Ile Gly Asp
    210                 215                 220

Ile Leu Tyr Gly Thr Arg Tyr Ala Ile Asp Lys Ala Ala Met Arg Asn
225                 230                 235                 240

Ile Ala Pro Leu Pro Ala Glu Gly Lys Phe Ala Val Ile Gly Gly Leu
                245                 250                 255

Gly Ser Val Ala Gly Phe Glu Lys Asn Thr Arg Glu Ala Val Asp Arg
            260                 265                 270

Trp Ile Gln Glu Asn Pro Asn Ala Ala Glu Thr Val Glu Ala Val Phe
        275                 280                 285

Asn Val Ala Ala Ala Ala Lys Val Ala Lys Leu Ala Lys Ala Ala Lys
    290                 295                 300

Pro Gly Lys Ala Ala Val Ser Gly Asp Phe Ala Asp Ser Tyr Lys Lys
305                 310                 315                 320

Lys Leu Ala Leu Ser Asp Ser Ala Arg Gln Leu Tyr Gln Asn Ala Lys
                325                 330                 335

Tyr Arg Glu Ala Leu Asp Ile His Tyr Glu Asp Leu Ile Arg Arg Lys
            340                 345                 350

Thr Asp Gly Ser Ser Lys Phe Ile Asn Gly Arg Glu Ile Asp Ala Val
        355                 360                 365

Thr Asn Asp Ala Leu Ile Gln Ala Arg
    370                 375


<210> SEQ ID NO 139
<211> LENGTH: 353
<212> TYPE: PRT
<213> ORGANISM: Artificial Sequence
<220> FEATURE:
<223> OTHER INFORMATION: 730-C2

<400> SEQUENCE: 139

Met Ala Asp Leu Ala Gln Asp Pro Phe Ile Thr Asp Asn Ala Gln Arg
```

-continued

```
1               5                   10                  15

Gln His Tyr Glu Pro Gly Gly Lys Tyr His Leu Phe Gly Asp Pro Arg
            20                  25                  30

Gly Ser Val Ser Asp Arg Thr Gly Lys Ile Asn Val Ile Gln Asp Tyr
        35                  40                  45

Thr His Gln Met Gly Asn Leu Leu Ile Gln Gln Ala Asn Ile Asn Gly
    50                  55                  60

Thr Ile Gly Tyr His Thr Arg Phe Ser Gly His Gly His Glu Glu His
65                  70                  75                  80

Ala Pro Phe Asp Asn His Ala Ala Asp Ser Ala Ser Glu Glu Lys Gly
                85                  90                  95

Asn Val Asp Glu Gly Phe Thr Val Tyr Arg Leu Asn Trp Glu Gly His
            100                 105                 110

Glu His His Pro Ala Asp Ala Tyr Asp Gly Pro Lys Gly Gly Asn Tyr
        115                 120                 125

Pro Lys Pro Thr Gly Ala Arg Asp Glu Tyr Thr Tyr His Val Asn Gly
    130                 135                 140

Thr Ala Arg Ser Ile Lys Leu Asn Pro Thr Asp Thr Arg Ser Ile Arg
145                 150                 155                 160

Gln Arg Ile Ser Asp Asn Tyr Ser Asn Leu Gly Ser Asn Phe Ser Asp
                165                 170                 175

Arg Ala Asp Glu Ala Asn Arg Lys Met Phe Glu His Asn Ala Lys Leu
            180                 185                 190

Asp Arg Trp Gly Asn Ser Met Glu Phe Ile Asn Gly Val Ala Ala Gly
        195                 200                 205

Ala Leu Asn Pro Phe Ile Ser Ala Gly Glu Ala Leu Gly Ile Gly Asp
    210                 215                 220

Ile Leu Tyr Gly Thr Arg Tyr Ala Ile Asp Lys Ala Ala Met Arg Asn
225                 230                 235                 240

Ile Ala Pro Leu Pro Ala Glu Gly Lys Phe Ala Val Ile Gly Gly Leu
                245                 250                 255

Gly Ser Val Ala Gly Phe Glu Lys Asn Thr Arg Glu Ala Val Asp Arg
            260                 265                 270

Trp Ile Gln Glu Asn Pro Asn Ala Ala Glu Thr Val Glu Ala Val Phe
        275                 280                 285

Asn Val Ala Ala Ala Ala Lys Val Ala Lys Leu Ala Lys Ala Ala Lys
    290                 295                 300

Pro Gly Lys Ala Ala Val Ser Gly Asp Phe Ala Asp Ser Tyr Lys Lys
305                 310                 315                 320

Lys Leu Ala Leu Ser Asp Ser Ala Arg Gln Leu Tyr Gln Asn Ala Lys
                325                 330                 335

Tyr Arg Glu Ala Leu Gly Lys Val Arg Ile Ser Gly Glu Ile Leu Leu
            340                 345                 350

Gly
```

<210> SEQ ID NO 140
<211> LENGTH: 2019
<212> TYPE: DNA
<213> ORGANISM: Artificial Sequence
<220> FEATURE:
<223> OTHER INFORMATION: ORF46.1-741

<400> SEQUENCE: 140

```
atgtcagatt tggcaaacga ttcttttatc cggcaggttc tcgaccgtca gcatttcgaa     60
```

-continued

```
cccgacggga aataccacct attcggcagc aggggggaac ttgccgagcg cagcggccat    120

atcggattgg gaaaaataca aagccatcag ttgggcaacc tgatgattca acaggcggcc    180

attaaaggaa atatcggcta cattgtccgc ttttccgatc acgggcacga agtccattcc    240

cccttcgaca accatgcctc acattccgat tctgatgaag ccggtagtcc cgttgacgga    300

tttagccttt accgcatcca ttgggacgga tacgaacacc atcccgccga cggctatgac    360

gggccacagg gcggcggcta tcccgctccc aaaggcgcga gggatatata cagctacgac    420

ataaaaggcg ttgcccaaaa tatccgcctc aacctgaccg acaaccgcag caccggacaa    480

cggcttgccg accgtttcca caatgccggt agtatgctga cgcaaggagt aggcgacgga    540

ttcaaacgcg ccacccgata cagccccgag ctggacagat cgggcaatgc cgccgaagcc    600

ttcaacggca ctgcagatat cgttaaaaac atcatcggcg cggcaggaga aattgtcggc    660

gcaggcgatg ccgtgcaggg cataagcgaa ggctcaaaca ttgctgtcat gcacggcttg    720

ggtctgcttt ccaccgaaaa caagatggcg cgcatcaacg atttggcaga tatggcgcaa    780

ctcaaagact atgccgcagc agccatccgc gattgggcag tccaaaaccc caatgccgca    840

caaggcatag aagccgtcag caatatcttt atggcagcca tccccatcaa agggattgga    900

gctgttcggg gaaaatacgg cttgggcggc atcacggcac atcctatcaa gcggtcgcag    960

atgggcgcga tcgcattgcc gaaagggaaa tccgccgtca gcgacaattt tgccgatgcg   1020

gcatacgcca aatacccgtc cccttaccat tcccgaaata tccgttcaaa cttggagcag   1080

cgttacggca aagaaaacat cacctcctca accgtgccgc cgtcaaacgg caaaaatgtc   1140

aaactggcag accaacgcca cccgaagaca ggcgtaccgt ttgacggtaa agggtttccg   1200

aattttgaga agcacgtgaa atatgatacg ggatccggag ggggtggtgt cgccgccgac   1260

atcggtgcgg ggcttgccga tgcactaacc gcaccgctcg accataaaga caaaggtttg   1320

cagtctttga cgctggatca gtccgtcagg aaaaacgaga aactgaagct ggcggcacaa   1380

ggtgcggaaa aaacttatgg aaacggtgac agcctcaata cgggcaaatt gaagaacgac   1440

aaggtcagcc gtttcgactt tatccgccaa atcgaagtgg acgggcagct cattaccttg   1500

gagagtggag agttccaagt atacaaacaa agccattccg ccttaaccgc ctttcagacc   1560

gagcaaatac aagattcgga gcattccggg aagatggttg cgaaacgcca gttcagaatc   1620

ggcgacatag cgggcgaaca tacatctttt gacaagcttc ccgaaggcgg cagggcgaca   1680

tatcgcggga cggcgttcgg ttcagacgat gccggcggaa aactgaccta caccatagat   1740

ttcgccgcca agcagggaaa cggcaaaatc gaacatttga aatcgccaga actcaatgtc   1800

gacctggccg ccgccgatat caagccggat ggaaaacgcc atgccgtcat cagcggttcc   1860

gtcctttaca accaagccga gaaaggcagt tactccctcg gtatctttgg cggaaaagcc   1920

caggaagttg ccggcagcgc ggaagtgaaa accgtaaacg gcatacgcca tatcggcctt   1980

gccgccaagc aactcgagca ccaccaccac caccactga                          2019
```

<210> SEQ ID NO 141
<211> LENGTH: 672
<212> TYPE: PRT
<213> ORGANISM: Artificial Sequence
<220> FEATURE:
<223> OTHER INFORMATION: ORF46.1-741

<400> SEQUENCE: 141

```
Met Ser Asp Leu Ala Asn Asp Ser Phe Ile Arg Gln Val Leu Asp Arg
1               5                   10                  15
```

-continued

```
Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ala Ile Arg Asp Trp
            260                 265                 270

Ala Val Gln Asn Pro Asn Ala Ala Gln Gly Ile Glu Ala Val Ser Asn
        275                 280                 285

Ile Phe Met Ala Ala Ile Pro Ile Lys Gly Ile Gly Ala Val Arg Gly
    290                 295                 300

Lys Tyr Gly Leu Gly Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
        355                 360                 365

Ser Ser Thr Val Pro Pro Ser Asn Gly Lys Asn Val Lys Leu Ala Asp
    370                 375                 380

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly Gly
                405                 410                 415

Val Ala Ala Asp Ile Gly Ala Gly Leu Ala Asp Ala Leu Thr Ala Pro
            420                 425                 430

Leu Asp His Lys Asp Lys Gly Leu Gln Ser Leu Thr Leu Asp Gln Ser
```

-continued

```
        435                 440                 445

Val Arg Lys Asn Glu Lys Leu Lys Leu Ala Ala Gln Gly Ala Glu Lys
    450                 455                 460

Thr Tyr Gly Asn Gly Asp Ser Leu Asn Thr Gly Lys Leu Lys Asn Asp
465                 470                 475                 480

Lys Val Ser Arg Phe Asp Phe Ile Arg Gln Ile Glu Val Asp Gly Gln
                485                 490                 495

Leu Ile Thr Leu Glu Ser Gly Glu Phe Gln Val Tyr Lys Gln Ser His
            500                 505                 510

Ser Ala Leu Thr Ala Phe Gln Thr Glu Gln Ile Gln Asp Ser Glu His
        515                 520                 525

Ser Gly Lys Met Val Ala Lys Arg Gln Phe Arg Ile Gly Asp Ile Ala
    530                 535                 540

Gly Glu His Thr Ser Phe Asp Lys Leu Pro Glu Gly Gly Arg Ala Thr
545                 550                 555                 560

Tyr Arg Gly Thr Ala Phe Gly Ser Asp Asp Ala Gly Gly Lys Leu Thr
                565                 570                 575

Tyr Thr Ile Asp Phe Ala Ala Lys Gln Gly Asn Gly Lys Ile Glu His
            580                 585                 590

Leu Lys Ser Pro Glu Leu Asn Val Asp Leu Ala Ala Ala Asp Ile Lys
        595                 600                 605

Pro Asp Gly Lys Arg His Ala Val Ile Ser Gly Ser Val Leu Tyr Asn
    610                 615                 620

Gln Ala Glu Lys Gly Ser Tyr Ser Leu Gly Ile Phe Gly Gly Lys Ala
625                 630                 635                 640

Gln Glu Val Ala Gly Ser Ala Glu Val Lys Thr Val Asn Gly Ile Arg
                645                 650                 655

His Ile Gly Leu Ala Ala Lys Gln Leu Glu His His His His His His
            660                 665                 670
```

<210> SEQ ID NO 142
<211> LENGTH: 2421
<212> TYPE: DNA
<213> ORGANISM: Artificial Sequence
<220> FEATURE:
<223> OTHER INFORMATION: ORF46.1-961

<400> SEQUENCE: 142

```
atgtcagatt tggcaaacga ttcttttatc cggcaggttc tcgaccgtca gcatttcgaa      60

cccgacggga aataccacct attcggcagc aggggggaac ttgccgagcg cagcggccat     120

atcggattgg gaaaaataca aagccatcag ttgggcaacc tgatgattca acaggcggcc     180

attaaaggaa atatcggcta cattgtccgc ttttccgatc acgggcacga agtccattcc     240

cccttcgaca accatgcctc acattccgat tctgatgaag ccggtagtcc cgttgacgga     300

tttagccttt accgcatcca ttgggacgga tacgaacacc atcccgccga cggctatgac     360

gggccacagg gcggcggcta tcccgctccc aaaggcgcga gggatatata cagctacgac     420

ataaaaggcg ttgcccaaaa tatccgcctc aacctgaccg acaaccgcag caccggacaa     480

cggcttgccg accgtttcca caatgccggt agtatgctga cgcaaggagt aggcgacgga     540

ttcaaacgcg ccacccgata cagccccgag ctggacagat cgggcaatgc cgccgaagcc     600

ttcaacggca ctgcagatat cgttaaaaac atcatcggcg cggcaggaga aattgtcggc     660

gcaggcgatg ccgtgcaggg cataagcgaa ggctcaaaca ttgctgtcat gcacggcttg     720

ggtctgcttt ccaccgaaaa caagatggcg cgcatcaacg atttggcaga tatggcgcaa     780
```

-continued

```
ctcaaagact atgccgcagc agccatccgc gattgggcag tccaaaaccc caatgccgca    840
caaggcatag aagccgtcag caatatcttt atggcagcca tccccatcaa agggattgga    900
gctgttcggg gaaaatacgg cttgggcggc atcacggcac atcctatcaa gcggtcgcag    960
atgggcgcga tcgcattgcc gaaagggaaa tccgccgtca gcgacaattt tgccgatgcg   1020
gcatacgcca aatacccgtc cccttaccat tcccgaaata tccgttcaaa cttggagcag   1080
cgttacggca aagaaaacat cacctcctca accgtgccgc cgtcaaacgg caaaaatgtc   1140
aaactggcag accaacgcca cccgaagaca ggcgtaccgt ttgacggtaa agggtttccg   1200
aattttgaga agcacgtgaa atatgatacg ggatccggag gaggaggagc cacaaacgac   1260
gacgatgtta aaaaagctgc cactgtggcc attgctgctg cctacaacaa tggccaagaa   1320
atcaacggtt tcaaagctgg agagaccatc tacgacattg atgaagacgg cacaattacc   1380
aaaaaagacg caactgcagc cgatgttgaa gccgacgact ttaaaggtct gggtctgaaa   1440
aaagtcgtga ctaacctgac caaaaccgtc aatgaaaaca aacaaaacgt cgatgccaaa   1500
gtaaaagctg cagaatctga aatagaaaag ttaacaacca agttagcaga cactgatgcc   1560
gctttagcag atactgatgc cgctctggat gcaaccacca acgccttgaa taaattggga   1620
gaaaatataa cgacatttgc tgaagagact aagacaaata tcgtaaaaat tgatgaaaaa   1680
ttagaagccg tggctgatac cgtcgacaag catgccgaag cattcaacga tatcgccgat   1740
tcattggatg aaaccaacac taaggcagac gaagccgtca aaaccgccaa tgaagccaaa   1800
cagacggccg aagaaaccaa acaaaacgtc gatgccaaag taaaagctgc agaaactgca   1860
gcaggcaaag ccgaagctgc cgctggcaca gctaatactg cagccgacaa ggccgaagct   1920
gtcgctgcaa aagttaccga catcaaagct gatatcgcta cgaacaaaga taatattgct   1980
aaaaaagcaa acagtgccga cgtgtacacc agagaagagt ctgacagcaa atttgtcaga   2040
attgatggtc tgaacgctac taccgaaaaa ttggacacac gcttggcttc tgctgaaaaa   2100
tccattgccg atcacgatac tcgcctgaac ggtttggata aaacagtgtc agacctgcgc   2160
aaagaaaccc gccaaggcct tgcagaacaa gccgcgctct ccggtctgtt ccaaccttac   2220
aacgtgggtc ggttcaatgt aacggctgca gtcggcggct acaaatccga atcggcagtc   2280
gccatcggta ccggcttccg ctttaccgaa aactttgccg ccaaagcagg cgtggcagtc   2340
ggcacttcgt ccggttcttc cgcagcctac catgtcggcg tcaattacga gtggctcgag   2400
caccaccacc accaccactg a                                             2421
```

<210> SEQ ID NO 143
<211> LENGTH: 806
<212> TYPE: PRT
<213> ORGANISM: Artificial Sequence
<220> FEATURE:
<223> OTHER INFORMATION: ORF46.1-961

<400> SEQUENCE: 143

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60
```

-continued

```
Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ala Ile Arg Asp Trp
            260                 265                 270

Ala Val Gln Asn Pro Asn Ala Ala Gln Gly Ile Glu Ala Val Ser Asn
        275                 280                 285

Ile Phe Met Ala Ala Ile Pro Ile Lys Gly Ile Gly Ala Val Arg Gly
    290                 295                 300

Lys Tyr Gly Leu Gly Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
        355                 360                 365

Ser Ser Thr Val Pro Pro Ser Asn Gly Lys Asn Val Lys Leu Ala Asp
    370                 375                 380

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly Gly
                405                 410                 415

Ala Thr Asn Asp Asp Asp Val Lys Lys Ala Ala Thr Val Ala Ile Ala
            420                 425                 430

Ala Ala Tyr Asn Asn Gly Gln Glu Ile Asn Gly Phe Lys Ala Gly Glu
        435                 440                 445

Thr Ile Tyr Asp Ile Asp Glu Asp Gly Thr Ile Thr Lys Lys Asp Ala
    450                 455                 460

Thr Ala Ala Asp Val Glu Ala Asp Asp Phe Lys Gly Leu Gly Leu Lys
465                 470                 475                 480

Lys Val Val Thr Asn Leu Thr Lys Thr Val Asn Glu Asn Lys Gln Asn
```

-continued

```
                485                 490                 495

Val Asp Ala Lys Val Lys Ala Ala Glu Ser Glu Ile Glu Lys Leu Thr
            500                 505                 510

Thr Lys Leu Ala Asp Thr Asp Ala Ala Leu Ala Asp Thr Asp Ala Ala
        515                 520                 525

Leu Asp Ala Thr Thr Asn Ala Leu Asn Lys Leu Gly Glu Asn Ile Thr
    530                 535                 540

Thr Phe Ala Glu Glu Thr Lys Thr Asn Ile Val Lys Ile Asp Glu Lys
545                 550                 555                 560

Leu Glu Ala Val Ala Asp Thr Val Asp Lys His Ala Glu Ala Phe Asn
                565                 570                 575

Asp Ile Ala Asp Ser Leu Asp Glu Thr Asn Thr Lys Ala Asp Glu Ala
            580                 585                 590

Val Lys Thr Ala Asn Glu Ala Lys Gln Thr Ala Glu Glu Thr Lys Gln
        595                 600                 605

Asn Val Asp Ala Lys Val Lys Ala Ala Glu Thr Ala Ala Gly Lys Ala
    610                 615                 620

Glu Ala Ala Ala Gly Thr Ala Asn Thr Ala Ala Asp Lys Ala Glu Ala
625                 630                 635                 640

Val Ala Ala Lys Val Thr Asp Ile Lys Ala Asp Ile Ala Thr Asn Lys
                645                 650                 655

Asp Asn Ile Ala Lys Lys Ala Asn Ser Ala Asp Val Tyr Thr Arg Glu
            660                 665                 670

Glu Ser Asp Ser Lys Phe Val Arg Ile Asp Gly Leu Asn Ala Thr Thr
        675                 680                 685

Glu Lys Leu Asp Thr Arg Leu Ala Ser Ala Glu Lys Ser Ile Ala Asp
    690                 695                 700

His Asp Thr Arg Leu Asn Gly Leu Asp Lys Thr Val Ser Asp Leu Arg
705                 710                 715                 720

Lys Glu Thr Arg Gln Gly Leu Ala Glu Gln Ala Ala Leu Ser Gly Leu
                725                 730                 735

Phe Gln Pro Tyr Asn Val Gly Arg Phe Asn Val Thr Ala Ala Val Gly
            740                 745                 750

Gly Tyr Lys Ser Glu Ser Ala Val Ala Ile Gly Thr Gly Phe Arg Phe
        755                 760                 765

Thr Glu Asn Phe Ala Ala Lys Ala Gly Val Ala Val Gly Thr Ser Ser
    770                 775                 780

Gly Ser Ser Ala Ala Tyr His Val Gly Val Asn Tyr Glu Trp Leu Glu
785                 790                 795                 800

His His His His His His
                805
```

<210> SEQ ID NO 144
<211> LENGTH: 2256
<212> TYPE: DNA
<213> ORGANISM: Artificial Sequence
<220> FEATURE:
<223> OTHER INFORMATION: ORF46.1-961c

<400> SEQUENCE: 144

```
atgtcagatt tggcaaacga ttcttttatc cggcaggttc tcgaccgtca gcatttcgaa      60

cccgacggga aataccacct attcggcagc aggggggaac ttgccgagcg cagcggccat     120

atcggattgg gaaaaataca aagccatcag ttgggcaacc tgatgattca acaggcggcc     180

attaaaggaa atatcggcta cattgtccgc ttttccgatc acgggcacga agtccattcc     240
```

-continued

```
cccttcgaca accatgcctc acattccgat tctgatgaag ccggtagtcc cgttgacgga    300
tttagccttt accgcatcca ttgggacgga tacgaacacc atcccgccga cggctatgac    360
gggccacagg gcggcggcta tcccgctccc aaaggcgcga gggatatata cagctacgac    420
ataaaaggcg ttgcccaaaa tatccgcctc aacctgaccg acaaccgcag caccggacaa    480
cggcttgccg accgtttcca caatgccggt agtatgctga cgcaaggagt aggcgacgga    540
ttcaaacgcg ccacccgata cagccccgag ctggacagat cgggcaatgc cgccgaagcc    600
ttcaacggca ctgcagatat cgttaaaaac atcatcggcg cggcaggaga aattgtcggc    660
gcaggcgatg ccgtgcaggg cataagcgaa ggctcaaaca ttgctgtcat gcacggcttg    720
ggtctgcttt ccaccgaaaa caagatggcg cgcatcaacg atttggcaga tatggcgcaa    780
ctcaaagact atgccgcagc agccatccgc gattgggcag tccaaaaccc caatgccgca    840
caaggcatag aagccgtcag caatatcttt atggcagcca tccccatcaa agggattgga    900
gctgttcggg gaaaatacgg cttgggcggc atcacggcac atcctatcaa gcggtcgcag    960
atgggcgcga tcgcattgcc gaaagggaaa tccgccgtca gcgacaattt tgccgatgcg   1020
gcatacgcca aatacccgtc cccttaccat tcccgaaata tccgttcaaa cttggagcag   1080
cgttacggca aagaaaacat cacctcctca accgtgccgc cgtcaaacgg caaaaatgtc   1140
aaactggcag accaacgcca cccgaagaca ggcgtaccgt ttgacggtaa agggtttccg   1200
aattttgaga agcacgtgaa atatgatacg ggatccggag gaggaggagc cacaaacgac   1260
gacgatgtta aaaaagctgc cactgtggcc attgctgctg cctacaacaa tggccaagaa   1320
atcaacggtt tcaaagctgg agagaccatc tacgacattg atgaagacgg cacaattacc   1380
aaaaaagacg caactgcagc cgatgttgaa gccgacgact ttaaaggtct gggtctgaaa   1440
aaagtcgtga ctaacctgac caaaaccgtc aatgaaaaca aacaaaacgt cgatgccaaa   1500
gtaaaagctg cagaatctga aatagaaaag ttaacaacca agttagcaga cactgatgcc   1560
gctttagcag atactgatgc cgctctggat gcaaccacca acgccttgaa taaattggga   1620
gaaaatataa cgacatttgc tgaagagact aagacaaata tcgtaaaaat tgatgaaaaa   1680
ttagaagccg tggctgatac cgtcgacaag catgccgaag cattcaacga tatcgccgat   1740
tcattggatg aaaccaacac taaggcagac gaagccgtca aaaccgccaa tgaagccaaa   1800
cagacggccg aagaaaccaa acaaaacgtc gatgccaaag taaaagctgc agaaactgca   1860
gcaggcaaag ccgaagctgc cgctggcaca gctaatactg cagccgacaa ggccgaagct   1920
gtcgctgcaa aagttaccga catcaaagct gatatcgcta cgaacaaaga taatattgct   1980
aaaaaagcaa acagtgccga cgtgtacacc agagaagagt ctgacagcaa atttgtcaga   2040
attgatggtc tgaacgctac taccgaaaaa ttggacacac gcttggcttc tgctgaaaaa   2100
tccattgccg atcacgatac tcgcctgaac ggtttggata aaacagtgtc agacctgcgc   2160
aaagaaaccc gccaaggcct tgcagaacaa gccgcgctct ccggtctgtt ccaaccttac   2220
aacgtgggtc tcgagcacca ccaccaccac cactga                             2256
```

<210> SEQ ID NO 145
<211> LENGTH: 751
<212> TYPE: PRT
<213> ORGANISM: Artificial Sequence
<220> FEATURE:
<223> OTHER INFORMATION: ORF46.1-961c

<400> SEQUENCE: 145

-continued

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ala Ile Arg Asp Trp
            260                 265                 270

Ala Val Gln Asn Pro Asn Ala Ala Gln Gly Ile Glu Ala Val Ser Asn
        275                 280                 285

Ile Phe Met Ala Ala Ile Pro Ile Lys Gly Ile Gly Ala Val Arg Gly
    290                 295                 300

Lys Tyr Gly Leu Gly Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
        355                 360                 365

Ser Ser Thr Val Pro Pro Ser Asn Gly Lys Asn Val Lys Leu Ala Asp
    370                 375                 380

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly Gly
                405                 410                 415

Ala Thr Asn Asp Asp Asp Val Lys Lys Ala Ala Thr Val Ala Ile Ala
```

-continued

```
            420                 425                 430

Ala Ala Tyr Asn Asn Gly Gln Glu Ile Asn Gly Phe Lys Ala Gly Glu
        435                 440                 445

Thr Ile Tyr Asp Ile Asp Glu Asp Gly Thr Ile Thr Lys Lys Asp Ala
    450                 455                 460

Thr Ala Ala Asp Val Glu Ala Asp Asp Phe Lys Gly Leu Gly Leu Lys
465                 470                 475                 480

Lys Val Val Thr Asn Leu Thr Lys Thr Val Asn Glu Asn Lys Gln Asn
                485                 490                 495

Val Asp Ala Lys Val Lys Ala Ala Glu Ser Glu Ile Glu Lys Leu Thr
            500                 505                 510

Thr Lys Leu Ala Asp Thr Asp Ala Ala Leu Ala Asp Thr Asp Ala Ala
        515                 520                 525

Leu Asp Ala Thr Thr Asn Ala Leu Asn Lys Leu Gly Glu Asn Ile Thr
    530                 535                 540

Thr Phe Ala Glu Glu Thr Lys Thr Asn Ile Val Lys Ile Asp Glu Lys
545                 550                 555                 560

Leu Glu Ala Val Ala Asp Thr Val Asp Lys His Ala Glu Ala Phe Asn
                565                 570                 575

Asp Ile Ala Asp Ser Leu Asp Glu Thr Asn Thr Lys Ala Asp Glu Ala
            580                 585                 590

Val Lys Thr Ala Asn Glu Ala Lys Gln Thr Ala Glu Glu Thr Lys Gln
        595                 600                 605

Asn Val Asp Ala Lys Val Lys Ala Ala Glu Thr Ala Ala Gly Lys Ala
    610                 615                 620

Glu Ala Ala Ala Gly Thr Ala Asn Thr Ala Ala Asp Lys Ala Glu Ala
625                 630                 635                 640

Val Ala Ala Lys Val Thr Asp Ile Lys Ala Asp Ile Ala Thr Asn Lys
                645                 650                 655

Asp Asn Ile Ala Lys Lys Ala Asn Ser Ala Asp Val Tyr Thr Arg Glu
            660                 665                 670

Glu Ser Asp Ser Lys Phe Val Arg Ile Asp Gly Leu Asn Ala Thr Thr
        675                 680                 685

Glu Lys Leu Asp Thr Arg Leu Ala Ser Ala Glu Lys Ser Ile Ala Asp
    690                 695                 700

His Asp Thr Arg Leu Asn Gly Leu Asp Lys Thr Val Ser Asp Leu Arg
705                 710                 715                 720

Lys Glu Thr Arg Gln Gly Leu Ala Glu Gln Ala Ala Leu Ser Gly Leu
                725                 730                 735

Phe Gln Pro Tyr Asn Val Gly Leu Glu His His His His His His
            740                 745                 750
```

```
<210> SEQ ID NO 146
<211> LENGTH: 2421
<212> TYPE: DNA
<213> ORGANISM: Artificial Sequence
<220> FEATURE:
<223> OTHER INFORMATION: 961-ORF46.1

<400> SEQUENCE: 146

atggccacaa acgacgacga tgttaaaaaa gctgccactg tggccattgc tgctgcctac      60

aacaatggcc aagaaatcaa cggtttcaaa gctggagaga ccatctacga cattgatgaa     120

gacggcacaa ttaccaaaaa agacgcaact gcagccgatg ttgaagccga cgactttaaa     180

ggtctgggtc tgaaaaaagt cgtgactaac ctgaccaaaa ccgtcaatga aaacaaacaa     240
```

-continued

```
aacgtcgatg ccaaagtaaa agctgcagaa tctgaaatag aaaagttaac aaccaagtta    300
gcagacactg atgccgcttt agcagatact gatgccgctc tggatgcaac caccaacgcc    360
ttgaataaat tgggagaaaa tataacgaca tttgctgaag agactaagac aaatatcgta    420
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg gcacagctaa tactgcagcc    660
gacaaggccg aagctgtcgc tgcaaaagtt accgacatca aagctgatat cgctacgaac    720
aaagataata ttgctaaaaa agcaaacagt gccgacgtgt acaccagaga agagtctgac    780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtcggttc aatgtaacgg ctgcagtcgg cggctacaaa   1020
tccgaatcgg cagtcgccat cggtaccggc ttccgcttta ccgaaaactt tgccgccaaa   1080
gcaggcgtgg cagtcggcac ttcgtccggt tcttccgcag cctaccatgt cggcgtcaat   1140
tacgagtggg gatccggagg aggaggatca gatttggcaa acgattcttt tatccggcag   1200
gttctcgacc gtcagcattt cgaacccgac gggaaatacc acctattcgg cagcaggggg   1260
gaacttgccg agcgcagcgg ccatatcgga ttgggaaaaa tacaaagcca tcagttgggc   1320
aacctgatga ttcaacaggc ggccattaaa ggaaatatcg gctacattgt ccgcttttcc   1380
gatcacgggc acgaagtcca ttccccttc gacaaccatg cctcacattc cgattctgat   1440
gaagccggta gtcccgttga cggatttagc ctttaccgca tccattggga cggatacgaa   1500
caccatcccg ccgacggcta tgacgggcca cagggcggcg gctatcccgc tcccaaaggc   1560
gcgagggata tatacagcta cgacataaaa ggcgttgccc aaaatatccg cctcaacctg   1620
accgacaacc gcagcaccgg acaacggctt gccgaccgtt tccacaatgc cggtagtatg   1680
ctgacgcaag gagtaggcga cggattcaaa cgcgccaccc gatacagccc cgagctggac   1740
agatcgggca atgccgccga agccttcaac ggcactgcag atatcgttaa aaacatcatc   1800
ggcgcggcag gagaaattgt cggcgcaggc gatgccgtgc agggcataag cgaaggctca   1860
aacattgctg tcatgcacgg cttgggtctg ctttccaccg aaaacaagat ggcgcgcatc   1920
aacgatttgg cagatatggc gcaactcaaa gactatgccg cagcagccat ccgcgattgg   1980
gcagtccaaa accccaatgc cgcacaaggc atagaagccg tcagcaatat ctttatggca   2040
gccatcccca tcaaagggat tggagctgtt cggggaaaat acggcttggg cggcatcacg   2100
gcacatccta tcaagcggtc gcagatgggc gcgatcgcat tgccgaaagg gaaatccgcc   2160
gtcagcgaca attttgccga tgcggcatac gccaaatacc cgtcccctta ccattcccga   2220
aatatccgtt caaacttgga gcagcgttac ggcaaagaaa acatcacctc ctcaaccgtg   2280
ccgccgtcaa acggcaaaaa tgtcaaactg gcagaccaac gccacccgaa gacaggcgta   2340
ccgtttgacg gtaaagggtt tccgaatttt gagaagcacg tgaaatatga tacgctcgag   2400
caccaccacc accaccactg a                                             2421
```

<210> SEQ ID NO 147
<211> LENGTH: 806
<212> TYPE: PRT

-continued

<213> ORGANISM: Artificial Sequence
<220> FEATURE:
<223> OTHER INFORMATION: 961-ORF46.1

<400> SEQUENCE: 147

```
Met Ala Thr Asn Asp Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
                325                 330                 335

Gly Gly Tyr Lys Ser Glu Ser Ala Val Ala Ile Gly Thr Gly Phe Arg
            340                 345                 350

Phe Thr Glu Asn Phe Ala Ala Lys Ala Gly Val Ala Val Gly Thr Ser
        355                 360                 365

Ser Gly Ser Ser Ala Ala Tyr His Val Gly Val Asn Tyr Glu Trp Gly
    370                 375                 380

Ser Gly Gly Gly Gly Ser Asp Leu Ala Asn Asp Ser Phe Ile Arg Gln
```

-continued

```
385                 390                 395                 400

Val Leu Asp Arg Gln His Phe Glu Pro Asp Gly Lys Tyr His Leu Phe
                405                 410                 415

Gly Ser Arg Gly Glu Leu Ala Glu Arg Ser Gly His Ile Gly Leu Gly
            420                 425                 430

Lys Ile Gln Ser His Gln Leu Gly Asn Leu Met Ile Gln Gln Ala Ala
        435                 440                 445

Ile Lys Gly Asn Ile Gly Tyr Ile Val Arg Phe Ser Asp His Gly His
    450                 455                 460

Glu Val His Ser Pro Phe Asp Asn His Ala Ser His Ser Asp Ser Asp
465                 470                 475                 480

Glu Ala Gly Ser Pro Val Asp Gly Phe Ser Leu Tyr Arg Ile His Trp
                485                 490                 495

Asp Gly Tyr Glu His His Pro Ala Asp Gly Tyr Asp Gly Pro Gln Gly
            500                 505                 510

Gly Gly Tyr Pro Ala Pro Lys Gly Ala Arg Asp Ile Tyr Ser Tyr Asp
        515                 520                 525

Ile Lys Gly Val Ala Gln Asn Ile Arg Leu Asn Leu Thr Asp Asn Arg
    530                 535                 540

Ser Thr Gly Gln Arg Leu Ala Asp Arg Phe His Asn Ala Gly Ser Met
545                 550                 555                 560

Leu Thr Gln Gly Val Gly Asp Gly Phe Lys Arg Ala Thr Arg Tyr Ser
                565                 570                 575

Pro Glu Leu Asp Arg Ser Gly Asn Ala Ala Glu Ala Phe Asn Gly Thr
            580                 585                 590

Ala Asp Ile Val Lys Asn Ile Ile Gly Ala Ala Gly Glu Ile Val Gly
        595                 600                 605

Ala Gly Asp Ala Val Gln Gly Ile Ser Glu Gly Ser Asn Ile Ala Val
    610                 615                 620

Met His Gly Leu Gly Leu Leu Ser Thr Glu Asn Lys Met Ala Arg Ile
625                 630                 635                 640

Asn Asp Leu Ala Asp Met Ala Gln Leu Lys Asp Tyr Ala Ala Ala Ala
                645                 650                 655

Ile Arg Asp Trp Ala Val Gln Asn Pro Asn Ala Ala Gln Gly Ile Glu
            660                 665                 670

Ala Val Ser Asn Ile Phe Met Ala Ala Ile Pro Ile Lys Gly Ile Gly
        675                 680                 685

Ala Val Arg Gly Lys Tyr Gly Leu Gly Gly Ile Thr Ala His Pro Ile
    690                 695                 700

Lys Arg Ser Gln Met Gly Ala Ile Ala Leu Pro Lys Gly Lys Ser Ala
705                 710                 715                 720

Val Ser Asp Asn Phe Ala Asp Ala Ala Tyr Ala Lys Tyr Pro Ser Pro
                725                 730                 735

Tyr His Ser Arg Asn Ile Arg Ser Asn Leu Glu Gln Arg Tyr Gly Lys
            740                 745                 750

Glu Asn Ile Thr Ser Ser Thr Val Pro Pro Ser Asn Gly Lys Asn Val
        755                 760                 765

Lys Leu Ala Asp Gln Arg His Pro Lys Thr Gly Val Pro Phe Asp Gly
    770                 775                 780

Lys Gly Phe Pro Asn Phe Glu Lys His Val Lys Tyr Asp Thr Leu Glu
785                 790                 795                 800

His His His His His His
                805
```

-continued

<210> SEQ ID NO 148
<211> LENGTH: 1938
<212> TYPE: DNA
<213> ORGANISM: Artificial Sequence
<220> FEATURE:
<223> OTHER INFORMATION: 961-741

<400> SEQUENCE: 148
atggccacaa acgacgacga tgttaaaaaa gctgccactg tggccattgc tgctgcctac 60
aacaatggcc aagaaatcaa cggtttcaaa gctggagaga ccatctacga cattgatgaa 120
gacggcacaa ttaccaaaaa agacgcaact gcagccgatg ttgaagccga cgactttaaa 180
ggtctgggtc tgaaaaaagt cgtgactaac ctgaccaaaa ccgtcaatga aaacaaacaa 240
aacgtcgatg ccaaagtaaa agctgcagaa tctgaaatag aaaagttaac aaccaagtta 300
gcagacactg atgccgcttt agcagatact gatgccgctc tggatgcaac caccaacgcc 360
ttgaataaat tgggagaaaa tataacgaca tttgctgaag agactaagac aaatatcgta 420
aaaattgatg aaaaattaga agccgtggct gataccgtcg acaagcatgc cgaagcattc 480
aacgatatcg ccgattcatt ggatgaaacc aacactaagg cagacgaagc cgtcaaaacc 540
gccaatgaag ccaaacagac ggccgaagaa accaaacaaa acgtcgatgc caaagtaaaa 600
gctgcagaaa ctgcagcagg caaagccgaa gctgccgctg gcacagctaa tactgcagcc 660
gacaaggccg aagctgtcgc tgcaaaagtt accgacatca aagctgatat cgctacgaac 720
aaagataata ttgctaaaaa agcaaacagt gccgacgtgt acaccagaga agagtctgac 780
agcaaatttg tcagaattga tggtctgaac gctactaccg aaaaattgga cacacgcttg 840
gcttctgctg aaaaatccat tgccgatcac gatactcgcc tgaacggttt ggataaaaca 900
gtgtcagacc tgcgcaaaga aacccgccaa ggccttgcag aacaagccgc gctctccggt 960
ctgttccaac cttacaacgt gggtcggttc aatgtaacgg ctgcagtcgg cggctacaaa 1020
tccgaatcgg cagtcgccat cggtaccggc ttccgcttta ccgaaaactt tgccgccaaa 1080
gcaggcgtgg cagtcggcac ttcgtccggt tcttccgcag cctaccatgt cggcgtcaat 1140
tacgagtggg gatccggagg gggtggtgtc gccgccgaca tcggtgcggg gcttgccgat 1200
gcactaaccg caccgctcga ccataaagac aaaggtttgc agtctttgac gctggatcag 1260
tccgtcagga aaaacgagaa actgaagctg gcggcacaag gtgcggaaaa aacttatgga 1320
aacggtgaca gcctcaatac gggcaaattg aagaacgaca aggtcagccg tttcgacttt 1380
atccgccaaa tcgaagtgga cgggcagctc attaccttgg agagtggaga gttccaagta 1440
tacaaacaaa gccattccgc cttaaccgcc tttcagaccg agcaaataca agattcggag 1500
cattccggga agatggttgc gaaacgccag ttcagaatcg gcgacatagc gggcgaacat 1560
acatcttttg acaagcttcc cgaaggcggc agggcgacat atcgcgggac ggcgttcggt 1620
tcagacgatg ccggcggaaa actgacctac accatagatt tcgccgccaa gcagggaaac 1680
ggcaaaatcg aacatttgaa atcgccagaa ctcaatgtcg acctggccgc cgccgatatc 1740
aagccggatg gaaaacgcca tgccgtcatc agcggttccg tcctttacaa ccaagccgag 1800
aaaggcagtt actccctcgg tatctttggc ggaaaagccc aggaagttgc cggcagcgcg 1860
gaagtgaaaa ccgtaaacgg catacgccat atcggccttg ccgccaagca actcgagcac 1920
caccaccacc accactga 1938

<210> SEQ ID NO 149

-continued

<211> LENGTH: 645
<212> TYPE: PRT
<213> ORGANISM: Artificial Sequence
<220> FEATURE:
<223> OTHER INFORMATION: 961-741

<400> SEQUENCE: 149

```
Met Ala Thr Asn Asp Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
                325                 330                 335

Gly Gly Tyr Lys Ser Glu Ser Ala Val Ala Ile Gly Thr Gly Phe Arg
            340                 345                 350

Phe Thr Glu Asn Phe Ala Ala Lys Ala Gly Val Ala Val Gly Thr Ser
        355                 360                 365

Ser Gly Ser Ser Ala Ala Tyr His Val Gly Val Asn Tyr Glu Trp Gly
    370                 375                 380
```

-continued

```
Ser Gly Gly Gly Gly Val Ala Ala Asp Ile Gly Ala Gly Leu Ala Asp
385                 390                 395                 400

Ala Leu Thr Ala Pro Leu Asp His Lys Asp Lys Gly Leu Gln Ser Leu
                405                 410                 415

Thr Leu Asp Gln Ser Val Arg Lys Asn Glu Lys Leu Lys Leu Ala Ala
            420                 425                 430

Gln Gly Ala Glu Lys Thr Tyr Gly Asn Gly Asp Ser Leu Asn Thr Gly
        435                 440                 445

Lys Leu Lys Asn Asp Lys Val Ser Arg Phe Asp Phe Ile Arg Gln Ile
    450                 455                 460

Glu Val Asp Gly Gln Leu Ile Thr Leu Glu Ser Gly Glu Phe Gln Val
465                 470                 475                 480

Tyr Lys Gln Ser His Ser Ala Leu Thr Ala Phe Gln Thr Glu Gln Ile
                485                 490                 495

Gln Asp Ser Glu His Ser Gly Lys Met Val Ala Lys Arg Gln Phe Arg
            500                 505                 510

Ile Gly Asp Ile Ala Gly Glu His Thr Ser Phe Asp Lys Leu Pro Glu
        515                 520                 525

Gly Gly Arg Ala Thr Tyr Arg Gly Thr Ala Phe Gly Ser Asp Asp Ala
    530                 535                 540

Gly Gly Lys Leu Thr Tyr Thr Ile Asp Phe Ala Ala Lys Gln Gly Asn
545                 550                 555                 560

Gly Lys Ile Glu His Leu Lys Ser Pro Glu Leu Asn Val Asp Leu Ala
                565                 570                 575

Ala Ala Asp Ile Lys Pro Asp Gly Lys Arg His Ala Val Ile Ser Gly
            580                 585                 590

Ser Val Leu Tyr Asn Gln Ala Glu Lys Gly Ser Tyr Ser Leu Gly Ile
        595                 600                 605

Phe Gly Gly Lys Ala Gln Glu Val Ala Gly Ser Ala Glu Val Lys Thr
    610                 615                 620

Val Asn Gly Ile Arg His Ile Gly Leu Ala Ala Lys Gln Leu Glu His
625                 630                 635                 640

His His His His His
                645
```

<210> SEQ ID NO 150
<211> LENGTH: 4335
<212> TYPE: DNA
<213> ORGANISM: Artificial Sequence
<220> FEATURE:
<223> OTHER INFORMATION: 961-983

<400> SEQUENCE: 150

```
atggccacaa acgacgacga tgttaaaaaa gctgccactg tggccattgc tgctgcctac      60

aacaatggcc aagaaatcaa cggtttcaaa gctggagaga ccatctacga cattgatgaa     120

gacggcacaa ttaccaaaaa agacgcaact gcagccgatg ttgaagccga cgactttaaa     180

ggtctgggtc tgaaaaaagt cgtgactaac ctgaccaaaa ccgtcaatga aaacaaacaa     240

aacgtcgatg ccaaagtaaa agctgcagaa tctgaaatag aaaagttaac aaccaagtta     300

gcagacactg atgccgcttt agcagatact gatgccgctc tggatgcaac caccaacgcc     360

ttgaataaat tgggagaaaa tataacgaca tttgctgaag agactaagac aaatatcgta     420

aaaattgatg aaaaattaga agccgtggct gataccgtcg acaagcatgc cgaagcattc     480

aacgatatcg ccgattcatt ggatgaaacc aacactaagg cagacgaagc cgtcaaaacc     540
```

-continued

```
gccaatgaag ccaaacagac ggccgaagaa accaaacaaa acgtcgatgc caaagtaaaa    600
gctgcagaaa ctgcagcagg caaagccgaa gctgccgctg gcacagctaa tactgcagcc    660
gacaaggccg aagctgtcgc tgcaaaagtt accgacatca aagctgatat cgctacgaac    720
aaagataata ttgctaaaaa agcaaacagt gccgacgtgt acaccagaga agagtctgac    780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtcggttc aatgtaacgg ctgcagtcgg cggctacaaa   1020
tccgaatcgg cagtcgccat cggtaccggc ttccgcttta ccgaaaactt tgccgccaaa   1080
gcaggcgtgg cagtcggcac ttcgtccggt tcttccgcag cctaccatgt cggcgtcaat   1140
tacgagtggg gatccggcgg aggcggcact tctgcgcccg acttcaatgc aggcggtacc   1200
ggtatcggca gcaacagcag agcaacaaca gcgaaatcag cagcagtatc ttacgccggt   1260
atcaagaacg aaatgtgcaa agacagaagc atgctctgtg ccggtcggga tgacgttgcg   1320
gttacagaca gggatgccaa aatcaatgcc cccccccga atctgcatac cggagacttt   1380
ccaaacccaa atgacgcata caagaatttg atcaacctca aacctgcaat tgaagcaggc   1440
tatacaggac gcggggtaga ggtaggtatc gtcgacacag gcgaatccgt cggcagcata   1500
tcctttcccg aactgtatgg cagaaaagaa cacggctata acgaaaatta caaaaactat   1560
acggcgtata tgcggaagga agcgcctgaa gacggaggcg gtaaagacat tgaagcttct   1620
ttcgacgatg aggccgttat agagactgaa gcaaagccga cggatatccg ccacgtaaaa   1680
gaaatcggac acatcgattt ggtctcccat attattggcg ggcgttccgt ggacggcaga   1740
cctgcaggcg gtattgcgcc cgatgcgacg ctacacataa tgaatacgaa tgatgaaacc   1800
aagaacgaaa tgatggttgc agccatccgc aatgcatggg tcaagctggg cgaacgtggc   1860
gtgcgcatcg tcaataacag ttttggaaca acatcgaggg caggcactgc cgaccttttc   1920
caaatagcca attcggagga gcagtaccgc caagcgttgc tcgactattc cggcggtgat   1980
aaaacagacg agggtatccg cctgatgcaa cagagcgatt acggcaacct gtcctaccac   2040
atccgtaata aaaacatgct tttcatcttt tcgacaggca atgacgcaca agctcagccc   2100
aacacatatg ccctattgcc attttatgaa aaagacgctc aaaaaggcat tatcacagtc   2160
gcaggcgtag accgcagtgg agaaaagttc aaacgggaaa tgtatggaga accgggtaca   2220
gaaccgcttg agtatggctc caaccattgc ggaattactg ccatgtggtg cctgtcggca   2280
ccctatgaag caagcgtccg tttcacccgt acaaacccga ttcaaattgc cggaacatcc   2340
ttttccgcac ccatcgtaac cggcacggcg gctctgctgc tgcagaaata cccgtggatg   2400
agcaacgaca acctgcgtac cacgttgctg acgacggctc aggacatcgg tgcagtcggc   2460
gtggacagca agttcggctg gggactgctg gatgcgggta aggccatgaa cggacccgcg   2520
tcctttccgt tcggcgactt taccgccgat acgaaaggta catccgatat tgcctactcc   2580
ttccgtaacg acatttcagg cacgggcggc ctgatcaaaa aaggcggcag ccaactgcaa   2640
ctgcacggca acaacaccta tacgggcaaa accattatcg aaggcggttc gctggtgttg   2700
tacggcaaca acaaatcgga tatgcgcgtc gaaaccaaag gtgcgctgat ttataacggg   2760
gcggcatccg gcggcagcct gaacagcgac ggcattgtct atctggcaga taccgaccaa   2820
tccggcgcaa acgaaaccgt acacatcaaa ggcagtctgc agctggacgg caaaggtacg   2880
```

-continued

```
ctgtacacac gtttgggcaa actgctgaaa gtggacggta cggcgattat cggcggcaag   2940

ctgtacatgt cggcacgcgg caagggggca ggctatctca acagtaccgg acgacgtgtt   3000

cccttcctga gtgccgccaa aatcgggcag gattattctt tcttcacaaa catcgaaacc   3060

gacggcggcc tgctggcttc cctcgacagc gtcgaaaaaa cagcgggcag tgaaggcgac   3120

acgctgtcct attatgtccg tcgcggcaat gcggcacgga ctgcttcggc agcggcacat   3180

tccgcgcccg ccggtctgaa acacgccgta gaacagggcg gcagcaatct ggaaaacctg   3240

atggtcgaac tggatgcctc cgaatcatcc gcaacacccg agacggttga aactgcggca   3300

gccgaccgca cagatatgcc gggcatccgc ccctacggcg caactttccg cgcagcggca   3360

gccgtacagc atgcgaatgc cgccgacggt gtacgcatct tcaacagtct cgccgctacc   3420

gtctatgccg acagtaccgc cgcccatgcc gatatgcagg gacgccgcct gaaagccgta   3480

tcggacgggt tggaccacaa cggcacgggt ctgcgcgtca tcgcgcaaac ccaacaggac   3540

ggtggaacgt gggaacaggg cggtgttgaa ggcaaaatgc gcggcagtac ccaaaccgtc   3600

ggcattgccg cgaaaaccgg cgaaaatacg acagcagccg ccacactggg catgggacgc   3660

agcacatgga gcgaaaacag tgcaaatgca aaaaccgaca gcattagtct gtttgcaggc   3720

atacggcacg atgcgggcga tatcggctat ctcaaaggcc tgttctccta cggacgctac   3780

aaaaacagca tcagccgcag caccggtgcg gacgaacatg cggaaggcag cgtcaacggc   3840

acgctgatgc agctgggcgc actgggcggt gtcaacgttc cgtttgccgc aacgggagat   3900

ttgacggtcg aaggcggtct gcgctacgac ctgctcaaac aggatgcatt cgccgaaaaa   3960

ggcagtgctt tgggctggag cggcaacagc ctcactgaag gcacgctggt cggactcgcg   4020

ggtctgaagc tgtcgcaacc cttgagcgat aaagccgtcc tgtttgcaac ggcgggcgtg   4080

gaacgcgacc tgaacggacg cgactacacg gtaacgggcg gctttaccgg cgcgactgca   4140

gcaaccggca agacgggggc acgcaatatg ccgcacaccc gtctggttgc cggcctgggc   4200

gcggatgtcg aattcggcaa cggctggaac ggcttggcac gttacagcta cgccggttcc   4260

aaacagtacg gcaaccacag cggacgagtc ggcgtaggct accggttcct cgagcaccac   4320

caccaccacc actga                                                    4335
```

<210> SEQ ID NO 151
<211> LENGTH: 1444
<212> TYPE: PRT
<213> ORGANISM: Artificial Sequence
<220> FEATURE:
<223> OTHER INFORMATION: 961-983

<400> SEQUENCE: 151

```
Met Ala Thr Asn Asp Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
```

-continued

```
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
                325                 330                 335

Gly Gly Tyr Lys Ser Glu Ser Ala Val Ala Ile Gly Thr Gly Phe Arg
            340                 345                 350

Phe Thr Glu Asn Phe Ala Ala Lys Ala Gly Val Ala Val Gly Thr Ser
        355                 360                 365

Ser Gly Ser Ser Ala Ala Tyr His Val Gly Val Asn Tyr Glu Trp Gly
    370                 375                 380

Ser Gly Gly Gly Gly Thr Ser Ala Pro Asp Phe Asn Ala Gly Gly Thr
385                 390                 395                 400

Gly Ile Gly Ser Asn Ser Arg Ala Thr Thr Ala Lys Ser Ala Ala Val
                405                 410                 415

Ser Tyr Ala Gly Ile Lys Asn Glu Met Cys Lys Asp Arg Ser Met Leu
            420                 425                 430

Cys Ala Gly Arg Asp Asp Val Ala Val Thr Asp Arg Asp Ala Lys Ile
        435                 440                 445

Asn Ala Pro Pro Pro Asn Leu His Thr Gly Asp Phe Pro Asn Pro Asn
    450                 455                 460

Asp Ala Tyr Lys Asn Leu Ile Asn Leu Lys Pro Ala Ile Glu Ala Gly
465                 470                 475                 480

Tyr Thr Gly Arg Gly Val Glu Val Gly Ile Val Asp Thr Gly Glu Ser
                485                 490                 495

Val Gly Ser Ile Ser Phe Pro Glu Leu Tyr Gly Arg Lys Glu His Gly
            500                 505                 510

Tyr Asn Glu Asn Tyr Lys Asn Tyr Thr Ala Tyr Met Arg Lys Glu Ala
        515                 520                 525
```

-continued

```
Pro Glu Asp Gly Gly Gly Lys Asp Ile Glu Ala Ser Phe Asp Asp Glu
    530                 535                 540

Ala Val Ile Glu Thr Glu Ala Lys Pro Thr Asp Ile Arg His Val Lys
545                 550                 555                 560

Glu Ile Gly His Ile Asp Leu Val Ser His Ile Ile Gly Gly Arg Ser
                565                 570                 575

Val Asp Gly Arg Pro Ala Gly Gly Ile Ala Pro Asp Ala Thr Leu His
            580                 585                 590

Ile Met Asn Thr Asn Asp Glu Thr Lys Asn Glu Met Met Val Ala Ala
        595                 600                 605

Ile Arg Asn Ala Trp Val Lys Leu Gly Glu Arg Gly Val Arg Ile Val
    610                 615                 620

Asn Asn Ser Phe Gly Thr Thr Ser Arg Ala Gly Thr Ala Asp Leu Phe
625                 630                 635                 640

Gln Ile Ala Asn Ser Glu Glu Gln Tyr Arg Gln Ala Leu Leu Asp Tyr
                645                 650                 655

Ser Gly Gly Asp Lys Thr Asp Glu Gly Ile Arg Leu Met Gln Gln Ser
            660                 665                 670

Asp Tyr Gly Asn Leu Ser Tyr His Ile Arg Asn Lys Asn Met Leu Phe
        675                 680                 685

Ile Phe Ser Thr Gly Asn Asp Ala Gln Ala Gln Pro Asn Thr Tyr Ala
    690                 695                 700

Leu Leu Pro Phe Tyr Glu Lys Asp Ala Gln Lys Gly Ile Ile Thr Val
705                 710                 715                 720

Ala Gly Val Asp Arg Ser Gly Glu Lys Phe Lys Arg Glu Met Tyr Gly
                725                 730                 735

Glu Pro Gly Thr Glu Pro Leu Glu Tyr Gly Ser Asn His Cys Gly Ile
            740                 745                 750

Thr Ala Met Trp Cys Leu Ser Ala Pro Tyr Glu Ala Ser Val Arg Phe
        755                 760                 765

Thr Arg Thr Asn Pro Ile Gln Ile Ala Gly Thr Ser Phe Ser Ala Pro
    770                 775                 780

Ile Val Thr Gly Thr Ala Ala Leu Leu Leu Gln Lys Tyr Pro Trp Met
785                 790                 795                 800

Ser Asn Asp Asn Leu Arg Thr Thr Leu Leu Thr Thr Ala Gln Asp Ile
                805                 810                 815

Gly Ala Val Gly Val Asp Ser Lys Phe Gly Trp Gly Leu Leu Asp Ala
            820                 825                 830

Gly Lys Ala Met Asn Gly Pro Ala Ser Phe Pro Phe Gly Asp Phe Thr
        835                 840                 845

Ala Asp Thr Lys Gly Thr Ser Asp Ile Ala Tyr Ser Phe Arg Asn Asp
    850                 855                 860

Ile Ser Gly Thr Gly Gly Leu Ile Lys Lys Gly Gly Ser Gln Leu Gln
865                 870                 875                 880

Leu His Gly Asn Asn Thr Tyr Thr Gly Lys Thr Ile Ile Glu Gly Gly
                885                 890                 895

Ser Leu Val Leu Tyr Gly Asn Asn Lys Ser Asp Met Arg Val Glu Thr
            900                 905                 910

Lys Gly Ala Leu Ile Tyr Asn Gly Ala Ala Ser Gly Gly Ser Leu Asn
        915                 920                 925

Ser Asp Gly Ile Val Tyr Leu Ala Asp Thr Asp Gln Ser Gly Ala Asn
    930                 935                 940
```

-continued

```
Glu Thr Val His Ile Lys Gly Ser Leu Gln Leu Asp Gly Lys Gly Thr
945                 950                 955                 960

Leu Tyr Thr Arg Leu Gly Lys Leu Leu Lys Val Asp Gly Thr Ala Ile
                965                 970                 975

Ile Gly Gly Lys Leu Tyr Met Ser Ala Arg Gly Lys Gly Ala Gly Tyr
            980                 985                 990

Leu Asn Ser Thr Gly Arg Arg Val Pro Phe Leu Ser Ala Ala Lys Ile
        995                 1000                1005

Gly Gln Asp Tyr Ser Phe Phe Thr Asn Ile Glu Thr Asp Gly Gly Leu
    1010                1015                1020

Leu Ala Ser Leu Asp Ser Val Glu Lys Thr Ala Gly Ser Glu Gly Asp
1025                1030                1035                1040

Thr Leu Ser Tyr Tyr Val Arg Arg Gly Asn Ala Ala Arg Thr Ala Ser
                1045                1050                1055

Ala Ala Ala His Ser Ala Pro Ala Gly Leu Lys His Ala Val Glu Gln
            1060                1065                1070

Gly Gly Ser Asn Leu Glu Asn Leu Met Val Glu Leu Asp Ala Ser Glu
        1075                1080                1085

Ser Ser Ala Thr Pro Glu Thr Val Glu Thr Ala Ala Ala Asp Arg Thr
    1090                1095                1100

Asp Met Pro Gly Ile Arg Pro Tyr Gly Ala Thr Phe Arg Ala Ala Ala
1105                1110                1115                1120

Ala Val Gln His Ala Asn Ala Ala Asp Gly Val Arg Ile Phe Asn Ser
                1125                1130                1135

Leu Ala Ala Thr Val Tyr Ala Asp Ser Thr Ala Ala His Ala Asp Met
            1140                1145                1150

Gln Gly Arg Arg Leu Lys Ala Val Ser Asp Gly Leu Asp His Asn Gly
        1155                1160                1165

Thr Gly Leu Arg Val Ile Ala Gln Thr Gln Gln Asp Gly Gly Thr Trp
    1170                1175                1180

Glu Gln Gly Gly Val Glu Gly Lys Met Arg Gly Ser Thr Gln Thr Val
1185                1190                1195                1200

Gly Ile Ala Ala Lys Thr Gly Glu Asn Thr Thr Ala Ala Ala Thr Leu
                1205                1210                1215

Gly Met Gly Arg Ser Thr Trp Ser Glu Asn Ser Ala Asn Ala Lys Thr
            1220                1225                1230

Asp Ser Ile Ser Leu Phe Ala Gly Ile Arg His Asp Ala Gly Asp Ile
        1235                1240                1245

Gly Tyr Leu Lys Gly Leu Phe Ser Tyr Gly Arg Tyr Lys Asn Ser Ile
    1250                1255                1260

Ser Arg Ser Thr Gly Ala Asp Glu His Ala Glu Gly Ser Val Asn Gly
1265                1270                1275                1280

Thr Leu Met Gln Leu Gly Ala Leu Gly Gly Val Asn Val Pro Phe Ala
                1285                1290                1295

Ala Thr Gly Asp Leu Thr Val Glu Gly Gly Leu Arg Tyr Asp Leu Leu
            1300                1305                1310

Lys Gln Asp Ala Phe Ala Glu Lys Gly Ser Ala Leu Gly Trp Ser Gly
        1315                1320                1325

Asn Ser Leu Thr Glu Gly Thr Leu Val Gly Leu Ala Gly Leu Lys Leu
    1330                1335                1340

Ser Gln Pro Leu Ser Asp Lys Ala Val Leu Phe Ala Thr Ala Gly Val
1345                1350                1355                1360

Glu Arg Asp Leu Asn Gly Arg Asp Tyr Thr Val Thr Gly Gly Phe Thr
```

-continued

```
                1365                1370                1375

Gly Ala Thr Ala Ala Thr Gly Lys Thr Gly Ala Arg Asn Met Pro His
            1380                1385                1390

Thr Arg Leu Val Ala Gly Leu Gly Ala Asp Val Glu Phe Gly Asn Gly
        1395                1400                1405

Trp Asn Gly Leu Ala Arg Tyr Ser Tyr Ala Gly Ser Lys Gln Tyr Gly
    1410                1415                1420

Asn His Ser Gly Arg Val Gly Val Gly Tyr Arg Phe Leu Glu His His
1425                1430                1435                1440

His His His His
```

<210> SEQ ID NO 152
<211> LENGTH: 2256
<212> TYPE: DNA
<213> ORGANISM: Artificial Sequence
<220> FEATURE:
<223> OTHER INFORMATION: 961c-ORF46.1

<400> SEQUENCE: 152

```
atggccacaa acgacgacga tgttaaaaaa gctgccactg tggccattgc tgctgcctac     60

aacaatggcc aagaaatcaa cggtttcaaa gctggagaga ccatctacga cattgatgaa    120

gacggcacaa ttaccaaaaa agacgcaact gcagccgatg ttgaagccga cgactttaaa    180

ggtctgggtc tgaaaaaagt cgtgactaac ctgaccaaaa ccgtcaatga aaacaaacaa    240

aacgtcgatg ccaaagtaaa agctgcagaa tctgaaatag aaaagttaac aaccaagtta    300

gcagacactg atgccgcttt agcagatact gatgccgctc tggatgcaac caccaacgcc    360

ttgaataaat tgggagaaaa tataacgaca tttgctgaag agactaagac aaatatcgta    420

aaaattgatg aaaaattaga agccgtggct gataccgtcg acaagcatgc cgaagcattc    480

aacgatatcg ccgattcatt ggatgaaacc aacactaagg cagacgaagc cgtcaaaacc    540

gccaatgaag ccaaacagac ggccgaagaa accaaacaaa acgtcgatgc caaagtaaaa    600

gctgcagaaa ctgcagcagg caaagccgaa gctgccgctg gcacagctaa tactgcagcc    660

gacaaggccg aagctgtcgc tgcaaaagtt accgacatca aagctgatat cgctacgaac    720

aaagataata ttgctaaaaa agcaaacagt gccgacgtgt acaccagaga agagtctgac    780

agcaaatttg tcagaattga tggtctgaac gctactaccg aaaaattgga cacacgcttg    840

gcttctgctg aaaaatccat tgccgatcac gatactcgcc tgaacggttt ggataaaaca    900

gtgtcagacc tgcgcaaaga aacccgccaa ggccttgcag aacaagccgc gctctccggt    960

ctgttccaac cttacaacgt gggtggatcc ggaggaggag gatcagattt ggcaaacgat   1020

tcttttatcc ggcaggttct cgaccgtcag catttcgaac ccgacgggaa ataccaccta   1080

ttcggcagca ggggggaact tgccgagcgc agcggccata tcggattggg aaaaatacaa   1140

agccatcagt tgggcaacct gatgattcaa caggcggcca ttaaaggaaa tatcggctac   1200

attgtccgct tttccgatca cgggcacgaa gtccattccc ccttcgacaa ccatgcctca   1260

cattccgatt ctgatgaagc cggtagtccc gttgacggat ttagccttta ccgcatccat   1320

tgggacggat acgaacacca tcccgccgac ggctatgacg ggccacaggg cggcggctat   1380

cccgctccca aaggcgcgag ggatatatac agctacgaca taaaaggcgt tgcccaaaat   1440

atccgcctca acctgaccga caaccgcagc accggacaac ggcttgccga ccgtttccac   1500

aatgccggta gtatgctgac gcaaggagta ggcgacggat tcaaacgcgc cacccgatac   1560

agccccgagc tggacagatc gggcaatgcc gccgaagcct tcaacggcac tgcagatatc   1620
```

-continued

```
gttaaaaaca tcatcggcgc ggcaggagaa attgtcggcg caggcgatgc cgtgcagggc   1680

ataagcgaag gctcaaacat tgctgtcatg cacggcttgg gtctgctttc caccgaaaac   1740

aagatggcgc gcatcaacga tttggcagat atggcgcaac tcaaagacta tgccgcagca   1800

gccatccgcg attgggcagt ccaaaacccc aatgccgcac aaggcataga agccgtcagc   1860

aatatcttta tggcagccat ccccatcaaa gggattggag ctgttcgggg aaaatacggc   1920

ttgggcggca tcacggcaca tcctatcaag cggtcgcaga tgggcgcgat cgcattgccg   1980

aaagggaaat ccgccgtcag cgacaatttt gccgatgcgg catacgccaa atacccgtcc   2040

ccttaccatt cccgaaatat ccgttcaaac ttggagcagc gttacggcaa agaaaacatc   2100

acctcctcaa ccgtgccgcc gtcaaacggc aaaaatgtca aactggcaga ccaacgccac   2160

ccgaagacag gcgtaccgtt tgacggtaaa gggtttccga attttgagaa gcacgtgaaa   2220

tatgatacgc tcgagcacca ccaccaccac cactga                             2256
```

```
<210> SEQ ID NO 153
<211> LENGTH: 751
<212> TYPE: PRT
<213> ORGANISM: Artificial Sequence
<220> FEATURE:
<223> OTHER INFORMATION: 961c-ORF46.1

<400> SEQUENCE: 153

Met Ala Thr Asn Asp Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
```

-continued

```
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Gly Ser Asp
                325                 330                 335

Leu Ala Asn Asp Ser Phe Ile Arg Gln Val Leu Asp Arg Gln His Phe
            340                 345                 350

Glu Pro Asp Gly Lys Tyr His Leu Phe Gly Ser Arg Gly Glu Leu Ala
        355                 360                 365

Glu Arg Ser Gly His Ile Gly Leu Gly Lys Ile Gln Ser His Gln Leu
    370                 375                 380

Gly Asn Leu Met Ile Gln Gln Ala Ala Ile Lys Gly Asn Ile Gly Tyr
385                 390                 395                 400

Ile Val Arg Phe Ser Asp His Gly His Glu Val His Ser Pro Phe Asp
                405                 410                 415

Asn His Ala Ser His Ser Asp Ser Asp Glu Ala Gly Ser Pro Val Asp
            420                 425                 430

Gly Phe Ser Leu Tyr Arg Ile His Trp Asp Gly Tyr Glu His His Pro
        435                 440                 445

Ala Asp Gly Tyr Asp Gly Pro Gln Gly Gly Gly Tyr Pro Ala Pro Lys
    450                 455                 460

Gly Ala Arg Asp Ile Tyr Ser Tyr Asp Ile Lys Gly Val Ala Gln Asn
465                 470                 475                 480

Ile Arg Leu Asn Leu Thr Asp Asn Arg Ser Thr Gly Gln Arg Leu Ala
                485                 490                 495

Asp Arg Phe His Asn Ala Gly Ser Met Leu Thr Gln Gly Val Gly Asp
            500                 505                 510

Gly Phe Lys Arg Ala Thr Arg Tyr Ser Pro Glu Leu Asp Arg Ser Gly
        515                 520                 525

Asn Ala Ala Glu Ala Phe Asn Gly Thr Ala Asp Ile Val Lys Asn Ile
    530                 535                 540

Ile Gly Ala Ala Gly Glu Ile Val Gly Ala Gly Asp Ala Val Gln Gly
545                 550                 555                 560

Ile Ser Glu Gly Ser Asn Ile Ala Val Met His Gly Leu Gly Leu Leu
                565                 570                 575

Ser Thr Glu Asn Lys Met Ala Arg Ile Asn Asp Leu Ala Asp Met Ala
            580                 585                 590

Gln Leu Lys Asp Tyr Ala Ala Ala Ala Ile Arg Asp Trp Ala Val Gln
        595                 600                 605

Asn Pro Asn Ala Ala Gln Gly Ile Glu Ala Val Ser Asn Ile Phe Met
    610                 615                 620

Ala Ala Ile Pro Ile Lys Gly Ile Gly Ala Val Arg Gly Lys Tyr Gly
625                 630                 635                 640

Leu Gly Gly Ile Thr Ala His Pro Ile Lys Arg Ser Gln Met Gly Ala
                645                 650                 655

Ile Ala Leu Pro Lys Gly Lys Ser Ala Val Ser Asp Asn Phe Ala Asp
            660                 665                 670
```

-continued

```
Ala Ala Tyr Ala Lys Tyr Pro Ser Pro Tyr His Ser Arg Asn Ile Arg
        675                 680                 685

Ser Asn Leu Glu Gln Arg Tyr Gly Lys Glu Asn Ile Thr Ser Ser Thr
    690                 695                 700

Val Pro Pro Ser Asn Gly Lys Asn Val Lys Leu Ala Asp Gln Arg His
705                 710                 715                 720

Pro Lys Thr Gly Val Pro Phe Asp Gly Lys Gly Phe Pro Asn Phe Glu
                725                 730                 735

Lys His Val Lys Tyr Asp Thr Leu Glu His His His His His His
            740                 745                 750


<210> SEQ ID NO 154
<211> LENGTH: 1773
<212> TYPE: DNA
<213> ORGANISM: Artificial Sequence
<220> FEATURE:
<223> OTHER INFORMATION: 961c-741

<400> SEQUENCE: 154

atggccacaa acgacgacga tgttaaaaaa gctgccactg tggccattgc tgctgcctac      60

aacaatggcc aagaaatcaa cggtttcaaa gctggagaga ccatctacga cattgatgaa     120

gacggcacaa ttaccaaaaa agacgcaact gcagccgatg ttgaagccga cgactttaaa     180

ggtctgggtc tgaaaaaagt cgtgactaac ctgaccaaaa ccgtcaatga aaacaaacaa     240

aacgtcgatg ccaaagtaaa agctgcagaa tctgaaatag aaaagttaac aaccaagtta     300

gcagacactg atgccgcttt agcagatact gatgccgctc tggatgcaac caccaacgcc     360

ttgaataaat tgggagaaaa tataacgaca tttgctgaag agactaagac aaatatcgta     420

aaaattgatg aaaaattaga agccgtggct gataccgtcg acaagcatgc cgaagcattc     480

aacgatatcg ccgattcatt ggatgaaacc aacactaagg cagacgaagc cgtcaaaacc     540

gccaatgaag ccaaacagac ggccgaagaa accaaacaaa acgtcgatgc caaagtaaaa     600

gctgcagaaa ctgcagcagg caaagccgaa gctgccgctg gcacagctaa tactgcagcc     660

gacaaggccg aagctgtcgc tgcaaaagtt accgacatca aagctgatat cgctacgaac     720

aaagataata ttgctaaaaa agcaaacagt gccgacgtgt acaccagaga agagtctgac     780

agcaaatttg tcagaattga tggtctgaac gctactaccg aaaaattgga cacacgcttg     840

gcttctgctg aaaaatccat tgccgatcac gatactcgcc tgaacggttt ggataaaaca     900

gtgtcagacc tgcgcaaaga aacccgccaa ggccttgcag aacaagccgc gctctccggt     960

ctgttccaac cttacaacgt gggtggatcc ggagggggtg gtgtcgccgc cgacatcggt    1020

gcggggcttg ccgatgcact aaccgcaccg ctcgaccata aagacaaagg tttgcagtct    1080

ttgacgctgg atcagtccgt caggaaaaac gagaaactga agctggcggc acaaggtgcg    1140

gaaaaaactt atggaaacgg tgacagcctc aatacgggca aattgaagaa cgacaaggtc    1200

agccgtttcg actttatccg ccaaatcgaa gtggacgggc agctcattac cttggagagt    1260

ggagagttcc aagtatacaa acaaagccat tccgccttaa ccgcctttca gaccgagcaa    1320

atacaagatt cggagcattc cgggaagatg gttgcgaaac gccagttcag aatcggcgac    1380

atagcgggcg aacatacatc ttttgacaag cttcccgaag gcggcagggc gacatatcgc    1440

gggacggcgt tcggttcaga cgatgccggc ggaaaactga cctacaccat agatttcgcc    1500

gccaagcagg gaaacggcaa aatcgaacat ttgaaatcgc cagaactcaa tgtcgacctg    1560

gccgccgccg atatcaagcc ggatggaaaa cgccatgccg tcatcagcgg ttccgtcctt    1620
```

tacaaccaag ccgagaaagg cagttactcc ctcggtatct ttggcggaaa agcccaggaa 1680
gttgccggca gcgcggaagt gaaaaccgta aacggcatac gccatatcgg ccttgccgcc 1740
aagcaactcg agcaccacca ccaccaccac tga 1773

<210> SEQ ID NO 155
<211> LENGTH: 590
<212> TYPE: PRT
<213> ORGANISM: Artificial Sequence
<220> FEATURE:
<223> OTHER INFORMATION: 961c-741

<400> SEQUENCE: 155

Met Ala Thr Asn Asp Asp Asp Val Lys Lys Ala Ala Thr Val Ala Ile
1 5 10 15

Ala Ala Ala Tyr Asn Asn Gly Gln Glu Ile Asn Gly Phe Lys Ala Gly
20 25 30

Glu Thr Ile Tyr Asp Ile Asp Glu Asp Gly Thr Ile Thr Lys Lys Asp
35 40 45

Ala Thr Ala Ala Asp Val Glu Ala Asp Asp Phe Lys Gly Leu Gly Leu
50 55 60

Lys Lys Val Val Thr Asn Leu Thr Lys Thr Val Asn Glu Asn Lys Gln
65 70 75 80

Asn Val Asp Ala Lys Val Lys Ala Ala Glu Ser Glu Ile Glu Lys Leu
85 90 95

Thr Thr Lys Leu Ala Asp Thr Asp Ala Ala Leu Ala Asp Thr Asp Ala
100 105 110

Ala Leu Asp Ala Thr Thr Asn Ala Leu Asn Lys Leu Gly Glu Asn Ile
115 120 125

Thr Thr Phe Ala Glu Glu Thr Lys Thr Asn Ile Val Lys Ile Asp Glu
130 135 140

Lys Leu Glu Ala Val Ala Asp Thr Val Asp Lys His Ala Glu Ala Phe
145 150 155 160

Asn Asp Ile Ala Asp Ser Leu Asp Glu Thr Asn Thr Lys Ala Asp Glu
165 170 175

Ala Val Lys Thr Ala Asn Glu Ala Lys Gln Thr Ala Glu Glu Thr Lys
180 185 190

Gln Asn Val Asp Ala Lys Val Lys Ala Ala Glu Thr Ala Ala Gly Lys
195 200 205

Ala Glu Ala Ala Ala Gly Thr Ala Asn Thr Ala Ala Asp Lys Ala Glu
210 215 220

Ala Val Ala Ala Lys Val Thr Asp Ile Lys Ala Asp Ile Ala Thr Asn
225 230 235 240

Lys Asp Asn Ile Ala Lys Lys Ala Asn Ser Ala Asp Val Tyr Thr Arg
245 250 255

Glu Glu Ser Asp Ser Lys Phe Val Arg Ile Asp Gly Leu Asn Ala Thr
260 265 270

Thr Glu Lys Leu Asp Thr Arg Leu Ala Ser Ala Glu Lys Ser Ile Ala
275 280 285

Asp His Asp Thr Arg Leu Asn Gly Leu Asp Lys Thr Val Ser Asp Leu
290 295 300

Arg Lys Glu Thr Arg Gln Gly Leu Ala Glu Gln Ala Ala Leu Ser Gly
305 310 315 320

Leu Phe Gln Pro Tyr Asn Val Gly Gly Ser Gly Gly Gly Gly Val Ala
325 330 335

-continued

```
Ala Asp Ile Gly Ala Gly Leu Ala Asp Ala Leu Thr Ala Pro Leu Asp
            340                 345                 350

His Lys Asp Lys Gly Leu Gln Ser Leu Thr Leu Asp Gln Ser Val Arg
        355                 360                 365

Lys Asn Glu Lys Leu Lys Leu Ala Ala Gln Gly Ala Glu Lys Thr Tyr
    370                 375                 380

Gly Asn Gly Asp Ser Leu Asn Thr Gly Lys Leu Lys Asn Asp Lys Val
385                 390                 395                 400

Ser Arg Phe Asp Phe Ile Arg Gln Ile Glu Val Asp Gly Gln Leu Ile
                405                 410                 415

Thr Leu Glu Ser Gly Glu Phe Gln Val Tyr Lys Gln Ser His Ser Ala
            420                 425                 430

Leu Thr Ala Phe Gln Thr Glu Gln Ile Gln Asp Ser Glu His Ser Gly
        435                 440                 445

Lys Met Val Ala Lys Arg Gln Phe Arg Ile Gly Asp Ile Ala Gly Glu
    450                 455                 460

His Thr Ser Phe Asp Lys Leu Pro Glu Gly Gly Arg Ala Thr Tyr Arg
465                 470                 475                 480

Gly Thr Ala Phe Gly Ser Asp Asp Ala Gly Gly Lys Leu Thr Tyr Thr
                485                 490                 495

Ile Asp Phe Ala Ala Lys Gln Gly Asn Gly Lys Ile Glu His Leu Lys
            500                 505                 510

Ser Pro Glu Leu Asn Val Asp Leu Ala Ala Ala Asp Ile Lys Pro Asp
        515                 520                 525

Gly Lys Arg His Ala Val Ile Ser Gly Ser Val Leu Tyr Asn Gln Ala
    530                 535                 540

Glu Lys Gly Ser Tyr Ser Leu Gly Ile Phe Gly Gly Lys Ala Gln Glu
545                 550                 555                 560

Val Ala Gly Ser Ala Glu Val Lys Thr Val Asn Gly Ile Arg His Ile
                565                 570                 575

Gly Leu Ala Ala Lys Gln Leu Glu His His His His His His
            580                 585                 590
```

<210> SEQ ID NO 156
<211> LENGTH: 4170
<212> TYPE: DNA
<213> ORGANISM: Artificial Sequence
<220> FEATURE:
<223> OTHER INFORMATION: 961c-983

<400> SEQUENCE: 156

```
atggccacaa acgacgacga tgttaaaaaa gctgccactg tggccattgc tgctgcctac      60

aacaatggcc aagaaatcaa cggtttcaaa gctggagaga ccatctacga cattgatgaa     120

gacggcacaa ttaccaaaaa agacgcaact gcagccgatg ttgaagccga cgactttaaa     180

ggtctgggtc tgaaaaaagt cgtgactaac ctgaccaaaa ccgtcaatga aaacaaacaa     240

aacgtcgatg ccaaagtaaa agctgcagaa tctgaaatag aaaagttaac aaccaagtta     300

gcagacactg atgccgcttt agcagatact gatgccgctc tggatgcaac caccaacgcc     360

ttgaataaat tgggagaaaa tataacgaca tttgctgaag agactaagac aaatatcgta     420

aaaattgatg aaaaattaga agccgtggct gataccgtcg acaagcatgc cgaagcattc     480

aacgatatcg ccgattcatt ggatgaaacc aacactaagg cagacgaagc cgtcaaaacc     540

gccaatgaag ccaaacagac ggccgaagaa accaaacaaa acgtcgatgc caaagtaaaa     600
```

-continued

```
gctgcagaaa ctgcagcagg caaagccgaa gctgccgctg gcacagctaa tactgcagcc    660
gacaaggccg aagctgtcgc tgcaaaagtt accgacatca aagctgatat cgctacgaac    720
aaagataata ttgctaaaaa agcaaacagt gccgacgtgt acaccagaga agagtctgac    780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtggatcc ggcggaggcg gcacttctgc gcccgacttc   1020
aatgcaggcg gtaccggtat cggcagcaac agcagagcaa caacagcgaa atcagcagca   1080
gtatcttacg ccggtatcaa gaacgaaatg tgcaaagaca gaagcatgct ctgtgccggt   1140
cgggatgacg ttgcggttac agacagggat gccaaaatca atgccccccc cccgaatctg   1200
cataccggag actttccaaa cccaaatgac gcatacaaga atttgatcaa cctcaaacct   1260
gcaattgaag caggctatac aggacgcggg gtagaggtag gtatcgtcga cacaggcgaa   1320
tccgtcggca gcatatcctt tcccgaactg tatggcagaa aagaacacgg ctataacgaa   1380
aattacaaaa actatacggc gtatatgcgg aaggaagcgc ctgaagacgg aggcggtaaa   1440
gacattgaag cttctttcga cgatgaggcc gttatagaga ctgaagcaaa gccgacggat   1500
atccgccacg taaaagaaat cggacacatc gatttggtct cccatattat tggcgggcgt   1560
tccgtggacg gcagacctgc aggcggtatt gcgcccgatg cgacgctaca cataatgaat   1620
acgaatgatg aaaccaagaa cgaaatgatg gttgcagcca tccgcaatgc atgggtcaag   1680
ctgggcgaac gtggcgtgcg catcgtcaat aacagttttg gaacaacatc gagggcaggc   1740
actgccgacc ttttccaaat agccaattcg gaggagcagt accgccaagc gttgctcgac   1800
tattccggcg gtgataaaac agacgagggt atccgcctga tgcaacagag cgattacggc   1860
aacctgtcct accacatccg taataaaaac atgcttttca tcttttcgac aggcaatgac   1920
gcacaagctc agcccaacac atatgcccta ttgccatttt atgaaaaaga cgctcaaaaa   1980
ggcattatca cagtcgcagg cgtagaccgc agtggagaaa agttcaaacg ggaaatgtat   2040
ggagaaccgg gtacagaacc gcttgagtat ggctccaacc attgcggaat tactgccatg   2100
tggtgcctgt cggcacccta tgaagcaagc gtccgtttca cccgtacaaa cccgattcaa   2160
attgccggaa catccttttc cgcacccatc gtaaccggca cggcggctct gctgctgcag   2220
aaatacccgt ggatgagcaa cgacaacctg cgtaccacgt tgctgacgac ggctcaggac   2280
atcggtgcag tcggcgtgga cagcaagttc ggctggggac tgctggatgc gggtaaggcc   2340
atgaacggac ccgcgtcctt tccgttcggc gactttaccg ccgatacgaa aggtacatcc   2400
gatattgcct actccttccg taacgacatt tcaggcacgg gcggcctgat caaaaaaggc   2460
ggcagccaac tgcaactgca cggcaacaac acctatacgg gcaaaaccat tatcgaaggc   2520
ggttcgctgg tgttgtacgg caacaacaaa tcggatatgc gcgtcgaaac caaaggtgcg   2580
ctgatttata acggggcggc atccggcggc agcctgaaca gcgacggcat tgtctatctg   2640
gcagataccg accaatccgg cgcaaacgaa accgtacaca tcaaaggcag tctgcagctg   2700
gacggcaaag gtacgctgta cacacgtttg ggcaaactgc tgaaagtgga cggtacggcg   2760
attatcggcg gcaagctgta catgtcggca cgcggcaagg gggcaggcta tctcaacagt   2820
accggacgac gtgttccctt cctgagtgcc gccaaaatcg ggcaggatta ttctttcttc   2880
acaaacatcg aaaccgacgg cggcctgctg gcttccctcg acagcgtcga aaaaacagcg   2940
ggcagtgaag gcgacacgct gtcctattat gtccgtcgcg gcaatgcggc acggactgct   3000
```

-continued

```
tcggcagcgg cacattccgc gcccgccggt ctgaaacacg ccgtagaaca gggcggcagc   3060
aatctggaaa acctgatggt cgaactggat gcctccgaat catccgcaac acccgagacg   3120
gttgaaactg cggcagccga ccgcacagat atgccgggca tccgccccta cggcgcaact   3180
ttccgcgcag cggcagccgt acagcatgcg aatgccgccg acggtgtacg catcttcaac   3240
agtctcgccg ctaccgtcta tgccgacagt accgccgccc atgccgatat gcagggacgc   3300
cgcctgaaag ccgtatcgga cgggttggac cacaacggca cgggtctgcg cgtcatcgcg   3360
caaacccaac aggacggtgg aacgtgggaa cagggcggtg ttgaaggcaa aatgcgcggc   3420
agtacccaaa ccgtcggcat tgccgcgaaa accggcgaaa atacgacagc agccgccaca   3480
ctgggcatgg gacgcagcac atggagcgaa aacagtgcaa atgcaaaaac cgacagcatt   3540
agtctgtttg caggcatacg gcacgatgcg ggcgatatcg gctatctcaa aggcctgttc   3600
tcctacggac gctacaaaaa cagcatcagc cgcagcaccg gtgcggacga acatgcggaa   3660
ggcagcgtca acggcacgct gatgcagctg ggcgcactgg gcggtgtcaa cgttccgttt   3720
gccgcaacgg gagatttgac ggtcgaaggc ggtctgcgct acgacctgct caaacaggat   3780
gcattcgccg aaaaaggcag tgctttgggc tggagcggca acagcctcac tgaaggcacg   3840
ctggtcggac tcgcgggtct gaagctgtcg caacccttga gcgataaagc cgtcctgttt   3900
gcaacggcgg gcgtggaacg cgacctgaac ggacgcgact acacggtaac gggcggcttt   3960
accggcgcga ctgcagcaac cggcaagacg gggcacgca atatgccgca cacccgtctg   4020
gttgccggcc tgggcgcgga tgtcgaattc ggcaacggct ggaacggctt ggcacgttac   4080
agctacgccg gttccaaaca gtacggcaac cacagcggac gagtcggcgt aggctaccgg   4140
ttcctcgagc accaccacca ccaccactga                                    4170
```

<210> SEQ ID NO 157
<211> LENGTH: 1389
<212> TYPE: PRT
<213> ORGANISM: Artificial Sequence
<220> FEATURE:
<223> OTHER INFORMATION: 961c-983

<400> SEQUENCE: 157

```
Met Ala Thr Asn Asp Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
```

-continued

```
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Gly Thr Ser
                325                 330                 335

Ala Pro Asp Phe Asn Ala Gly Gly Thr Gly Ile Gly Ser Asn Ser Arg
            340                 345                 350

Ala Thr Thr Ala Lys Ser Ala Ala Val Ser Tyr Ala Gly Ile Lys Asn
        355                 360                 365

Glu Met Cys Lys Asp Arg Ser Met Leu Cys Ala Gly Arg Asp Asp Val
    370                 375                 380

Ala Val Thr Asp Arg Asp Ala Lys Ile Asn Ala Pro Pro Pro Asn Leu
385                 390                 395                 400

His Thr Gly Asp Phe Pro Asn Pro Asn Asp Ala Tyr Lys Asn Leu Ile
                405                 410                 415

Asn Leu Lys Pro Ala Ile Glu Ala Gly Tyr Thr Gly Arg Gly Val Glu
            420                 425                 430

Val Gly Ile Val Asp Thr Gly Glu Ser Val Gly Ser Ile Ser Phe Pro
        435                 440                 445

Glu Leu Tyr Gly Arg Lys Glu His Gly Tyr Asn Glu Asn Tyr Lys Asn
    450                 455                 460

Tyr Thr Ala Tyr Met Arg Lys Glu Ala Pro Glu Asp Gly Gly Gly Lys
465                 470                 475                 480

Asp Ile Glu Ala Ser Phe Asp Asp Glu Ala Val Ile Glu Thr Glu Ala
                485                 490                 495

Lys Pro Thr Asp Ile Arg His Val Lys Glu Ile Gly His Ile Asp Leu
            500                 505                 510

Val Ser His Ile Ile Gly Gly Arg Ser Val Asp Gly Arg Pro Ala Gly
        515                 520                 525

Gly Ile Ala Pro Asp Ala Thr Leu His Ile Met Asn Thr Asn Asp Glu
    530                 535                 540

Thr Lys Asn Glu Met Met Val Ala Ala Ile Arg Asn Ala Trp Val Lys
545                 550                 555                 560

Leu Gly Glu Arg Gly Val Arg Ile Val Asn Asn Ser Phe Gly Thr Thr
                565                 570                 575
```

-continued

```
Ser Arg Ala Gly Thr Ala Asp Leu Phe Gln Ile Ala Asn Ser Glu Glu
            580                 585                 590

Gln Tyr Arg Gln Ala Leu Leu Asp Tyr Ser Gly Gly Asp Lys Thr Asp
        595                 600                 605

Glu Gly Ile Arg Leu Met Gln Gln Ser Asp Tyr Gly Asn Leu Ser Tyr
    610                 615                 620

His Ile Arg Asn Lys Asn Met Leu Phe Ile Phe Ser Thr Gly Asn Asp
625                 630                 635                 640

Ala Gln Ala Gln Pro Asn Thr Tyr Ala Leu Leu Pro Phe Tyr Glu Lys
                645                 650                 655

Asp Ala Gln Lys Gly Ile Ile Thr Val Ala Gly Val Asp Arg Ser Gly
            660                 665                 670

Glu Lys Phe Lys Arg Glu Met Tyr Gly Glu Pro Gly Thr Glu Pro Leu
        675                 680                 685

Glu Tyr Gly Ser Asn His Cys Gly Ile Thr Ala Met Trp Cys Leu Ser
    690                 695                 700

Ala Pro Tyr Glu Ala Ser Val Arg Phe Thr Arg Thr Asn Pro Ile Gln
705                 710                 715                 720

Ile Ala Gly Thr Ser Phe Ser Ala Pro Ile Val Thr Gly Thr Ala Ala
                725                 730                 735

Leu Leu Leu Gln Lys Tyr Pro Trp Met Ser Asn Asp Asn Leu Arg Thr
            740                 745                 750

Thr Leu Leu Thr Thr Ala Gln Asp Ile Gly Ala Val Gly Val Asp Ser
        755                 760                 765

Lys Phe Gly Trp Gly Leu Leu Asp Ala Gly Lys Ala Met Asn Gly Pro
    770                 775                 780

Ala Ser Phe Pro Phe Gly Asp Phe Thr Ala Asp Thr Lys Gly Thr Ser
785                 790                 795                 800

Asp Ile Ala Tyr Ser Phe Arg Asn Asp Ile Ser Gly Thr Gly Gly Leu
                805                 810                 815

Ile Lys Lys Gly Gly Ser Gln Leu Gln Leu His Gly Asn Asn Thr Tyr
            820                 825                 830

Thr Gly Lys Thr Ile Ile Glu Gly Gly Ser Leu Val Leu Tyr Gly Asn
        835                 840                 845

Asn Lys Ser Asp Met Arg Val Glu Thr Lys Gly Ala Leu Ile Tyr Asn
    850                 855                 860

Gly Ala Ala Ser Gly Gly Ser Leu Asn Ser Asp Gly Ile Val Tyr Leu
865                 870                 875                 880

Ala Asp Thr Asp Gln Ser Gly Ala Asn Glu Thr Val His Ile Lys Gly
                885                 890                 895

Ser Leu Gln Leu Asp Gly Lys Gly Thr Leu Tyr Thr Arg Leu Gly Lys
            900                 905                 910

Leu Leu Lys Val Asp Gly Thr Ala Ile Ile Gly Gly Lys Leu Tyr Met
        915                 920                 925

Ser Ala Arg Gly Lys Gly Ala Gly Tyr Leu Asn Ser Thr Gly Arg Arg
    930                 935                 940

Val Pro Phe Leu Ser Ala Ala Lys Ile Gly Gln Asp Tyr Ser Phe Phe
945                 950                 955                 960

Thr Asn Ile Glu Thr Asp Gly Gly Leu Leu Ala Ser Leu Asp Ser Val
                965                 970                 975

Glu Lys Thr Ala Gly Ser Glu Gly Asp Thr Leu Ser Tyr Tyr Val Arg
            980                 985                 990
```

-continued

```
Arg Gly Asn Ala Ala Arg Thr Ala Ser Ala Ala Ala His Ser Ala Pro
        995                 1000                1005

Ala Gly Leu Lys His Ala Val Glu Gln Gly Gly Ser Asn Leu Glu Asn
    1010                1015                1020

Leu Met Val Glu Leu Asp Ala Ser Glu Ser Ser Ala Thr Pro Glu Thr
1025                1030                1035                1040

Val Glu Thr Ala Ala Ala Asp Arg Thr Asp Met Pro Gly Ile Arg Pro
                1045                1050                1055

Tyr Gly Ala Thr Phe Arg Ala Ala Ala Ala Val Gln His Ala Asn Ala
            1060                1065                1070

Ala Asp Gly Val Arg Ile Phe Asn Ser Leu Ala Ala Thr Val Tyr Ala
        1075                1080                1085

Asp Ser Thr Ala Ala His Ala Asp Met Gln Gly Arg Arg Leu Lys Ala
    1090                1095                1100

Val Ser Asp Gly Leu Asp His Asn Gly Thr Gly Leu Arg Val Ile Ala
1105                1110                1115                1120

Gln Thr Gln Gln Asp Gly Gly Thr Trp Glu Gln Gly Gly Val Glu Gly
                1125                1130                1135

Lys Met Arg Gly Ser Thr Gln Thr Val Gly Ile Ala Ala Lys Thr Gly
            1140                1145                1150

Glu Asn Thr Thr Ala Ala Ala Thr Leu Gly Met Gly Arg Ser Thr Trp
        1155                1160                1165

Ser Glu Asn Ser Ala Asn Ala Lys Thr Asp Ser Ile Ser Leu Phe Ala
    1170                1175                1180

Gly Ile Arg His Asp Ala Gly Asp Ile Gly Tyr Leu Lys Gly Leu Phe
1185                1190                1195                1200

Ser Tyr Gly Arg Tyr Lys Asn Ser Ile Ser Arg Ser Thr Gly Ala Asp
                1205                1210                1215

Glu His Ala Glu Gly Ser Val Asn Gly Thr Leu Met Gln Leu Gly Ala
            1220                1225                1230

Leu Gly Gly Val Asn Val Pro Phe Ala Ala Thr Gly Asp Leu Thr Val
        1235                1240                1245

Glu Gly Gly Leu Arg Tyr Asp Leu Leu Lys Gln Asp Ala Phe Ala Glu
    1250                1255                1260

Lys Gly Ser Ala Leu Gly Trp Ser Gly Asn Ser Leu Thr Glu Gly Thr
1265                1270                1275                1280

Leu Val Gly Leu Ala Gly Leu Lys Leu Ser Gln Pro Leu Ser Asp Lys
                1285                1290                1295

Ala Val Leu Phe Ala Thr Ala Gly Val Glu Arg Asp Leu Asn Gly Arg
            1300                1305                1310

Asp Tyr Thr Val Thr Gly Gly Phe Thr Gly Ala Thr Ala Ala Thr Gly
        1315                1320                1325

Lys Thr Gly Ala Arg Asn Met Pro His Thr Arg Leu Val Ala Gly Leu
    1330                1335                1340

Gly Ala Asp Val Glu Phe Gly Asn Gly Trp Asn Gly Leu Ala Arg Tyr
1345                1350                1355                1360

Ser Tyr Ala Gly Ser Lys Gln Tyr Gly Asn His Ser Gly Arg Val Gly
                1365                1370                1375

Val Gly Tyr Arg Phe Leu Glu His His His His His His
            1380                1385
```

<210> SEQ ID NO 158
<211> LENGTH: 2304
<212> TYPE: DNA

-continued

<213> ORGANISM: Artificial Sequence
<220> FEATURE:
<223> OTHER INFORMATION: 961cL-ORF46.1

<400> SEQUENCE: 158

```
atgaaacact ttccatccaa agtactgacc acagccatcc ttgccacttt ctgtagcggc     60
gcactggcag ccacaaacga cgacgatgtt aaaaaagctg ccactgtggc cattgctgct    120
gcctacaaca atggccaaga aatcaacggt ttcaaagctg gagagaccat ctacgacatt    180
gatgaagacg gcacaattac caaaaaagac gcaactgcag ccgatgttga agccgacgac    240
tttaaaggtc tgggtctgaa aaaagtcgtg actaacctga ccaaaaccgt caatgaaaac    300
aaacaaaacg tcgatgccaa agtaaaagct gcagaatctg aaatagaaaa gttaacaacc    360
aagttagcag acactgatgc cgctttagca gatactgatg ccgctctgga tgcaaccacc    420
aacgccttga ataaattggg agaaaatata acgacatttg ctgaagagac taagacaaat    480
atcgtaaaaa ttgatgaaaa attagaagcc gtggctgata ccgtcgacaa gcatgccgaa    540
gcattcaacg atatcgccga ttcattggat gaaaccaaca ctaaggcaga cgaagccgtc    600
aaaaccgcca atgaagccaa acagacggcc gaagaaacca aacaaaacgt cgatgccaaa    660
gtaaaagctg cagaaactgc agcaggcaaa gccgaagctg ccgctggcac agctaatact    720
gcagccgaca aggccgaagc tgtcgctgca aaagttaccg acatcaaagc tgatatcgct    780
acgaacaaag ataatattgc taaaaaagca aacagtgccg acgtgtacac cagagaagag    840
tctgacagca aatttgtcag aattgatggt ctgaacgcta ctaccgaaaa attggacaca    900
cgcttggctt ctgctgaaaa atccattgcc gatcacgata ctcgcctgaa cggtttggat    960
aaaacagtgt cagacctgcg caaagaaacc cgccaaggcc ttgcagaaca agccgcgctc   1020
tccggtctgt tccaacctta caacgtgggt ggatccggag gaggaggatc agatttggca   1080
aacgattctt ttatccggca ggttctcgac cgtcagcatt tcgaacccga cgggaaatac   1140
cacctattcg gcagcagggg ggaacttgcc gagcgcagcg gccatatcgg attgggaaaa   1200
atacaaagcc atcagttggg caacctgatg attcaacagg cggccattaa aggaaatatc   1260
ggctacattg tccgcttttc cgatcacggg cacgaagtcc attcccccttt cgacaaccat   1320
gcctcacatt ccgattctga tgaagccggt agtcccgttg acggatttag cctttaccgc   1380
atccattggg acggatacga acaccatccc gccgacggct atgacgggcc acagggcggc   1440
ggctatcccg ctcccaaagg cgcgagggat atatacagct acgacataaa aggcgttgcc   1500
caaaatatcc gcctcaacct gaccgacaac cgcagcaccg gacaacggct tgccgaccgt   1560
ttccacaatg ccggtagtat gctgacgcaa ggagtaggcg acggattcaa acgcgccacc   1620
cgatacagcc ccgagctgga cagatcgggc aatgccgccg aagccttcaa cggcactgca   1680
gatatcgtta aaaacatcat cggcgcggca ggagaaattg tcggcgcagg cgatgccgtg   1740
cagggcataa gcgaaggctc aaacattgct gtcatgcacg gcttgggtct gctttccacc   1800
gaaaacaaga tggcgcgcat caacgatttg gcagatatgg cgcaactcaa agactatgcc   1860
gcagcagcca tccgcgattg ggcagtccaa aaccccaatg ccgcacaagg catagaagcc   1920
gtcagcaata tctttatggc agccatcccc atcaaaggga ttggagctgt tcggggaaaa   1980
tacggcttgg gcggcatcac ggcacatcct atcaagcggt cgcagatggg cgcgatcgca   2040
ttgccgaaag ggaaatccgc cgtcagcgac aattttgccg atgcggcata cgccaaatac   2100
ccgtcccctt accattcccg aaatatccgt tcaaacttgg agcagcgtta cggcaaagaa   2160
aacatcacct cctcaaccgt gccgccgtca aacggcaaaa atgtcaaact ggcagaccaa   2220
```

-continued cgccacccga agacaggcgt accgtttgac ggtaaagggt ttccgaattt tgagaagcac 2280
gtgaaatatg atacgtaact cgag 2304

<210> SEQ ID NO 159
<211> LENGTH: 765
<212> TYPE: PRT
<213> ORGANISM: Artificial Sequence
<220> FEATURE:
<223> OTHER INFORMATION: 961cL-ORF46.1

<400> SEQUENCE: 159

Met Lys His Phe Pro Ser Lys Val Leu Thr Thr Ala Ile Leu Ala Thr
1 5 10 15

Phe Cys Ser Gly Ala Leu Ala Ala Thr Asn Asp Asp Asp Val Lys Lys
20 25 30

Ala Ala Thr Val Ala Ile Ala Ala Ala Tyr Asn Asn Gly Gln Glu Ile
35 40 45

Asn Gly Phe Lys Ala Gly Glu Thr Ile Tyr Asp Ile Asp Glu Asp Gly
50 55 60

Thr Ile Thr Lys Lys Asp Ala Thr Ala Ala Asp Val Glu Ala Asp Asp
65 70 75 80

Phe Lys Gly Leu Gly Leu Lys Lys Val Val Thr Asn Leu Thr Lys Thr
85 90 95

Val Asn Glu Asn Lys Gln Asn Val Asp Ala Lys Val Lys Ala Ala Glu
100 105 110

Ser Glu Ile Glu Lys Leu Thr Thr Lys Leu Ala Asp Thr Asp Ala Ala
115 120 125

Leu Ala Asp Thr Asp Ala Ala Leu Asp Ala Thr Thr Asn Ala Leu Asn
130 135 140

Lys Leu Gly Glu Asn Ile Thr Thr Phe Ala Glu Glu Thr Lys Thr Asn
145 150 155 160

Ile Val Lys Ile Asp Glu Lys Leu Glu Ala Val Ala Asp Thr Val Asp
165 170 175

Lys His Ala Glu Ala Phe Asn Asp Ile Ala Asp Ser Leu Asp Glu Thr
180 185 190

Asn Thr Lys Ala Asp Glu Ala Val Lys Thr Ala Asn Glu Ala Lys Gln
195 200 205

Thr Ala Glu Glu Thr Lys Gln Asn Val Asp Ala Lys Val Lys Ala Ala
210 215 220

Glu Thr Ala Ala Gly Lys Ala Glu Ala Ala Ala Gly Thr Ala Asn Thr
225 230 235 240

Ala Ala Asp Lys Ala Glu Ala Val Ala Ala Lys Val Thr Asp Ile Lys
245 250 255

Ala Asp Ile Ala Thr Asn Lys Asp Asn Ile Ala Lys Lys Ala Asn Ser
260 265 270

Ala Asp Val Tyr Thr Arg Glu Glu Ser Asp Ser Lys Phe Val Arg Ile
275 280 285

Asp Gly Leu Asn Ala Thr Thr Glu Lys Leu Asp Thr Arg Leu Ala Ser
290 295 300

Ala Glu Lys Ser Ile Ala Asp His Asp Thr Arg Leu Asn Gly Leu Asp
305 310 315 320

Lys Thr Val Ser Asp Leu Arg Lys Glu Thr Arg Gln Gly Leu Ala Glu
325 330 335

Gln Ala Ala Leu Ser Gly Leu Phe Gln Pro Tyr Asn Val Gly Gly Ser

-continued

```
            340                 345                 350

Gly Gly Gly Gly Ser Asp Leu Ala Asn Asp Ser Phe Ile Arg Gln Val
        355                 360                 365

Leu Asp Arg Gln His Phe Glu Pro Asp Gly Lys Tyr His Leu Phe Gly
    370                 375                 380

Ser Arg Gly Glu Leu Ala Glu Arg Ser Gly His Ile Gly Leu Gly Lys
385                 390                 395                 400

Ile Gln Ser His Gln Leu Gly Asn Leu Met Ile Gln Gln Ala Ala Ile
                405                 410                 415

Lys Gly Asn Ile Gly Tyr Ile Val Arg Phe Ser Asp His Gly His Glu
            420                 425                 430

Val His Ser Pro Phe Asp Asn His Ala Ser His Ser Asp Ser Asp Glu
        435                 440                 445

Ala Gly Ser Pro Val Asp Gly Phe Ser Leu Tyr Arg Ile His Trp Asp
    450                 455                 460

Gly Tyr Glu His His Pro Ala Asp Gly Tyr Asp Gly Pro Gln Gly Gly
465                 470                 475                 480

Gly Tyr Pro Ala Pro Lys Gly Ala Arg Asp Ile Tyr Ser Tyr Asp Ile
                485                 490                 495

Lys Gly Val Ala Gln Asn Ile Arg Leu Asn Leu Thr Asp Asn Arg Ser
            500                 505                 510

Thr Gly Gln Arg Leu Ala Asp Arg Phe His Asn Ala Gly Ser Met Leu
        515                 520                 525

Thr Gln Gly Val Gly Asp Gly Phe Lys Arg Ala Thr Arg Tyr Ser Pro
    530                 535                 540

Glu Leu Asp Arg Ser Gly Asn Ala Ala Glu Ala Phe Asn Gly Thr Ala
545                 550                 555                 560

Asp Ile Val Lys Asn Ile Ile Gly Ala Ala Gly Glu Ile Val Gly Ala
                565                 570                 575

Gly Asp Ala Val Gln Gly Ile Ser Glu Gly Ser Asn Ile Ala Val Met
            580                 585                 590

His Gly Leu Gly Leu Leu Ser Thr Glu Asn Lys Met Ala Arg Ile Asn
        595                 600                 605

Asp Leu Ala Asp Met Ala Gln Leu Lys Asp Tyr Ala Ala Ala Ala Ile
    610                 615                 620

Arg Asp Trp Ala Val Gln Asn Pro Asn Ala Ala Gln Gly Ile Glu Ala
625                 630                 635                 640

Val Ser Asn Ile Phe Met Ala Ala Ile Pro Ile Lys Gly Ile Gly Ala
                645                 650                 655

Val Arg Gly Lys Tyr Gly Leu Gly Gly Ile Thr Ala His Pro Ile Lys
            660                 665                 670

Arg Ser Gln Met Gly Ala Ile Ala Leu Pro Lys Gly Lys Ser Ala Val
        675                 680                 685

Ser Asp Asn Phe Ala Asp Ala Ala Tyr Ala Lys Tyr Pro Ser Pro Tyr
    690                 695                 700

His Ser Arg Asn Ile Arg Ser Asn Leu Glu Gln Arg Tyr Gly Lys Glu
705                 710                 715                 720

Asn Ile Thr Ser Ser Thr Val Pro Pro Ser Asn Gly Lys Asn Val Lys
                725                 730                 735

Leu Ala Asp Gln Arg His Pro Lys Thr Gly Val Pro Phe Asp Gly Lys
            740                 745                 750

Gly Phe Pro Asn Phe Glu Lys His Val Lys Tyr Asp Thr
        755                 760                 765
```

-continued

<210> SEQ ID NO 160
<211> LENGTH: 1839
<212> TYPE: DNA
<213> ORGANISM: Artificial Sequence
<220> FEATURE:
<223> OTHER INFORMATION: 961cL-741

<400> SEQUENCE: 160
atgaaacact ttccatccaa agtactgacc acagccatcc ttgccacttt ctgtagcggc 60
gcactggcag ccacaaacga cgacgatgtt aaaaaagctg ccactgtggc cattgctgct 120
gcctacaaca atggccaaga aatcaacggt ttcaaagctg gagagaccat ctacgacatt 180
gatgaagacg gcacaattac caaaaaagac gcaactgcag ccgatgttga agccgacgac 240
tttaaaggtc tgggtctgaa aaaagtcgtg actaacctga ccaaaaccgt caatgaaaac 300
aaacaaaacg tcgatgccaa agtaaaagct gcagaatctg aaatagaaaa gttaacaacc 360
aagttagcag acactgatgc cgctttagca gatactgatg ccgctctgga tgcaaccacc 420
aacgccttga ataaattggg agaaaatata acgacatttg ctgaagagac taagacaaat 480
atcgtaaaaa ttgatgaaaa attagaagcc gtggctgata ccgtcgacaa gcatgccgaa 540
gcattcaacg atatcgccga ttcattggat gaaaccaaca ctaaggcaga cgaagccgtc 600
aaaaccgcca atgaagccaa acagacggcc gaagaaacca aacaaaacgt cgatgccaaa 660
gtaaaagctg cagaaactgc agcaggcaaa gccgaagctg ccgctggcac agctaatact 720
gcagccgaca aggccgaagc tgtcgctgca aaagttaccg acatcaaagc tgatatcgct 780
acgaacaaag ataatattgc taaaaaagca aacagtgccg acgtgtacac cagagaagag 840
tctgacagca aatttgtcag aattgatggt ctgaacgcta ctaccgaaaa attggacaca 900
cgcttggctt ctgctgaaaa atccattgcc gatcacgata ctcgcctgaa cggtttggat 960
aaaacagtgt cagacctgcg caaagaaacc cgccaaggcc ttgcagaaca agccgcgctc 1020
tccggtctgt tccaacctta caacgtgggt ggatccggag ggggtggtgt cgccgccgac 1080
atcggtgcgg ggcttgccga tgcactaacc gcaccgctcg accataaaga caaaggtttg 1140
cagtctttga cgctggatca gtccgtcagg aaaaacgaga aactgaagct ggcggcacaa 1200
ggtgcggaaa aaacttatgg aaacggtgac agcctcaata cgggcaaatt gaagaacgac 1260
aaggtcagcc gtttcgactt tatccgccaa atcgaagtgg acgggcagct cattaccttg 1320
gagagtggag agttccaagt atacaaacaa agccattccg ccttaaccgc ctttcagacc 1380
gagcaaatac aagattcgga gcattccggg aagatggttg cgaaacgcca gttcagaatc 1440
ggcgacatag cgggcgaaca tacatctttt gacaagcttc ccgaaggcgg cagggcgaca 1500
tatcgcggga cggcgttcgg ttcagacgat gccggcggaa aactgaccta caccatagat 1560
ttcgccgcca agcagggaaa cggcaaaatc gaacatttga aatcgccaga actcaatgtc 1620
gacctggccg ccgccgatat caagccggat ggaaaacgcc atgccgtcat cagcggttcc 1680
gtcctttaca accaagccga gaaaggcagt tactccctcg gtatctttgg cggaaaagcc 1740
caggaagttg ccggcagcgc ggaagtgaaa accgtaaacg gcatacgcca tatcggcctt 1800
gccgccaagc aactcgagca ccaccaccac caccactga 1839

<210> SEQ ID NO 161
<211> LENGTH: 612
<212> TYPE: PRT
<213> ORGANISM: Artificial Sequence
<220> FEATURE:

-continued

<223> OTHER INFORMATION: 961cL-741

<400> SEQUENCE: 161

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Asp Val Lys Lys
            20                  25                  30

Ala Ala Thr Val Ala Ile Ala Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Thr Asn Ala Leu Asn
    130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
    210                 215                 220

Glu Thr Ala Ala Gly Lys Ala Glu Ala Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
        275                 280                 285

Asp Gly Leu Asn Ala Thr Thr Glu Lys Leu Asp Thr Arg Leu Ala Ser
    290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly Gly Ser
            340                 345                 350

Gly Gly Gly Gly Val Ala Ala Asp Ile Gly Ala Gly Leu Ala Asp Ala
        355                 360                 365

Leu Thr Ala Pro Leu Asp His Lys Asp Lys Gly Leu Gln Ser Leu Thr
    370                 375                 380

Leu Asp Gln Ser Val Arg Lys Asn Glu Lys Leu Lys Leu Ala Ala Gln
385                 390                 395                 400
```

-continued

```
Gly Ala Glu Lys Thr Tyr Gly Asn Gly Asp Ser Leu Asn Thr Gly Lys
                405                 410                 415

Leu Lys Asn Asp Lys Val Ser Arg Phe Asp Phe Ile Arg Gln Ile Glu
            420                 425                 430

Val Asp Gly Gln Leu Ile Thr Leu Glu Ser Gly Glu Phe Gln Val Tyr
        435                 440                 445

Lys Gln Ser His Ser Ala Leu Thr Ala Phe Gln Thr Glu Gln Ile Gln
    450                 455                 460

Asp Ser Glu His Ser Gly Lys Met Val Ala Lys Arg Gln Phe Arg Ile
465                 470                 475                 480

Gly Asp Ile Ala Gly Glu His Thr Ser Phe Asp Lys Leu Pro Glu Gly
                485                 490                 495

Gly Arg Ala Thr Tyr Arg Gly Thr Ala Phe Gly Ser Asp Asp Ala Gly
            500                 505                 510

Gly Lys Leu Thr Tyr Thr Ile Asp Phe Ala Ala Lys Gln Gly Asn Gly
        515                 520                 525

Lys Ile Glu His Leu Lys Ser Pro Glu Leu Asn Val Asp Leu Ala Ala
    530                 535                 540

Ala Asp Ile Lys Pro Asp Gly Lys Arg His Ala Val Ile Ser Gly Ser
545                 550                 555                 560

Val Leu Tyr Asn Gln Ala Glu Lys Gly Ser Tyr Ser Leu Gly Ile Phe
                565                 570                 575

Gly Gly Lys Ala Gln Glu Val Ala Gly Ser Ala Glu Val Lys Thr Val
            580                 585                 590

Asn Gly Ile Arg His Ile Gly Leu Ala Ala Lys Gln Leu Glu His His
        595                 600                 605

His His His His
    610
```

<210> SEQ ID NO 162
<211> LENGTH: 4218
<212> TYPE: DNA
<213> ORGANISM: Artificial Sequence
<220> FEATURE:
<223> OTHER INFORMATION: 961cL-983

<400> SEQUENCE: 162

```
atgaaacact ttccatccaa agtactgacc acagccatcc ttgccacttt ctgtagcggc     60

gcactggcag ccacaaacga cgacgatgtt aaaaaagctg ccactgtggc cattgctgct    120

gcctacaaca atggccaaga aatcaacggt ttcaaagctg gagagaccat ctacgacatt    180

gatgaagacg gcacaattac caaaaaagac gcaactgcag ccgatgttga agccgacgac    240

tttaaaggtc tgggtctgaa aaaagtcgtg actaacctga ccaaaaccgt caatgaaaac    300

aaacaaaacg tcgatgccaa agtaaaagct gcagaatctg aaatagaaaa gttaacaacc    360

aagttagcag acactgatgc cgctttagca gatactgatg ccgctctgga tgcaaccacc    420

aacgccttga ataaattggg agaaaatata acgacatttg ctgaagagac taagacaaat    480

atcgtaaaaa ttgatgaaaa attagaagcc gtggctgata ccgtcgacaa gcatgccgaa    540

gcattcaacg atatcgccga ttcattggat gaaaccaaca ctaaggcaga cgaagccgtc    600

aaaaccgcca atgaagccaa acagacggcc gaagaaacca aacaaaacgt cgatgccaaa    660

gtaaaagctg cagaaactgc agcaggcaaa gccgaagctg ccgctggcac agctaatact    720

gcagccgaca aggccgaagc tgtcgctgca aaagttaccg acatcaaagc tgatatcgct    780

acgaacaaag ataatattgc taaaaaagca aacagtgccg acgtgtacac cagagaagag    840
```

-continued

```
tctgacagca aatttgtcag aattgatggt ctgaacgcta ctaccgaaaa attggacaca    900
cgcttggctt ctgctgaaaa atccattgcc gatcacgata ctcgcctgaa cggtttggat    960
aaaacagtgt cagacctgcg caaagaaacc cgccaaggcc ttgcagaaca agccgcgctc   1020
tccggtctgt tccaacctta caacgtgggt ggatccggcg gaggcggcac ttctgcgccc   1080
gacttcaatg caggcggtac cggtatcggc agcaacagca gagcaacaac agcgaaatca   1140
gcagcagtat cttacgccgg tatcaagaac gaaatgtgca aagacagaag catgctctgt   1200
gccggtcggg atgacgttgc ggttacagac agggatgcca aaatcaatgc cccccccccg   1260
aatctgcata ccggagactt tccaaaccca aatgacgcat acaagaattt gatcaacctc   1320
aaacctgcaa ttgaagcagg ctatacagga cgcggggtag aggtaggtat cgtcgacaca   1380
ggcgaatccg tcggcagcat atcctttccc gaactgtatg gcagaaaaga acacggctat   1440
aacgaaaatt acaaaaacta tacggcgtat atgcggaagg aagcgcctga agacggaggc   1500
ggtaaagaca ttgaagcttc tttcgacgat gaggccgtta tagagactga agcaaagccg   1560
acggatatcc gccacgtaaa agaaatcgga cacatcgatt tggtctccca tattattggc   1620
gggcgttccg tggacggcag acctgcaggc ggtattgcgc ccgatgcgac gctacacata   1680
atgaatacga atgatgaaac caagaacgaa atgatggttg cagccatccg caatgcatgg   1740
gtcaagctgg gcgaacgtgg cgtgcgcatc gtcaataaca gttttggaac aacatcgagg   1800
gcaggcactg ccgacctttt ccaaatagcc aattcggagg agcagtaccg ccaagcgttg   1860
ctcgactatt ccggcggtga taaaacagac gagggtatcc gcctgatgca acagagcgat   1920
tacggcaacc tgtcctacca catccgtaat aaaaacatgc ttttcatctt ttcgacaggc   1980
aatgacgcac aagctcagcc caacacatat gccctattgc cattttatga aaaagacgct   2040
caaaaaggca ttatcacagt cgcaggcgta gaccgcagtg gagaaaagtt caaacgggaa   2100
atgtatggag aaccgggtac agaaccgctt gagtatggct ccaaccattg cggaattact   2160
gccatgtggt gcctgtcggc accctatgaa gcaagcgtcc gtttcacccg tacaaacccg   2220
attcaaattg ccggaacatc cttttccgca cccatcgtaa ccggcacggc ggctctgctg   2280
ctgcagaaat acccgtggat gagcaacgac aacctgcgta ccacgttgct gacgacggct   2340
caggacatcg gtgcagtcgg cgtggacagc aagttcggct ggggactgct ggatgcgggt   2400
aaggccatga acggacccgc gtcctttccg ttcggcgact ttaccgccga tacgaaaggt   2460
acatccgata ttgcctactc cttccgtaac gacatttcag gcacgggcgg cctgatcaaa   2520
aaaggcggca gccaactgca actgcacggc aacaacacct atacgggcaa aaccattatc   2580
gaaggcggtt cgctggtgtt gtacggcaac aacaaatcgg atatgcgcgt cgaaaccaaa   2640
ggtgcgctga tttataacgg ggcggcatcc ggcggcagcc tgaacagcga cggcattgtc   2700
tatctggcag ataccgacca atccggcgca aacgaaaccg tacacatcaa aggcagtctg   2760
cagctggacg gcaaaggtac gctgtacaca cgtttgggca aactgctgaa agtggacggt   2820
acggcgatta tcggcggcaa gctgtacatg tcggcacgcg gcaagggggc aggctatctc   2880
aacagtaccg gacgacgtgt tcccttcctg agtgccgcca aaatcgggca ggattattct   2940
ttcttcacaa acatcgaaac cgacggcggc ctgctggctt ccctcgacag cgtcgaaaaa   3000
acagcgggca gtgaaggcga cacgctgtcc tattatgtcc gtcgcggcaa tgcggcacgg   3060
actgcttcgg cagcggcaca ttccgcgccc gccggtctga aacacgccgt agaacagggc   3120
ggcagcaatc tggaaaacct gatggtcgaa ctggatgcct ccgaatcatc cgcaacaccc   3180
```

-continued

```
gagacggttg aaactgcggc agccgaccgc acagatatgc cgggcatccg cccctacggc   3240

gcaactttcc gcgcagcggc agccgtacag catgcgaatg ccgccgacgg tgtacgcatc   3300

ttcaacagtc tcgccgctac cgtctatgcc gacagtaccg ccgcccatgc cgatatgcag   3360

ggacgccgcc tgaaagccgt atcggacggg ttggaccaca acggcacggg tctgcgcgtc   3420

atcgcgcaaa cccaacagga cggtggaacg tgggaacagg gcggtgttga aggcaaaatg   3480

cgcggcagta cccaaaccgt cggcattgcc gcgaaaaccg gcgaaaatac gacagcagcc   3540

gccacactgg gcatgggacg cagcacatgg agcgaaaaca gtgcaaatgc aaaaaccgac   3600

agcattagtc tgtttgcagg catacggcac gatgcgggcg atatcggcta tctcaaaggc   3660

ctgttctcct acggacgcta caaaaacagc atcagccgca gcaccggtgc ggacgaacat   3720

gcggaaggca gcgtcaacgg cacgctgatg cagctgggcg cactgggcgg tgtcaacgtt   3780

ccgtttgccg caacgggaga tttgacggtc gaaggcggtc tgcgctacga cctgctcaaa   3840

caggatgcat tcgccgaaaa aggcagtgct ttgggctgga gcggcaacag cctcactgaa   3900

ggcacgctgg tcggactcgc gggtctgaag ctgtcgcaac ccttgagcga taaagccgtc   3960

ctgtttgcaa cggcgggcgt ggaacgcgac ctgaacggac gcgactacac ggtaacgggc   4020

ggctttaccg gcgcgactgc agcaaccggc aagacggggg cacgcaatat gccgcacacc   4080

cgtctggttg ccggcctggg cgcggatgtc gaattcggca acggctggaa cggcttggca   4140

cgttacagct acgccggttc caaacagtac ggcaaccaca gcggacgagt cggcgtaggc   4200

taccggttct gactcgag                                                  4218
```

```
<210> SEQ ID NO 163
<211> LENGTH: 1403
<212> TYPE: PRT
<213> ORGANISM: Artificial Sequence
<220> FEATURE:
<223> OTHER INFORMATION: 961cL-983

<400> SEQUENCE: 163

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Asp Val Lys Lys
            20                  25                  30

Ala Ala Thr Val Ala Ile Ala Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Thr Asn Ala Leu Asn
    130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175
```

-continued

```
Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
    210                 215                 220

Glu Thr Ala Ala Gly Lys Ala Glu Ala Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
        275                 280                 285

Asp Gly Leu Asn Ala Thr Thr Glu Lys Leu Asp Thr Arg Leu Ala Ser
    290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly Gly Ser
            340                 345                 350

Gly Gly Gly Gly Thr Ser Ala Pro Asp Phe Asn Ala Gly Gly Thr Gly
        355                 360                 365

Ile Gly Ser Asn Ser Arg Ala Thr Thr Ala Lys Ser Ala Ala Val Ser
    370                 375                 380

Tyr Ala Gly Ile Lys Asn Glu Met Cys Lys Asp Arg Ser Met Leu Cys
385                 390                 395                 400

Ala Gly Arg Asp Asp Val Ala Val Thr Asp Arg Asp Ala Lys Ile Asn
                405                 410                 415

Ala Pro Pro Pro Asn Leu His Thr Gly Asp Phe Pro Asn Pro Asn Asp
            420                 425                 430

Ala Tyr Lys Asn Leu Ile Asn Leu Lys Pro Ala Ile Glu Ala Gly Tyr
        435                 440                 445

Thr Gly Arg Gly Val Glu Val Gly Ile Val Asp Thr Gly Glu Ser Val
    450                 455                 460

Gly Ser Ile Ser Phe Pro Glu Leu Tyr Gly Arg Lys Glu His Gly Tyr
465                 470                 475                 480

Asn Glu Asn Tyr Lys Asn Tyr Thr Ala Tyr Met Arg Lys Glu Ala Pro
                485                 490                 495

Glu Asp Gly Gly Gly Lys Asp Ile Glu Ala Ser Phe Asp Asp Glu Ala
            500                 505                 510

Val Ile Glu Thr Glu Ala Lys Pro Thr Asp Ile Arg His Val Lys Glu
        515                 520                 525

Ile Gly His Ile Asp Leu Val Ser His Ile Ile Gly Gly Arg Ser Val
    530                 535                 540

Asp Gly Arg Pro Ala Gly Gly Ile Ala Pro Asp Ala Thr Leu His Ile
545                 550                 555                 560

Met Asn Thr Asn Asp Glu Thr Lys Asn Glu Met Met Val Ala Ala Ile
                565                 570                 575

Arg Asn Ala Trp Val Lys Leu Gly Glu Arg Gly Val Arg Ile Val Asn
            580                 585                 590

Asn Ser Phe Gly Thr Thr Ser Arg Ala Gly Thr Ala Asp Leu Phe Gln
```

-continued

```
        595                 600                 605

Ile Ala Asn Ser Glu Glu Gln Tyr Arg Gln Ala Leu Leu Asp Tyr Ser
    610                 615                 620

Gly Gly Asp Lys Thr Asp Glu Gly Ile Arg Leu Met Gln Gln Ser Asp
625                 630                 635                 640

Tyr Gly Asn Leu Ser Tyr His Ile Arg Asn Lys Asn Met Leu Phe Ile
                645                 650                 655

Phe Ser Thr Gly Asn Asp Ala Gln Ala Gln Pro Asn Thr Tyr Ala Leu
            660                 665                 670

Leu Pro Phe Tyr Glu Lys Asp Ala Gln Lys Gly Ile Ile Thr Val Ala
        675                 680                 685

Gly Val Asp Arg Ser Gly Glu Lys Phe Lys Arg Glu Met Tyr Gly Glu
    690                 695                 700

Pro Gly Thr Glu Pro Leu Glu Tyr Gly Ser Asn His Cys Gly Ile Thr
705                 710                 715                 720

Ala Met Trp Cys Leu Ser Ala Pro Tyr Glu Ala Ser Val Arg Phe Thr
                725                 730                 735

Arg Thr Asn Pro Ile Gln Ile Ala Gly Thr Ser Phe Ser Ala Pro Ile
            740                 745                 750

Val Thr Gly Thr Ala Ala Leu Leu Leu Gln Lys Tyr Pro Trp Met Ser
        755                 760                 765

Asn Asp Asn Leu Arg Thr Thr Leu Leu Thr Thr Ala Gln Asp Ile Gly
    770                 775                 780

Ala Val Gly Val Asp Ser Lys Phe Gly Trp Gly Leu Leu Asp Ala Gly
785                 790                 795                 800

Lys Ala Met Asn Gly Pro Ala Ser Phe Pro Phe Gly Asp Phe Thr Ala
                805                 810                 815

Asp Thr Lys Gly Thr Ser Asp Ile Ala Tyr Ser Phe Arg Asn Asp Ile
            820                 825                 830

Ser Gly Thr Gly Gly Leu Ile Lys Lys Gly Gly Ser Gln Leu Gln Leu
        835                 840                 845

His Gly Asn Asn Thr Tyr Thr Gly Lys Thr Ile Ile Glu Gly Gly Ser
    850                 855                 860

Leu Val Leu Tyr Gly Asn Asn Lys Ser Asp Met Arg Val Glu Thr Lys
865                 870                 875                 880

Gly Ala Leu Ile Tyr Asn Gly Ala Ala Ser Gly Gly Ser Leu Asn Ser
                885                 890                 895

Asp Gly Ile Val Tyr Leu Ala Asp Thr Asp Gln Ser Gly Ala Asn Glu
            900                 905                 910

Thr Val His Ile Lys Gly Ser Leu Gln Leu Asp Gly Lys Gly Thr Leu
        915                 920                 925

Tyr Thr Arg Leu Gly Lys Leu Leu Lys Val Asp Gly Thr Ala Ile Ile
    930                 935                 940

Gly Gly Lys Leu Tyr Met Ser Ala Arg Gly Lys Gly Ala Gly Tyr Leu
945                 950                 955                 960

Asn Ser Thr Gly Arg Arg Val Pro Phe Leu Ser Ala Ala Lys Ile Gly
                965                 970                 975

Gln Asp Tyr Ser Phe Phe Thr Asn Ile Glu Thr Asp Gly Gly Leu Leu
            980                 985                 990

Ala Ser Leu Asp Ser Val Glu Lys Thr Ala Gly Ser Glu Gly Asp Thr
        995                 1000                1005

Leu Ser Tyr Tyr Val Arg Arg Gly Asn Ala Ala Arg Thr Ala Ser Ala
    1010                1015                1020
```

-continued

```
Ala Ala His Ser Ala Pro Ala Gly Leu Lys His Ala Val Glu Gln Gly
1025                1030                1035                1040

Gly Ser Asn Leu Glu Asn Leu Met Val Glu Leu Asp Ala Ser Glu Ser
                1045                1050                1055

Ser Ala Thr Pro Glu Thr Val Glu Thr Ala Ala Ala Asp Arg Thr Asp
            1060                1065                1070

Met Pro Gly Ile Arg Pro Tyr Gly Ala Thr Phe Arg Ala Ala Ala Ala
        1075                1080                1085

Val Gln His Ala Asn Ala Ala Asp Gly Val Arg Ile Phe Asn Ser Leu
    1090                1095                1100

Ala Ala Thr Val Tyr Ala Asp Ser Thr Ala Ala His Ala Asp Met Gln
1105                1110                1115                1120

Gly Arg Arg Leu Lys Ala Val Ser Asp Gly Leu Asp His Asn Gly Thr
                1125                1130                1135

Gly Leu Arg Val Ile Ala Gln Thr Gln Gln Asp Gly Gly Thr Trp Glu
            1140                1145                1150

Gln Gly Gly Val Glu Gly Lys Met Arg Gly Ser Thr Gln Thr Val Gly
        1155                1160                1165

Ile Ala Ala Lys Thr Gly Glu Asn Thr Thr Ala Ala Ala Thr Leu Gly
    1170                1175                1180

Met Gly Arg Ser Thr Trp Ser Glu Asn Ser Ala Asn Ala Lys Thr Asp
1185                1190                1195                1200

Ser Ile Ser Leu Phe Ala Gly Ile Arg His Asp Ala Gly Asp Ile Gly
                1205                1210                1215

Tyr Leu Lys Gly Leu Phe Ser Tyr Gly Arg Tyr Lys Asn Ser Ile Ser
            1220                1225                1230

Arg Ser Thr Gly Ala Asp Glu His Ala Glu Gly Ser Val Asn Gly Thr
        1235                1240                1245

Leu Met Gln Leu Gly Ala Leu Gly Gly Val Asn Val Pro Phe Ala Ala
    1250                1255                1260

Thr Gly Asp Leu Thr Val Glu Gly Gly Leu Arg Tyr Asp Leu Leu Lys
1265                1270                1275                1280

Gln Asp Ala Phe Ala Glu Lys Gly Ser Ala Leu Gly Trp Ser Gly Asn
                1285                1290                1295

Ser Leu Thr Glu Gly Thr Leu Val Gly Leu Ala Gly Leu Lys Leu Ser
            1300                1305                1310

Gln Pro Leu Ser Asp Lys Ala Val Leu Phe Ala Thr Ala Gly Val Glu
        1315                1320                1325

Arg Asp Leu Asn Gly Arg Asp Tyr Thr Val Thr Gly Gly Phe Thr Gly
    1330                1335                1340

Ala Thr Ala Ala Thr Gly Lys Thr Gly Ala Arg Asn Met Pro His Thr
1345                1350                1355                1360

Arg Leu Val Ala Gly Leu Gly Ala Asp Val Glu Phe Gly Asn Gly Trp
                1365                1370                1375

Asn Gly Leu Ala Arg Tyr Ser Tyr Ala Gly Ser Lys Gln Tyr Gly Asn
            1380                1385                1390

His Ser Gly Arg Val Gly Val Gly Tyr Arg Phe
        1395                1400
```

<210> SEQ ID NO 164
<211> LENGTH: 33
<212> TYPE: DNA
<213> ORGANISM: Artificial Sequence
<220> FEATURE:

-continued

<223> OTHER INFORMATION: Oligonucleotide

<400> SEQUENCE: 164
cgcggatccg ctagcaaaac aaccgacaaa cgg 33

<210> SEQ ID NO 165
<211> LENGTH: 27
<212> TYPE: DNA
<213> ORGANISM: Artificial Sequence
<220> FEATURE:
<223> OTHER INFORMATION: Oligonucleotide

<400> SEQUENCE: 165
cccgctcgag ttaccagcgg tagccta 27

<210> SEQ ID NO 166
<211> LENGTH: 30
<212> TYPE: DNA
<213> ORGANISM: Artificial Sequence
<220> FEATURE:
<223> OTHER INFORMATION: Oligonucleotide

<400> SEQUENCE: 166
ctagctagcg gacacactta tttcggcatc 30

<210> SEQ ID NO 167
<211> LENGTH: 32
<212> TYPE: DNA
<213> ORGANISM: Artificial Sequence
<220> FEATURE:
<223> OTHER INFORMATION: Oligonucleotide

<400> SEQUENCE: 167
cccgctcgag ttaccagcgg tagcctaatt tg 32

<210> SEQ ID NO 168
<211> LENGTH: 10
<212> TYPE: DNA
<213> ORGANISM: Artificial Sequence
<220> FEATURE:
<223> OTHER INFORMATION: Oligonucleotide

<400> SEQUENCE: 168
cccgctcgag 10

<210> SEQ ID NO 169
<211> LENGTH: 33
<212> TYPE: DNA
<213> ORGANISM: Artificial Sequence
<220> FEATURE:
<223> OTHER INFORMATION: Oligonucleotide

<400> SEQUENCE: 169
cgcggatccc atatgaaaac cttcttcaaa acc 33

<210> SEQ ID NO 170
<211> LENGTH: 28
<212> TYPE: DNA
<213> ORGANISM: Artificial Sequence
<220> FEATURE:
<223> OTHER INFORMATION: Oligonucleotide

<400> SEQUENCE: 170
cccgctcgag ttatttggct gcgccttc 28

-continued

<210> SEQ ID NO 171
<211> LENGTH: 35
<212> TYPE: DNA
<213> ORGANISM: Artificial Sequence
<220> FEATURE:
<223> OTHER INFORMATION: Oligonucleotide

<400> SEQUENCE: 171
gcggcattaa tatgttgaga aaattgttga aatgg 35

<210> SEQ ID NO 172
<211> LENGTH: 34
<212> TYPE: DNA
<213> ORGANISM: Artificial Sequence
<220> FEATURE:
<223> OTHER INFORMATION: Oligonucleotide

<400> SEQUENCE: 172
gcggcctcga gttatttttt caaaatatat ttgc 34

<210> SEQ ID NO 173
<211> LENGTH: 33
<212> TYPE: DNA
<213> ORGANISM: Artificial Sequence
<220> FEATURE:
<223> OTHER INFORMATION: Oligonucleotide

<400> SEQUENCE: 173
gcggccatat gttacctaac cgtttcaaaa tgt 33

<210> SEQ ID NO 174
<211> LENGTH: 31
<212> TYPE: DNA
<213> ORGANISM: Artificial Sequence
<220> FEATURE:
<223> OTHER INFORMATION: Oligonucleotide

<400> SEQUENCE: 174
gcggcctcga gttatttccg aggttttcgg g 31

<210> SEQ ID NO 175
<211> LENGTH: 32
<212> TYPE: DNA
<213> ORGANISM: Artificial Sequence
<220> FEATURE:
<223> OTHER INFORMATION: Oligonucleotide

<400> SEQUENCE: 175
cgcggatccc atatgacacg cttcaaatat tc 32

<210> SEQ ID NO 176
<211> LENGTH: 31
<212> TYPE: DNA
<213> ORGANISM: Artificial Sequence
<220> FEATURE:
<223> OTHER INFORMATION: Oligonucleotide

<400> SEQUENCE: 176
cccgctcgag ttatttaaac cgataggtaa a 31

<210> SEQ ID NO 177
<211> LENGTH: 31
<212> TYPE: DNA
<213> ORGANISM: Artificial Sequence
<220> FEATURE:
<223> OTHER INFORMATION: Oligonucleotide -continued

<400> SEQUENCE: 177
cgcggatccc atatgggcag ggaagaaccg c 31

<210> SEQ ID NO 178
<211> LENGTH: 28
<212> TYPE: DNA
<213> ORGANISM: Artificial Sequence
<220> FEATURE:
<223> OTHER INFORMATION: Oligonucleotide

<400> SEQUENCE: 178
gcccaagctt atcgatggaa tagccgcg 28

<210> SEQ ID NO 179
<211> LENGTH: 32
<212> TYPE: DNA
<213> ORGANISM: Artificial Sequence
<220> FEATURE:
<223> OTHER INFORMATION: Oligonucleotide

<400> SEQUENCE: 179
cgcggatccg ctagcaacgg tttggatgcc cg 32

<210> SEQ ID NO 180
<211> LENGTH: 30
<212> TYPE: DNA
<213> ORGANISM: Artificial Sequence
<220> FEATURE:
<223> OTHER INFORMATION: Oligonucleotide

<400> SEQUENCE: 180
cccgctcgag tttgtctaag ttcctgatat 30

<210> SEQ ID NO 181
<211> LENGTH: 26
<212> TYPE: DNA
<213> ORGANISM: Artificial Sequence
<220> FEATURE:
<223> OTHER INFORMATION: Oligonucleotide

<400> SEQUENCE: 181
cccgctcgag attcccacct gccatc 26

<210> SEQ ID NO 182
<211> LENGTH: 37
<212> TYPE: DNA
<213> ORGANISM: Artificial Sequence
<220> FEATURE:
<223> OTHER INFORMATION: Oligonucleotide

<400> SEQUENCE: 182
cgcggatccg ctagcatgaa tttgcctatt caaaaat 37

<210> SEQ ID NO 183
<211> LENGTH: 29
<212> TYPE: DNA
<213> ORGANISM: Artificial Sequence
<220> FEATURE:
<223> OTHER INFORMATION: Oligonucleotide

<400> SEQUENCE: 183
cccgctcgag ttaattccca cctgccatc 29

<210> SEQ ID NO 184
<211> LENGTH: 37

-continued

<212> TYPE: DNA
<213> ORGANISM: Artificial Sequence
<220> FEATURE:
<223> OTHER INFORMATION: Oligonucleotide

<400> SEQUENCE: 184
cgcggatccg ctagcatgaa tttgcctatt caaaaat 37

<210> SEQ ID NO 185
<211> LENGTH: 27
<212> TYPE: DNA
<213> ORGANISM: Artificial Sequence
<220> FEATURE:
<223> OTHER INFORMATION: Oligonucleotide

<400> SEQUENCE: 185
cccgctcgag ttggacgatg cccgcga 27

<210> SEQ ID NO 186
<211> LENGTH: 37
<212> TYPE: DNA
<213> ORGANISM: Artificial Sequence
<220> FEATURE:
<223> OTHER INFORMATION: Oligonucleotide

<400> SEQUENCE: 186
cgcggatccg ctagcatgaa tttgcctatt caaaaat 37

<210> SEQ ID NO 187
<211> LENGTH: 28
<212> TYPE: DNA
<213> ORGANISM: Artificial Sequence
<220> FEATURE:
<223> OTHER INFORMATION: Oligonucleotide

<400> SEQUENCE: 187
cccgctcgag ttattggacg atgcccgc 28

<210> SEQ ID NO 188
<211> LENGTH: 32
<212> TYPE: DNA
<213> ORGANISM: Artificial Sequence
<220> FEATURE:
<223> OTHER INFORMATION: Oligonucleotide

<400> SEQUENCE: 188
cgcggatccc atatgtatcg caaactgatt gc 32

<210> SEQ ID NO 189
<211> LENGTH: 28
<212> TYPE: DNA
<213> ORGANISM: Artificial Sequence
<220> FEATURE:
<223> OTHER INFORMATION: Oligonucleotide

<400> SEQUENCE: 189
cccgctcgag ctaatcgatg gaatagcc 28

<210> SEQ ID NO 190
<211> LENGTH: 32
<212> TYPE: DNA
<213> ORGANISM: Artificial Sequence
<220> FEATURE:
<223> OTHER INFORMATION: Oligonucleotide

<400> SEQUENCE: 190

-continued cgcggatccc atatgaaaca gacagtcaaa tg 32

<210> SEQ ID NO 191
<211> LENGTH: 28
<212> TYPE: DNA
<213> ORGANISM: Artificial Sequence
<220> FEATURE:
<223> OTHER INFORMATION: Oligonucleotide

<400> SEQUENCE: 191
cccgctcgag tcaataaccc gccttcag 28

<210> SEQ ID NO 192
<211> LENGTH: 45
<212> TYPE: DNA
<213> ORGANISM: Artificial Sequence
<220> FEATURE:
<223> OTHER INFORMATION: Oligonucleotide

<400> SEQUENCE: 192
cgcggatccc atatgttacg tttgactgct ttagccgtat gcacc 45

<210> SEQ ID NO 193
<211> LENGTH: 40
<212> TYPE: DNA
<213> ORGANISM: Artificial Sequence
<220> FEATURE:
<223> OTHER INFORMATION: Oligonucleotide

<400> SEQUENCE: 193
cccgctcgag ttattttgcc gcgttaaaag cgtcggcaac 40

<210> SEQ ID NO 194
<211> LENGTH: 32
<212> TYPE: DNA
<213> ORGANISM: Artificial Sequence
<220> FEATURE:
<223> OTHER INFORMATION: Oligonucleotide

<400> SEQUENCE: 194
cgcggatccc atatgaacaa aatataccgc at 32

<210> SEQ ID NO 195
<211> LENGTH: 28
<212> TYPE: DNA
<213> ORGANISM: Artificial Sequence
<220> FEATURE:
<223> OTHER INFORMATION: Oligonucleotide

<400> SEQUENCE: 195
cccgctcgag ttaccactga taaccgac 28

<210> SEQ ID NO 196
<211> LENGTH: 34
<212> TYPE: DNA
<213> ORGANISM: Artificial Sequence
<220> FEATURE:
<223> OTHER INFORMATION: Oligonucleotide

<400> SEQUENCE: 196
cgcggatccc atatgaccga tgacgacgat ttat 34

<210> SEQ ID NO 197
<211> LENGTH: 28
<212> TYPE: DNA
<213> ORGANISM: Artificial Sequence -continued
<220> FEATURE:
<223> OTHER INFORMATION: Oligonucleotide

<400> SEQUENCE: 197
gcccaagctt ccactgataa ccgacaga 28

<210> SEQ ID NO 198
<211> LENGTH: 32
<212> TYPE: DNA
<213> ORGANISM: Artificial Sequence
<220> FEATURE:
<223> OTHER INFORMATION: Oligonucleotide

<400> SEQUENCE: 198
cgcggatccc atatgaacaa aatataccgc at 32

<210> SEQ ID NO 199
<211> LENGTH: 28
<212> TYPE: DNA
<213> ORGANISM: Artificial Sequence
<220> FEATURE:
<223> OTHER INFORMATION: Oligonucleotide

<400> SEQUENCE: 199
gcccaagctt ttaccactga taaccgac 28

<210> SEQ ID NO 200
<211> LENGTH: 34
<212> TYPE: DNA
<213> ORGANISM: Artificial Sequence
<220> FEATURE:
<223> OTHER INFORMATION: Oligonucleotide

<400> SEQUENCE: 200
gggaattcca tatgggcatt tcccgcaaaa tatc 34

<210> SEQ ID NO 201
<211> LENGTH: 40
<212> TYPE: DNA
<213> ORGANISM: Artificial Sequence
<220> FEATURE:
<223> OTHER INFORMATION: Oligonucleotide

<400> SEQUENCE: 201
cccgctcgag ttatttactc ctataacgag gtctcttaac 40

<210> SEQ ID NO 202
<211> LENGTH: 36
<212> TYPE: DNA
<213> ORGANISM: Artificial Sequence
<220> FEATURE:
<223> OTHER INFORMATION: Oligonucleotide

<400> SEQUENCE: 202
gggaattcca tatgtcagat ttggcaaacg attctt 36

<210> SEQ ID NO 203
<211> LENGTH: 40
<212> TYPE: DNA
<213> ORGANISM: Artificial Sequence
<220> FEATURE:
<223> OTHER INFORMATION: Oligonucleotide

<400> SEQUENCE: 203
cccgctcgag ttatttactc ctataacgag gtctcttaac 40

-continued

<210> SEQ ID NO 204
<211> LENGTH: 34
<212> TYPE: DNA
<213> ORGANISM: Artificial Sequence
<220> FEATURE:
<223> OTHER INFORMATION: Oligonucleotide

<400> SEQUENCE: 204
gggaattcca tatgggcatt tcccgcaaaa tatc 34

<210> SEQ ID NO 205
<211> LENGTH: 32
<212> TYPE: DNA
<213> ORGANISM: Artificial Sequence
<220> FEATURE:
<223> OTHER INFORMATION: Oligonucleotide

<400> SEQUENCE: 205
cccgctcgag ttacgtatca tatttcacgt gc 32

<210> SEQ ID NO 206
<211> LENGTH: 35
<212> TYPE: DNA
<213> ORGANISM: Artificial Sequence
<220> FEATURE:
<223> OTHER INFORMATION: Oligonucleotide

<400> SEQUENCE: 206
gggaattcca tatgcacgtg aaatatgata cgaag 35

<210> SEQ ID NO 207
<211> LENGTH: 37
<212> TYPE: DNA
<213> ORGANISM: Artificial Sequence
<220> FEATURE:
<223> OTHER INFORMATION: Oligonucleotide

<400> SEQUENCE: 207
cccgctcgag tttactccta taacgaggtc tcttaac 37

<210> SEQ ID NO 208
<211> LENGTH: 36
<212> TYPE: DNA
<213> ORGANISM: Artificial Sequence
<220> FEATURE:
<223> OTHER INFORMATION: Oligonucleotide

<400> SEQUENCE: 208
gggaattcca tatgtcagat ttggcaaacg attctt 36

<210> SEQ ID NO 209
<211> LENGTH: 29
<212> TYPE: DNA
<213> ORGANISM: Artificial Sequence
<220> FEATURE:
<223> OTHER INFORMATION: Oligonucleotide

<400> SEQUENCE: 209
cccgctcgag cgtatcatat ttcacgtgc 29

<210> SEQ ID NO 210
<211> LENGTH: 36
<212> TYPE: DNA
<213> ORGANISM: Artificial Sequence
<220> FEATURE:
<223> OTHER INFORMATION: Oligonucleotide -continued

<400> SEQUENCE: 210
gggaattcca tatgtcagat ttggcaaacg attctt 36

<210> SEQ ID NO 211
<211> LENGTH: 37
<212> TYPE: DNA
<213> ORGANISM: Artificial Sequence
<220> FEATURE:
<223> OTHER INFORMATION: Oligonucleotide

<400> SEQUENCE: 211
cccgctcgag tttactccta taacgaggtc tcttaac 37

<210> SEQ ID NO 212
<211> LENGTH: 35
<212> TYPE: DNA
<213> ORGANISM: Artificial Sequence
<220> FEATURE:
<223> OTHER INFORMATION: Oligonucleotide

<400> SEQUENCE: 212
cgcggatccc atatgcaaaa tgcgttcaaa atccc 35

<210> SEQ ID NO 213
<211> LENGTH: 32
<212> TYPE: DNA
<213> ORGANISM: Artificial Sequence
<220> FEATURE:
<223> OTHER INFORMATION: Oligonucleotide

<400> SEQUENCE: 213
cgcggatccc atatgaacaa aatataccgc at 32

<210> SEQ ID NO 214
<211> LENGTH: 29
<212> TYPE: DNA
<213> ORGANISM: Artificial Sequence
<220> FEATURE:
<223> OTHER INFORMATION: Oligonucleotide

<400> SEQUENCE: 214
cccgctcgag tttgctttcg atagaacgg 29

<210> SEQ ID NO 215
<211> LENGTH: 34
<212> TYPE: DNA
<213> ORGANISM: Artificial Sequence
<220> FEATURE:
<223> OTHER INFORMATION: Oligonucleotide

<400> SEQUENCE: 215
gcggccatat ggtcataaaa tatacaaatt tgaa 34

<210> SEQ ID NO 216
<211> LENGTH: 34
<212> TYPE: DNA
<213> ORGANISM: Artificial Sequence
<220> FEATURE:
<223> OTHER INFORMATION: Oligonucleotide

<400> SEQUENCE: 216
gcggcctcga gttagcctga gacctttgca aatt 34

<210> SEQ ID NO 217

-continued

<211> LENGTH: 30
<212> TYPE: DNA
<213> ORGANISM: Artificial Sequence
<220> FEATURE:
<223> OTHER INFORMATION: Oligonucleotide

<400> SEQUENCE: 217
gcggccatat gaaacagaaa aaaaccgctg 30

<210> SEQ ID NO 218
<211> LENGTH: 32
<212> TYPE: DNA
<213> ORGANISM: Artificial Sequence
<220> FEATURE:
<223> OTHER INFORMATION: Oligonucleotide

<400> SEQUENCE: 218
gcggcctcga gttacggttt gacaccgttt tc 32

<210> SEQ ID NO 219
<211> LENGTH: 30
<212> TYPE: DNA
<213> ORGANISM: Artificial Sequence
<220> FEATURE:
<223> OTHER INFORMATION: Oligonucleotide

<400> SEQUENCE: 219
cgcggatccc atatgaaaac cctgctcctc 30

<210> SEQ ID NO 220
<211> LENGTH: 27
<212> TYPE: DNA
<213> ORGANISM: Artificial Sequence
<220> FEATURE:
<223> OTHER INFORMATION: Oligonucleotide

<400> SEQUENCE: 220
cccgctcgag ttatcctcct ttgcggc 27

<210> SEQ ID NO 221
<211> LENGTH: 30
<212> TYPE: DNA
<213> ORGANISM: Artificial Sequence
<220> FEATURE:
<223> OTHER INFORMATION: Oligonucleotide

<400> SEQUENCE: 221
gcggccatat ggcaaaaatg atgaaatggg 30

<210> SEQ ID NO 222
<211> LENGTH: 29
<212> TYPE: DNA
<213> ORGANISM: Artificial Sequence
<220> FEATURE:
<223> OTHER INFORMATION: Oligonucleotide

<400> SEQUENCE: 222
gcggcctcga gttatcggcg cggcgggcc 29

<210> SEQ ID NO 223
<211> LENGTH: 30
<212> TYPE: DNA
<213> ORGANISM: Artificial Sequence
<220> FEATURE:
<223> OTHER INFORMATION: Oligonucleotide

<400> SEQUENCE: 223

-continued gcggccatat gaaaaaatcc tccctcatca 30

<210> SEQ ID NO 224
<211> LENGTH: 32
<212> TYPE: DNA
<213> ORGANISM: Artificial Sequence
<220> FEATURE:
<223> OTHER INFORMATION: Oligonucleotide

<400> SEQUENCE: 224
gcggcctcga gttatttgcc gccgtttttg gc 32

<210> SEQ ID NO 225
<211> LENGTH: 31
<212> TYPE: DNA
<213> ORGANISM: Artificial Sequence
<220> FEATURE:
<223> OTHER INFORMATION: Oligonucleotide

<400> SEQUENCE: 225
gcggccatat ggcccctgcc gacgcggtaa g 31

<210> SEQ ID NO 226
<211> LENGTH: 33
<212> TYPE: DNA
<213> ORGANISM: Artificial Sequence
<220> FEATURE:
<223> OTHER INFORMATION: Oligonucleotide

<400> SEQUENCE: 226
gcggcctcga gtttgccgcc gtttttggct ttc 33

<210> SEQ ID NO 227
<211> LENGTH: 30
<212> TYPE: DNA
<213> ORGANISM: Artificial Sequence
<220> FEATURE:
<223> OTHER INFORMATION: Oligonucleotide

<400> SEQUENCE: 227
gcggccatat gaaacacata ctccccctga 30

<210> SEQ ID NO 228
<211> LENGTH: 32
<212> TYPE: DNA
<213> ORGANISM: Artificial Sequence
<220> FEATURE:
<223> OTHER INFORMATION: Oligonucleotide

<400> SEQUENCE: 228
gcggcctcga gttattcgcc tacggttttt tg 32

<210> SEQ ID NO 229
<211> LENGTH: 30
<212> TYPE: DNA
<213> ORGANISM: Artificial Sequence
<220> FEATURE:
<223> OTHER INFORMATION: Oligonucleotide

<400> SEQUENCE: 229
gcggccatat gatttacatc gtactgtttc 30

<210> SEQ ID NO 230
<211> LENGTH: 32
<212> TYPE: DNA

-continued

<213> ORGANISM: Artificial Sequence
<220> FEATURE:
<223> OTHER INFORMATION: Oligonucleotide

<400> SEQUENCE: 230
gcggcctcga gttaggagaa caggcgcaat gc 32

<210> SEQ ID NO 231
<211> LENGTH: 32
<212> TYPE: DNA
<213> ORGANISM: Artificial Sequence
<220> FEATURE:
<223> OTHER INFORMATION: Oligonucleotide

<400> SEQUENCE: 231
gcggccatat gtacaacatg tatcaggaaa ac 32

<210> SEQ ID NO 232
<211> LENGTH: 31
<212> TYPE: DNA
<213> ORGANISM: Artificial Sequence
<220> FEATURE:
<223> OTHER INFORMATION: Oligonucleotide

<400> SEQUENCE: 232
gcggcctcga gggagaacag gcgcaatgcg g 31

<210> SEQ ID NO 233
<211> LENGTH: 29
<212> TYPE: DNA
<213> ORGANISM: Artificial Sequence
<220> FEATURE:
<223> OTHER INFORMATION: Oligonucleotide

<400> SEQUENCE: 233
cgcggatccg ctagctgcgg cacggcggg 29

<210> SEQ ID NO 234
<211> LENGTH: 28
<212> TYPE: DNA
<213> ORGANISM: Artificial Sequence
<220> FEATURE:
<223> OTHER INFORMATION: Oligonucleotide

<400> SEQUENCE: 234
cccgctcgag ataacggtat gccgccag 28

<210> SEQ ID NO 235
<211> LENGTH: 31
<212> TYPE: DNA
<213> ORGANISM: Artificial Sequence
<220> FEATURE:
<223> OTHER INFORMATION: Oligonucleotide

<400> SEQUENCE: 235
cgcggatccc atatggaatc aacactttca c 31

<210> SEQ ID NO 236
<211> LENGTH: 27
<212> TYPE: DNA
<213> ORGANISM: Artificial Sequence
<220> FEATURE:
<223> OTHER INFORMATION: Oligonucleotide

<400> SEQUENCE: 236
cccgctcgag ttacacgcgg ttgctgt 27

-continued

<210> SEQ ID NO 237
<211> LENGTH: 31
<212> TYPE: DNA
<213> ORGANISM: Artificial Sequence
<220> FEATURE:
<223> OTHER INFORMATION: Oligonucleotide

<400> SEQUENCE: 237
cgcggatccc atatgaacaa cagacatttt g 31

<210> SEQ ID NO 238
<211> LENGTH: 28
<212> TYPE: DNA
<213> ORGANISM: Artificial Sequence
<220> FEATURE:
<223> OTHER INFORMATION: Oligonucleotide

<400> SEQUENCE: 238
cccgctcgag ttacctgtcc ggtaaaag 28

<210> SEQ ID NO 239
<211> LENGTH: 33
<212> TYPE: DNA
<213> ORGANISM: Artificial Sequence
<220> FEATURE:
<223> OTHER INFORMATION: Oligonucleotide

<400> SEQUENCE: 239
cgcggatccg ctagcaccgt catcaaacag gaa 33

<210> SEQ ID NO 240
<211> LENGTH: 27
<212> TYPE: DNA
<213> ORGANISM: Artificial Sequence
<220> FEATURE:
<223> OTHER INFORMATION: Oligonucleotide

<400> SEQUENCE: 240
cccgctcgag tcaagattcg acgggga 27

<210> SEQ ID NO 241
<211> LENGTH: 31
<212> TYPE: DNA
<213> ORGANISM: Artificial Sequence
<220> FEATURE:
<223> OTHER INFORMATION: Oligonucleotide

<400> SEQUENCE: 241
cgcggatccc atatgtccgc aaacgaatac g 31

<210> SEQ ID NO 242
<211> LENGTH: 28
<212> TYPE: DNA
<213> ORGANISM: Artificial Sequence
<220> FEATURE:
<223> OTHER INFORMATION: Oligonucleotide

<400> SEQUENCE: 242
cccgctcgag tcagtgttct gccagttt 28

<210> SEQ ID NO 243
<211> LENGTH: 29
<212> TYPE: DNA
<213> ORGANISM: Artificial Sequence
<220> FEATURE:

-continued

<223> OTHER INFORMATION: Oligonucleotide

<400> SEQUENCE: 243
cgcggatccc atatgccgtc tgaaacacg 29

<210> SEQ ID NO 244
<211> LENGTH: 28
<212> TYPE: DNA
<213> ORGANISM: Artificial Sequence
<220> FEATURE:
<223> OTHER INFORMATION: Oligonucleotide

<400> SEQUENCE: 244
cccgctcgag ttagcggagc agtttttc 28

<210> SEQ ID NO 245
<211> LENGTH: 28
<212> TYPE: DNA
<213> ORGANISM: Artificial Sequence
<220> FEATURE:
<223> OTHER INFORMATION: Oligonucleotide

<400> SEQUENCE: 245
cgcggatccc atatgaccgc catcagcc 28

<210> SEQ ID NO 246
<211> LENGTH: 27
<212> TYPE: DNA
<213> ORGANISM: Artificial Sequence
<220> FEATURE:
<223> OTHER INFORMATION: Oligonucleotide

<400> SEQUENCE: 246
cccgctcgag ttaaagccgg gtaacgc 27

<210> SEQ ID NO 247
<211> LENGTH: 31
<212> TYPE: DNA
<213> ORGANISM: Artificial Sequence
<220> FEATURE:
<223> OTHER INFORMATION: Oligonucleotide

<400> SEQUENCE: 247
gcggccatat ggaaacacag ctttacatcg g 31

<210> SEQ ID NO 248
<211> LENGTH: 30
<212> TYPE: DNA
<213> ORGANISM: Artificial Sequence
<220> FEATURE:
<223> OTHER INFORMATION: Oligonucleotide

<400> SEQUENCE: 248
gcggcctcga gtcaataata atatcccgcg 30

<210> SEQ ID NO 249
<211> LENGTH: 30
<212> TYPE: DNA
<213> ORGANISM: Artificial Sequence
<220> FEATURE:
<223> OTHER INFORMATION: Oligonucleotide

<400> SEQUENCE: 249
gcggccatat gattaaaatc cgcaatatcc 30

-continued

<210> SEQ ID NO 250
<211> LENGTH: 36
<212> TYPE: DNA
<213> ORGANISM: Artificial Sequence
<220> FEATURE:
<223> OTHER INFORMATION: Oligonucleotide

<400> SEQUENCE: 250
gcggcctcga gttaaatctt ggtagattgg atttgg 36

<210> SEQ ID NO 251
<211> LENGTH: 30
<212> TYPE: DNA
<213> ORGANISM: Artificial Sequence
<220> FEATURE:
<223> OTHER INFORMATION: Oligonucleotide

<400> SEQUENCE: 251
gcggccatat gactgacaac gcactgctcc 30

<210> SEQ ID NO 252
<211> LENGTH: 31
<212> TYPE: DNA
<213> ORGANISM: Artificial Sequence
<220> FEATURE:
<223> OTHER INFORMATION: Oligonucleotide

<400> SEQUENCE: 252
gcggcctcga gtcagaccgc gttgtcgaaa c 31

<210> SEQ ID NO 253
<211> LENGTH: 32
<212> TYPE: DNA
<213> ORGANISM: Artificial Sequence
<220> FEATURE:
<223> OTHER INFORMATION: Oligonucleotide

<400> SEQUENCE: 253
cgcggatccc atatggcgtt aaaaacatca aa 32

<210> SEQ ID NO 254
<211> LENGTH: 27
<212> TYPE: DNA
<213> ORGANISM: Artificial Sequence
<220> FEATURE:
<223> OTHER INFORMATION: Oligonucleotide

<400> SEQUENCE: 254
cccgctcgag tcagcccttc atacagc 27

<210> SEQ ID NO 255
<211> LENGTH: 32
<212> TYPE: DNA
<213> ORGANISM: Artificial Sequence
<220> FEATURE:
<223> OTHER INFORMATION: Oligonucleotide

<400> SEQUENCE: 255
gcggcattaa tggcacaaac tacactcaaa cc 32

<210> SEQ ID NO 256
<211> LENGTH: 33
<212> TYPE: DNA
<213> ORGANISM: Artificial Sequence
<220> FEATURE:
<223> OTHER INFORMATION: Oligonucleotide -continued

<400> SEQUENCE: 256
gcggcctcga gttaaaactt cacgttcacg ccg 33

<210> SEQ ID NO 257
<211> LENGTH: 34
<212> TYPE: DNA
<213> ORGANISM: Artificial Sequence
<220> FEATURE:
<223> OTHER INFORMATION: Oligonucleotide

<400> SEQUENCE: 257
gcggcattaa tgcatgaaac tgagcaatcg gtgg 34

<210> SEQ ID NO 258
<211> LENGTH: 38
<212> TYPE: DNA
<213> ORGANISM: Artificial Sequence
<220> FEATURE:
<223> OTHER INFORMATION: Oligonucleotide

<400> SEQUENCE: 258
gcggcctcga gaaacttcac gttcacgccg ccggtaaa 38

<210> SEQ ID NO 259
<211> LENGTH: 33
<212> TYPE: DNA
<213> ORGANISM: Artificial Sequence
<220> FEATURE:
<223> OTHER INFORMATION: Oligonucleotide

<400> SEQUENCE: 259
cgcggatccc atatgggcaa atccgaaaat acg 33

<210> SEQ ID NO 260
<211> LENGTH: 26
<212> TYPE: DNA
<213> ORGANISM: Artificial Sequence
<220> FEATURE:
<223> OTHER INFORMATION: Oligonucleotide

<400> SEQUENCE: 260
cccgctcgag ataatggcgg cggcgg 26

<210> SEQ ID NO 261
<211> LENGTH: 29
<212> TYPE: DNA
<213> ORGANISM: Artificial Sequence
<220> FEATURE:
<223> OTHER INFORMATION: Oligonucleotide

<400> SEQUENCE: 261
cgcggatccc atatgtttcc ccccgacaa 29

<210> SEQ ID NO 262
<211> LENGTH: 31
<212> TYPE: DNA
<213> ORGANISM: Artificial Sequence
<220> FEATURE:
<223> OTHER INFORMATION: Oligonucleotide

<400> SEQUENCE: 262
cccgctcgag tcattctgta aaaaaagtat g 31

<210> SEQ ID NO 263
<211> LENGTH: 32

-continued

<212> TYPE: DNA
<213> ORGANISM: Artificial Sequence
<220> FEATURE:
<223> OTHER INFORMATION: Oligonucleotide

<400> SEQUENCE: 263
cgcggatccc atatgcttca aagcgacagc ag 32

<210> SEQ ID NO 264
<211> LENGTH: 29
<212> TYPE: DNA
<213> ORGANISM: Artificial Sequence
<220> FEATURE:
<223> OTHER INFORMATION: Oligonucleotide

<400> SEQUENCE: 264
cccgctcgag ttcggatttt tgcgtactc 29

<210> SEQ ID NO 265
<211> LENGTH: 31
<212> TYPE: DNA
<213> ORGANISM: Artificial Sequence
<220> FEATURE:
<223> OTHER INFORMATION: Oligonucleotide

<400> SEQUENCE: 265
cgcggatccc atatggcaat ggcagaaaac g 31

<210> SEQ ID NO 266
<211> LENGTH: 27
<212> TYPE: DNA
<213> ORGANISM: Artificial Sequence
<220> FEATURE:
<223> OTHER INFORMATION: Oligonucleotide

<400> SEQUENCE: 266
cccgctcgag ctatacaatc cgtgccg 27

<210> SEQ ID NO 267
<211> LENGTH: 32
<212> TYPE: DNA
<213> ORGANISM: Artificial Sequence
<220> FEATURE:
<223> OTHER INFORMATION: Oligonucleotide

<400> SEQUENCE: 267
cgcggatccc atatggattc ttttttcaaa cc 32

<210> SEQ ID NO 268
<211> LENGTH: 27
<212> TYPE: DNA
<213> ORGANISM: Artificial Sequence
<220> FEATURE:
<223> OTHER INFORMATION: Oligonucleotide

<400> SEQUENCE: 268
cccgctcgag tcagttcaga aagcggg 27

<210> SEQ ID NO 269
<211> LENGTH: 32
<212> TYPE: DNA
<213> ORGANISM: Artificial Sequence
<220> FEATURE:
<223> OTHER INFORMATION: Oligonucleotide

<400> SEQUENCE: 269

-continued cgcggatccc atatgaaacc tttgatttta gg 32

<210> SEQ ID NO 270
<211> LENGTH: 28
<212> TYPE: DNA
<213> ORGANISM: Artificial Sequence
<220> FEATURE:
<223> OTHER INFORMATION: Oligonucleotide

<400> SEQUENCE: 270
cccgctcgag ttatttgggc tgctcttc 28

<210> SEQ ID NO 271
<211> LENGTH: 30
<212> TYPE: DNA
<213> ORGANISM: Artificial Sequence
<220> FEATURE:
<223> OTHER INFORMATION: Oligonucleotide

<400> SEQUENCE: 271
cgcggatccc atatggtaat cgtctggttg 30

<210> SEQ ID NO 272
<211> LENGTH: 27
<212> TYPE: DNA
<213> ORGANISM: Artificial Sequence
<220> FEATURE:
<223> OTHER INFORMATION: Oligonucleotide

<400> SEQUENCE: 272
cccgctcgag ctacgacttg gttaccg 27

<210> SEQ ID NO 273
<211> LENGTH: 33
<212> TYPE: DNA
<213> ORGANISM: Artificial Sequence
<220> FEATURE:
<223> OTHER INFORMATION: Oligonucleotide

<400> SEQUENCE: 273
gcggccatat gagacgtaaa atgctaaagc tac 33

<210> SEQ ID NO 274
<211> LENGTH: 31
<212> TYPE: DNA
<213> ORGANISM: Artificial Sequence
<220> FEATURE:
<223> OTHER INFORMATION: Oligonucleotide

<400> SEQUENCE: 274
gcggcctcga gtcaaagtgt tctgtttgcg c 31

<210> SEQ ID NO 275
<211> LENGTH: 30
<212> TYPE: DNA
<213> ORGANISM: Artificial Sequence
<220> FEATURE:
<223> OTHER INFORMATION: Oligonucleotide

<400> SEQUENCE: 275
gccgccatat gttgacttta acccgaaaaa 30

<210> SEQ ID NO 276
<211> LENGTH: 34
<212> TYPE: DNA
<213> ORGANISM: Artificial Sequence
<220> FEATURE:
<223> OTHER INFORMATION: Oligonucleotide

<400> SEQUENCE: 276
gccgcctcga ggccggcggt caataccgcc cgaa 34

<210> SEQ ID NO 277
<211> LENGTH: 32
<212> TYPE: DNA
<213> ORGANISM: Artificial Sequence
<220> FEATURE:
<223> OTHER INFORMATION: Oligonucleotide

<400> SEQUENCE: 277
cgcggatccc atatggcgca atgcgatttg ac 32

<210> SEQ ID NO 278
<211> LENGTH: 27
<212> TYPE: DNA
<213> ORGANISM: Artificial Sequence
<220> FEATURE:
<223> OTHER INFORMATION: Oligonucleotide

<400> SEQUENCE: 278
cccgctcgag ttcggcggta aatgccg 27

<210> SEQ ID NO 279
<211> LENGTH: 28
<212> TYPE: DNA
<213> ORGANISM: Artificial Sequence
<220> FEATURE:
<223> OTHER INFORMATION: Oligonucleotide

<400> SEQUENCE: 279
gcggccatat ggcggggccg atttttgt 28

<210> SEQ ID NO 280
<211> LENGTH: 33
<212> TYPE: DNA
<213> ORGANISM: Artificial Sequence
<220> FEATURE:
<223> OTHER INFORMATION: Oligonucleotide

<400> SEQUENCE: 280
gcggcctcga gttatttgct ttcagtatta ttg 33

<210> SEQ ID NO 281
<211> LENGTH: 30
<212> TYPE: DNA
<213> ORGANISM: Artificial Sequence
<220> FEATURE:
<223> OTHER INFORMATION: Oligonucleotide

<400> SEQUENCE: 281
gcggccatat gaactttgct ttatccgtca 30

<210> SEQ ID NO 282
<211> LENGTH: 32
<212> TYPE: DNA
<213> ORGANISM: Artificial Sequence
<220> FEATURE:
<223> OTHER INFORMATION: Oligonucleotide

<400> SEQUENCE: 282
gcggcctcga gttaacggca gtatttgttt ac 32

-continued

<210> SEQ ID NO 283
<211> LENGTH: 31
<212> TYPE: DNA
<213> ORGANISM: Artificial Sequence
<220> FEATURE:
<223> OTHER INFORMATION: Oligonucleotide

<400> SEQUENCE: 283
cgcggatccc atatgggttt gcgcttcggg c 31

<210> SEQ ID NO 284
<211> LENGTH: 29
<212> TYPE: DNA
<213> ORGANISM: Artificial Sequence
<220> FEATURE:
<223> OTHER INFORMATION: Oligonucleotide

<400> SEQUENCE: 284
gcccaagctt ttttcctttg ccgtttccg 29

<210> SEQ ID NO 285
<211> LENGTH: 32
<212> TYPE: DNA
<213> ORGANISM: Artificial Sequence
<220> FEATURE:
<223> OTHER INFORMATION: Oligonucleotide

<400> SEQUENCE: 285
cgcggatccc atatggccga cctttccgaa aa 32

<210> SEQ ID NO 286
<211> LENGTH: 27
<212> TYPE: DNA
<213> ORGANISM: Artificial Sequence
<220> FEATURE:
<223> OTHER INFORMATION: Oligonucleotide

<400> SEQUENCE: 286
cccgctcgag gaagcgcgtt cccaagc 27

<210> SEQ ID NO 287
<211> LENGTH: 29
<212> TYPE: DNA
<213> ORGANISM: Artificial Sequence
<220> FEATURE:
<223> OTHER INFORMATION: Oligonucleotide

<400> SEQUENCE: 287
cgcggatccc atatgcacga cacccgtac 29

<210> SEQ ID NO 288
<211> LENGTH: 28
<212> TYPE: DNA
<213> ORGANISM: Artificial Sequence
<220> FEATURE:
<223> OTHER INFORMATION: Oligonucleotide

<400> SEQUENCE: 288
cccgctcgag ttagaagcgc gttcccaa 28

<210> SEQ ID NO 289
<211> LENGTH: 34
<212> TYPE: DNA
<213> ORGANISM: Artificial Sequence
<220> FEATURE:
<223> OTHER INFORMATION: Oligonucleotide

```
<400> SEQUENCE: 289

ctagctagct ttaaacgcag cgtaatcgca atgg                           34

<210> SEQ ID NO 290
<211> LENGTH: 31
<212> TYPE: DNA
<213> ORGANISM: Artificial Sequence
<220> FEATURE:
<223> OTHER INFORMATION: Oligonucleotideucleotide

<400> SEQUENCE: 290

cccgctcgag tcaatcctgc tcttttttgc c                              31

<210> SEQ ID NO 291
<211> LENGTH: 25
<212> TYPE: DNA
<213> ORGANISM: Artificial Sequence
<220> FEATURE:
<223> OTHER INFORMATION: Oligonucleotide

<400> SEQUENCE: 291

ctagctagcg ggggcggcgg tggcg                                     25

<210> SEQ ID NO 292
<211> LENGTH: 31
<212> TYPE: DNA
<213> ORGANISM: Artificial Sequence
<220> FEATURE:
<223> OTHER INFORMATION: Oligonucleotide

<400> SEQUENCE: 292

cccgctcgag tcaatcctgc tcttttttgc c                              31

<210> SEQ ID NO 293
<211> LENGTH: 40
<212> TYPE: DNA
<213> ORGANISM: Artificial Sequence
<220> FEATURE:
<223> OTHER INFORMATION: Oligonucleotide

<400> SEQUENCE: 293

ctagctagcg ctcatcctcg ccgcctgcgg gggcggcggt                     40

<210> SEQ ID NO 294
<211> LENGTH: 31
<212> TYPE: DNA
<213> ORGANISM: Artificial Sequence
<220> FEATURE:
<223> OTHER INFORMATION: Oligonucleotide

<400> SEQUENCE: 294

cccgctcgag tcaatcctgc tcttttttgc c                              31

<210> SEQ ID NO 295
<211> LENGTH: 25
<212> TYPE: DNA
<213> ORGANISM: Artificial Sequence
<220> FEATURE:
<223> OTHER INFORMATION: Oligonucleotide

<400> SEQUENCE: 295

cggggatccg ggggcggcgg tggcg                                     25

<210> SEQ ID NO 296
```

-continued

<211> LENGTH: 31
<212> TYPE: DNA
<213> ORGANISM: Artificial Sequence
<220> FEATURE:
<223> OTHER INFORMATION: Oligonucleotide

<400> SEQUENCE: 296
cccgctcgag tcaatcctgc tcttttttgc c 31

<210> SEQ ID NO 297
<211> LENGTH: 25
<212> TYPE: DNA
<213> ORGANISM: Artificial Sequence
<220> FEATURE:
<223> OTHER INFORMATION: Oligonucleotide

<400> SEQUENCE: 297
ctagctagcg ggggcggcgg tggcg 25

<210> SEQ ID NO 298
<211> LENGTH: 28
<212> TYPE: DNA
<213> ORGANISM: Artificial Sequence
<220> FEATURE:
<223> OTHER INFORMATION: Oligonucleotide

<400> SEQUENCE: 298
cccgctcgag atcctgctct tttttgcc 28

<210> SEQ ID NO 299
<211> LENGTH: 28
<212> TYPE: DNA
<213> ORGANISM: Artificial Sequence
<220> FEATURE:
<223> OTHER INFORMATION: Oligonucleotide

<400> SEQUENCE: 299
ctagctagct gcgggggcgg cggtggcg 28

<210> SEQ ID NO 300
<211> LENGTH: 28
<212> TYPE: DNA
<213> ORGANISM: Artificial Sequence
<220> FEATURE:
<223> OTHER INFORMATION: Oligonucleotide

<400> SEQUENCE: 300
cccgctcgag atcctgctct tttttgcc 28

<210> SEQ ID NO 301
<211> LENGTH: 32
<212> TYPE: DNA
<213> ORGANISM: Artificial Sequence
<220> FEATURE:
<223> OTHER INFORMATION: Oligonucleotide

<400> SEQUENCE: 301
cgcggatccg ctagccccga tgttaaatcg gc 32

<210> SEQ ID NO 302
<211> LENGTH: 32
<212> TYPE: DNA
<213> ORGANISM: Artificial Sequence
<220> FEATURE:
<223> OTHER INFORMATION: Oligonucleotide

<400> SEQUENCE: 302

-continued cgcggatccg ctagccaaga tatggcggca gt 32

<210> SEQ ID NO 303
<211> LENGTH: 32
<212> TYPE: DNA
<213> ORGANISM: Artificial Sequence
<220> FEATURE:
<223> OTHER INFORMATION: Oligonucleotide

<400> SEQUENCE: 303
cgcggatccg ctagcgccga atccgcaaat ca 32

<210> SEQ ID NO 304
<211> LENGTH: 32
<212> TYPE: DNA
<213> ORGANISM: Artificial Sequence
<220> FEATURE:
<223> OTHER INFORMATION: Oligonucleotide

<400> SEQUENCE: 304
cgcgctagcg gaagggttga tttggctaat gg 32

<210> SEQ ID NO 305
<211> LENGTH: 32
<212> TYPE: DNA
<213> ORGANISM: Artificial Sequence
<220> FEATURE:
<223> OTHER INFORMATION: Oligonucleotide

<400> SEQUENCE: 305
cgcgctagcg gaagggttga tttggctaat gg 32

<210> SEQ ID NO 306
<211> LENGTH: 29
<212> TYPE: DNA
<213> ORGANISM: Artificial Sequence
<220> FEATURE:
<223> OTHER INFORMATION: Oligonucleotide

<400> SEQUENCE: 306
cgccatatgt ttaaacgcag cgtaatcgc 29

<210> SEQ ID NO 307
<211> LENGTH: 34
<212> TYPE: DNA
<213> ORGANISM: Artificial Sequence
<220> FEATURE:
<223> OTHER INFORMATION: Oligonucleotide

<400> SEQUENCE: 307
cccgctcgag aaaattgcta ccgccattcg cagg 34

<210> SEQ ID NO 308
<211> LENGTH: 32
<212> TYPE: DNA
<213> ORGANISM: Artificial Sequence
<220> FEATURE:
<223> OTHER INFORMATION: Oligonucleotide

<400> SEQUENCE: 308
cgccatatgg gaagggttga tttggctaat gg 32

<210> SEQ ID NO 309
<211> LENGTH: 38
<212> TYPE: DNA

```
<213> ORGANISM: Artificial Sequence
<220> FEATURE:
<223> OTHER INFORMATION: Oligonucleotide

<400> SEQUENCE: 309

cccgctcgag cttgtcttta taaatgatga catatttg                                38

<210> SEQ ID NO 310
<211> LENGTH: 40
<212> TYPE: DNA
<213> ORGANISM: Artificial Sequence
<220> FEATURE:
<223> OTHER INFORMATION: Oligonucleotide

<400> SEQUENCE: 310

cccgctcgag tttataaaag ataatatatt gattgattcc                              40

<210> SEQ ID NO 311
<211> LENGTH: 31
<212> TYPE: DNA
<213> ORGANISM: Artificial Sequence
<220> FEATURE:
<223> OTHER INFORMATION: Oligonucleotide

<400> SEQUENCE: 311

cgcgctagca tgccgctgat tcccgtcaat c                                       31

<210> SEQ ID NO 312
<211> LENGTH: 25
<212> TYPE: DNA
<213> ORGANISM: Artificial Sequence
<220> FEATURE:
<223> OTHER INFORMATION: Oligonucleotide

<400> SEQUENCE: 312

ctagctagcg ggggcggcgg tggcg                                              25

<210> SEQ ID NO 313
<211> LENGTH: 31
<212> TYPE: DNA
<213> ORGANISM: Artificial Sequence
<220> FEATURE:
<223> OTHER INFORMATION: Oligonucleotide

<400> SEQUENCE: 313

cccgctcgag tcaatcctgc tcttttttgc c                                       31

<210> SEQ ID NO 314
<211> LENGTH: 32
<212> TYPE: DNA
<213> ORGANISM: Artificial Sequence
<220> FEATURE:
<223> OTHER INFORMATION: Oligonucleotide

<400> SEQUENCE: 314

cgcggatccg ctagccccga tgttaaatcg gc                                      32

<210> SEQ ID NO 315
<211> LENGTH: 28
<212> TYPE: DNA
<213> ORGANISM: Artificial Sequence
<220> FEATURE:
<223> OTHER INFORMATION: Oligonucleotide

<400> SEQUENCE: 315

cccgctcgag atcctgctct ttttgcc                                            28
```

<210> SEQ ID NO 316
<211> LENGTH: 32
<212> TYPE: DNA
<213> ORGANISM: Artificial Sequence
<220> FEATURE:
<223> OTHER INFORMATION: Oligonucleotide

<400> SEQUENCE: 316
cgcggatccg ctagccccga tgttaaatcg gc                                    32

<210> SEQ ID NO 317
<211> LENGTH: 31
<212> TYPE: DNA
<213> ORGANISM: Artificial Sequence
<220> FEATURE:
<223> OTHER INFORMATION: Oligonucleotide

<400> SEQUENCE: 317
cccgctcgag tcaatcctgc tcttttttgc c                                     31

<210> SEQ ID NO 318
<211> LENGTH: 87
<212> TYPE: DNA
<213> ORGANISM: Artificial Sequence
<220> FEATURE:
<223> OTHER INFORMATION: Oligonucleotide

<400> SEQUENCE: 318
cgcggatccg ctagctttga acgcagtgtg attgcaatgg cttgtatttt tgccctttca      60
gcctgttcgc ccgatgttaa atcggcg                                          87

<210> SEQ ID NO 319
<211> LENGTH: 31
<212> TYPE: DNA
<213> ORGANISM: Artificial Sequence
<220> FEATURE:
<223> OTHER INFORMATION: Oligonucleotide

<400> SEQUENCE: 319
cccgctcgag tcaatcctgc tcttttttgc c                                     31

<210> SEQ ID NO 320
<211> LENGTH: 90
<212> TYPE: DNA
<213> ORGANISM: Artificial Sequence
<220> FEATURE:
<223> OTHER INFORMATION: Oligonucleotide

<400> SEQUENCE: 320
cgcggatccg ctagcaaaac cttcttcaaa acctttccg ccgccgcact cgcgctcatc       60
ctcgccgcct gctcgcccga tgttaaatcg                                       90

<210> SEQ ID NO 321
<211> LENGTH: 31
<212> TYPE: DNA
<213> ORGANISM: Artificial Sequence
<220> FEATURE:
<223> OTHER INFORMATION: Oligonucleotide

<400> SEQUENCE: 321
cccgctcgag tcaatcctgc tcttttttgc c                                     31

<210> SEQ ID NO 322

-continued

<211> LENGTH: 33
<212> TYPE: DNA
<213> ORGANISM: Artificial Sequence
<220> FEATURE:
<223> OTHER INFORMATION: Oligonucleotide

<400> SEQUENCE: 322
cgcggatccc atatgaaaac caagttaatc aaa 33

<210> SEQ ID NO 323
<211> LENGTH: 30
<212> TYPE: DNA
<213> ORGANISM: Artificial Sequence
<220> FEATURE:
<223> OTHER INFORMATION: Oligonucleotide

<400> SEQUENCE: 323
cccgctcgag ttattgattt ttgcggatga 30

<210> SEQ ID NO 324
<211> LENGTH: 34
<212> TYPE: DNA
<213> ORGANISM: Artificial Sequence
<220> FEATURE:
<223> OTHER INFORMATION: Oligonucleotide

<400> SEQUENCE: 324
cgcggatccc atatgttaaa tcgggtattt tatc 34

<210> SEQ ID NO 325
<211> LENGTH: 28
<212> TYPE: DNA
<213> ORGANISM: Artificial Sequence
<220> FEATURE:
<223> OTHER INFORMATION: Oligonucleotide

<400> SEQUENCE: 325
cccgctcgag ttaatccgcc attccctg 28

<210> SEQ ID NO 326
<211> LENGTH: 30
<212> TYPE: DNA
<213> ORGANISM: Artificial Sequence
<220> FEATURE:
<223> OTHER INFORMATION: Oligonucleotide

<400> SEQUENCE: 326
gcggccatat gaaattacaa caattggctg 30

<210> SEQ ID NO 327
<211> LENGTH: 31
<212> TYPE: DNA
<213> ORGANISM: Artificial Sequence
<220> FEATURE:
<223> OTHER INFORMATION: Oligonucleotide

<400> SEQUENCE: 327
gcggcctcga gttaccttac gtttttcaaa g 31

<210> SEQ ID NO 328
<211> LENGTH: 29
<212> TYPE: DNA
<213> ORGANISM: Artificial Sequence
<220> FEATURE:
<223> OTHER INFORMATION: Oligonucleotide

<400> SEQUENCE: 328

-continued cgcggatccc atatgcaagc acggctgct 29

<210> SEQ ID NO 329
<211> LENGTH: 29
<212> TYPE: DNA
<213> ORGANISM: Artificial Sequence
<220> FEATURE:
<223> OTHER INFORMATION: Oligonucleotide

<400> SEQUENCE: 329
cccgctcgag tcaaggttgt ccttgtcta 29

<210> SEQ ID NO 330
<211> LENGTH: 30
<212> TYPE: DNA
<213> ORGANISM: Artificial Sequence
<220> FEATURE:
<223> OTHER INFORMATION: Oligonucleotide

<400> SEQUENCE: 330
cgcggatccc atatgatgaa accgcacaac 30

<210> SEQ ID NO 331
<211> LENGTH: 28
<212> TYPE: DNA
<213> ORGANISM: Artificial Sequence
<220> FEATURE:
<223> OTHER INFORMATION: Oligonucleotide

<400> SEQUENCE: 331
cccgctcgag tcagttgctc aacacgtc 28

<210> SEQ ID NO 332
<211> LENGTH: 32
<212> TYPE: DNA
<213> ORGANISM: Artificial Sequence
<220> FEATURE:
<223> OTHER INFORMATION: Oligonucleotide

<400> SEQUENCE: 332
cgcggatccc atatggtaga cgcgcttaag ca 32

<210> SEQ ID NO 333
<211> LENGTH: 25
<212> TYPE: DNA
<213> ORGANISM: Artificial Sequence
<220> FEATURE:
<223> OTHER INFORMATION: Oligonucleotide

<400> SEQUENCE: 333
cccgctcgag agctgcatgg cggcg 25

<210> SEQ ID NO 334
<211> LENGTH: 30
<212> TYPE: DNA
<213> ORGANISM: Artificial Sequence
<220> FEATURE:
<223> OTHER INFORMATION: Oligonucleotide

<400> SEQUENCE: 334
cgcggatccc atatggcacg gtcgttatac 30

<210> SEQ ID NO 335
<211> LENGTH: 26
<212> TYPE: DNA

-continued

<213> ORGANISM: Artificial Sequence
<220> FEATURE:
<223> OTHER INFORMATION: Oligonucleotide

<400> SEQUENCE: 335
cccgctcgag ctaccgcgca ttcctg 26

<210> SEQ ID NO 336
<211> LENGTH: 31
<212> TYPE: DNA
<213> ORGANISM: Artificial Sequence
<220> FEATURE:
<223> OTHER INFORMATION: Oligonucleotide

<400> SEQUENCE: 336
gcggccatat ggaatttttc attatcttgt t 31

<210> SEQ ID NO 337
<211> LENGTH: 31
<212> TYPE: DNA
<213> ORGANISM: Artificial Sequence
<220> FEATURE:
<223> OTHER INFORMATION: Oligonucleotide

<400> SEQUENCE: 337
gcggcctcga gttatttggc ggttttgctg c 31

<210> SEQ ID NO 338
<211> LENGTH: 32
<212> TYPE: DNA
<213> ORGANISM: Artificial Sequence
<220> FEATURE:
<223> OTHER INFORMATION: Oligonucleotide

<400> SEQUENCE: 338
gcggccatat gaagtatgtc cggttatttt tc 32

<210> SEQ ID NO 339
<211> LENGTH: 30
<212> TYPE: DNA
<213> ORGANISM: Artificial Sequence
<220> FEATURE:
<223> OTHER INFORMATION: Oligonucleotide

<400> SEQUENCE: 339
gcggcctcga gttatcggct tgtgcaacgg 30

<210> SEQ ID NO 340
<211> LENGTH: 32
<212> TYPE: DNA
<213> ORGANISM: Artificial Sequence
<220> FEATURE:
<223> OTHER INFORMATION: Oligonucleotide

<400> SEQUENCE: 340
cgcggatccg ctagctccgg cagcaaaacc ga 32

<210> SEQ ID NO 341
<211> LENGTH: 28
<212> TYPE: DNA
<213> ORGANISM: Artificial Sequence
<220> FEATURE:
<223> OTHER INFORMATION: Oligonucleotide

<400> SEQUENCE: 341
gcccaagctt acgcagttcg gaatggag 28

-continued

<210> SEQ ID NO 342
<211> LENGTH: 35
<212> TYPE: DNA
<213> ORGANISM: Artificial Sequence
<220> FEATURE:
<223> OTHER INFORMATION: Oligonucleotide

<400> SEQUENCE: 342
gccgccatat gttgaatatt aaactgaaaa ccttg 35

<210> SEQ ID NO 343
<211> LENGTH: 32
<212> TYPE: DNA
<213> ORGANISM: Artificial Sequence
<220> FEATURE:
<223> OTHER INFORMATION: Oligonucleotide

<400> SEQUENCE: 343
gccgcctcga gttatttctg atgccttttc cc 32

<210> SEQ ID NO 344
<211> LENGTH: 29
<212> TYPE: DNA
<213> ORGANISM: Artificial Sequence
<220> FEATURE:
<223> OTHER INFORMATION: Oligonucleotide

<400> SEQUENCE: 344
gccgccatat ggacaataag accaaactg 29

<210> SEQ ID NO 345
<211> LENGTH: 30
<212> TYPE: DNA
<213> ORGANISM: Artificial Sequence
<220> FEATURE:
<223> OTHER INFORMATION: Oligonucleotide

<400> SEQUENCE: 345
gccgcctcga gttaacggtg cggacgtttc 30

<210> SEQ ID NO 346
<211> LENGTH: 32
<212> TYPE: DNA
<213> ORGANISM: Artificial Sequence
<220> FEATURE:
<223> OTHER INFORMATION: Oligonucleotide

<400> SEQUENCE: 346
cgcggatccc atatgaacaa actgtttctt ac 32

<210> SEQ ID NO 347
<211> LENGTH: 28
<212> TYPE: DNA
<213> ORGANISM: Artificial Sequence
<220> FEATURE:
<223> OTHER INFORMATION: Oligonucleotide

<400> SEQUENCE: 347
cccgctcgag tcattccgcc ttcagaaa 28

<210> SEQ ID NO 348
<211> LENGTH: 45
<212> TYPE: DNA
<213> ORGANISM: Artificial Sequence
<220> FEATURE:

-continued

<223> OTHER INFORMATION: Oligonucleotide

<400> SEQUENCE: 348
cgcggatccc atatgcaagg tatcgttgcc gacaaatccg cacct 45

<210> SEQ ID NO 349
<211> LENGTH: 42
<212> TYPE: DNA
<213> ORGANISM: Artificial Sequence
<220> FEATURE:
<223> OTHER INFORMATION: Oligonucleotide

<400> SEQUENCE: 349
cccgctcgag agctaattgt gcttggtttg cagataggag tt 42

<210> SEQ ID NO 350
<211> LENGTH: 52
<212> TYPE: DNA
<213> ORGANISM: Artificial Sequence
<220> FEATURE:
<223> OTHER INFORMATION: Oligonucleotide

<400> SEQUENCE: 350
cgcggatccc atatgaaccg caccctgtac aaagttgtat ttaacaaaca tc 52

<210> SEQ ID NO 351
<211> LENGTH: 45
<212> TYPE: DNA
<213> ORGANISM: Artificial Sequence
<220> FEATURE:
<223> OTHER INFORMATION: Oligonucleotide

<400> SEQUENCE: 351
cccgctcgag ttaagctaat tgtgcttggt ttgcagatag gagtt 45

<210> SEQ ID NO 352
<211> LENGTH: 46
<212> TYPE: DNA
<213> ORGANISM: Artificial Sequence
<220> FEATURE:
<223> OTHER INFORMATION: Oligonucleotide

<400> SEQUENCE: 352
cgcggatccc atatgacggg agaaaatcat gcggtttcac ttcatg 46

<210> SEQ ID NO 353
<211> LENGTH: 42
<212> TYPE: DNA
<213> ORGANISM: Artificial Sequence
<220> FEATURE:
<223> OTHER INFORMATION: Oligonucleotide

<400> SEQUENCE: 353
cccgctcgag agctaattgt gcttggtttg cagataggag tt 42

<210> SEQ ID NO 354
<211> LENGTH: 51
<212> TYPE: DNA
<213> ORGANISM: Artificial Sequence
<220> FEATURE:
<223> OTHER INFORMATION: Oligonucleotide

<400> SEQUENCE: 354
cgcggatccc atatggtttc agacggccta tacaaccaac atggtgaaat t 51

-continued

<210> SEQ ID NO 355
<211> LENGTH: 41
<212> TYPE: DNA
<213> ORGANISM: Artificial Sequence
<220> FEATURE:
<223> OTHER INFORMATION: Oligonucleotide

<400> SEQUENCE: 355
cccgctcgag gcggtaactg ccgcttgcac tgaatccgta a 41

<210> SEQ ID NO 356
<211> LENGTH: 46
<212> TYPE: DNA
<213> ORGANISM: Artificial Sequence
<220> FEATURE:
<223> OTHER INFORMATION: Oligonucleotide

<400> SEQUENCE: 356
cgcggatccc atatgacggg agaaaatcat gcggtttcac ttcatg 46

<210> SEQ ID NO 357
<211> LENGTH: 41
<212> TYPE: DNA
<213> ORGANISM: Artificial Sequence
<220> FEATURE:
<223> OTHER INFORMATION: Oligonucleotide

<400> SEQUENCE: 357
cccgctcgag gcggtaactg ccgcttgcac tgaatccgta a 41

<210> SEQ ID NO 358
<211> LENGTH: 49
<212> TYPE: DNA
<213> ORGANISM: Artificial Sequence
<220> FEATURE:
<223> OTHER INFORMATION: Oligonucleotide

<400> SEQUENCE: 358
cgcggatccc atatgcaaag caaagtcaaa gcagaccatg cctccgtaa 49

<210> SEQ ID NO 359
<211> LENGTH: 56
<212> TYPE: DNA
<213> ORGANISM: Artificial Sequence
<220> FEATURE:
<223> OTHER INFORMATION: Oligonucleotide

<400> SEQUENCE: 359
cccgctcgag tcttttcctt tcaattataa ctttagtagg ttcaattttg gtcccc 56

<210> SEQ ID NO 360
<211> LENGTH: 51
<212> TYPE: DNA
<213> ORGANISM: Artificial Sequence
<220> FEATURE:
<223> OTHER INFORMATION: Oligonucleotide

<400> SEQUENCE: 360
cgcggatccc atatggtttc agacggccta tacaaccaac atggtgaaat t 51

<210> SEQ ID NO 361
<211> LENGTH: 56
<212> TYPE: DNA
<213> ORGANISM: Artificial Sequence
<220> FEATURE:
<223> OTHER INFORMATION: Oligonucleotide -continued

<400> SEQUENCE: 361
cccgctcgag tcttttcctt tcaattataa ctttagtagg ttcaattttg gtcccc 56

<210> SEQ ID NO 362
<211> LENGTH: 27
<212> TYPE: DNA
<213> ORGANISM: Artificial Sequence
<220> FEATURE:
<223> OTHER INFORMATION: Oligonucleotide

<400> SEQUENCE: 362
gcggccatat gacccgtttg acccgcg 27

<210> SEQ ID NO 363
<211> LENGTH: 31
<212> TYPE: DNA
<213> ORGANISM: Artificial Sequence
<220> FEATURE:
<223> OTHER INFORMATION: Oligonucleotide

<400> SEQUENCE: 363
gcggcctcga gtcagcgggc gttcatttct t 31

<210> SEQ ID NO 364
<211> LENGTH: 33
<212> TYPE: DNA
<213> ORGANISM: Artificial Sequence
<220> FEATURE:
<223> OTHER INFORMATION: Oligonucleotide

<400> SEQUENCE: 364
cgcggatccc atatgaacac cattttcaaa atc 33

<210> SEQ ID NO 365
<211> LENGTH: 32
<212> TYPE: DNA
<213> ORGANISM: Artificial Sequence
<220> FEATURE:
<223> OTHER INFORMATION: Oligonucleotide

<400> SEQUENCE: 365
cccgctcgag ttaatttact tttttgatgt cg 32

<210> SEQ ID NO 366
<211> LENGTH: 28
<212> TYPE: DNA
<213> ORGANISM: Artificial Sequence
<220> FEATURE:
<223> OTHER INFORMATION: Oligonucleotide

<400> SEQUENCE: 366
gcggccatat ggattcgccc aaggtcgg 28

<210> SEQ ID NO 367
<211> LENGTH: 31
<212> TYPE: DNA
<213> ORGANISM: Artificial Sequence
<220> FEATURE:
<223> OTHER INFORMATION: Oligonucleotide

<400> SEQUENCE: 367
gcggcctcga gctacacttc ccccgaagtg g 31

<210> SEQ ID NO 368
<211> LENGTH: 31

-continued

<212> TYPE: DNA
<213> ORGANISM: Artificial Sequence
<220> FEATURE:
<223> OTHER INFORMATION: Oligonucleotide

<400> SEQUENCE: 368
cgcggatccc atatgatagt tgaccaaagc c 31

<210> SEQ ID NO 369
<211> LENGTH: 30
<212> TYPE: DNA
<213> ORGANISM: Artificial Sequence
<220> FEATURE:
<223> OTHER INFORMATION: Oligonucleotide

<400> SEQUENCE: 369
cccgctcgag ttatttttcc gatttttcgg 30

<210> SEQ ID NO 370
<211> LENGTH: 28
<212> TYPE: DNA
<213> ORGANISM: Artificial Sequence
<220> FEATURE:
<223> OTHER INFORMATION: Oligonucleotide

<400> SEQUENCE: 370
gcggccatat gcttgaactg aacggact 28

<210> SEQ ID NO 371
<211> LENGTH: 30
<212> TYPE: DNA
<213> ORGANISM: Artificial Sequence
<220> FEATURE:
<223> OTHER INFORMATION: Oligonucleotide

<400> SEQUENCE: 371
gcggcctcga gtcagcggaa gcggacgatt 30

<210> SEQ ID NO 372
<211> LENGTH: 34
<212> TYPE: DNA
<213> ORGANISM: Artificial Sequence
<220> FEATURE:
<223> OTHER INFORMATION: Oligonucleotide

<400> SEQUENCE: 372
cgcggatccc atatgtccaa actcaaaacc atcg 34

<210> SEQ ID NO 373
<211> LENGTH: 29
<212> TYPE: DNA
<213> ORGANISM: Artificial Sequence
<220> FEATURE:
<223> OTHER INFORMATION: Oligonucleotide

<400> SEQUENCE: 373
cccgctcgag gcttccaatc agtttgacc 29

<210> SEQ ID NO 374
<211> LENGTH: 32
<212> TYPE: DNA
<213> ORGANISM: Artificial Sequence
<220> FEATURE:
<223> OTHER INFORMATION: Oligonucleotide

<400> SEQUENCE: 374

-continued gcggccatat gagcgcaatc gttgatattt tc 32

<210> SEQ ID NO 375
<211> LENGTH: 34
<212> TYPE: DNA
<213> ORGANISM: Artificial Sequence
<220> FEATURE:
<223> OTHER INFORMATION: Oligonucleotide

<400> SEQUENCE: 375
gcggcctcga gttatttgcc cagttggtag aatg 34

<210> SEQ ID NO 376
<211> LENGTH: 32
<212> TYPE: DNA
<213> ORGANISM: Artificial Sequence
<220> FEATURE:
<223> OTHER INFORMATION: Oligonucleotide

<400> SEQUENCE: 376
gcggccatat ggtgatacat ccgcactact tc 32

<210> SEQ ID NO 377
<211> LENGTH: 32
<212> TYPE: DNA
<213> ORGANISM: Artificial Sequence
<220> FEATURE:
<223> OTHER INFORMATION: Oligonucleotide

<400> SEQUENCE: 377
gcggcctcga gtcaaaatcg agttttacac ca 32

<210> SEQ ID NO 378
<211> LENGTH: 31
<212> TYPE: DNA
<213> ORGANISM: Artificial Sequence
<220> FEATURE:
<223> OTHER INFORMATION: Oligonucleotide

<400> SEQUENCE: 378
gcggccatat gaccatctat ttcaaaaacg g 31

<210> SEQ ID NO 379
<211> LENGTH: 34
<212> TYPE: DNA
<213> ORGANISM: Artificial Sequence
<220> FEATURE:
<223> OTHER INFORMATION: Oligonucleotide

<400> SEQUENCE: 379
gcggcctcga gtcagccgat gtttagcgtc catt 34

<210> SEQ ID NO 380
<211> LENGTH: 31
<212> TYPE: DNA
<213> ORGANISM: Artificial Sequence
<220> FEATURE:
<223> OTHER INFORMATION: Oligonucleotide

<400> SEQUENCE: 380
cgcggatccc atatgagcag cggagggggt g 31

<210> SEQ ID NO 381
<211> LENGTH: 27
<212> TYPE: DNA
<213> ORGANISM: Artificial Sequence -continued
<220> FEATURE:
<223> OTHER INFORMATION: Oligonucleotide

<400> SEQUENCE: 381
cccgctcgag ttgcttggcg gcaaggc 27

<210> SEQ ID NO 382
<211> LENGTH: 31
<212> TYPE: DNA
<213> ORGANISM: Artificial Sequence
<220> FEATURE:
<223> OTHER INFORMATION: Oligonucleotide

<400> SEQUENCE: 382
cgcggatccc atatggtcgc cgccgacatc g 31

<210> SEQ ID NO 383
<211> LENGTH: 27
<212> TYPE: DNA
<213> ORGANISM: Artificial Sequence
<220> FEATURE:
<223> OTHER INFORMATION: Oligonucleotide

<400> SEQUENCE: 383
cccgctcgag ttgcttggcg gcaaggc 27

<210> SEQ ID NO 384
<211> LENGTH: 31
<212> TYPE: DNA
<213> ORGANISM: Artificial Sequence
<220> FEATURE:
<223> OTHER INFORMATION: Oligonucleotide

<400> SEQUENCE: 384
cgcggatccc atatgggcgg ttcggaaggc g 31

<210> SEQ ID NO 385
<211> LENGTH: 33
<212> TYPE: DNA
<213> ORGANISM: Artificial Sequence
<220> FEATURE:
<223> OTHER INFORMATION: Oligonucleotide

<400> SEQUENCE: 385
cccgctcgag ttgaacactg atgtcttttc cga 33

<210> SEQ ID NO 386
<211> LENGTH: 35
<212> TYPE: DNA
<213> ORGANISM: Artificial Sequence
<220> FEATURE:
<223> OTHER INFORMATION: Oligonucleotide

<400> SEQUENCE: 386
cgcggatccg ctagcaaact gtcgttggtg ttaac 35

<210> SEQ ID NO 387
<211> LENGTH: 26
<212> TYPE: DNA
<213> ORGANISM: Artificial Sequence
<220> FEATURE:
<223> OTHER INFORMATION: Oligonucleotide

<400> SEQUENCE: 387
cccgctcgag ttgacccgct ccacgg 26

-continued

<210> SEQ ID NO 388
<211> LENGTH: 31
<212> TYPE: DNA
<213> ORGANISM: Artificial Sequence
<220> FEATURE:
<223> OTHER INFORMATION: Oligonucleotide

<400> SEQUENCE: 388
gccgccatat ggcggacttg gcgcaagacc c 31

<210> SEQ ID NO 389
<211> LENGTH: 39
<212> TYPE: DNA
<213> ORGANISM: Artificial Sequence
<220> FEATURE:
<223> OTHER INFORMATION: Oligonucleotide

<400> SEQUENCE: 389
gccgcctcga gatctcctaa acctgtttta acaatgccg 39

<210> SEQ ID NO 390
<211> LENGTH: 31
<212> TYPE: DNA
<213> ORGANISM: Artificial Sequence
<220> FEATURE:
<223> OTHER INFORMATION: Oligonucleotide

<400> SEQUENCE: 390
gccgccatat ggcggacttg gcgcaagacc c 31

<210> SEQ ID NO 391
<211> LENGTH: 31
<212> TYPE: DNA
<213> ORGANISM: Artificial Sequence
<220> FEATURE:
<223> OTHER INFORMATION: Oligonucleotide

<400> SEQUENCE: 391
gcggcctcga gctccatgct gttgccccag c 31

<210> SEQ ID NO 392
<211> LENGTH: 31
<212> TYPE: DNA
<213> ORGANISM: Artificial Sequence
<220> FEATURE:
<223> OTHER INFORMATION: Oligonucleotide

<400> SEQUENCE: 392
gccgccatat ggcggacttg gcgcaagacc c 31

<210> SEQ ID NO 393
<211> LENGTH: 31
<212> TYPE: DNA
<213> ORGANISM: Artificial Sequence
<220> FEATURE:
<223> OTHER INFORMATION: Oligonucleotide

<400> SEQUENCE: 393
gcggcctcga gaaaatcccc gctaaccgca g 31

<210> SEQ ID NO 394
<211> LENGTH: 31
<212> TYPE: DNA
<213> ORGANISM: Artificial Sequence
<220> FEATURE:
<223> OTHER INFORMATION: Oligonucleotide -continued

<400> SEQUENCE: 394
cgcggatccc atatgagcag cggagggggt g 31

<210> SEQ ID NO 395
<211> LENGTH: 27
<212> TYPE: DNA
<213> ORGANISM: Artificial Sequence
<220> FEATURE:
<223> OTHER INFORMATION: Oligonucleotide

<400> SEQUENCE: 395
cccgctcgag ttgcttggcg gcaaggc 27

<210> SEQ ID NO 396
<211> LENGTH: 31
<212> TYPE: DNA
<213> ORGANISM: Artificial Sequence
<220> FEATURE:
<223> OTHER INFORMATION: Oligonucleotide

<400> SEQUENCE: 396
cgcggatccc atatggtcgc cgccgacatc g 31

<210> SEQ ID NO 397
<211> LENGTH: 27
<212> TYPE: DNA
<213> ORGANISM: Artificial Sequence
<220> FEATURE:
<223> OTHER INFORMATION: Oligonucleotide

<400> SEQUENCE: 397
cccgctcgag ttgcttggcg gcaaggc 27

<210> SEQ ID NO 398
<211> LENGTH: 33
<212> TYPE: DNA
<213> ORGANISM: Artificial Sequence
<220> FEATURE:
<223> OTHER INFORMATION: Oligonucleotide

<400> SEQUENCE: 398
cgcggatccc atatggacgg tgttgtgcct gtt 33

<210> SEQ ID NO 399
<211> LENGTH: 29
<212> TYPE: DNA
<213> ORGANISM: Artificial Sequence
<220> FEATURE:
<223> OTHER INFORMATION: Oligonucleotide

<400> SEQUENCE: 399
cccgctcgag cttacggatc aaattgacg 29

<210> SEQ ID NO 400
<211> LENGTH: 33
<212> TYPE: DNA
<213> ORGANISM: Artificial Sequence
<220> FEATURE:
<223> OTHER INFORMATION: Oligonucleotide

<400> SEQUENCE: 400
cgcggatccc atatgggcag ccaatctgaa gaa 33

<210> SEQ ID NO 401

-continued

<211> LENGTH: 28
<212> TYPE: DNA
<213> ORGANISM: Artificial Sequence
<220> FEATURE:
<223> OTHER INFORMATION: Oligonucleotide

<400> SEQUENCE: 401
cccgctcgag ctcagctttt gccgtcaa 28

<210> SEQ ID NO 402
<211> LENGTH: 33
<212> TYPE: DNA
<213> ORGANISM: Artificial Sequence
<220> FEATURE:
<223> OTHER INFORMATION: Oligonucleotide

<400> SEQUENCE: 402
cgcggatccg ctagctactc atccattgtc cgc 33

<210> SEQ ID NO 403
<211> LENGTH: 29
<212> TYPE: DNA
<213> ORGANISM: Artificial Sequence
<220> FEATURE:
<223> OTHER INFORMATION: Oligonucleotide

<400> SEQUENCE: 403
cccgctcgag ccagttgtag cctattttg 29

<210> SEQ ID NO 404
<211> LENGTH: 32
<212> TYPE: DNA
<213> ORGANISM: Artificial Sequence
<220> FEATURE:
<223> OTHER INFORMATION: Oligonucleotide

<400> SEQUENCE: 404
cgcggatccg ctagcatgcg cttcacacac ac 32

<210> SEQ ID NO 405
<211> LENGTH: 30
<212> TYPE: DNA
<213> ORGANISM: Artificial Sequence
<220> FEATURE:
<223> OTHER INFORMATION: Oligonucleotide

<400> SEQUENCE: 405
cccgctcgag ttaccagttg tagcctattt 30

<210> SEQ ID NO 406
<211> LENGTH: 32
<212> TYPE: DNA
<213> ORGANISM: Artificial Sequence
<220> FEATURE:
<223> OTHER INFORMATION: Oligonucleotide

<400> SEQUENCE: 406
gccgccatat ggcacaaacg gaaggtttgg aa 32

<210> SEQ ID NO 407
<211> LENGTH: 36
<212> TYPE: DNA
<213> ORGANISM: Artificial Sequence
<220> FEATURE:
<223> OTHER INFORMATION: Oligonucleotide

<400> SEQUENCE: 407

-continued gccgcctcga gaaaactgta acgcaggttt gccgtc 36

<210> SEQ ID NO 408
<211> LENGTH: 32
<212> TYPE: DNA
<213> ORGANISM: Artificial Sequence
<220> FEATURE:
<223> OTHER INFORMATION: Oligonucleotide

<400> SEQUENCE: 408
gcggccatat ggaagaaaca ccgcgcgaac cg 32

<210> SEQ ID NO 409
<211> LENGTH: 32
<212> TYPE: DNA
<213> ORGANISM: Artificial Sequence
<220> FEATURE:
<223> OTHER INFORMATION: Oligonucleotide

<400> SEQUENCE: 409
gcggcctcga ggaacgtttt attaaactcg ac 32

<210> SEQ ID NO 410
<211> LENGTH: 32
<212> TYPE: DNA
<213> ORGANISM: Artificial Sequence
<220> FEATURE:
<223> OTHER INFORMATION: Oligonucleotide

<400> SEQUENCE: 410
gcggccatat gagaaaaccg accgataccc ta 32

<210> SEQ ID NO 411
<211> LENGTH: 33
<212> TYPE: DNA
<213> ORGANISM: Artificial Sequence
<220> FEATURE:
<223> OTHER INFORMATION: Oligonucleotide

<400> SEQUENCE: 411
gcggcctcga gtcaacgcca ctgccagcgg ttg 33

<210> SEQ ID NO 412
<211> LENGTH: 48
<212> TYPE: DNA
<213> ORGANISM: Artificial Sequence
<220> FEATURE:
<223> OTHER INFORMATION: Oligonucleotide

<400> SEQUENCE: 412
cgcggatccc atatgaagaa gaacatattg gaattttggg tcggactg 48

<210> SEQ ID NO 413
<211> LENGTH: 38
<212> TYPE: DNA
<213> ORGANISM: Artificial Sequence
<220> FEATURE:
<223> OTHER INFORMATION: Oligonucleotide

<400> SEQUENCE: 413
cccgctcgag ttattcggcg gctttttccg cattgccg 38

<210> SEQ ID NO 414
<211> LENGTH: 103
<212> TYPE: DNA

-continued

<213> ORGANISM: Artificial Sequence
<220> FEATURE:
<223> OTHER INFORMATION: Oligonucleotide

<400> SEQUENCE: 414
gggaattcca tatgaaaaag acagctatcg cgattgcagt ggcactggct ggtttcgcta 60
ccgtagcgca ggccgctagc gctttccgcg tggccggcgg tgc 103

<210> SEQ ID NO 415
<211> LENGTH: 38
<212> TYPE: DNA
<213> ORGANISM: Artificial Sequence
<220> FEATURE:
<223> OTHER INFORMATION: Oligonucleotide

<400> SEQUENCE: 415
cccgctcgag ttattcggcg gctttttccg cattgccg 38

<210> SEQ ID NO 416
<211> LENGTH: 32
<212> TYPE: DNA
<213> ORGANISM: Artificial Sequence
<220> FEATURE:
<223> OTHER INFORMATION: Oligonucleotide

<400> SEQUENCE: 416
catgccatgg ctttccgcgt ggccggcggt gc 32

<210> SEQ ID NO 417
<211> LENGTH: 38
<212> TYPE: DNA
<213> ORGANISM: Artificial Sequence
<220> FEATURE:
<223> OTHER INFORMATION: Oligonucleotide

<400> SEQUENCE: 417
cccgctcgag ttattcggcg gctttttccg cattgccg 38

<210> SEQ ID NO 418
<211> LENGTH: 31
<212> TYPE: DNA
<213> ORGANISM: Artificial Sequence
<220> FEATURE:
<223> OTHER INFORMATION: Oligonucleotide

<400> SEQUENCE: 418
cgcggatccc atatgtttgc cgaaacccgc c 31

<210> SEQ ID NO 419
<211> LENGTH: 28
<212> TYPE: DNA
<213> ORGANISM: Artificial Sequence
<220> FEATURE:
<223> OTHER INFORMATION: Oligonucleotide

<400> SEQUENCE: 419
cccgctcgag aggttgtgtt ccaggttg 28

<210> SEQ ID NO 420
<211> LENGTH: 31
<212> TYPE: DNA
<213> ORGANISM: Artificial Sequence
<220> FEATURE:
<223> OTHER INFORMATION: Oligonucleotide

<400> SEQUENCE: 420
cgcggatccc atatgaaaaa aaccgcctat g 31

<210> SEQ ID NO 421
<211> LENGTH: 28
<212> TYPE: DNA
<213> ORGANISM: Artificial Sequence
<220> FEATURE:
<223> OTHER INFORMATION: Oligonucleotide

<400> SEQUENCE: 421
cccgctcgag ttaaggttgt gttccagg 28

<210> SEQ ID NO 422
<211> LENGTH: 33
<212> TYPE: DNA
<213> ORGANISM: Artificial Sequence
<220> FEATURE:
<223> OTHER INFORMATION: Oligonucleotide

<400> SEQUENCE: 422
cgcggatccc atatgaaaaa atacctattc cgc 33

<210> SEQ ID NO 423
<211> LENGTH: 27
<212> TYPE: DNA
<213> ORGANISM: Artificial Sequence
<220> FEATURE:
<223> OTHER INFORMATION: Oligonucleotide

<400> SEQUENCE: 423
cccgctcgag ttacgggcgg tattcgg 27

<210> SEQ ID NO 424
<211> LENGTH: 34
<212> TYPE: DNA
<213> ORGANISM: Artificial Sequence
<220> FEATURE:
<223> OTHER INFORMATION: Oligonucleotide

<400> SEQUENCE: 424
cgcggatccc atatgcaaag caagagcatc caaa 34

<210> SEQ ID NO 425
<211> LENGTH: 27
<212> TYPE: DNA
<213> ORGANISM: Artificial Sequence
<220> FEATURE:
<223> OTHER INFORMATION: Oligonucleotide

<400> SEQUENCE: 425
cccgctcgag ttacgggcgg tattcgg 27

<210> SEQ ID NO 426
<211> LENGTH: 86
<212> TYPE: DNA
<213> ORGANISM: Artificial Sequence
<220> FEATURE:
<223> OTHER INFORMATION: Oligonucleotide

<400> SEQUENCE: 426
gggaattcca tatgaaaacc ttcttcaaaa ccctttccgc cgccgcgcta gcgctcatcc 60
tcgccgcctg ccaaagcaag agcatc 86

<210> SEQ ID NO 427

-continued

<211> LENGTH: 38
<212> TYPE: DNA
<213> ORGANISM: Artificial Sequence
<220> FEATURE:
<223> OTHER INFORMATION: Oligonucleotide

<400> SEQUENCE: 427
cccgctcgag ttacgggcgg tattcgggct tcataccg 38

<210> SEQ ID NO 428
<211> LENGTH: 33
<212> TYPE: DNA
<213> ORGANISM: Artificial Sequence
<220> FEATURE:
<223> OTHER INFORMATION: Oligonucleotide

<400> SEQUENCE: 428
cgcggatccg tcgactgtgg gggcggcggt ggc 33

<210> SEQ ID NO 429
<211> LENGTH: 31
<212> TYPE: DNA
<213> ORGANISM: Artificial Sequence
<220> FEATURE:
<223> OTHER INFORMATION: Oligonucleotide

<400> SEQUENCE: 429
cccgctcgag tcaatcctgc tctttttgc c 31

<210> SEQ ID NO 430
<211> LENGTH: 30
<212> TYPE: DNA
<213> ORGANISM: Artificial Sequence
<220> FEATURE:
<223> OTHER INFORMATION: Oligonucleotide

<400> SEQUENCE: 430
gcggccatat gaagaaaaca ttgacactgc 30

<210> SEQ ID NO 431
<211> LENGTH: 32
<212> TYPE: DNA
<213> ORGANISM: Artificial Sequence
<220> FEATURE:
<223> OTHER INFORMATION: Oligonucleotide

<400> SEQUENCE: 431
gcggcctcga gttaatggtg cgaatgaccg at 32

<210> SEQ ID NO 432
<211> LENGTH: 46
<212> TYPE: DNA
<213> ORGANISM: Artificial Sequence
<220> FEATURE:
<223> OTHER INFORMATION: Oligonucleotide

<400> SEQUENCE: 432
ggggacaagt ttgtacaaaa aagcaggctt gcggcaagga tgccgg 46

<210> SEQ ID NO 433
<211> LENGTH: 47
<212> TYPE: DNA
<213> ORGANISM: Artificial Sequence
<220> FEATURE:
<223> OTHER INFORMATION: Oligonucleotide

<400> SEQUENCE: 433

-continued ggggaccact ttgtacaaga aagctgggtc taaagcaaca atgccgg 47

<210> SEQ ID NO 434
<211> LENGTH: 30
<212> TYPE: DNA
<213> ORGANISM: Artificial Sequence
<220> FEATURE:
<223> OTHER INFORMATION: Oligonucleotide

<400> SEQUENCE: 434
cgcggatccc atatgaaaca caccgtatcc 30

<210> SEQ ID NO 435
<211> LENGTH: 26
<212> TYPE: DNA
<213> ORGANISM: Artificial Sequence
<220> FEATURE:
<223> OTHER INFORMATION: Oligonucleotide

<400> SEQUENCE: 435
cccgctcgag ttatctcgtg cgcgcc 26

<210> SEQ ID NO 436
<211> LENGTH: 30
<212> TYPE: DNA
<213> ORGANISM: Artificial Sequence
<220> FEATURE:
<223> OTHER INFORMATION: Oligonucleotide

<400> SEQUENCE: 436
cgcggatccc atatgagccc cgcgccgatt 30

<210> SEQ ID NO 437
<211> LENGTH: 28
<212> TYPE: DNA
<213> ORGANISM: Artificial Sequence
<220> FEATURE:
<223> OTHER INFORMATION: Oligonucleotide

<400> SEQUENCE: 437
cccgctcgag tttttgtgcg gtcaggcg 28

<210> SEQ ID NO 438
<211> LENGTH: 62
<212> TYPE: DNA
<213> ORGANISM: Artificial Sequence
<220> FEATURE:
<223> OTHER INFORMATION: Oligonucleotide

<400> SEQUENCE: 438
ggggacaagt ttgtacaaaa aagcaggctt gttcgtttgg gggatttaaa ccaaaccaaa 60
tc 62

<210> SEQ ID NO 439
<211> LENGTH: 30
<212> TYPE: DNA
<213> ORGANISM: Artificial Sequence
<220> FEATURE:
<223> OTHER INFORMATION: Oligonucleotide

<400> SEQUENCE: 439
cgcggatccc atatggcgga tgcgcccgcg 30

<210> SEQ ID NO 440

-continued

<211> LENGTH: 26
<212> TYPE: DNA
<213> ORGANISM: Artificial Sequence
<220> FEATURE:
<223> OTHER INFORMATION: Oligonucleotide

<400> SEQUENCE: 440
cccgctcgag aaaccgccaa tccgcc 26

<210> SEQ ID NO 441
<211> LENGTH: 61
<212> TYPE: DNA
<213> ORGANISM: Artificial Sequence
<220> FEATURE:
<223> OTHER INFORMATION: Oligonucleotide

<400> SEQUENCE: 441
ggggaccact ttgtacaaga aagctgggtt cattttgttt ttccttcttc tcgaggccat 60
t 61

<210> SEQ ID NO 442
<211> LENGTH: 30
<212> TYPE: DNA
<213> ORGANISM: Artificial Sequence
<220> FEATURE:
<223> OTHER INFORMATION: Oligonucleotide

<400> SEQUENCE: 442
cgcggatccc atatgaaacc caaaccgcac 30

<210> SEQ ID NO 443
<211> LENGTH: 27
<212> TYPE: DNA
<213> ORGANISM: Artificial Sequence
<220> FEATURE:
<223> OTHER INFORMATION: Oligonucleotide

<400> SEQUENCE: 443
cccgctcgag tcagcgttgg acgtagt 27

<210> SEQ ID NO 444
<211> LENGTH: 33
<212> TYPE: DNA
<213> ORGANISM: Artificial Sequence
<220> FEATURE:
<223> OTHER INFORMATION: Oligonucleotide

<400> SEQUENCE: 444
gggaattcca tatgaaaaaa atcatcttcg ccg 33

<210> SEQ ID NO 445
<211> LENGTH: 31
<212> TYPE: DNA
<213> ORGANISM: Artificial Sequence
<220> FEATURE:
<223> OTHER INFORMATION: Oligonucleotide

<400> SEQUENCE: 445
cccgctcgag ttattgtttg gctgcctcga t 31

<210> SEQ ID NO 446
<211> LENGTH: 33
<212> TYPE: DNA
<213> ORGANISM: Artificial Sequence
<220> FEATURE:
<223> OTHER INFORMATION: Oligonucleotide -continued

<400> SEQUENCE: 446
gggaattcca tatggccacc tacaaagtgg acg 33

<210> SEQ ID NO 447
<211> LENGTH: 30
<212> TYPE: DNA
<213> ORGANISM: Artificial Sequence
<220> FEATURE:
<223> OTHER INFORMATION: Oligonucleotide

<400> SEQUENCE: 447
cggggatcct tgtttggctg cctcgatttg 30

<210> SEQ ID NO 448
<211> LENGTH: 34
<212> TYPE: DNA
<213> ORGANISM: Artificial Sequence
<220> FEATURE:
<223> OTHER INFORMATION: Oligonucleotide

<400> SEQUENCE: 448
cgcggatccc atatgcaaga acaatcgcag aaag 34

<210> SEQ ID NO 449
<211> LENGTH: 30
<212> TYPE: DNA
<213> ORGANISM: Artificial Sequence
<220> FEATURE:
<223> OTHER INFORMATION: Oligonucleotide

<400> SEQUENCE: 449
cccgctcgag ttttttcggc aaattggctt 30

<210> SEQ ID NO 450
<211> LENGTH: 45
<212> TYPE: DNA
<213> ORGANISM: Artificial Sequence
<220> FEATURE:
<223> OTHER INFORMATION: Oligonucleotide

<400> SEQUENCE: 450
ggggacaagt ttgtacaaaa aagcaggctg ccgatgccgt tgcgg 45

<210> SEQ ID NO 451
<211> LENGTH: 47
<212> TYPE: DNA
<213> ORGANISM: Artificial Sequence
<220> FEATURE:
<223> OTHER INFORMATION: Oligonucleotide

<400> SEQUENCE: 451
ggggaccact ttgtacaaga aagctgggtt cagggtcgtt tgttgcg 47

<210> SEQ ID NO 452
<211> LENGTH: 30
<212> TYPE: DNA
<213> ORGANISM: Artificial Sequence
<220> FEATURE:
<223> OTHER INFORMATION: Oligonucleotide

<400> SEQUENCE: 452
cgcggatccc atatgaaaca ctttccatcc 30

<210> SEQ ID NO 453

-continued

<211> LENGTH: 28
<212> TYPE: DNA
<213> ORGANISM: Artificial Sequence
<220> FEATURE:
<223> OTHER INFORMATION: Oligonucleotide

<400> SEQUENCE: 453
cccgctcgag ttaccactcg taattgac 28

<210> SEQ ID NO 454
<211> LENGTH: 30
<212> TYPE: DNA
<213> ORGANISM: Artificial Sequence
<220> FEATURE:
<223> OTHER INFORMATION: Oligonucleotide

<400> SEQUENCE: 454
cgcggatccc atatggccac aagcgacgac 30

<210> SEQ ID NO 455
<211> LENGTH: 28
<212> TYPE: DNA
<213> ORGANISM: Artificial Sequence
<220> FEATURE:
<223> OTHER INFORMATION: Oligonucleotide

<400> SEQUENCE: 455
cccgctcgag ttaccactcg taattgac 28

<210> SEQ ID NO 456
<211> LENGTH: 28
<212> TYPE: DNA
<213> ORGANISM: Artificial Sequence
<220> FEATURE:
<223> OTHER INFORMATION: Oligonucleotide

<400> SEQUENCE: 456
cgcggatccc atatggccac aaacgacg 28

<210> SEQ ID NO 457
<211> LENGTH: 28
<212> TYPE: DNA
<213> ORGANISM: Artificial Sequence
<220> FEATURE:
<223> OTHER INFORMATION: Oligonucleotide

<400> SEQUENCE: 457
cccgctcgag acccacgttg taaggttg 28

<210> SEQ ID NO 458
<211> LENGTH: 32
<212> TYPE: DNA
<213> ORGANISM: Artificial Sequence
<220> FEATURE:
<223> OTHER INFORMATION: Oligonucleotide

<400> SEQUENCE: 458
cgcggatccc atatggccac aagcgacgac ga 32

<210> SEQ ID NO 459
<211> LENGTH: 28
<212> TYPE: DNA
<213> ORGANISM: Artificial Sequence
<220> FEATURE:
<223> OTHER INFORMATION: Oligonucleotide

<400> SEQUENCE: 459

-continued cccgctcgag acccacgttg taaggttg 28

<210> SEQ ID NO 460
<211> LENGTH: 33
<212> TYPE: DNA
<213> ORGANISM: Artificial Sequence
<220> FEATURE:
<223> OTHER INFORMATION: Oligonucleotide

<400> SEQUENCE: 460
cgcggatccc atatgatgaa acactttcca tcc 33

<210> SEQ ID NO 461
<211> LENGTH: 29
<212> TYPE: DNA
<213> ORGANISM: Artificial Sequence
<220> FEATURE:
<223> OTHER INFORMATION: Oligonucleotide

<400> SEQUENCE: 461
cccgctcgag ttaacccacg ttgtaaggt 29

<210> SEQ ID NO 462
<211> LENGTH: 33
<212> TYPE: DNA
<213> ORGANISM: Artificial Sequence
<220> FEATURE:
<223> OTHER INFORMATION: Oligonucleotide

<400> SEQUENCE: 462
cgcggatccc atatgatgaa acactttcca tcc 33

<210> SEQ ID NO 463
<211> LENGTH: 29
<212> TYPE: DNA
<213> ORGANISM: Artificial Sequence
<220> FEATURE:
<223> OTHER INFORMATION: Oligonucleotide

<400> SEQUENCE: 463
cccgctcgag ttaacccacg ttgtaaggt 29

<210> SEQ ID NO 464
<211> LENGTH: 28
<212> TYPE: DNA
<213> ORGANISM: Artificial Sequence
<220> FEATURE:
<223> OTHER INFORMATION: Oligonucleotide

<400> SEQUENCE: 464
cgcggatccc atatggccac aaacgacg 28

<210> SEQ ID NO 465
<211> LENGTH: 29
<212> TYPE: DNA
<213> ORGANISM: Artificial Sequence
<220> FEATURE:
<223> OTHER INFORMATION: Oligonucleotide

<400> SEQUENCE: 465
cccgctcgag gtctgacact gttttatcc 29

<210> SEQ ID NO 466
<211> LENGTH: 33
<212> TYPE: DNA

-continued

<213> ORGANISM: Artificial Sequence
<220> FEATURE:
<223> OTHER INFORMATION: Oligonucleotide

<400> SEQUENCE: 466
cgcggatccc atatgatgaa acactttcca tcc 33

<210> SEQ ID NO 467
<211> LENGTH: 29
<212> TYPE: DNA
<213> ORGANISM: Artificial Sequence
<220> FEATURE:
<223> OTHER INFORMATION: Oligonucleotide

<400> SEQUENCE: 467
cccgctcgag ttatgctttg gcggcaaag 29

<210> SEQ ID NO 468
<211> LENGTH: 30
<212> TYPE: DNA
<213> ORGANISM: Artificial Sequence
<220> FEATURE:
<223> OTHER INFORMATION: Oligonucleotide

<400> SEQUENCE: 468
cgcggatccc atatggccac aaacgacgac 30

<210> SEQ ID NO 469
<211> LENGTH: 27
<212> TYPE: DNA
<213> ORGANISM: Artificial Sequence
<220> FEATURE:
<223> OTHER INFORMATION: Oligonucleotide

<400> SEQUENCE: 469
cgcggatccc cactcgtaat tgacgcc 27

<210> SEQ ID NO 470
<211> LENGTH: 30
<212> TYPE: DNA
<213> ORGANISM: Artificial Sequence
<220> FEATURE:
<223> OTHER INFORMATION: Oligonucleotide

<400> SEQUENCE: 470
cgcggatccc atatggccac aagcgacgac 30

<210> SEQ ID NO 471
<211> LENGTH: 27
<212> TYPE: DNA
<213> ORGANISM: Artificial Sequence
<220> FEATURE:
<223> OTHER INFORMATION: Oligonucleotide

<400> SEQUENCE: 471
cgcggatccc cactcgtaat tgacgcc 27

<210> SEQ ID NO 472
<211> LENGTH: 30
<212> TYPE: DNA
<213> ORGANISM: Artificial Sequence
<220> FEATURE:
<223> OTHER INFORMATION: Oligonucleotide

<400> SEQUENCE: 472
cgcggatccc atatggccac aaacgacgac 30

<210> SEQ ID NO 473
<211> LENGTH: 27
<212> TYPE: DNA
<213> ORGANISM: Artificial Sequence
<220> FEATURE:
<223> OTHER INFORMATION: Oligonucleotide

<400> SEQUENCE: 473
cgcggatcca cccacgttgt aaggttg 27

<210> SEQ ID NO 474
<211> LENGTH: 33
<212> TYPE: DNA
<213> ORGANISM: Artificial Sequence
<220> FEATURE:
<223> OTHER INFORMATION: Oligonucleotide

<400> SEQUENCE: 474
cgcggatccc atatgatgaa acactttcca tcc 33

<210> SEQ ID NO 475
<211> LENGTH: 27
<212> TYPE: DNA
<213> ORGANISM: Artificial Sequence
<220> FEATURE:
<223> OTHER INFORMATION: Oligonucleotide

<400> SEQUENCE: 475
cgcggatcca cccacgttgt aaggttg 27

<210> SEQ ID NO 476
<211> LENGTH: 25
<212> TYPE: DNA
<213> ORGANISM: Artificial Sequence
<220> FEATURE:
<223> OTHER INFORMATION: Oligonucleotide

<400> SEQUENCE: 476
cgcggatccg gagggggtgg tgtcg 25

<210> SEQ ID NO 477
<211> LENGTH: 27
<212> TYPE: DNA
<213> ORGANISM: Artificial Sequence
<220> FEATURE:
<223> OTHER INFORMATION: Oligonucleotide

<400> SEQUENCE: 477
cccgctcgag ttgcttggcg gcaaggc 27

<210> SEQ ID NO 478
<211> LENGTH: 25
<212> TYPE: DNA
<213> ORGANISM: Artificial Sequence
<220> FEATURE:
<223> OTHER INFORMATION: Oligonucleotide

<400> SEQUENCE: 478
cgcggatccg gcggaggcgg cactt 25

<210> SEQ ID NO 479
<211> LENGTH: 26
<212> TYPE: DNA
<213> ORGANISM: Artificial Sequence
<220> FEATURE:

-continued

<223> OTHER INFORMATION: Oligonucleotide

<400> SEQUENCE: 479
cccgctcgag gaaccggtag cctacg 26

<210> SEQ ID NO 480
<211> LENGTH: 41
<212> TYPE: DNA
<213> ORGANISM: Artificial Sequence
<220> FEATURE:
<223> OTHER INFORMATION: Oligonucleotide

<400> SEQUENCE: 480
cgcggatccg gtggtggtgg ttcagatttg gcaaacgatt c 41

<210> SEQ ID NO 481
<211> LENGTH: 29
<212> TYPE: DNA
<213> ORGANISM: Artificial Sequence
<220> FEATURE:
<223> OTHER INFORMATION: Oligonucleotide

<400> SEQUENCE: 481
cccgctcgag cgtatcatat ttcacgtgc 29

<210> SEQ ID NO 482
<211> LENGTH: 25
<212> TYPE: DNA
<213> ORGANISM: Artificial Sequence
<220> FEATURE:
<223> OTHER INFORMATION: Oligonucleotide

<400> SEQUENCE: 482
cgcggatccg gagggggtgg tgtcg 25

<210> SEQ ID NO 483
<211> LENGTH: 28
<212> TYPE: DNA
<213> ORGANISM: Artificial Sequence
<220> FEATURE:
<223> OTHER INFORMATION: Oligonucleotide

<400> SEQUENCE: 483
cccgctcgag ttattgcttg gcggcaag 28

<210> SEQ ID NO 484
<211> LENGTH: 25
<212> TYPE: DNA
<213> ORGANISM: Artificial Sequence
<220> FEATURE:
<223> OTHER INFORMATION: Oligonucleotide

<400> SEQUENCE: 484
cgcggatccg gcggaggcgg cactt 25

<210> SEQ ID NO 485
<211> LENGTH: 28
<212> TYPE: DNA
<213> ORGANISM: Artificial Sequence
<220> FEATURE:
<223> OTHER INFORMATION: Oligonucleotide

<400> SEQUENCE: 485
cccgctcgag tcagaaccgg tagcctac 28

-continued

<210> SEQ ID NO 486
<211> LENGTH: 41
<212> TYPE: DNA
<213> ORGANISM: Artificial Sequence
<220> FEATURE:
<223> OTHER INFORMATION: Oligonucleotide

<400> SEQUENCE: 486
cgcggatccg gtggtggtgg ttcagatttg gcaaacgatt c 41

<210> SEQ ID NO 487
<211> LENGTH: 32
<212> TYPE: DNA
<213> ORGANISM: Artificial Sequence
<220> FEATURE:
<223> OTHER INFORMATION: Oligonucleotide

<400> SEQUENCE: 487
cccgctcgag ttacgtatca tatttcacgt gc 32

<210> SEQ ID NO 488
<211> LENGTH: 31
<212> TYPE: DNA
<213> ORGANISM: Artificial Sequence
<220> FEATURE:
<223> OTHER INFORMATION: Oligonucleotide

<400> SEQUENCE: 488
cgcggatccc atatggccac aagcgacgac g 31

<210> SEQ ID NO 489
<211> LENGTH: 28
<212> TYPE: DNA
<213> ORGANISM: Artificial Sequence
<220> FEATURE:
<223> OTHER INFORMATION: Oligonucleotide

<400> SEQUENCE: 489
cccgctcgag ccactcgtaa ttgacgcc 28

<210> SEQ ID NO 490
<211> LENGTH: 30
<212> TYPE: DNA
<213> ORGANISM: Artificial Sequence
<220> FEATURE:
<223> OTHER INFORMATION: Oligonucleotide

<400> SEQUENCE: 490
cgcggatccc atatggccac aaacgacgac 30

<210> SEQ ID NO 491
<211> LENGTH: 28
<212> TYPE: DNA
<213> ORGANISM: Artificial Sequence
<220> FEATURE:
<223> OTHER INFORMATION: Oligonucleotide

<400> SEQUENCE: 491
cccgctcgag tgctttggcg gcaaagtt 28

<210> SEQ ID NO 492
<211> LENGTH: 30
<212> TYPE: DNA
<213> ORGANISM: Artificial Sequence
<220> FEATURE:
<223> OTHER INFORMATION: Oligonucleotide -continued

<400> SEQUENCE: 492
cgcggatccc atatggccac aaacgacgac 30

<210> SEQ ID NO 493
<211> LENGTH: 37
<212> TYPE: DNA
<213> ORGANISM: Artificial Sequence
<220> FEATURE:
<223> OTHER INFORMATION: Oligonucleotide

<400> SEQUENCE: 493
cccgctcgag tttagcaata ttatctttgt tcgtagc 37

<210> SEQ ID NO 494
<211> LENGTH: 32
<212> TYPE: DNA
<213> ORGANISM: Artificial Sequence
<220> FEATURE:
<223> OTHER INFORMATION: Oligonucleotide

<400> SEQUENCE: 494
cgcggatccc atatgaaagc aaaccgtgcc ga 32

<210> SEQ ID NO 495
<211> LENGTH: 28
<212> TYPE: DNA
<213> ORGANISM: Artificial Sequence
<220> FEATURE:
<223> OTHER INFORMATION: Oligonucleotide

<400> SEQUENCE: 495
cccgctcgag ccactcgtaa ttgacgcc 28

<210> SEQ ID NO 496
<211> LENGTH: 61
<212> TYPE: DNA
<213> ORGANISM: Artificial Sequence
<220> FEATURE:
<223> OTHER INFORMATION: Oligonucleotide

<400> SEQUENCE: 496
ggggacaagt ttgtacaaaa aagcaggctg cagccacaaa cgacgacgat gttaaaaaag 60
c 61

<210> SEQ ID NO 497
<211> LENGTH: 61
<212> TYPE: DNA
<213> ORGANISM: Artificial Sequence
<220> FEATURE:
<223> OTHER INFORMATION: Oligonucleotide

<400> SEQUENCE: 497
ggggaccact ttgtacaaga aagctgggtt taccactcgt aattgacgcc gacatggtag 60
g 61

<210> SEQ ID NO 498
<211> LENGTH: 31
<212> TYPE: DNA
<213> ORGANISM: Artificial Sequence
<220> FEATURE:
<223> OTHER INFORMATION: Oligonucleotide

<400> SEQUENCE: 498
gcggccatat ggcagcaaaa gacgtacagt t 31

-continued

<210> SEQ ID NO 499
<211> LENGTH: 33
<212> TYPE: DNA
<213> ORGANISM: Artificial Sequence
<220> FEATURE:
<223> OTHER INFORMATION: Oligonucleotide

<400> SEQUENCE: 499
gcggcctcga gttacatcat gccgcccata cca 33

<210> SEQ ID NO 500
<211> LENGTH: 31
<212> TYPE: DNA
<213> ORGANISM: Artificial Sequence
<220> FEATURE:
<223> OTHER INFORMATION: Oligonucleotide

<400> SEQUENCE: 500
cgcggatccg ctagcttagg cggcggcgga g 31

<210> SEQ ID NO 501
<211> LENGTH: 26
<212> TYPE: DNA
<213> ORGANISM: Artificial Sequence
<220> FEATURE:
<223> OTHER INFORMATION: Oligonucleotide

<400> SEQUENCE: 501
cccgctcgag gaaccggtag cctacg 26

<210> SEQ ID NO 502
<211> LENGTH: 29
<212> TYPE: DNA
<213> ORGANISM: Artificial Sequence
<220> FEATURE:
<223> OTHER INFORMATION: Oligonucleotide

<400> SEQUENCE: 502
cccctagcta gcacttctgc gcccgactt 29

<210> SEQ ID NO 503
<211> LENGTH: 26
<212> TYPE: DNA
<213> ORGANISM: Artificial Sequence
<220> FEATURE:
<223> OTHER INFORMATION: Oligonucleotide

<400> SEQUENCE: 503
cccgctcgag gaaccggtag cctacg 26

<210> SEQ ID NO 504
<211> LENGTH: 31
<212> TYPE: DNA
<213> ORGANISM: Artificial Sequence
<220> FEATURE:
<223> OTHER INFORMATION: Oligonucleotide

<400> SEQUENCE: 504
cgcggatccg ctagcttagg cggcggcgga g 31

<210> SEQ ID NO 505
<211> LENGTH: 26
<212> TYPE: DNA
<213> ORGANISM: Artificial Sequence
<220> FEATURE:

-continued

<223> OTHER INFORMATION: Oligonucleotide

<400> SEQUENCE: 505
cccgctcgag gaaccggtag cctacg 26

<210> SEQ ID NO 506
<211> LENGTH: 32
<212> TYPE: DNA
<213> ORGANISM: Artificial Sequence
<220> FEATURE:
<223> OTHER INFORMATION: Oligonucleotide

<400> SEQUENCE: 506
cgcggatccg ctagcacttc tgcgcccgac tt 32

<210> SEQ ID NO 507
<211> LENGTH: 26
<212> TYPE: DNA
<213> ORGANISM: Artificial Sequence
<220> FEATURE:
<223> OTHER INFORMATION: Oligonucleotide

<400> SEQUENCE: 507
cccgctcgag gaaccggtag cctacg 26

<210> SEQ ID NO 508
<211> LENGTH: 50
<212> TYPE: DNA
<213> ORGANISM: Artificial Sequence
<220> FEATURE:
<223> OTHER INFORMATION: Oligonucleotide

<400> SEQUENCE: 508
cgcggatccg ctagccgaac gaccccaacc ttccctacaa aaactttcaa 50

<210> SEQ ID NO 509
<211> LENGTH: 35
<212> TYPE: DNA
<213> ORGANISM: Artificial Sequence
<220> FEATURE:
<223> OTHER INFORMATION: Oligonucleotide

<400> SEQUENCE: 509
cccgctcgag tcagaaccga cgtgccaagc cgttc 35

<210> SEQ ID NO 510
<211> LENGTH: 32
<212> TYPE: DNA
<213> ORGANISM: Artificial Sequence
<220> FEATURE:
<223> OTHER INFORMATION: Oligonucleotide

<400> SEQUENCE: 510
gccgccatat gcccccactg gaagaacgga cg 32

<210> SEQ ID NO 511
<211> LENGTH: 35
<212> TYPE: DNA
<213> ORGANISM: Artificial Sequence
<220> FEATURE:
<223> OTHER INFORMATION: Oligonucleotide

<400> SEQUENCE: 511
gccgcctcga gtaataaacc ttctatgggc agcag 35

-continued

<210> SEQ ID NO 512
<211> LENGTH: 31
<212> TYPE: DNA
<213> ORGANISM: Artificial Sequence
<220> FEATURE:
<223> OTHER INFORMATION: Oligonucleotide

<400> SEQUENCE: 512
cgcggatccc atatgtccgt ccacgcatcc g 31

<210> SEQ ID NO 513
<211> LENGTH: 31
<212> TYPE: DNA
<213> ORGANISM: Artificial Sequence
<220> FEATURE:
<223> OTHER INFORMATION: Oligonucleotide

<400> SEQUENCE: 513
cccgctcgag tttgaatttg taggtgtatt g 31

<210> SEQ ID NO 514
<211> LENGTH: 29
<212> TYPE: DNA
<213> ORGANISM: Artificial Sequence
<220> FEATURE:
<223> OTHER INFORMATION: Oligonucleotide

<400> SEQUENCE: 514
cgcggatccc atatgacccc ttccgcact 29

<210> SEQ ID NO 515
<211> LENGTH: 32
<212> TYPE: DNA
<213> ORGANISM: Artificial Sequence
<220> FEATURE:
<223> OTHER INFORMATION: Oligonucleotide

<400> SEQUENCE: 515
cccgctcgag ttatttgaat ttgtaggtgt at 32

<210> SEQ ID NO 516
<211> LENGTH: 33
<212> TYPE: DNA
<213> ORGANISM: Artificial Sequence
<220> FEATURE:
<223> OTHER INFORMATION: Oligonucleotide

<400> SEQUENCE: 516
cgcggatccc atatgaaaac caattcagaa gaa 33

<210> SEQ ID NO 517
<211> LENGTH: 28
<212> TYPE: DNA
<213> ORGANISM: Artificial Sequence
<220> FEATURE:
<223> OTHER INFORMATION: Oligonucleotide

<400> SEQUENCE: 517
cccgctcgag tccacagaga ttgtttcc 28

<210> SEQ ID NO 518
<211> LENGTH: 17
<212> TYPE: DNA
<213> ORGANISM: Artificial Sequence
<220> FEATURE:
<223> OTHER INFORMATION: Oligonucleotide -continued

<400> SEQUENCE: 518
gatgcccgaa gggcggg 17

<210> SEQ ID NO 519
<211> LENGTH: 29
<212> TYPE: DNA
<213> ORGANISM: Artificial Sequence
<220> FEATURE:
<223> OTHER INFORMATION: Oligonucleotide

<400> SEQUENCE: 519
gcccaagctt tcagaagaag acttcacgc 29

<210> SEQ ID NO 520
<211> LENGTH: 36
<212> TYPE: DNA
<213> ORGANISM: Artificial Sequence
<220> FEATURE:
<223> OTHER INFORMATION: Oligonucleotide

<400> SEQUENCE: 520
cgcggatccc atatgcaaac ccataaatac gctatt 36

<210> SEQ ID NO 521
<211> LENGTH: 29
<212> TYPE: DNA
<213> ORGANISM: Artificial Sequence
<220> FEATURE:
<223> OTHER INFORMATION: Oligonucleotide

<400> SEQUENCE: 521
gcccaagctt gaagaagact tcacgccag 29

<210> SEQ ID NO 522
<211> LENGTH: 35
<212> TYPE: DNA
<213> ORGANISM: Artificial Sequence
<220> FEATURE:
<223> OTHER INFORMATION: Oligonucleotide

<400> SEQUENCE: 522
cgcggatccc atatggtctt tttcgacaat accga 35

<210> SEQ ID NO 523
<211> LENGTH: 10
<212> TYPE: DNA
<213> ORGANISM: Artificial Sequence
<220> FEATURE:
<223> OTHER INFORMATION: Oligonucleotide

<400> SEQUENCE: 523
gcccaagctt 10

<210> SEQ ID NO 524
<211> LENGTH: 36
<212> TYPE: DNA
<213> ORGANISM: Artificial Sequence
<220> FEATURE:
<223> OTHER INFORMATION: Oligonucleotide

<400> SEQUENCE: 524
cgcggatccc atatgaataa aactttaaaa aggcgg 36

<210> SEQ ID NO 525
<211> LENGTH: 29

-continued

<212> TYPE: DNA
<213> ORGANISM: Artificial Sequence
<220> FEATURE:
<223> OTHER INFORMATION: Oligonucleotide

<400> SEQUENCE: 525
gcccaagctt tcagaagaag acttcacgc 29

<210> SEQ ID NO 526
<211> LENGTH: 35
<212> TYPE: DNA
<213> ORGANISM: Artificial Sequence
<220> FEATURE:
<223> OTHER INFORMATION: Oligonucleotide

<400> SEQUENCE: 526
cgcgaatccc atatgttcga tcttgattct gtcga 35

<210> SEQ ID NO 527
<211> LENGTH: 28
<212> TYPE: DNA
<213> ORGANISM: Artificial Sequence
<220> FEATURE:
<223> OTHER INFORMATION: Oligonucleotide

<400> SEQUENCE: 527
cccgctcgag tcgcacaggc tgttggcg 28

<210> SEQ ID NO 528
<211> LENGTH: 32
<212> TYPE: DNA
<213> ORGANISM: Artificial Sequence
<220> FEATURE:
<223> OTHER INFORMATION: Oligonucleotide

<400> SEQUENCE: 528
cgcgaatccc atatgttggg cggaggcggc ag 32

<210> SEQ ID NO 529
<211> LENGTH: 28
<212> TYPE: DNA
<213> ORGANISM: Artificial Sequence
<220> FEATURE:
<223> OTHER INFORMATION: Oligonucleotide

<400> SEQUENCE: 529
cccgctcgag tcgcacaggc tgttggcg 28

<210> SEQ ID NO 530
<211> LENGTH: 32
<212> TYPE: DNA
<213> ORGANISM: Artificial Sequence
<220> FEATURE:
<223> OTHER INFORMATION: Oligonucleotide

<400> SEQUENCE: 530
cgcgaatccc atatgttggg cggaggcggc ag 32

<210> SEQ ID NO 531
<211> LENGTH: 28
<212> TYPE: DNA
<213> ORGANISM: Artificial Sequence
<220> FEATURE:
<223> OTHER INFORMATION: Oligonucleotide

<400> SEQUENCE: 531

-continued cccgctcgag tcgcacaggc tgttggcg 28

<210> SEQ ID NO 532
<211> LENGTH: 33
<212> TYPE: DNA
<213> ORGANISM: Artificial Sequence
<220> FEATURE:
<223> OTHER INFORMATION: Oligonucleotide

<400> SEQUENCE: 532
cgcggatccc atatggcaaa tttggaggtg cgc 33

<210> SEQ ID NO 533
<211> LENGTH: 27
<212> TYPE: DNA
<213> ORGANISM: Artificial Sequence
<220> FEATURE:
<223> OTHER INFORMATION: Oligonucleotide

<400> SEQUENCE: 533
cccgctcgag ttcggagcgg ttgaagc 27

<210> SEQ ID NO 534
<211> LENGTH: 34
<212> TYPE: DNA
<213> ORGANISM: Artificial Sequence
<220> FEATURE:
<223> OTHER INFORMATION: Oligonucleotide

<400> SEQUENCE: 534
cgcggatccc atatgcaacg tcgtattata accc 34

<210> SEQ ID NO 535
<211> LENGTH: 29
<212> TYPE: DNA
<213> ORGANISM: Artificial Sequence
<220> FEATURE:
<223> OTHER INFORMATION: Oligonucleotide

<400> SEQUENCE: 535
cccgctcgag ttattcggag cggttgaag 29

<210> SEQ ID NO 536
<211> LENGTH: 42
<212> TYPE: DNA
<213> ORGANISM: Artificial Sequence
<220> FEATURE:
<223> OTHER INFORMATION: Oligonucleotide

<400> SEQUENCE: 536
cgcggatccc atatgggcat caaagtcgcc atcaacggct ac 42

<210> SEQ ID NO 537
<211> LENGTH: 35
<212> TYPE: DNA
<213> ORGANISM: Artificial Sequence
<220> FEATURE:
<223> OTHER INFORMATION: Oligonucleotide

<400> SEQUENCE: 537
cccgctcgag tttgagcggg cgcacttcaa gtccg 35

<210> SEQ ID NO 538
<211> LENGTH: 33
<212> TYPE: DNA
<213> ORGANISM: Artificial Sequence -continued
<220> FEATURE:
<223> OTHER INFORMATION: Oligonucleotide

<400> SEQUENCE: 538
cgcggatccc atatgggcgg cagcgaaaaa aac 33

<210> SEQ ID NO 539
<211> LENGTH: 28
<212> TYPE: DNA
<213> ORGANISM: Artificial Sequence
<220> FEATURE:
<223> OTHER INFORMATION: Oligonucleotide

<400> SEQUENCE: 539
cccgctcgag gttggtgccg actttgat 28

<210> SEQ ID NO 540
<211> LENGTH: 31
<212> TYPE: DNA
<213> ORGANISM: Artificial Sequence
<220> FEATURE:
<223> OTHER INFORMATION: Oligonucleotide

<400> SEQUENCE: 540
cgcggatccc atatgggcgg cggaagcgat a 31

<210> SEQ ID NO 541
<211> LENGTH: 27
<212> TYPE: DNA
<213> ORGANISM: Artificial Sequence
<220> FEATURE:
<223> OTHER INFORMATION: Oligonucleotide

<400> SEQUENCE: 541
cccgctcgag tttgcccgct ttgagcc 27

<210> SEQ ID NO 542
<211> LENGTH: 33
<212> TYPE: DNA
<213> ORGANISM: Artificial Sequence
<220> FEATURE:
<223> OTHER INFORMATION: Oligonucleotide

<400> SEQUENCE: 542
cgcggatccc atatgggcaa atccgaaaat acg 33

<210> SEQ ID NO 543
<211> LENGTH: 27
<212> TYPE: DNA
<213> ORGANISM: Artificial Sequence
<220> FEATURE:
<223> OTHER INFORMATION: Oligonucleotide

<400> SEQUENCE: 543
cccgctcgag catcccgtac tgtttcg 27

<210> SEQ ID NO 544
<211> LENGTH: 62
<212> TYPE: DNA
<213> ORGANISM: Artificial Sequence
<220> FEATURE:
<223> OTHER INFORMATION: Oligonucleotide

<400> SEQUENCE: 544
ggggacaagt ttgtacaaaa aagcaggctc cgacattacc gtgtacaacg gccaacaaag 60

-continued aa 62

<210> SEQ ID NO 545
<211> LENGTH: 61
<212> TYPE: DNA
<213> ORGANISM: Artificial Sequence
<220> FEATURE:
<223> OTHER INFORMATION: Oligonucleotide

<400> SEQUENCE: 545
ggggaccact ttgtacaaga aagctgggtc ttatttcata ccggcttgct caagcagccg 60
g 61

<210> SEQ ID NO 546
<211> LENGTH: 61
<212> TYPE: DNA
<213> ORGANISM: Artificial Sequence
<220> FEATURE:
<223> OTHER INFORMATION: Oligonucleotide

<400> SEQUENCE: 546
ggggacaagt ttgtacaaaa aagcaggctg atacggtgtt ttcctgtaaa acggacaaca 60
a 61

<210> SEQ ID NO 547
<211> LENGTH: 60
<212> TYPE: DNA
<213> ORGANISM: Artificial Sequence
<220> FEATURE:
<223> OTHER INFORMATION: Oligonucleotide

<400> SEQUENCE: 547
ggggaccact ttgtacaaga aagctgggtc taggaaaaat cgtcatcgtt gaaattcgcc 60

<210> SEQ ID NO 548
<211> LENGTH: 47
<212> TYPE: DNA
<213> ORGANISM: Artificial Sequence
<220> FEATURE:
<223> OTHER INFORMATION: Oligonucleotide

<400> SEQUENCE: 548
ggggacaagt ttgtacaaaa aagcaggcta tgcaccccat cgaaacc 47

<210> SEQ ID NO 549
<211> LENGTH: 47
<212> TYPE: DNA
<213> ORGANISM: Artificial Sequence
<220> FEATURE:
<223> OTHER INFORMATION: Oligonucleotide

<400> SEQUENCE: 549
ggggaccact ttgtacaaga aagctgggtc tagtcttgca gtgcctc 47

<210> SEQ ID NO 550
<211> LENGTH: 41
<212> TYPE: DNA
<213> ORGANISM: Artificial Sequence
<220> FEATURE:
<223> OTHER INFORMATION: Oligonucleotide

<400> SEQUENCE: 550
cgcggatccc atatgggaaa tttcttatat agaggcatta g 41

-continued

<210> SEQ ID NO 551
<211> LENGTH: 40
<212> TYPE: DNA
<213> ORGANISM: Artificial Sequence
<220> FEATURE:
<223> OTHER INFORMATION: Oligonucleotide

<400> SEQUENCE: 551
cccgctcgag gttaatttct atcaactctt tagcaataat 40

<210> SEQ ID NO 552
<211> LENGTH: 31
<212> TYPE: DNA
<213> ORGANISM: Artificial Sequence
<220> FEATURE:
<223> OTHER INFORMATION: Oligonucleotide

<400> SEQUENCE: 552
cgcggatccc atatggcctg ccaagacgac a 31

<210> SEQ ID NO 553
<211> LENGTH: 26
<212> TYPE: DNA
<213> ORGANISM: Artificial Sequence
<220> FEATURE:
<223> OTHER INFORMATION: Oligonucleotide

<400> SEQUENCE: 553
cccgctcgag ccgcctcctg ccgaaa 26

<210> SEQ ID NO 554
<211> LENGTH: 34
<212> TYPE: DNA
<213> ORGANISM: Artificial Sequence
<220> FEATURE:
<223> OTHER INFORMATION: Oligonucleotide

<400> SEQUENCE: 554
cgcggatccc atatggcaga gatctgtttg ataa 34

<210> SEQ ID NO 555
<211> LENGTH: 27
<212> TYPE: DNA
<213> ORGANISM: Artificial Sequence
<220> FEATURE:
<223> OTHER INFORMATION: Oligonucleotide

<400> SEQUENCE: 555
cccgctcgag cggttttccg cccaatg 27

<210> SEQ ID NO 556
<211> LENGTH: 30
<212> TYPE: DNA
<213> ORGANISM: Artificial Sequence
<220> FEATURE:
<223> OTHER INFORMATION: Oligonucleotide

<400> SEQUENCE: 556
cgcggatccc atatgcagcc ggatacggtc 30

<210> SEQ ID NO 557
<211> LENGTH: 30
<212> TYPE: DNA
<213> ORGANISM: Artificial Sequence
<220> FEATURE:
<223> OTHER INFORMATION: Oligonucleotide -continued

<400> SEQUENCE: 557
cccgctcgag aatcacttcc aacacaaaat 30

<210> SEQ ID NO 558
<211> LENGTH: 33
<212> TYPE: DNA
<213> ORGANISM: Artificial Sequence
<220> FEATURE:
<223> OTHER INFORMATION: Oligonucleotide

<400> SEQUENCE: 558
cgcggatccc atatgtggtt gctgatgaag ggc 33

<210> SEQ ID NO 559
<211> LENGTH: 28
<212> TYPE: DNA
<213> ORGANISM: Artificial Sequence
<220> FEATURE:
<223> OTHER INFORMATION: Oligonucleotide

<400> SEQUENCE: 559
cccgctcgag gactgcttca tcttctgc 28

<210> SEQ ID NO 560
<211> LENGTH: 34
<212> TYPE: DNA
<213> ORGANISM: Artificial Sequence
<220> FEATURE:
<223> OTHER INFORMATION: Oligonucleotide

<400> SEQUENCE: 560
cgcggatccc atatggaact gatgactgtt ttgc 34

<210> SEQ ID NO 561
<211> LENGTH: 29
<212> TYPE: DNA
<213> ORGANISM: Artificial Sequence
<220> FEATURE:
<223> OTHER INFORMATION: Oligonucleotide

<400> SEQUENCE: 561
cccgctcgag tcagactgct tcatcttct 29

<210> SEQ ID NO 562
<211> LENGTH: 45
<212> TYPE: DNA
<213> ORGANISM: Artificial Sequence
<220> FEATURE:
<223> OTHER INFORMATION: Oligonucleotide

<400> SEQUENCE: 562
cgcggatccc atatgagcat taaagtagcg attaacggtt tcggc 45

<210> SEQ ID NO 563
<211> LENGTH: 40
<212> TYPE: DNA
<213> ORGANISM: Artificial Sequence
<220> FEATURE:
<223> OTHER INFORMATION: Oligonucleotide

<400> SEQUENCE: 563
cccgctcgag gattttgcct gcgaagtatt ccaaagtgcg 40

<210> SEQ ID NO 564
<211> LENGTH: 32

-continued

<212> TYPE: DNA
<213> ORGANISM: Artificial Sequence
<220> FEATURE:
<223> OTHER INFORMATION: Oligonucleotide

<400> SEQUENCE: 564
cgcggatccg ctagccccga tgttaaatcg gc 32

<210> SEQ ID NO 565
<211> LENGTH: 29
<212> TYPE: DNA
<213> ORGANISM: Artificial Sequence
<220> FEATURE:
<223> OTHER INFORMATION: Oligonucleotide

<400> SEQUENCE: 565
cggggatcca tcctgctctt ttttgccgg 29

<210> SEQ ID NO 566
<211> LENGTH: 42
<212> TYPE: DNA
<213> ORGANISM: Artificial Sequence
<220> FEATURE:
<223> OTHER INFORMATION: Oligonucleotide

<400> SEQUENCE: 566
cgcggatccg gtggtggtgg tcaaagcaag agcatccaaa cc 42

<210> SEQ ID NO 567
<211> LENGTH: 30
<212> TYPE: DNA
<213> ORGANISM: Artificial Sequence
<220> FEATURE:
<223> OTHER INFORMATION: Oligonucleotide

<400> SEQUENCE: 567
cccaagcttt tcgggcggta ttcgggcttc 30

<210> SEQ ID NO 568
<211> LENGTH: 39
<212> TYPE: DNA
<213> ORGANISM: Artificial Sequence
<220> FEATURE:
<223> OTHER INFORMATION: Oligonucleotide

<400> SEQUENCE: 568
cgcggatccg gtggtggtgg tgccacctac aaagtggac 39

<210> SEQ ID NO 569
<211> LENGTH: 28
<212> TYPE: DNA
<213> ORGANISM: Artificial Sequence
<220> FEATURE:
<223> OTHER INFORMATION: Oligonucleotide

<400> SEQUENCE: 569
gcccaagctt ttgtttggct gcctcgat 28

<210> SEQ ID NO 570
<211> LENGTH: 34
<212> TYPE: DNA
<213> ORGANISM: Artificial Sequence
<220> FEATURE:
<223> OTHER INFORMATION: Oligonucleotide

<400> SEQUENCE: 570

-continued cgcggatccg gtggtggtgg tacaagcgac gacg 34

<210> SEQ ID NO 571
<211> LENGTH: 28
<212> TYPE: DNA
<213> ORGANISM: Artificial Sequence
<220> FEATURE:
<223> OTHER INFORMATION: Oligonucleotide

<400> SEQUENCE: 571
gcccaagctt ccactcgtaa ttgacgcc 28

<210> SEQ ID NO 572
<211> LENGTH: 41
<212> TYPE: DNA
<213> ORGANISM: Artificial Sequence
<220> FEATURE:
<223> OTHER INFORMATION: Oligonucleotide

<400> SEQUENCE: 572
cgcggatccg gtggtggtgg ttcagatttg gcaaacgatt c 41

<210> SEQ ID NO 573
<211> LENGTH: 28
<212> TYPE: DNA
<213> ORGANISM: Artificial Sequence
<220> FEATURE:
<223> OTHER INFORMATION: Oligonucleotide

<400> SEQUENCE: 573
cccaagcttc gtatcatatt tcacgtgc 28

<210> SEQ ID NO 574
<211> LENGTH: 44
<212> TYPE: DNA
<213> ORGANISM: Artificial Sequence
<220> FEATURE:
<223> OTHER INFORMATION: Oligonucleotide

<400> SEQUENCE: 574
cccaagcttg gtggtggtgg tggttcagat ttggcaaacg attc 44

<210> SEQ ID NO 575
<211> LENGTH: 29
<212> TYPE: DNA
<213> ORGANISM: Artificial Sequence
<220> FEATURE:
<223> OTHER INFORMATION: Oligonucleotide

<400> SEQUENCE: 575
cccgctcgag cgtatcatat ttcacgtgc 29

<210> SEQ ID NO 576
<211> LENGTH: 45
<212> TYPE: DNA
<213> ORGANISM: Artificial Sequence
<220> FEATURE:
<223> OTHER INFORMATION: Oligonucleotide

<400> SEQUENCE: 576
cccaagcttg gtggtggtgg tggtcaaagc aagagcatcc aaacc 45

<210> SEQ ID NO 577
<211> LENGTH: 28
<212> TYPE: DNA
<213> ORGANISM: Artificial Sequence -continued
<220> FEATURE:
<223> OTHER INFORMATION: Oligonucleotide

<400> SEQUENCE: 577
cccgctcgag cgggcggtat tcgggctt 28

<210> SEQ ID NO 578
<211> LENGTH: 32
<212> TYPE: DNA
<213> ORGANISM: Artificial Sequence
<220> FEATURE:
<223> OTHER INFORMATION: Oligonucleotide

<400> SEQUENCE: 578
cgcggatccg ctagccccga tgttaaatcg gc 32

<210> SEQ ID NO 579
<211> LENGTH: 29
<212> TYPE: DNA
<213> ORGANISM: Artificial Sequence
<220> FEATURE:
<223> OTHER INFORMATION: Oligonucleotide

<400> SEQUENCE: 579
cggggatcca tcctgctctt ttttgccgg 29

<210> SEQ ID NO 580
<211> LENGTH: 36
<212> TYPE: DNA
<213> ORGANISM: Artificial Sequence
<220> FEATURE:
<223> OTHER INFORMATION: Oligonucleotide

<400> SEQUENCE: 580
cgcggatccg ctagcggaca cacttatttc ggcatc 36

<210> SEQ ID NO 581
<211> LENGTH: 30
<212> TYPE: DNA
<213> ORGANISM: Artificial Sequence
<220> FEATURE:
<223> OTHER INFORMATION: Oligonucleotide

<400> SEQUENCE: 581
cgcggatccc cagcggtagc ctaatttgat 30

<210> SEQ ID NO 582
<211> LENGTH: 41
<212> TYPE: DNA
<213> ORGANISM: Artificial Sequence
<220> FEATURE:
<223> OTHER INFORMATION: Oligonucleotide

<400> SEQUENCE: 582
cgcggatccg gtggtggtgg ttcagatttg gcaaacgatt c 41

<210> SEQ ID NO 583
<211> LENGTH: 28
<212> TYPE: DNA
<213> ORGANISM: Artificial Sequence
<220> FEATURE:
<223> OTHER INFORMATION: Oligonucleotide

<400> SEQUENCE: 583
cccaagcttc gtatcatatt tcacgtgc 28

-continued

<210> SEQ ID NO 584
<211> LENGTH: 36
<212> TYPE: DNA
<213> ORGANISM: Artificial Sequence
<220> FEATURE:
<223> OTHER INFORMATION: Oligonucleotide

<400> SEQUENCE: 584
gcggcgtcga cggtggcgga ggcactggat cctcag 36

<210> SEQ ID NO 585
<211> LENGTH: 35
<212> TYPE: DNA
<213> ORGANISM: Artificial Sequence
<220> FEATURE:
<223> OTHER INFORMATION: Oligonucleotide

<400> SEQUENCE: 585
ggaggcactg gatcctcaga tttggcaaac gattc 35

<210> SEQ ID NO 586
<211> LENGTH: 29
<212> TYPE: DNA
<213> ORGANISM: Artificial Sequence
<220> FEATURE:
<223> OTHER INFORMATION: Oligonucleotide

<400> SEQUENCE: 586
cccgctcgag cgtatcatat ttcacgtgc 29

<210> SEQ ID NO 587
<211> LENGTH: 33
<212> TYPE: DNA
<213> ORGANISM: Artificial Sequence
<220> FEATURE:
<223> OTHER INFORMATION: Oligonucleotide

<400> SEQUENCE: 587
ggaattccat atgtcagatt tggcaaacga ttc 33

<210> SEQ ID NO 588
<211> LENGTH: 28
<212> TYPE: DNA
<213> ORGANISM: Artificial Sequence
<220> FEATURE:
<223> OTHER INFORMATION: Oligonucleotide

<400> SEQUENCE: 588
cgcggatccc gtatcatatt tcacgtgc 28

<210> SEQ ID NO 589
<211> LENGTH: 25
<212> TYPE: DNA
<213> ORGANISM: Artificial Sequence
<220> FEATURE:
<223> OTHER INFORMATION: Oligonucleotide

<400> SEQUENCE: 589
cggggatccg ggggcggcgg tggcg 25

<210> SEQ ID NO 590
<211> LENGTH: 30
<212> TYPE: DNA
<213> ORGANISM: Artificial Sequence
<220> FEATURE:
<223> OTHER INFORMATION: Oligonucleotide

<400> SEQUENCE: 590
cccaagctta tcctgctctt ttttgccggc 30

<210> SEQ ID NO 591
<211> LENGTH: 42
<212> TYPE: DNA
<213> ORGANISM: Artificial Sequence
<220> FEATURE:
<223> OTHER INFORMATION: Oligonucleotide

<400> SEQUENCE: 591
cgcggatccg gtggtggtgg tcaaagcaag agcatccaaa cc 42

<210> SEQ ID NO 592
<211> LENGTH: 28
<212> TYPE: DNA
<213> ORGANISM: Artificial Sequence
<220> FEATURE:
<223> OTHER INFORMATION: Oligonucleotide

<400> SEQUENCE: 592
cccaagcttc gggcggtatt cgggcttc 28

<210> SEQ ID NO 593
<211> LENGTH: 26
<212> TYPE: DNA
<213> ORGANISM: Artificial Sequence
<220> FEATURE:
<223> OTHER INFORMATION: Oligonucleotide

<400> SEQUENCE: 593
ccccaagctt gggggcggcg gtggcg 26

<210> SEQ ID NO 594
<211> LENGTH: 31
<212> TYPE: DNA
<213> ORGANISM: Artificial Sequence
<220> FEATURE:
<223> OTHER INFORMATION: Oligonucleotide

<400> SEQUENCE: 594
cccgctcgag atcctgctct tttttgccgg c 31

<210> SEQ ID NO 595
<211> LENGTH: 45
<212> TYPE: DNA
<213> ORGANISM: Artificial Sequence
<220> FEATURE:
<223> OTHER INFORMATION: Oligonucleotide

<400> SEQUENCE: 595
cccaagcttg gtggtggtgg tggtcaaagc aagagcatcc aaacc 45

<210> SEQ ID NO 596
<211> LENGTH: 28
<212> TYPE: DNA
<213> ORGANISM: Artificial Sequence
<220> FEATURE:
<223> OTHER INFORMATION: Oligonucleotide

<400> SEQUENCE: 596
cccgctcgag cgggcggtat tcgggctt 28

<210> SEQ ID NO 597

-continued

<211> LENGTH: 35
<212> TYPE: DNA
<213> ORGANISM: Artificial Sequence
<220> FEATURE:
<223> OTHER INFORMATION: Oligonucleotide

<400> SEQUENCE: 597
ggaggcactg gatccgcagc cacaaacgac gacga 35

<210> SEQ ID NO 598
<211> LENGTH: 36
<212> TYPE: DNA
<213> ORGANISM: Artificial Sequence
<220> FEATURE:
<223> OTHER INFORMATION: Oligonucleotide

<400> SEQUENCE: 598
gcggcctcga gggtggcgga ggcactggat ccgcag 36

<210> SEQ ID NO 599
<211> LENGTH: 28
<212> TYPE: DNA
<213> ORGANISM: Artificial Sequence
<220> FEATURE:
<223> OTHER INFORMATION: Oligonucleotide

<400> SEQUENCE: 599
cccgctcgag acccagcttg taaggttg 28

<210> SEQ ID NO 600
<211> LENGTH: 35
<212> TYPE: DNA
<213> ORGANISM: Artificial Sequence
<220> FEATURE:
<223> OTHER INFORMATION: Oligonucleotide

<400> SEQUENCE: 600
ggaggcactg gatccgcagc cacaaacgac gacga 35

<210> SEQ ID NO 601
<211> LENGTH: 36
<212> TYPE: DNA
<213> ORGANISM: Artificial Sequence
<220> FEATURE:
<223> OTHER INFORMATION: Oligonucleotide

<400> SEQUENCE: 601
gcggcctcga gggtggcgga ggcactggat ccgcag 36

<210> SEQ ID NO 602
<211> LENGTH: 28
<212> TYPE: DNA
<213> ORGANISM: Artificial Sequence
<220> FEATURE:
<223> OTHER INFORMATION: Oligonucleotide

<400> SEQUENCE: 602
cccgctcgag ccactcgtaa ttgacgcc 28

<210> SEQ ID NO 603
<211> LENGTH: 38
<212> TYPE: DNA
<213> ORGANISM: Artificial Sequence
<220> FEATURE:
<223> OTHER INFORMATION: Oligonucleotide

<400> SEQUENCE: 603
gcggcctcga gggatccggc ggaggcggca cttctgcg 38

<210> SEQ ID NO 604
<211> LENGTH: 26
<212> TYPE: DNA
<213> ORGANISM: Artificial Sequence
<220> FEATURE:
<223> OTHER INFORMATION: Oligonucleotide

<400> SEQUENCE: 604
cccgctcgag gaaccggtag cctacg 26

<210> SEQ ID NO 605
<211> LENGTH: 35
<212> TYPE: DNA
<213> ORGANISM: Artificial Sequence
<220> FEATURE:
<223> OTHER INFORMATION: Oligonucleotide

<400> SEQUENCE: 605
ggaggcactg gatcctcaga tttggcaaac gattc 35

<210> SEQ ID NO 606
<211> LENGTH: 37
<212> TYPE: DNA
<213> ORGANISM: Artificial Sequence
<220> FEATURE:
<223> OTHER INFORMATION: Oligonucleotide

<400> SEQUENCE: 606
gcggcgtcga cggtggcgga ggcactggat cctcaga 37

<210> SEQ ID NO 607
<211> LENGTH: 29
<212> TYPE: DNA
<213> ORGANISM: Artificial Sequence
<220> FEATURE:
<223> OTHER INFORMATION: Oligonucleotide

<400> SEQUENCE: 607
cccgctcgag cgtatcatat ttcacgtgc 29

<210> SEQ ID NO 608
<211> LENGTH: 35
<212> TYPE: DNA
<213> ORGANISM: Artificial Sequence
<220> FEATURE:
<223> OTHER INFORMATION: Oligonucleotide

<400> SEQUENCE: 608
gcggcctcga gggatccgga gggggtggtg tcgcc 35

<210> SEQ ID NO 609
<211> LENGTH: 25
<212> TYPE: DNA
<213> ORGANISM: Artificial Sequence
<220> FEATURE:
<223> OTHER INFORMATION: Oligonucleotide

<400> SEQUENCE: 609
cccgctcgag ttgcttggcg gcaag 25

<210> SEQ ID NO 610
<211> LENGTH: 35
<212> TYPE: DNA

-continued

<213> ORGANISM: Artificial Sequence
<220> FEATURE:
<223> OTHER INFORMATION: Oligonucleotide

<400> SEQUENCE: 610
ggaggcactg gatccgcagc cacaaacgac gacga 35

<210> SEQ ID NO 611
<211> LENGTH: 36
<212> TYPE: DNA
<213> ORGANISM: Artificial Sequence
<220> FEATURE:
<223> OTHER INFORMATION: Oligonucleotide

<400> SEQUENCE: 611
gcggcctcga gggtggcgga ggcactggat ccgcag 36

<210> SEQ ID NO 612
<211> LENGTH: 28
<212> TYPE: DNA
<213> ORGANISM: Artificial Sequence
<220> FEATURE:
<223> OTHER INFORMATION: Oligonucleotide

<400> SEQUENCE: 612
cccgctcgag acccagcttg taaggttg 28

<210> SEQ ID NO 613
<211> LENGTH: 35
<212> TYPE: DNA
<213> ORGANISM: Artificial Sequence
<220> FEATURE:
<223> OTHER INFORMATION: Oligonucleotide

<400> SEQUENCE: 613
ggaggcactg gatccgcagc cacaaacgac gacga 35

<210> SEQ ID NO 614
<211> LENGTH: 36
<212> TYPE: DNA
<213> ORGANISM: Artificial Sequence
<220> FEATURE:
<223> OTHER INFORMATION: Oligonucleotide

<400> SEQUENCE: 614
gcggcctcga gggtggcgga ggcactggat ccgcag 36

<210> SEQ ID NO 615
<211> LENGTH: 28
<212> TYPE: DNA
<213> ORGANISM: Artificial Sequence
<220> FEATURE:
<223> OTHER INFORMATION: Oligonucleotide

<400> SEQUENCE: 615
cccgctcgag ccactcgtaa ttgacgcc 28

<210> SEQ ID NO 616
<211> LENGTH: 35
<212> TYPE: DNA
<213> ORGANISM: Artificial Sequence
<220> FEATURE:
<223> OTHER INFORMATION: Oligonucleotide

<400> SEQUENCE: 616
ggaggcactg gatcctcaga tttggcaaac gattc 35

-continued

<210> SEQ ID NO 617
<211> LENGTH: 37
<212> TYPE: DNA
<213> ORGANISM: Artificial Sequence
<220> FEATURE:
<223> OTHER INFORMATION: Oligonucleotide

<400> SEQUENCE: 617
gcggcgtcga cggtggcgga ggcactggat cctcaga 37

<210> SEQ ID NO 618
<211> LENGTH: 29
<212> TYPE: DNA
<213> ORGANISM: Artificial Sequence
<220> FEATURE:
<223> OTHER INFORMATION: Oligonucleotide

<400> SEQUENCE: 618
cccgctcgag cgtatcatat ttcacgtgc 29

<210> SEQ ID NO 619
<211> LENGTH: 488
<212> TYPE: PRT
<213> ORGANISM: Artificial Sequence
<220> FEATURE:
<223> OTHER INFORMATION: MC58

<400> SEQUENCE: 619

```
Met Phe Lys Arg Ser Val Ile Ala Met Ala Cys Ile Phe Ala Leu Ser
1               5                   10                  15

Ala Cys Gly Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240
```

-continued

```
Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485


<210> SEQ ID NO 620
<211> LENGTH: 427
<212> TYPE: PRT
<213> ORGANISM: Artificial Sequence
<220> FEATURE:
<223> OTHER INFORMATION: 2996

<400> SEQUENCE: 620

Met Phe Glu Arg Ser Val Ile Ala Met Ala Cys Ile Phe Ala Leu Ser
1               5                   10                  15

Ala Cys Gly Gly Gly Gly Gly Gly Ser Pro Asp Val Lys Ser Ala Asp
            20                  25                  30

Thr Leu Ser Lys Pro Ala Ala Pro Val Val Ala Glu Lys Glu Thr Glu
        35                  40                  45

Val Lys Glu Asp Ala Pro Gln Ala Gly Ser Gln Gly Gln Gly Ala Pro
    50                  55                  60

Ser Thr Gln Gly Ser Gln Asp Met Ala Ala Val Ser Ala Glu Asn Thr
65                  70                  75                  80

Gly Asn Gly Gly Ala Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110
```

```
Thr Gly Asn Asn Gln Pro Ala Asp Ser Ser Asp Ser Ala Pro Ala Ser
        115                 120                 125

Asn Pro Ala Pro Ala Asn Gly Gly Ser Asn Phe Gly Arg Val Asp Leu
    130                 135                 140

Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
        195                 200                 205

Ala Thr Ala Val Gln Ala Asn Gly Thr Asn Lys Tyr Val Ile Ile Tyr
    210                 215                 220

Lys Asp Lys Ser Ala Ser Ser Ser Ser Ala Arg Phe Arg Arg Ser Ala
225                 230                 235                 240

Arg Ser Arg Arg Ser Leu Pro Ala Glu Met Pro Leu Ile Pro Val Asn
                245                 250                 255

Gln Ala Asp Thr Leu Ile Val Asp Gly Glu Ala Val Ser Leu Thr Gly
            260                 265                 270

His Ser Gly Asn Ile Phe Ala Pro Glu Gly Asn Tyr Arg Tyr Leu Thr
        275                 280                 285

Tyr Gly Ala Glu Lys Leu Pro Gly Gly Ser Tyr Ala Leu Arg Val Gln
    290                 295                 300

Gly Glu Pro Ala Lys Gly Glu Met Leu Ala Gly Thr Ala Val Tyr Asn
305                 310                 315                 320

Gly Glu Val Leu His Phe His Thr Glu Asn Gly Arg Pro Tyr Pro Thr
                325                 330                 335

Arg Gly Arg Phe Ala Ala Lys Val Asp Phe Gly Ser Lys Ser Val Asp
            340                 345                 350

Gly Ile Ile Asp Ser Gly Asp Asp Leu His Met Gly Thr Gln Lys Phe
        355                 360                 365

Lys Ala Ala Ile Asp Gly Asn Gly Phe Lys Gly Thr Trp Thr Glu Asn
    370                 375                 380

Gly Gly Gly Asp Val Ser Gly Arg Phe Tyr Gly Pro Ala Gly Glu Glu
385                 390                 395                 400

Val Ala Gly Lys Tyr Ser Tyr Arg Pro Thr Asp Ala Glu Lys Gly Gly
                405                 410                 415

Phe Gly Val Phe Ala Gly Lys Lys Glu Gln Asp
            420                 425


<210> SEQ ID NO 621
<211> LENGTH: 9
<212> TYPE: PRT
<213> ORGANISM: artificial sequence
<220> FEATURE:
<223> OTHER INFORMATION: replacement leader peptide

<400> SEQUENCE: 621

Met Lys Lys Tyr Leu Phe Ser Ala Ala
1               5


<210> SEQ ID NO 622
<211> LENGTH: 6
<212> TYPE: PRT
<213> ORGANISM: artificial sequence
```

<220> FEATURE:
<223> OTHER INFORMATION: sample poly-glycine stretch

<400> SEQUENCE: 622

Cys Gly Gly Gly Gly Ser
1               5

<210> SEQ ID NO 623
<211> LENGTH: 5
<212> TYPE: PRT
<213> ORGANISM: artificial sequence
<220> FEATURE:
<223> OTHER INFORMATION: deletion example

<400> SEQUENCE: 623

Cys Gly Gly Gly Ser
1               5

<210> SEQ ID NO 624
<211> LENGTH: 4
<212> TYPE: PRT
<213> ORGANISM: artificial sequence
<220> FEATURE:
<223> OTHER INFORMATION: deletion example

<400> SEQUENCE: 624

Cys Gly Gly Ser
1

<210> SEQ ID NO 625
<211> LENGTH: 6
<212> TYPE: PRT
<213> ORGANISM: artificial sequence
<220> FEATURE:
<223> OTHER INFORMATION: substitution example
<220> FEATURE:
<221> NAME/KEY: misc_feature
<222> LOCATION: (3)..(3)
<223> OTHER INFORMATION: Xaa can be any naturally occurring amino acid

<400> SEQUENCE: 625

Cys Gly Xaa Gly Gly Ser
1               5

<210> SEQ ID NO 626
<211> LENGTH: 6
<212> TYPE: PRT
<213> ORGANISM: artificial sequence
<220> FEATURE:
<223> OTHER INFORMATION: substitution example
<220> FEATURE:
<221> NAME/KEY: misc_feature
<222> LOCATION: (3)..(4)
<223> OTHER INFORMATION: Xaa can be any naturally occurring amino acid

<400> SEQUENCE: 626

Cys Gly Xaa Xaa Gly Ser
1               5

<210> SEQ ID NO 627
<211> LENGTH: 6
<212> TYPE: PRT
<213> ORGANISM: artificial sequence
<220> FEATURE:
<223> OTHER INFORMATION: substitution example
<220> FEATURE:
<221> NAME/KEY: misc_feature
<222> LOCATION: (3)..(3)
<223> OTHER INFORMATION: Xaa can be any naturally occurring amino acid -continued
<220> FEATURE:
<221> NAME/KEY: misc_feature
<222> LOCATION: (5)..(5)
<223> OTHER INFORMATION: Xaa can be any naturally occurring amino acid

<400> SEQUENCE: 627

Cys Gly Xaa Gly Xaa Ser
1 5

<210> SEQ ID NO 628
<211> LENGTH: 7
<212> TYPE: PRT
<213> ORGANISM: artificial sequence
<220> FEATURE:
<223> OTHER INFORMATION: insertion example
<220> FEATURE:
<221> NAME/KEY: misc_feature
<222> LOCATION: (4)..(4)
<223> OTHER INFORMATION: Xaa can be any naturally occurring amino acid

<400> SEQUENCE: 628

Cys Gly Gly Xaa Gly Gly Ser
1 5

<210> SEQ ID NO 629
<211> LENGTH: 7
<212> TYPE: PRT
<213> ORGANISM: artificial sequence
<220> FEATURE:
<223> OTHER INFORMATION: insertion example
<220> FEATURE:
<221> NAME/KEY: misc_feature
<222> LOCATION: (3)..(3)
<223> OTHER INFORMATION: Xaa can be any naturally occurring amino acid

<400> SEQUENCE: 629

Cys Gly Xaa Gly Gly Gly Ser
1 5

<210> SEQ ID NO 630
<211> LENGTH: 19
<212> TYPE: PRT
<213> ORGANISM: artificial sequence
<220> FEATURE:
<223> OTHER INFORMATION: leader peptide from ORF4

<400> SEQUENCE: 630

Met Lys Thr Phe Phe Lys Thr Leu Ser Ala Ala Ala Leu Ala Leu Ile
1 5 10 15

Leu Ala Ala

<210> SEQ ID NO 631
<211> LENGTH: 7
<212> TYPE: PRT
<213> ORGANISM: artificial sequence
<220> FEATURE:
<223> OTHER INFORMATION: short N-terminal deletion

<400> SEQUENCE: 631

Gly Gly Gly Gly Gly Gly Ser
1 5

<210> SEQ ID NO 632
<211> LENGTH: 6
<212> TYPE: PRT
<213> ORGANISM: artificial sequence
<220> FEATURE:
<223> OTHER INFORMATION: deletion sequence -continued

```
<400> SEQUENCE: 632

Gly Gly Gly Gly Gly Gly
1               5


<210> SEQ ID NO 633
<211> LENGTH: 20
<212> TYPE: PRT
<213> ORGANISM: artificial sequence
<220> FEATURE:
<223> OTHER INFORMATION: 20mer leader peptide from 919

<400> SEQUENCE: 633

Met Lys Lys Tyr Leu Phe Arg Ala Ala Leu Tyr Gly Ile Ala Ala Ala
1               5                   10                  15

Ile Leu Ala Ala
            20
```